US012780929B2

(12) United States Patent
Huang et al.

(10) Patent No.: US 12,780,929 B2
(45) Date of Patent: Nov. 3, 2026

(54) ANTIBODIES AGAINST TL1A AND USES THEREOF

(71) Applicant: Earendil Labs Inc., Wilmington, DE (US)

(72) Inventors: Jian Huang, Suzhou (CN); Zhenping Zhu, Suzhou (CN); Jian Peng, Suzhou (CN); Liang Tian, Suzhou (CN); Chenpeng Su, Suzhou (CN); Hao Ran, Suzhou (CN)

( * ) Notice: Subject to any disclaimer, the term of this patent is extended or adjusted under 35 U.S.C. 154(b) by 0 days.

(21) Appl. No.: 19/312,502

(22) Filed: Aug. 28, 2025

(65) Prior Publication Data

US 2026/0062492 A1 Mar. 5, 2026

(51) Int. Cl.

*A61P 1/00* (2006.01)
*C07K 16/28* (2006.01)
*A61K 39/00* (2006.01)

(52) U.S. Cl.

CPC ............ *C07K 16/2875* (2013.01); *A61P 1/00* (2018.01); *A61K 2039/505* (2013.01); *C07K 2317/33* (2013.01); *C07K 2317/52* (2013.01); *C07K 2317/565* (2013.01); *C07K 2317/76* (2013.01); *C07K 2317/92* (2013.01); *C07K 2317/94* (2013.01)

(58) Field of Classification Search

CPC .......................................................... A61P 1/00
See application file for complete search history.

(56) References Cited

U.S. PATENT DOCUMENTS 5,639,641 A 6/1997 Pedersen et al.
2002/0052480 A1* 5/2002 Park ....................... C07K 16/40 424/183.1
2014/0051834 A1* 2/2014 Hoffman .................. A61P 7/02 530/387.3
2015/0132311 A1 5/2015 Arch et al.
2018/0110855 A1 4/2018 Bilsborough et al.
2019/0202898 A9 7/2019 Bansal
2021/0122828 A1 4/2021 Watkins et al.
2021/0140201 A1 5/2021 Chen
2021/0209892 A1 7/2021 Danielson et al.
2021/0244976 A1 8/2021 Castiglione
2022/0089764 A1 3/2022 Viswanathan et al.
2023/0332104 A1 10/2023 Estevez Silva et al.
2026/0062471 A1 3/2026 Ran et al.
2026/0062472 A1 3/2026 Ran et al.

FOREIGN PATENT DOCUMENTS

CN 117924509 A 4/2024
CN 117964774 A 5/2024
WO WO-2006003388 A2 1/2006
WO WO-2006030220 A1 3/2006
WO WO-2010115786 A1 10/2010
WO WO-2015073580 A1 5/2015
WO WO-2017106383 A1 6/2017
WO WO-2018138496 A1 8/2018
WO WO-2022112356 A1 6/2022
WO WO-2022159620 A1 7/2022
WO WO-2022159630 A1 7/2022
WO WO-2022178158 A1 8/2022
WO WO-2023133538 A2 7/2023
WO WO-2023220663 A1 11/2023
WO WO-2024061288 A1 3/2024
WO WO-2024148222 A1 7/2024

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Ahmed et al., "Dual Biologic or Small Molecule Therapy for Treatment of Inflammatory Bowel Disease: A Systematic Review and Meta-analysis", Clin Gastroenterol Hepatol., Mar. 2022, 20(3): e361-e379, Epublished Mar. 31, 2021.
Banfield et al., "First-in-human, randomized dose-escalation study of the safety, tolerability, pharmacokinetics, pharmacodynamics and immunogenicity of PF-06480605 in healthy subjects" British Journal of Clinical Pharmacology, vol. 86, Apr. 2020, pp. 812-824.
Bird et al., "Single-chain antigen-binding proteins" Science, Oct. 21, 1988, vol. 242, Issue 4877, pp. 423-426.
Cheng et al., "Relationship between the inhibition constant (K1) and the concentration of inhibitor which causes 50 per cent inhibition (150) of an enzymatic reaction" Biochemical Pharmacology, vol. 22, Issue 23, Dec. 1, 1973, pp. 3099-3108.
Chothia, C. & Lesk, A., "Canonical structures for the hypervariable regions of immunoglobulins" Journal of Molecular Biology 196(4):901-917 (Aug. 20, 1987).
Chothia, C. et al. "Conformations of immunoglobulin hypervariable regions," Nature, 342(6252):878-883 (Dec. 28, 1989).
Clackson et al., "Making antibody fragments using phage display libraries" Nature, Aug. 15, 1991, vol. 352, pp. 624-628.
Co et al., "Chimeric and humanized antibodies with specificity for the CD33 antigen" The Journal of Immunology, Feb. 15, 1992, vol. 148, pp. 1149-1154.
Co et al., "Humanized antibodies for antiviral therapy" Proceedings of the National Academy of Sciences of the United States of America, Apr. 1, 1991, vol. 88, pp. 2869-2873.
Danese et al., "Anti-TL1A Antibody PF-06480605 Safety and Efficacy for Ulcerative Colitis: A Phase 2a Single-Arm Study" Clinical Gastroenterology and Hepatology, Nov. 2021, vol. 19, No. 11, pp. 2324-2332.
Freireich et al., "Quantitative comparison of toxicity of anticancer agents in mouse, rat, hamster, dog, monkey, and man" Cancer Chemotherapy Reports, vol. 50, May 1966, pp. 219-244.

(Continued)

*Primary Examiner* — Nelson B Moseley, II
*Assistant Examiner* — Dennis J Sullivan
(74) *Attorney, Agent, or Firm* — COOLEY LLP

(57) ABSTRACT

The present disclosure provides an isolated antigen-binding protein specifically binding to TNF-like protein A (TL1A), comprising a heavy chain variable region (VH) comprising at least one heavy chain complementarity-determining region (HCDR) comprising an amino acid sequence shown in SEQ ID NO:1, SEQ ID NO:5, or SEQ ID NO:14.

5 Claims, 56 Drawing Sheets

Specification includes a Sequence Listing.

(56) References Cited

OTHER PUBLICATIONS

Hamers-Casterman, et al. (Jun. 3, 1993) "Naturally Occurring Antibodies Devoid of Light Chains", Nature, vol. 363, No. 6428, pp. 446-448.
Hassan-Zahraee et al., "Antitumor Necrosis Factor-like Ligand 1A Therapy Targets Tissue Inflammation and Fibrosis Pathways and Reduces Gut Pathobionts in Ulcerative Colitis" Inflammatory Bowel Diseases, Mar. 2, 2022, 28, pp. 434-446.
Holt et al., "Domain antibodies: proteins for therapy", Trends Biotechnol., Nov. 2003, 21 (11): 484-490.
Huston et al., "Protein engineering of antibody binding sites: Recovery of specific activity in an anti-digoxin single-chain Fv analogue produced in *Escherichia coli*" Proceedings of the National Academy of Sciences of the United States of America, Aug. 1988, vol. 85, pp. 5879-5883.
Jones, P.T. et al.; "Replacing the complementarity-determining regions in a human antibody with those from a mouse," Nature; 321(6069):522-525 (Apr. 1986).
Kang et al., "Single-domain antibody - advances in research and application" Chinese Journal of Biotechnology, Dec. 25, 2018, 34(12), pp. 1974-1984, with English abstract.
Kastelein et al., "Discovery and biology of IL-23 and IL-27: related but functionally distinct regulators of inflammation", Ann. Rev. Immunol., Apr. 2007, vol. 25, pp. 221-242.
Kikly et al., "The IL-23/Th17 axis: therapeutic targets for autoimmune inflammation", Curr. Opin. Immunol., Dec. 2006, 18(6): 670-675.
Korndorfer et al., "Crystallographic analysis of an "anticalin" with tailored specificity for fluorescein reveals high structural plasticity of the lipocalin loop region", Proteins: Structure, Function, and Bioinformatics, Aug. 5, 2003, 53(1), pp. 121-129.
MacCallum et al., "Antibody-antigen interactions: contact analysis and binding site topography" Journal of Molecular Biology, Oct. 11, 1996, vol. 262, Issue 5, pp. 732-745.
Marks et al., "By-passing Immunization. Human Antibodies from V-gene Libraries Displayed on Phage" Journal of Molecular Biology, vol. 222, Issue 3, Dec. 5, 1991, pp. 581-597.
(No Author Available) PRA023 Progress Update, Phase 1 Data & Announcement of New Indication, Prometheus Biosciences, (unknown publication date), 33 pages.
(No Author Available) RVT-3101, roivant, Jan. 2023, 24 pages.
Oppman et al., "Novel p19 protein engages IL-12p40 to form a cytokine, IL-23, with biological activities similar as well as distinct from IL-12", Immunity, Nov. 2000, 13(5), pp. 715-725.
Padlan et al., "Identification of specificity-determining residues in antibodies" The FASEB Journal, Jan. 1, 1995, vol. 9, Issue 1, pp. 133-139.
Parham et al., "A Receptor for the Heterodimeric Cytokine IL-23 Is Composed of IL-12Rβ1 and a Novel Cytokine Receptor Subunit, IL-23R", J. Immunol., Jun. 2002, vol. 168, Issue 11, 5699-5708.
PCT Application No. PCT/US2025/043850, International Search Report and Written Opinion mailed Dec. 16, 2025, Applicant Earendil Labs Inc.; 15 pages.
PCT Application No. PCT/US2025/043850, Invitation to Pay Additional Fees mailed Oct. 22, 2025, Applicant Earendil Labs Inc., 2 pages.
Queen et al., "A humanized antibody that binds to the interleukin 2 receptor" Proceedings of the National Academy of Sciences of the United States of America, Dec. 1989, vol. 86, pp. 10029-10033.
Riechmann et al., "Reshaping human antibodies for therapy" Nature, Mar. 24, 1988, vol. 332, pp. 323-327.
Roque et al., "Antibodies and Genetically Engineered Related Molecules: Production and Purification", Biotechnol. Progress, May-Jun. 2004, 20(3), pp. 639-654.
Sheriff et al, "Redefining the minimal antigen-binding fragment", Nature Struct & Molec Biol., Sept. 1, 1996, 3, pp. 733-736.
Tempest P.R., et al., "Reshaping a Human Monoclonal Antibody to Inhibit Human Respiratory Syncytial Virus Infection In Vivo," Nature Biotechnology, Mar. 1991, vol. 9, No. 3, pp. 266-271.
Verhoeyen et al., "Reshaping human antibodies: grafting an antilysozyme activity" Science, Mar. 25, 1988, vol. 239, Issue 4847, pp. 1534-1536.
Ward et al., "Binding activities of a repertoire of single immunoglobulin variable domains secreted from *Escherichia coli*" Nature, Oct. 12, 1989, vol. 341, pp. 544-546.
Kobayashi et al., "Ulcerative colitis", Nature Reviews, Disease Primers, vol. 6, No. 1, (Sep. 10, 2020), 20 pages. doi:10.1038/s41572-020-0205-x.
Leppkes et al., "Cytokines in inflammatory bowel diseases—Update 2020", Pharmacological Research, vol. 158, (Aug. 2020), 8 pages. doi:10.1016/j.phrs.2020.104835.
Lu et al., "Immunology of Inflammatory Bowel Disease: Molecular Mechanisms and Therapeutics", Journal of Inflammation Research, vol. 15, (Mar. 12, 2022), pp. 1825-1844.
Ma et al., "Bispecific Antibodies: From Research to Clinical Application", Frontiers in Immunology, vol. 12, Article 626616, (May 5, 2021), 19 pages. doi:10.3389/fimmu.2021.626616.
Mahita et al., "Characterizing antibodies binding to the same epitope reveals limited contribution by heavy chain CDR3 sequence relative to other CDRs", BioRxiv, (May 2025), 29 pages. DOI:10.1101/2025.05.24.655967.
PCT Application No. PCT/US2025/043885, International Search Report and Written Opinion mailed May 6, 2026, Applicant Earendil Labs Inc, 23 pages.
PCT Application No. PCT/US2025/043885, Invitation to Pay Additional fees mailed Jan. 30, 2026, Applicant Earendil Labs Inc, 14 pages.
PCT Application No. PCT/US2025/043896, International Search Report and Written Opinion mailed Jan. 16, 2026, Applicant Earendil Labs Inc., 20 pages.
Petronio et al., "Drug Development in Inflammatory Bowel Diseases: What Is Next?", Pharmaceuticals, vol. 18, No. 2, (Jan. 30, 2025), 35 pages.
Ran et al., "Clinical: Therapy and Observation, Abstract citation ID: jjae190.1022, P0848, Engineering and Development of a Novel Bispecific Antibody Targeting both TL1A and [alpha]4[beta]7 for the Treatment of IBD", Journal of Crohn's and Colitis, vol. 19, No. Supp 1, (Oct. 1, 2025), p. i1618.
Ran et al., "Su 1884: Development of a Novel BiSpecific Antibody Targeting TL1A and [alpha]4[beta]7 for Enhanced IBD Therapy", Gastroenterology, vol. 169, No. 1, (May 3, 2025), 1 page.
Spyre Therapeutics, "Corporate Overview", (Oct. 24, 2023), [Retrieved from and publicly available at URL: https://s26.q4cdn.com/935390172/files/doc_presentation/2023/09/SPYRECorporate-Overview-Sept-2023.pdf], 38 pages.
U.S. Appl. No. 19/312,682, filed Aug. 28, 2025, Inventor Ran, Hao et al.
U.S. Appl. No. 19/312,684, filed Aug. 28, 2025, Inventor Ran, Hao et al.
Wan et al., "177a: First-In-Class Oral TL1A Nanobody and Long-Acting TL1A/IL-23 Bispecific Nanobody: Novel Therapies for Inflammatory Bowel Disease", Gastroenterology, vol. 169, No. 1, (May 3, 2025), 1 page. DOI:10.1016/80016-5085(25)05711-7.
Xu et al., "Role of TL1A in Inflammatory Autoimmune Diseases: A Comprehensive Review", Frontiers in Immunology, vol. 13, Article 891328, (Jul. 14, 2022), 10 pages.

* cited by examiner

| | IC50 |
|---|---|
| TLA0238-39 | 22.05 |
| TLA0238-40 | 66.96 |
| TLA0238-41 | 1068 |
| TLA0238-42 | 185.8 |
| TLA0238-43 | 1.017 |
| TLA0238-28 | 1.032 |

| | IC50 |
|---|---|
| TLA0238-44 | 1.102 |
| TLA0238-45 | 0.8999 |
| TLA0238-46 | 1.051 |
| TLA0238-47 | 1.062 |
| TLA0238-48 | 1.026 |
| TLA0238-28 | 0.9224 |

| | IC50 |
|---|---|
| TLA0238-49 | 0.9190 |
| TLA0238-50 | 0.9476 |
| RVT-3101(analogue) | 0.9623 |
| MK-7240(analogue) | 1.801 |
| TLA0015-11 | 0.7296 |
| TLA0238-28 | 0.9381 |

| | RVT-3101 analogue | MK-7240 analogue | TLA0015-11 |
|---|---|---|---|
| IC50 | 0.9528 | 3.178 | 0.8164 |

SEQUENCE LISTING

```
Sequence total quantity: 565
SEQ ID NO: 1            moltype = AA  length = 5
FEATURE                 Location/Qualifiers
REGION                  1..5
                        note = TLA0015-HCDR1
VARIANT                 1
                        note = Xaa = Ser, Thr or Tyr
source                  1..5
                        mol_type = protein
                        organism = synthetic construct
SEQUENCE: 1
XYGVD                                                        5

SEQ ID NO: 2            moltype = AA  length = 5
FEATURE                 Location/Qualifiers
REGION                  1..5
                        note = TLA0015-HCDR1-1
source                  1..5
                        mol_type = protein
                        organism = synthetic construct
SEQUENCE: 2
SYGVD                                                        5

SEQ ID NO: 3            moltype = AA  length = 5
FEATURE                 Location/Qualifiers
REGION                  1..5
                        note = TLA0015-HCDR1-2
source                  1..5
                        mol_type = protein
                        organism = synthetic construct
SEQUENCE: 3
YYGVD                                                        5

SEQ ID NO: 4            moltype = AA  length = 5
FEATURE                 Location/Qualifiers
REGION                  1..5
                        note = TLA0015-HCDR1-3
source                  1..5
                        mol_type = protein
                        organism = synthetic construct
SEQUENCE: 4
TYGVD                                                        5

SEQ ID NO: 5            moltype = AA  length = 16
FEATURE                 Location/Qualifiers
REGION                  1..16
                        note = TLA0015-HCDR2
VARIANT                 1
                        note = Xaa = Arg or Val
VARIANT                 7
                        note = Xaa = Gly or Lys
VARIANT                 9
                        note = Xaa = Asp, His or Asn
VARIANT                 11
                        note = Xaa = Asn or Gln
VARIANT                 12
                        note = Xaa = Ala, Pro or Ser
source                  1..16
```

```
                        mol_type = protein
                        organism = synthetic construct
SEQUENCE: 5
XIWGFGXTXY XXALKS                                                   16

SEQ ID NO: 6            moltype = AA  length = 16
FEATURE                 Location/Qualifiers
REGION                  1..16
                        note = TLA0015-HCDR2-1
source                  1..16
                        mol_type = protein
                        organism = synthetic construct
SEQUENCE: 6
VIWGFGGTNY NSALKS                                                   16

SEQ ID NO: 7            moltype = AA  length = 16
FEATURE                 Location/Qualifiers
REGION                  1..16
                        note = TLA0015-HCDR2-2
source                  1..16
                        mol_type = protein
                        organism = synthetic construct
SEQUENCE: 7
VIWGFGGTNY QSALKS                                                   16

SEQ ID NO: 8            moltype = AA  length = 16
FEATURE                 Location/Qualifiers
REGION                  1..16
                        note = TLA0015-HCDR2-3
source                  1..16
                        mol_type = protein
                        organism = synthetic construct
SEQUENCE: 8
VIWGFGGTNY NAALKS                                                   16

SEQ ID NO: 9            moltype = AA  length = 16
FEATURE                 Location/Qualifiers
REGION                  1..16
                        note = TLA0015-HCDR2-4
source                  1..16
                        mol_type = protein
                        organism = synthetic construct
SEQUENCE: 9
VIWGFGGTNY NPALKS                                                   16

SEQ ID NO: 10           moltype = AA  length = 16
FEATURE                 Location/Qualifiers
REGION                  1..16
                        note = TLA0015-HCDR2-5
source                  1..16
                        mol_type = protein
                        organism = synthetic construct
SEQUENCE: 10
VIWGFGGTHY NSALKS                                                   16

SEQ ID NO: 11           moltype = AA  length = 16
FEATURE                 Location/Qualifiers
REGION                  1..16
                        note = TLA0015-HCDR2-6
source                  1..16
                        mol_type = protein
                        organism = synthetic construct
SEQUENCE: 11
RIWGFGGTNY NSALKS                                                   16

SEQ ID NO: 12           moltype = AA  length = 16
FEATURE                 Location/Qualifiers
REGION                  1..16
                        note = TLA0015-HCDR2-7
source                  1..16
                        mol_type = protein
                        organism = synthetic construct
SEQUENCE: 12
VIWGFGKTNY NSALKS                                                   16

SEQ ID NO: 13           moltype = AA  length = 16
FEATURE                 Location/Qualifiers
REGION                  1..16
                        note = TLA0015-HCDR2-8
```

```
source                  1..16
                        mol_type = protein
                        organism = synthetic construct
SEQUENCE: 13
VIWGFGGTDY NSALKS                                                           16

SEQ ID NO: 14           moltype = AA  length = 8
FEATURE                 Location/Qualifiers
REGION                  1..8
                        note = TLA0015-HCDR3
VARIANT                 2
                        note = Xaa = Asp, Leu or Asn
VARIANT                 3
                        note = Xaa = Phe or Tyr
source                  1..8
                        mol_type = protein
                        organism = synthetic construct
SEQUENCE: 14
GXXDAMDY                                                                    8

SEQ ID NO: 15           moltype = AA  length = 8
FEATURE                 Location/Qualifiers
REGION                  1..8
                        note = TLA0015-HCDR3-1
source                  1..8
                        mol_type = protein
                        organism = synthetic construct
SEQUENCE: 15
GNFDAMDY                                                                    8

SEQ ID NO: 16           moltype = AA  length = 8
FEATURE                 Location/Qualifiers
REGION                  1..8
                        note = TLA0015-HCDR3-2
source                  1..8
                        mol_type = protein
                        organism = synthetic construct
SEQUENCE: 16
GNYDAMDY                                                                    8

SEQ ID NO: 17           moltype = AA  length = 8
FEATURE                 Location/Qualifiers
REGION                  1..8
                        note = TLA0015-HCDR3-3
source                  1..8
                        mol_type = protein
                        organism = synthetic construct
SEQUENCE: 17
GDFDAMDY                                                                    8

SEQ ID NO: 18           moltype = AA  length = 8
FEATURE                 Location/Qualifiers
REGION                  1..8
                        note = TLA0015-HCDR3-4
source                  1..8
                        mol_type = protein
                        organism = synthetic construct
SEQUENCE: 18
GLFDAMDY                                                                    8

SEQ ID NO: 19           moltype = AA  length = 30
FEATURE                 Location/Qualifiers
REGION                  1..30
                        note = TLA0015-HFR1
VARIANT                 2
                        note = Xaa = Ile or Val
VARIANT                 5
                        note = Xaa = Leu or Val
VARIANT                 12
                        note = Xaa = Ile or Val
VARIANT                 20
                        note = Xaa = Ile or Leu
VARIANT                 28
                        note = Xaa = Asp or Ser
VARIANT                 30
                        note = Xaa = Ile, Lys or Ser
source                  1..30
                        mol_type = protein
                        organism = synthetic construct
```

```
SEQUENCE: 19
EXQLXESGGG LXQPGGSLRX SCAVSGFXLX                                    30

SEQ ID NO: 20          moltype = AA  length = 30
FEATURE                Location/Qualifiers
REGION                 1..30
                       note = TLA0015-HFR1-1
source                 1..30
                       mol_type = protein
                       organism = synthetic construct
SEQUENCE: 20
EIQLLESGGG LVQPGGSLRL SCAVSGFSLS                                    30

SEQ ID NO: 21          moltype = AA  length = 30
FEATURE                Location/Qualifiers
REGION                 1..30
                       note = TLA0015-HFR1-2
source                 1..30
                       mol_type = protein
                       organism = synthetic construct
SEQUENCE: 21
EIQLLESGGG LVQPGGSLRI SCAVSGFSLS                                    30

SEQ ID NO: 22          moltype = AA  length = 30
FEATURE                Location/Qualifiers
REGION                 1..30
                       note = TLA0015-HFR1-3
source                 1..30
                       mol_type = protein
                       organism = synthetic construct
SEQUENCE: 22
EIQLVESGGG LVQPGGSLRI SCAVSGFSLS                                    30

SEQ ID NO: 23          moltype = AA  length = 30
FEATURE                Location/Qualifiers
REGION                 1..30
                       note = TLA0015-HFR1-4
source                 1..30
                       mol_type = protein
                       organism = synthetic construct
SEQUENCE: 23
EVQLLESGGG LVQPGGSLRL SCAVSGFSLS                                    30

SEQ ID NO: 24          moltype = AA  length = 30
FEATURE                Location/Qualifiers
REGION                 1..30
                       note = TLA0015-HFR1-5
source                 1..30
                       mol_type = protein
                       organism = synthetic construct
SEQUENCE: 24
EIQLVESGGG LIQPGGSLRL SCAVSGFSLS                                    30

SEQ ID NO: 25          moltype = AA  length = 30
FEATURE                Location/Qualifiers
REGION                 1..30
                       note = TLA0015-HFR1-6
source                 1..30
                       mol_type = protein
                       organism = synthetic construct
SEQUENCE: 25
EIQLVESGGG LIQPGGSLRI SCAVSGFSLS                                    30

SEQ ID NO: 26          moltype = AA  length = 30
FEATURE                Location/Qualifiers
REGION                 1..30
                       note = TLA0015-HFR1-7
source                 1..30
                       mol_type = protein
                       organism = synthetic construct
SEQUENCE: 26
EIQLVESGGG LIQPGGSLRI SCAVSGFSLI                                    30

SEQ ID NO: 27          moltype = AA  length = 30
FEATURE                Location/Qualifiers
REGION                 1..30
                       note = TLA0015-HFR1-8
source                 1..30
                       mol_type = protein
```

```
                         organism = synthetic construct
SEQUENCE: 27
EIQLVESGGG LIQPGGSLRI SCAVSGFSLK                                       30

SEQ ID NO: 28            moltype = AA  length = 30
FEATURE                  Location/Qualifiers
REGION                   1..30
                         note = TLA0015-HFR1-9
source                   1..30
                         mol_type = protein
                         organism = synthetic construct
SEQUENCE: 28
EIQLVESGGG LIQPGGSLRI SCAVSGFDLS                                       30

SEQ ID NO: 29            moltype = AA  length = 14
FEATURE                  Location/Qualifiers
REGION                   1..14
                         note = TLA0015-HFR2
VARIANT                  5
                         note = Xaa = Ala or Ser
VARIANT                  13
                         note = Xaa = Leu or Val
source                   1..14
                         mol_type = protein
                         organism = synthetic construct
SEQUENCE: 29
WVRQXPGKGL EWXG                                                        14

SEQ ID NO: 30            moltype = AA  length = 14
FEATURE                  Location/Qualifiers
REGION                   1..14
                         note = TLA0015-HFR2-1/TLA-0238-HFR2-3
source                   1..14
                         mol_type = protein
                         organism = synthetic construct
SEQUENCE: 30
WVRQAPGKGL EWVG                                                        14

SEQ ID NO: 31            moltype = AA  length = 14
FEATURE                  Location/Qualifiers
REGION                   1..14
                         note = TLA0015-HFR2-2
source                   1..14
                         mol_type = protein
                         organism = synthetic construct
SEQUENCE: 31
WVRQAPGKGL EWLG                                                        14

SEQ ID NO: 32            moltype = AA  length = 14
FEATURE                  Location/Qualifiers
REGION                   1..14
                         note = TLA0015-HFR2-3
source                   1..14
                         mol_type = protein
                         organism = synthetic construct
SEQUENCE: 32
WVRQSPGKGL EWLG                                                        14

SEQ ID NO: 33            moltype = AA  length = 32
FEATURE                  Location/Qualifiers
REGION                   1..32
                         note = TLA0015-HFR3
VARIANT                  2
                         note = Xaa = Phe or Leu
VARIANT                  6
                         note = Xaa = Ala, Lys, Arg or Val
VARIANT                  13
                         note = Xaa = Leu or Val
VARIANT                  32
                         note = Xaa = Arg or Ser
source                   1..32
                         mol_type = protein
                         organism = synthetic construct
SEQUENCE: 33
RXTISXDNSK NTXYLQMNSL RAEDTAVYYC AX                                    32

SEQ ID NO: 34            moltype = AA  length = 32
FEATURE                  Location/Qualifiers
REGION                   1..32
```

```
                        note = TLA0015-HFR3-1
source                  1..32
                        mol_type = protein
                        organism = synthetic construct
SEQUENCE: 34
RLTISRDNSK NTLYLQMNSL RAEDTAVYYC AS                              32

SEQ ID NO: 35           moltype = AA  length = 32
FEATURE                 Location/Qualifiers
REGION                  1..32
                        note = TLA0015-HFR3-2
source                  1..32
                        mol_type = protein
                        organism = synthetic construct
SEQUENCE: 35
RLTISKDNSK NTVYLQMNSL RAEDTAVYYC AS                              32

SEQ ID NO: 36           moltype = AA  length = 32
FEATURE                 Location/Qualifiers
REGION                  1..32
                        note = TLA0015-HFR3-3
source                  1..32
                        mol_type = protein
                        organism = synthetic construct
SEQUENCE: 36
RFTISRDNSK NTVYLQMNSL RAEDTAVYYC AS                              32

SEQ ID NO: 37           moltype = AA  length = 32
FEATURE                 Location/Qualifiers
REGION                  1..32
                        note = TLA0015-HFR3-4
source                  1..32
                        mol_type = protein
                        organism = synthetic construct
SEQUENCE: 37
RLTISRDNSK NTVYLQMNSL RAEDTAVYYC AS                              32

SEQ ID NO: 38           moltype = AA  length = 32
FEATURE                 Location/Qualifiers
REGION                  1..32
                        note = TLA0015-HFR3-5
source                  1..32
                        mol_type = protein
                        organism = synthetic construct
SEQUENCE: 38
RLTISRDNSK NTVYLQMNSL RAEDTAVYYC AR                              32

SEQ ID NO: 39           moltype = AA  length = 32
FEATURE                 Location/Qualifiers
REGION                  1..32
                        note = TLA0015-HFR3-6
source                  1..32
                        mol_type = protein
                        organism = synthetic construct
SEQUENCE: 39
RLTISVDNSK NTVYLQMNSL RAEDTAVYYC AS                              32

SEQ ID NO: 40           moltype = AA  length = 32
FEATURE                 Location/Qualifiers
REGION                  1..32
                        note = TLA0015-HFR3-7
source                  1..32
                        mol_type = protein
                        organism = synthetic construct
SEQUENCE: 40
RLTISADNSK NTVYLQMNSL RAEDTAVYYC AS                              32

SEQ ID NO: 41           moltype = AA  length = 11
FEATURE                 Location/Qualifiers
REGION                  1..11
                        note = TLA0015-HFR4-1/TLA-0238-HFR4-2
source                  1..11
                        mol_type = protein
                        organism = synthetic construct
SEQUENCE: 41
WGQGTLVTVS S                                                     11

SEQ ID NO: 42           moltype = AA  length = 11
FEATURE                 Location/Qualifiers
```

```
REGION               1..11
                     note = TLA0015-LCDR1-1
source               1..11
                     mol_type = protein
                     organism = synthetic construct
SEQUENCE: 42
RASQDISNYL N                                                11

SEQ ID NO: 43        moltype = AA  length = 7
FEATURE              Location/Qualifiers
REGION               1..7
                     note = TL0015-LCDR2-1
source               1..7
                     mol_type = protein
                     organism = synthetic construct
SEQUENCE: 43
YTSRLHS                                                     7

SEQ ID NO: 44        moltype = AA  length = 9
FEATURE              Location/Qualifiers
REGION               1..9
                     note = TL0015-LCDR3-1
source               1..9
                     mol_type = protein
                     organism = synthetic construct
SEQUENCE: 44
QQGNTLPFT                                                   9

SEQ ID NO: 45        moltype = AA  length = 23
FEATURE              Location/Qualifiers
REGION               1..23
                     note = TL0015-LFR1
VARIANT              7
                     note = Xaa = Ser or Thr
VARIANT              8
                     note = Xaa = Pro or Thr
VARIANT              22
                     note = Xaa = Ser or Thr
source               1..23
                     mol_type = protein
                     organism = synthetic construct
SEQUENCE: 45
DIQMTQXXSS LSASVGDRVT IXC                                   23

SEQ ID NO: 46        moltype = AA  length = 23
FEATURE              Location/Qualifiers
REGION               1..23
                     note = TL0015-LFR1-1
source               1..23
                     mol_type = protein
                     organism = synthetic construct
SEQUENCE: 46
DIQMTQTTSS LSASLGDRVT ISC                                   23

SEQ ID NO: 47        moltype = AA  length = 23
FEATURE              Location/Qualifiers
REGION               1..23
                     note = TL0015-LFR1-2/TLA0241-LFR1-1
source               1..23
                     mol_type = protein
                     organism = synthetic construct
SEQUENCE: 47
DIQMTQSPSS LSASVGDRVT ITC                                   23

SEQ ID NO: 48        moltype = AA  length = 15
FEATURE              Location/Qualifiers
REGION               1..15
                     note = TL0015-LFR2
VARIANT              9
                     note = Xaa = Ala or Val
VARIANT              10
                     note = Xaa = Pro or Val
source               1..15
                     mol_type = protein
                     organism = synthetic construct
SEQUENCE: 48
WYQQKPGKXX KLLIY                                            15

SEQ ID NO: 49        moltype = AA  length = 15
```

```
FEATURE               Location/Qualifiers
REGION                1..15
                      note = TL0015-LFR2-1
source                1..15
                      mol_type = protein
                      organism = synthetic construct
SEQUENCE: 49
WYQQKPDGTV KLLIY                                                    15

SEQ ID NO: 50         moltype = AA  length = 15
FEATURE               Location/Qualifiers
REGION                1..15
                      note = TL0015-LFR2-2
source                1..15
                      mol_type = protein
                      organism = synthetic construct
SEQUENCE: 50
WYQQKPGKVV KLLIY                                                    15

SEQ ID NO: 51         moltype = AA  length = 15
FEATURE               Location/Qualifiers
REGION                1..15
                      note = TL0015-LFR2-3
source                1..15
                      mol_type = protein
                      organism = synthetic construct
SEQUENCE: 51
WYQQKPGKAV KLLIY                                                    15

SEQ ID NO: 52         moltype = AA  length = 15
FEATURE               Location/Qualifiers
REGION                1..15
                      note = TL0015-LFR2-4/TLA0241-LFR2-1
source                1..15
                      mol_type = protein
                      organism = synthetic construct
SEQUENCE: 52
WYQQKPGKAP KLLIY                                                    15

SEQ ID NO: 53         moltype = AA  length = 32
FEATURE               Location/Qualifiers
REGION                1..32
                      note = TL0015-LFR3
VARIANT               15
                      note = Xaa = Phe or Tyr
VARIANT               27
                      note = Xaa = Phe or Val
VARIANT               31
                      note = Xaa = Phe or Tyr
source                1..32
                      mol_type = protein
                      organism = synthetic construct
SEQUENCE: 53
GVPSRFSGSG SGTDXTLTIS SLQPEDXATY XC                                 32

SEQ ID NO: 54         moltype = AA  length = 32
FEATURE               Location/Qualifiers
REGION                1..32
                      note = TL0015-LFR3-1
source                1..32
                      mol_type = protein
                      organism = synthetic construct
SEQUENCE: 54
GVPSRFSGSG SGTDYSLTIS NLEQEDIATY FC                                 32

SEQ ID NO: 55         moltype = AA  length = 32
FEATURE               Location/Qualifiers
REGION                1..32
                      note = TL0015-LFR3-2
source                1..32
                      mol_type = protein
                      organism = synthetic construct
SEQUENCE: 55
GVPSRFSGSG SGTDYTLTIS SLQPEDVATY FC                                 32

SEQ ID NO: 56         moltype = AA  length = 32
FEATURE               Location/Qualifiers
REGION                1..32
                      note = TL0015-LFR3-3
```

```
source                1..32
                      mol_type = protein
                      organism = synthetic construct
SEQUENCE: 56
GVPSRFSGSG SGTDYTLTIS SLQPEDFATY FC                             32

SEQ ID NO: 57         moltype = AA  length = 32
FEATURE               Location/Qualifiers
REGION                1..32
                      note = TL0015-LFR3-4/TLA0238-LFR3-4/TLA0241-LFR3-2
source                1..32
                      mol_type = protein
                      organism = synthetic construct
SEQUENCE: 57
GVPSRFSGSG SGTDFTLTIS SLQPEDFATY YC                             32

SEQ ID NO: 58         moltype = AA  length = 10
FEATURE               Location/Qualifiers
REGION                1..10
                      note = TL0015-LFR4
VARIANT               3
                      note = Xaa = Pro or Gln
source                1..10
                      mol_type = protein
                      organism = synthetic construct
SEQUENCE: 58
FGXGTKLEIK                                                      10

SEQ ID NO: 59         moltype = AA  length = 10
FEATURE               Location/Qualifiers
REGION                1..10
                      note = TL0015-LFR4-1
source                1..10
                      mol_type = protein
                      organism = synthetic construct
SEQUENCE: 59
FGSGTKLEIK                                                      10

SEQ ID NO: 60         moltype = AA  length = 10
FEATURE               Location/Qualifiers
REGION                1..10
                      note = TL0015-LFR4-2
source                1..10
                      mol_type = protein
                      organism = synthetic construct
SEQUENCE: 60
FGPGTKLEIK                                                      10

SEQ ID NO: 61         moltype = AA  length = 10
FEATURE               Location/Qualifiers
REGION                1..10
                      note = TL0015-LFR4-3/TLA0238-LFR4-3
source                1..10
                      mol_type = protein
                      organism = synthetic construct
SEQUENCE: 61
FGQGTKLEIK                                                      10

SEQ ID NO: 62         moltype = AA  length = 116
FEATURE               Location/Qualifiers
REGION                1..116
                      note = TLA0015-VH-1
source                1..116
                      mol_type = protein
                      organism = synthetic construct
SEQUENCE: 62
QIQLKESGPG LVAPSQSLSI TCTVSGFSLS SYGVDWVRQS PGKGLEWLGV IWGFGGTNYN  60
SALKSRLSIS KDNSKSQVFL KMNSLQSDDS AIYYCASGNF DAMDYWGQGT SVTVSS      116

SEQ ID NO: 63         moltype = AA  length = 116
FEATURE               Location/Qualifiers
REGION                1..116
                      note = TLA0015-VH-2
source                1..116
                      mol_type = protein
                      organism = synthetic construct
SEQUENCE: 63
EIQLLESGGG LVQPGGSLRL SCAVSGFSLS SYGVDWVRQA PGKGLEWVGV IWGFGGTNYN  60
SALKSRLTIS RDNSKNTLYL QMNSLRAEDT AVYYCASGNF DAMDYWGQGT LVTVSS      116
```

```
SEQ ID NO: 64          moltype = AA  length = 116
FEATURE                Location/Qualifiers
REGION                 1..116
                       note = TLA0015-VH-3
source                 1..116
                       mol_type = protein
                       organism = synthetic construct
SEQUENCE: 64
EIQLLESGGG LVQPGGSLRI SCAVSGFSLS SYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 65          moltype = AA  length = 116
FEATURE                Location/Qualifiers
REGION                 1..116
                       note = TLA0015-VH-4
source                 1..116
                       mol_type = protein
                       organism = synthetic construct
SEQUENCE: 65
EIQLVESGGG LVQPGGSLRI SCAVSGFSLS SYGVDWVRQS PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 66          moltype = AA  length = 116
FEATURE                Location/Qualifiers
REGION                 1..116
                       note = TLA0015-VH-5
source                 1..116
                       mol_type = protein
                       organism = synthetic construct
SEQUENCE: 66
EVQLLESGGG LVQPGGSLRL SCAVSGFSLS SYGVDWVRQA PGKGLEWLGV IWGFGGTNYN  60
SALKSRFTIS RDNSKNTVYL QMNSLRAEDT AVYYCASGNF DAMDYWGQGT LVTVSS      116

SEQ ID NO: 67          moltype = AA  length = 116
FEATURE                Location/Qualifiers
REGION                 1..116
                       note = TLA0015-VH-6
source                 1..116
                       mol_type = protein
                       organism = synthetic construct
SEQUENCE: 67
EVQLLESGGG LVQPGGSLRL SCAVSGFSLS SYGVDWVRQA PGKGLEWLGV IWGFGGTNYN  60
SALKSRLTIS RDNSKNTVYL QMNSLRAEDT AVYYCASGNF DAMDYWGQGT LVTVSS      116

SEQ ID NO: 68          moltype = AA  length = 116
FEATURE                Location/Qualifiers
REGION                 1..116
                       note = TLA0015-VH-7
source                 1..116
                       mol_type = protein
                       organism = synthetic construct
SEQUENCE: 68
EVQLLESGGG LVQPGGSLRL SCAVSGFSLS SYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 69          moltype = AA  length = 116
FEATURE                Location/Qualifiers
REGION                 1..116
                       note = TLA0015-VH-8
source                 1..116
                       mol_type = protein
                       organism = synthetic construct
SEQUENCE: 69
EIQLVESGGG LIQPGGSLRL SCAVSGFSLS SYGVDWVRQA PGKGLEWLGV IWGFGGTNYN  60
SALKSRLTIS RDNSKNTVYL QMNSLRAEDT AVYYCARGNF DAMDYWGQGT LVTVSS      116

SEQ ID NO: 70          moltype = AA  length = 116
FEATURE                Location/Qualifiers
REGION                 1..116
                       note = TLA0015-VH-9
source                 1..116
                       mol_type = protein
                       organism = synthetic construct
SEQUENCE: 70
EIQLVESGGG LIQPGGSLRI SCAVSGFSLS SYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 71          moltype = AA  length = 116
```

```
FEATURE                Location/Qualifiers
REGION                 1..116
                       note = TLA0015-VH-10
source                 1..116
                       mol_type = protein
                       organism = synthetic construct
SEQUENCE: 71
EIQLVESGGG LIQPGGSLRI SCAVSGFSLS SYGVDWVRQA PGKGLEWLGV IWGFGGTNYN  60
SALKSRLTIS RDNSKNTVYL QMNSLRAEDT AVYYCASGNF DAMDYWGQGT LVTVSS      116

SEQ ID NO: 72          moltype = AA  length = 116
FEATURE                Location/Qualifiers
REGION                 1..116
                       note = TLA0015-VH-11
source                 1..116
                       mol_type = protein
                       organism = synthetic construct
SEQUENCE: 72
EIQLVESGGG LIQPGGSLRI SCAVSGFSLS SYGVDWVRQA PGKGLEWLGV IWGFGGTNYN  60
SALKSRLTIS VDNSKNTVYL QMNSLRAEDT AVYYCASGNF DAMDYWGQGT LVTVSS      116

SEQ ID NO: 73          moltype = AA  length = 116
FEATURE                Location/Qualifiers
REGION                 1..116
                       note = TLA0015-VH-12
source                 1..116
                       mol_type = protein
                       organism = synthetic construct
SEQUENCE: 73
EIQLVESGGG LIQPGGSLRI SCAVSGFSLS SYGVDWVRQA PGKGLEWLGV IWGFGGTNYQ  60
SALKSRLTIS KDNSKNTVYL QMNSLRAEDT AVYYCASGNF DAMDYWGQGT LVTVSS      116

SEQ ID NO: 74          moltype = AA  length = 116
FEATURE                Location/Qualifiers
REGION                 1..116
                       note = TLA0015-VH-13
source                 1..116
                       mol_type = protein
                       organism = synthetic construct
SEQUENCE: 74
EIQLVESGGG LIQPGGSLRI SCAVSGFSLS SYGVDWVRQA PGKGLEWLGV IWGFGGTNYN  60
AALKSRLTIS KDNSKNTVYL QMNSLRAEDT AVYYCASGNF DAMDYWGQGT LVTVSS      116

SEQ ID NO: 75          moltype = AA  length = 116
FEATURE                Location/Qualifiers
REGION                 1..116
                       note = TLA0015-VH-14
source                 1..116
                       mol_type = protein
                       organism = synthetic construct
SEQUENCE: 75
EIQLVESGGG LIQPGGSLRI SCAVSGFSLS SYGVDWVRQA PGKGLEWLGV IWGFGGTNYN  60
SALKSRLTIS ADNSKNTVYL QMNSLRAEDT AVYYCASGNF DAMDYWGQGT LVTVSS      116

SEQ ID NO: 76          moltype = AA  length = 116
FEATURE                Location/Qualifiers
REGION                 1..116
                       note = TLA0015-VH-15
source                 1..116
                       mol_type = protein
                       organism = synthetic construct
SEQUENCE: 76
EIQLVESGGG LIQPGGSLRI SCAVSGFSLS YYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 77          moltype = AA  length = 116
FEATURE                Location/Qualifiers
REGION                 1..116
                       note = TLA0015-VH-16
source                 1..116
                       mol_type = protein
                       organism = synthetic construct
SEQUENCE: 77
EIQLVESGGG LIQPGGSLRI SCAVSGFSLS SYGVDWVRQA PGKGLEWLGV IWGFGGTNYN  60
SALKSRLTIS KDNSKNTVYL QMNSLRAEDT AVYYCASGNY DAMDYWGQGT LVTVSS      116

SEQ ID NO: 78          moltype = AA  length = 116
FEATURE                Location/Qualifiers
REGION                 1..116
```

```
                         note = TLA0015-VH-17
source                   1..116
                         mol_type = protein
                         organism = synthetic construct
SEQUENCE: 78
EIQLVESGGG LIQPGGSLRI SCAVSGFSLS SYGVDWVRQA PGKGLEWLGV IWGFGGTNYN  60
SALKSRLTIS KDNSKNTVYL QMNSLRAEDT AVYYCASGDF DAMDYWGQGT LVTVSS      116

SEQ ID NO: 79            moltype = AA  length = 116
FEATURE                  Location/Qualifiers
REGION                   1..116
                         note = TLA0015-VH-18
source                   1..116
                         mol_type = protein
                         organism = synthetic construct
SEQUENCE: 79
EIQLVESGGG LIQPGGSLRI SCAVSGFSLS SYGVDWVRQA PGKGLEWLGV IWGFGGTNYN  60
SALKSRLTIS KDNSKNTVYL QMNSLRAEDT AVYYCASGLF DAMDYWGQGT LVTVSS      116

SEQ ID NO: 80            moltype = AA  length = 116
FEATURE                  Location/Qualifiers
REGION                   1..116
                         note = TLA0015-VH-19
source                   1..116
                         mol_type = protein
                         organism = synthetic construct
SEQUENCE: 80
EIQLVESGGG LIQPGGSLRI SCAVSGFSLS TYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 81            moltype = AA  length = 116
FEATURE                  Location/Qualifiers
REGION                   1..116
                         note = TLA0015-VH-20
source                   1..116
                         mol_type = protein
                         organism = synthetic construct
SEQUENCE: 81
EIQLVESGGG LIQPGGSLRI SCAVSGFSLI SYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 82            moltype = AA  length = 116
FEATURE                  Location/Qualifiers
REGION                   1..116
                         note = TLA0015-VH-21
source                   1..116
                         mol_type = protein
                         organism = synthetic construct
SEQUENCE: 82
EIQLVESGGG LIQPGGSLRI SCAVSGFSLS SYGVDWVRQA PGKGLEWLGV IWGFGGTNYN  60
PALKSRLTIS KDNSKNTVYL QMNSLRAEDT AVYYCASGNF DAMDYWGQGT LVTVSS      116

SEQ ID NO: 83            moltype = AA  length = 116
FEATURE                  Location/Qualifiers
REGION                   1..116
                         note = TLA0015-VH-22
source                   1..116
                         mol_type = protein
                         organism = synthetic construct
SEQUENCE: 83
EIQLVESGGG LIQPGGSLRI SCAVSGFSLK SYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 84            moltype = AA  length = 116
FEATURE                  Location/Qualifiers
REGION                   1..116
                         note = TLA0015-VH-23
source                   1..116
                         mol_type = protein
                         organism = synthetic construct
SEQUENCE: 84
EIQLVESGGG LIQPGGSLRI SCAVSGFSLS SYGVDWVRQA PGKGLEWLGV IWGFGGTHYN  60
SALKSRLTIS KDNSKNTVYL QMNSLRAEDT AVYYCASGNF DAMDYWGQGT LVTVSS      116

SEQ ID NO: 85            moltype = AA  length = 116
FEATURE                  Location/Qualifiers
REGION                   1..116
                         note = TLA0015-VH-24
source                   1..116
```

```
                        mol_type = protein
                        organism = synthetic construct
SEQUENCE: 85
EIQLVESGGG LIQPGGSLRI SCAVSGFSLS SYGVDWVRQA PGKGLEWLGR IWGFGGTNYN  60
SALKSRLTIS KDNSKNTVYL QMNSLRAEDT AVYYCASGNF DAMDYWGQGT LVTVSS      116

SEQ ID NO: 86           moltype = AA  length = 116
FEATURE                 Location/Qualifiers
REGION                  1..116
                        note = TLA0015-VH-25
source                  1..116
                        mol_type = protein
                        organism = synthetic construct
SEQUENCE: 86
EIQLVESGGG LIQPGGSLRI SCAVSGFDLS SYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 87           moltype = AA  length = 116
FEATURE                 Location/Qualifiers
REGION                  1..116
                        note = TLA0015-VH-26
source                  1..116
                        mol_type = protein
                        organism = synthetic construct
SEQUENCE: 87
EIQLVESGGG LIQPGGSLRI SCAVSGFSLS SYGVDWVRQA PGKGLEWLGV IWGFGKTNYN  60
SALKSRLTIS KDNSKNTVYL QMNSLRAEDT AVYYCASGNF DAMDYWGQGT LVTVSS      116

SEQ ID NO: 88           moltype = AA  length = 116
FEATURE                 Location/Qualifiers
REGION                  1..116
                        note = TLA0015-VH-27
source                  1..116
                        mol_type = protein
                        organism = synthetic construct
SEQUENCE: 88
EIQLVESGGG LIQPGGSLRI SCAVSGFSLS SYGVDWVRQA PGKGLEWLGV IWGFGGTDYN  60
SALKSRLTIS KDNSKNTVYL QMNSLRAEDT AVYYCASGNF DAMDYWGQGT LVTVSS      116

SEQ ID NO: 89           moltype = AA  length = 116
FEATURE                 Location/Qualifiers
REGION                  1..116
                        note = TLA0015-VH-28
source                  1..116
                        mol_type = protein
                        organism = synthetic construct
SEQUENCE: 89
EIQLVESGGG LIQPGGSLRI SCAVSGFSLS YYGVDWVRQA PGKGLEWLGV IWGFGGTNYN  60
SALKSRLTIS KDNSKNTVYL QMNSLRAEDT AVYYCASGNY DAMDYWGQGT LVTVSS      116

SEQ ID NO: 90           moltype = AA  length = 116
FEATURE                 Location/Qualifiers
REGION                  1..116
                        note = TLA0015-VH-29
source                  1..116
                        mol_type = protein
                        organism = synthetic construct
SEQUENCE: 90
EIQLVESGGG LIQPGGSLRI SCAVSGFSLS YYGVDWVRQA PGKGLEWLGV IWGFGGTNYN  60
SALKSRLTIS KDNSKNTVYL QMNSLRAEDT AVYYCASGDF DAMDYWGQGT LVTVSS      116

SEQ ID NO: 91           moltype = AA  length = 116
FEATURE                 Location/Qualifiers
REGION                  1..116
                        note = TLA0015-VH-30
source                  1..116
                        mol_type = protein
                        organism = synthetic construct
SEQUENCE: 91
EIQLVESGGG LIQPGGSLRI SCAVSGFSLS YYGVDWVRQA PGKGLEWLGV IWGFGGTNYN  60
PALKSRLTIS KDNSKNTVYL QMNSLRAEDT AVYYCASGNF DAMDYWGQGT LVTVSS      116

SEQ ID NO: 92           moltype = AA  length = 116
FEATURE                 Location/Qualifiers
REGION                  1..116
                        note = TLA0015-VH-31
source                  1..116
                        mol_type = protein
                        organism = synthetic construct
```

```
SEQUENCE: 92
EIQLVESGGG LIQPGGSLRI SCAVSGFSLS YYGVDWVRQA PGKGLEWLGV IWGFGGTHYN  60
SALKSRLTIS KDNSKNTVYL QMNSLRAEDT AVYYCASGNF DAMDYWGQGT LVTVSS      116

SEQ ID NO: 93          moltype = AA  length = 116
FEATURE                Location/Qualifiers
REGION                 1..116
                       note = TLA0015-VH-32
source                 1..116
                       mol_type = protein
                       organism = synthetic construct
SEQUENCE: 93
EIQLVESGGG LIQPGGSLRI SCAVSGFSLS YYGVDWVRQA PGKGLEWLGR IWGFGGTNYN  60
SALKSRLTIS KDNSKNTVYL QMNSLRAEDT AVYYCASGNF DAMDYWGQGT LVTVSS      116

SEQ ID NO: 94          moltype = AA  length = 116
FEATURE                Location/Qualifiers
REGION                 1..116
                       note = TLA0015-VH-33
source                 1..116
                       mol_type = protein
                       organism = synthetic construct
SEQUENCE: 94
EIQLVESGGG LIQPGGSLRI SCAVSGFDLS YYGVDWVRQA PGKGLEWLGV IWGFGGTNYN  60
SALKSRLTIS KDNSKNTVYL QMNSLRAEDT AVYYCASGNF DAMDYWGQGT LVTVSS      116

SEQ ID NO: 95          moltype = AA  length = 116
FEATURE                Location/Qualifiers
REGION                 1..116
                       note = TLA0015-VH-34
source                 1..116
                       mol_type = protein
                       organism = synthetic construct
SEQUENCE: 95
EIQLVESGGG LIQPGGSLRI SCAVSGFSLI SYGVDWVRQA PGKGLEWLGV IWGFGGTNYN  60
SALKSRLTIS KDNSKNTVYL QMNSLRAEDT AVYYCASGNY DAMDYWGQGT LVTVSS      116

SEQ ID NO: 96          moltype = AA  length = 116
FEATURE                Location/Qualifiers
REGION                 1..116
                       note = TLA0015-VH-35
source                 1..116
                       mol_type = protein
                       organism = synthetic construct
SEQUENCE: 96
EIQLVESGGG LIQPGGSLRI SCAVSGFSLS SYGVDWVRQA PGKGLEWLGV IWGFGGTNYN  60
PALKSRLTIS KDNSKNTVYL QMNSLRAEDT AVYYCASGNY DAMDYWGQGT LVTVSS      116

SEQ ID NO: 97          moltype = AA  length = 116
FEATURE                Location/Qualifiers
REGION                 1..116
                       note = TLA0015-VH-36
source                 1..116
                       mol_type = protein
                       organism = synthetic construct
SEQUENCE: 97
EIQLVESGGG LIQPGGSLRI SCAVSGFSLS SYGVDWVRQA PGKGLEWLGV IWGFGGTHYN  60
SALKSRLTIS KDNSKNTVYL QMNSLRAEDT AVYYCASGNY DAMDYWGQGT LVTVSS      116

SEQ ID NO: 98          moltype = AA  length = 116
FEATURE                Location/Qualifiers
REGION                 1..116
                       note = TLA0015-VH-37
source                 1..116
                       mol_type = protein
                       organism = synthetic construct
SEQUENCE: 98
EIQLVESGGG LIQPGGSLRI SCAVSGFSLS SYGVDWVRQA PGKGLEWLGR IWGFGGTNYN  60
SALKSRLTIS KDNSKNTVYL QMNSLRAEDT AVYYCASGNY DAMDYWGQGT LVTVSS      116

SEQ ID NO: 99          moltype = AA  length = 116
FEATURE                Location/Qualifiers
REGION                 1..116
                       note = TLA0015-VH-38
source                 1..116
                       mol_type = protein
                       organism = synthetic construct
SEQUENCE: 99
EIQLVESGGG LIQPGGSLRI SCAVSGFSLS SYGVDWVRQA PGKGLEWLGV IWGFGKTNYN  60
```

```
SALKSRLTIS KDNSKNTVYL QMNSLRAEDT AVYYCASGNY DAMDYWGQGT LVTVSS      116

SEQ ID NO: 100         moltype = AA  length = 116
FEATURE                Location/Qualifiers
REGION                 1..116
                       note = TLA0015-VH-39
source                 1..116
                       mol_type = protein
                       organism = synthetic construct
SEQUENCE: 100
EIQLVESGGG LIQPGGSLRI SCAVSGFSLI SYGVDWVRQA PGKGLEWLGV IWGFGGTNYN  60
SALKSRLTIS KDNSKNTVYL QMNSLRAEDT AVYYCASGDF DAMDYWGQGT LVTVSS      116

SEQ ID NO: 101         moltype = AA  length = 116
FEATURE                Location/Qualifiers
REGION                 1..116
                       note = TLA0015-VH-40
source                 1..116
                       mol_type = protein
                       organism = synthetic construct
SEQUENCE: 101
EIQLVESGGG LIQPGGSLRI SCAVSGFSLS SYGVDWVRQA PGKGLEWLGV IWGFGGTHYN  60
SALKSRLTIS KDNSKNTVYL QMNSLRAEDT AVYYCASGDF DAMDYWGQGT LVTVSS      116

SEQ ID NO: 102         moltype = AA  length = 107
FEATURE                Location/Qualifiers
REGION                 1..107
                       note = TLA0015-VL-1
source                 1..107
                       mol_type = protein
                       organism = synthetic construct
SEQUENCE: 102
DIQMTQTTSS LSASLGDRVT ISCRASQDIS NYLNWYQQKP DGTVKLLIYY TSRLHSGVPS  60
RFSGSGSGTD YSLTISNLEQ EDIATYFCQQ GNTLPFTFGS GTKLEIK                107

SEQ ID NO: 103         moltype = AA  length = 107
FEATURE                Location/Qualifiers
REGION                 1..107
                       note = TLA0015-VL-2
source                 1..107
                       mol_type = protein
                       organism = synthetic construct
SEQUENCE: 103
DIQMTQSPSS LSASVGDRVT ITCRASQDIS NYLNWYQQKP GKVVKLLIYY TSRLHSGVPS  60
RFSGSGSGTD YTLTISSLQP EDVATYFCQQ GNTLPFTFGP GTKLEIK                107

SEQ ID NO: 104         moltype = AA  length = 107
FEATURE                Location/Qualifiers
REGION                 1..107
                       note = TLA0015-VL-3
source                 1..107
                       mol_type = protein
                       organism = synthetic construct
SEQUENCE: 104
DIQMTQSPSS LSASVGDRVT ITCRASQDIS NYLNWYQQKP GKAPKLLIYY TSRLHSGVPS  60
RFSGSGSGTD FTLTISSLQP EDFATYYCQQ GNTLPFTFGQ GTKLEIK                107

SEQ ID NO: 105         moltype = AA  length = 107
FEATURE                Location/Qualifiers
REGION                 1..107
                       note = TLA0015-VL-4
source                 1..107
                       mol_type = protein
                       organism = synthetic construct
SEQUENCE: 105
DIQMTQSPSS LSASVGDRVT ITCRASQDIS NYLNWYQQKP GKAPKLLIYY TSRLHSGVPS  60
RFSGSGSGTD YTLTISSLQP EDFATYFCQQ GNTLPFTFGQ GTKLEIK                107

SEQ ID NO: 106         moltype = AA  length = 107
FEATURE                Location/Qualifiers
REGION                 1..107
                       note = TLA0015-VL-5
source                 1..107
                       mol_type = protein
                       organism = synthetic construct
SEQUENCE: 106
DIQMTQSPSS LSASVGDRVT ITCRASQDIS NYLNWYQQKP GKAVKLLIYY TSRLHSGVPS  60
RFSGSGSGTD YTLTISSLQP EDFATYFCQQ GNTLPFTFGQ GTKLEIK                107
```

```
SEQ ID NO: 107          moltype =   length =
SEQUENCE: 107
000

SEQ ID NO: 108          moltype = AA  length = 5
FEATURE                 Location/Qualifiers
REGION                  1..5
                        note = TLA-0238-HCDR1-1
source                  1..5
                        mol_type = protein
                        organism = synthetic construct
SEQUENCE: 108
NYWMN                                                     5

SEQ ID NO: 109          moltype = AA  length = 5
FEATURE                 Location/Qualifiers
REGION                  1..5
                        note = TLA-0238-HCDR1-2
source                  1..5
                        mol_type = protein
                        organism = synthetic construct
SEQUENCE: 109
NYWMH                                                     5

SEQ ID NO: 110          moltype = AA  length = 5
FEATURE                 Location/Qualifiers
REGION                  1..5
                        note = TLA-0238-HCDR1-3
source                  1..5
                        mol_type = protein
                        organism = synthetic construct
SEQUENCE: 110
NYWMS                                                     5

SEQ ID NO: 111          moltype = AA  length = 5
FEATURE                 Location/Qualifiers
REGION                  1..5
                        note = TLA-0238-HCDR1-4
source                  1..5
                        mol_type = protein
                        organism = synthetic construct
SEQUENCE: 111
NYIMN                                                     5

SEQ ID NO: 112          moltype = AA  length = 5
FEATURE                 Location/Qualifiers
REGION                  1..5
                        note = TLA-0238-HCDR1-5
source                  1..5
                        mol_type = protein
                        organism = synthetic construct
SEQUENCE: 112
NYLMN                                                     5

SEQ ID NO: 113          moltype = AA  length = 5
FEATURE                 Location/Qualifiers
REGION                  1..5
                        note = TLA-0238-HCDR1-6
source                  1..5
                        mol_type = protein
                        organism = synthetic construct
SEQUENCE: 113
NYMMN                                                     5

SEQ ID NO: 114          moltype = AA  length = 5
FEATURE                 Location/Qualifiers
REGION                  1..5
                        note = TLA-0238-HCDR1-7
source                  1..5
                        mol_type = protein
                        organism = synthetic construct
SEQUENCE: 114
NYYMN                                                     5

SEQ ID NO: 115          moltype = AA  length = 19
FEATURE                 Location/Qualifiers
REGION                  1..19
                        note = TLA-0238-HCDR2
VARIANT                 15
```

```
                          note = Xaa = Ala, Asp or Glu
VARIANT                   16
                          note = Xaa = Pro or Ser
source                    1..19
                          mol_type = protein
                          organism = synthetic construct
SEQUENCE: 115
QIRLKSDNYA THYAXXVKG                                                19

SEQ ID NO: 116            moltype = AA  length = 19
FEATURE                   Location/Qualifiers
REGION                    1..19
                          note = TLA-0238-HCDR2-1
source                    1..19
                          mol_type = protein
                          organism = synthetic construct
SEQUENCE: 116
QIRLKSDNYA THYAESVKG                                                19

SEQ ID NO: 117            moltype = AA  length = 19
FEATURE                   Location/Qualifiers
REGION                    1..19
                          note = TLA-0238-HCDR2-2
source                    1..19
                          mol_type = protein
                          organism = synthetic construct
SEQUENCE: 117
QIRLKSDNYA THYADSVKG                                                19

SEQ ID NO: 118            moltype = AA  length = 19
FEATURE                   Location/Qualifiers
REGION                    1..19
                          note = TLA-0238-HCDR2-3
source                    1..19
                          mol_type = protein
                          organism = synthetic construct
SEQUENCE: 118
QIRLKSDNYA THYAASVKG                                                19

SEQ ID NO: 119            moltype = AA  length = 19
FEATURE                   Location/Qualifiers
REGION                    1..19
                          note = TLA-0238-HCDR2-4
source                    1..19
                          mol_type = protein
                          organism = synthetic construct
SEQUENCE: 119
QIRLKSDNYA THYAAPVKG                                                19

SEQ ID NO: 120            moltype = AA  length = 8
FEATURE                   Location/Qualifiers
REGION                    1..8
                          note = TLA-0238-HCDR3-1
source                    1..8
                          mol_type = protein
                          organism = synthetic construct
SEQUENCE: 120
LLLRYRDY                                                            8

SEQ ID NO: 121            moltype = AA  length = 30
FEATURE                   Location/Qualifiers
REGION                    1..30
                          note = TLA-0238-HFR1
VARIANT                   1
                          note = Xaa = Glu or Gln
VARIANT                   3
                          note = Xaa = Lys or Gln
VARIANT                   4
                          note = Xaa = Leu or Val
VARIANT                   5
                          note = Xaa = Glu or Val
VARIANT                   11
                          note = Xaa = Leu or Val
VARIANT                   13
                          note = Xaa = Lys or Gln
VARIANT                   16
                          note = Xaa = Gly or Arg
VARIANT                   17
                          note = Xaa = Ala or Ser
```

```
VARIANT              19
                     note = Xaa = Lys or Arg
VARIANT              23
                     note = Xaa = Ala or Ile
source               1..30
                     mol_type = protein
                     organism = synthetic construct
SEQUENCE: 121
XVXXXESGGG XVXPGXXLXL SCXASGFTFS                                   30

SEQ ID NO: 122       moltype = AA  length = 30
FEATURE              Location/Qualifiers
REGION               1..30
                     note = TLA-0238-HFR1-1
source               1..30
                     mol_type = protein
                     organism = synthetic construct
SEQUENCE: 122
EVKVEESGGG LVQPGGSMKL SCIASGFTFS                                   30

SEQ ID NO: 123       moltype = AA  length = 30
FEATURE              Location/Qualifiers
REGION               1..30
                     note = TLA-0238-HFR1-2
source               1..30
                     mol_type = protein
                     organism = synthetic construct
SEQUENCE: 123
EVQVVESGGG LVKPGGSLRL SCAASGFTFS                                   30

SEQ ID NO: 124       moltype = AA  length = 30
FEATURE              Location/Qualifiers
REGION               1..30
                     note = TLA-0238-HFR1-3
source               1..30
                     mol_type = protein
                     organism = synthetic construct
SEQUENCE: 124
EVQVVESGGG LVQPGGSLRL SCIASGFTFS                                   30

SEQ ID NO: 125       moltype = AA  length = 30
FEATURE              Location/Qualifiers
REGION               1..30
                     note = TLA-0238-HFR1-4
source               1..30
                     mol_type = protein
                     organism = synthetic construct
SEQUENCE: 125
EVQLVESGGG LVQPGGSLRL SCAASGFTFS                                   30

SEQ ID NO: 126       moltype = AA  length = 30
FEATURE              Location/Qualifiers
REGION               1..30
                     note = TLA-0238-HFR1-5
source               1..30
                     mol_type = protein
                     organism = synthetic construct
SEQUENCE: 126
QVQLVESGGG VVQPGRSLRL SCAASGFTFS                                   30

SEQ ID NO: 127       moltype = AA  length = 30
FEATURE              Location/Qualifiers
REGION               1..30
                     note = TLA-0238-HFR1-6
source               1..30
                     mol_type = protein
                     organism = synthetic construct
SEQUENCE: 127
EVKVEESGGG LVQPGGSLRL SCIASGFTFS                                   30

SEQ ID NO: 128       moltype = AA  length = 30
FEATURE              Location/Qualifiers
REGION               1..30
                     note = TLA-0238-HFR1-7
source               1..30
                     mol_type = protein
                     organism = synthetic construct
SEQUENCE: 128
EVKVEESGGG LVQPGGSLKL SCIASGFTFS                                   30
```

```
SEQ ID NO: 129          moltype = AA  length = 30
FEATURE                 Location/Qualifiers
REGION                  1..30
                        note = TLA-0238-HFR1-8
source                  1..30
                        mol_type = protein
                        organism = synthetic construct
SEQUENCE: 129
EVKVEESGGG LVQPGGALRL SCIASGFTFS                                   30

SEQ ID NO: 130          moltype = AA  length = 30
FEATURE                 Location/Qualifiers
REGION                  1..30
                        note = TLA-0238-HFR1-9
source                  1..30
                        mol_type = protein
                        organism = synthetic construct
SEQUENCE: 130
EVKLEESGGG LVQPGGSLKL SCIASGFTFS                                   30

SEQ ID NO: 131          moltype = AA  length = 30
FEATURE                 Location/Qualifiers
REGION                  1..30
                        note = TLA-0238-HFR1-10
source                  1..30
                        mol_type = protein
                        organism = synthetic construct
SEQUENCE: 131
EVQLVESGGG LVKPGGSLRL SCAASGFTFS                                   30

SEQ ID NO: 132          moltype = AA  length = 30
FEATURE                 Location/Qualifiers
REGION                  1..30
                        note = TLA-0238-HFR1-11
source                  1..30
                        mol_type = protein
                        organism = synthetic construct
SEQUENCE: 132
EVKLEESGGG LVQPGGALRL SCIASGFTFS                                   30

SEQ ID NO: 133          moltype = AA  length = 14
FEATURE                 Location/Qualifiers
REGION                  1..14
                        note = TLA-0238-HFR2
VARIANT                 5
                        note = Xaa = Ala or Ser
VARIANT                 7
                        note = Xaa = Glu or Gly
VARIANT                 14
                        note = Xaa = Ala or Gly
source                  1..14
                        mol_type = protein
                        organism = synthetic construct
SEQUENCE: 133
WVRQXPXKGL EWVX                                                    14

SEQ ID NO: 134          moltype = AA  length = 14
FEATURE                 Location/Qualifiers
REGION                  1..14
                        note = TLA-0238-HFR2-1
source                  1..14
                        mol_type = protein
                        organism = synthetic construct
SEQUENCE: 134
WVRQSPEKGL EWVA                                                    14

SEQ ID NO: 135          moltype = AA  length = 14
FEATURE                 Location/Qualifiers
REGION                  1..14
                        note = TLA-0238-HFR2-2
source                  1..14
                        mol_type = protein
                        organism = synthetic construct
SEQUENCE: 135
WVRQAPGKGL EWVA                                                    14

SEQ ID NO: 136          moltype = AA  length = 32
FEATURE                 Location/Qualifiers
```

```
REGION                  1..32
                        note = TLA-0238-HFR3
VARIANT                 1
                        note = Xaa = Asn or Arg
VARIANT                 3
                        note = Xaa = Ala or Thr
VARIANT                 8
                        note = Xaa = Asp or Asn
VARIANT                 9
                        note = Xaa = Ala or Ser
VARIANT                 11
                        note = Xaa = Asn or Ser
VARIANT                 12
                        note = Xaa = Ser or Thr
VARIANT                 13
                        note = Xaa = Ala, Leu or Val
VARIANT                 21
                        note = Xaa = Lys or Arg
VARIANT                 22
                        note = Xaa = Ala, Asp or Thr
VARIANT                 25
                        note = Xaa = Met or Thr
source                  1..32
                        mol_type = protein
                        organism = synthetic construct
SEQUENCE: 136
XFXISRDXXK XXXYLQMNSL XXEDXAVYYC TP                               32

SEQ ID NO: 137          moltype = AA  length = 32
FEATURE                 Location/Qualifiers
REGION                  1..32
                        note = TLA-0238-HFR3-1
source                  1..32
                        mol_type = protein
                        organism = synthetic construct
SEQUENCE: 137
NFTISRDDSK SSVYLQMNNL RAEDTGIYYC TP                               32

SEQ ID NO: 138          moltype = AA  length = 32
FEATURE                 Location/Qualifiers
REGION                  1..32
                        note = TLA-0238-HFR3-2
source                  1..32
                        mol_type = protein
                        organism = synthetic construct
SEQUENCE: 138
NFTISRDDSK STVYLQMNSL KTEDTAVYYC TP                               32

SEQ ID NO: 139          moltype = AA  length = 32
FEATURE                 Location/Qualifiers
REGION                  1..32
                        note = TLA-0238-HFR3-3
source                  1..32
                        mol_type = protein
                        organism = synthetic construct
SEQUENCE: 139
NFTISRDNAK SSVYLQMNSL RAEDTAVYYC TP                               32

SEQ ID NO: 140          moltype = AA  length = 32
FEATURE                 Location/Qualifiers
REGION                  1..32
                        note = TLA-0238-HFR3-4
source                  1..32
                        mol_type = protein
                        organism = synthetic construct
SEQUENCE: 140
RFTISRDDSK STVYLQMNSL KTEDTAVYYC TP                               32

SEQ ID NO: 141          moltype = AA  length = 32
FEATURE                 Location/Qualifiers
REGION                  1..32
                        note = TLA-0238-HFR3-5
source                  1..32
                        mol_type = protein
                        organism = synthetic construct
SEQUENCE: 141
NFAISRDDSK STVYLQMNSL KTEDTAVYYC TP                               32

SEQ ID NO: 142          moltype = AA  length = 32
```

```
FEATURE                Location/Qualifiers
REGION                 1..32
                       note = TLA-0238-HFR3-6
source                 1..32
                       mol_type = protein
                       organism = synthetic construct
SEQUENCE: 142
RFTISRDNSK NTLYLQMNSL RAEDTAVYYC TP                                32

SEQ ID NO: 143         moltype = AA  length = 32
FEATURE                Location/Qualifiers
REGION                 1..32
                       note = TLA-0238-HFR3-7
source                 1..32
                       mol_type = protein
                       organism = synthetic construct
SEQUENCE: 143
RFTISRDNSK NTLYLQMNSL KTEDTAVYYC TP                                32

SEQ ID NO: 144         moltype = AA  length = 32
FEATURE                Location/Qualifiers
REGION                 1..32
                       note = TLA-0238-HFR3-8
source                 1..32
                       mol_type = protein
                       organism = synthetic construct
SEQUENCE: 144
RFTISRDDSK NSLYLQMNSL RDEDTAVYYC TP                                32

SEQ ID NO: 145         moltype = AA  length = 32
FEATURE                Location/Qualifiers
REGION                 1..32
                       note = TLA-0238-HFR3-9
source                 1..32
                       mol_type = protein
                       organism = synthetic construct
SEQUENCE: 145
RFTISRDDSK NTLYLQMNSL RAEDTAVYYC TP                                32

SEQ ID NO: 146         moltype = AA  length = 32
FEATURE                Location/Qualifiers
REGION                 1..32
                       note = TLA-0238-HFR3-10
source                 1..32
                       mol_type = protein
                       organism = synthetic construct
SEQUENCE: 146
RFTISRDDSK NSLYLQMNSL RAEDMAVYYC TP                                32

SEQ ID NO: 147         moltype = AA  length = 32
FEATURE                Location/Qualifiers
REGION                 1..32
                       note = TLA-0238-HFR3-11
source                 1..32
                       mol_type = protein
                       organism = synthetic construct
SEQUENCE: 147
RFTISRDDSK NTAYLQMNSL RAEDTAVYYC TP                                32

SEQ ID NO: 148         moltype = AA  length = 32
FEATURE                Location/Qualifiers
REGION                 1..32
                       note = TLA-0238-HFR3-12
source                 1..32
                       mol_type = protein
                       organism = synthetic construct
SEQUENCE: 148
RFTISRDDSK NTLYLQMNSL KTEDTAVYYC TP                                32

SEQ ID NO: 149         moltype = AA  length = 11
FEATURE                Location/Qualifiers
REGION                 1..11
                       note = TLA-0238-HFR4
VARIANT                6
                       note = Xaa = Leu, Met or Thr
VARIANT                7
                       note = Xaa = Leu or Val
source                 1..11
                       mol_type = protein
```

```
                        organism = synthetic construct
SEQUENCE: 149
WGQGTXXTVS S                                                       11

SEQ ID NO: 150          moltype = AA  length = 11
FEATURE                 Location/Qualifiers
REGION                  1..11
                        note = TLA-0238-HFR4-1
source                  1..11
                        mol_type = protein
                        organism = synthetic construct
SEQUENCE: 150
WGQGTTLTVS S                                                       11

SEQ ID NO: 151          moltype = AA  length = 11
FEATURE                 Location/Qualifiers
REGION                  1..11
                        note = TLA-0238-HFR4-3
source                  1..11
                        mol_type = protein
                        organism = synthetic construct
SEQUENCE: 151
WGQGTLLTVS S                                                       11

SEQ ID NO: 152          moltype = AA  length = 11
FEATURE                 Location/Qualifiers
REGION                  1..11
                        note = TLA-0238-HFR4-4
source                  1..11
                        mol_type = protein
                        organism = synthetic construct
SEQUENCE: 152
WGQGTMVTVS S                                                       11

SEQ ID NO: 153          moltype = AA  length = 11
FEATURE                 Location/Qualifiers
REGION                  1..11
                        note = TLA-0238-HFR4-5
source                  1..11
                        mol_type = protein
                        organism = synthetic construct
SEQUENCE: 153
WGQGTTVTVS S                                                       11

SEQ ID NO: 154          moltype = AA  length = 10
FEATURE                 Location/Qualifiers
REGION                  1..10
                        note = TLA0238-LCDR1
VARIANT                 9
                        note = Xaa = Leu or Met
VARIANT                 10
                        note = Xaa = Ala, His or Thr
source                  1..10
                        mol_type = protein
                        organism = synthetic construct
SEQUENCE: 154
SASSSVSYXX                                                         10

SEQ ID NO: 155          moltype = AA  length = 10
FEATURE                 Location/Qualifiers
REGION                  1..10
                        note = TLA0238-LCDR1-1
source                  1..10
                        mol_type = protein
                        organism = synthetic construct
SEQUENCE: 155
SASSSVSYMH                                                         10

SEQ ID NO: 156          moltype = AA  length = 10
FEATURE                 Location/Qualifiers
REGION                  1..10
                        note = TLA0238-LCDR1-2
source                  1..10
                        mol_type = protein
                        organism = synthetic construct
SEQUENCE: 156
SASSSVSYLH                                                         10

SEQ ID NO: 157          moltype = AA  length = 10
```

```
FEATURE                 Location/Qualifiers
REGION                  1..10
                        note = TLA0238-LCDR1-3
source                  1..10
                        mol_type = protein
                        organism = synthetic construct
SEQUENCE: 157
SASSSVSYLA                                                          10

SEQ ID NO: 158          moltype = AA  length = 10
FEATURE                 Location/Qualifiers
REGION                  1..10
                        note = TLA0238-LCDR1-4
source                  1..10
                        mol_type = protein
                        organism = synthetic construct
SEQUENCE: 158
SASSSVSYLT                                                          10

SEQ ID NO: 159          moltype = AA  length = 7
FEATURE                 Location/Qualifiers
REGION                  1..7
                        note = TLA0238-LCDR2
VARIANT                 5
                        note = Xaa = Leu or Arg
VARIANT                 7
                        note = Xaa = Ser or Thr
source                  1..7
                        mol_type = protein
                        organism = synthetic construct
SEQUENCE: 159
DTSNXAX                                                             7

SEQ ID NO: 160          moltype = AA  length = 7
FEATURE                 Location/Qualifiers
REGION                  1..7
                        note = TLA0238-LCDR2-1
source                  1..7
                        mol_type = protein
                        organism = synthetic construct
SEQUENCE: 160
DTSNLAS                                                             7

SEQ ID NO: 161          moltype = AA  length = 7
FEATURE                 Location/Qualifiers
REGION                  1..7
                        note = TLA0238-LCDR2-2
source                  1..7
                        mol_type = protein
                        organism = synthetic construct
SEQUENCE: 161
DTSNRAS                                                             7

SEQ ID NO: 162          moltype = AA  length = 7
FEATURE                 Location/Qualifiers
REGION                  1..7
                        note = TLA0238-LCDR2-3
source                  1..7
                        mol_type = protein
                        organism = synthetic construct
SEQUENCE: 162
DTSNLAT                                                             7

SEQ ID NO: 163          moltype = AA  length = 9
FEATURE                 Location/Qualifiers
REGION                  1..9
                        note = TLA0238-LCDR3
VARIANT                 4
                        note = Xaa = Glu, Asn or Ser
VARIANT                 5
                        note = Xaa = Ala, Glu or Gly
source                  1..9
                        mol_type = protein
                        organism = synthetic construct
SEQUENCE: 163
FQEXXHPFT                                                           9

SEQ ID NO: 164          moltype = AA  length = 9
FEATURE                 Location/Qualifiers
```

```
REGION                1..9
                      note = TLA0238-LCDR3-1
source                1..9
                      mol_type = protein
                      organism = synthetic construct
SEQUENCE: 164
FQENGHPFT                                                         9

SEQ ID NO: 165        moltype = AA  length = 9
FEATURE               Location/Qualifiers
REGION                1..9
                      note = TLA0238-LCDR3-2
source                1..9
                      mol_type = protein
                      organism = synthetic construct
SEQUENCE: 165
FQESGHPFT                                                         9

SEQ ID NO: 166        moltype = AA  length = 9
FEATURE               Location/Qualifiers
REGION                1..9
                      note = TLA0238-LCDR3-3
source                1..9
                      mol_type = protein
                      organism = synthetic construct
SEQUENCE: 166
FQENEHPFT                                                         9

SEQ ID NO: 167        moltype = AA  length = 9
FEATURE               Location/Qualifiers
REGION                1..9
                      note = TLA0238-LCDR3-4
source                1..9
                      mol_type = protein
                      organism = synthetic construct
SEQUENCE: 167
FQEEGHPFT                                                         9

SEQ ID NO: 168        moltype = AA  length = 9
FEATURE               Location/Qualifiers
REGION                1..9
                      note = TLA0238-LCDR3-5
source                1..9
                      mol_type = protein
                      organism = synthetic construct
SEQUENCE: 168
FQENAHPFT                                                         9

SEQ ID NO: 169        moltype = AA  length = 23
FEATURE               Location/Qualifiers
REGION                1..23
                      note = TLA0238-LFR1
VARIANT               1
                      note = Xaa = Asp or Glu
VARIANT               2
                      note = Xaa = Ile, Asn, Thr or Val
VARIANT               3
                      note = Xaa = Gln or Val
VARIANT               4
                      note = Xaa = Leu or Met
VARIANT               9
                      note = Xaa = Ala or Ser
VARIANT               10
                      note = Xaa = Phe, Ile, Ser or Thr
VARIANT               11
                      note = Xaa = Leu, Met or Val
VARIANT               13
                      note = Xaa = Ala, Leu or Val
VARIANT               14
                      note = Xaa = Ser or Thr
VARIANT               15
                      note = Xaa = Pro or Val
VARIANT               17
                      note = Xaa = Asp or Glu
VARIANT               18
                      note = Xaa = Lys or Arg
VARIANT               19
                      note = Xaa = Ala or Val
VARIANT               21
```

```
                        note = Xaa = Ile or Met
VARIANT                 22
                        note = Xaa = Ser or Thr
source                  1..23
                        mol_type = protein
                        organism = synthetic construct
SEQUENCE: 169
XXXXTQSPXX XSXXXGXXXT XXC                                              23

SEQ ID NO: 170          moltype = AA  length = 23
FEATURE                 Location/Qualifiers
REGION                  1..23
                        note = TLA0238-LFR1-1
source                  1..23
                        mol_type = protein
                        organism = synthetic construct
SEQUENCE: 170
ENVLTQSPAI MSASPGEKVT MTC                                              23

SEQ ID NO: 171          moltype = AA  length = 23
FEATURE                 Location/Qualifiers
REGION                  1..23
                        note = TLA0238-LFR1-2
source                  1..23
                        mol_type = protein
                        organism = synthetic construct
SEQUENCE: 171
ENVLTQSPAT LSLSPGERAT MSC                                              23

SEQ ID NO: 172          moltype = AA  length = 23
FEATURE                 Location/Qualifiers
REGION                  1..23
                        note = TLA0238-LFR1-3
source                  1..23
                        mol_type = protein
                        organism = synthetic construct
SEQUENCE: 172
DNQLTQSPSS LSASVGDRVT ITC                                              23

SEQ ID NO: 173          moltype = AA  length = 23
FEATURE                 Location/Qualifiers
REGION                  1..23
                        note = TLA0238-LFR1-4/TLA0241-LFR1-2
source                  1..23
                        mol_type = protein
                        organism = synthetic construct
SEQUENCE: 173
DIQMTQSPSS VSASVGDRVT ITC                                              23

SEQ ID NO: 174          moltype = AA  length = 23
FEATURE                 Location/Qualifiers
REGION                  1..23
                        note = TLA0238-LFR1-5
source                  1..23
                        mol_type = protein
                        organism = synthetic construct
SEQUENCE: 174
ENVLTQSPAI MSATPGEKVT ITC                                              23

SEQ ID NO: 175          moltype = AA  length = 23
FEATURE                 Location/Qualifiers
REGION                  1..23
                        note = TLA0238-LFR1-6
source                  1..23
                        mol_type = protein
                        organism = synthetic construct
SEQUENCE: 175
EVVLTQSPAF LSVTPGEKVT ITC                                              23

SEQ ID NO: 176          moltype = AA  length = 23
FEATURE                 Location/Qualifiers
REGION                  1..23
                        note = TLA0238-LFR1-7
source                  1..23
                        mol_type = protein
                        organism = synthetic construct
SEQUENCE: 176
ENVLTQSPAF MSATPGEKVT ITC                                              23
```

```
SEQ ID NO: 177          moltype = AA  length = 23
FEATURE                 Location/Qualifiers
REGION                  1..23
                        note = TLA0238-LFR1-8
source                  1..23
                        mol_type = protein
                        organism = synthetic construct
SEQUENCE: 177
EIVLTQSPAF MSATPGEKVT ITC                                          23

SEQ ID NO: 178          moltype = AA  length = 23
FEATURE                 Location/Qualifiers
REGION                  1..23
                        note = TLA0238-LFR1-9
source                  1..23
                        mol_type = protein
                        organism = synthetic construct
SEQUENCE: 178
ETVLTQSPAF MSATPGEKVT ITC                                          23

SEQ ID NO: 179          moltype = AA  length = 23
FEATURE                 Location/Qualifiers
REGION                  1..23
                        note = TLA0238-LFR1-10
source                  1..23
                        mol_type = protein
                        organism = synthetic construct
SEQUENCE: 179
ENVLTQSPAF LSVTPGEKVT ITC                                          23

SEQ ID NO: 180          moltype = AA  length = 15
FEATURE                 Location/Qualifiers
REGION                  1..15
                        note = TLA0238-LFR2
VARIANT                 7
                        note = Xaa = Asp or Gly
VARIANT                 8
                        note = Xaa = Lys or Gln
VARIANT                 9
                        note = Xaa = Ala or Ser
VARIANT                 11
                        note = Xaa = Lys, Gln or Arg
source                  1..15
                        mol_type = protein
                        organism = synthetic construct
SEQUENCE: 180
WYQQKPXXXP XLWIY                                                   15

SEQ ID NO: 181          moltype = AA  length = 15
FEATURE                 Location/Qualifiers
REGION                  1..15
                        note = TLA0238-LFR2-1
source                  1..15
                        mol_type = protein
                        organism = synthetic construct
SEQUENCE: 181
WYQQKSSTSP KLWIY                                                   15

SEQ ID NO: 182          moltype = AA  length = 15
FEATURE                 Location/Qualifiers
REGION                  1..15
                        note = TLA0238-LFR2-2
source                  1..15
                        mol_type = protein
                        organism = synthetic construct
SEQUENCE: 182
WYQQKPGQAP RLWIY                                                   15

SEQ ID NO: 183          moltype = AA  length = 15
FEATURE                 Location/Qualifiers
REGION                  1..15
                        note = TLA0238-LFR2-3
source                  1..15
                        mol_type = protein
                        organism = synthetic construct
SEQUENCE: 183
WYQQKPGKAP KLWIY                                                   15

SEQ ID NO: 184          moltype = AA  length = 15
```

```
FEATURE                 Location/Qualifiers
REGION                  1..15
                        note = TLA0238-LFR2-4
source                  1..15
                        mol_type = protein
                        organism = synthetic construct
SEQUENCE: 184
WYQQKPGQSP QLWIY                                                   15

SEQ ID NO: 185          moltype = AA  length = 15
FEATURE                 Location/Qualifiers
REGION                  1..15
                        note = TLA0238-LFR2-5
source                  1..15
                        mol_type = protein
                        organism = synthetic construct
SEQUENCE: 185
WYQQKPGQSP RLWIY                                                   15

SEQ ID NO: 186          moltype = AA  length = 15
FEATURE                 Location/Qualifiers
REGION                  1..15
                        note = TLA0238-LFR2-6
source                  1..15
                        mol_type = protein
                        organism = synthetic construct
SEQUENCE: 186
WYQQKPGKSP KLWIY                                                   15

SEQ ID NO: 187          moltype = AA  length = 15
FEATURE                 Location/Qualifiers
REGION                  1..15
                        note = TLA0238-LFR2-7
source                  1..15
                        mol_type = protein
                        organism = synthetic construct
SEQUENCE: 187
WYQQKPDQSP KLWIY                                                   15

SEQ ID NO: 188          moltype = AA  length = 15
FEATURE                 Location/Qualifiers
REGION                  1..15
                        note = TLA0238-LFR2-8
source                  1..15
                        mol_type = protein
                        organism = synthetic construct
SEQUENCE: 188
WYQQKPGQSP KLWIY                                                   15

SEQ ID NO: 189          moltype = AA  length = 32
FEATURE                 Location/Qualifiers
REGION                  1..32
                        note = TLA0238-LFR3
VARIANT                 4
                        note = Xaa = Ala, Asp, Gly or Ser
VARIANT                 13
                        note = Xaa = Asn or Thr
VARIANT                 14
                        note = Xaa = Asp or Ser
VARIANT                 15
                        note = Xaa = Phe or Tyr
VARIANT                 22
                        note = Xaa = Leu or Met
VARIANT                 23
                        note = Xaa = Glu or Gln
VARIANT                 24
                        note = Xaa = Ala or Pro
VARIANT                 27
                        note = Xaa = Ala, Phe or Val
VARIANT                 29
                        note = Xaa = Thr or Val
source                  1..32
                        mol_type = protein
                        organism = synthetic construct
SEQUENCE: 189
GVPXRFSGSG SGXXXTLTIS SXXXEDXAXY YC                                32

SEQ ID NO: 190          moltype = AA  length = 32
FEATURE                 Location/Qualifiers
```

```
REGION                  1..32
                        note = TLA0238-LFR3-1
source                  1..32
                        mol_type = protein
                        organism = synthetic construct
SEQUENCE: 190
GVPGRFSGSG SGNSYSLTIS SMEAEDVATY YC                        32

SEQ ID NO: 191          moltype = AA  length = 32
FEATURE                 Location/Qualifiers
REGION                  1..32
                        note = TLA0238-LFR3-2
source                  1..32
                        mol_type = protein
                        organism = synthetic construct
SEQUENCE: 191
GVPARFSGSG SGNDYTLTIS SMEPEDFAVY YC                        32

SEQ ID NO: 192          moltype = AA  length = 32
FEATURE                 Location/Qualifiers
REGION                  1..32
                        note = TLA0238-LFR3-3
source                  1..32
                        mol_type = protein
                        organism = synthetic construct
SEQUENCE: 192
GVPGRFSGSG SGNDYTLTIS SLQPEDFATY YC                        32

SEQ ID NO: 193          moltype = AA  length = 32
FEATURE                 Location/Qualifiers
REGION                  1..32
                        note = TLA0238-LFR3-5
source                  1..32
                        mol_type = protein
                        organism = synthetic construct
SEQUENCE: 193
GVPDRFSGSG SGTDYTLTIS SLQPEDVATY YC                        32

SEQ ID NO: 194          moltype = AA  length = 32
FEATURE                 Location/Qualifiers
REGION                  1..32
                        note = TLA0238-LFR3-6
source                  1..32
                        mol_type = protein
                        organism = synthetic construct
SEQUENCE: 194
GVPDRFSGSG SGTDYTLTIS SLQPEDFAVY YC                        32

SEQ ID NO: 195          moltype = AA  length = 32
FEATURE                 Location/Qualifiers
REGION                  1..32
                        note = TLA0238-LFR3-7
source                  1..32
                        mol_type = protein
                        organism = synthetic construct
SEQUENCE: 195
GVPSRFSGSG SGTSYTLTIS SLQPEDVATY YC                        32

SEQ ID NO: 196          moltype = AA  length = 32
FEATURE                 Location/Qualifiers
REGION                  1..32
                        note = TLA0238-LFR3-8
source                  1..32
                        mol_type = protein
                        organism = synthetic construct
SEQUENCE: 196
GVPDRFSGSG SGTDYTLTIS SLEAEDAATY YC                        32

SEQ ID NO: 197          moltype = AA  length = 32
FEATURE                 Location/Qualifiers
REGION                  1..32
                        note = TLA0238-LFR3-9
source                  1..32
                        mol_type = protein
                        organism = synthetic construct
SEQUENCE: 197
GVPSRFSGSG SGTDYTLTIS SLQPEDFATY YC                        32

SEQ ID NO: 198          moltype = AA  length = 10
```

```
FEATURE                 Location/Qualifiers
REGION                  1..10
                        note = TLA0238-LFR4
VARIANT                 3
                        note = Xaa = Gly or Gln
VARIANT                 7
                        note = Xaa = Leu or Val
VARIANT                 9
                        note = Xaa = Ile or Met
source                  1..10
                        mol_type = protein
                        organism = synthetic construct
SEQUENCE: 198
FGXGTKXEXK                                                        10

SEQ ID NO: 199          moltype = AA  length = 10
FEATURE                 Location/Qualifiers
REGION                  1..10
                        note = TLA0238-LFR4-1
source                  1..10
                        mol_type = protein
                        organism = synthetic construct
SEQUENCE: 199
FGGGTKLEMK                                                        10

SEQ ID NO: 200          moltype = AA  length = 10
FEATURE                 Location/Qualifiers
REGION                  1..10
                        note = TLA0238-LFR4-2
source                  1..10
                        mol_type = protein
                        organism = synthetic construct
SEQUENCE: 200
FGGGTKVEMK                                                        10

SEQ ID NO: 201          moltype = AA  length = 10
FEATURE                 Location/Qualifiers
REGION                  1..10
                        note = TLA0238-LFR4-4/TLA0241-LFR4-1
source                  1..10
                        mol_type = protein
                        organism = synthetic construct
SEQUENCE: 201
FGQGTKVEIK                                                        10

SEQ ID NO: 202          moltype = AA  length = 119
FEATURE                 Location/Qualifiers
REGION                  1..119
                        note = TLA0238-VH-1
source                  1..119
                        mol_type = protein
                        organism = synthetic construct
SEQUENCE: 202
EVKVEESGGG LVQPGGSMKL SCIASGFTFS NYWMNWVRQS PEKGLEWVAQ IRLKSDNYAT  60
HYAESVKGNF TISRDDSKSS VYLQMNNLRA EDTGIYYCTP LLLRYRDYWG QGTTLTVSS   119

SEQ ID NO: 203          moltype = AA  length = 119
FEATURE                 Location/Qualifiers
REGION                  1..119
                        note = TLA0238-VH-2
source                  1..119
                        mol_type = protein
                        organism = synthetic construct
SEQUENCE: 203
EVQVVESGGG LVKPGGSLRL SCAASGFTFS NYWMNWVRQA PGKGLEWVAQ IRLKSDNYAT  60
HYAESVKGNF TISRDDSKST VYLQMNSLKT EDTAVYYCTP LLLRYRDYWG QGTLVTVSS   119

SEQ ID NO: 204          moltype = AA  length = 119
FEATURE                 Location/Qualifiers
REGION                  1..119
                        note = TLA0238-VH-3
source                  1..119
                        mol_type = protein
                        organism = synthetic construct
SEQUENCE: 204
EVQVVESGGG LVQPGGSLRL SCIASGFTFS NYWMNWVRQA PGKGLEWVAQ IRLKSDNYAT  60
HYAESVKGNF TISRDNAKSS VYLQMNSLRA EDTAVYYCTP LLLRYRDYWG QGTLLTVSS   119

SEQ ID NO: 205          moltype = AA  length = 119
```

```
FEATURE                 Location/Qualifiers
REGION                  1..119
                        note = TLA0238-VH-4
source                  1..119
                        mol_type = protein
                        organism = synthetic construct
SEQUENCE: 205
EVQVVESGGG LVKPGGSLRL SCAASGFTFS NYWMNWVRQA PGKGLEWVAQ IRLKSDNYAT  60
HYAESVKGRF TISRDDSKST VYLQMNSLKT EDTAVYYCTP LLLRYRDYWG QGTLVTVSS   119

SEQ ID NO: 206          moltype = AA  length = 119
FEATURE                 Location/Qualifiers
REGION                  1..119
                        note = TLA0238-VH-5
source                  1..119
                        mol_type = protein
                        organism = synthetic construct
SEQUENCE: 206
EVQVVESGGG LVKPGGSLRL SCAASGFTFS NYWMNWVRQA PGKGLEWVAQ IRLKSDNYAT  60
HYAESVKGNF AISRDDSKST VYLQMNSLKT EDTAVYYCTP LLLRYRDYWG QGTLVTVSS   119

SEQ ID NO: 207          moltype = AA  length = 119
FEATURE                 Location/Qualifiers
REGION                  1..119
                        note = TLA0238-VH-6
source                  1..119
                        mol_type = protein
                        organism = synthetic construct
SEQUENCE: 207
QVQLVESGGG VVQPGRSLRL SCAASGFTFS NYWMNWVRQA PGKGLEWVAQ IRLKSDNYAT  60
HYADSVKGRF TISRDNSKNT LYLQMNSLRA EDTAVYYCTP LLLRYRDYWG QGTMVTVSS   119

SEQ ID NO: 208          moltype = AA  length = 119
FEATURE                 Location/Qualifiers
REGION                  1..119
                        note = TLA0238-VH-7
source                  1..119
                        mol_type = protein
                        organism = synthetic construct
SEQUENCE: 208
EVKVEESGGG LVQPGGSLRL SCIASGFTFS NYWMHWVRQA PGKGLEWVGQ IRLKSDNYAT  60
HYAASVKGRF TISRDNSKNT LYLQMNSLKT EDTAVYYCTP LLLRYRDYWG QGTLVTVSS   119

SEQ ID NO: 209          moltype = AA  length = 119
FEATURE                 Location/Qualifiers
REGION                  1..119
                        note = TLA0238-VH-8
source                  1..119
                        mol_type = protein
                        organism = synthetic construct
SEQUENCE: 209
EVKVEESGGG LVQPGGSLKL SCIASGFTFS NYWMHWVRQA PGKGLEWVGQ IRLKSDNYAT  60
HYAASVKGRF TISRDDSKNS LYLQMNSLRD EDTAVYYCTP LLLRYRDYWG QGTLVTVSS   119

SEQ ID NO: 210          moltype = AA  length = 119
FEATURE                 Location/Qualifiers
REGION                  1..119
                        note = TLA0238-VH-9
source                  1..119
                        mol_type = protein
                        organism = synthetic construct
SEQUENCE: 210
EVKVEESGGG LVQPGGALRL SCIASGFTFS NYWMHWVRQA PGKGLEWVGQ IRLKSDNYAT  60
HYAASVKGRF TISRDDSKNT LYLQMNSLRA EDTAVYYCTP LLLRYRDYWG QGTLVTVSS   119

SEQ ID NO: 211          moltype = AA  length = 119
FEATURE                 Location/Qualifiers
REGION                  1..119
                        note = TLA0238-VH-10
source                  1..119
                        mol_type = protein
                        organism = synthetic construct
SEQUENCE: 211
EVKVEESGGG LVQPGGSLRL SCIASGFTFS NYWMHWVRQA PGKGLEWVGQ IRLKSDNYAT  60
HYAASVKGRF TISRDDSKNS LYLQMNSLRA EDMAVYYCTP LLLRYRDYWG QGTLVTVSS   119

SEQ ID NO: 212          moltype = AA  length = 119
FEATURE                 Location/Qualifiers
REGION                  1..119
```

```
                        note = TLA0238-VH-11
source                  1..119
                        mol_type = protein
                        organism = synthetic construct
SEQUENCE: 212
EVQLVESGGG LVQPGGSLRL SCAASGFTFS NYWMNWVRQA PGKGLEWVAQ IRLKSDNYAT  60
HYADSVKGRF TISRDNSKNT LYLQMNSLRA EDTAVYYCTP LLLRYRDYWG QGTMVTVSS   119

SEQ ID NO: 213          moltype = AA  length = 119
FEATURE                 Location/Qualifiers
REGION                  1..119
                        note = TLA0238-VH-12
source                  1..119
                        mol_type = protein
                        organism = synthetic construct
SEQUENCE: 213
EVKLEESGGG LVQPGGSLKL SCIASGFTFS NYWMHWVRQA PGKGLEWVGQ IRLKSDNYAT  60
HYAASVKGRF TISRDDSKNT AYLQMNSLRA EDTAVYYCTP LLLRYRDYWG QGTLVTVSS   119

SEQ ID NO: 214          moltype = AA  length = 119
FEATURE                 Location/Qualifiers
REGION                  1..119
                        note = TLA0238-VH-13
source                  1..119
                        mol_type = protein
                        organism = synthetic construct
SEQUENCE: 214
EVQLVESGGG LVKPGGSLRL SCAASGFTFS NYWMNWVRQA PGKGLEWVAQ IRLKSDNYAT  60
HYAAPVKGRF TISRDDSKNT LYLQMNSLKT EDTAVYYCTP LLLRYRDYWG QGTTVTVSS   119

SEQ ID NO: 215          moltype = AA  length = 119
FEATURE                 Location/Qualifiers
REGION                  1..119
                        note = TLA0238-VH-14
source                  1..119
                        mol_type = protein
                        organism = synthetic construct
SEQUENCE: 215
EVKLEESGGG LVQPGGALRL SCIASGFTFS NYWMSWVRQA PGKGLEWVGQ IRLKSDNYAT  60
HYAASVKGRF TISRDDSKNT LYLQMNSLRA EDTAVYYCTP LLLRYRDYWG QGTLVTVSS   119

SEQ ID NO: 216          moltype = AA  length = 119
FEATURE                 Location/Qualifiers
REGION                  1..119
                        note = TLA0238-VH-15
source                  1..119
                        mol_type = protein
                        organism = synthetic construct
SEQUENCE: 216
EVQLVESGGG LVQPGGSLRL SCAASGFTFS NYIMNWVRQA PGKGLEWVAQ IRLKSDNYAT  60
HYADSVKGRF TISRDNSKNT LYLQMNSLRA EDTAVYYCTP LLLRYRDYWG QGTLVTVSS   119

SEQ ID NO: 217          moltype = AA  length = 119
FEATURE                 Location/Qualifiers
REGION                  1..119
                        note = TLA0238-VH-16
source                  1..119
                        mol_type = protein
                        organism = synthetic construct
SEQUENCE: 217
EVQLVESGGG LVQPGGSLRL SCAASGFTFS NYLMNWVRQA PGKGLEWVAQ IRLKSDNYAT  60
HYADSVKGRF TISRDNSKNT LYLQMNSLRA EDTAVYYCTP LLLRYRDYWG QGTLVTVSS   119

SEQ ID NO: 218          moltype = AA  length = 119
FEATURE                 Location/Qualifiers
REGION                  1..119
                        note = TLA0238-VH-17
source                  1..119
                        mol_type = protein
                        organism = synthetic construct
SEQUENCE: 218
EVQLVESGGG LVQPGGSLRL SCAASGFTFS NYMMNWVRQA PGKGLEWVAQ IRLKSDNYAT  60
HYADSVKGRF TISRDNSKNT LYLQMNSLRA EDTAVYYCTP LLLRYRDYWG QGTLVTVSS   119

SEQ ID NO: 219          moltype = AA  length = 119
FEATURE                 Location/Qualifiers
REGION                  1..119
                        note = TLA0238-VH-18
source                  1..119
```

```
                         mol_type = protein
                         organism = synthetic construct
SEQUENCE: 219
EVQLVESGGG LVQPGGSLRL SCAASGFTFS NYWMNWVRQA PGKGLEWVAQ IRLKSDNYAT  60
HYADSVKGRF TISRDNSKNT LYLQMNSLRA EDTAVYYCTP LLLRYRDYWG QGTLVTVSS   119

SEQ ID NO: 220           moltype = AA  length = 119
FEATURE                  Location/Qualifiers
REGION                   1..119
                         note = TLA0238-VH-19
source                   1..119
                         mol_type = protein
                         organism = synthetic construct
SEQUENCE: 220
EVQLVESGGG LVQPGGSLRL SCAASGFTFS NYYMNWVRQA PGKGLEWVAQ IRLKSDNYAT  60
HYADSVKGRF TISRDNSKNT LYLQMNSLRA EDTAVYYCTP LLLRYRDYWG QGTLVTVSS   119

SEQ ID NO: 221           moltype = AA  length = 106
FEATURE                  Location/Qualifiers
REGION                   1..106
                         note = TLA0238-VL-1
source                   1..106
                         mol_type = protein
                         organism = synthetic construct
SEQUENCE: 221
ENVLTQSPAI MSASPGEKVT MTCSASSSVS YMHWYQQKSS TSPKLWIYDT SNLASGVPGR  60
FSGSGSGNSY SLTISSMEAE DVATYYCFQE NGHPFTFGGG TKLEMK                 106

SEQ ID NO: 222           moltype = AA  length = 106
FEATURE                  Location/Qualifiers
REGION                   1..106
                         note = TLA0238-VL-2
source                   1..106
                         mol_type = protein
                         organism = synthetic construct
SEQUENCE: 222
ENVLTQSPAT LSLSPGERAT MSCSASSSVS YMHWYQQKPG QAPRLWIYDT SNLASGVPAR  60
FSGSGSGNDY TLTISSMEPE DFAVYYCFQE NGHPFTFGGG TKVEMK                 106

SEQ ID NO: 223           moltype = AA  length = 106
FEATURE                  Location/Qualifiers
REGION                   1..106
                         note = TLA0238-VL-3
source                   1..106
                         mol_type = protein
                         organism = synthetic construct
SEQUENCE: 223
DNQLTQSPSS LSASVGDRVT ITCSASSSVS YMHWYQQKPG KAPKLWIYDT SNLASGVPGR  60
FSGSGSGNDY TLTISSLQPE DFATYYCFQE NGHPFTFGQG TKLEIK                 106

SEQ ID NO: 224           moltype = AA  length = 106
FEATURE                  Location/Qualifiers
REGION                   1..106
                         note = TLA0238-VL-4
source                   1..106
                         mol_type = protein
                         organism = synthetic construct
SEQUENCE: 224
ENVLTQSPAI MSATPGEKVT ITCSASSSVS YLHWYQQKPG QSPQLWIYDT SNRASGVPDR  60
FSGSGSGTDY TLTISSLQPE DVATYYCFQE NGHPFTFGGG TKLEMK                 106

SEQ ID NO: 225           moltype = AA  length = 106
FEATURE                  Location/Qualifiers
REGION                   1..106
                         note = TLA0238-VL-5
source                   1..106
                         mol_type = protein
                         organism = synthetic construct
SEQUENCE: 225
EVVLTQSPAF LSVTPGEKVT ITCSASSSVS YLAWYQQKPG QSPRLWIYDT SNRASGVPDR  60
FSGSGSGTDY TLTISSLQPE DFAVYYCFQE NGHPFTFGGG TKLEMK                 106

SEQ ID NO: 226           moltype = AA  length = 106
FEATURE                  Location/Qualifiers
REGION                   1..106
                         note = TLA0238-VL-6
source                   1..106
                         mol_type = protein
                         organism = synthetic construct
```

```
SEQUENCE: 226
ENVLTQSPAF MSATPGEKVT ITCSASSSVS YLAWYQQKPG KSPKLWIYDT SNLATGVPSR  60
FSGSGSGTSY TLTISSLQPE DVATYYCFQE NGHPFTFGGG TKLEMK                106

SEQ ID NO: 227          moltype = AA  length = 106
FEATURE                 Location/Qualifiers
REGION                  1..106
                        note = TLA0238-VL-7
source                  1..106
                        mol_type = protein
                        organism = synthetic construct
SEQUENCE: 227
EIVLTQSPAF MSATPGEKVT ITCSASSSVS YLHWYQQKPD QSPKLWIYDT SNRASGVPDR  60
FSGSGSGTDY TLTISSLEAE DAATYYCFQE NGHPFTFGGG TKLEMK                106

SEQ ID NO: 228          moltype = AA  length = 106
FEATURE                 Location/Qualifiers
REGION                  1..106
                        note = TLA0238-VL-8
source                  1..106
                        mol_type = protein
                        organism = synthetic construct
SEQUENCE: 228
ETVLTQSPAF MSATPGEKVT ITCSASSSVS YLTWYQQKPG QSPKLWIYDT SNLASGVPDR  60
FSGSGSGTDY TLTISSLEAE DAATYYCFQE NGHPFTFGGG TKLEMK                106

SEQ ID NO: 229          moltype = AA  length = 106
FEATURE                 Location/Qualifiers
REGION                  1..106
                        note = TLA0238-VL-9
source                  1..106
                        mol_type = protein
                        organism = synthetic construct
SEQUENCE: 229
DIQMTQSPSS VSASVGDRVT ITCSASSSVS YMHWYQQKPG KAPKLWIYDT SNLASGVPSR  60
FSGSGSGTDF TLTISSLQPE DFATYYCFQE NGHPFTFGQG TKVEIK                106

SEQ ID NO: 230          moltype = AA  length = 106
FEATURE                 Location/Qualifiers
REGION                  1..106
                        note = TLA0238-VL-10
source                  1..106
                        mol_type = protein
                        organism = synthetic construct
SEQUENCE: 230
ENVLTQSPAF LSVTPGEKVT ITCSASSSVS YLHWYQQKPD QSPKLWIYDT SNLATGVPSR  60
FSGSGSGTDY TLTISSLQPE DFATYYCFQE NGHPFTFGGG TKLEMK                106

SEQ ID NO: 231          moltype = AA  length = 106
FEATURE                 Location/Qualifiers
REGION                  1..106
                        note = TLA0238-VL-11
source                  1..106
                        mol_type = protein
                        organism = synthetic construct
SEQUENCE: 231
DIQMTQSPSS VSASVGDRVT ITCSASSSVS YMHWYQQKPG KAPKLWIYDT SNLASGVPSR  60
FSGSGSGTDF TLTISSLQPE DFATYYCFQE SGHPFTFGQG TKVEIK                106

SEQ ID NO: 232          moltype = AA  length = 106
FEATURE                 Location/Qualifiers
REGION                  1..106
                        note = TLA0238-VL-12
source                  1..106
                        mol_type = protein
                        organism = synthetic construct
SEQUENCE: 232
DIQMTQSPSS VSASVGDRVT ITCSASSSVS YMHWYQQKPG KAPKLWIYDT SNLASGVPSR  60
FSGSGSGTDF TLTISSLQPE DFATYYCFQE NEHPFTFGQG TKVEIK                106

SEQ ID NO: 233          moltype = AA  length = 106
FEATURE                 Location/Qualifiers
REGION                  1..106
                        note = TLA0238-VL-13
source                  1..106
                        mol_type = protein
                        organism = synthetic construct
SEQUENCE: 233
DIQMTQSPSS VSASVGDRVT ITCSASSSVS YMHWYQQKPG KAPKLWIYDT SNLASGVPSR  60
```

```
FSGSGSGTDF TLTISSLQPE DFATYYCFQE EGHPFTFGQG TKVEIK                106

SEQ ID NO: 234          moltype = AA  length = 106
FEATURE                 Location/Qualifiers
REGION                  1..106
                        note = TLA0238-VL-14
source                  1..106
                        mol_type = protein
                        organism = synthetic construct
SEQUENCE: 234
DIQMTQSPSS VSASVGDRVT ITCSASSSVS YMHWYQQKPG KAPKLWIYDT SNLASGVPSR  60
FSGSGSGTDF TLTISSLQPE DFATYYCFQE NAHPFTFGQG TKVEIK                106

SEQ ID NO: 235          moltype =   length =
SEQUENCE: 235
000

SEQ ID NO: 236          moltype = AA  length = 5
FEATURE                 Location/Qualifiers
REGION                  1..5
                        note = TLA0241-HCDR1-1
source                  1..5
                        mol_type = protein
                        organism = synthetic construct
SEQUENCE: 236
DYYLN                                                             5

SEQ ID NO: 237          moltype = AA  length = 5
FEATURE                 Location/Qualifiers
REGION                  1..5
                        note = TLA0241-HCDR1-2
source                  1..5
                        mol_type = protein
                        organism = synthetic construct
SEQUENCE: 237
DYYMH                                                             5

SEQ ID NO: 238          moltype = AA  length = 17
FEATURE                 Location/Qualifiers
REGION                  1..17
                        note = TLA0241-HCDR2
VARIANT                 12
                        note = Xaa = Ala or Asn
VARIANT                 13
                        note = Xaa = Asp or Gln
VARIANT                 14
                        note = Xaa = Lys or Ser
VARIANT                 15
                        note = Xaa = Phe or Val
VARIANT                 16
                        note = Xaa = Lys, Gln or Thr
source                  1..17
                        mol_type = protein
                        organism = synthetic construct
SEQUENCE: 238
DINPNNGRTT YXXXXXG                                                17

SEQ ID NO: 239          moltype = AA  length = 17
FEATURE                 Location/Qualifiers
REGION                  1..17
                        note = TLA0241-HCDR2-1
source                  1..17
                        mol_type = protein
                        organism = synthetic construct
SEQUENCE: 239
DINPNNGRTT YNQKFTG                                                17

SEQ ID NO: 240          moltype = AA  length = 17
FEATURE                 Location/Qualifiers
REGION                  1..17
                        note = TLA0241-HCDR2-2
source                  1..17
                        mol_type = protein
                        organism = synthetic construct
SEQUENCE: 240
DINPNNGRTT YADSVKG                                                17

SEQ ID NO: 241          moltype = AA  length = 17
FEATURE                 Location/Qualifiers
```

```
REGION                  1..17
                        note = TLA0241-HCDR2-3
source                  1..17
                        mol_type = protein
                        organism = synthetic construct
SEQUENCE: 241
DINPNNGRTT YNQKFQG                                            17

SEQ ID NO: 242          moltype = AA  length = 10
FEATURE                 Location/Qualifiers
REGION                  1..10
                        note = TLA0241-HCDR3-1
source                  1..10
                        mol_type = protein
                        organism = synthetic construct
SEQUENCE: 242
EGGYGWYFDV                                                    10

SEQ ID NO: 243          moltype = AA  length = 30
FEATURE                 Location/Qualifiers
REGION                  1..30
                        note = TLA0241-HFR1
VARIANT                 1
                        note = Xaa = Glu or Gln
VARIANT                 2
                        note = Xaa = Ile, Leu or Val
VARIANT                 5
                        note = Xaa = Leu, Gln or Val
VARIANT                 6
                        note = Xaa = Glu or Gln
VARIANT                 9
                        note = Xaa = Ala, Gly or Pro
VARIANT                 10
                        note = Xaa = Glu or Gly
VARIANT                 11
                        note = Xaa = Glu, Leu or Val
VARIANT                 12
                        note = Xaa = Lys or Val
VARIANT                 13
                        note = Xaa = Lys or Gln
VARIANT                 16
                        note = Xaa = Ala, Gly or Arg
VARIANT                 18
                        note = Xaa = Leu or Val
VARIANT                 20
                        note = Xaa = Ile or Leu
VARIANT                 23
                        note = Xaa = Ala, Lys or Ser
source                  1..30
                        mol_type = protein
                        organism = synthetic construct
SEQUENCE: 243
XXQLXXSGXX XXXPGXSXRX SCXASGYTFT                              30

SEQ ID NO: 244          moltype = AA  length = 30
FEATURE                 Location/Qualifiers
REGION                  1..30
                        note = TLA0241-HFR1-1
source                  1..30
                        mol_type = protein
                        organism = synthetic construct
SEQUENCE: 244
EVQLVESGGG LVQPGGSLRL SCSASGYTFT                              30

SEQ ID NO: 245          moltype = AA  length = 30
FEATURE                 Location/Qualifiers
REGION                  1..30
                        note = TLA0241-HFR1-2
source                  1..30
                        mol_type = protein
                        organism = synthetic construct
SEQUENCE: 245
QVQLVESGGG VVQPGRSLRL SCAASGYTFT                              30

SEQ ID NO: 246          moltype = AA  length = 30
FEATURE                 Location/Qualifiers
REGION                  1..30
                        note = TLA0241-HFR1-3
source                  1..30
```

```
                        mol_type = protein
                        organism = synthetic construct
SEQUENCE: 246
EVQLQQSGPE VKKPGASVRI SCKASGYTFT                                     30

SEQ ID NO: 247          moltype = AA  length = 30
FEATURE                 Location/Qualifiers
REGION                  1..30
                        note = TLA0241-HFR1-4
source                  1..30
                        mol_type = protein
                        organism = synthetic construct
SEQUENCE: 247
ELQLQQSGPE VKKPGASVRI SCKASGYTFT                                     30

SEQ ID NO: 248          moltype = AA  length = 30
FEATURE                 Location/Qualifiers
REGION                  1..30
                        note = TLA0241-HFR1-5
source                  1..30
                        mol_type = protein
                        organism = synthetic construct
SEQUENCE: 248
EVQLLESGGG LVQPGGSLRL SCAASGYTFT                                     30

SEQ ID NO: 249          moltype = AA  length = 30
FEATURE                 Location/Qualifiers
REGION                  1..30
                        note = TLA0241-HFR1-6
source                  1..30
                        mol_type = protein
                        organism = synthetic construct
SEQUENCE: 249
EIQLQQSGAE EKKPGASVRI SCKASGYTFT                                     30

SEQ ID NO: 250          moltype = AA  length = 30
FEATURE                 Location/Qualifiers
REGION                  1..30
                        note = TLA0241-HFR1-7
source                  1..30
                        mol_type = protein
                        organism = synthetic construct
SEQUENCE: 250
ELQLQQSGAE VKKPGASVRI SCKASGYTFT                                     30

SEQ ID NO: 251          moltype = AA  length = 14
FEATURE                 Location/Qualifiers
REGION                  1..14
                        note = TLA0241-HFR2
VARIANT                 3
                        note = Xaa = Gln or Arg
VARIANT                 8
                        note = Xaa = Glu, Lys or Gln
source                  1..14
                        mol_type = protein
                        organism = synthetic construct
SEQUENCE: 251
WVXQAPGXGL EWIG                                                      14

SEQ ID NO: 252          moltype = AA  length = 14
FEATURE                 Location/Qualifiers
REGION                  1..14
                        note = TLA0241-HFR2-1
source                  1..14
                        mol_type = protein
                        organism = synthetic construct
SEQUENCE: 252
WVRQAPGKGL EWIG                                                      14

SEQ ID NO: 253          moltype = AA  length = 14
FEATURE                 Location/Qualifiers
REGION                  1..14
                        note = TLA0241-HFR2-2
source                  1..14
                        mol_type = protein
                        organism = synthetic construct
SEQUENCE: 253
WVRQAPGQGL EWIG                                                      14
```

```
SEQ ID NO: 254         moltype = AA  length = 14
FEATURE                Location/Qualifiers
REGION                 1..14
                       note = TLA0241-HFR2-3
source                 1..14
                       mol_type = protein
                       organism = synthetic construct
SEQUENCE: 254
WVQQAPGKGL EWIG                                                 14

SEQ ID NO: 255         moltype = AA  length = 14
FEATURE                Location/Qualifiers
REGION                 1..14
                       note = TLA0241-HFR2-4
source                 1..14
                       mol_type = protein
                       organism = synthetic construct
SEQUENCE: 255
WVRQAPGEGL EWIG                                                 14

SEQ ID NO: 256         moltype = AA  length = 32
FEATURE                Location/Qualifiers
REGION                 1..32
                       note = TLA0241-HFR3
VARIANT                2
                       note = Xaa = Phe or Val
VARIANT                5
                       note = Xaa = Ser or Thr
VARIANT                6
                       note = Xaa = Ala or Arg
VARIANT                8
                       note = Xaa = Lys, Asn or Thr
VARIANT                10
                       note = Xaa = Lys, Ser or Thr
VARIANT                11
                       note = Xaa = Asn or Ser
VARIANT                13
                       note = Xaa = Ala or Leu
VARIANT                15
                       note = Xaa = Leu or Met
VARIANT                16
                       note = Xaa = Glu or Gln
VARIANT                17
                       note = Xaa = Leu or Met
VARIANT                18
                       note = Xaa = Asn, Arg or Ser
VARIANT                21
                       note = Xaa = Arg or Thr
VARIANT                22
                       note = Xaa = Ala or Ser
VARIANT                23
                       note = Xaa = Asp or Glu
VARIANT                25
                       note = Xaa = Met or Thr
source                 1..32
                       mol_type = protein
                       organism = synthetic construct
SEQUENCE: 256
RXTIXXDXSX XTXYXXXXSL XXXDXAVYYC AR                             32

SEQ ID NO: 257         moltype = AA  length = 32
FEATURE                Location/Qualifiers
REGION                 1..32
                       note = TLA0241-HFR3-1
source                 1..32
                       mol_type = protein
                       organism = synthetic construct
SEQUENCE: 257
RFTISRDNSK NTLYLQMSSL RAEDTAVYYC AR                             32

SEQ ID NO: 258         moltype = AA  length = 32
FEATURE                Location/Qualifiers
REGION                 1..32
                       note = TLA0241-HFR3-2
source                 1..32
                       mol_type = protein
                       organism = synthetic construct
SEQUENCE: 258
RFTISRDNSK NTLYLQMNSL RAEDTAVYYC AR                             32
```

```
SEQ ID NO: 259          moltype = AA  length = 32
FEATURE                 Location/Qualifiers
REGION                  1..32
                        note = TLA0241-HFR3-3
source                  1..32
                        mol_type = protein
                        organism = synthetic construct
SEQUENCE: 259
RVTITRDTSS STAYMELRSL RSDDTAVYYC AR                              32

SEQ ID NO: 260          moltype = AA  length = 32
FEATURE                 Location/Qualifiers
REGION                  1..32
                        note = TLA0241-HFR3-4
source                  1..32
                        mol_type = protein
                        organism = synthetic construct
SEQUENCE: 260
RVTITADKST STAYMELRSL RSDDTAVYYC AR                              32

SEQ ID NO: 261          moltype = AA  length = 32
FEATURE                 Location/Qualifiers
REGION                  1..32
                        note = TLA0241-HFR3-5
source                  1..32
                        mol_type = protein
                        organism = synthetic construct
SEQUENCE: 261
RVTITADKST STAYMELRSL TSDDTAVYYC AR                              32

SEQ ID NO: 262          moltype = AA  length = 32
FEATURE                 Location/Qualifiers
REGION                  1..32
                        note = TLA0241-HFR3-6
source                  1..32
                        mol_type = protein
                        organism = synthetic construct
SEQUENCE: 262
RVTITADKST STAYMELRSL RSDDMAVYYC AR                              32

SEQ ID NO: 263          moltype = AA  length = 11
FEATURE                 Location/Qualifiers
REGION                  1..11
                        note = TLA0241-HFR4
VARIANT                 3
                        note = Xaa = Gln, Arg or Thr
VARIANT                 6
                        note = Xaa = Leu, Met or Thr
source                  1..11
                        mol_type = protein
                        organism = synthetic construct
SEQUENCE: 263
WGXGTXVTVS S                                                     11

SEQ ID NO: 264          moltype = AA  length = 11
FEATURE                 Location/Qualifiers
REGION                  1..11
                        note = TLA0241-HFR4-1
source                  1..11
                        mol_type = protein
                        organism = synthetic construct
SEQUENCE: 264
WGRGTLVTVS S                                                     11

SEQ ID NO: 265          moltype = AA  length = 11
FEATURE                 Location/Qualifiers
REGION                  1..11
                        note = TLA0241-HFR4-2
source                  1..11
                        mol_type = protein
                        organism = synthetic construct
SEQUENCE: 265
WGQGTMVTVS S                                                     11

SEQ ID NO: 266          moltype = AA  length = 11
FEATURE                 Location/Qualifiers
REGION                  1..11
                        note = TLA0241-HFR4-3
```

```
source                  1..11
                        mol_type = protein
                        organism = synthetic construct
SEQUENCE: 266
WGTGTLVTVS S                                                              11

SEQ ID NO: 267          moltype = AA  length = 11
FEATURE                 Location/Qualifiers
REGION                  1..11
                        note = TLA0241-HFR4-4
source                  1..11
                        mol_type = protein
                        organism = synthetic construct
SEQUENCE: 267
WGQGTTVTVS S                                                              11

SEQ ID NO: 268          moltype = AA  length = 11
FEATURE                 Location/Qualifiers
REGION                  1..11
                        note = TLA0241-HFR4-5
source                  1..11
                        mol_type = protein
                        organism = synthetic construct
SEQUENCE: 268
WGTGTTVTVS S                                                              11

SEQ ID NO: 269          moltype = AA  length = 12
FEATURE                 Location/Qualifiers
REGION                  1..12
                        note = TLA0241-LCDR1
VARIANT                 2
                        note = Xaa = Ala or Thr
VARIANT                 11
                        note = Xaa = Leu or Ser
VARIANT                 12
                        note = Xaa = Ala or His
source                  1..12
                        mol_type = protein
                        organism = synthetic construct
SEQUENCE: 269
SXSSSIISNY XX                                                             12

SEQ ID NO: 270          moltype = AA  length = 12
FEATURE                 Location/Qualifiers
REGION                  1..12
                        note = TLA0241-LCDR1-1
source                  1..12
                        mol_type = protein
                        organism = synthetic construct
SEQUENCE: 270
STSSSIISNY SH                                                             12

SEQ ID NO: 271          moltype = AA  length = 12
FEATURE                 Location/Qualifiers
REGION                  1..12
                        note = TLA0241-LCDR1-2
source                  1..12
                        mol_type = protein
                        organism = synthetic construct
SEQUENCE: 271
SASSSIISNY LH                                                             12

SEQ ID NO: 272          moltype = AA  length = 12
FEATURE                 Location/Qualifiers
REGION                  1..12
                        note = TLA0241-LCDR1-3
source                  1..12
                        mol_type = protein
                        organism = synthetic construct
SEQUENCE: 272
SASSSIISNY SA                                                             12

SEQ ID NO: 273          moltype = AA  length = 12
FEATURE                 Location/Qualifiers
REGION                  1..12
                        note = TLA0241-LCDR1-4
source                  1..12
                        mol_type = protein
                        organism = synthetic construct
```

```
SEQUENCE: 273
SASSSIISNY LA                                                   12

SEQ ID NO: 274          moltype = AA  length = 7
FEATURE                 Location/Qualifiers
REGION                  1..7
                        note = TLA0241-LCDR2
VARIANT                 5
                        note = Xaa = Leu or Arg
source                  1..7
                        mol_type = protein
                        organism = synthetic construct
SEQUENCE: 274
KTSNXPS                                                         7

SEQ ID NO: 275          moltype = AA  length = 7
FEATURE                 Location/Qualifiers
REGION                  1..7
                        note = TLA0241-LCDR2-1
source                  1..7
                        mol_type = protein
                        organism = synthetic construct
SEQUENCE: 275
KTSNLPS                                                         7

SEQ ID NO: 276          moltype = AA  length = 7
FEATURE                 Location/Qualifiers
REGION                  1..7
                        note = TLA0241-LCDR2-2
source                  1..7
                        mol_type = protein
                        organism = synthetic construct
SEQUENCE: 276
KTSNRPS                                                         7

SEQ ID NO: 277          moltype = AA  length = 9
FEATURE                 Location/Qualifiers
REGION                  1..9
                        note = TLA0241-LCDR3-1
source                  1..9
                        mol_type = protein
                        organism = synthetic construct
SEQUENCE: 277
QQGSDMPIT                                                       9

SEQ ID NO: 278          moltype = AA  length = 23
FEATURE                 Location/Qualifiers
REGION                  1..23
                        note = TLA0241-LFR1
VARIANT                 1
                        note = Xaa = Ala, Asp or Glu
VARIANT                 3
                        note = Xaa = Gln or Val
VARIANT                 4
                        note = Xaa = Leu or Met
VARIANT                 9
                        note = Xaa = Ala, Gly, Pro, Ser or Thr
VARIANT                 10
                        note = Xaa = Ser or Thr
VARIANT                 11
                        note = Xaa = Leu or Val
VARIANT                 13
                        note = Xaa = Ala or Leu
VARIANT                 15
                        note = Xaa = Pro or Val
VARIANT                 17
                        note = Xaa = Asp or Glu
VARIANT                 18
                        note = Xaa = Lys or Arg
source                  1..23
                        mol_type = protein
                        organism = synthetic construct
SEQUENCE: 278
XIXXTQSPXX XSXSXGXXVT ITC                                       23

SEQ ID NO: 279          moltype = AA  length = 23
FEATURE                 Location/Qualifiers
REGION                  1..23
                        note = TLA0241-LFR1-3
```

```
source                  1..23
                        mol_type = protein
                        organism = synthetic construct
SEQUENCE: 279
EIVLTQSPTT LSLSPGEKVT ITC                                             23

SEQ ID NO: 280          moltype = AA  length = 23
FEATURE                 Location/Qualifiers
REGION                  1..23
                        note = TLA0241-LFR1-4
source                  1..23
                        mol_type = protein
                        organism = synthetic construct
SEQUENCE: 280
EIVLTQSPPT LSLSPGEKVT ITC                                             23

SEQ ID NO: 281          moltype = AA  length = 23
FEATURE                 Location/Qualifiers
REGION                  1..23
                        note = TLA0241-LFR1-5
source                  1..23
                        mol_type = protein
                        organism = synthetic construct
SEQUENCE: 281
EIVLTQSPGT LSLSPGEKVT ITC                                             23

SEQ ID NO: 282          moltype = AA  length = 23
FEATURE                 Location/Qualifiers
REGION                  1..23
                        note = TLA0241-LFR1-6
source                  1..23
                        mol_type = protein
                        organism = synthetic construct
SEQUENCE: 282
AIQLTQSPSS LSASVGDRVT ITC                                             23

SEQ ID NO: 283          moltype = AA  length = 23
FEATURE                 Location/Qualifiers
REGION                  1..23
                        note = TLA0241-LFR1-7
source                  1..23
                        mol_type = protein
                        organism = synthetic construct
SEQUENCE: 283
EIVLTQSPAT LSLSPGEKVT ITC                                             23

SEQ ID NO: 284          moltype = AA  length = 15
FEATURE                 Location/Qualifiers
REGION                  1..15
                        note = TLA0241-LFR2
VARIANT                 7
                        note = Xaa = Asp or Gly
VARIANT                 8
                        note = Xaa = Lys or Gln
VARIANT                 9
                        note = Xaa = Ala or Ser
VARIANT                 11
                        note = Xaa = Lys or Gln
source                  1..15
                        mol_type = protein
                        organism = synthetic construct
SEQUENCE: 284
WYQQKPXXXP XLLIY                                                      15

SEQ ID NO: 285          moltype = AA  length = 15
FEATURE                 Location/Qualifiers
REGION                  1..15
                        note = TLA0241-LFR2-2
source                  1..15
                        mol_type = protein
                        organism = synthetic construct
SEQUENCE: 285
WYQQKPGKSP KLLIY                                                      15

SEQ ID NO: 286          moltype = AA  length = 15
FEATURE                 Location/Qualifiers
REGION                  1..15
                        note = TLA0241-LFR2-3
source                  1..15
```

```
                          mol_type = protein
                          organism = synthetic construct
SEQUENCE: 286
WYQQKPGQSP QLLIY                                                15

SEQ ID NO: 287            moltype = AA  length = 15
FEATURE                   Location/Qualifiers
REGION                    1..15
                          note = TLA0241-LFR2-4
source                    1..15
                          mol_type = protein
                          organism = synthetic construct
SEQUENCE: 287
WYQQKPDQSP KLLIY                                                15

SEQ ID NO: 288            moltype = AA  length = 32
FEATURE                   Location/Qualifiers
REGION                    1..32
                          note = TLA0241-LFR3
VARIANT                   4
                          note = Xaa = Ala, Asp or Ser
VARIANT                   14
                          note = Xaa = Asp, Glu or Ser
VARIANT                   20
                          note = Xaa = Asn or Ser
VARIANT                   23
                          note = Xaa = Glu or Gln
VARIANT                   24
                          note = Xaa = Ala or Pro
VARIANT                   27
                          note = Xaa = Ala or Phe
source                    1..32
                          mol_type = protein
                          organism = synthetic construct
SEQUENCE: 288
GVPXRFSGSG SGTXFTLTIX SLXXEDXATY YC                             32

SEQ ID NO: 289            moltype = AA  length = 32
FEATURE                   Location/Qualifiers
REGION                    1..32
                          note = TLA0241-LFR3-1
source                    1..32
                          mol_type = protein
                          organism = synthetic construct
SEQUENCE: 289
GVPSRFSGSG SGTEFTLTIS SLQPEDFATY YC                             32

SEQ ID NO: 290            moltype = AA  length = 32
FEATURE                   Location/Qualifiers
REGION                    1..32
                          note = TLA0241-LFR3-3
source                    1..32
                          mol_type = protein
                          organism = synthetic construct
SEQUENCE: 290
GVPSRFSGSG SGTDFTLTIN SLEAEDAATY YC                             32

SEQ ID NO: 291            moltype = AA  length = 32
FEATURE                   Location/Qualifiers
REGION                    1..32
                          note = TLA0241-LFR3-4
source                    1..32
                          mol_type = protein
                          organism = synthetic construct
SEQUENCE: 291
GVPDRFSGSG SGTDFTLTIN SLEAEDAATY YC                             32

SEQ ID NO: 292            moltype = AA  length = 32
FEATURE                   Location/Qualifiers
REGION                    1..32
                          note = TLA0241-LFR3-5
source                    1..32
                          mol_type = protein
                          organism = synthetic construct
SEQUENCE: 292
GVPARFSGSG SGTDFTLTIN SLEAEDAATY YC                             32

SEQ ID NO: 293            moltype = AA  length = 32
FEATURE                   Location/Qualifiers
```

```
REGION                 1..32
                       note = TLA0241-LFR3-6
source                 1..32
                       mol_type = protein
                       organism = synthetic construct
SEQUENCE: 293
GVPSRFSGSG SGTSFTLTIN SLEAEDAATY YC                         32

SEQ ID NO: 294         moltype = AA  length = 10
FEATURE                Location/Qualifiers
REGION                 1..10
                       note = TLA0241-LFR4
VARIANT                3
                       note = Xaa = Ala or Gln
VARIANT                6
                       note = Xaa = Lys or Arg
VARIANT                7
                       note = Xaa = Leu or Val
VARIANT                9
                       note = Xaa = Ile or Leu
source                 1..10
                       mol_type = protein
                       organism = synthetic construct
SEQUENCE: 294
FGXGTXXEXK                                                  10

SEQ ID NO: 295         moltype = AA  length = 10
FEATURE                Location/Qualifiers
REGION                 1..10
                       note = TLA0241-LFR4-2
source                 1..10
                       mol_type = protein
                       organism = synthetic construct
SEQUENCE: 295
FGAGTRLELK                                                  10

SEQ ID NO: 296         moltype = AA  length = 10
FEATURE                Location/Qualifiers
REGION                 1..10
                       note = TLA0241-LFR4-3
source                 1..10
                       mol_type = protein
                       organism = synthetic construct
SEQUENCE: 296
FGAGTKLELK                                                  10

SEQ ID NO: 297         moltype = AA  length = 119
FEATURE                Location/Qualifiers
REGION                 1..119
                       note = TLA0241-VH-1
source                 1..119
                       mol_type = protein
                       organism = synthetic construct
SEQUENCE: 297
EFQLQQSGPE LVKPGASVRI SCKASGYTFT DYYLNWVKQS RGESLEWIGD INPNNGRTTY  60
NQKFTGKATW TVDKSSSTVY MELRSLTSDD SAVYYCAREG GYGWYFDVWG TGTTVTVSS   119

SEQ ID NO: 298         moltype = AA  length = 119
FEATURE                Location/Qualifiers
REGION                 1..119
                       note = TLA0241-VH-2
source                 1..119
                       mol_type = protein
                       organism = synthetic construct
SEQUENCE: 298
EVQLVESGGG LVQPGGSLRL SCSASGYTFT DYYLNWVRQA PGKGLEWIGD INPNNGRTTY  60
ADSVKGRFTI SRDNSKNTLY LQMSSLRAED TAVYYCAREG GYGWYFDVWG RGTLVTVSS   119

SEQ ID NO: 299         moltype = AA  length = 119
FEATURE                Location/Qualifiers
REGION                 1..119
                       note = TLA0241-VH-3
source                 1..119
                       mol_type = protein
                       organism = synthetic construct
SEQUENCE: 299
QVQLVESGGG VVQPGRSLRL SCAASGYTFT DYYLNWVRQA PGKGLEWIGD INPNNGRTTY  60
ADSVKGRFTI SRDNSKNTLY LQMNSLRAED TAVYYCAREG GYGWYFDVWG QGTMVTVSS   119
```

```
SEQ ID NO: 300         moltype = AA  length = 119
FEATURE                Location/Qualifiers
REGION                 1..119
                       note = TLA0241-VH-4
source                 1..119
                       mol_type = protein
                       organism = synthetic construct
SEQUENCE: 300
EVQLQQSGPE VKKPGASVRI SCKASGYTFT DYYMHWVRQA PGQGLEWIGD INPNNGRTTY  60
NQKFQGRVTI TRDTSSSTAY MELRSLRSDD TAVYYCAREG GYGWYFDVWG TGTTVTVSS   119

SEQ ID NO: 301         moltype = AA  length = 119
FEATURE                Location/Qualifiers
REGION                 1..119
                       note = TLA0241-VH-5
source                 1..119
                       mol_type = protein
                       organism = synthetic construct
SEQUENCE: 301
EVQLQQSGPE VKKPGASVRI SCKASGYTFT DYYMHWVQQA PGKGLEWIGD INPNNGRTTY  60
NQKFQGRVTI TADKSTSTAY MELRSLRSDD TAVYYCAREG GYGWYFDVWG TGTLVTVSS   119

SEQ ID NO: 302         moltype = AA  length = 119
FEATURE                Location/Qualifiers
REGION                 1..119
                       note = TLA0241-VH-6
source                 1..119
                       mol_type = protein
                       organism = synthetic construct
SEQUENCE: 302
ELQLQQSGPE VKKPGASVRI SCKASGYTFT DYYMHWVQQA PGKGLEWIGD INPNNGRTTY  60
NQKFQGRVTI TADKSTSTAY MELRSLTSDD TAVYYCAREG GYGWYFDVWG TGTTVTVSS   119

SEQ ID NO: 303         moltype = AA  length = 119
FEATURE                Location/Qualifiers
REGION                 1..119
                       note = TLA0241-VH-7
source                 1..119
                       mol_type = protein
                       organism = synthetic construct
SEQUENCE: 303
EVQLLESGGG LVQPGGSLRL SCAASGYTFT DYYLNWVRQA PGKGLEWIGD INPNNGRTTY  60
ADSVKGRFTI SRDNSKNTLY LQMNSLRAED TAVYYCAREG GYGWYFDVWG QGTMVTVSS   119

SEQ ID NO: 304         moltype = AA  length = 119
FEATURE                Location/Qualifiers
REGION                 1..119
                       note = TLA0241-VH-8
source                 1..119
                       mol_type = protein
                       organism = synthetic construct
SEQUENCE: 304
EVQLQQSGPE VKKPGASVRI SCKASGYTFT DYYMHWVRQA PGEGLEWIGD INPNNGRTTY  60
NQKFQGRVTI TADKSTSTAY MELRSLRSDD TAVYYCAREG GYGWYFDVWG TGTTVTVSS   119

SEQ ID NO: 305         moltype = AA  length = 119
FEATURE                Location/Qualifiers
REGION                 1..119
                       note = TLA0241-VH-9
source                 1..119
                       mol_type = protein
                       organism = synthetic construct
SEQUENCE: 305
QVQLVESGGG VVQPGRSLRL SCAASGYTFT DYYLNWVRQA PGKGLEWIGD INPNNGRTTY  60
ADSVKGRFTI SRDNSKNTLY LQMNSLRAED TAVYYCAREG GYGWYFDVWG QGTTVTVSS   119

SEQ ID NO: 306         moltype = AA  length = 119
FEATURE                Location/Qualifiers
REGION                 1..119
                       note = TLA0241-VH-10
source                 1..119
                       mol_type = protein
                       organism = synthetic construct
SEQUENCE: 306
EIQLQQSGAE EKKPGASVRI SCKASGYTFT DYYMHWVQQA PGKGLEWIGD INPNNGRTTY  60
NQKFQGRVTI TADKSTSTAY MELRSLRSDD TAVYYCAREG GYGWYFDVWG TGTTVTVSS   119

SEQ ID NO: 307         moltype = AA  length = 119
FEATURE                Location/Qualifiers
```

```
REGION                  1..119
                        note = TLA0241-VH-11
source                  1..119
                        mol_type = protein
                        organism = synthetic construct
SEQUENCE: 307
ELQLQQSGAE VKKPGASVRI SCKASGYTFT DYYMHWVRQA PGQGLEWIGD INPNNGRTTY  60
NQKFQGRVTI TADKSTSTAY MELRSLRSDD MAVYYCAREG GYGWYFDVWG TGTLVTVSS   119

SEQ ID NO: 308          moltype = AA  length = 108
FEATURE                 Location/Qualifiers
REGION                  1..108
                        note = TLA0241-VL-1
source                  1..108
                        mol_type = protein
                        organism = synthetic construct
SEQUENCE: 308
EIVLTQSPTT MAASPGEKIT ITCSTSSSII SNYSHWYQQK PGFSPKLLIY KTSNLPSGVP  60
ARFSGSGSGT SYSLTIGTME AEDAATYYCQ QGSDMPITFG AGTKLELK              108

SEQ ID NO: 309          moltype = AA  length = 108
FEATURE                 Location/Qualifiers
REGION                  1..108
                        note = TLA0241-VL-2
source                  1..108
                        mol_type = protein
                        organism = synthetic construct
SEQUENCE: 309
DIQMTQSPSS LSASVGDRVT ITCSTSSSII SNYSHWYQQK PGKAPKLLIY KTSNLPSGVP  60
SRFSGSGSGT EFTLTISSLQ PEDFATYYCQ QGSDMPITFG QGTKVEIK              108

SEQ ID NO: 310          moltype = AA  length = 108
FEATURE                 Location/Qualifiers
REGION                  1..108
                        note = TLA0241-VL-3
source                  1..108
                        mol_type = protein
                        organism = synthetic construct
SEQUENCE: 310
EIVLTQSPTT LSLSPGEKVT ITCSASSSII SNYLHWYQQK PGKSPKLLIY KTSNLPSGVP  60
SRFSGSGSGT DFTLTINSLE AEDAATYYCQ QGSDMPITFG AGTRLELK              108

SEQ ID NO: 311          moltype = AA  length = 108
FEATURE                 Location/Qualifiers
REGION                  1..108
                        note = TLA0241-VL-4
source                  1..108
                        mol_type = protein
                        organism = synthetic construct
SEQUENCE: 311
EIVLTQSPPT LSLSPGEKVT ITCSASSSII SNYLHWYQQK PGQSPQLLIY KTSNRPSGVP  60
DRFSGSGSGT DFTLTINSLE AEDAATYYCQ QGSDMPITFG AGTRLELK              108

SEQ ID NO: 312          moltype = AA  length = 108
FEATURE                 Location/Qualifiers
REGION                  1..108
                        note = TLA0241-VL-5
source                  1..108
                        mol_type = protein
                        organism = synthetic construct
SEQUENCE: 312
EIVLTQSPGT LSLSPGEKVT ITCSASSSII SNYLHWYQQK PDQSPKLLIY KTSNLPSGVP  60
SRFSGSGSGT DFTLTINSLE AEDAATYYCQ QGSDMPITFG AGTKLELK              108

SEQ ID NO: 313          moltype = AA  length = 108
FEATURE                 Location/Qualifiers
REGION                  1..108
                        note = TLA0241-VL-6
source                  1..108
                        mol_type = protein
                        organism = synthetic construct
SEQUENCE: 313
AIQLTQSPSS LSASVGDRVT ITCSTSSSII SNYSHWYQQK PGKAPKLLIY KTSNLPSGVP  60
SRFSGSGSGT DFTLTISSLQ PEDFATYYCQ QGSDMPITFG QGTKVEIK              108

SEQ ID NO: 314          moltype = AA  length = 108
FEATURE                 Location/Qualifiers
REGION                  1..108
                        note = TLA0241-VL-7
```

```
source                  1..108
                        mol_type = protein
                        organism = synthetic construct
SEQUENCE: 314
EIVLTQSPAT LSLSPGEKVT ITCSASSSII SNYSAWYQQK PGKSPKLLIY KTSNLPSGVP  60
ARFSGSGSGT DFTLTINSLE AEDAATYYCQ QGSDMPITFG AGTRLELK               108

SEQ ID NO: 315          moltype = AA  length = 108
FEATURE                 Location/Qualifiers
REGION                  1..108
                        note = TLA0241-VL-8
source                  1..108
                        mol_type = protein
                        organism = synthetic construct
SEQUENCE: 315
DIQMTQSPSS VSASVGDRVT ITCSTSSSII SNYSHWYQQK PGKAPKLLIY KTSNLPSGVP  60
SRFSGSGSGT DFTLTISSLQ PEDFATYYCQ QGSDMPITFG QGTKVEIK               108

SEQ ID NO: 316          moltype = AA  length = 108
FEATURE                 Location/Qualifiers
REGION                  1..108
                        note = TLA0241-VL-9
source                  1..108
                        mol_type = protein
                        organism = synthetic construct
SEQUENCE: 316
EIVLTQSPTT LSLSPGEKVT ITCSASSSII SNYLHWYQQK PDQSPKLLIY KTSNLPSGVP  60
SRFSGSGSGT DFTLTINSLE AEDAATYYCQ QGSDMPITFG AGTKLELK               108

SEQ ID NO: 317          moltype = AA  length = 108
FEATURE                 Location/Qualifiers
REGION                  1..108
                        note = TLA0241-VL-10
source                  1..108
                        mol_type = protein
                        organism = synthetic construct
SEQUENCE: 317
EIVLTQSPPT LSLSPGEKVT ITCSASSSII SNYLAWYQQK PGKSPKLLIY KTSNLPSGVP  60
SRFSGSGSGT SFTLTINSLE AEDAATYYCQ QGSDMPITFG AGTKLELK               108

SEQ ID NO: 318          moltype = AA  length = 107
FEATURE                 Location/Qualifiers
REGION                  1..107
                        note = C
source                  1..107
                        mol_type = protein
                        organism = synthetic construct
SEQUENCE: 318
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 319          moltype = AA  length = 103
FEATURE                 Location/Qualifiers
REGION                  1..103
                        note = CH1
source                  1..103
                        mol_type = protein
                        organism = synthetic construct
SEQUENCE: 319
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSC                    103

SEQ ID NO: 320          moltype = AA  length = 227
FEATURE                 Location/Qualifiers
REGION                  1..227
                        note = Fc(L234A, L235A)
source                  1..227
                        mol_type = protein
                        organism = synthetic construct
SEQUENCE: 320
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 321          moltype = AA  length = 227
FEATURE                 Location/Qualifiers
REGION                  1..227
                        note = Fc(L234A, L235A, M252Y, S254T, T256E)
```

```
source                  1..227
                        mol_type = protein
                        organism = synthetic construct
SEQUENCE: 321
DKTHTCPPCP APEAAGGPSV FLFPPKPKDT LYITREPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 322          moltype = AA  length = 124
FEATURE                 Location/Qualifiers
REGION                  1..124
                        note = RVT-3101-VH
source                  1..124
                        mol_type = protein
                        organism = synthetic construct
SEQUENCE: 322
QVQLVQSGAE VKKPGASVKV SCKASGYDFT YYGISWVRQA PGQGLEWMGW ISTYNGNTHY  60
ARMLQGRVTM TTDTSTRTAY MELRSLRSDD TAVYYCAREN YYGSGAYRGG MDVWGQGTTV  120
TVSS                                                              124

SEQ ID NO: 323          moltype = AA  length = 107
FEATURE                 Location/Qualifiers
REGION                  1..107
                        note = RVT-3101-VL
source                  1..107
                        mol_type = protein
                        organism = synthetic construct
SEQUENCE: 323
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPWTFGQ GTKVEIK              107

SEQ ID NO: 324          moltype = AA  length = 116
FEATURE                 Location/Qualifiers
REGION                  1..116
                        note = MK-7240-VH
source                  1..116
                        mol_type = protein
                        organism = synthetic construct
SEQUENCE: 324
QVQLVQSGAE VKKPGASVKV SCKASGFDIQ DTYMHWVKQR PGQGLEWMGR IDPASGHTKY  60
DPKFQVRVTI TRDTSTSTVY LELSSLRSED TAVYYCARSG GLPDVWGQGT TVTVSS     116

SEQ ID NO: 325          moltype = AA  length = 106
FEATURE                 Location/Qualifiers
REGION                  1..106
                        note = MK-7240-VL
source                  1..106
                        mol_type = protein
                        organism = synthetic construct
SEQUENCE: 325
EIVLTQSPGT LSLSPGERAT LSCRASSSVS YMYWYQQKPG QAPRPLIYAT SNLASGIPDR  60
FSGSGSGTDF TLTISRLEPE DFAVYYCQQW EGNPRTFGGG TKLEIK               106

SEQ ID NO: 326          moltype = AA  length = 251
FEATURE                 Location/Qualifiers
REGION                  1..251
                        note = Human TL1A (M1-L251)
source                  1..251
                        mol_type = protein
                        organism = Homo sapiens
SEQUENCE: 326
MAEDLGLSFG ETASVEMLPE HGSCRPKARS SSARWALTCC LVLLPFLAGL TTYLLVSQLR  60
AQGEACVQFQ ALKGQEFAPS HQQVYAPLRA DGDKPRAHLT VVRQTPTQHF KNQFPALHWE  120
HELGLAFTKN RMNYTNKFLL IPESGDYFIY SQVTFRGMTS ECSEIRQAGR PNKPDSITVV  180
ITKVTDSYPE PTQLLMGTKS VCEVGSNWFQ PIYLGAMFSL QEGDKLMVNV SDISLVDYTK  240
EDKTFFGAFL L                                                      251

SEQ ID NO: 327          moltype = AA  length = 180
FEATURE                 Location/Qualifiers
REGION                  1..180
                        note = Human sTL1A (L72-L251)
source                  1..180
                        mol_type = protein
                        organism = Homo sapiens
SEQUENCE: 327
LKGQEFAPSH QQVYAPLRAD GDKPRAHLTV VRQTPTQHFK NQFPALHWEH ELGLAFTKNR  60
MNYTNKFLLI PESGDYFIYS QVTFRGMTSE CSEIRQAGRP NKPDSITVVI TKVTDSYPEP  120
TQLLMGTKSV CEVGSNWFQP IYLGAMFSLQ EGDKLMVNVS DISLVDYTKE DKTFFGAFLL  180
```

```
SEQ ID NO: 328         moltype = AA  length = 180
FEATURE                Location/Qualifiers
REGION                 1..180
                       note = sTL1A (L72-L251)
source                 1..180
                       mol_type = protein
                       organism = synthetic construct
SEQUENCE: 328
LKGQEFAPSH QQVYAPLRAD GDKPRAHLTV VRQTPTQHLK NQFPALHWEH ELGLAFTKNR  60
MNYTNKFLLI PESGDYFVYS QVTFRGMTSE CSEIRQAGRP NKPDSITVVI TKVTDSYPEP  120
TQLLMGTKSV CEVGSNWFQP IYLGAMFSLQ EGDKLMVNVS DISLVDYTKE DKTFFGAFLL  180

SEQ ID NO: 329         moltype = AA  length = 192
FEATURE                Location/Qualifiers
REGION                 1..192
                       note = Mouse sTL1A (A61-L252)
source                 1..192
                       mol_type = protein
                       organism = Mus musculus
SEQUENCE: 329
AGQLRVPGKD CMLRAITEER SEPSPQQVYS PPRGKPRAHL TIKKQTPAPH LKNQLSALHW  60
EHDLGMAFTK NGMKYINKSL VIPESGDYFI YSQITFRGTT SVCGDISRGR RPNKPDSITV  120
VITKVADSYP EPARLLTGSK SVCEISNNWF QSLYLGAMFS LEEGDRLMVN VSDISLVDYT  180
KEDKTFFGAF LL                                                     192

SEQ ID NO: 330         moltype = AA  length = 192
FEATURE                Location/Qualifiers
REGION                 1..192
                       note = Rat sTL1A (T61-I252)
source                 1..192
                       mol_type = protein
                       organism = Rattus norvegicus
SEQUENCE: 330
TGQLRIPGKD CMFPTVTEER SAPSAQPVYT PSRDKPKAHL TIMRQTPVPH LKNELAALHW  60
ENNLGMAFTK NRMNYTNKFL VIPESGDYFI YSQITFRGTT SECGDISRVR RPKKPDSITV  120
VITKVADSYP EPAHLLTGTK SVCEISSNWF QPIYLGAMFS LEEGDRLMVN VSDISLVDYT  180
KEDKTFFGAF LI                                                     192

SEQ ID NO: 331         moltype = AA  length = 175
FEATURE                Location/Qualifiers
REGION                 1..175
                       note = Human DR3-ECD (Q25-Q199)
source                 1..175
                       mol_type = protein
                       organism = Homo sapiens
SEQUENCE: 331
QGGTRSPRCD CAGDFHKKIG LFCCRGCPAG HYLKAPCTEP CGNSTCLVCP QDTFLAWENH  60
HNSECARCQA CDEQASQVAL ENCSAVADTR CGCKPGWFVE CQVSQCVSSS PFYCQPCLDC  120
GALHRHTRLL CSRRDTDCGT CLPGFYEHGD GCVSCPTSTL GSCPERCAAV CGWRQ       175

SEQ ID NO: 332         moltype = AA  length = 119
FEATURE                Location/Qualifiers
source                 1..119
                       mol_type = protein
                       organism = synthetic construct
SEQUENCE: 332
EVQLVESGGG LVKPGGSLRL SCAASGFTFS NYWMNWVRQA PGKGLEWVGQ IRLKSDNYAT  60
HYAESVKGRF TISRDDSKNT LYLQMNSLKT EDTAVYYCTT LLLRYRDYWG QGTLVTVSS   119

SEQ ID NO: 333         moltype = AA  length = 119
FEATURE                Location/Qualifiers
source                 1..119
                       mol_type = protein
                       organism = synthetic construct
SEQUENCE: 333
EVQLVESGGG LVKPGGSLRL SCAASGFTFS NYWMNWVRQA PGKGLEWVGQ IRLKSDNYAT  60
HYAESVKGRF TISRDDSKNT LYLQMNSLKT EDTAVYYCTP LLLRYRDYWG QGTLVTVSS   119

SEQ ID NO: 334         moltype = AA  length = 119
FEATURE                Location/Qualifiers
source                 1..119
                       mol_type = protein
                       organism = synthetic construct
SEQUENCE: 334
EVQLVESGGG LVKPGGSLRL SCAASGFTFS NYWMNWVRQA PGKGLEWVAQ IRLKSDNYAT  60
HYAESVKGRF TISRDDSKNT LYLQMNSLKT EDTAVYYCTP LLLRYRDYWG QGTLVTVSS   119

SEQ ID NO: 335         moltype = AA  length = 106
```

```
FEATURE                Location/Qualifiers
source                 1..106
                       mol_type = protein
                       organism = synthetic construct
SEQUENCE: 335
EIVLTQSPAT LSLSPGERAT LSCSASSSVS YMHWYQQKPG QSPRLWIYDT SNLASGIPAR  60
FSGSGSGTDY TLTISSLEPE DFAVYYCFQE NAHPFTFGGG TKVEIK                 106

SEQ ID NO: 336         moltype = AA  length = 106
FEATURE                Location/Qualifiers
source                 1..106
                       mol_type = protein
                       organism = synthetic construct
SEQUENCE: 336
EIVLTQSPAT LSLSPGERAT LSCSASSSVS YMHWYQQKPG QSPRLWIYDT SNLASGVPAR  60
FSGSGSGTDY TLTISSLEPE DFAVYYCFQE NAHPFTFGGG TKVEIK                 106

SEQ ID NO: 337         moltype = AA  length = 106
FEATURE                Location/Qualifiers
source                 1..106
                       mol_type = protein
                       organism = synthetic construct
SEQUENCE: 337
DIQMTQSPSS LSASVGDRVT ITCSASSSVS YMHWYQQKPG KAPKLWIYDT SNLASGVPSR  60
FSGSGSGTDY TLTISSLQPE DFATYYCFQE NAHPFTFGQG TKLEIK                 106

SEQ ID NO: 338         moltype = AA  length = 106
FEATURE                Location/Qualifiers
source                 1..106
                       mol_type = protein
                       organism = synthetic construct
SEQUENCE: 338
DIQLTQSPSS LSASVGDRVT ITCSASSSVS YMHWYQQKPG KAPKLWIYDT SNLASGVPSR  60
FSGSGSGTDY TLTISSLQPE DFATYYCFQE NAHPFTFGQG TKLEIK                 106

SEQ ID NO: 339         moltype = AA  length = 446
FEATURE                Location/Qualifiers
source                 1..446
                       mol_type = protein
                       organism = synthetic construct
SEQUENCE: 339
EIQLVESGGG LIQPGGSLRI SCAVSGFSLS SYGVDWVRQA PGKGLEWLGV IWGFGGTNYN  60
SALKSRLTIS KDNSKNTVYL QMNSLRAEDT AVYYCASGNF DAMDYWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL YITREPEVTC VVVDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 340         moltype = AA  length = 214
FEATURE                Location/Qualifiers
source                 1..214
                       mol_type = protein
                       organism = synthetic construct
SEQUENCE: 340
DIQMTQSPSS LSASVGDRVT ITCRASQDIS NYLNWYQQKP GKAVKLLIYY TSRLHSGVPS  60
RFSGSGSGTD YTLTISSLQP EDFATYFCQQ GNTLPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 341         moltype = AA  length = 227
FEATURE                Location/Qualifiers
source                 1..227
                       mol_type = protein
                       organism = synthetic construct
SEQUENCE: 341
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 342         moltype = AA  length = 119
FEATURE                Location/Qualifiers
REGION                 1..119
                       note = mice-1
source                 1..119
                       mol_type = protein
                       organism = synthetic construct
```

```
SEQUENCE: 342
QIQLVQSGPE LKKPGETVKI SCKASGYTFT TYGMNWVKQS PGKGLKWMGW INTYSGVPTY  60
ADDFKGRFAF SLETSVNTAY LQINSLKTDD TATYFCAKDA YDNYAMDYWG QGTSVTVSS   119

SEQ ID NO: 343          moltype = AA  length = 116
FEATURE                 Location/Qualifiers
REGION                  1..116
                        note = mice-2
source                  1..116
                        mol_type = protein
                        organism = synthetic construct
SEQUENCE: 343
QIQLKESGPG LVAPSQSLSI TCTVSGFSLS SYGVDWVRQS PGKGLEWLGV IWGFGGTNYN  60
SALKSRLSIS KDNSKSQVFL KMNSLQSDDS AIYYCASGNF DAMDYWGQGT SVTVSS      116

SEQ ID NO: 344          moltype = AA  length = 117
FEATURE                 Location/Qualifiers
REGION                  1..117
                        note = mice-3
source                  1..117
                        mol_type = protein
                        organism = synthetic construct
SEQUENCE: 344
DVQLQESGPG LVKPSQSLSL TCSVTDYSIT SGYYWNWIRQ FPGNKLEWMG YIHFDGSNDY  60
NPSLKNRISI TRDTSRNQFF LKLNSVTSED TATYYCAREG TSYFDYWGQG TTLTVSS     117

SEQ ID NO: 345          moltype = AA  length = 115
FEATURE                 Location/Qualifiers
REGION                  1..115
                        note = mice-4
source                  1..115
                        mol_type = protein
                        organism = synthetic construct
SEQUENCE: 345
QIQLVQSGPE LKKPGETVKI SCKASGYTFT TYGMSWVKQA PGKYLKWMGW IDTYSGVPTY  60
ADDFKGRFAF SLETSANTAY LQINNLKNED TATYFCANSF QFAYWGQGTL VTVSA       115

SEQ ID NO: 346          moltype = AA  length = 117
FEATURE                 Location/Qualifiers
REGION                  1..117
                        note = mice-5
source                  1..117
                        mol_type = protein
                        organism = synthetic construct
SEQUENCE: 346
DVQLQESGPG LVKPSQSLSL TCSVTGYSIT SGYYWNWIRQ FPGNKLEWMG CISYDGSNYY  60
NPSLKNRISF TRDTSKNQFF LKLNSVTTDD TATYYCVREG TSYVDYWGQG TTLTVSS     117

SEQ ID NO: 347          moltype = AA  length = 117
FEATURE                 Location/Qualifiers
REGION                  1..117
                        note = mice-6
source                  1..117
                        mol_type = protein
                        organism = synthetic construct
SEQUENCE: 347
DVQLQESGPG LVKPSQSLSL TCSVTDYSIT SGYYWNWIRQ FPGNKLEWMG YIHYDGSNDY  60
NPSLKNRISI TRDTSRNQFF LKLNSVTSED TATYYCAREG TSYFDYWGQG TTLTVSS     117

SEQ ID NO: 348          moltype = AA  length = 128
FEATURE                 Location/Qualifiers
REGION                  1..128
                        note = mice-7
source                  1..128
                        mol_type = protein
                        organism = synthetic construct
SEQUENCE: 348
QVQLQQSGPE LVRPGASVKI SCKAPGYTFT SHWMQWVRQR PGQGLEWIGE IFPGSGTTYY  60
NEKFQGKATL TVDTSSSTAY MQLSSLTSED SSVHFCARGE GIYYPARSYG PLGYFDVWGT  120
GTTVTVSS                                                          128

SEQ ID NO: 349          moltype = AA  length = 119
FEATURE                 Location/Qualifiers
REGION                  1..119
                        note = mice-8
source                  1..119
                        mol_type = protein
                        organism = synthetic construct
SEQUENCE: 349
```

```
QVQLQQPGAE LVMPGASVKL SCKASGYTFT NYWMNWVKQR PRQGLEWIGE TDPSNTYINY  60
NQKFKGKATL TVDKSSNTAY MQLNSLTSED SAVYYCARGG LPYYGMDYWG QGTSVTVSS   119

SEQ ID NO: 350          moltype = AA  length = 115
FEATURE                 Location/Qualifiers
REGION                  1..115
                        note = mice-9
source                  1..115
                        mol_type = protein
                        organism = synthetic construct
SEQUENCE: 350
QIQLVQSGPE LKKPGETVKI SCKASGSAFT TYGMSWVKQA PGEGLKWMGY IITYSGVPTY  60
ADDFKGRFAF SLETSASTAY LQINNLKNED TATYFCTNFY YFDYWGQGTT LTVSS       115

SEQ ID NO: 351          moltype = AA  length = 121
FEATURE                 Location/Qualifiers
REGION                  1..121
                        note = mice-10
source                  1..121
                        mol_type = protein
                        organism = synthetic construct
SEQUENCE: 351
QIQLVQSGPE LKKPGETVKI SCKASGYTFT TFGMNWVKQA PGKDLKWMGW INTNSGVPTY  60
ADDFRGRFAF SMETSATTAY LQINNLKNED TATYFCARGN WEGPGIWFAY WGQGTLVTVS  120
A                                                                 121

SEQ ID NO: 352          moltype = AA  length = 115
FEATURE                 Location/Qualifiers
REGION                  1..115
                        note = mice-11
source                  1..115
                        mol_type = protein
                        organism = synthetic construct
SEQUENCE: 352
QVQLQQPGTE LVKPGASVKL SCKASGYTFT SYWMHWVKQR PGQGLEWIGN IDPNNDVINY  60
NDKFKSKATL TVDKSSSTAY MQLSSLTSED SGVYYCARGI YAGYWGQGTL VTVSA       115

SEQ ID NO: 353          moltype = AA  length = 121
FEATURE                 Location/Qualifiers
REGION                  1..121
                        note = mice-12
source                  1..121
                        mol_type = protein
                        organism = synthetic construct
SEQUENCE: 353
EVQLQQSGAE LMKPGASVKL SCKATGYTFT GYWLEWVKQR PGHGLEWIGE TLPGSGYNKY  60
NEKFKGKATF TADTSSNTAH MQLSSLTTED SAIYYCARRG SNYPYWYFDV WGTGTTVTVS  120
S                                                                 121

SEQ ID NO: 354          moltype = AA  length = 117
FEATURE                 Location/Qualifiers
REGION                  1..117
                        note = mice-13
source                  1..117
                        mol_type = protein
                        organism = synthetic construct
SEQUENCE: 354
QVQLKESGPG LVQPSQSLSI TCTVSGFSLT SYGVHWVRQS PGKGLEWLGV IWSGGSTDYN  60
AAFISRLSIS KDNSKSQVFF KMNSLQADDT AIYYCARNDY DYAMDYWGQG TSVTVSS     117

SEQ ID NO: 355          moltype = AA  length = 116
FEATURE                 Location/Qualifiers
REGION                  1..116
                        note = mice-14
source                  1..116
                        mol_type = protein
                        organism = synthetic construct
SEQUENCE: 355
QVQLQQSGPE LVKPGASVKL SCKASGYTFT SIDINWVKQR PGQGLEWIGW IYPRDGRTDY  60
NEKFKGKATL TVDTSSSTAY MELHSLTSED SAVYFCARYT SSLDYWGQGT TLTVSS      116

SEQ ID NO: 356          moltype = AA  length = 119
FEATURE                 Location/Qualifiers
REGION                  1..119
                        note = mice-15
source                  1..119
                        mol_type = protein
                        organism = synthetic construct
SEQUENCE: 356
```

```
EVKLEESGGG LVQPGGSMKL SCVASGFTFS NYWMNWVRQS PEKGLEWVAQ IRLKSDNYAT  60
HYAESVKGRF TISRDDSKSN VYLQMNNLRA EDTGIYYCTP LLLRSIDYWG QGTTLTVSS   119

SEQ ID NO: 357         moltype = AA  length = 116
FEATURE                Location/Qualifiers
REGION                 1..116
                       note = mice-16
source                 1..116
                       mol_type = protein
                       organism = synthetic construct
SEQUENCE: 357
EVQLQQSGPE LVKPGASVKL SCKASGYTFT SIDINWVKQR PGQGLEWIGW IYPRDGRTDY  60
NEKFKGKATL TVDTSSSTAY MELHSLTSED SAVYFCARYG SSLDYWGQGT TLTVSS      116

SEQ ID NO: 358         moltype = AA  length = 116
FEATURE                Location/Qualifiers
REGION                 1..116
                       note = mice-17
source                 1..116
                       mol_type = protein
                       organism = synthetic construct
SEQUENCE: 358
QVQLQQSGPE LVKPGASVKL SCKASGYTFT NQDMNWVKQR PGQGLEWIGW IFPRDGRTHH  60
NENFKGKATL TVDTSSSTAY MELHSLTAED SAVYFCAIYG FAMDQWGQGT SVTVSS      116

SEQ ID NO: 359         moltype = AA  length = 116
FEATURE                Location/Qualifiers
REGION                 1..116
                       note = mice-18
source                 1..116
                       mol_type = protein
                       organism = synthetic construct
SEQUENCE: 359
QVQLQQPGPE LVKPGASVKL SCKASGYTFT NQDINWVKQR PGQGLEWIGW IFPRDGRTHY  60
NENFKGKATL TVDTSSSTAY MELHSLTAED SAVYFCAIYG IALDHWGQGT SVTVSS      116

SEQ ID NO: 360         moltype = AA  length = 116
FEATURE                Location/Qualifiers
REGION                 1..116
                       note = mice-19
source                 1..116
                       mol_type = protein
                       organism = synthetic construct
SEQUENCE: 360
QVQLQQPGPE LVKPGASVKL SCKASGYTFT NQDINWVKQR PGQGLEWIGW IFPRDGRTHY  60
NENFKGKATL TVDTSSSTAY MELHSLTAED SAVYFCAIYG AAMDHWGQGT SVTVSS      116

SEQ ID NO: 361         moltype = AA  length = 119
FEATURE                Location/Qualifiers
REGION                 1..119
                       note = mice-20
source                 1..119
                       mol_type = protein
                       organism = synthetic construct
SEQUENCE: 361
EVKLEESGGG LVQPGGSMKL SCVASGFTFS NYWMNWVRQS PEKGLEWVAQ IRLKSDNYAT  60
HYAESVKGRF TISRDDSKSS VYLQMNNLRA EDTGIYYCTP LLLRYFDVWG TGTTVTVSS   119

SEQ ID NO: 362         moltype = AA  length = 114
FEATURE                Location/Qualifiers
REGION                 1..114
                       note = mice-21
source                 1..114
                       mol_type = protein
                       organism = synthetic construct
SEQUENCE: 362
EVQLQQSVAE LVRPGASVKL SCTASGFNIE DTYIHWVKQR PEQGLEWIGR IDPAHDKTKY  60
APKFQGKATI TADTSSNTAY LQLSSLTSED TAIYYCASTG PDWWGQGTTL TVSS        114

SEQ ID NO: 363         moltype = AA  length = 122
FEATURE                Location/Qualifiers
REGION                 1..122
                       note = mice-22
source                 1..122
                       mol_type = protein
                       organism = synthetic construct
SEQUENCE: 363
QVQLQQSGAE LVRPGTSVKM SCKASGYTFT NYWIGWTKQR PGHGLEWIGD IYPGGGYINY  60
NEKFKGKATL TADKSSSTAY MQFSSLTSED SAIYYCAREG GYGSGQAWFP YWGQGTLVTV  120
```

```
SA                                                                122

SEQ ID NO: 364         moltype = AA  length = 118
FEATURE                Location/Qualifiers
REGION                 1..118
                       note = mice-23
source                 1..118
                       mol_type = protein
                       organism = synthetic construct
SEQUENCE: 364
QVQLQQPGTE LVRPGTSVKL SCKASGYTFT SYWMHWVKQR PGQGLEWIGV IEPSDSYTDY  60
NQKFKGKATL TVDTSSSTAY MQLSSLTSED SAVYYCARGD YDEVFAYWGQ GTLVTVSA    118

SEQ ID NO: 365         moltype = AA  length = 118
FEATURE                Location/Qualifiers
REGION                 1..118
                       note = mice-24
source                 1..118
                       mol_type = protein
                       organism = synthetic construct
SEQUENCE: 365
QVQLQQPGAE LVRPGTSVKL SCKASGYTFT SYWMHWVKQR PGQGLEWIGV IEPSDSYTDY  60
DQKFKGKATL TVDTSSNTAY MQLSSLTSED SAVYYCSRGD YDEVFAYWGQ GTLVTVST    118

SEQ ID NO: 366         moltype = AA  length = 119
FEATURE                Location/Qualifiers
REGION                 1..119
                       note = mice-25
source                 1..119
                       mol_type = protein
                       organism = synthetic construct
SEQUENCE: 366
QVQLQQSGAD LVRPGASVTL SCKASGYTFS DSEIHWVRQT PVHGLEWIGA IDPETGDIAY  60
NQMFKDKATL TADKSSSTAY VELRSLTSED SAVYYCTRYG GNSWHFDVWG TGTTVTVSS   119

SEQ ID NO: 367         moltype = AA  length = 119
FEATURE                Location/Qualifiers
REGION                 1..119
                       note = mice-26
source                 1..119
                       mol_type = protein
                       organism = synthetic construct
SEQUENCE: 367
EFQLQQSGPE LLKPGASVKI SCKASGYSFT DYNINWVKQR NGKSLEWIGM INPKYGITDY  60
NQKFKGKATL TVDQFSSTAY MQVNSLTSDD SAVYYCAREE LGHWCFDVWG TGTTVTVSS   119

SEQ ID NO: 368         moltype = AA  length = 118
FEATURE                Location/Qualifiers
REGION                 1..118
                       note = mice-27
source                 1..118
                       mol_type = protein
                       organism = synthetic construct
SEQUENCE: 368
QVQLQQSGAE LVRPGTSVKV SCKASGYAFT NYLIEWVNQR PGQGLEWIGV INPGSGGTKY  60
NEKFKGKATL TADKSSSTAY MQLSSLTSED SAVYFCAREG SAGPFDYWGQ GTTLTVSS    118

SEQ ID NO: 369         moltype = AA  length = 119
FEATURE                Location/Qualifiers
REGION                 1..119
                       note = mice-28
source                 1..119
                       mol_type = protein
                       organism = synthetic construct
SEQUENCE: 369
EFQLQQSGPE LVKPGASVKI SCKASGYSFT DYNINWVKQR NGKSLEWIGM INPKYGITDY  60
NQKFKGKATL TVDQFSSTAY MQVNSLTSDD SAVYYCAREE LGHWCFDVWG TGTTVTVSS   119

SEQ ID NO: 370         moltype = AA  length = 115
FEATURE                Location/Qualifiers
REGION                 1..115
                       note = mice-29
source                 1..115
                       mol_type = protein
                       organism = synthetic construct
SEQUENCE: 370
EVQLQQSGPV LVKPGASVKM SCEASGYTLT DYYMNWVKQS HGKSLEWIGI INPYNGASNF  60
NQRFRGKASL TFGKSSNTAY MELNSLTSED SAVYYCASDW DVGYWGQGTA LTVSS       115
```

```
SEQ ID NO: 371         moltype = AA  length = 119
FEATURE                Location/Qualifiers
REGION                 1..119
                       note = mice-30
source                 1..119
                       mol_type = protein
                       organism = synthetic construct
SEQUENCE: 371
EVQLVESGGD LVKPGGSLKL SCAASGFTFS RYGMSWVRQT PDKRLEWVAT ISSGGSDTYY  60
PDSVKGRFTI SRDNAKNTLY LQMSSLKSED TAMYYCARHG YDYGHFDYWG QGTTLTVSS   119

SEQ ID NO: 372         moltype = AA  length = 119
FEATURE                Location/Qualifiers
REGION                 1..119
                       note = mice-31
source                 1..119
                       mol_type = protein
                       organism = synthetic construct
SEQUENCE: 372
EFQLQQSGPE LVKPGASVKI SCKASGYSFT DYNINWVKQS NGKSLEWIGV INPNYGITDY  60
NQKFKGKATL TVDQSSSTAY MQLNSLTSED SAVYYCAREE LGHWCFDVWG TGTTVTVSS   119

SEQ ID NO: 373         moltype = AA  length = 114
FEATURE                Location/Qualifiers
REGION                 1..114
                       note = mice-32
source                 1..114
                       mol_type = protein
                       organism = synthetic construct
SEQUENCE: 373
QVTLKESGPG ILQPSQTLNL TCSFSGFSLS TFGMGVGWIR QPSGEGLEWL AHIWWDDHEY  60
YNPALKSRLT ISKDTSKNQV FLKIANVDTA DTATYYCNRG FVYWGQGTLV TVSA        114

SEQ ID NO: 374         moltype = AA  length = 116
FEATURE                Location/Qualifiers
REGION                 1..116
                       note = mice-33
source                 1..116
                       mol_type = protein
                       organism = synthetic construct
SEQUENCE: 374
QVQLQQSGPE LVKPGTSVKL SCKASGYTFT SYDINWMKQR PGQGLEWIGW IFPRDGITKY  60
NEKFKDKATL TVDTSSSAAY MELHSLTSED SAVYFCARYG PAMDYWGQGT SVTVSS      116

SEQ ID NO: 375         moltype = AA  length = 116
FEATURE                Location/Qualifiers
REGION                 1..116
                       note = mice-34
source                 1..116
                       mol_type = protein
                       organism = synthetic construct
SEQUENCE: 375
QIQLVQSGPE LVKPGASVKV SCKASGYTFT RQDINWVKQR PGQGLEWIGW IYPRDGRTEY  60
NEKFKGKVTL TVDTSSSTAY MELHSLTSED SAVYFCATYG SSLDNWGQGT TLTVSS      116

SEQ ID NO: 376         moltype = AA  length = 116
FEATURE                Location/Qualifiers
REGION                 1..116
                       note = mice-35
source                 1..116
                       mol_type = protein
                       organism = synthetic construct
SEQUENCE: 376
EVQLQQSGPE LVKPGASVKV SCKASGYTFT RQDINWVKQR PGQGLEWIGW IYPRDGSTKY  60
NEKFKGKVTL TVDTSSSTAY MELHSLTSED SAVYFCATYG SSLDNWGQGT TLTVSS      116

SEQ ID NO: 377         moltype = AA  length = 116
FEATURE                Location/Qualifiers
REGION                 1..116
                       note = mice-36
source                 1..116
                       mol_type = protein
                       organism = synthetic construct
SEQUENCE: 377
EVQLQQSGPE LVKPGASVKL SCKASGYTFT NQDINWVKQR PGQGLEWIGW IFPRDGRTHY  60
NENFKGKATL TVDTSSSTAY MELHSLTAED SAVYFCAIYG IAMDHWGQGT SVTVSS      116

SEQ ID NO: 378         moltype = AA  length = 116
FEATURE                Location/Qualifiers
```

```
REGION                  1..116
                        note = mice-37
source                  1..116
                        mol_type = protein
                        organism = synthetic construct
SEQUENCE: 378
QIQLVQSGPE LVKPGASVKL SCKASGYTFT NYDINWVKQR PGQGLEWIGW IYPRDGSTYY  60
NEKFKGKATL TVDTSSTTAY MEFHSLTSED SAVYFCARYA YALNSWGQGT SVTVSS      116

SEQ ID NO: 379          moltype = AA  length = 116
FEATURE                 Location/Qualifiers
REGION                  1..116
                        note = mice-38
source                  1..116
                        mol_type = protein
                        organism = synthetic construct
SEQUENCE: 379
QVQLKQSGPE LVRPGASVKL SCKASGYSFT SGDINWVKQR PGQGLEWIAW IYPRDGSTEY  60
NEKFKGKATL TVDTSSSTAY MELHSLTSED SAVYFCARYD CAFVYWGQGT LVTVSA      116

SEQ ID NO: 380          moltype = AA  length = 116
FEATURE                 Location/Qualifiers
REGION                  1..116
                        note = mice-39
source                  1..116
                        mol_type = protein
                        organism = synthetic construct
SEQUENCE: 380
QVQLQQSGPE LVKPGASVKL SCKASGYTFT NQDINWVKQR PGQGLEWIGW IFPRDGRTHY  60
NENFKGKATL TVDTSSSTAF MELHSLTAED SAVYFCAIYG IALDHWGQGT SVTVSS      116

SEQ ID NO: 381          moltype = AA  length = 116
FEATURE                 Location/Qualifiers
REGION                  1..116
                        note = mice-40
source                  1..116
                        mol_type = protein
                        organism = synthetic construct
SEQUENCE: 381
QVQLQQSGPE LVKPGASVKL SCKASGYTFT DYDVNWVKQR PGQGLEWIGW NYPRDGRTNY  60
NEKFKGKATL TVDISSSTAY MELHSLTSED SAVYFCARYG SALNVWGTGT SVTVSS      116

SEQ ID NO: 382          moltype = AA  length = 116
FEATURE                 Location/Qualifiers
REGION                  1..116
                        note = mice-41
source                  1..116
                        mol_type = protein
                        organism = synthetic construct
SEQUENCE: 382
QIQLVQSGPE LVKPGASVKL SCKASGYTFT KYDINWVKQR PGQGLEWIGW IYPRDGSTKY  60
NEKFKGKATL TVDTSSNTAY MELHSLTSED SAVYFCARYS AAMDYWGQGT SVTVSS      116

SEQ ID NO: 383          moltype = AA  length = 116
FEATURE                 Location/Qualifiers
REGION                  1..116
                        note = mice-42
source                  1..116
                        mol_type = protein
                        organism = synthetic construct
SEQUENCE: 383
QVQLQQPGAE LGKPGASVKL SCKASGYTFT NYDINWVKQR PGQGLEWIGW NYPRDGRTKY  60
NEKFKGKATL TVDTSSSTAY MELHSLTSED SAVYFCARYG YAMDYWGQGT SVTVSS      116

SEQ ID NO: 384          moltype = AA  length = 116
FEATURE                 Location/Qualifiers
REGION                  1..116
                        note = mice-43
source                  1..116
                        mol_type = protein
                        organism = synthetic construct
SEQUENCE: 384
QVQLQQPGAE LGKPGASVKL SCKASGYTFT NYDINWMKLR PGQGLEWIGW NYPRDGRTKY  60
NEKFKGKATF TVDTSSSTAY MELHSLTSED SAVYFCARYG YAMDYWGQGT SVTVSS      116

SEQ ID NO: 385          moltype = AA  length = 116
FEATURE                 Location/Qualifiers
REGION                  1..116
                        note = mice-44
```

```
source                 1..116
                       mol_type = protein
                       organism = synthetic construct
SEQUENCE: 385
QIQLVQSGPE LVKPGASVKL SCRASGYTFT SYDINWVKQR PGQGLEWIGW IFPRDGRTEY  60
NAKFKGKATL TVDTSSNTAY MELHSLTSDD SAVYFCARYG STLDVLGAGT TVTVSS      116

SEQ ID NO: 386         moltype = AA  length = 116
FEATURE                Location/Qualifiers
REGION                 1..116
                       note = mice-45
source                 1..116
                       mol_type = protein
                       organism = synthetic construct
SEQUENCE: 386
EVQLQQSGPE LVKPGASVKL SCKASGYTFT NQDINWVKQR PGQGLEWIGW IFPRDGRTHY  60
NENFKDKATL TVDTSSSTAY MEVHSLTAED SAVYFCAIYG IALDHWGQGT SVTVSS      116

SEQ ID NO: 387         moltype = AA  length = 116
FEATURE                Location/Qualifiers
REGION                 1..116
                       note = mice-46
source                 1..116
                       mol_type = protein
                       organism = synthetic construct
SEQUENCE: 387
QIQLVQSGPE LVKPGASVKL SCKASGYTFT RQDINWVKQR PGQGLEWIGW IYPRDGSTKY  60
NEKFKGKVTL TVDTSSSTAY MELHSLTSED SAVYFCATYG SSLDNWGQGT TLTVSS      116

SEQ ID NO: 388         moltype = AA  length = 120
FEATURE                Location/Qualifiers
REGION                 1..120
                       note = mice-47
source                 1..120
                       mol_type = protein
                       organism = synthetic construct
SEQUENCE: 388
QVQLQQSGPE LVKPGASVKI PCKTSGYTFT DYNINWVKRS HGKSLEWIGD INPDSGGTSY  60
NQRFKDKATL TVDKSSSTAY MELRSLTSGD TAVYYCARWG YYGGRGFDYW GQGTTLTVSS  120

SEQ ID NO: 389         moltype = AA  length = 116
FEATURE                Location/Qualifiers
REGION                 1..116
                       note = mice-48
source                 1..116
                       mol_type = protein
                       organism = synthetic construct
SEQUENCE: 389
QVQLQQSGAE LGKPGASVKL SCKASGYTFT NYDINWMKQR PGQGLEWIGW NYPRDGRTKY  60
NEKFKGKATL TVDTSSSTAY MELHSLTSED SAVYFCARYG YAMDYWGQGT SVTVSS      116

SEQ ID NO: 390         moltype = AA  length = 116
FEATURE                Location/Qualifiers
REGION                 1..116
                       note = mice-49
source                 1..116
                       mol_type = protein
                       organism = synthetic construct
SEQUENCE: 390
EVQLQQSGPD LVKPGASVKL SCKASGYTFA SYDINWVKQR PGQGLEWIGW IYPRDGRTDY  60
NEKFKGKATL TVDTSSSTAY MELHSLTSED SAVYFCARYG YALGYWGQGT SVTVSS      116

SEQ ID NO: 391         moltype = AA  length = 116
FEATURE                Location/Qualifiers
REGION                 1..116
                       note = mice-50
source                 1..116
                       mol_type = protein
                       organism = synthetic construct
SEQUENCE: 391
QVQLQQSGPE LAKPGASVKL SCKASGYTFT SRDINWVKQR PGQGLEWIGW IYPRDGRTNY  60
NEKFKDKATL TVDTSSSTAY MDLHSLTSED SAVYFCATYG SSLDHWGQGT TLTVSS      116

SEQ ID NO: 392         moltype = AA  length = 116
FEATURE                Location/Qualifiers
REGION                 1..116
                       note = mice-51
source                 1..116
                       mol_type = protein
```

```
                        organism = synthetic construct
SEQUENCE: 392
EVQLQQSGPE LVKPGASVKL SCKASGYTFT NQDINWVKQR PGQGLEWIGW IFPRDGRTHY  60
NENFKGKATL TVDTSSSTAY MELHSLTAED SAVYFCAIYG AAMDHWGQGT SVTVSS      116

SEQ ID NO: 393          moltype = AA  length = 116
FEATURE                 Location/Qualifiers
REGION                  1..116
                        note = mice-52
source                  1..116
                        mol_type = protein
                        organism = synthetic construct
SEQUENCE: 393
QVQLQQSGPE LVKPGTSVKL SCKASGYTFT DQDINWVKQR PGQGLEWIGW IFPRDGRTHY  60
NEKFKGKATL TVDTSSSTAY MELHSLTSED SAVYFCSIYG SAMDLWGQGT SVTVSS      116

SEQ ID NO: 394          moltype = AA  length = 116
FEATURE                 Location/Qualifiers
REGION                  1..116
                        note = mice-53
source                  1..116
                        mol_type = protein
                        organism = synthetic construct
SEQUENCE: 394
QVQLQQSGPE LVKPGASVKL SCKASGYTFT NQDINWVKQR PGQGLEWIGW IFPRDGRTHN  60
NENFKGKATL TVDTSSSTAY MELHSLTAED SAVYFCAIYG FAMDHWGQGT SVTVSS      116

SEQ ID NO: 395          moltype = AA  length = 116
FEATURE                 Location/Qualifiers
REGION                  1..116
                        note = mice-54
source                  1..116
                        mol_type = protein
                        organism = synthetic construct
SEQUENCE: 395
EVQLQQSGPE LVKPGASVKL SCKASGYTST SYDINWVKQR PGQGLEWIGW IYPRDGRTNY  60
NEKFKGKATL TVDTSSSTAF MELHSLTSED SAVYFCARYS AAMDYWGQGT SVTVSS      116

SEQ ID NO: 396          moltype = AA  length = 120
FEATURE                 Location/Qualifiers
REGION                  1..120
                        note = mice-55
source                  1..120
                        mol_type = protein
                        organism = synthetic construct
SEQUENCE: 396
QVQLQQPGSE LVRPGASVKI PCKTSGYSFT DFNINWVRQS HGKSLEWIGD INPDSGGTIY  60
NQKFKGKATL TVDKSSSTAY MELRSLTSED TAVYYCARWG YYGGEGFDYW GQGTTLTVSS  120

SEQ ID NO: 397          moltype = AA  length = 116
FEATURE                 Location/Qualifiers
REGION                  1..116
                        note = mice-56
source                  1..116
                        mol_type = protein
                        organism = synthetic construct
SEQUENCE: 397
QIQLVQSGPE LVKPGASVKL SCKASGYTFT SSDINWVKQR PGQGPEWIGW IYPRDGRTHY  60
NEKFKGKATL TVDTSSSTAY MELHSLTSED SAVYFCARYA YALNSWGQGT SVTVSS      116

SEQ ID NO: 398          moltype = AA  length = 116
FEATURE                 Location/Qualifiers
REGION                  1..116
                        note = mice-57
source                  1..116
                        mol_type = protein
                        organism = synthetic construct
SEQUENCE: 398
QVQLQQPGPE LVKPGASVRV SCKASGYTFT RQDINWVKQR AGQGLEWIGW IYPRDGRTEY  60
NEKFKGKVTL TVDTSSSTAY MELHSLTSED SAVYFCATYG SSLDNWGQGA TLTVSS      116

SEQ ID NO: 399          moltype = AA  length = 116
FEATURE                 Location/Qualifiers
REGION                  1..116
                        note = mice-58
source                  1..116
                        mol_type = protein
                        organism = synthetic construct
SEQUENCE: 399
```

```
QVQLQQSGPE LVKPGASVKL SCKASGYTFT SYDINWVKQR PGQGLEWIGW IFPRDGDTKY  60
NEKFKGKATL TVDTSSSTAF MELHSLTSED SAVYFCARYG STLDVWGTGT TVTVSS      116

SEQ ID NO: 400         moltype = AA  length = 116
FEATURE                Location/Qualifiers
REGION                 1..116
                       note = mice-59
source                 1..116
                       mol_type = protein
                       organism = synthetic construct
SEQUENCE: 400
QIQLVQSGPE LVMPGASVKL SCQASGYTFT NSDINWVKQR PGQGLEWIGW VYPGDGSTYY  60
NEKFKGKATL TVDTSSSTAY MDLYSLTSED SAVYFCARYA YALNSWGQGT SVTVSS      116

SEQ ID NO: 401         moltype = AA  length = 116
FEATURE                Location/Qualifiers
REGION                 1..116
                       note = mice-60
source                 1..116
                       mol_type = protein
                       organism = synthetic construct
SEQUENCE: 401
QIQLVQSGPE LVKPGASVKL SCKASGYTFT NSDINWVKQR PGQGLEWIGW IYPRDGSTYY  60
NEKFKGKATL TVDTSSTTAY MEFHSLTSED SAVYFCARYA YALNSWGQGT SVTVSS      116

SEQ ID NO: 402         moltype = AA  length = 116
FEATURE                Location/Qualifiers
REGION                 1..116
                       note = mice-61
source                 1..116
                       mol_type = protein
                       organism = synthetic construct
SEQUENCE: 402
QVQLQQSGPE VVKPGASVKL SCKASGYTFT SYDINWVKQR PGQGLEWIGW IFPRDGRTEY  60
NEKFKDKATL TVDTSSSTAY MELHSLTSED SAFYFCARYG SSLDYWGQGT TLTVSS      116

SEQ ID NO: 403         moltype = AA  length = 116
FEATURE                Location/Qualifiers
REGION                 1..116
                       note = mice-62
source                 1..116
                       mol_type = protein
                       organism = synthetic construct
SEQUENCE: 403
QIQLVQSGPE LVKPGASVKL SCQASGYTFT NSDINWVKQR PGQGLDWIGW VYPRDGSTYY  60
NEKFKGKATL TVDTSSSTAY MELYSLTSED SAVYFCARYA YALNYWGQGT SVTVSS      116

SEQ ID NO: 404         moltype = AA  length = 116
FEATURE                Location/Qualifiers
REGION                 1..116
                       note = mice-63
source                 1..116
                       mol_type = protein
                       organism = synthetic construct
SEQUENCE: 404
QIQLVQSGPE LVKPGASVKL SCKASGYTFT SIDINWVKQR PGQGLEWIGW IYPRDGRTDY  60
NEKFKGKATL TVDTSSSTAY MELHSLTSED SAVYFCARYT SSLDYWGQGT TLTVSS      116

SEQ ID NO: 405         moltype = AA  length = 116
FEATURE                Location/Qualifiers
REGION                 1..116
                       note = mice-64
source                 1..116
                       mol_type = protein
                       organism = synthetic construct
SEQUENCE: 405
QVQLQQSGPE LVKPGASVKL SCKASGYTFT SIDINWVKQR PGQGLEWIGW IYPRDGRTNY  60
NEKFKGKATL TVDTSSSTAY MDLHSLTSED SAVYFCARYT SSLDYWGQGT TLTVSS      116

SEQ ID NO: 406         moltype = AA  length = 116
FEATURE                Location/Qualifiers
REGION                 1..116
                       note = mice-65
source                 1..116
                       mol_type = protein
                       organism = synthetic construct
SEQUENCE: 406
QVQLQQSGPE LVKPGASVKL SCRASGYTFT SYDINWVKQR PGQGLEWIGW NYPRDGRTDY  60
NEKFKGKATL TVDTSSNTAY MDLHSLTSED SAVYFCTRYG STLDVWGTGT SVTVSS      116
```

```
SEQ ID NO: 407          moltype = AA  length = 116
FEATURE                 Location/Qualifiers
REGION                  1..116
                        note = mice-66
source                  1..116
                        mol_type = protein
                        organism = synthetic construct
SEQUENCE: 407
QIQLVQSGPE LVKPGASVKL SCQASGYTFT NSDINWVKQR PGQGLEWIGW VYPRDGSAYY  60
NEKFKGKATL TVDTSSSTAY MELYSLTSED SAVYFCARYA YALNFWGQGT SVTVSS      116

SEQ ID NO: 408          moltype = AA  length = 116
FEATURE                 Location/Qualifiers
REGION                  1..116
                        note = mice-67
source                  1..116
                        mol_type = protein
                        organism = synthetic construct
SEQUENCE: 408
QVQLKQSGPE LVKPGASVKV SCKASGYTFT RQDINWVKQR PGQGLEWIGW IYPRDGRTEY  60
NEKFKGKVTL TVDTSSSTAY MELHSLTSED SAVYFCATYG SSLDNWGQGT TLTVSS      116

SEQ ID NO: 409          moltype = AA  length = 116
FEATURE                 Location/Qualifiers
REGION                  1..116
                        note = mice-68
source                  1..116
                        mol_type = protein
                        organism = synthetic construct
SEQUENCE: 409
QVQLQQPGPE LVKPGASVKL SCKASGYTFT NQDINWVKQR PGQGLEWIGW IFPRDGRTHY  60
NEKFKGKATL TVDTSSSTAY MELHSLTAED SAVYFCAIYG SAMDQWGQGT SVTVSS      116

SEQ ID NO: 410          moltype = AA  length = 116
FEATURE                 Location/Qualifiers
REGION                  1..116
                        note = mice-69
source                  1..116
                        mol_type = protein
                        organism = synthetic construct
SEQUENCE: 410
EVQLQQSGPE LVKPGASVKL SCKASGYTFT NSDINWVKQR PGQGLEWIGW IYPRDGSTYY  60
NEKFKGKATL TVDTSSTTAY MEFHSLTSED SAVYFCARYA YALNSWGQGT SVTVSS      116

SEQ ID NO: 411          moltype = AA  length = 121
FEATURE                 Location/Qualifiers
REGION                  1..121
                        note = mice-70
source                  1..121
                        mol_type = protein
                        organism = synthetic construct
SEQUENCE: 411
QVQLQQPGAE LMKPGASVKL SCKATGYTFT AYWLEWVKQR PGHGLEWIGE ILPGSGYAYY  60
NAKFKGKATF TADISSNTAY MQLSGLTTED SAIYYCARRG SNYPYWYFDV WGTGTTVTVS  120
S                                                                  121

SEQ ID NO: 412          moltype = AA  length = 121
FEATURE                 Location/Qualifiers
REGION                  1..121
                        note = mice-71
source                  1..121
                        mol_type = protein
                        organism = synthetic construct
SEQUENCE: 412
QVQLQQSGAE LMKPGASVKL SCKATGYTFT GYWLEWVKQR PGHGLEWIGE TLPGSGYNKY  60
NEKFKGKATF TADTSSNTAH MQLSSLTTED SAIYYCARRG SNYPYWYFDV WGTGTTVTVS  120
S                                                                  121

SEQ ID NO: 413          moltype = AA  length = 121
FEATURE                 Location/Qualifiers
REGION                  1..121
                        note = mice-72
source                  1..121
                        mol_type = protein
                        organism = synthetic construct
SEQUENCE: 413
QVQLQQSGAE LMKPGASVKL SCKATGYTFT GYWLEWVKQR PGHGLEWIGE TLPGSGYNKY  60
NEKFKGKATF TADTSSNTAH MQLSSLTTED SAIYYCARRG SNYPYWYFDV WGTGTSVTVS  120
```

```
S                                                           121

SEQ ID NO: 414         moltype = AA  length = 116
FEATURE                Location/Qualifiers
REGION                 1..116
                       note = mice-73
source                 1..116
                       mol_type = protein
                       organism = synthetic construct
SEQUENCE: 414
QVQLQQSGPE LVKPGASVKL SCRASGYTFT SYDINWVKQR PGQGLEWIGW NYPRDGRTDY  60
NEKFKGKATL TVDTSSNTAY MELHSLTSED SAVYFCTRYG STLDVWGTGT TVTVSS      116

SEQ ID NO: 415         moltype = AA  length = 116
FEATURE                Location/Qualifiers
REGION                 1..116
                       note = mice-74
source                 1..116
                       mol_type = protein
                       organism = synthetic construct
SEQUENCE: 415
QIQLVQSGPE LVKPGASVKL SCRASGYTFT SYDINWVKQR PGQGLEWIGW NYPRDGRTDY  60
NEKFKGKATL TVDTSSNTAY MELHSLTSED SAVYFCTRYG STLDVWGTGT TVTVSS      116

SEQ ID NO: 416         moltype = AA  length = 116
FEATURE                Location/Qualifiers
REGION                 1..116
                       note = mice-75
source                 1..116
                       mol_type = protein
                       organism = synthetic construct
SEQUENCE: 416
QVQLQQPGPE LVKPGASVKL SCRASGYTFT SYDINWVKQR PGQGLEWIGW IFPRDGRTEY  60
NAKFKGKATL TVDTSSNTAY MELHSLTSDD SAVYFCARYG STLDVLGAGT TVTVSS      116

SEQ ID NO: 417         moltype = AA  length = 116
FEATURE                Location/Qualifiers
REGION                 1..116
                       note = mice-76
source                 1..116
                       mol_type = protein
                       organism = synthetic construct
SEQUENCE: 417
EVQLQQSGPE LVKPGASVKL SCRASGYTFT SYDINWVKQR PGQGLEWIGW IFPRDGRTEY  60
NEKFKGKATL TVDTSSNTAY MELHSLTSED SAVYFCARYG STLDVWGTGT TVTVSS      116

SEQ ID NO: 418         moltype = AA  length = 116
FEATURE                Location/Qualifiers
REGION                 1..116
                       note = mice-77
source                 1..116
                       mol_type = protein
                       organism = synthetic construct
SEQUENCE: 418
QIQLVQSGPE LVKPGASVKL SCRASGYTFT SYDINWVKQR PGQGLEWIGW IFPRDGRTEY  60
NEKFKGKVTL TVDTSSNTAY MELHSLTSED SAVYFCARYG STLDVWGPGT TVTVSS      116

SEQ ID NO: 419         moltype = AA  length = 116
FEATURE                Location/Qualifiers
REGION                 1..116
                       note = mice-78
source                 1..116
                       mol_type = protein
                       organism = synthetic construct
SEQUENCE: 419
QVQLQQFGPE LVKPGSSVKL SCKASGYTFT DYDVNWVKQR PGQGLEWIGW NYPRDGRTNY  60
NEKFKGKATL TVDTSSSTAY MELHSLTSED SAVYFCARYG SALNVWGTGT TVTVSS      116

SEQ ID NO: 420         moltype = AA  length = 116
FEATURE                Location/Qualifiers
REGION                 1..116
                       note = mice-79
source                 1..116
                       mol_type = protein
                       organism = synthetic construct
SEQUENCE: 420
QVQLQQSGPE LVKPGASVKL SCKASGYTFT DYDVNWVKQR PGQGLEWIGW NYPRDGRTNY  60
NEKFKGKATL TVDISSSTAY MELHSLTSED SAVYFCARYG SALNVWGTGT TVTVSS      116
```

```
SEQ ID NO: 421         moltype = AA  length = 116
FEATURE                Location/Qualifiers
REGION                 1..116
                       note = mice-80
source                 1..116
                       mol_type = protein
                       organism = synthetic construct
SEQUENCE: 421
QIQLVQSGPE LVKPGASVKL SCQASGYTFT NSDINWVKQR PGQGLEWIGW VYPRDGSTYY  60
NEKFKGKATL TVDTSSSTAY MELYSLTSED SAVYFCARYA YALNSWGQGT SVTVSS      116

SEQ ID NO: 422         moltype = AA  length = 116
FEATURE                Location/Qualifiers
REGION                 1..116
                       note = mice-81
source                 1..116
                       mol_type = protein
                       organism = synthetic construct
SEQUENCE: 422
QIQLVQSGPE LVKPGASVKL SCQASGYTFT NSDINWVKQR PGQGLEWIGW VYPRDGSTYY  60
NEKFKAKATL TVDTSSSTAY MELYSLTSED SAVYFCARYA YALNYWGQGT SVTVSS      116

SEQ ID NO: 423         moltype = AA  length = 116
FEATURE                Location/Qualifiers
REGION                 1..116
                       note = mice-82
source                 1..116
                       mol_type = protein
                       organism = synthetic construct
SEQUENCE: 423
QIQLVQSGPE LVKPGASVKL SCQASGYTFT NSDINWVKQR PGQGLEWIGW VYPRDGRTYY  60
NEKFKGKATL TVDTSSSTAY MELYSLTSED SAVYFCARYA YALNSWGQGT SVTVSS      116

SEQ ID NO: 424         moltype = AA  length = 116
FEATURE                Location/Qualifiers
REGION                 1..116
                       note = mice-83
source                 1..116
                       mol_type = protein
                       organism = synthetic construct
SEQUENCE: 424
QIQLVQSGPE LVKPGASVKL SCKASGYTFT NSDINWVKQR PGQGLEWIGW VYPRDGSTYY  60
NEKFKGKATL TVDTSSSTAY MELHSLTSED SAVYFCTRYA YALNSWGQGT SVTVSS      116

SEQ ID NO: 425         moltype = AA  length = 116
FEATURE                Location/Qualifiers
REGION                 1..116
                       note = mice-84
source                 1..116
                       mol_type = protein
                       organism = synthetic construct
SEQUENCE: 425
QIQLVQSGPE LVKPGASVKL SCKASGYTFT NSDINWVKQR PGQGLEWIGW IYPRDGSTYY  60
NEKFKGKATL TVDTSSTTAY MEFHSLTSED SAVYFCARYA YTLNSWGQGT SVTVSS      116

SEQ ID NO: 426         moltype = AA  length = 116
FEATURE                Location/Qualifiers
REGION                 1..116
                       note = mice-85
source                 1..116
                       mol_type = protein
                       organism = synthetic construct
SEQUENCE: 426
EVQLQQSGAE LARPGASVKM SCKASGYTFT NSDINWVKQR PGQGLEWIGW IYPRDGSTYY  60
NEKFKGKATL TVDTSSSTAY MELHSLTSED SAVYFCTRYA YALNSWGQGT SVTVSS      116

SEQ ID NO: 427         moltype = AA  length = 116
FEATURE                Location/Qualifiers
REGION                 1..116
                       note = mice-86
source                 1..116
                       mol_type = protein
                       organism = synthetic construct
SEQUENCE: 427
QVQLQQSGPE LVKPGASVKL SCKASGYTFT NSDINWVKQR PGQGLEWIGW IYPRDGSTYY  60
NEKFKGKATL TVDTSSSTAY MELHSLTSED SAVYFCTRYA YALNSWGQGT SVTVSS      116

SEQ ID NO: 428         moltype = AA  length = 116
FEATURE                Location/Qualifiers
```

```
REGION                  1..116
                        note = mice-87
source                  1..116
                        mol_type = protein
                        organism = synthetic construct
SEQUENCE: 428
EVQLQQSGPE LVKPGASVKL SCQASGYTFT NSDINWVKQR PGQGLEWIGW VYPRDGRTYY  60
NEKFKGKATL TVDTSSSTAY MELYSLTSED SAVYFCARYA YALNSWGQGT SVTVSS      116

SEQ ID NO: 429          moltype = AA  length = 116
FEATURE                 Location/Qualifiers
REGION                  1..116
                        note = mice-88
source                  1..116
                        mol_type = protein
                        organism = synthetic construct
SEQUENCE: 429
EVQLQQSGPE LVRPGASVKL SCKASGYSFT SGDINWVKQR PGQGLEWIAW IYPRDGSTEY  60
NEKFKGKATL TVDTSSSTAY MELHSLTSED SAVYFCARYD YAFVYWGQGT LVTVSA      116

SEQ ID NO: 430          moltype = AA  length = 116
FEATURE                 Location/Qualifiers
REGION                  1..116
                        note = mice-89
source                  1..116
                        mol_type = protein
                        organism = synthetic construct
SEQUENCE: 430
EVQLQQSGPE LVRPGTSVRL SCKTSGYTFT SRDINWVKQR PGQGLEWIAW IYPRDGSTEY  60
NEKFKGKATL TVDTSSSTAY MELHSLTSED SAVYFCTRYD YAFTYWGQGT LVTVSA      116

SEQ ID NO: 431          moltype = AA  length = 116
FEATURE                 Location/Qualifiers
REGION                  1..116
                        note = mice-90
source                  1..116
                        mol_type = protein
                        organism = synthetic construct
SEQUENCE: 431
EVQLQQSGPE VVKPGASVKL SCKASGYTFT RNDINWVKQR PGQGLEWIGW IYPRDGSSKN  60
NEKFKGKATL TVDTSSSTAY MELHSLTSED SAVYFCARYD YAFVYWGQGT TVTVSS      116

SEQ ID NO: 432          moltype = AA  length = 116
FEATURE                 Location/Qualifiers
REGION                  1..116
                        note = mice-91
source                  1..116
                        mol_type = protein
                        organism = synthetic construct
SEQUENCE: 432
EVQLQQSGPE LVKPGASVKL SCKASGYTFT SYDINWVKQR PGQGLEWIGW IYPRDGRTKY  60
SEKFKGKATL TVDTSSSTAY MELHSLTSED SAVYFCARYG ASMDYWGQGT SVTVSS      116

SEQ ID NO: 433          moltype = AA  length = 116
FEATURE                 Location/Qualifiers
REGION                  1..116
                        note = mice-92
source                  1..116
                        mol_type = protein
                        organism = synthetic construct
SEQUENCE: 433
EVQLQQSGPE LVKPGASVKL SCKASGYTFT SYDINWVKQS PGQGPEWIGW VYPRDGRTQY  60
NEKFKGKATL TVDTSSSTAY MELHSLTSED SAVYFCARYG ASMDYWGQGT SVTVSS      116

SEQ ID NO: 434          moltype = AA  length = 116
FEATURE                 Location/Qualifiers
REGION                  1..116
                        note = mice-93
source                  1..116
                        mol_type = protein
                        organism = synthetic construct
SEQUENCE: 434
EVQLQQSGPE LAKPGASVKL SCKASGYTFT SYDINWVKQR PGQGLEWIGW IYPRDGNTNY  60
NEKFKGKATL TVDTSSNTAS MELHSLTSED SAVYFCARYS AAMDYWGQGT SVTVSS      116

SEQ ID NO: 435          moltype = AA  length = 116
FEATURE                 Location/Qualifiers
REGION                  1..116
                        note = mice-94
```

```
source                  1..116
                        mol_type = protein
                        organism = synthetic construct
SEQUENCE: 435
QVQLQQPGPE LVKPGASVKL SCKASGYTST SYDINWVKQR PGQGLEWIGW IYPRDGRTNY  60
NEKFKGKATL TVDTSSSTAF MELHSLTSED SAVYFCARYS AAMDYWGQGT SVTVSS      116

SEQ ID NO: 436          moltype = AA  length = 116
FEATURE                 Location/Qualifiers
REGION                  1..116
                        note = mice-95
source                  1..116
                        mol_type = protein
                        organism = synthetic construct
SEQUENCE: 436
QVQLQQSGPE LVKPGASVKL SCKASGYTFT SYDINWVKQR PGQGLEWIGW IFPRDGRTNY  60
NEKFKDKATL TVDTSSSTAF MELHRLTSED SAVYFCARYS AAMDYWGQGT SVTVSS      116

SEQ ID NO: 437          moltype = AA  length = 116
FEATURE                 Location/Qualifiers
REGION                  1..116
                        note = mice-96
source                  1..116
                        mol_type = protein
                        organism = synthetic construct
SEQUENCE: 437
EVQLQQSGAE LGKPGASVKL SCKASGYTFT NYDINWMKQR PGQGLEWIGW NYPRDGRTKY  60
NEKFKGKATL TVDTSSSTAY MELHSLTSED SAVYFCARYG YAMDYWGQGT SVTVSS      116

SEQ ID NO: 438          moltype = AA  length = 116
FEATURE                 Location/Qualifiers
REGION                  1..116
                        note = mice-97
source                  1..116
                        mol_type = protein
                        organism = synthetic construct
SEQUENCE: 438
QVQLQQSGPD LVKPGASVKL SCKASGYIFA SYDLNWVKQR PGQGLEWIGW IYPRDGRTDY  60
NEKFKGKATL TVDTSSSTAY MELHSLTSED SAVYFCARYG YALDYWGQGT SVTVSS      116

SEQ ID NO: 439          moltype = AA  length = 116
FEATURE                 Location/Qualifiers
REGION                  1..116
                        note = mice-98
source                  1..116
                        mol_type = protein
                        organism = synthetic construct
SEQUENCE: 439
QIQLVQSGPE LVKPGASVKV SCKASGYTFT RQDINWVKQR PGQGLEWIGW IYPRDGRTEY  60
NEKFKGKATL TVDTSSSTAF MELHSLTSED SAVYFCARYS AAMDYWGQGT SVTVSS      116

SEQ ID NO: 440          moltype = AA  length = 116
FEATURE                 Location/Qualifiers
REGION                  1..116
                        note = mice-99
source                  1..116
                        mol_type = protein
                        organism = synthetic construct
SEQUENCE: 440
QIQLVQSGPE LVKPGASVKL SCKASGYTFT NSDINWVKQR PGQGLEWIGW NYPRDGRTKY  60
NEKFKGKATF TVDTSSSTAY MDLQSLTSED SAVYFCTRYG SAMDYWGQGT SVTVSS      116

SEQ ID NO: 441          moltype = AA  length = 116
FEATURE                 Location/Qualifiers
REGION                  1..116
                        note = mice-100
source                  1..116
                        mol_type = protein
                        organism = synthetic construct
SEQUENCE: 441
EVQLQQSGPE LVKPGASVKL SCKASGYTFT NQDINWVKQR PGQGLEWIGW IFPRDGRTHY  60
NENFKGKATL TVDTSSSTAY MELHSLTAED SAVYFCAIYG IALDHWGQGT SVTVSS      116

SEQ ID NO: 442          moltype = AA  length = 116
FEATURE                 Location/Qualifiers
REGION                  1..116
                        note = mice-101
source                  1..116
                        mol_type = protein
```

```
                        organism = synthetic construct
SEQUENCE: 442
QVQLQQSGPE LVKPGASVKL SCKASGYTFT NQDINWVKQR PGQGLEWIGW IFPRDGRTHY  60
NENFKGKATL TVDTSSNTAY MELHSLTAED SAVYFCAIYG IALDHWGQGT SVTVSS      116

SEQ ID NO: 443          moltype = AA  length = 116
FEATURE                 Location/Qualifiers
REGION                  1..116
                        note = mice-102
source                  1..116
                        mol_type = protein
                        organism = synthetic construct
SEQUENCE: 443
QVQLQQSGPE LVKPGASVKL SCKASGYTFT NQDINWVKQR PGQGLEWIGW IFPRDGRTHY  60
NENFKGKATL TVDTSSSTAY MELHSLTAED SAVYFCAIYG IALDHWGQGT SVTVSS      116

SEQ ID NO: 444          moltype = AA  length = 116
FEATURE                 Location/Qualifiers
REGION                  1..116
                        note = mice-103
source                  1..116
                        mol_type = protein
                        organism = synthetic construct
SEQUENCE: 444
QVQLQQSGPE LVKPGASVKL SCKASGYTFT NQDINWVKQR PGQGLEWIGW IFPRDGRTHY  60
NENFKGKATL TVDTSSSTAY MELHSLTAED SAVYFCAIYG AAMDHWGQGT SVTVSS      116

SEQ ID NO: 445          moltype = AA  length = 116
FEATURE                 Location/Qualifiers
REGION                  1..116
                        note = mice-104
source                  1..116
                        mol_type = protein
                        organism = synthetic construct
SEQUENCE: 445
QVQLQQSGPE LVKPGTSVKL SCKASGYTFT NQDINWVKQR PGQGLEWIGW IFPRDGRTHY  60
NENFKGKATL TVDTSSSTAY MELHSLTAED SAVYFCSIYG IAMDHWGQGT SVTVSS      116

SEQ ID NO: 446          moltype = AA  length = 116
FEATURE                 Location/Qualifiers
REGION                  1..116
                        note = mice-105
source                  1..116
                        mol_type = protein
                        organism = synthetic construct
SEQUENCE: 446
QVQLQQPGPE LVKPGASVKL SCKASGYTFT NQDINWVKQR PGQGLEWIGW IFPRDGRTHN  60
NENFKGKATL TVDTSSSTAY MELHSLTAED SAVYFCAIYG FAMDHWGQGT SVTVSS      116

SEQ ID NO: 447          moltype = AA  length = 116
FEATURE                 Location/Qualifiers
REGION                  1..116
                        note = mice-106
source                  1..116
                        mol_type = protein
                        organism = synthetic construct
SEQUENCE: 447
QVQLQQSGPE LVKPGASVKL SCKASGYTFT NQDINWVKQR PGQGLEWIGW IFPRDGRTHY  60
NENFKGKATL TVDTSSSTAY MELHSLTAED SAVYFCAIYG FAMDHWGQGT SVTVSS      116

SEQ ID NO: 448          moltype = AA  length = 116
FEATURE                 Location/Qualifiers
REGION                  1..116
                        note = mice-107
source                  1..116
                        mol_type = protein
                        organism = synthetic construct
SEQUENCE: 448
QVQLQQPGPE LVKPGASVKL SCKASGYTFT NQDINWVKQR PGQGLEWIGW IFPRDGRTHY  60
NENFKGKATL TVDTSSSTAY MELHSLTAED SAVYFCAIYG AAMDDWGQGT SVTVSS      116

SEQ ID NO: 449          moltype = AA  length = 116
FEATURE                 Location/Qualifiers
REGION                  1..116
                        note = mice-108
source                  1..116
                        mol_type = protein
                        organism = synthetic construct
SEQUENCE: 449
```

```
QVQLQQPGPE LVKPGASVKL SCKASGYTFT NQDINWVKQR PGQGLEWIGW IFPRDGRTHY  60
NENFKGKATL TVDTSSSTAF MELHSLTAED SAVYFCAIYG IALDHWGQGT SVTVSS      116

SEQ ID NO: 450         moltype = AA  length = 116
FEATURE                Location/Qualifiers
REGION                 1..116
                       note = mice-109
source                 1..116
                       mol_type = protein
                       organism = synthetic construct
SEQUENCE: 450
EVQLQQSGPE LVKPGASVKL SCKASGYTFT NQDINWVKQR PGQGLEWIGW IFPRDGRTHY  60
NENFKGKATL TVDTSSSTAY MELHSLTAED SAVYFCAIYG FAMDHWGQGT SVTVSS      116

SEQ ID NO: 451         moltype = AA  length = 116
FEATURE                Location/Qualifiers
REGION                 1..116
                       note = mice-110
source                 1..116
                       mol_type = protein
                       organism = synthetic construct
SEQUENCE: 451
EVQLQQSGPE LVKPGASVKL SCKASGYTFT NQDINWVKQR PGQGLEWIGW NFPRDGRTHY  60
NENFKGKATL TVDTSSSTAY MELHSLTAED SAVFFCAIYG FALDHWGQGT SVTVSS      116

SEQ ID NO: 452         moltype = AA  length = 116
FEATURE                Location/Qualifiers
REGION                 1..116
                       note = mice-111
source                 1..116
                       mol_type = protein
                       organism = synthetic construct
SEQUENCE: 452
QVQLQQSGPE LVKPGASVKL SCKASGYTFT NQDINWVKQR PGQGLEWIGW IFPRDGRTHY  60
NENFKGKATL TVDTSSSTAY MELHSLTAED SAVYFCALYG FAMDQWGQGT SVTVSS      116

SEQ ID NO: 453         moltype = AA  length = 116
FEATURE                Location/Qualifiers
REGION                 1..116
                       note = mice-112
source                 1..116
                       mol_type = protein
                       organism = synthetic construct
SEQUENCE: 453
EVQLQQSGPE LVKPGASVKL SCKASGYTFT NQDINWVKQR PGQGLEWIGW IFPRDGRTHY  60
NEKFKGKATL TVDTSSSTAY MELHSLTAED SAVYFCAIYG SAMDQWGQGT SVTVSS      116

SEQ ID NO: 454         moltype = AA  length = 120
FEATURE                Location/Qualifiers
REGION                 1..120
                       note = mice-113
source                 1..120
                       mol_type = protein
                       organism = synthetic construct
SEQUENCE: 454
EVQLQQSGPE LVKPGTSVKI PCKTSGYTFT DYNINWVKQS HGKSLEWIGD INPDSGGTVY  60
NQRFKDKATL TVDKSSSTAY MELRSLTSGD TAVYYCARWG YYDGRGFDYW GQGTTLTVSS  120

SEQ ID NO: 455         moltype = AA  length = 117
FEATURE                Location/Qualifiers
REGION                 1..117
                       note = mice-114
source                 1..117
                       mol_type = protein
                       organism = synthetic construct
SEQUENCE: 455
EVQLQQSGAE LVRPGASVTL SCKASGYTFT DYEIHWVKQI PVHGLEWIGV FDPETGGAAY  60
NQKFKGKAIL TADKSSSTAY MELRSLTSED SAVYYCTTPW LNYFEYWGQG TTLTVSS     117

SEQ ID NO: 456         moltype = AA  length = 115
FEATURE                Location/Qualifiers
REGION                 1..115
                       note = mice-115
source                 1..115
                       mol_type = protein
                       organism = synthetic construct
SEQUENCE: 456
QVQLQQSVAE LVRPGASVKL SCTASGFNIE DTYMHWVKQR PEQGLEWIGR VDPASGNTKY  60
GPKFQGKATI TADTSSNTAY LQLSSLSSAD TAIYYCSTWG LFDYWGQGTT LTVSS       115
```

```
SEQ ID NO: 457         moltype = AA  length = 116
FEATURE                Location/Qualifiers
REGION                 1..116
                       note = mice-116
source                 1..116
                       mol_type = protein
                       organism = synthetic construct
SEQUENCE: 457
QVQLQQPGPE LVKPGASVKL SCKASGYTFT SIDINWVKQR PGQGLEWIGW IYPRDGRTHY  60
NEKFKGKATL TVDTSSSTAY MELHSLTSED SAVYFCARYT SSLDYWGQGT TLTVSS      116

SEQ ID NO: 458         moltype = AA  length = 116
FEATURE                Location/Qualifiers
REGION                 1..116
                       note = mice-117
source                 1..116
                       mol_type = protein
                       organism = synthetic construct
SEQUENCE: 458
QVQLQQSGPE LVKPGASVKL SCKASGYTFT SIDINWVKQR PGQGLEWIGW IYPRDGRTDY  60
NEKFKGKATL TVDTSSSTAY MELHSLTSED SAVYFCARYG SSLDYWGQGT TLTVSS      116

SEQ ID NO: 459         moltype = AA  length = 115
FEATURE                Location/Qualifiers
REGION                 1..115
                       note = mice-118
source                 1..115
                       mol_type = protein
                       organism = synthetic construct
SEQUENCE: 459
QVQLQQSGPE LVKPGTSVRL SCKASGYTFT NSDINWVKQR PGQGLEWIGW IYPRDGRTDY  60
NEKFKGKATL TVDTSSSTAY MELHSLTSED SAVYFCARYG SSLYWGQGTT LTVSS       115

SEQ ID NO: 460         moltype = AA  length = 116
FEATURE                Location/Qualifiers
REGION                 1..116
                       note = mice-119
source                 1..116
                       mol_type = protein
                       organism = synthetic construct
SEQUENCE: 460
EVQLQQSGPE LVKPGASVKL SCKASGYTFT SSDINWVKQR PGQGPEWIGW IYPRDGRTHY  60
NEKFKGKATL TVDTSSSTAY MELHSLTSED SAVYFCAPYG SSLAYWGQGT TLTVSS      116

SEQ ID NO: 461         moltype = AA  length = 116
FEATURE                Location/Qualifiers
REGION                 1..116
                       note = mice-120
source                 1..116
                       mol_type = protein
                       organism = synthetic construct
SEQUENCE: 461
QIQLVQSGPE LVKPGASVKL SCKASGYTFT SSDINWVKQR PGQGLEWIGW IYPRDGSTHY  60
NENFKGKATL TVDTSSSTAY MELHSLTSED SAVYFCAPYG SSLAYWGQGT TLTVSS      116

SEQ ID NO: 462         moltype = AA  length = 116
FEATURE                Location/Qualifiers
REGION                 1..116
                       note = mice-121
source                 1..116
                       mol_type = protein
                       organism = synthetic construct
SEQUENCE: 462
QVQLKESGPE VVKPGASVKL SCKASGYTFT SYDINWVKQR PGQGLEWIGW IYPRDGRTEY  60
NEKFKDKATL TVDTSSSTAY MELHSLTSED SAVYFCARYG SSLDYWGQGT TLTVSS      116

SEQ ID NO: 463         moltype = AA  length = 116
FEATURE                Location/Qualifiers
REGION                 1..116
                       note = mice-122
source                 1..116
                       mol_type = protein
                       organism = synthetic construct
SEQUENCE: 463
QIQLVQSGPE LVKPGASVKV SCKASGYTFT RQDINWVKQR PGQGLEWIGW IYPRDGSTKY  60
NEKFKGKVTL TVDTSSSTAY MELHSLTSED SAVYFCATYG SSLDNWGQGT TLTVSS      116

SEQ ID NO: 464         moltype = AA  length = 116
```

```
FEATURE                Location/Qualifiers
REGION                 1..116
                       note = mice-123
source                 1..116
                       mol_type = protein
                       organism = synthetic construct
SEQUENCE: 464
QVQLQQSGPE LVKPGASVKV SCKASGYTFT RQDINWVKQR PGQGLEWIGW IYPRDGSTKY  60
NEKFKGKVTL TVDTSSSTAY MELHSLTSED SAVYFCATYG SSLDNWGQGT TLTVSS      116

SEQ ID NO: 465         moltype = AA  length = 116
FEATURE                Location/Qualifiers
REGION                 1..116
                       note = mice-124
source                 1..116
                       mol_type = protein
                       organism = synthetic construct
SEQUENCE: 465
QIQLVQSGPE LVKPGASVKV SCKASGYTFT RQDINWVKQR PGQGLEWIGW IYPRDGRTEY  60
NEKFKGKVTL TVDTSSSTAY MELHSLTPED SAVYFCATYG SSLDNWGQGT TLTVSS      116

SEQ ID NO: 466         moltype = AA  length = 116
FEATURE                Location/Qualifiers
REGION                 1..116
                       note = mice-125
source                 1..116
                       mol_type = protein
                       organism = synthetic construct
SEQUENCE: 466
QVQLKESGPE LVKPGASVKV SCKASGYTFT RQDINWVKQR PGQGLEWIGW IYPRDGRTEY  60
NEKFKGKVTL TVDTSSSTAY MELHSLTSED SAVYFCATYG SSLDNWGQGT TLTVSS      116

SEQ ID NO: 467         moltype = AA  length = 116
FEATURE                Location/Qualifiers
REGION                 1..116
                       note = mice-126
source                 1..116
                       mol_type = protein
                       organism = synthetic construct
SEQUENCE: 467
QVQLQQSGAE LAKPGASVKL SCKASGYTFT RQDINWVKQR PGQGLEWIGW IYPRDGRTEY  60
NEKFKGKVTL TVDTSSSTAY MELHSLTSED SAVYFCATYG SSLDNWGQGT TLTVSS      116

SEQ ID NO: 468         moltype = AA  length = 116
FEATURE                Location/Qualifiers
REGION                 1..116
                       note = mice-127
source                 1..116
                       mol_type = protein
                       organism = synthetic construct
SEQUENCE: 468
QVQLQQPGPE LVKPGASVKV SCKASGYTFT RQDINWVKQR PGQGLEWIGW IYPRDGRTEY  60
NEKFKGKVTL TVDTSSNTAY MELHSLTSED SAVYFCATYG SSLDNWGQGT TLTVSS      116

SEQ ID NO: 469         moltype = AA  length = 116
FEATURE                Location/Qualifiers
REGION                 1..116
                       note = mice-128
source                 1..116
                       mol_type = protein
                       organism = synthetic construct
SEQUENCE: 469
QVQLQQSGPE LVKPGASVKV SCKASGYTFT RQDINWVKQR PGQGLEWIGW IYPRDGRTEY  60
NEKFKGKVTL TVDTSSSTAY MELHSLTSED SAVYFCATYG SSLDNWGQGT TLTVSS      116

SEQ ID NO: 470         moltype = AA  length = 116
FEATURE                Location/Qualifiers
REGION                 1..116
                       note = mice-129
source                 1..116
                       mol_type = protein
                       organism = synthetic construct
SEQUENCE: 470
EVQLQQSGPE LVKPGASVKV SCKASGYTFT RQDINWAKQR PGQGLEWIGW IYPRDGRTEY  60
NEKFKGKVTL TVDTSSSTAY MELHSLTPED SAVYFCATYG SSLDNWGQGT TLTVSS      116

SEQ ID NO: 471         moltype = AA  length = 116
FEATURE                Location/Qualifiers
REGION                 1..116
```

```
                        note = mice-130
source                  1..116
                        mol_type = protein
                        organism = synthetic construct
SEQUENCE: 471
EVQLQQSGPE LVKPGASVKV SCKASGYTFT RQDINWVKQR PGQGLEWIGW IYPRDGRTEY  60
NEKFKGKVTL TVDTSSSTAY MELHSLTSED SAVYFCATYG SSLDNWGQGT TLTVSS      116

SEQ ID NO: 472          moltype = AA  length = 114
FEATURE                 Location/Qualifiers
REGION                  1..114
                        note = mice-131
source                  1..114
                        mol_type = protein
                        organism = synthetic construct
SEQUENCE: 472
EVQLQQSVAE LVRPGASVKL SCTASGFNIE NTYIHWVKQR PEQGLEWIGR IDPASGNTKY  60
APKFQGKATI TADTSSNTAY LQLSSLTSED TAIYYCASTG PDYWGQGTTL TVSS        114

SEQ ID NO: 473          moltype = AA  length = 119
FEATURE                 Location/Qualifiers
REGION                  1..119
                        note = mice-132
source                  1..119
                        mol_type = protein
                        organism = synthetic construct
SEQUENCE: 473
QIQLVQSGPE LKKPGETVEI SCKASGYTFT THGMNWVKQA PGKGLKWMGW INTFSGVPTY  60
ADDFRGRFDF FLATSASTAY LQINNLKNED TATYFCARDY GTAYAMDSWG QGTSVTVSS   119

SEQ ID NO: 474          moltype = AA  length = 119
FEATURE                 Location/Qualifiers
REGION                  1..119
                        note = mice-133
source                  1..119
                        mol_type = protein
                        organism = synthetic construct
SEQUENCE: 474
EVKVEESGGG LVQPGGSMKL SCIASGFTFS NYWMNWVRQS PEKGLEWVAQ IRLKSDNYAT  60
HYAESVKGNF TISRDDSKSS VYLQMNNLRA EDTGIYYCTP LLLRYRDYWG QGTTLTVSS   119

SEQ ID NO: 475          moltype = AA  length = 119
FEATURE                 Location/Qualifiers
REGION                  1..119
                        note = mice-134
source                  1..119
                        mol_type = protein
                        organism = synthetic construct
SEQUENCE: 475
EVQLQQSGPE LVKPGASVKI SCKASGYTFT DYYMNWVKQS HGKSLEWIGD VNPNSGGTSQ  60
NQKFKGKATL TVDKSSTTAY MELRSLTSED SAVYHCARGS NYVGGFTYWG QGTLVAVSA   119

SEQ ID NO: 476          moltype = AA  length = 122
FEATURE                 Location/Qualifiers
REGION                  1..122
                        note = mice-135
source                  1..122
                        mol_type = protein
                        organism = synthetic construct
SEQUENCE: 476
QVQLQQPGAE LVKPGASVKL SCKASGYTFS NDWMHWVKQR PGRGLEWIGR IDPDSGGTKY  60
NEKFKNKATL TVDKPSSTVY MQLSSLTSED SAVYYCARSE GYYGSRSYFD YWGQGTTLTV  120
SS                                                                 122

SEQ ID NO: 477          moltype = AA  length = 119
FEATURE                 Location/Qualifiers
REGION                  1..119
                        note = mice-136
source                  1..119
                        mol_type = protein
                        organism = synthetic construct
SEQUENCE: 477
EFQLQQSGPE LVKPGASVRI SCKASGYTFT DYYLNWVKQS RGESLEWIGD INPNNGRTTY  60
NQKFTGKATW TVDKSSSTVY MELRSLTSDD SAVYYCAREG GYGWYFDVWG TGTTVTVSS   119

SEQ ID NO: 478          moltype = AA  length = 107
FEATURE                 Location/Qualifiers
REGION                  1..107
                        note = mice-137
```

```
source                  1..107
                        mol_type = protein
                        organism = synthetic construct
SEQUENCE: 478
DIQMTQTTSS LSASLGDRVT ISCRASQDIS NYLNWYQQKP DGTVKLLIYY TSRLHSGVPS  60
RFSGSGSGTD YSLTISNLEQ EDIATYFCQQ GNTLPFTFGS GTKLEIK               107

SEQ ID NO: 479          moltype = AA  length = 111
FEATURE                 Location/Qualifiers
REGION                  1..111
                        note = mice-138
source                  1..111
                        mol_type = protein
                        organism = synthetic construct
SEQUENCE: 479
DIVLTQSPAS LPVSLGQRAT ISCRASKSVS TSSYSYMHWY QQKPGQPPKL LIKYASNLES  60
GVPARFSGSG SGTDFTLNIH PVEEEDAATY YCQHSKEFPW TFGGGTKLEI K          111

SEQ ID NO: 480          moltype = AA  length = 107
FEATURE                 Location/Qualifiers
REGION                  1..107
                        note = mice-139
source                  1..107
                        mol_type = protein
                        organism = synthetic construct
SEQUENCE: 480
DIKMTQSPSS MYASLGERVT ITCKASQDIN SFLSWFQQKP GKSPKTLIYR ANRLVDGVPS  60
RFSGSGSGQD YSLTISSLEY EDMGIYYCLQ CDEFPYTFGG GTKLEIK               107

SEQ ID NO: 481          moltype = AA  length = 107
FEATURE                 Location/Qualifiers
REGION                  1..107
                        note = mice-140
source                  1..107
                        mol_type = protein
                        organism = synthetic construct
SEQUENCE: 481
DIKMTQSPSS MYASLGERVT ITCKASQDIN SYLSWFQQKP GKSPKTLIYR ANRLVDGVPS  60
RFSASGSGQD YSLTISSLEY EDMGIYYCLQ CDEFPYTFGG GTKLEIK               107

SEQ ID NO: 482          moltype = AA  length = 107
FEATURE                 Location/Qualifiers
REGION                  1..107
                        note = mice-141
source                  1..107
                        mol_type = protein
                        organism = synthetic construct
SEQUENCE: 482
DIVMTQSHKF MSTSVGDRVS ITCKASQDVS TAVAWYQQKP GQSPKLLIYW ASARHTGVPA  60
RFTGSGSGTD YTLTISSVQA EDLALYYCQQ HYGTPPTFGG GTKLEIK               107

SEQ ID NO: 483          moltype = AA  length = 106
FEATURE                 Location/Qualifiers
REGION                  1..106
                        note = mice-142
source                  1..106
                        mol_type = protein
                        organism = synthetic construct
SEQUENCE: 483
QIVLTQSPAI MSVSPGEKVT ITCSATSRVT YMHWFQQKPG TAPKLWIYST SNVASGVPAR  60
FSGSGSVTSY SLTISRMEAA DAATYYCQQR SSYPPTFGGG TKLEIK                106

SEQ ID NO: 484          moltype = AA  length = 111
FEATURE                 Location/Qualifiers
REGION                  1..111
                        note = mice-143
source                  1..111
                        mol_type = protein
                        organism = synthetic construct
SEQUENCE: 484
DIMLTQSPAS LTVSLGQRAT ISCRASKSVS TSSYTYMHWY QQKPGQPPKL LIKYASNLES  60
GVPARFSGSG SGTDFILNIH PVEEEDAATY YCQHSREFPW TFGGGTKLEI K          111

SEQ ID NO: 485          moltype = AA  length = 111
FEATURE                 Location/Qualifiers
REGION                  1..111
                        note = mice-144
source                  1..111
                        mol_type = protein
```

```
                         organism = synthetic construct
SEQUENCE: 485
DIVLTQSPAS LAVSLGQRAT ISCRASKSVS TSSYNYMHWY QQKPGQPPKL LIKYASNLES  60
GVPARFSGSG SGTDFTLNIH PVEEEDAATY YCQHSREFPW TFGGGTKLEI K           111

SEQ ID NO: 486           moltype = AA  length = 108
FEATURE                  Location/Qualifiers
REGION                   1..108
                         note = mice-145
source                   1..108
                         mol_type = protein
                         organism = synthetic construct
SEQUENCE: 486
QIVLTQSPAL MSASPGEKVT MTCSASSSVS YMYWYQQKPR SSPKPWIYLT SNLASGVPAR  60
FSGSGSGTSY SLTISSMEAE DAATYYCQQW IIYPPMLTFG AGTKLELK               108

SEQ ID NO: 487           moltype = AA  length = 110
FEATURE                  Location/Qualifiers
REGION                   1..110
                         note = mice-146
source                   1..110
                         mol_type = protein
                         organism = synthetic construct
SEQUENCE: 487
DIVLTQSPAS LAVSLGQRAT ISCKASQSVS FAGISLMHWY QQKPGQQPKL LIYRASNLEA  60
GVPTRFSGSG SRTDFTLTIN PVETDDVATY YCQQSNKDPT FGGGTKLELK             110

SEQ ID NO: 488           moltype = AA  length = 108
FEATURE                  Location/Qualifiers
REGION                   1..108
                         note = mice-147
source                   1..108
                         mol_type = protein
                         organism = synthetic construct
SEQUENCE: 488
DIVMTQSHKF MSTSVGDRVS ITCKASQDVS TAVAWYQQKP GQSPKLLIYS ASYRYTGVPD  60
RFTGSGSGTD FTFTISSVQA EDLAVYYCHQ HYSTPYTFGG GTKLEIKR               108

SEQ ID NO: 489           moltype = AA  length = 113
FEATURE                  Location/Qualifiers
REGION                   1..113
                         note = mice-148
source                   1..113
                         mol_type = protein
                         organism = synthetic construct
SEQUENCE: 489
DVVMTQTPLS LPVSLGDQAS ISCRSSQNIV HSNGDTYLDW FLQKPGQSPK LLIYKVSNRF  60
SGVPDRFSGS GSGTDFTLKI TRVESEDLGV YYCFQGSHDP YTFGGGTKLE IKR         113

SEQ ID NO: 490           moltype = AA  length = 106
FEATURE                  Location/Qualifiers
REGION                   1..106
                         note = mice-149
source                   1..106
                         mol_type = protein
                         organism = synthetic construct
SEQUENCE: 490
ENVLTQSPAI MSASPGERVT MTCSASSSVS YMHWYQQKSS TSPKLWISDT SKLASGVPGR  60
FSGSGSGNSY SLTISSMEAE DVATYYCFQE SGYPFTFGAG TKLELK                 106

SEQ ID NO: 491           moltype = AA  length = 113
FEATURE                  Location/Qualifiers
REGION                   1..113
                         note = mice-150
source                   1..113
                         mol_type = protein
                         organism = synthetic construct
SEQUENCE: 491
DVVMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP YTFGGGTKLE IKR         113

SEQ ID NO: 492           moltype = AA  length = 106
FEATURE                  Location/Qualifiers
REGION                   1..106
                         note = mice-151
source                   1..106
                         mol_type = protein
                         organism = synthetic construct
SEQUENCE: 492
```

```
ENVLTQSPAI MSASPGEKVT MTCSASSSVS YMHWYQQKSS TSPKLWIYDT SKLASGVPGR  60
FSGSGSGNSY SLTISSMEAE DVATYYCFQE SGYPLTFGAG TKLELK                106

SEQ ID NO: 493          moltype = AA  length = 106
FEATURE                 Location/Qualifiers
REGION                  1..106
                        note = mice-152
source                  1..106
                        mol_type = protein
                        organism = synthetic construct
SEQUENCE: 493
EILLTQSPAI IVASPGEKVT ITCSATSSVI YMNWYQQKPG SSPKIWIYGI SNLASGVPAR  60
FSGSGSGTSF SFTINSMEAE DVATYYCQQR SSYPFTFGSG TKLEIK                106

SEQ ID NO: 494          moltype = AA  length = 107
FEATURE                 Location/Qualifiers
REGION                  1..107
                        note = mice-153
source                  1..107
                        mol_type = protein
                        organism = synthetic construct
SEQUENCE: 494
DVQITQSPSY LAASPGETIT MNCRASKSIR KYLAWYQEKP GKSNKILIYS GSTLQSGIPS  60
RFSGSGSGTD FTLTISSLEP EDFAMYYCQQ HNEYPLTFGA GTKLELK               107

SEQ ID NO: 495          moltype = AA  length = 106
FEATURE                 Location/Qualifiers
REGION                  1..106
                        note = mice-154
source                  1..106
                        mol_type = protein
                        organism = synthetic construct
SEQUENCE: 495
QIVLTQSPAI MSASPGEKVT MTCSASSSVS YMHWYQQKSG TSLKRWIYDT SKLASGVPAR  60
FSGSGSGTSY SLTVSSMEAE DAATYYCQQW TSTPYTFGGG TKLEIK                106

SEQ ID NO: 496          moltype = AA  length = 106
FEATURE                 Location/Qualifiers
REGION                  1..106
                        note = mice-155
source                  1..106
                        mol_type = protein
                        organism = synthetic construct
SEQUENCE: 496
QIVLTQSPAI MSASPGEKVT MTCSASSSVS YMHWYQQKSG TSPKRWIYDT SKLASGVPAR  60
FSGSGSGTSY SLTISTMEAE DAATYYCQQW TSTPYTFGGG TKLEIK                106

SEQ ID NO: 497          moltype = AA  length = 107
FEATURE                 Location/Qualifiers
REGION                  1..107
                        note = mice-156
source                  1..107
                        mol_type = protein
                        organism = synthetic construct
SEQUENCE: 497
DIQMTQTTSS LSASLGDRVT ISCRASQDIT NYLNWYQQKP DGTVKLLIYS TSRLHSGVPS  60
RFSGSGSGTD YSLTISNLEQ EDIATYFCQQ GNTLPLTFGA GTKLELK               107

SEQ ID NO: 498          moltype = AA  length = 107
FEATURE                 Location/Qualifiers
REGION                  1..107
                        note = mice-157
source                  1..107
                        mol_type = protein
                        organism = synthetic construct
SEQUENCE: 498
DIKMTQSPSS MYASLGERVT ITCKASQDIN SYLSWFQQKP GKSPKTLIYR ANRLLDGVPS  60
RFSGSGSGQD YSLTISSLEY EDMGIYYCLQ YDEFPYTFGG GTKLEIK               107

SEQ ID NO: 499          moltype = AA  length = 107
FEATURE                 Location/Qualifiers
REGION                  1..107
                        note = mice-158
source                  1..107
                        mol_type = protein
                        organism = synthetic construct
SEQUENCE: 499
DIVMTQPQKF MPTSVGDRVS VTCKASQNVG TNVAWYQQKA GQSPKVLIYS ASYRYSGVPD  60
RFTGSGSGTA FTLTISNVQS EDLAEYFCHQ YNNFPFSFGS GTMLEIK               107
```

```
SEQ ID NO: 500          moltype = AA  length = 107
FEATURE                 Location/Qualifiers
REGION                  1..107
                        note = mice-159
source                  1..107
                        mol_type = protein
                        organism = synthetic construct
SEQUENCE: 500
DIKMTQSPSS MYASLGDRVT ITCKASQDID SYLSWFQQKP GKSPKTLMYH TNRLIVGVPS  60
RFSGTGSGQD YALTISSLEY EDLGIYYCQQ YDEFPSTFGS GTKLEIK               107

SEQ ID NO: 501          moltype = AA  length = 107
FEATURE                 Location/Qualifiers
REGION                  1..107
                        note = mice-160
source                  1..107
                        mol_type = protein
                        organism = synthetic construct
SEQUENCE: 501
DIQMTQTTSS LSASLGDRVT ISCRASQDIS NYLNWYQQKP DGTVKLLIYY TSRLHSGVPS  60
RFSGSGSGTD YSLTISNLDQ EDIATYFCQQ GNTLPLTFGA GTKLELK               107

SEQ ID NO: 502          moltype = AA  length = 107
FEATURE                 Location/Qualifiers
REGION                  1..107
                        note = mice-161
source                  1..107
                        mol_type = protein
                        organism = synthetic construct
SEQUENCE: 502
DNVMTQSQKF MSTSVGDRVS VTCKASQNVG TNVAWYQQKA GQSPKVLIYS ASYRYSGVPD  60
RFTGSGSGTA FTLTISNVQS EDLAEYFCQQ YNSFPFTFGS GTKLEIK               107

SEQ ID NO: 503          moltype = AA  length = 112
FEATURE                 Location/Qualifiers
REGION                  1..112
                        note = mice-162
source                  1..112
                        mol_type = protein
                        organism = synthetic construct
SEQUENCE: 503
DVVMTQTPLT LSVTIGQPAS ISCKSSQSLL DSDGKTYLSW LLQRPGQSPK RLIILVSKLD  60
SGVPDRFTGS GSGTDFTLKI SRVEAEDLGV YYCWQGTHFP QTFGGGTKLE IK          112

SEQ ID NO: 504          moltype = AA  length = 112
FEATURE                 Location/Qualifiers
REGION                  1..112
                        note = mice-163
source                  1..112
                        mol_type = protein
                        organism = synthetic construct
SEQUENCE: 504
DVLMTQAPLS LPVSLGDQAS ISCRSSQSIV HSNGDTYLDW YLQKPGQSLK LLIYKLSNRF  60
SGVPDRFSGS GSGTDFTLKI SRVEAEDLGV YHCFQGSHVP YTFGGGTKLE IK          112

SEQ ID NO: 505          moltype = AA  length = 113
FEATURE                 Location/Qualifiers
REGION                  1..113
                        note = mice-164
source                  1..113
                        mol_type = protein
                        organism = synthetic construct
SEQUENCE: 505
DVVMTQTPLS LPVSLGDQAS ISCRSSQSIV HGNGNTYLEW YLQKPGQSPK LLIYKVSNRF  60
SGVPDRFSGS GSGTDFTLKI SRVEAEDLGV YYCFQGSHVP YTFGGGTKLE LKR         113

SEQ ID NO: 506          moltype = AA  length = 113
FEATURE                 Location/Qualifiers
REGION                  1..113
                        note = mice-165
source                  1..113
                        mol_type = protein
                        organism = synthetic construct
SEQUENCE: 506
DVVMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP YTFGGGTKLE LKR         113

SEQ ID NO: 507          moltype = AA  length = 112
```

```
FEATURE                 Location/Qualifiers
REGION                  1..112
                        note = mice-166
source                  1..112
                        mol_type = protein
                        organism = synthetic construct
SEQUENCE: 507
DVVMTQTPLS LPVSLGDQAS ISCRSSQSIV HSNGSTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 508          moltype = AA  length = 112
FEATURE                 Location/Qualifiers
REGION                  1..112
                        note = mice-167
source                  1..112
                        mol_type = protein
                        organism = synthetic construct
SEQUENCE: 508
DVVMTQTPLS LPVSLGDQAS ISCRSSQNIV HSNGDTYLDW FLQKPGQSPQ LLIYKVSNRF  60
SGVPDRFSGS GSGTDFTLKI SRVEAEDLGI YYCFQGSHVP YTFGGGTKLE IK          112

SEQ ID NO: 509          moltype = AA  length = 112
FEATURE                 Location/Qualifiers
REGION                  1..112
                        note = mice-168
source                  1..112
                        mol_type = protein
                        organism = synthetic construct
SEQUENCE: 509
DVVMTQTPLS LPVSLGDQAS ISCRSSQSIV HSNGHTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 510          moltype = AA  length = 112
FEATURE                 Location/Qualifiers
REGION                  1..112
                        note = mice-169
source                  1..112
                        mol_type = protein
                        organism = synthetic construct
SEQUENCE: 510
DVVMTQTPLS LPVSLGDQAS ISCRPSQTIV HSNGDTYLDW FLQKPGQSPK LLIYKVSNRF  60
SGVPDRFSGS GSGTDFTLKI SRVEAEDLGV YYCFQGSHVP YTFGGGTRLE IK          112

SEQ ID NO: 511          moltype = AA  length = 112
FEATURE                 Location/Qualifiers
REGION                  1..112
                        note = mice-170
source                  1..112
                        mol_type = protein
                        organism = synthetic construct
SEQUENCE: 511
DVVMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP LTFGDGTKLE IK          112

SEQ ID NO: 512          moltype = AA  length = 112
FEATURE                 Location/Qualifiers
REGION                  1..112
                        note = mice-171
source                  1..112
                        mol_type = protein
                        organism = synthetic construct
SEQUENCE: 512
DVVMTQTPLS LPVSLGDQAS ISCRSSQSIV HSNGDTYLDW FLQKPGQSPK LLIYKVSNRF  60
SGVPDRFSGS GSGTDFTLKI TRVESEDLGV YYCFQGSHDP YTFGGGTKLE IK          112

SEQ ID NO: 513          moltype = AA  length = 112
FEATURE                 Location/Qualifiers
REGION                  1..112
                        note = mice-172
source                  1..112
                        mol_type = protein
                        organism = synthetic construct
SEQUENCE: 513
DVVMTQTPLS LPVSLGDQAS ISCRSSQSVV HNNGNTYLEW YLQKPGQSPK LLIYKVSNRF  60
SGVPDRFSGS GSGTDFTLKI SRVEAEDLGV YYCFQGSHVP YTFGGGTKLE LK          112

SEQ ID NO: 514          moltype = AA  length = 112
FEATURE                 Location/Qualifiers
REGION                  1..112
```

```
                        note = mice-173
source                  1..112
                        mol_type = protein
                        organism = synthetic construct
SEQUENCE: 514
DVVMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 515          moltype = AA  length = 112
FEATURE                 Location/Qualifiers
REGION                  1..112
                        note = mice-174
source                  1..112
                        mol_type = protein
                        organism = synthetic construct
SEQUENCE: 515
DVVMTQTPLS LPVSLGDQAS ISCRSSQSIV HTNGDTYLDW YLQKPGQSPK LLIYKVSNRF  60
SGVPDRFSGS GSGTDFTLKI SRVEAEDLGV YYCFQGSHVP YTFGGGTKLE IK          112

SEQ ID NO: 516          moltype = AA  length = 112
FEATURE                 Location/Qualifiers
REGION                  1..112
                        note = mice-175
source                  1..112
                        mol_type = protein
                        organism = synthetic construct
SEQUENCE: 516
DVVMTQTPLS LPVSLGDQAS ISCRSSQSIV HDNGDTYLEW YLQKPGQSPK LLIYKVSNRF  60
SGVPDRFSGS GSGTDFTLKI NRVEAEDLGV YYCFQGSHVP YTFGGGTKLE IK          112

SEQ ID NO: 517          moltype = AA  length = 112
FEATURE                 Location/Qualifiers
REGION                  1..112
                        note = mice-176
source                  1..112
                        mol_type = protein
                        organism = synthetic construct
SEQUENCE: 517
DVVMTQTPLS LPVSLGDQAS ISCRSSQNIV HSNGNTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 518          moltype = AA  length = 111
FEATURE                 Location/Qualifiers
REGION                  1..111
                        note = mice-177
source                  1..111
                        mol_type = protein
                        organism = synthetic construct
SEQUENCE: 518
DIVLTQSPAS LAVSLGQRAT ISCRASESVD DYGISFMHWY QQKPGQPPKL LIYRASNLES  60
GIPARFSGSG SRTDFTLTID PVETDDVATY YCQQSYEDPP TFGAGTKLEI K           111

SEQ ID NO: 519          moltype = AA  length = 111
FEATURE                 Location/Qualifiers
REGION                  1..111
                        note = mice-178
source                  1..111
                        mol_type = protein
                        organism = synthetic construct
SEQUENCE: 519
DIVLTQSPAS LAVSLGQRAT ISCRASESVD NYGISFMHWY QQKPGQPPKL LVYRASNLES  60
GIPARFSGSG SRTDFTLTIN PVETDDVATY YCQQSNKDPP TFGGGTKLEI K           111

SEQ ID NO: 520          moltype = AA  length = 111
FEATURE                 Location/Qualifiers
REGION                  1..111
                        note = mice-179
source                  1..111
                        mol_type = protein
                        organism = synthetic construct
SEQUENCE: 520
DIVLTQSPAS LAVSLGQRAT ISCRASESVD NYGISFMHWY QQKPGQPPKL LIYRASNLES  60
GIPARFSGSG SRTDFTLTIN PVETDDVATY YCQQSNKDPP TFGAGTKLEL K           111

SEQ ID NO: 521          moltype = AA  length = 110
FEATURE                 Location/Qualifiers
REGION                  1..110
                        note = mice-180
source                  1..110
```

```
                        mol_type = protein
                        organism = synthetic construct
SEQUENCE: 521
DIVLTQSPAS LAVSLGQRAT ISCRASKSVS TSSYSYMHWY QQKPGQPPKL LIKYASNLES  60
GVPARFSGSG SGTDFTLNIH PVEEEDAATY YCQHSREFPT FGGGTKLEIK             110

SEQ ID NO: 522          moltype = AA  length = 113
FEATURE                 Location/Qualifiers
REGION                  1..113
                        note = mice-181
source                  1..113
                        mol_type = protein
                        organism = synthetic construct
SEQUENCE: 522
DVVMTQTPLS LPVSLGDQAS ISCRSSQSIV HSNGDTYLDW YLEKPGQSPK LLIYKVSNRF  60
SGVPDRFSGS GSGTDFTLKI SRVEAEDLGV YYCFQGSHVP YTFGGGTKLE IKR         113

SEQ ID NO: 523          moltype = AA  length = 112
FEATURE                 Location/Qualifiers
REGION                  1..112
                        note = mice-182
source                  1..112
                        mol_type = protein
                        organism = synthetic construct
SEQUENCE: 523
DVVMTQTPLS LPVSLGDQAS ISCRSSQSIV HNNGDTYLDW YLQKPGQSPK LLIYKVSNRF  60
SGVPDRFSGS GSGTDFTLKI SRVEAEDLGV YYCFQGSHVP YTFGGGTKLE LK          112

SEQ ID NO: 524          moltype = AA  length = 112
FEATURE                 Location/Qualifiers
REGION                  1..112
                        note = mice-183
source                  1..112
                        mol_type = protein
                        organism = synthetic construct
SEQUENCE: 524
DVVMTQTPLS LPVSLGDQAS ISCRSSQSIV HGNGNTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 525          moltype = AA  length = 112
FEATURE                 Location/Qualifiers
REGION                  1..112
                        note = mice-184
source                  1..112
                        mol_type = protein
                        organism = synthetic construct
SEQUENCE: 525
DVVMTQTPLS LPVSLGDQAS ISCRSSQNII HSNGDTYLDW FLQKPGQSPK LLIYKVSNRF  60
SGVPDRFSGS GSGTDFTLKI SRVEAEDLGV YYCFQGSHVP YTFGGGTKLE IK          112

SEQ ID NO: 526          moltype = AA  length = 113
FEATURE                 Location/Qualifiers
REGION                  1..113
                        note = mice-185
source                  1..113
                        mol_type = protein
                        organism = synthetic construct
SEQUENCE: 526
DVVMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP YTFGRGDQAG NKT         113

SEQ ID NO: 527          moltype = AA  length = 112
FEATURE                 Location/Qualifiers
REGION                  1..112
                        note = mice-186
source                  1..112
                        mol_type = protein
                        organism = synthetic construct
SEQUENCE: 527
DVVMTQTPLS LPVSLGDQAS ISCRSSQSIV HSNGDTYLEW YLQKPGQSPK LLIYKVSNRF  60
SGVPDRFSGS GSGTDFTLKI SRVEAEDLGI YYCFQGSHVP YTFGGGTKLE IK          112

SEQ ID NO: 528          moltype = AA  length = 112
FEATURE                 Location/Qualifiers
REGION                  1..112
                        note = mice-187
source                  1..112
                        mol_type = protein
                        organism = synthetic construct
```

```
SEQUENCE: 528
DVVMTQTPLS LPVSLGNQAS ISCRSSQDIV HTNGDTYLDW YLQKPGQSPK LLIYKVSNRF  60
SGVPDRFSGS GSGTDFTLKI NRVEAEDLGV YYCFQGSHVP YTFGGGTKLE LK          112

SEQ ID NO: 529         moltype = AA  length = 112
FEATURE                Location/Qualifiers
REGION                 1..112
                       note = mice-188
source                 1..112
                       mol_type = protein
                       organism = synthetic construct
SEQUENCE: 529
DVVMTQTPLS LPVSLGDQAS ISCRSSQSIV HSNGDTYLDW FLQKPGQSPK LLIYKVSNRF  60
SGVPDRFSGS GSGTDFTLKI SRVEAEDLGV YYCFQGSHVP YTFGGGTKLE LK          112

SEQ ID NO: 530         moltype = AA  length = 112
FEATURE                Location/Qualifiers
REGION                 1..112
                       note = mice-189
source                 1..112
                       mol_type = protein
                       organism = synthetic construct
SEQUENCE: 530
DVVMTQTPLY LPVSLGDQAS ISCRSSQSIV HSNGDTYLDW FLQKPGQSPK LLIYKVSNRF  60
SGVPDRFSGS GSGTDFTLKI SRVEAEDLGV YYCFQGSHVP YTFGGGTKLE LK          112

SEQ ID NO: 531         moltype = AA  length = 112
FEATURE                Location/Qualifiers
REGION                 1..112
                       note = mice-190
source                 1..112
                       mol_type = protein
                       organism = synthetic construct
SEQUENCE: 531
DVVMTQTPLS LPVSLGDQAS ISCRSSQTIV HSNGDTYLDW YLQKPGQSPK LLISKVSNRF  60
SGVPDRFSGS GSGTDFTLKI SSVEAEDLGV YYCFQGSHVP YTFGGGTKLE IK          112

SEQ ID NO: 532         moltype = AA  length = 112
FEATURE                Location/Qualifiers
REGION                 1..112
                       note = mice-191
source                 1..112
                       mol_type = protein
                       organism = synthetic construct
SEQUENCE: 532
DVVMTQTPLS LPVSLADQAS ISCRSSQSIV HDNGDTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 533         moltype = AA  length = 112
FEATURE                Location/Qualifiers
REGION                 1..112
                       note = mice-192
source                 1..112
                       mol_type = protein
                       organism = synthetic construct
SEQUENCE: 533
DVVMTQTPLS LPVSLGDQAS ISCRSSQSIV HNNGDTYLDW YLEKPGQSPK LLIYKVSNRF  60
SGVPDRFSGS GSGTDFTLKI SRVEAEDLGV YYCFQGSHVP YTFGGGTKLE IK          112

SEQ ID NO: 534         moltype = AA  length = 112
FEATURE                Location/Qualifiers
REGION                 1..112
                       note = mice-193
source                 1..112
                       mol_type = protein
                       organism = synthetic construct
SEQUENCE: 534
DVVMTQTPLS LPVSLGDQAS ISCRSSQNIV HNNGDTYLDW FLQKPGQSPK LLIYKVSNRF  60
SGVPDRFSGS GSGTDFTLKI SRVEAEDLGV YYCFQGSHVP YTFGGGTKLE LK          112

SEQ ID NO: 535         moltype = AA  length = 112
FEATURE                Location/Qualifiers
REGION                 1..112
                       note = mice-194
source                 1..112
                       mol_type = protein
                       organism = synthetic construct
SEQUENCE: 535
DVVMTQTPLS LPVSLGDQAS ISCKSSQSIV HSNGNTYLEW YLQKPGQSPK LLIYKVSNRF  60
```

```
SGVPDRFSGS GSGTDFTLKI SRVEAEDLGV YYCFQGSHVP YTFGGGTKLE IK         112

SEQ ID NO: 536         moltype = AA  length = 112
FEATURE                Location/Qualifiers
REGION                 1..112
                       note = mice-195
source                 1..112
                       mol_type = protein
                       organism = synthetic construct
SEQUENCE: 536
DVVMTQTPLS LPVSLGDQAS ISCRSSQNIV HSNGDTYLEW YLQKPGQSPK LLIYKVSNRF  60
SGVPDRFSGS GSGTDFTLKI SRVEAEDLGV YYCFQGSYVP YTFGGGTKLE IK         112

SEQ ID NO: 537         moltype = AA  length = 112
FEATURE                Location/Qualifiers
REGION                 1..112
                       note = mice-196
source                 1..112
                       mol_type = protein
                       organism = synthetic construct
SEQUENCE: 537
DVVMTQTPLS LPVSLGDQAS ISCRSSQNIV HSNGDTYLEW YLQKPGQSPK LLIYKVSNRF  60
SGVPDRFSGS GSGTDFTLKI SRVEAEDLGV YYCFQGSHVP YTFGGGTKLE IK         112

SEQ ID NO: 538         moltype = AA  length = 112
FEATURE                Location/Qualifiers
REGION                 1..112
                       note = mice-197
source                 1..112
                       mol_type = protein
                       organism = synthetic construct
SEQUENCE: 538
DVVMTQTPLS LPVSLGDQAS ISCRSSQNIV HSNGDTYLDW FLQKPGQSPK LLIYKVSNRF  60
SGVPDRFSGS GSGTDFTLKI SRVEAEDLGV YYCFQGSHVP YTFGGGTKLE IK         112

SEQ ID NO: 539         moltype = AA  length = 112
FEATURE                Location/Qualifiers
REGION                 1..112
                       note = mice-198
source                 1..112
                       mol_type = protein
                       organism = synthetic construct
SEQUENCE: 539
DVVMTQTPLS LPVSLGDQAS ISCRSSQSIV HSNGDTYLDW FLQKPGQSPK LLIYKVSNRF  60
SGVPDRFSGS GSGTDFTLKI SRVESEDLGV YYCFQGSHDP YTFGGGTKLE IK         112

SEQ ID NO: 540         moltype = AA  length = 112
FEATURE                Location/Qualifiers
REGION                 1..112
                       note = mice-199
source                 1..112
                       mol_type = protein
                       organism = synthetic construct
SEQUENCE: 540
DVVMTQTPLS LPVSLGDQAS ISCRSSQSIV HSNGNTYLEW YLQKPGQSPK LLIYKVSDRF  60
SGVPDRFSGS GSGTDFTLKI SRVEAEDLGV YYCFQGSHVP YTFGGGTKLE IK         112

SEQ ID NO: 541         moltype = AA  length = 112
FEATURE                Location/Qualifiers
REGION                 1..112
                       note = mice-200
source                 1..112
                       mol_type = protein
                       organism = synthetic construct
SEQUENCE: 541
DVVMTQTPLS LPVSLGHQAS ISCRSSQSIV HSNGNTYLEW YLQKPGQSPK LLIYKVSNRF  60
SGVPDRFSGS GSGTDFTLKI SRVEAEDLGV YYCFQGSHVP YTFGGGTKLE LK         112

SEQ ID NO: 542         moltype = AA  length = 113
FEATURE                Location/Qualifiers
REGION                 1..113
                       note = mice-201
source                 1..113
                       mol_type = protein
                       organism = synthetic construct
SEQUENCE: 542
DVVMTQTPLS LPVSLADQAS ISCRSSQSIV HDNGDTYLEW YLQKPGQSPK LLIYKVSNRF  60
SGVPDRFSGS GSGTDFTLKI SRVEAEDLGV YYCFQGSHVP YTFGWRDQAG NKT        113
```

```
SEQ ID NO: 543         moltype = AA  length = 112
FEATURE                Location/Qualifiers
REGION                 1..112
                       note = mice-202
source                 1..112
                       mol_type = protein
                       organism = synthetic construct
SEQUENCE: 543
DVVMTQTPLS LPVSLGDQAS ISCRSSQSIV HSNGNTYLEW YLQKPGQSPK LLIYKASNRF  60
SGVPDRFSGS GSGTDFTLRI SSVEAEDLGV YYCFQGSHVP YTFGGGTKLE IK          112

SEQ ID NO: 544         moltype = AA  length = 112
FEATURE                Location/Qualifiers
REGION                 1..112
                       note = mice-203
source                 1..112
                       mol_type = protein
                       organism = synthetic construct
SEQUENCE: 544
DVVMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP LTFGAGTKLE LK          112

SEQ ID NO: 545         moltype = AA  length = 112
FEATURE                Location/Qualifiers
REGION                 1..112
                       note = mice-204
source                 1..112
                       mol_type = protein
                       organism = synthetic construct
SEQUENCE: 545
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVP FTFGSGTKLE IK          112

SEQ ID NO: 546         moltype = AA  length = 106
FEATURE                Location/Qualifiers
REGION                 1..106
                       note = mice-205
source                 1..106
                       mol_type = protein
                       organism = synthetic construct
SEQUENCE: 546
EIVLTQSPAL MSASPGEKVT ITCSASSSVS YMHWFQQKPG TSPKLWIYST SNLASGVPAR  60
FSGSGSGTSY SLTISRMEAE DAATYYCQQR SSYPFTFGSG TKLEIK                 106

SEQ ID NO: 547         moltype = AA  length = 113
FEATURE                Location/Qualifiers
REGION                 1..113
                       note = mice-206
source                 1..113
                       mol_type = protein
                       organism = synthetic construct
SEQUENCE: 547
DVVMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP YTFGGGTKLE IKR         113

SEQ ID NO: 548         moltype = AA  length = 112
FEATURE                Location/Qualifiers
REGION                 1..112
                       note = mice-207
source                 1..112
                       mol_type = protein
                       organism = synthetic construct
SEQUENCE: 548
DVVMTQTPLS LPVSLGDQAS ISCRSSQNIV HSNGDTYLDW YLQKPGQSPK LLISKVSNRF  60
SGVPDRFSGS GSGTDFTLKI SRVEAEDLGV YYCFQGSHVP YTFGGGTKLE IK          112

SEQ ID NO: 549         moltype = AA  length = 112
FEATURE                Location/Qualifiers
REGION                 1..112
                       note = mice-208
source                 1..112
                       mol_type = protein
                       organism = synthetic construct
SEQUENCE: 549
DVVMTQTPLS LPVSLGDQAS ISCRSSQNIV HSNGDTYLDW FLQKPGQSPK LLISKVSNRF  60
SGVPDRFSGS GSGTDFTLKI SRVEAEDLGV YYCFQGSHVP YTFGGGTKLE IK          112

SEQ ID NO: 550         moltype = AA  length = 112
FEATURE                Location/Qualifiers
```

```
REGION                  1..112
                        note = mice-209
source                  1..112
                        mol_type = protein
                        organism = synthetic construct
SEQUENCE: 550
DVVMTQTPLS LPVSLGDQAS ISCRSSQSIV HSNGDTYLDW FLQKPGQSPK LLIYKVSNRF  60
SGVPDRFSGS GSGTDFTLKI SRVEAEDLGV YYCFQGSHVP YTFGGGTKLE IK          112

SEQ ID NO: 551          moltype = AA  length = 112
FEATURE                 Location/Qualifiers
REGION                  1..112
                        note = mice-210
source                  1..112
                        mol_type = protein
                        organism = synthetic construct
SEQUENCE: 551
DVVMTQTPLS LPVSLGDQAS ISCRSSQNIV HSNGDTYLDW FLQKPGQSPK LLIYKVSNRF  60
SGVPDRFSGS GSGTDFTLKI SRVEAEDLGV YYCFQGSHVP YTFGGGTKLE LK          112

SEQ ID NO: 552          moltype = AA  length = 112
FEATURE                 Location/Qualifiers
REGION                  1..112
                        note = mice-211
source                  1..112
                        mol_type = protein
                        organism = synthetic construct
SEQUENCE: 552
DVVMTQTPLS LPVSLADQAS ISCRSSQSIV HDNGDTYLEW YLQKPGQSPR LLIYKVSNRF  60
SGVPDRFSGS GSGTDFTLKI NRVEAEDLGV YYCFQGSHVP YTFGGGTKLE IK          112

SEQ ID NO: 553          moltype = AA  length = 112
FEATURE                 Location/Qualifiers
REGION                  1..112
                        note = mice-212
source                  1..112
                        mol_type = protein
                        organism = synthetic construct
SEQUENCE: 553
DVVMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 554          moltype = AA  length = 112
FEATURE                 Location/Qualifiers
REGION                  1..112
                        note = mice-213
source                  1..112
                        mol_type = protein
                        organism = synthetic construct
SEQUENCE: 554
DVVMTQTPLS LPVSLGDQAS ISCRSSQSIV HNNGDTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 555          moltype = AA  length = 112
FEATURE                 Location/Qualifiers
REGION                  1..112
                        note = mice-214
source                  1..112
                        mol_type = protein
                        organism = synthetic construct
SEQUENCE: 555
DVVMTQTPLS LPVSLGDQAS ISCRSSQNIV HTNGDTYLDW YLQKPGQSPK LLIYKVSNRF  60
SGVPDRFSGS GSGTDFTLKI SRVEAEDLGV YYCFQGSHVP YTFGGGTKLE LK          112

SEQ ID NO: 556          moltype = AA  length = 112
FEATURE                 Location/Qualifiers
REGION                  1..112
                        note = mice-215
source                  1..112
                        mol_type = protein
                        organism = synthetic construct
SEQUENCE: 556
DVVMTQTPLS LPVSLGDQAS ISCRSSQTIV HSNGNTYLDW YLQKPGHSPQ LLIYKVSNRF  60
SGVPDRFSGS GSGTDFTLKI SRVEAEDLGV YYCFQGSHVP YTFGGGTKLE IK          112

SEQ ID NO: 557          moltype = AA  length = 112
FEATURE                 Location/Qualifiers
REGION                  1..112
                        note = mice-216
```

```
source                  1..112
                        mol_type = protein
                        organism = synthetic construct
SEQUENCE: 557
DVVMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP YTFGSGTKLE IK          112

SEQ ID NO: 558          moltype = AA  length = 112
FEATURE                 Location/Qualifiers
REGION                  1..112
                        note = mice-217
source                  1..112
                        mol_type = protein
                        organism = synthetic construct
SEQUENCE: 558
DVVMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP YTFGGGTKLE LK          112

SEQ ID NO: 559          moltype = AA  length = 112
FEATURE                 Location/Qualifiers
REGION                  1..112
                        note = mice-218
source                  1..112
                        mol_type = protein
                        organism = synthetic construct
SEQUENCE: 559
DVVMTQTPLS LPVSLGDQAS ISCRSSQNIV HSNGDTYLEW YLQKPGQSPK LLIYKVSSRF  60
SGVPDRFSGS GSGTDFTLKI SRVEAEDLGI YYCFQGSHVP YTFGGGTKLE IK          112

SEQ ID NO: 560          moltype = AA  length = 106
FEATURE                 Location/Qualifiers
REGION                  1..106
                        note = mice-219
source                  1..106
                        mol_type = protein
                        organism = synthetic construct
SEQUENCE: 560
EILLTQSPAI IAASPGEKVT ITCSASSSVS YMNWYQQKPG SSPKIWIYGI SNLASGVPAR  60
FSGSGSGTSF SFTINSMEAE DVATYYCQQR SSYPFTFGSG TKLEIK                106

SEQ ID NO: 561          moltype = AA  length = 112
FEATURE                 Location/Qualifiers
REGION                  1..112
                        note = mice-220
source                  1..112
                        mol_type = protein
                        organism = synthetic construct
SEQUENCE: 561
DVLMTQAPLS LPVSLGDQAS ISCRSNQTIV HSNGNTYLEW YLQKPGQSPK LLIYKVSNRF  60
SGVPDRFSGS GSGTDFTLKI SGVEAEDLGV YYCFQGSHVP LTFGAGTKLE LN          112

SEQ ID NO: 562          moltype = AA  length = 106
FEATURE                 Location/Qualifiers
REGION                  1..106
                        note = mice-221
source                  1..106
                        mol_type = protein
                        organism = synthetic construct
SEQUENCE: 562
ENVLTQSPAI MSASPGEKVT MTCSASSSVS YMHWYQQKSS TSPKLWIYDT SNLASGVPGR  60
FSGSGSGNSY SLTISSMEAE DVATYYCFQE NGHPFTFGGG TKLEMK                106

SEQ ID NO: 563          moltype = AA  length = 107
FEATURE                 Location/Qualifiers
REGION                  1..107
                        note = mice-222
source                  1..107
                        mol_type = protein
                        organism = synthetic construct
SEQUENCE: 563
DILMTQSPSS MSVSLGDTVS ITCHASQDIF SYIGWLQQKP GKSFKGLIHH GTNLEDGVPS  60
RFRGNGSGAD YSLTISSLES EDFADYYCVQ YAQFPYTFGG GTKLEIK               107

SEQ ID NO: 564          moltype = AA  length = 113
FEATURE                 Location/Qualifiers
REGION                  1..113
                        note = mice-223
source                  1..113
                        mol_type = protein
```

```
                        organism = synthetic construct
SEQUENCE: 564
DIVMTQSPSS LRVSAGEKVT MSCKSSQSLL NSGNQKNYLA WYQQKPGQPP KLLIYGASTR  60
ESGVPDRFTG SGSGTDFTLT ISSVQAEDLA VYYCQNDHSY PYTFGGGTKL EIK         113

SEQ ID NO: 565          moltype = AA  length = 108
FEATURE                 Location/Qualifiers
REGION                  1..108
                        note = mice-224
source                  1..108
                        mol_type = protein
                        organism = synthetic construct
SEQUENCE: 565
EIVLTQSPTT MAASPGEKIT ITCSTSSSII SNYSHWYQQK PGFSPKLLIY KTSNLPSGVP  60
ARFSGSGSGT SYSLTIGTME AEDAATYYCQ QGSDMPITFG AGTKLELK              108
```

ANTIBODIES AGAINST TL1A AND USES THEREOF

CROSS-REFERENCE TO RELATED APPLICATIONS

This application claims priority to Chinese patent application No. 2024111953052, filed Aug. 28, 2024, the disclosure of which is herein incorporated by reference in its entirety. This application also claims priority to Chinese patent application No. 2025101307369, filed Feb. 5, 2025, the disclosure of which is herein incorporated by reference in its entirety.

FIELD OF THE INVENTION

The present application relates to the field of biomedicine, and specifically to a TL1A antigen-binding protein.

INCORPORATION BY REFERENCE OF SEQUENCE LISTING

The content of the electronic sequence listing (HEXO_001_02US_SubSeqList_ST26.xml: Size: 795,360 bytes; and Date of Creation: Sep. 29, 2025) is herein incorporated by reference in its entirety.

BACKGROUND OF THE INVENTION

TL1A, also known as TNFSF15, is a member of the tumor necrosis factor (TNF) ligand superfamily, also known as vascular growth inhibitory factor (VEGI), which is a cytokine secreted mainly by vascular endothelial cells. TL1A possesses physiological activities such as activation of T-cells and promotion of secretion of inflammatory factors, and plays an important role in immune regulation and inflammatory diseases. Inflammation-related diseases can be treated by targeting antibodies to this target, and constructing effective antibodies for new drug development remains the biggest challenge.

SUMMARY OF THE INVENTION

In one aspect, the present application provides an isolated antigen-binding protein capable of specifically binding to TNF-like protein A (TL1A) comprising a heavy chain variable region (VH) comprising at least one heavy chain complementarity-determining region (the HCDR) comprising an amino acid sequence shown in SEQ ID NO: 1, SEQ ID NO:5, or SEQ ID NO: 14.

In some embodiments, the VH comprises an HCDR3 including an amino acid sequence as set forth in SEQ ID NO:14.

In some embodiments, the HCDR3 comprises an amino acid sequence as set forth in any one of SEQ ID NOs: 15-18.

I In some embodiments, the VH comprises an HCDR2 including an amino acid sequence as set forth in SEQ ID NO:5.

In some embodiments, the HCDR2 comprises an amino acid sequence as set forth in any one of SEQ ID NOs: 6-13.

In some embodiments, the VH comprises an HCDR1 including an amino acid sequence as set forth in SEQ ID NO:1.

In some embodiments, the HCDR1 comprises an amino acid sequence as set forth in any one of SEQ ID NO:2-4.

In some embodiments, the VH comprises the HCDR1 as set forth in SEQ ID NO:2, the HCDR2 as set forth in SEQ ID NO:6, and the HCDR3 as set forth in SEQ ID NO:15.

In some embodiments, the VH comprises the HCDR1 as set forth in SEQ ID NO:2, the HCDR2 as set forth in SEQ ID NO:7, and the HCDR3 as set forth in SEQ ID NO:15.

In some embodiments, the VH comprises the HCDR1 as set forth in SEQ ID NO:2, the HCDR2 as set forth in SEQ ID NO:8, and the HCDR3 as set forth in SEQ ID NO:15.

In some embodiments, the VH comprises the HCDR1 as set forth in SEQ ID NO:3, the HCDR2 as set forth in SEQ ID NO:6, and the HCDR3 as set forth in SEQ ID NO:15.

In some embodiments, the VH comprises the HCDR1 as set forth in SEQ ID NO:2, the HCDR2 as set forth in SEQ ID NO:6, and the HCDR3 as set forth in SEQ ID NO:16.

In some embodiments, the VH comprises the HCDR1 as set forth in SEQ ID NO:2, the HCDR2 as set forth in SEQ ID NO:6, and the HCDR3 as set forth in SEQ ID NO:17.

In some embodiments, the VH comprises the HCDR1 as set forth in SEQ ID NO:2, the HCDR2 as set forth in SEQ ID NO:6, and the HCDR3 as set forth in SEQ ID NO:18.

In some embodiments, the VH comprises the HCDR1 as set forth in SEQ ID NO:4, the HCDR2 as set forth in SEQ ID NO:6, and the HCDR3 as set forth in SEQ ID NO:15.

In some embodiments, the VH comprises the HCDR1 as set forth in SEQ ID NO:2, the HCDR2 as set forth in SEQ ID NO:9, and the HCDR3 as set forth in SEQ ID NO:15.

In some embodiments, the VH comprises the HCDR1 as set forth in SEQ ID NO:2, the HCDR2 as set forth in SEQ ID NO: 10, and the HCDR3 as set forth in SEQ ID NO: 15.

In some embodiments, the VH comprises the HCDR1 as set forth in SEQ ID NO:2, the HCDR2 as set forth in SEQ ID NO: 11, and the HCDR3 as set forth in SEQ ID NO: 15.

In some embodiments, the VH comprises the HCDR1 as set forth in SEQ ID NO:2, the HCDR2 as set forth in SEQ ID NO: 12, and the HCDR3 as set forth in SEQ ID NO: 15.

In some embodiments, the VH comprises the HCDR1 as set forth in SEQ ID NO:2, the HCDR2 as set forth in SEQ ID NO: 13, and the HCDR3 as set forth in SEQ ID NO: 15.

In some embodiments, the VH comprises the HCDR1 as set forth in SEQ ID NO:3, the HCDR2 as set forth in SEQ ID NO:6, and the HCDR3 as set forth in SEQ ID NO:16.

In some embodiments, the VH comprises the HCDR1 as set forth in SEQ ID NO:3, the HCDR2 as set forth in SEQ ID NO:6, and the HCDR3 as set forth in SEQ ID NO:17.

In some embodiments, the VH comprises the HCDR1 as set forth in SEQ ID NO:3, the HCDR2 as set forth in SEQ ID NO:9, and the HCDR3 as set forth in SEQ ID NO: 15.

In some embodiments, the VH comprises the HCDR1 as set forth in SEQ ID NO:3, the HCDR2 as set forth in SEQ ID NO: 10, and the HCDR3 as set forth in SEQ ID NO: 15.

In some embodiments, the VH comprises the HCDR1 as set forth in SEQ ID NO:3, the HCDR2 as set forth in SEQ ID NO: 11, and the HCDR3 as set forth in SEQ ID NO: 15.

In some embodiments, the VH comprises the HCDR1 as set forth in SEQ ID NO:2, the HCDR2 as set forth in SEQ ID NO:9, and the HCDR3 as set forth in SEQ ID NO: 16.

In some embodiments, the VH comprises the HCDR1 as set forth in SEQ ID NO:2, the HCDR2 as set forth in SEQ ID NO: 10, and the HCDR3 as set forth in SEQ ID NO: 16.

In some embodiments, the VH comprises the HCDR1 as set forth in SEQ ID NO:2, the HCDR2 as set forth in SEQ ID NO: 11, and the HCDR3 as set forth in SEQ ID NO: 16.

In some embodiments, the VH comprises the HCDR1 as set forth in SEQ ID NO:2, the HCDR2 as set forth in SEQ ID NO: 12, and the HCDR3 as set forth in SEQ ID NO: 16.

In some embodiments, the VH comprises the HCDR1 as set forth in SEQ ID NO:2, the HCDR2 as set forth in SEQ ID NO: 10, and the HCDR3 as set forth in SEQ ID NO: 17.

In some embodiments, the VH comprises an HFR1 including an amino acid sequence as set forth in SEQ ID NO:19.

In some embodiments, the HFR1 is selected from an amino acid sequence shown in any one of the SEQ ID NOs: 20-28.

In some embodiments, the VH comprises the HFR2 including an amino acid sequence as set forth in SEQ ID NO:29.

In some embodiments, the HFR2 is selected from an amino acid sequence shown in any one of the SEQ ID NOs: 30-32.

In some embodiments, the VH comprises HFR3 including an amino acid sequence as set forth in SEQ ID NO:33.

In some embodiments, the HFR3 is selected from an amino acid sequence shown in any one of SEQ ID NOs: 34-40.

In some embodiments, the VH contains HFR4 including an amino acid sequence shown in SEQ ID NO: 41.

In some embodiments, the VH comprises HFR1 as set forth in SEQ ID NO:20, HFR2 as set forth in SEQ ID NO:30, HFR3 as set forth in SEQ ID NO:34, and HFR4 as set forth in SEQ ID NO:41.

In some embodiments, the VH comprises HFR1 as set forth in SEQ ID NO:21, HFR2 as set forth in SEQ ID NO:31, HFR3 as set forth in SEQ ID NO:35, and HFR4 as set forth in SEQ ID NO:41.

In some embodiments, the VH comprises HFR1 as set forth in SEQ ID NO:22, HFR2 as set forth in SEQ ID NO:32, HFR3 as set forth in SEQ ID NO:35, and HFR4 as set forth in SEQ ID NO:41.

In some embodiments, the VH comprises HFR1 as set forth in SEQ ID NO:23, HFR2 as set forth in SEQ ID NO:31, HFR3 as set forth in SEQ ID NO:3636NO: 35, and HFR4 as set forth in SEQ ID NO: 41.

In some embodiments, the VH comprises HFR1 as set forth in SEQ ID NO:23, HFR2 as set forth in SEQ ID NO:31, HFR3 as set forth in SEQ ID NO:37, and HFR4 as set forth in SEQ ID NO:41.

In some embodiments, the VH comprises HFR1 as set forth in SEQ ID NO:23, HFR2 as set forth in SEQ ID NO:31, HFR3 as set forth in SEQ ID NO:35, and HFR4 as set forth in SEQ ID NO:41.

In some embodiments, the VH comprises HFR1 as set forth in SEQ ID NO:24, HFR2 as set forth in SEQ ID NO:31, HFR3 as set forth in SEQ ID NO:38, and HFR4 as set forth in SEQ ID NO:41.

In some embodiments, the VH comprises HFR1 as set forth in SEQ ID NO: 25, HFR2 as set forth in SEQ ID NO: 31, HFR3 as set forth in SEQ ID NO: 37, and HFR4 as set forth in SEQ ID NO: 41.

In some embodiments, the VH comprises HFR1 as set forth in SEQ ID NO:25, HFR2 as set forth in SEQ ID NO:31, HFR3 as set forth in SEQ ID NO:39, and HFR4 as set forth in SEQ ID NO:41.

In some embodiments, the VH comprises HFR1 as set forth in SEQ ID NO:25, HFR2 as set forth in SEQ ID NO:31, HFR3 as set forth in SEQ ID NO:40, and HFR4 as set forth in SEQ ID NO:41.

In some embodiments, the VH comprises HFR1 as set forth in SEQ ID NO:26, HFR2 as set forth in SEQ ID NO:31, HFR3 as set forth in SEQ ID NO:35, and HFR4 as set forth in SEQ ID NO:41.

In some embodiments, the VH comprises HFR1 as set forth in SEQ ID NO:25, HFR2 as set forth in SEQ ID NO:31, HFR3 as set forth in SEQ ID NO:35, and HFR4 as set forth in SEQ ID NO:41.

In some embodiments, the VH comprises HFR1 as set forth in SEQ ID NO: 27, HFR2 as set forth in SEQ ID NO: 31, HFR3 as set forth in SEQ ID NO: 35, and HFR4 as set forth in SEQ ID NO: 41.

In some embodiments, the VH comprises HFR1 as set forth in SEQ ID NO:28, HFR2 as set forth in SEQ ID NO:31, HFR3 as set forth in SEQ ID NO:35, and HFR4 as set forth in SEQ ID NO:41.

In some embodiments, the isolated antigen-binding proteins further comprises a light chain variable region (VL) that comprises at least one light chain complementarity-determining region (LCDR) comprising an amino acid sequence selected from SEQ ID NO:42, SEQ ID NO:43, and SEQ ID NO: 44.

In some embodiments, the VL comprises LCDR3 including an amino acid sequence as set forth in SEQ ID NO:44.

In some embodiments, the VL comprises LCDR2 including an amino acid sequence as set forth in SEQ ID NO:43.

In some embodiments, the VL comprises LCDR1 including an amino acid sequence as set forth in SEQ ID NO:42.

in some embodiments, the VL comprises the LFR1 including an amino acid sequence as set forth in SEQ ID NO:45.

In some embodiments, the LFR1 comprises an amino acid sequence as set forth in any one of SEQ ID NOs: 46-47.

In some embodiments, the VL comprises LFR2, which comprises the amino acid sequence of SEQ ID NO:48.

In some embodiments, the LFR2 comprises an amino acid sequence shown in any one of the SEQ ID NOs: 49-52.

In some embodiments, the VL contains the LFR3, which comprises the amino acid sequence of SEQ ID NO:53.

In some embodiments, the LFR3 comprises an amino acid sequence as set forth in any one of SEQ ID NOs: 54-57.

In some embodiments, the VL contains the amino acid sequence of the LFR4, which comprises SEQ ID NO:58.

In some embodiments, the LFR1 comprises an amino acid sequence shown in any one of the SEQ ID NOs: 59-61.

In some embodiments, the VL comprises the LFR1 as set forth in SEQ ID NO:46, the LFR2 as set forth in SEQ ID NO:49, the LFR3 as set forth in SEQ ID NO:54, and the LFR4 as set forth in SEQ ID NO:59.

In some embodiments, the VL comprises the LFR1 as set forth in SEQ ID NO: 47, the LFR2 as set forth in SEQ ID NO: 50, the LFR3 as set forth in SEQ ID NO: 55, and the LFR4 as set forth in SEQ ID NO: 60.

In some embodiments, the VL comprises the LFR1 as set forth in SEQ ID NO:47, the LFR2 as set forth in SEQ ID NO:51, the LFR3 as set forth in SEQ ID NO:56, and the LFR4 as set forth in SEQ ID NO:61.

In some embodiments, the VL comprises the LFR1 as set forth in SEQ ID NO:47, the LFR2 as set forth in SEQ ID NO:52, the LFR3 as set forth in SEQ ID NO:57, and the LFR4 as set forth in SEQ ID NO:61.

In some embodiments, the VL comprises the LFR1 as set forth in SEQ ID NO: 47, the LFR2 as set forth in SEQ ID NO: 52, the LFR3 as set forth in SEQ ID NO: 56, and the LFR4 as set forth in SEQ ID NO: 61.

In some embodiments, the VH comprises sequences as set forth in any one of SEQ ID NOs: 62-99.

In some embodiments, the VL comprises sequences as set forth in any one of SEQ ID NOs: 102-106.

In some embodiments, the isolated antigen-binding protein includes VH including HCDR1 as set forth in SEQ ID NO: 2, HCDR2 as set forth in SEQ ID NO: 6, HCDR3 as set forth in SEQ ID NO: 15, and VL including LCDR1 as set forth in SEQ ID NO: 42, LCDR2 as set forth in SEQ ID NO: 43, and LCDR3 as set forth in SEQ ID NO: 44.

In some embodiments, the isolated antigen-binding protein includes VH as set forth in SEQ ID NO: 70 and VL as set forth in SEQ ID NO: 106.

In another aspect, the present application provides an isolated antigen-binding protein capable of specifically binding to TNF-like protein A (TL1A) comprising a heavy chain variable region (VH) comprising at least one heavy chain complementarity-determining region (HCDR) comprising an amino acid sequence selected from SEQ ID NO: 107, SEQ ID NO:115, and SEQ ID NO:120.

In some embodiments, the VH comprises HCDR3 including an amino acid sequence as set forth in SEQ ID NO:120.

In some embodiments, the VH comprises HCDR2 including an amino acid sequence as set forth in SEQ ID NO:115.

In some embodiments, the HCDR2 comprises an amino acid sequence as set forth in any one of SEQ ID NOs: 116-119.

In some embodiments, the VH comprises HCDR1 including an amino acid sequence as set forth in SEQ ID NO:107.

In some embodiments, the HCDR1 comprises an amino acid sequence as set forth in any one of SEQ ID NOs: 108-114.

In some embodiments, the VH comprises the HCDR1 as set forth in SEQ ID NO:108, the HCDR2 as set forth in SEQ ID NO:116, and the HCDR3 as set forth in SEQ ID NO: 120.

In some embodiments, the VH comprises the HCDR1 as set forth in SEQ ID NO:109, the HCDR2 as set forth in SEQ ID NO:118, and the HCDR3 as set forth in SEQ ID NO: 120.

In some embodiments, the VH comprises the HCDR1 as set forth in SEQ ID NO: 108, the HCDR2 as set forth in SEQ ID NO: 119, and the HCDR3 AS SHOWN IN SEQ ID NO: 120.

In some embodiments, the VH comprises the HCDR1 as set forth in SEQ ID NO:110, the HCDR2 as set forth in SEQ ID NO:118, and the HCDR3 as set forth in SEQ ID NO: 120.

In some embodiments, the VH comprises the HCDR1 as set forth in SEQ ID NO:111, the HCDR2 as set forth in SEQ ID NO:117, and the HCDR3 as set forth in SEQ ID NO: 120.

In some embodiments, the VH comprises the HCDR1 as set forth in SEQ ID NO:112, the HCDR2 as set forth in SEQ ID NO:117, and the HCDR3 as set forth in SEQ ID NO: 120.

In some embodiments, the VH comprises the HCDR1 as set forth in SEQ ID NO:113, the HCDR2 as set forth in SEQ ID NO:117, and the HCDR3 as set forth in SEQ ID NO:120.

In some embodiments, the VH comprises the HCDR1 as set forth in SEQ ID NO:108, the HCDR2 as set forth in SEQ ID NO:117, and the HCDR3 as set forth in SEQ ID NO:120.

In some embodiments, the VH comprises the HCDR1 as set forth in SEQ ID NO:114, the HCDR2 as set forth in SEQ ID NO:117, and the HCDR3 as set forth in SEQ ID NO:120.

In some embodiments, the VH comprises HFR1 including an amino acid sequence as set forth in SEQ ID NO:121.

In some embodiments, the HFR1 is selected from an amino acid sequence shown in any one of SEQ ID NOs: 122-132.

In some embodiments, the VH comprises HFR2 including an amino acid sequence as set forth in SEQ ID NO:133.

In some embodiments, the HFR2 is selected from an amino acid sequence shown in any one of SEQ ID NOs: 134-135, 30.

In some embodiments, the VH comprises HFR3 including an amino acid sequence as set forth in SEQ ID NO:136.

In some embodiments, the HFR3 is selected from an amino acid sequence shown in any one of SEQ ID NOs: 137-148.

In some embodiments, the VH comprises HFR4 including an amino acid sequence shown in SEQ ID NO: 149.

In some embodiments, the HFR4 is selected from an amino acid sequence shown in any one of SEQ ID NOs: 150-153, 41.

In some embodiments, the VH comprises HFR1 as set forth in SEQ ID NO: 122, HFR2 as set forth in SEQ ID NO: 134, HFR3 as set forth in SEQ ID NO: 137, and HFR4 as set forth in SEQ ID NO: 150.

In some embodiments, the VH comprises HFR1 as set forth in SEQ ID NO: 123, HFR2 as set forth in SEQ ID NO: 135, HFR3 as set forth in SEQ ID NO: 138, and HFR4 as set forth in SEQ ID NO: 41.

In some embodiments, the VH comprises HFR1 as set forth in SEQ ID NO: 124, HFR2 as set forth in SEQ ID NO: 135, HFR3 as set forth in SEQ ID NO: 139, and HFR4 as set forth in SEQ ID NO: 151.

In some embodiments, the VH comprises HFR1 as set forth in SEQ ID NO: 125, HFR2 as set forth in SEQ ID NO: 135, HFR3 as set forth in SEQ ID NO: 142, and HFR4 as set forth in SEQ ID NO: 41.

In some embodiments, the VH comprises HFR1 as set forth in SEQ ID NO: 123, HFR2 as set forth in SEQ ID NO: 135, HFR3 as set forth in SEQ ID NO: 140, and HFR4 as set forth in SEQ ID NO: 41.

In some embodiments, the VH comprises HFR1 as set forth in SEQ ID NO: 123, HFR2 as set forth in SEQ ID NO: 135, HFR3 as set forth in SEQ ID NO: 141, and HFR4 as set forth in SEQ ID NO: 41.

In some embodiments, the VH comprises HFR1 as set forth in SEQ ID NO: 126, HFR2 as set forth in SEQ ID NO: 135, HFR3 as set forth in SEQ ID NO: 142, and HFR4 as set forth in SEQ ID NO: 152.

In some embodiments, the VH comprises HFR1 as set forth in SEQ ID NO: 127, HFR2 as set forth in SEQ ID NO: 30, HFR3 as set forth in SEQ ID NO: 143, and HFR4 as set forth in SEQ ID NO: 41.

In some embodiments, the VH comprises HFR1 as set forth in SEQ ID NO: 128, HFR2 as set forth in SEQ ID NO: 30, HFR3 as set forth in SEQ ID NO: 144, and HFR4 as set forth in SEQ ID NO: 41.

In some embodiments, the VH comprises HFR1 as set forth in SEQ ID NO: 129, HFR2 as set forth in SEQ ID NO: 30, HFR3 as set forth in SEQ ID NO: 145, and HFR4 as set forth in SEQ ID NO: 41.

In some embodiments, the VH comprises HFR1 as set forth in SEQ ID NO: 127, HFR2 as set forth in SEQ ID NO: 30, HFR3 as set forth in SEQ ID NO: 146, and HFR4 as set forth in SEQ ID NO: 41.

In some embodiments, the VH comprises HFR1 as set forth in SEQ ID NO: 125, HFR2 as set forth in SEQ ID NO: 135, HFR3 as set forth in SEQ ID NO: 142, and HFR4 as set forth in SEQ ID NO: 152.

In some embodiments, the VH comprises HFR1 as set forth in SEQ ID NO: 130, HFR2 as set forth in SEQ ID NO: 30, HFR3 as set forth in SEQ ID NO: 147, and HFR4 as set forth in SEQ ID NO: 41.

In some embodiments, the VH comprises HFR1 as set forth in SEQ ID NO: 131, HFR2 as set forth in SEQ ID NO: 135, HFR3 as set forth in SEQ ID NO: 148, and HFR4 as set forth in SEQ ID NO: 153.

In some embodiments, the VH comprises HFR1 as set forth in SEQ ID NO:132, HFR2 as set forth in SEQ ID NO:30, HFR3 as set forth in SEQ ID NO:145, and HFR4 as set forth in SEQ ID NO: 41.

In some embodiments, the isolated antigen-binding protein further comprises a light chain variable region (VL) that comprises at least one light chain complementarity-determining region (LCDR) comprising an amino acid sequence selected from SEQ ID NO:154, SEQ ID NO:159, and SEQ ID NO:163.

In some embodiments, the VL comprises LCDR3 including an amino acid sequence as set forth in SEQ ID NOs: 163.

In some embodiments, the LCDR3 comprises an amino acid sequence shown in any one of the SEQ ID NOs: 164-168.

1 In some embodiments, the VL comprises LCDR2 including an amino acid sequence as set forth in SEQ ID NO:159.

In some embodiments, the LCDR2 comprises an amino acid sequence shown in any one of the SEQ ID NOs: 160-162.

In some embodiments, the VL comprises LCDR1 including an amino acid sequence as set forth in SEQ ID NO:154.

In some embodiments, the LCDR1 comprises an amino acid sequence shown in any one of the SEQ ID NOs: 155-158.

In some embodiments, the VL comprises LCDR1 as set forth in SEQ ID NO: 157, LCDR2 as set forth in SEQ ID NO: 161 and LCDR3 as set forth in SEQ ID NO: 164.

In some embodiments, the VL comprises LCDR1 as set forth in SEQ ID NO: 157, LCDR2 as set forth in SEQ ID NO: 162 and LCDR3 as set forth in SEQ ID NO: 164.

In some embodiments, the VL comprises LCDR1 as set forth in SEQ ID NO: 156, LCDR2 as set forth in SEQ ID NO: 161 and LCDR3 as set forth in SEQ ID NO: 164.

In some embodiments, the VL comprises LCDR1 as set forth in SEQ ID NO: 158, LCDR2 as set forth in SEQ ID NO: 160 and LCDR3 as set forth in SEQ ID NO: 164.

In some embodiments, the VL comprises LCDR1 as set forth in SEQ ID NO: 155, LCDR2 as set forth in SEQ ID NO: 160 and LCDR3 as set forth in SEQ ID NO: 164.

In some embodiments, the VL comprises LCDR1 as set forth in SEQ ID NO: 156, LCDR2 as set forth in SEQ ID NO: 162, and LCDR3 as set forth in SEQ ID NO: 164.

In some embodiments, the VL comprises LCDR1 as set forth in SEQ ID NO: 155, LCDR2 as set forth in SEQ ID NO: 160 and LCDR3 as set forth in SEQ ID NO: 165.

In some embodiments, the VL comprises LCDR1 as set forth in SEQ ID NO: 155, LCDR2 as set forth in SEQ ID NO: 160 and LCDR3 as set forth in SEQ ID NO: 166.

In some embodiments, the VL comprises LCDR1 as set forth in SEQ ID NO: 155, LCDR2 as set forth in SEQ ID NO: 160 and LCDR3 as set forth in SEQ ID NO: 167.

In some embodiments, the VL comprises LCDR1 as set forth in SEQ ID NO: 155, LCDR2 as set forth in SEQ ID NO: 160 and LCDR3 as set forth in SEQ ID NO: 168.

In some embodiments, the VL comprises LFR1 including an amino acid sequence of SEQ ID NO: 169.

In some embodiments, the LFR1 comprises an amino acid sequence as set forth in SEQ ID NOs: 170-179.

In some embodiments, the VL comprises LFR2 including an amino acid sequence of SEQ ID NO: 180.

In some embodiments, the LFR2 comprises an amino acid sequence as set forth in any one of SEQ ID NOs: 181-188.

In some embodiments, the VL comprises LFR3 including an amino acid sequence of SEQ ID NO: 189.

In some embodiments, the LFR3 comprises an amino acid sequence shown in SEQ ID NOs: 190-197, 57.

In some embodiments, the VL comprises LFR4 including an amino acid sequence of SEQ ID NO: 198.

In some embodiments, the LFR4 comprises an amino acid sequence indicated in SEQ ID NOs: 199-201, 61.

In some embodiments, the VL comprises the LFR1 as set forth in SEQ ID NO: 170, the LFR2 as set forth in SEQ ID NO:181, the LFR3 as set forth in SEQ ID NO:190, and the LFR4 as set forth in SEQ ID NO:199.

In some embodiments, the VL comprises the LFR1 as set forth in SEQ ID NO: 171, the LFR2 as set forth in SEQ ID NO:182, the LFR3 as set forth in SEQ ID NO:191, and the LFR4 as set forth in SEQ ID NO:200.

In some embodiments, the VL comprises the LFR1 as set forth in SEQ ID NO: 172, the LFR2 as set forth in SEQ ID NO:183, the LFR3 as set forth in SEQ ID NO:192, and the LFR4 as set forth in SEQ ID NO:61.

In some embodiments, the VL comprises the LFR1 as set forth in SEQ ID NO: 174, the LFR2 as set forth in SEQ ID NO:184, the LFR3 as set forth in SEQ ID NO:57, and the LFR4 as set forth in SEQ ID NO:199.

In some embodiments, the VL comprises the LFR1 as set forth in SEQ ID NO: 175, the LFR2 as set forth in SEQ ID NO: 185, the LFR3 as set forth in SEQ ID NO: 193, and the LFR4 as set forth in SEQ ID NO: 199.

In some embodiments, the VL comprises the LFR1 as set forth in SEQ ID NO: 176, the LFR2 as set forth in SEQ ID NO: 186, the LFR3 as set forth in SEQ ID NO: 194, and the LFR4 as set forth in SEQ ID NO: 199.

In some embodiments, the VL comprises the LFR1 as set forth in SEQ ID NO: 177, the LFR2 as set forth in SEQ ID NO: 187, the LFR3 as set forth in SEQ ID NO: 195, and the LFR4 as set forth in SEQ ID NO: 199.

In some embodiments, the VL comprises the LFR1 as set forth in SEQ ID NO: 178, the LFR2 as set forth in SEQ ID NO: 188, the LFR3 as set forth in SEQ ID NO: 196, and the LFR4 as set forth in SEQ ID NO: 199.

In some embodiments, the VL comprises the LFR1 as set forth in SEQ ID NO: 179, the LFR2 as set forth in SEQ ID NO: 187, the LFR3 as set forth in SEQ ID NO: 195, and the LFR4 as set forth in SEQ ID NO: 199.

In some embodiments, the VL comprises the LFR1 as set forth in SEQ ID NO: 173, the LFR2 as set forth in SEQ ID NO:183, the LFR3 as set forth in SEQ ID NO:192, and the LFR4 as set forth in SEQ ID NO:201.

In some embodiments, the VH comprises sequence as set forth in any one of SEQ ID NOs: 202-220, 332-334.

In some embodiments, the VL comprises sequence as set forth in any one of SEQ ID NOs: 221-234, 335-338.

In another aspect, the present application provides an isolated antigen-binding protein capable of specifically binding to TNF-like protein A (TL1A) comprising a heavy chain variable region (VH) comprising at least one heavy chain complementarity-determining region (HCDR) comprising an amino acid sequence selected from an amino acid sequence shown in SEQ ID NO:242, SEQ ID NO: 238, and SEQ ID NO:235.

In some embodiments, the VH comprises the HCDR3 including an amino acid sequence as set forth in SEQ ID NO:242.

In some embodiments, the VH comprises the HCDR2 including an amino acid sequence as set forth in SEQ ID NO:238.

In some embodiments, the HCDR2 comprises an amino acid sequence as set forth in any one of SEQ ID NOs: 239-241.

in some embodiments, the VH comprises the HCDR1 including an amino acid sequence of SEQ ID NO: 235.

In some embodiments, the HCDR1 comprises an amino acid sequence as set forth in any one of SEQ ID NOs: 236-237.

In some embodiments, the VH comprises the HCDR1 as set forth in SEQ ID NO:108, the HCDR2 as set forth in SEQ ID NO:116, and the HCDR3 as set forth in SEQ ID NO:120.

In some embodiments, the VH comprises the HCDR1 as set forth in SEQ ID NO: 236, the HCDR2 as set forth in SEQ ID NO: 239, and the HCDR3 as set forth in SEQ ID NO: 242.

In some embodiments, the VH comprises the HCDR1 as set forth in SEQ ID NO: 236, the HCDR2 as set forth in SEQ ID NO: 240, and the HCDR3 as set forth in SEQ ID NO: 242.

In some embodiments, the VH comprises the HCDR1 as set forth in SEQ ID NO:237, the HCDR2 as set forth in SEQ ID NO:241, and HCDR3 as set forth in SEQ ID NO:242.

In some embodiments, the VH comprises HFR1 including an amino acid sequence as set forth in SEQ ID NO:243.

In some embodiments, the HFR1 is selected from an amino acid sequence shown in any one of SEQ ID NOs: 244-250.

In some embodiments, the VH comprises HFR2 including an amino acid sequence as set forth in SEQ ID NO:251.

In some embodiments, the HFR2 is selected from an amino acid sequence shown in any one of SEQ ID NOs: 252-255.

In some embodiments, the VH contains HFR3 including an amino acid sequence of SEQ ID NO: 256.

In some embodiments, the HFR3 is selected from an amino acid sequence shown in any one of SEQ ID NOs: 257-262.

In some embodiments, the VH comprises HFR4 including an amino acid sequence shown in SEQ ID NO:263.

In some embodiments, the HFR4 is selected from an amino acid sequence shown in any one of SEQ ID NOs: 264-268.

In some embodiments, the VH comprises HFR1 as set forth in SEQ ID NO: 244, HFR2 as set forth in SEQ ID NO: 252, HFR3 as set forth in SEQ ID NO: 257, and HFR4 as set forth in SEQ ID NO: 264.

In some embodiments, the VH comprises HFR1 as set forth in SEQ ID NO: 245, HFR2 as set forth in SEQ ID NO: 252, HFR3 as set forth in SEQ ID NO: 258, and HFR4 as set forth in SEQ ID NO: 265.

In some embodiments, the VH comprises HFR1 as set forth in SEQ ID NO: 246, HFR2 as set forth in SEQ ID NO: 253, HFR3 as set forth in SEQ ID NO: 259, and HFR4 as set forth in SEQ ID NO: 268.

In some embodiments, the VH comprises HFR1 as set forth in SEQ ID NO: 246, HFR2 as set forth in SEQ ID NO: 254, HFR3 as set forth in SEQ ID NO: 260, and HFR4 as set forth in SEQ ID NO: 266.

In some embodiments, the VH comprises HFR1 as set forth in SEQ ID NO: 247, HFR2 as set forth in SEQ ID NO: 254, HFR3 as set forth in SEQ ID NO: 261, and HFR4 as set forth in SEQ ID NO: 268.

In some embodiments, the VH comprises HFR1 as set forth in SEQ ID NO: 248, HFR2 as set forth in SEQ ID NO: 252, HFR3 as set forth in SEQ ID NO: 258, and HFR4 as set forth in SEQ ID NO: 265.

In some embodiments, the VH comprises HFR1 as set forth in SEQ ID NO: 246, HFR2 as set forth in SEQ ID NO: 255, HFR3 as set forth in SEQ ID NO: 260, and HFR4 as set forth in SEQ ID NO: 268.

In some embodiments, the VH comprises HFR1 as set forth in SEQ ID NO: 245, HFR2 as set forth in SEQ ID NO: 252, HFR3 as set forth in SEQ ID NO: 258, and HFR4 as set forth in SEQ ID NO: 267.

In some embodiments, the VH comprises HFR1 as set forth in SEQ ID NO: 249, HFR2 as set forth in SEQ ID NO: 254, HFR3 as set forth in SEQ ID NO: 260, and HFR4 as set forth in SEQ ID NO: 268.

In some embodiments, the VH comprises HFR1 as set forth in SEQ ID NO: 250, HFR2 as set forth in SEQ ID NO: 253, HFR3 as set forth in SEQ ID NO: 262, and HFR4 as set forth in SEQ ID NO: 266.

In some embodiments, the isolated antigen-binding protein further comprises a light chain variable region (VL) comprising at least one light chain complementarity-determining region (LCDR) comprising an amino acid sequence selected from SEQ ID NO: 269, SEQ ID NO: 274, and SEQ ID NO: 277.

In some embodiments, the VL comprises LCDR3 including an amino acid sequence as set forth in SEQ ID NO:277.

In some embodiments, the VL comprises LCDR2 including an amino acid sequence as set forth in SEQ ID NO:274.

In some embodiments, the LCDR2 comprises an amino acid sequence shown in any one of the SEQ ID NO:275-276.

In some embodiments, the VL comprises LCDR1 including an amino acid sequence as set forth in SEQ ID NO:269.

In some embodiments, the LCDR1 comprises an amino acid sequence shown in any one of the SEQ ID NOs: 270-273.

In some embodiments, the VL comprises LCDR1 as set forth in SEQ ID NO: 270, LCDR2 as set forth in SEQ ID NO: 275 and LCDR3 as set forth in SEQ ID NO: 277.

In some embodiments, the VL comprises LCDR1 as set forth in SEQ ID NO: 271, LCDR2 as set forth in SEQ ID NO: 275 and LCDR3 as set forth in SEQ ID NO: 277.

In some embodiments, the VL comprises LCDR1 as set forth in SEQ ID NO: 272, LCDR2 as set forth in SEQ ID NO: 275 and LCDR3 as set forth in SEQ ID NO: 277.

In some embodiments, the VL comprises LCDR1 as set forth in SEQ ID NO: 273, LCDR2 as set forth in SEQ ID NO: 275 and LCDR3 as set forth in SEQ ID NO: 277.

In some embodiments, the VL comprises LCDR1 as set forth in SEQ ID NO: 271, LCDR2 as set forth in SEQ ID NO: 276 and LCDR3 as set forth in SEQ ID NO: 277.

In some embodiments, the VL contains the LFR1 including an amino acid sequence of SEQ ID NO: 278.

In some embodiments, the LFR1 comprises an amino acid sequence shown in SEQ ID NOs: 47, 173, 279-283.

In some embodiments, the VL comprises the LFR2 including an amino acid sequence as set forth in SEQ ID NO:284.

In some embodiments, the LFR2 comprises an amino acid sequence shown in SEQ ID NOs: 52, 285-287.

In some embodiments, the VL comprises the LFR3 including an amino acid sequence as set forth in SEQ ID NO:288.

In some embodiments, the LFR3 comprises an amino acid sequence shown in SEQ ID NOs: 289-293, 57.

In some embodiments, the VL comprises the LFR4 including an amino acid sequence as set forth in SEQ ID NO:294.

In some embodiments, the LFR4 comprises an amino acid sequence shown in SEQ ID NO:201, 295-296.

In some embodiments, the VL comprises the LFR1 as set forth in SEQ ID NO: 170, the LFR2 as set forth in SEQ ID NO:181, the LFR3 as set forth in SEQ ID NO:190, and the LFR4 as set forth in SEQ ID NO:199.

In some embodiments, the VL comprises the LFR1 as set forth in SEQ ID NO: 171, the LFR2 as set forth in SEQ ID NO:182, the LFR3 as set forth in SEQ ID NO:191, and the LFR4 as set forth in SEQ ID NO:200.

In some embodiments, the VL comprises the LFR1 as set forth in SEQ ID NO: 172, the LFR2 as set forth in SEQ ID NO:183, the LFR3 as set forth in SEQ ID NO:192, and the LFR4 as set forth in SEQ ID NO:61.

In some embodiments, the VL comprises the LFR1 as set forth in SEQ ID NO: 174, the LFR2 as set forth in SEQ ID NO:184, the LFR3 as set forth in SEQ ID NO:57, and the LFR4 as set forth in SEQ ID NO:199.

In some embodiments, the VL comprises the LFR1 as set forth in SEQ ID NO: 175, the LFR2 as set forth in SEQ ID NO: 185, the LFR3 as set forth in SEQ ID NO: 193, and the LFR4 as set forth in SEQ ID NO: 199.

In some embodiments, the VL comprises the LFR1 as set forth in SEQ ID NO: 176, the LFR2 as set forth in SEQ ID NO: 186, the LFR3 as set forth in SEQ ID NO: 194, and the LFR4 as set forth in SEQ ID NO: 199.

In some embodiments, the VL comprises the LFR1 as set forth in SEQ ID NO: 177, the LFR2 as set forth in SEQ ID NO: 187, the LFR3 as set forth in SEQ ID NO: 195, and the LFR4 as set forth in SEQ ID NO: 199.

In some embodiments, the VL comprises the LFR1 as set forth in SEQ ID NO: 178, the LFR2 as set forth in SEQ ID NO: 188, the LFR3 as set forth in SEQ ID NO: 196, and the LFR4 as set forth in SEQ ID NO: 199.

In some embodiments, the VL comprises the LFR1 as set forth in SEQ ID NO: 179, the LFR2 as set forth in SEQ ID NO: 187, the LFR3 as set forth in SEQ ID NO: 195, and the LFR4 as set forth in SEQ ID NO: 199.

In some embodiments, the VL comprises the LFR1 as set forth in SEQ ID NO: 173, the LFR2 as set forth in SEQ ID NO:183, the LFR3 as set forth in SEQ ID NO:192, and the LFR4 as set forth in SEQ ID NO:201.

In some embodiments, the VH comprises a sequence as set forth in any one of SEQ ID NOs: 202-220, 332-334.

In some embodiments, the VL comprises a sequences as set forth in any one of SEQ ID NOs: 221-234, 335-338.

In some embodiments, the isolated antigen-binding protein comprises a heavy chain constant region of IgG and/or the light chain constant region of human antibodies.

In some embodiments, the isolated antigen-binding protein comprising a heavy chain constant region of IgG1, IgG2, IgG3, or IgG4.

In some embodiments, the isolated antigen-binding protein comprising Kappa or Lambda light chain constant regions.

In some embodiments, Fc of the isolated antigen-binding protein is derived from IgG, IgM, IgA, IgD, or IgE.

In another aspect, the present application provides an isolated nucleic acid molecule encoding the previously isolated antigen-binding protein.

In another aspect, the present application provides an expression vector which comprises the aforementioned nucleic acids.

In another aspect, the present application provides a host cell comprising the aforementioned isolated nucleic acids and/or the expression vector.

In another aspect, the present application provides a composition comprising the aforementioned isolated antigen-binding protein and optionally a pharmaceutically acceptable carrier.

In another aspect, the application provides a method for preparing isolated antigen-binding protein TL1A, comprising: culturing the host cells claimed above, and recovering the isolated antigen-binding protein.

In another aspect, the present application provides a method for the treatment of TL1A-mediated disease or conditions, which comprises: administration of the aforementioned isolated antigen-binding protein, aforementioned isolated nucleic acids, and/or aforementioned expression vectors, aforementioned host cells, or aforementioned compositions.

In another aspect, the present application provides antigen-binding protein isolated as described above, nucleic acids isolated as described above, and/or expression vectors described above, host cells as described above, or combinations described above, which are used for the treatment of TL1A-mediated diseases or conditions.

In another aspect, the present application provides the use of the aforementioned isolated antigen-binding protein, aforementioned isolated nucleic acids, and/or aforementioned expression vectors, aforementioned host cells, or aforementioned compositions in the treatment of TL1A-mediated diseases or conditions.

The aforementioned isolated antigen-binding proteins, the aforementioned isolated nucleic acids, and/or the aforementioned expression vectors, aforementioned host cells, or the aforementioned combinations are used in the preparation of drugs for the treatment of TL1A-mediated diseases or conditions.

In some embodiments, the disease or condition mediated by TL1A is inflammatory disease.

In some embodiments, TL1A-mediated inflammatory disease is selected from one of the following: allergy, ankylosing spondylitis, asthma, atopic dermatitis, autoimmune diseases or disorders, cancer, celiac disease, chronic obstructive pulmonary disease (COPD), chronic peptic ulcer, cystic fibrosis, diabetes (e.g., type 1 diabetes and type 2 diabetes), glomerulonephritis, gout, hepatitis (e.g., active hepatitis), an immune-mediated disease or disorder, inflammatory bowel disease (IBD) such as Crohn's disease and ulcerative colitis, myositis, osteoarthritis, pelvic inflammatory disease (PID), multiple sclerosis, neurodegenerative diseases of aging, periodontal disease (e.g., periodontitis), preperfusion injury transplant rejection, psoriasis, pulmonary fibrosis (e.g., idiopathic pulmonary fibrosis), rheumatic disease, scleroderma, sinusitis, tuberculosis.

In some embodiments, the TL1A-mediated disease or condition is an autoimmune disease.

In some embodiments, TL1A-mediated autoimmune disease is selected from one of the following: Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenia purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal MotorNeuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenia purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Vogt-Koyanagi-Harada Disease.

In some embodiments, the disease or condition mediated by TL1A is cancer.

In some embodiments, TL1A-mediated cancer is selected from one or more of the following: Adenoid Cystic Carcinoma, Adrenal Gland Cancer, Amyloidosis, Anal Cancer, Ataxia-Telangiectasia, Atypical Mole Syndrome, Basal Cell Carcinoma, Bile Duct Cancer, Birt Hogg Dube Syndrome, Bladder Cancer, Bone Cancer, Brain Tumor, Breast Cancer, Breast Cancer in Men, Carcinoid Tumor, Cervical Cancer, Colorectal Cancer, Ductal Carcinoma, Endometrial Cancer, Esophageal Cancer, Gastric Cancer, Gastrointestinal Stromal Tumor (GIST), HER2-Positive Breast Cancer, Islet Cell Tumor, Juvenile Polyposis Syndrome, Kidney Cancer, Laryngeal Cancer, Leukemia-Acute Lymphoblastic Leukemia, Leukemia-Acute Lymphocytic (ALL), Leukemia-Acute Myeloid AML, Leukemia-Adult, Leukemia-Childhood, Leukemia-Chronic Lymphocytic (CLL), Leukemia-Chronic Myeloid (CIVIL), Liver Cancer, Lobular Carcinoma, Lung Cancer, Lung Cancer-Small Cell (SCLC), Lung Cancer-Non-small Cell (NSCLC), Lymphoma-Hodgkin's, Lymphoma-Non-Hodgkin's, Malignant Glioma, Melanoma, Meningioma, Multiple Myeloma, Myelodysplastic Syndrome (MDS), Nasopharyngeal Cancer, Neuroendocrine Tumor, Oral Cancer, Osteosarcoma, Ovarian Cancer, Pancreatic Cancer, Pancreatic Neuroendocrine Tumors, Parathyroid Cancer, Penile Cancer, Peritoneal Cancer, Peutz-Jeghers Syndrome, Pituitary Gland Tumor, Polycythemia Vera, Prostate Cancer, Renal Cell Carcinoma, Retinoblastoma, Salivary Gland Cancer, Sarcoma, Sarcoma-Kaposi, Skin Cancer, Small Intestine Cancer, Stomach Cancer, Testicular Cancer, Thymoma, Thyroid Cancer, Uterine (Endometrial) Cancer, Vaginal Cancer, and Wilms' Tumor.

Other aspects and advantages of the present application will become readily apparent to those skilled in the art from the following detailed description. Only exemplary embodiments of the present application are shown and described in the following detailed description. As will be recognized by those skilled in the art, the contents of the present application enable those skilled in the art to make modifications to the specific embodiments disclosed without departing from the spirit and scope of the present application to which the present application pertains. Accordingly, the drawings and description herein are to be regarded as illustrative in nature, and not as restrictive.

BRIEF DESCRIPTION OF THE DRAWINGS

Specific features of the present application to which the present application relates are as set forth in the appended claims. The features and advantages of the present application to which the present application relates will be better understood by reference to the exemplary embodiments and drawings described in detail below. A brief description of the drawings is as follows:

DETAILED DESCRIPTION OF THE INVENTION

Figure 1A:
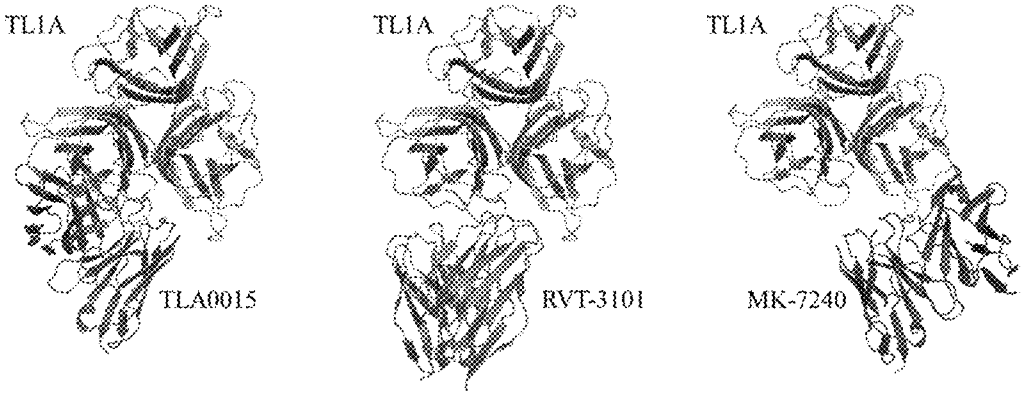
FIG. 1A shows the predicted structure of different anti-TL1A antibodies binding with TL1A antigen as described in the present application (top view)

The embodiments of the invention of the present application are illustrated by particular examples. Other advantages and effects of the present application will become readily apparent to those skilled in the art from disclosure of the present specification.

Definition of Terms

In the present application, the term "isolated" generally refers to a product obtained from a natural state by artificial means. If an "isolated" substance or component occurs in nature, it may be altered from its natural environment, or the substance may be isolated from its natural environment, or both. For example, an unisolated polynucleotide or polypeptide naturally occurs in a living animal and the same polynucleotide or polypeptide isolated from its natural state in high purity is the to be isolated. The term "isolated" does not exclude the admixture of artificial or synthetic substances, nor the presence of other impure substances which do not affect the activity of the substance.

In the present application, the term "antigen-binding protein" generally refers to a polypeptide molecule capable of specifically recognizing and/or neutralizing a particular antigen. In the present application, the term "antigen-binding protein" may include an "antibody" or an "antigen-binding fragment". For example, the antibody may comprise an immunoglobulin composed of at least two heavy (H) chains and two light (L) chains interconnected by disulfide bonds, and may include any molecule comprising an antigen-binding portion thereof. The term "antibody" may include monoclonal antibodies, antibody fragments, or antibody derivatives, including, but not limited to, murine antibodies, human antibodies (fully human antibodies), humanized antibodies, chimeric antibodies, single chain antibodies (e.g., scFv), and antibody fragments that bind to an antigen (e.g., Fab, Fab', and (Fab)2 fragments). The term "antibody" may also include all recombinant forms of antibodies, such as antibodies expressed in prokaryotic cells, non-glycosylated antibodies, and any antigen-binding antibody fragments and derivatives thereof described herein. Each heavy chain may be composed of a heavy chain variable region and a heavy chain constant region. Each light chain may be composed of a light chain variable region and a light chain constant region. The VH and VL regions can be further distinguished as hypervariable regions called complementarity determining regions (CDRs), interspersed with more conserved regions called framework regions (FRs). Each VH and VL may be composed of three CDRs and four FRs, which may be arranged from amino-terminus to carboxy-terminus in the following order: FR1, CDR1, FR2, CDR2, FR3, CDR3, and FR4. The variable regions of the heavy and light chains contain binding domains that interact with an antigen. The constant region of an antibody can mediate the binding of the immunoglobulin to host tissues or factors, including various cells of the immune system (e.g., effector cells) and the first component of the classical complement system (C1q). The exact boundaries of the CDRs have been defined differently for different systems. The system described by Kabat (Kabat et al., Sequences of Proteins of Immunological Interest (National Institutes of Health, Bethesda, Md. (1987) and (1991)) provides not only an unambiguous residue numbering system applicable to any variable region of an antigen-binding fragment, but also provides precise residue boundaries defining CDRs. These CDRs may be referred to as Kabat CDRs. Chothia and co-workers (Chothia and Lesk, J. Mol. Biol. 196:901-917 (1987) and Chothia et al., Nature 342: 877-883 (1989)) found that certain sub-portions within Kabat CDRs adopt nearly identical conformations in the backbone of a peptide despite the large diversity at the amino acid sequence level. These sub-portions are designated as L1, L2, and L3 or H1, H2, and H3, where "L" and "H" refer to the light chain and heavy chain regions, respectively. These regions may be referred to as Chothia CDRs, which have boundaries that overlap with Kabat CDRs. Other boundaries that define CDRs and overlap with Kabat CDRs have been described by Padlan (FASEB J. 9:133-139 (1995)) and MacCallum (J Mol Biol 262 (5): 732-45 (1996)). In addition, other CDR boundary definitions may not strictly follow one of the above systems, but will still overlap with Kabat CDRs, although they may be shortened or lengthened in light of prediction or experimental findings that a particular residue or group of residues or even the entire CDRs, do not significantly affect the antigen binding. In the present application, the Kabat numbering system is used.

In the present application, the term "antigen-binding fragment" generally refers to one or more fragments of an antibody that function to specifically bind to an antigen. The antigen-binding function of an antibody can be achieved by a full-length fragment of the antibody. The antigen-binding function of an antibody may also be achieved by: a heavy chain comprising a fragment of Fv, scFv, dsFv, Fab, Fab' or F(ab')2, or a light chain comprising a fragment of Fv, scFv, dsFv, Fab, Fab', or F(ab')2. (1) An Fab fragment, i.e., a monovalent fragment consisting of the VL, VH, CL, and CH domains: (2) an F(ab') 2 fragment, a bivalent fragment comprising two Fab fragments linked by a disulfide bond at the hinge region: (3) an Fd fragment consisting of the VH and CH domains: (4) an Fv fragment consisting of the VL and VH domains of a single arm of an antibody: (5) a dAb fragment consisting of VH domains (Ward et al., (1989) Nature 341:544-546): (6) an isolated complementarity determining region (CDR), and (7) a combination of two or more isolated CDRs which may optionally be joined by a linker. For example, monovalent single chain molecules Fv (scFv) formed by the pairing of VL and VH may also be included (see, Bird et al., (1988) Science 242:423-426; and Huston et al., (1988) Proc. Natl. Acad. Sci. 85:5879-5883). For example, a class of antibody VHH lacking the antibody light chain but only the heavy chain variable region can also be included (see, e.g., Kang Xiaozhen et al., Chinese Journal of Biotechnology, 2018, 34 (12): 1974-1984). The "antigen-binding fragment" may also include an immunoglobulin fusion protein comprising a binding domain selected from the group consisting of: (1) a binding domain polypeptide fused to an immunoglobulin hinge region polypeptide: (2) an immunoglobulin heavy chain CH2 constant region fused to the hinge region; and (3) an immunoglobulin heavy chain CH3 constant region fused to the CH2 constant region.

In the present application, the term "monoclonal antibody" generally refers to a population of substantially homologous antibodies, i.e., the individual antibodies comprising the population are identical except for possible naturally occurring mutations that may be present in minor amounts. Monoclonal antibodies are highly specific, being directed against a single antigenic site. For example, the monoclonal antibodies can be prepared by hybridoma techniques or can be produced in bacteria, eukaryotic animal or plant cells using recombinant DNA methods, or can be derived from phage antibody libraries using the techniques, for example, described in Clackson et al., Nature, 352:624-628 (1991) and Marks et al., Mol. Biol., 222:581-597 (1991).

In the present application, the term "chimeric antibody" generally refers to an antibody in which a portion of the amino acid sequence of each heavy or light chain is homologous to the corresponding amino acid sequence in an antibody from a particular species, or belongs to a particular class, while the remaining segments of the chain are homologous to the corresponding sequence in another species. For example, the variable regions of both the light and heavy chains are derived from the variable region of an antibody of one animal species (e.g., mouse, rat, etc.), while the constant portions are homologous to antibody sequences from another species (e.g., human). For example, to obtain chimeric antibodies, non-human-derived B cells or hybridoma cells can be used to generate variable regions, while which the constant regions in combination therewith are of human origin. The variable region has the advantage of being easy to prepare and its specificity is not influenced by the origin of the constant region with which it is combined. Also, since the constant region of the chimeric antibody can be derived from human, the chimeric antibodies are less likely to elicit an immune response upon injection than using antibodies whose constant regions are of non-human origin.

In the present application, the term "humanized antibody" generally refers to a chimeric antibody that comprises fewer sequences from non-human immunoglobulins, thereby reducing the immunogenicity of a xenogenous antibody when introduced into humans, while maintaining the full antigen-binding affinity and specificity of the antibody. For example, non-human binding domains can be humanized using the technical means, such as CDR transplantion (Jones et al., Nature 321: 522 (1986)) and variants thereof: including "reshaping", (Verhoeyen, et al., 1988 Science 239:1534-1536: Riechmann, et al., 1988 Nature 332:323-337: Tempest, et al., Bio/Technol 1991 9:266-271), "hyperchimerization" (Queen, et al., 1989 Proc Natl Acad Sci USA 86:10029-10033: Co, et al., 1991 Proc Natl Acad Sci USA 88:2869-2873: Co, et al., 1992 J Immunol 148: 1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994:291-312), and resurfacing (U.S. Pat. No. 5,639,641). Other regions, such as hinge and constant region domains, may also be humanized if they are also derived from non-human sources.

In the present application, the term "mouse antibody" generally refers to an antibody whose variable region framework and CDR region are derived from mouse germline immunoglobulin sequences. In addition, if the antibody comprises a constant region, it is also derived from mouse germline immunoglobulin sequences. The mouse antibody of the present application may comprise amino acid residues not encoded by mouse germline immunoglobulin sequences, for example, may comprise mutations introduced by in vitro random mutations or point mutations or by in vivo somatic mutations.

In this application, the term "TL1A" refers to TNF-like protein 1A. TL1A (TNFSF15) is a member of the TNF family that is expressed predominantly by endothelial cells, macrophages and dendritic cells (DCs). Its expression is induced by immune complexes (ICs) and cytokines. TL1A receptor DR3 is expressed mainly on T cells and NKT cells. In vitro, TL1A has been shown to enhance T cell proliferation and cytokine production in both humans and mice. In vivo, TL1A transgenic mice produce an IBD phenotype similar to human Crohn's disease.

In addition to the specific proteins and nucleotides mentioned herein, the present application may also include functional variants, derivatives, analogs, homologs, and fragments thereof.

The term "functional variant" refers to an amino acid sequence that is substantially identical to a naturally occurring sequence or a polypeptide encoded by a substantially identical nucleotide sequence and capable of having one or more activities of the naturally occurring sequence. In the context of the present application, a variant of any given sequence refers to a sequence in which the particular sequence of residues, whether amino acid or nucleotide residues, has been modified such that the polypeptide or polynucleotide substantially retains at least one endogenous function. Variant sequences may be obtained by the addition, deletion, substitution, modification, substitution and/or variation of at least one amino acid residue and/or nucleotide residue present in a naturally occurring protein and/or polynucleotide, so long as the original functional activity is retained.

In the present application, the term "derivative" generally refers to a polypeptide or polynucleotide of the present application comprising any substitution, variation, modification, replacement, deletion and/or addition of one (or more) amino acid residues from/on the sequence, so long as the resulting polypeptide or polynucleotide substantially retains at least one of its endogenous functions.

In the present application, the term "analog" generally refers to a polypeptide or polynucleotide including any mimetic of a polypeptide or polynucleotide, i.e., a chemical compound that possesses at least one endogenous function of the polypeptide or polynucleotide that the mimetic mimics.

Generally, amino acid substitutions, e.g., at least one (e.g., 1, 2, 3, 4, 5, 6, 7, 8, 9, 10, or 20 or more) amino acid substitution can be made, so long as the modified sequence substantially retains the desired activity or ability. Amino acid substitutions can include the use of non-naturally occurring analogs.

In the present application, the term "homologue" generally refers to an amino acid sequence or nucleotide sequence having certain homology to a naturally occurring sequence. The term "homology" can be equivalent to sequence "identity". Homologous sequences may include amino acid sequences that may be at least 80%, 85%, 90%, 99.1%, 99.2%, 99.3%, 99.4%, 99.5%, 99.6%, 99.7%, 99.8%, or 99.9% identical to the subject sequence. Typically, the homologue will comprise the same active site or the like as the subject amino acid sequence. Homology may be considered in terms of similarity (i.e., amino acid residues having similar chemical properties/functions) or may be expressed in terms of sequence identity. In the present application, a sequence having percent identity in any one of the SEQ ID NO of a mentioned amino acid sequence or nucleotide sequence refers to a sequence having the percent identity over the entire length of the mentioned SEQ ID NO. To determine sequence identity, sequence alignments may be performed by a variety of ways known to those skilled in the art, e.g., using BLAST, BLAST-2, ALIGN, NEEDLE, or Megalign (DNASTAR) software, etc. Those skilled in the art can determine the appropriate parameters for the alignment, including any algorithm required to achieve the optimal alignment over the full length of the sequence being compared.

The proteins or polypeptides used in the present application may also have deletions, insertions, or substitutions of amino acid residues which produce silent changes and result in functionally equivalent proteins. Intentional amino acid substitutions may be made on the basis of similarity in polarity, charge, solubility, hydrophobicity, hydrophilicity, and/or amphipathic nature of the residues, so long as the endogenous function is retained. For example, negatively charged amino acids include aspartic acid and glutamic acid: positively charged amino acids include lysine and arginine; and amino acids containing uncharged polar head groups with similar hydrophilicity values include asparagine, glutamine, serine, threonine, and tyrosine.

In the present application, the term "immunoconjugate" generally refers to a conjugate formed by the conjugation of other agents (e.g., a chemotherapeutic agent, a radioactive element, a cytostatic agent, and a cytotoxic agent) to the isolated antigen-binding protein (e.g., via covalent attachment of a linking molecule), wherein the conjugate can deliver the other agents to a target cell (e.g., a tumor cell) via specific binding of the isolated antigen-binding protein to an antigen on the target cell. The immunoconjugate then undergoes such internalization and eventually enters the interior of the target cell (e.g., into vesicles such as a lysosome), at which point the linker molecule in the immunoconjugate can be cleaved to release the other agent, thereby exerting its cytotoxic effect. In addition, the antigen may also be secreted by the target cell and located in the space outside the target cell.

In the present application, the term "subject" generally refers to human or non-human animals, including, but not limited to, cats, dogs, horses, pigs, cows, caprid, rabbits, mice, rats, or monkeys.

In the present application, the term "nucleic acid molecule" generally refers to an isolated form of nucleotides, deoxyribonucleotides, or ribonucleotides or analogs thereof, of any length, isolated from their natural environment or artificially synthesized.

In the present application, the term "vector" generally refers to a nucleic acid molecule capable of self-replication in a suitable host. The vector can transfer the inserted nucleic acid molecule into and/or between cells. The vector may include a vector for primarily inserting DNA or RNA into a cell, a vector for primarily replicating DNA or RNA, and a vector for primarily expressing transcription and/or translation of DNA or RNA. The vector can be a polynucleotide capable of being transcribed and translated into a polypeptide when introduced into an appropriate cell. In general, the vector may produce the desired expression product by culturing an appropriate cell containing the vector. In the present application, the vector may include a lentiviral vector.

In the present application, the term "cell" generally refers to an individual cell, cell line or cell culture that may or may already contain a plasmid or vector comprising a nucleic acid molecule as described herein, or that is capable of expressing a polypeptide as described herein or an antigen-binding protein as described herein. The cell may include the progeny of a single cell. Due to natural, accidental, or deliberate mutations, the progeny cells may not necessarily be identical in morphology or in genome to the original parent cell, but are capable of expressing the polypeptide or antigen-binding protein as described herein. The cells can be obtained by transfecting cells in vitro with the vectors as described herein. The cells may be prokaryotic cells (e.g., *E. coli*) or eukaryotic cells (e.g., yeast cell, COS cells, Chinese Hamster Ovary (CHO) cells, HeLa cells, HEK293 cells, COS-1 cells, NS0 cells, or myeloma cells). In some embodiments, the cells may be immune cells. For example, the immune cell may be selected from the group consisting of T cells, B cells, natural killer cells (NK cells), macrophages, NKT cells, monocytes, dendritic cells, granulocytes, lymphocytes, leukocytes and/or peripheral blood mononuclear cells.

In the present application, the term "treatment" generally refers to: (i) the prevention of the development of a disease, disorder, and/or condition in a patient who may be susceptible to, but has not yet been diagnosed with, that disease, disorder, or condition: (ii) the suppression of the disease, disorder, or condition, i.e., the curb of the development; and (iii) remission of the disease, disorder, or condition, i.e., causing regression of the disease, disorder, and/or condition and/or symptoms associated with the disease, disorder, and/or condition.

In the present application, the terms "polypeptide", "peptide", and "protein" are used interchangeably and generally refer to a polymer of amino acids of any length. The polymer may be linear or branched, and may comprise modified amino acids and it may be interrupted by non-amino acids. These terms also encompass amino acid polymers that have been modified. These modifications may comprise: disulfide bond formation, glycosylation, lipidation, acetylation, phosphorylation, or any other manipulation (e.g., binding to a labeling component). The term "amino acid" comprises natural and/or non-natural or synthetic amino acids, including glycine as well as the D and L optical isomers, as well as amino acid analogs and peptidomimetics.

In the present application, the terms "polynucleotide", "nucleotide", "nucleotide sequence", "nucleic acid", and "oligonucleotide" are used interchangeably and refer generally to polymeric forms of nucleotides of any length, such as deoxyribonucleotides or ribonucleotides, or analogs thereof. A polynucleotide may have any three-dimensional structure and may perform any function that is known or unknown. Non-limiting examples of polynucleotides are as follows: a coding or noncoding region of a gene or gene fragment, a plurality of loci (one locus) as defined by ligation analysis, exons, introns, messenger RNA (mRNA), transport RNA, ribosomal RNA, short interfering RNA (siRNA), short hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modification of the nucleotide structure may be performed before or after assembly of the polymer. The sequence of nucleotides may be interrupted by non-nucleotide components. The polynucleotides may be further modified after polymerization, e.g., by conjugation to labeled components.

In the present application, the term "$K_D$" (likewise, "$K_D$" or "KD") generally refers to an "affinity constant" or an "equilibrium dissociation constant" and refers to a value obtained at equilibrium in a titration measurement, or by dividing the dissociation rate constant ($k_d$) by the binding rate constant ($k_a$). The binding affinity of a binding protein (e.g., an isolated antigen-binding protein as described herein) for an antigen is expressed using an association rate constant ($k_a$), a dissociation rate constant ($k_d$), and an equilibrium dissociation constant ($K_D$). Methods for determining association and dissociation rate constants are well known in the art. The use of fluorescence-based techniques provides high sensitivity and the ability to examine samples at equilibrium in physiological buffers. For example, the $K_D$ value can be determined by Octet assay, and other experimental approaches and instruments such as BIAcore (Biomolecular Interaction Analysis) can be used (e.g., instruments available from BIAcoreInternationalAB, aGEHealthcarecompany, Uppsala, Sweden). Alternatively, the $K_D$ value can be determined using KinExA (dynamic exclusion assay (KineticExclusionAssay)) available from SapidyneInstruments (Boise, Idaho) or using a surface plasmon resonance (SPR) instrument.

In the present application, the term "IC50 value" or the term "half-maximal inhibitory concentration" (IC50) indicates the concentration of a particular compound that is required to achieve 50% inhibition of a biological process in vitro. The IC50 value can be logarithmically converted to a pIC50 value (−log IC50), where higher values indicate exponentially greater potency. The IC50 value is not an absolute value, but rather depends on experimental conditions, such as the concentration used. The IC50 value can be converted to an absolute inhibitory constant (Ki) using the Cheng-Prusoff equation (Biochem. Pharmacol. (1973) 22:3099).

The term "EC50", in the context of in vitro or in vivo analyses using isolated antigen-binding fragments, refers to the concentration of the antibody or antigen-binding portion thereof when the induced response is 50% of the maximal response, i.e., halfway between the maximal response and the baseline.

In the present application, the term "and/or" should be understood as meaning any one of the alternatives or both of the alternatives.

In the present application, the term "comprising" or "containing" generally refers to the inclusion of explicitly specified features, but not excluding other elements. In certain instances, "comprising" or "contain" also encompasses the inclusion of only the specified components.

In the present application, the term "about" generally refers to a range from 0.5% to 10% above or below the specified value, for example, a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below the specified value.

DETAILED DESCRIPTION OF THE INVENTION

Isolated Antigen-Binding Protein

In one aspect, the present application provides an isolated antigen-binding protein that can bind to a monomer TL1A and/or trimer TL1A with a $K_D$ value of about 1.0E-8M or less (For example, said $K_D$ is no greater than about 5E-08M, no greater than about 4.5E-08M, no greater than about 4E-08M, no greater than about 3.5E-08M, no greater than about 3E-08M, no greater than about 2E-08M, no greater than about 2E-08M, no greater than about 1.5E-08M, no greater than about 1E-08M, no greater than about 5E-09M, no greater than about 4.5E-09M, no greater than about 4E-09M, no greater than about 3.5E-09M, no greater than about 3E-09M, no greater than about 2.5E-09M, no greater than about 2E-09M, no greater than about 1.5E-09M, no greater than about 1E-09M, no greater than about 9E-10M, no greater than about 5E-10M, no greater than about 1E-10M, no greater than about 5E-11M, no greater than about 1E-11M, or no greater than 5E-12M or less.)

In the present application, the isolated antigen-binding protein of the present disclosure can be detected in a flow-through assay at an EC50 value of about 20 nM or less (e.g., said EC50 value is no higher than about 20 nM, no higher than about 15 nM, no higher than about 10 nM, no higher than about 5 nM, no higher than about 2.5 nM, no higher than about 2 nM, no higher than about 1 nM, no higher than about 0.5 nM, or less) in relation to the antigen-binding proteins expressed in theCHOK1 cells specifically binds to human TL1A expressed on CHOKI cells.

In the present application, the isolated antigen-binding protein of the present disclosure is an antagonist of the TL1A receptor, including, but not limited to, DR3 and TR6/DcR3. In the present application, the isolated antigen-binding protein of the present disclosure blocks the interaction of TL1A with death receptor 3 ("DR3"). In the present application, said isolated antigen-binding protein blocks monomeric TL1A-protein and/or trimeric TL1A in a flow-through assay at an IC50 value of about 50 nM or less (e.g., said IC50 value is no higher than about 50 nM, no higher than about 45 nM, no higher than about 40 nM, no higher than about 35 nM, no higher than about 30 nM, no higher than about 25 nM or less) binding to DR3 (DR3: UniprotKB NO. Q93038).

In the present application, the isolated antigen-binding proteins can inhibit the activity of the soluble TL1A-activated NF-κB signaling pathway. For example, the soluble TL1A-activated NF-κB signaling pathway can be tested for inhibition by a luciferase reporter gene system.

In the present application, said isolated antigen-binding protein can inhibit the activity of the membrane-bound TL1A-activated NF-κB signaling pathway. For example, whether the membrane-bound TL1A-activated NF-κB signaling pathway is inhibited can be detected by a luciferase reporter gene system.

In the present application, said isolated antigen-binding protein may function to inhibit Caspase3/7 activity. For example, the function of the Caspase3/7 activity can be tested for inhibition by a luciferase reporter gene system.

On the other hand, the present application provides an antigen-binding protein which competitively binds TL1A with the antigen-binding protein described herein.

Isolated Antigen-Binding Protein-TLA-0015

In one aspect, the present disclosure provides an antigen-binding protein which specifically binds to TL1A and comprises a heavy chain variable region (VH). The VH comprises at least one heavy chain complementarity determining regions (HCDR). The VH may include at least one, two or three of HCDR1, HCDR2 or HCDR3. In some embodiments, HCDR3, HCDR2 and HCDR1 are sequences as set forth in SEQ ID NO: 14, 5 and 1 respectively.

HCDR3 of the antigen-binding protein may include amino acid sequence as set forth in SEQ ID NO: 14. For example, the sequence of HCDR3 of the antigen-binding protein may be defined by Kabat.

In some embodiments, HCDR3 may be GX1X2DAMDY (SEQ ID NO:14). X1 may be D or L or N, X2 may be F or Y.

In some embodiments, HCDR3 may include an amino acid sequence as set forth in any one of SEQ ID NOs: 15-18.

HCDR2 of the antigen-binding protein may include amino acid sequence as set forth in SEQ ID NO: 5. For example, the sequence of HCDR2 of the antigen-binding protein may be defined by Kabat.

In some embodiments, HCDR2 may be X3IWGFGX4TX5YX6X7ALKS (SEQ ID NO:5). X3 may be R or V, X4 may be G or K, X5 may be D or H or N, X6 may be Nor Q, X7 may be A or P or S.

In some embodiments, HCDR2 may include an amino acid sequence as set forth in any one of SEQ ID NOs: 6-13.

HCDR1 of the antigen-binding protein may include amino acid sequence as set forth in SEQ ID NO: 1. For example, the sequence of HCDR1 of the antigen-binding protein may be defined by Kabat.

In some embodiments, HCDR1 may be X8YGVD (SEQ ID NO:1). X8 may be S or T or Y.

In some embodiments, HCDR1 may include an amino acid as set forth in any one of SEQ ID NO: 2-4.

In some embodiments, the VH comprises HFR1, and C-terminus of HFR1 is directly or indirectly linked to the N-terminus of HCDR1. For example, the sequence of HFR1 of the antigen-binding protein may be defined by Kabat. HFR1 comprises an amino acid as set forth in SEQ ID NO: 19.

In some embodiments, HFR1 is EX9QLX10ESGGGLX11QPGGSLRX12SCAVSSGFXx1LXx2 (SEQ ID NO:19). X9 may be I or V, X10 may be Lor V, X11 may be I or V, X12 may be I or L. Xx1 is D or S, Xx2 is I or K or S.

In some embodiments, HFR1 is selected from an amino acid sequence as set forth in any one of SEQ ID NOs: 20-28.

In some embodiments, VH comprises HFR2, and HFR2 is located between HCDR1 and HCDR2. For example, the sequence of HFR2 of the antigen-binding protein may be defined by Kabat. HFR2 comprises an amino acid sequence as set forth in SEQ ID NO:29.

In some embodiments, HFR2 is WVRQX13PGKGLEWX14G (SEQ ID NO:29).X13 may be A or S,X14 may be L or V.

In some embodiments, HFR2 is selected from an amino acid sequence as set forth in any one of SEQ ID NOs: 30-32.

In some embodiments, VH comprises HFR3, and HFR3 is located between HCDR2 and HCDR3. For example, the sequence of HFR3 of the antigen-binding protein may be defined by Kabat. HFR3 comprises an amino acid as set forth in SEQ ID NO:33.

In some embodiments, HFR3 is RX15TISX16DNSKNTX17YLQMNSLRAEDTAVYYCAX18 (SEQ ID NO:33). X15 may be F or L,X16 may be A or K or R or V, X17 may be Lor V, X18 may be R or S.

In some embodiments, HFR3 is selected from an amino acid sequence as set forth in any one of SEQ ID NOs: 34-40.

In some embodiments, VH comprises HFR4, and N-terminus of HFR4 is directly or indirectly linked to C-terminus of HCDR3. For example, the sequence of HFR4 of the antigen-binding protein may be defined by Kabat. HFR4 comprises an amino acid sequence as set forth in SEQ ID NO:41.

In some embodiments, the isolated antigen-binding protein further comprises a light chain variable region (VL), and VL comprises at least one light chain complementarity determining regions (LCDR). VL comprises LCDR1, LCDR2 and LCDR3, which is selected from an amino acid sequence as set forth in any one of SEQ ID NO:42, SEQ ID NO:43 and SEQ ID NO:44 accordingly.

In some embodiments, VL comprises LCDR3 including an amino acid sequence as set forth in SEQ ID NO:44. For example, the sequence of LCDR3 of the antigen-binding protein may be defined by Kabat.

In some embodiments, VL comprises LCDR2 including an amino acid sequence as set forth in SEQ ID NO:43. For example, the sequence of LCDR2 of the antigen-binding protein may be defined by Kabat.

In some embodiments, VL comprises LCDR1 including an amino acid sequence as set forth in SEQ ID NO:42. For example, the sequence of LCDR1 of the antigen-binding protein may be defined by Kabat.

In some embodiments, VL comprises the LFR1, and C-terminus of the LFR1 is directly or indirectly linked to N-terminus of LCDR1. For example, the sequence of the LFR1 of the antigen-binding protein may be defined by Kabat. The LFR1 comprises an amino acid sequence as set forth in SEQ ID NO:45.

In some embodiments, the LFR1 is DIQMTQX19X20SSLSASVGDRVTIX21C (SEQ ID NO: 45). X19 may be S or T, X20 may be Por T, X21 may be T or S.

In some embodiments, the LFR1 comprises an amino acid sequence as set forth in any one of SEQ ID NOs: 46-47.

In some embodiments, VL comprises the LFR2, and the LFR2 is located between LCDR1 and LCDR2. For example, the sequence of the LFR2 of the antigen-binding protein may be defined by Kabat, the LFR2 comprises an amino acid sequence as set forth in SEQ ID NO:48.

In some embodiments, the LFR2 is WYQQKPGKX22X23KLLIY (SEQ ID NO:48). X22 may be A or V,X23 may be Por V.

In some embodiments, the LFR2 comprises an amino acid sequence as set forth in any one of SEQ ID NOs: 49-52.

In some embodiments, VL comprises the LFR3, and the LFR3 is located between LCDR2 and LCDR3. For example, the sequence of the LFR3 of the antigen-binding protein may be defined by Kabat. The LFR3 comprises an amino acid sequence as set forth in SEQ ID NO:53.

In some embodiments, the LFR3 is GVPSRFSGSGSGTDX24TLTISSLQPEDX25ATYX26C (SEQ ID NO:53). X24 may be F or Y. X25 may be F or V. X26 may be F or Y.

In some embodiments, the LFR3 comprises an amino acid sequence as set forth in any one of SEQ ID NOs: 54-57.

In some embodiments, the isolated antigen-binding protein comprises the LFR4, and N-terminus of the LFR4 is directly or indirectly linked to C terminus of LCDR3. For example, the sequence of the LFR4 of the antigen-binding protein may be defined by Kabat. The LFR4 comprises an amino acid sequence as set forth in SEQ ID NO:58.

In some embodiments, the LFR4 is FGX27GTKLEIK (SEQ ID NO:58). X27 may be Por Q.

In some embodiments, the LFR4 comprises an amino acid sequence as set forth in any one of SEQ ID NOs: 59-61.

In some embodiments, VH comprises sequences as set forth in SEQ ID NOs: 62-99.

In some embodiments, VL comprises sequences as set forth in SEQ ID NOs: 102-106.

In some embodiments, said isolated antigen-binding protein comprises a VH as shown in SEQ ID NO: 70 and a VL as shown in SEQ ID NO: 106.

In some embodiments, the VH of said isolated antigen-binding protein comprises an HCDR1 as shown in SEQ ID NO:2, an HCDR2 as shown in SEQ ID NO:6, and an HCDR3 as shown in SEQ ID NO: 15, and further comprises a light chain variable region (VL), said VL comprising at least one light chain complementary determining region (LCDR) comprising an LCDR1 shown in SEQ ID NO:42, an LCDR2 shown in SEQ ID NO:43 and an LCDR3 shown in SEQ ID NO:44.

In some embodiments, the antigen-binding proteins described above are mentioned in example 4, Tables 3 and 4.

In some embodiments, the distribution of antibodies for the TLA-0015 line is shown in the following table, with Table 1-1 showing the distribution of heavy chain components and Table 1-2 showing the distribution of light chain components. The technical solution of the present application includes, for the same antibody, a combination of HCDR1-3 in Table 1-1 and LCDR1-3 in Table 1-2. The technical solution of the present application includes, for the same antibody, a combination of VH in Table 1-1 and VL in Table 1-2.

TABLE 1-1

| | VH | | | | | | | | | | | | | |
|---|---|---|---|---|---|---|---|---|---|---|---|---|---|---|
| antibody | HFR1 | SEQ ID | HCDR1 | SEQ ID | HFR2 | SEQ ID | HCDR2 | SEQ ID | HFR3 | SEQ ID | HCDR3 | SEQ ID | HFR4 | SEQ ID |
| TLA0015 (mouse) | | | TLA0015-HCDR1-1 | 2 | TLA0015-HFR2-3 | 32 | TLA0015-HCDR2-1 | 6 | | | TLA0015-HCDR3-1 | 15 | | |
| TLA0015-1 | TLA0015-HFR1-1 | 20 | TLA0015-HCDR1-1 | 2 | TLA0015-HFR2-1/ | 30 | TLA0015-HCDR2-1 | 6 | TLA0015-HFR3-1 | 34 | TLA0015-HCDR3-1 | 15 | TLA0015-HFR4-1/TLA-0238-HFR4-2 | 41 |
| TLA0015-2 | TLA0015-HFR1-1 | 20 | TLA0015-HCDR1-1 | 2 | TLA0015-HFR2-1/ | 30 | TLA0015-HCDR2-1 | 6 | TLA0015-HFR3-1 | 34 | TLA0015-HCDR3-1 | 15 | TLA0015-HFR4-1/TLA-0238-HFR4-2 | 41 |
| TLA0015-3 | TLA0015-HFR1-2 | 21 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA0015-4 | TLA0015-HFR1-2 | 21 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA0015-5 | TLA0015-HFR1-3 | 22 | TLA0015-HCDR1-1 | 2 | TLA0015-HFR2-3 | 32 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA0015-6 | TLA0015-HFR1-3 | 22 | TLA0015-HCDR1-1 | 2 | TLA0015-HFR2-3 | 32 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA0015-7 | TLA0015-HFR1-4 | 23 | TLA0015-HCDR1-1 | 2 | TLA0015-HFR2-2 | 31 | TLA0015-HCDR2-1 | 6 | TLA0015-HFR3-3 | 36 | TLA0015-HCDR3-1 | 15 | TLA0015-HFR4-1/TLA-0238-HFR4-2 | 41 |
| TLA0015-8 | TLA0015-HFR1-4 | 23 | TLA0015-HCDR1-1 | 2 | TLA0015-HFR2-2 | 31 | TLA0015-HCDR2-1 | 6 | TLA0015-HFR3-4 | 37 | TLA0015-HCDR3-1 | 15 | TLA0015-HFR4-1/TLA-0238-HFR4-2 | 41 |
| TLA0015-9 | TLA0015-HFR1-4 | 23 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA0015-10 | TLA0015-HFR1-5 | 24 | TLA0015-HCDR1-1 | 2 | TLA0015-HFR2-2 | 31 | TLA0015-HCDR2-1 | 6 | TLA0015-HFR3-5 | 38 | TLA0015-HCDR3-1 | 15 | TLA0015-HFR4-1/TLA-0238-HFR4-2 | 41 |
| TLA0015-11 | TLA0015-HFR1-6 | 25 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA0015-12 | TLA0015-HFR1-6 | 25 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA0015-13 | TLA0015-HFR1-6 | 25 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA0015-14 | TLA0015-HFR1-4 | 23 | TLA0015-HCDR1-1 | 2 | TLA0015-HFR2-2 | 31 | TLA0015-HCDR2-1 | 6 | TLA0015-HFR3-3 | 36 | TLA0015-HCDR3-1 | 15 | TLA0015-HFR4-1/TLA-0238-HFR4-2 | 41 |
| TLA0015-15 | TLA0015-HFR1-4 | 23 | TLA0015-HCDR1-1 | 2 | TLA0015-HFR2-2 | 31 | TLA0015-HCDR2-1 | 6 | TLA0015-HFR3-4 | 37 | TLA0015-HCDR3-1 | 15 | TLA0015-HFR4-1/TLA-0238-HFR4-2 | 41 |
| TLA0015-16 | TLA0015-HFR1-4 | 23 | TLA0015-HCDR1-1 | 2 | TLA0015-HFR2-2 | 31 | TLA0015-HCDR2-1 | 6 | TLA0015-HFR3-3 | 36 | TLA0015-HCDR3-1 | 15 | TLA0015-HFR4-1/TLA-0238-HFR4-2 | 41 |
| TLa0015-17 | TLA0015-HFR1-6 | 25 | TLA0015-HCDR1-1 | 2 | TLA0015-HFR2-2 | 31 | TLA0015-HCDR2-1 | 6 | TLA0015-HFR3-4 | 37 | TLA0015-HCDR3-1 | 15 | TLA0015-HFR4-1 | 41 |
| TLa0015-18 | TLA0015-HFR1-6 | 25 | TLA0015-HCDR1-1 | 2 | TLA0015-HFR2-2 | 31 | TLA0015-HCDR2-1 | 6 | TLA0015-HFR3-6 | 39 | TLA0015-HCDR3-1 | 15 | TLA0015-HFR4-1 | 41 |
| TLa0015-19 | TLA0015-HFR1-6 | 25 | TLA0015-HCDR1-1 | 2 | TLA0015-HFR2-2 | 31 | TLA0015-HCDR2-2 | 7 | TLA0015-HFR3-2 | 35 | TLA0015-HCDR3-1 | 15 | TLA0015-HFR4-1 | 41 |
| TLa0015-20 | TLA0015-HFR1-6 | 25 | TLA0015-HCDR1-1 | 2 | TLA0015-HFR2-2 | 31 | TLA0015-HCDR2-3 | 8 | TLA0015-HFR3-2 | 35 | TLA0015-HCDR3-1 | 15 | TLA0015-HFR4-1/TLA-0238-HFR4-2 | 41 |
| TLa0015-21 | TLA0015-HFR1-6 | 25 | TLA0015-HCDR1-1 | 2 | TLA0015-HFR2-2 | 31 | TLA0015-HCDR2-1 | 6 | TLA0015-HFR3-7 | 40 | TLA0015-HCDR3-1 | 15 | TLA0015-HFR4-1 | 41 |
| TLA015-22 | TLA0015-HFR1-6 | 25 | TLA0015-HCDR1-2 | 3 | TLA0015-HFR2-2 | 31 | TLA0015-HCDR2-1 | 6 | TLA0015-HFR3-2 | 35 | TLA0015-HCDR3-1 | 15 | TLA0015-HFR4-1 | 41 |
| TLA015-23 | TLA0015-HFR1-6 | 25 | TLA0015-HCDR1-1 | 2 | TLA0015-HFR2-2 | 31 | TLA0015-HCDR2-1 | 6 | TLA0015-HFR3-2 | 35 | TLA0015-HCDR3-2 | 16 | TLA0015-HFR4-1 | 41 |
| TLA015-24 | TLA0015-HFR1-6 | 25 | TLA0015-HCDR1-1 | 2 | TLA0015-HFR2-2 | 31 | TLA0015-HCDR2-1 | 6 | TLA0015-HFR3-2 | 35 | TLA0015-HCDR3-3 | 17 | TLA0015-HFR4-1 | 41 |
| TLA015-25 | TLA0015-HFR1-6 | 25 | TLA0015-HCDR1-1 | 2 | TLA0015-HFR2-2 | 31 | TLA0015-HCDR2-1 | 6 | TLA0015-HFR3-2 | 35 | TLA0015-HCDR3-4 | 18 | TLA0015-HFR4-1 | 41 |
| TLA015-26 | TLA0015-HFR1-6 | 25 | TLA0015-HCDR1-3 | 4 | TLA0015-HFR2-2 | 31 | TLA0015-HCDR2-1 | 6 | TLA0015-HFR3-2 | 35 | TLA0015-HCDR3-1 | 15 | TLA0015-HFR4-1 | 41 |
| TLA015-27 | TLA0015-HFR1-7 | 26 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1 | 41 |
| TLA015-28 | TLA0015-HFR1-6 | 25 | TLA0015-HCDR1-1 | 2 | TLA0015-HFR2-2 | 31 | TLA0015-HCDR2-4 | 9 | TLA0015-HFR3-2 | 35 | TLA0015-HCDR3-1 | 15 | TLA0015-HFR4-1 | 41 |

TABLE 1-1-continued

| antibody | VH HFR1 | SEQ ID | HCDR1 | SEQ ID | HFR2 | SEQ ID | HCDR2 | SEQ ID | HFR3 | SEQ ID | HCDR3 | SEQ ID | HFR4 | SEQ ID |
|---|---|---|---|---|---|---|---|---|---|---|---|---|---|---|
| TLA015-29 | TLA0015-HFR1-8 | 27 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1 | 41 |
| TLA015-30 | TLA0015-HFR1-6 | 25 | TLA0015-HCDR1-1 | 2 | TLA0015-HFR2-2 | 31 | TLA0015-HCDR2-5 | 10 | TLA0015-HFR3-2 | 35 | TLA0015-HCDR3-1 | 15 | TLA0015-HFR4-1/ | 41 |
| TLA015-31 | TLA0015-HFR1-6 | 25 | TLA0015-HCDR1-1 | 2 | TLA0015-HFR2-2 | 31 | TLA0015-HCDR2-6 | 11 | TLA0015-HFR3-2 | 35 | TLA0015-HCDR3-1 | 15 | TLA0015-HFR4-1/TLA-0238-HFR4-2 | 41 |
| TLA015-32 | TLA0015-HFR1-9 | 28 | TLA0015-HCDR1-1 | 2 | TLA0015-HFR2-2 | 31 | TLA0015-HCDR2-1 | 6 | TLA0015-HFR3-2 | 35 | TLA0015-HCDR3-1 | 15 | TLA0015-HFR4-1/TLA-0238-HFR4-2 | 41 |
| TLA015-33 | TLA0015-HFR1-6 | 25 | TLA0015-HCDR1-1 | 2 | TLA0015-HFR2-2 | 31 | TLA0015-HCDR2-7 | 12 | TLA0015-HFR3-2 | 35 | TLA0015-HCDR3-1 | 15 | TLA0015-HFR4-1/TLA-0238-HFR4-2 | 41 |
| TLA015-34 | TLA0015-HFR1-6 | 25 | TLA0015-HCDR1-1 | 2 | TLA0015-HFR2-2 | 31 | TLA0015-HCDR2-8 | 13 | TLA0015-HFR3-2 | 35 | TLA0015-HCDR3-1 | 15 | TLA0015-HFR4-1/TLA-0238-HFR4-2 | 41 |
| TLA015-35 | TLA0015-HFR1-6 | 25 | TLA0015-HCDR1-2 | 3 | TLA0015-HFR2-2 | 31 | TLA0015-HCDR2-1 | 6 | TLA0015-HFR3-2 | 35 | TLA0015-HCDR3-2 | 16 | TLA0015-HFR4-1/ | 41 |
| TLA015-36 | TLA0015-HFR1-6 | 25 | TLA0015-HCDR1-2 | 3 | TLA0015-HFR2-2 | 31 | TLA0015-HCDR2-1 | 6 | TLA0015-HFR3-2 | 35 | TLA0015-HCDR3-3 | 17 | TLA0015-HFR4-1 | 41 |
| TLA015-37 | TLA0015-HFR1-6 | 25 | TLA0015-HCDR1-2 | 3 | TLA0015-HFR2-2 | 31 | TLA0015-HCDR2-4 | 9 | TLA0015-HFR3-2 | 35 | TLA0015-HCDR3-1 | 15 | TLA0015-HFR4-1 | 41 |
| TLA015-38 | TLA0015-HFR1-6 | 25 | TLA0015-HCDR1-2 | 3 | TLA0015-HFR2-2 | 31 | TLA0015-HCDR2-5 | 10 | TLA0015-HFR3-2 | 35 | TLA0015-HCDR3-1 | 15 | TLA0015-HFR4-1 | 41 |
| TLA015-39 | TLA0015-HFR1-6 | 25 | TLA0015-HCDR1-2 | 3 | TLA0015-HFR2-2 | 31 | TLA0015-HCDR2-6 | 11 | TLA0015-HFR3-2 | 35 | TLA0015-HCDR3-1 | 15 | TLA0015-HFR4-1/TLA-0238-HFR4-2 | 41 |
| TLA015-40 | TLA0015-HFR1-9 | 28 | TLA0015-HCDR1-2 | 3 | TLA0015-HFR2-2 | 31 | TLA0015-HCDR2-1 | 6 | TLA0015-HFR3-2 | 35 | TLA0015-HCDR3-1 | 15 | TLA0015-HFR4-1 | 41 |
| TLA015-41 | TLA0015-HFR1-7 | 26 | TLA0015-HCDR1-1 | 2 | TLA0015-HFR2-2 | 31 | TLA0015-HCDR2-1 | 6 | TLA0015-HFR3-2 | 35 | TLA0015-HCDR3-2 | 16 | TLA0015-HFR4-1 | 41 |
| TLA015-42 | TLA0015-HFR1-6 | 25 | TLA0015-HCDR1-1 | 2 | TLA0015-HFR2-2 | 31 | TLA0015-HCDR2-4 | 9 | TLA0015-HFR3-2 | 35 | TLA0015-HCDR3-2 | 16 | TLA0015-HFR4-1 | 41 |
| TLA015-43 | TLA0015-HFR1-6 | 25 | TLA0015-HCDR1-1 | 2 | TLA0015-HFR2-2 | 31 | TLA0015-HCDR2-5 | 10 | TLA0015-HFR3-2 | 35 | TLA0015-HCDR3-2 | 16 | TLA0015-HFR4-1 | 41 |
| TLA015-44 | TLA0015-HFR1-6 | 25 | TLA0015-HCDR1-1 | 2 | TLA0015-HFR2-2 | 31 | TLA0015-HCDR2-6 | 11 | TLA0015-HFR3-2 | 35 | TLA0015-HCDR3-2 | 16 | TLA0015-HFR4-1 | 41 |
| TLA015-45 | TLA0015-HFR1-6 | 25 | TLA0015-HCDR1-1 | 2 | TLA0015-HFR2-2 | 31 | TLA0015-HCDR2-7 | 12 | TLA0015-HFR3-2 | 35 | TLA0015-HCDR3-2 | 16 | TLA0015-HFR4-1 | 41 |
| TLA015-46 | TLA0015-HFR1-7 | 26 | TLA0015-HCDR1-1 | 2 | TLA0015-HFR2-2 | 31 | TLA0015-HCDR2-1 | 6 | TLA0015-HFR3-2 | 35 | TLA0015-HCDR3-3 | 17 | TLA0015-HFR4-1 | 41 |
| TLA015-47 | TLA0015-HFR1-6 | 25 | TLA0015-HCDR1-1 | 2 | TLA0015-HFR2-2 | 31 | TLA0015-HCDR2-5 | 10 | TLA0015-HFR3-2 | 35 | TLA0015-HCDR3-3 | 17 | TLA0015-HFR4-1/TLA-0238-HFR4-2 | 41 |

TABLE 1-2

| antibody | VL LFR1 | SEQ ID | CDR1 | SEQ ID | LFR2 | SEQ ID | LCDR2 | SEQ ID | LFR3 | SEQ ID | LCDR3 | SEQ ID | LFR4 | SEQ ID |
|---|---|---|---|---|---|---|---|---|---|---|---|---|---|---|
| TLA0015 (mouse) | TL0015-LFR1-1 | 46 | TLA0015-LCDR1-1 | 42 | TL0015-LFR2-1 | 49 | TL0015-LCDR2-1 | 43 | TL0015-LFR3-1 | 54 | TL0015-LCDR3-1 | 44 | TL0015-LFR4-1 | 59 |
| TLA0015-1 | TL0015-LFR1-2/TLA0241-LFR1-1 | 47 | TLA0015-LCDR1-1 | 42 | TL0015-LFR2-2 | 50 | TL0015-LCDR2-1 | 43 | TL0015-LFR3-2 | 55 | TL0015-LCDR3-1 | 44 | TL0015-LFR4-2 | 60 |
| TLA0015-2 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA0015-3 | TL0015-LFR1-2/TLA0241-LFR1-1 | 47 | TLA0015-LCDR1-1 | 42 | TL0015-LFR2-2 | 50 | TL0015-LCDR2-1 | 43 | TL0015-LFR3-2 | 55 | TL0015-LCDR3-1 | 44 | TL0015-LFR4-2 | 60 |
| TLA0015-4 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |

TABLE 1-2-continued

| | VL | | | | | | | | | | | | | |
|---|---|---|---|---|---|---|---|---|---|---|---|---|---|---|
| antibody | LFR1 | SEQ ID | CDR1 | SEQ ID | LFR2 | SEQ ID | LCDR2 | SEQ ID | LFR3 | SEQ ID | LCDR3 | SEQ ID | LFR4 | SEQ ID |
| TLA0015-5 | TL0015-LFR1-2/TLA0241-LFR1-1 | 47 | TLA0015-LCDR1-1 | 42 | TL0015-LFR2-2 | 50 | TL0015-LCDR2-1 | 43 | TL0015-LFR3-2 | 55 | TL0015-LCDR3-1 | 44 | TL0015-LFR4-2 | 60 |
| TLA0015-6 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA0015-7 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA0015-8 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA0015-9 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA0015-10 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA0015-11 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA0015-12 | TL0015-LFR1-2/TLA0241-LFR1-1 | 47 | TLA0015-LCDR1-1 | 42 | TL0015-LFR2-4/TLA0241-LFR2-1 | 52 | TL0015-LCDR2-1 | 43 | TL0015-LFR3-4/TLA0238-LFR3-4/TLA0241-LFR3-2 | 57 | TL0015-LCDR3-1 | 44 | TL0015-LFR4-3/TLA0238-LFR4-3 | 61 |
| TLA0015-13 | TL0015-LFR1-2/TLA0241-LFR1-1 | 47 | TLA0015-LCDR1-1 | 42 | TL0015-LFR2-4/TLA0241-LFR2-1 | 52 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA0015-14 | TL0015-LFR1-2/TLA0241-LFR1-1 | 47 | TLA0015-LCDR1-1 | 42 | TL0015-LFR2-4/TLA0241-LFR2-1 | 52 | TL0015-LCDR2-1 | 43 | TL0015-LFR3-4/TLA0238-LFR3-4/TLA0241-LFR3-2 | 57 | TL0015-LCDR3-1 | 44 | TL0015-LFR4-3/TLA0238-LFR4-3 | 61 |
| TLA0015-15 | TL0015-LFR1-2/TLA0241-LFR1-1 | 47 | TLA0015-LCDR1-1 | 42 | TL0015-LFR2-4/TLA0241-LFR2-1 | 52 | TL0015-LCDR2-1 | 43 | TL0015-LFR3-4/TLA0238-LFR3-4/TLA0241-LFR3-2 | 57 | TL0015-LCDR3-1 | 44 | TL0015-LFR4-3/TLA0238-LFR4-3 | 61 |
| TLA0015-16 | TL0015-LFR1-2/TLA0241-LFR1-1 | 47 | TLA0015-LCDR1-1 | 42 | TL0015-LFR2-4/TLA0241-LFR2-1 | 52 | TL0015-LCDR2-1 | 43 | TL0015-LFR3-3 | 56 | TL0015-LCDR3-1 | 44 | TL0015-LFR4-3/TLA0238-LFR4-3 | 61 |
| TLa0015-17 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLa0015-18 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLa0015-19 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLa0015-20 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLa0015-21 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |

TABLE 1-2-continued

| | VL | | | | | | | | | | | | | |
|---|---|---|---|---|---|---|---|---|---|---|---|---|---|---|
| antibody | LFR1 | SEQ ID | CDR1 | SEQ ID | LFR2 | SEQ ID | LCDR2 | SEQ ID | LFR3 | SEQ ID | LCDR3 | SEQ ID | LFR4 | SEQ ID |
| TLA015-22 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-23 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-24 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-25 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-26 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-27 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-28 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-29 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-30 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-31 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-32 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-33 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-34 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-35 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-36 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-37 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-38 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |
| TLA015-39 | TL0015-LFR1-2/ TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/ TLA0238-LFR4-3 | 61 |

TABLE 1-2-continued

| | VL | | | | | | | | | | | | | |
|---|---|---|---|---|---|---|---|---|---|---|---|---|---|---|
| antibody | LFR1 | SEQ ID | CDR1 | SEQ ID | LFR2 | SEQ ID | LCDR2 | SEQ ID | LFR3 | SEQ ID | LCDR3 | SEQ ID | LFR4 | SEQ ID |
| TLA015-40 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA015-41 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA015-42 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA015-43 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA015-44 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA015-45 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA015-46 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |
| TLA015-47 | TL0015-LFR1-2/TLA0241-LFR1-1 | 47 | TLA0015-LCDR1-1 | 42 | TL0015-LFR2-3 | 51 | TL0015-LCDR2-1 | 43 | TL0015-LFR3-3 | 56 | TL0015-LCDR3-1 | 44 | TL0015-LFR4-3/TLA0238-LFR4-3 | 61 |

Isolated Antigen-Binding Protein-TLA-0238

In one aspect, the present disclosure provides an antigen-binding protein which specifically binds to TL1A and comprises a heavy chain variable region (VH). The VH comprises at least one heavy chain complementarity determining regions (HCDR). The VH may include at least one, two or three of HCDR1, HCDR2 or HCDR3. In some embodiments, HCDR 1, HCDR3 and HCDR3 are sequences as set forth in SEQ ID NO: 107, 115 and 120 respectively.

HCDR3 of the antigen-binding protein may include amino acid sequence as set forth in SEQ ID NO: 120. For example, the sequence of HCDR3 of the antigen-binding protein may be defined by Kabat.

HCDR2 of the antigen-binding protein may include amino acid sequence as set forth in SEQ ID NO: 115. For example, the sequence of HCDR2 of the antigen-binding protein may be defined by Kabat.

In some embodiments, HCDR2 may be QIRLKSDNYATHYAX28X29VKG (SEQ ID NO:115). X28 may be A or D or E. X29 may be Por S.

In some embodiments, HCDR2 may include an amino acid sequence as set forth in any one of SEQ ID NOs: 116-119.

HCDR1 of the antigen-binding protein may include amino acid sequence as set forth in SEQ ID NO: 107. For example, the sequence of HCDR1 of the antigen-binding protein may be defined by Kabat.

In some embodiments, HCDR1 may be NYX30MX31 (SEQ ID NO:107). X30 may be I or L or M or Y or W. X31 may be N or H or S.

In some embodiments, HCDR1 may include an amino acid as set forth in any one of SEQ ID NOs: 108-114.

In some embodiments, the VH comprises HFR1, and C-terminus of HFR1 is directly or indirectly linked to the N-terminus of HCDR1. For example, the sequence of HFR1 of the antigen-binding protein may be defined by Kabat. HFR1 comprises an amino acid as set forth in SEQ ID NO: 121.

In some embodiments, HFR1 is X32VX33X34X35ESGGGX36VX37PGX38X39L X40LSCX41ASGFTFS (SEQ ID NO:121). X32 may be E or Q. X33 may be K or Q.X34 may be Lor V.X35 may be E or V.X36 may be Lor V.X37 may be K or Q. X38 may be G or R.X39 may be A or S.X40 may be K or R.X41 may be A or I.

In some embodiments, HFR1 is selected from an amino acid sequence as set forth in any one of SEQ ID NOs: 122-132.

In some embodiments, VH comprises HFR2, and HFR2 is located between HCDR1 and HCDR2. For example, the sequence of HFR2 of the antigen-binding protein may be defined by Kabat. HFR2 comprises an amino acid sequence as set forth in SEQ ID NO:133.

In some embodiments, HFR2 is WVRQX42PX43KGLEWVX44 (SEQ ID NO:133). X42 may be A or S.X43 may be E or G.X44 may be A or G.

In some embodiments, HFR2 is selected from an amino acid sequence as set forth in any one of SEQ ID NOs: 134-135 and 30.

In some embodiments, VH comprises HFR3, and HFR3 is located between HCDR2 and HCDR3. For example, the sequence of HFR3 of the antigen-binding protein may be defined by Kabat. HFR3 comprises an amino acid as set forth in SEQ ID NO:136.

In some embodiments, HFR3 is X45FX46ISRDX47X48KX49X50X51YLQMNSLX52 X53EDX54AVYYCTP (SEQ ID NO:136). X45 may be N or R.X46 may be A or T.X47 may be D or N.X48 may be A or S.X49 may be Nor S.X50 may be S or T.X51 may be A or Lor V.X52 may be Kor R.X53 may be A or D or T.X54 may be M or T.

In some embodiments, HFR3 is selected from an amino acid sequence as set forth in any one of SEQ ID NOs: 137-148.

In some embodiments, VH comprises HFR4, and N-terminus of HFR4 is directly or indirectly linked to C-terminus of HCDR3. For example, the sequence of HFR4 of the antigen-binding protein may be defined by Kabat. HFR4 comprises an amino acid sequence as set forth in SEQ ID NO:149.

In some embodiments, HFR4 is WGQGT X55X56TVSS (SEQ ID NO:149). X55 may be L or M OR H or T.X56 may be Lor V.

In some embodiments, the isolated antigen-binding protein further comprises a light chain variable region (VL), an VL comprises at least one light chain complementarity determining regions (LCDR). VL comprises LCDR1, LCDR2 and LCDR3, which is selected from an amino acid sequence as set forth in any one of SEQ ID NO: 154, SEQ ID NO: 159 and SEQ ID NO:163 accordingly.

In some embodiments, VL comprises LCDR3 including an amino acid sequence as set forth in SEQ ID NO: 163. For example, the sequence of LCDR3 of the antigen-binding protein may be defined by Kabat.

In some embodiments, LCDR3 is FQEX57X58HPFT (SEQ ID NO:163). X57 may be N or S or E.X58 may be G or E or A.

In some embodiments, LCDR3 is selected from an amino acid sequence as set forth in any one of SEQ ID NOs: 164-168.

In some embodiments, VL comprises LCDR2 including an amino acid sequence as set forth in SEQ ID NO: 159. For example, the sequence of LCDR2 of the antigen-binding protein may be defined by Kabat.

In some embodiments, LCDR2 is DTSNX59AX60 (SEQ ID NO:159). X59 may be L or R.X60 may be S or T.

In some embodiments, LCDR2 is selected from an amino acid sequence as set forth in any one of SEQ ID NOs: 160-162.

In some embodiments, VL comprises LCDR1 including an amino acid sequence as set forth in SEQ ID NO:42. For example, the sequence of LCDR1 of the antigen-binding protein may be defined by Kabat.

In some embodiments, LCDR1 is SASSSVSYX61X62 (SEQ ID NO:154). X61 may be Lor M.X62 may be A or H or T.

In some embodiments, LCDR1 is selected from an amino acid sequence as set forth in any one of SEQ ID NOs: 155-158.

In some embodiments, VL comprises the LFR1, and C-terminus of the LFR1 is directly or indirectly linked to N-terminus of LCDR1. For example, the sequence of the LFR1 of the antigen-binding protein may be defined by Kabat. the LFR1 comprises an amino acid sequence as set forth in SEQ ID NO:169.

In some embodiments, the LFR1 is X63X64X65X66TQSPX67X68X69SX70X71X72 GX73X74X75TX76X77C (SEQ ID NO:169). X63 may be E or D.X64 may be I or N or Tor V.X65 may be Q or V.X66 may be Lor M.X67 may be A or S. X68 may be F or I or S or T.X69 may be Lor M or V. X70 may be A or Lor V. X71 may be S or T.X72 may be Por V.X73 may be D or E. X74 may be Kor R.X75 may be A or V.X76 may be I or M.X77 may be S or T.

In some embodiments, the LFR1 comprises an amino acid sequence as set forth in any one of SEQ ID NOs: 170-179.

In some embodiments, VL comprises the LFR2, and the LFR2 is located between LCDR1 and LCDR2. For example, the sequence of the LFR2 of the antigen-binding protein may be defined by Kabat, the LFR2 comprises an amino acid sequence as set forth in SEQ ID NO:180.

In some embodiments, the LFR2 is WYQQKP X78 X79 X80P X81LWIY (SEQ ID NO: 180).X78 may be D or G.X79 may be K or Q.X80 may be A or S.X81 may be K or Q or R.

In some embodiments, the LFR2 comprises an amino acid sequence as set forth in any one of SEQ ID NOs: 181-188.

In some embodiments, VL comprises the LFR3, the LFR3 is located between LCDR2 and LCDR3. For example, the sequence of the LFR3 of the antigen-binding protein may be defined by Kabat. The LFR3 comprises an amino acid sequence as set forth in SEQ ID NO:189.

In some embodiments, the LFR3 is GVP X82RFSGSGSGX83X84X85TLTISSX86X8 7X88EDX89AX90YYC (SEQ ID NO:189). X82 may be A or D or G or S. X83 may be N or T.X84 may be D or S. X85 may be F or Y. X86 may be Lor M.X87 may be E or Q. X88 may be A or P.X89 may be A or For V. X90 may be Tor V.

In some embodiments, the LFR3 comprises an amino acid sequence as set forth in any one of SEQ ID NOs: 190-197 and 57.

In some embodiments, the isolated antigen-binding protein comprises the LFR4, and N-terminus of the LFR4 is directly or indirectly linked to C terminus of LCDR3. For example, the sequence of the LFR4 of the antigen-binding protein may be defined by Kabat. The LFR4 comprises an amino acid sequence as set forth in SEQ ID NO:198.

In some embodiments, the LFR4 is FG X91GTK X92EX93K (SEQ ID NO: 198). X91 may be G or Q. X92 may be Lor V. X93 may be I or M.

In some embodiments, the LFR4 comprises an amino acid sequence as set forth in any one of SEQ ID NOs: 199-201 and 61.

In some embodiments, VH comprises sequences as set forth in SEQ ID NOs: 202-220, 332-334.

In some embodiments, VL comprises sequences as set forth in SEQ ID NOs: 221-234, 335-338. In some embodiments, the antigen-binding proteins described above are mentioned in Example 4, Tables 5, 6 and 7.

In some embodiments, the distribution of antibodies for the TLA-0015 line is shown in the following table, with Table 1-3 showing the distribution of heavy chain components and Table 1-4 showing the distribution of light chain components. The technical solution of the present application includes, for the same antibody, a combination of HCDR1-3 in Table 1-3 and LCDR1-3 in Table 1-4. The technical solution of the present application includes, for the same antibody, a combination of VH in Table 1-3 and VL in Table 1-4.

TABLE 1-3

| antibody | VH HFR1 | SEQ ID | HCDR1 | SEQ ID | HFR2 | SEQ ID | HCDR2 |
|---|---|---|---|---|---|---|---|
| TLA0238 (mouse) | | | TLA-0238-HCDR1-1 | 108 | | 134 | TLA-0238-HCDR2-1 |
| TLA0238-1 | TLA-0238-HFR1-2 | 123 | TLA-0238-HCDR1-1 | 108 | TLA-0238-HFR2-2 | 135 | TLA-0238-HCDR2-1 |
| TLA0238-2 | TLA-0238-HFR1-2 | 123 | TLA-0238-HCDR1-1 | 108 | TLA-0238-HFR2-2 | 135 | TLA-0238-HCDR2-1 |
| TLA0238-3 | TLA-0238-HFR1-3 | 124 | TLA-0238-HCDR1-1 | 108 | TLA-0238-HFR2-2 | 135 | TLA-0238-HCDR2-1 |
| TLA0238-4 | TLA-0238-HFR1-3 | 124 | TLA-0238-HCDR1-1 | 108 | TLA-0238-HFR2-2 | 135 | TLA-0238-HCDR2-1 |
| TLA0238-2-1 | TLA-0238-HFR1-2 | 123 | TLA-0238-HCDR1-1 | 108 | TLA-0238-HFR2-2 | 135 | TLA-0238-HCDR2-1 |
| TLA0238-2-2 | TLA-0238-HFR1-2 | 123 | TLA-0238-HCDR1-1 | 108 | TLA-0238-HFR2-2 | 135 | TLA-0238-HCDR2-1 |
| TLA0238-5 | TLA-0238-HFR1-4 | 125 | TLA-0238-HCDR1-1 | 108 | TLA-0238-HFR2-2 | 135 | TLA-0238-HCDR2-2 |
| TLA0238-6 | TLA-0238-HFR1-5 | 126 | TLA-0238-HCDR1-1 | 108 | TLA-0238-HFR2-2 | 135 | TLA-0238-HCDR2-2 |
| TLA0238-7 | TLA-0238-HFR1-6 | 127 | TLA-0238-HCDR1-2 | 109 | TLA0015-HFR2-1/TLA-0238-HFR2-3 | 30 | TLA-0238-HCDR2-3 |
| TLA0238-8 | TLA-0238-HFR1-7 | 128 | TLA-0238-HCDR1-2 | 109 | TLA0015-HFR2-1/TLA-0238-HFR2-3 | 30 | TLA-0238-HCDR2-3 |
| TLA0238-9 | TLA-0238-HFR1-8 | 129 | TLA-0238-HCDR1-2 | 109 | TLA0015-HFR2-1/TLA-0238-HFR2-3 | 30 | TLA-0238-HCDR2-3 |
| TLA0238-10 | TLA-0238-HFR1-6 | 127 | TLA-0238-HCDR1-2 | 109 | TLA0015-HFR2-1/TLA-0238-HFR2-3 | 30 | TLA-0238-HCDR2-3 |
| TLA0238-11 | TLA-0238-HFR1-4 | 125 | TLA-0238-HCDR1-1 | 108 | TLA-0238-HFR2-2 | 135 | TLA-0238-HCDR2-2 |
| TLA0238-12 | TLA-0238-HFR1-9 | 130 | TLA-0238-HCDR1-2 | 109 | TLA0015-HFR2-1/TLA-0238-HFR2-3 | 30 | TLA-0238-HCDR2-3 |
| TLA0238-13 | TLA-0238-HFR1-10 | 131 | TLA-0238-HCDR1-1 | 108 | TLA-0238-HFR2-2 | 135 | TLA-0238-HCDR2-4 |
| TLA0238-14 | TLA-0238-HFR1-11 | 132 | TLA-0238-HCDR1-3 | 110 | TLA0015-HFR2-1/TLA-0238-HFR2-3 | 30 | TLA-0238-HCDR2-3 |
| TLA0238-15 | TLA-0238-HFR1-4 | 125 | TLA-0238-HCDR1-4 | 111 | TLA-0238-HFR2-2 | 135 | TLA-0238-HCDR2-2 |
| TLA0238-16 | TLA-0238-HFR1-4 | 125 | TLA-0238-HCDR1-4 | 111 | TLA-0238-HFR2-2 | 135 | TLA-0238-HCDR2-2 |
| TLA0238-17 | TLA-0238-HFR1-4 | 125 | TLA-0238-HCDR1-5 | 112 | TLA-0238-HFR2-2 | 135 | TLA-0238-HCDR2-2 |
| TLA0238-18 | TLA-0238-HFR1-4 | 125 | TLA-0238-HCDR1-5 | 112 | TLA-0238-HFR2-2 | 135 | TLA-0238-HCDR2-2 |
| TLA0238-19 | TLA-0238-HFR1-4 | 125 | TLA-0238-HCDR1-6 | 113 | TLA-0238-HFR2-2 | 135 | TLA-0238-HCDR2-2 |
| TLA0238-20 | TLA-0238-HFR1-4 | 125 | TLA-0238-HCDR1-6 | 113 | TLA-0238-HFR2-2 | 135 | TLA-0238-HCDR2-2 |
| TLA0238-21 | TLA-0238-HFR1-4 | 125 | TLA-0238-HCDR1-4 | 111 | TLA-0238-HFR2-2 | 135 | TLA-0238-HCDR2-2 |
| TLA0238-22 | TLA-0238-HFR1-4 | 125 | TLA-0238-HCDR1-4 | 111 | TLA-0238-HFR2-2 | 135 | TLA-0238-HCDR2-2 |
| TLA0238-23 | TLA-0238-HFR1-4 | 125 | TLA-0238-HCDR1-5 | 112 | TLA-0238-HFR2-2 | 135 | TLA-0238-HCDR2-2 |
| TLA0238-24 | TLA-0238-HFR1-4 | 125 | TLA-0238-HCDR1-5 | 112 | TLA-0238-HFR2-2 | 135 | TLA-0238-HCDR2-2 |
| TLA0238-25 | TLA-0238-HFR1-4 | 125 | TLA-0238-HCDR1-6 | 113 | TLA-0238-HFR2-2 | 135 | TLA-0238-HCDR2-2 |
| TLA0238-26 | TLA-0238-HFR1-4 | 125 | TLA-0238-HCDR1-6 | 113 | TLA-0238-HFR2-2 | 135 | TLA-0238-HCDR2-2 |
| TLA0238-27 | TLA-0238-HFR1-4 | 125 | TLA-0238-HCDR1-1 | 108 | TLA-0238-HFR2-2 | 135 | TLA-0238-HCDR2-2 |
| TLA0238-28 | TLA-0238-HFR1-4 | 125 | TLA-0238-HCDR1-1 | 108 | TLA-0238-HFR2-2 | 135 | TLA-0238-HCDR2-2 |

TABLE 1-3-continued

| | | | | | | | |
|---|---|---|---|---|---|---|---|
| TLA0238-29 | TLA-0238-HFR1-4 | 125 | TLA-0238-HCDR1-7 | 114 | TLA-0238-HFR2-2 | 135 | TLA-0238-HCDR2-2 |
| TLA0238-30 | TLA-0238-HFR1-4 | 125 | TLA-0238-HCDR1-7 | 114 | TLA-0238-HFR2-2 | 135 | TLA-0238-HCDR2-2 |

| | VH | | | | | |
|---|---|---|---|---|---|---|
| antibody | SEQ ID | HFR3 | SEQ ID | HCDR3 | SEQ ID | HFR4 | SEQ ID |
| TLA0238 (mouse) | 116 | | | TLA-0238-HCDR3-1 | 120 | | |
| TLA0238-1 | 116 | TLA-0238-HFR3-2 | 138 | TLA-0238-HCDR3-1 | 120 | TLA0015-HFR4-1/TLA-0238-HFR4-2 | 41 |
| TLA0238-2 | 116 | TLA-0238-HFR3-2 | 138 | TLA-0238-HCDR3-1 | 120 | TLA0015-HFR4-1/TLA-0238-HFR4-2 | 41 |
| TLA0238-3 | 116 | TLA-0238-HFR3-3 | 139 | TLA-0238-HCDR3-1 | 120 | TLA-0238-HFR4-3 | 151 |
| TLA0238-4 | 116 | TLA-0238-HFR3-3 | 139 | TLA-0238-HCDR3-1 | 120 | TLA-0238-HFR4-3 | 151 |
| TLA0238-2-1 | 116 | TLA-0238-HFR3-4 | 140 | TLA-0238-HCDR3-1 | 120 | TLA0015-HFR4-1/TLA-0238-HFR4-2 | 41 |
| TLA0238-2-2 | 116 | TLA-0238-HFR3-5 | 141 | TLA-0238-HCDR3-1 | 120 | TLA0015-HFR4-1/TLA-0238-HFR4-2 | 41 |
| TLA0238-5 | 117 | TLA-0238-HFR3-6 | 142 | TLA-0238-HCDR3-1 | 120 | TLA0015-HFR4-1/TLA-0238-HFR4-2 | 41 |
| TLA0238-6 | 117 | TLA-0238-HFR3-6 | 142 | TLA-0238-HCDR3-1 | 120 | TLA-0238-HFR4-4 | 152 |
| TLA0238-7 | 118 | TLA-0238-HFR3-7 | 143 | TLA-0238-HCDR3-1 | 120 | TLA0015-HFR4-1/TLA-0238-HFR4-2 | 41 |
| TLA0238-8 | 118 | TLA-0238-HFR3-8 | 144 | TLA-0238-HCDR3-1 | 120 | TLA0015-HFR4-1/TLA-0238-HFR4-2 | 41 |
| TLA0238-9 | 118 | TLA-0238-HFR3-9 | 145 | TLA-0238-HCDR3-1 | 120 | TLA0015-HFR4-1/TLA-0238-HFR4-2 | 41 |
| TLA0238-10 | 118 | TLA-0238-HFR3-10 | 146 | TLA-0238-HCDR3-1 | 120 | TLA0015-HFR4-1/TLA-0238-HFR4-2 | 41 |
| TLA0238-11 | 117 | TLA-0238-HFR3-6 | 142 | TLA-0238-HCDR3-1 | 120 | TLA-0238-HFR4-4 | 152 |
| TLA0238-12 | 118 | TLA-0238-HFR3-11 | 147 | TLA-0238-HCDR3-1 | 120 | TLA0015-HFR4-1/TLA-0238-HFR4-2 | 41 |
| TLA0238-13 | 119 | TLA-0238-HFR3-12 | 148 | TLA-0238-HCDR3-1 | 120 | TLA-0238-HFR4-5 | 153 |
| TLA0238-14 | 118 | TLA-0238-HFR3-9 | 145 | TLA-0238-HCDR3-1 | 120 | TLA0015-HFR4-1/TLA-0238-HFR4-2 | 41 |
| TLA0238-15 | 117 | TLA-0238-HFR3-6 | 142 | TLA-0238-HCDR3-1 | 120 | TLA0015-HFR4-1/TLA-0238-HFR4-2 | 41 |
| TLA0238-16 | 117 | TLA-0238-HFR3-6 | 142 | TLA-0238-HCDR3-1 | 120 | TLA0015-HFR4-1/TLA-0238-HFR4-2 | 41 |
| TLA0238-17 | 117 | TLA-0238-HFR3-6 | 142 | TLA-0238-HCDR3-1 | 120 | TLA0015-HFR4-1/TLA-0238-HFR4-2 | 41 |
| TLA0238-18 | 117 | TLA-0238-HFR3-6 | 142 | TLA-0238-HCDR3-1 | 120 | TLA0015-HFR4-1/TLA-0238-HFR4-2 | 41 |
| TLA0238-19 | 117 | TLA-0238-HFR3-6 | 142 | TLA-0238-HCDR3-1 | 120 | TLA0015-HFR4-1/TLA-0238-HFR4-2 | 41 |
| TLA0238-20 | 117 | TLA-0238-HFR3-6 | 142 | TLA-0238-HCDR3-1 | 120 | TLA0015-HFR4-1/TLA-0238-HFR4-2 | 41 |
| TLA0238-21 | 117 | TLA-0238-HFR3-6 | 142 | TLA-0238-HCDR3-1 | 120 | TLA0015-HFR4-1/TLA-0238-HFR4-2 | 41 |

TABLE 1-3-continued

| | | | | | | | |
|---|---|---|---|---|---|---|---|
| TLA0238-22 | 117 | TLA-0238-HFR3-6 | 142 | TLA-0238-HCDR3-1 | 120 | TLA0015-HFR4-1/TLA-0238-HFR4-2 | 41 |
| TLA0238-23 | 117 | TLA-0238-HFR3-6 | 142 | TLA-0238-HCDR3-1 | 120 | TLA0015-HFR4-1/TLA-0238-HFR4-2 | 41 |
| TLA0238-24 | 117 | TLA-0238-HFR3-6 | 142 | TLA-0238-HCDR3-1 | 120 | TLA0015-HFR4-1/TLA-0238-HFR4-2 | 41 |
| TLA0238-25 | 117 | TLA-0238-HFR3-6 | 142 | TLA-0238-HCDR3-1 | 120 | TLA0015-HFR4-1/TLA-0238-HFR4-2 | 41 |
| TLA0238-26 | 117 | TLA-0238-HFR3-6 | 142 | TLA-0238-HCDR3-1 | 120 | TLA0015-HFR4-1/TLA-0238-HFR4-2 | 41 |
| TLA0238-27 | 111 | TLA-0238-HFR3-6 | 142 | TLA-0238-HCDR3-1 | 120 | TLA0015-HFR4-1/TLA-0238-HFR4-2 | 41 |
| TLA0238-28 | 117 | TLA-0238-HFR3-6 | 142 | TLA-0238-HCDR3-1 | 120 | TLA0015-HFR4-1/TLA-0238-HFR4-2 | 41 |
| TLA0238-29 | 117 | TLA-0238-HFR3-6 | 142 | TLA-0238-HCDR3-1 | 120 | TLA0015-HFR4-1/TLA-0238-HFR4-2 | 41 |
| TLA0238-30 | 117 | TLA-0238-HFR3-6 | 142 | TLA-0238-HCDR3-1 | 120 | TLA0015-HFR4-1/TLA-0238-HFR4-2 | 41 |

TABLE 1-4

| | VL | | | | | | | | | | | | | |
|---|---|---|---|---|---|---|---|---|---|---|---|---|---|---|
| antibody | LFR1 | SEQ ID | CDR1 | SEQ ID | LFR2 | SEQ ID | LCDR2 | SEQ ID | LFR3 | SEQ ID | LCDR3 | SEQ ID | LFR4 | SEQ ID |
| TLA0238 (mouse) | | | TLA0238-LCDR1-1 | 155 | | | TLA0238-LCDR2-1 | 160 | | | TLA0238-LCDR3-1 | 164 | | |
| TLA0238-1 | TLA0238-LFR1-2 | 171 | TLA0238-LCDR1-1 | 155 | TLA0238-LFR2-2 | 182 | TLA0238-LCDR2-1 | 160 | TLA0238-LFR3-2 | 191 | TLA0238-LCDR3-1 | 164 | TLA0238-LFR4-2 | 200 |
| TLA0238-2 | TLA0238-LFR1-3 | 172 | TLA0238-LCDR1-1 | 155 | TLA0238-LFR2-3 | 183 | TLA0238-LCDR2-1 | 160 | TLA0238-LFR3-3 | 192 | TLA0238-LCDR3-1 | 164 | TL0015-LFR4-3/TLA0238-LFR4-3 | 61 |
| TLA0238-3 | TLA0238-LFR1-2 | 171 | TLA0238-LCDR1-1 | 155 | TLA0238-LFR2-2 | 182 | TLA0238-LCDR2-1 | 160 | TLA0238-LFR3-2 | 191 | TLA0238-LCDR3-1 | 164 | TLA0238-LFR4-2 | 200 |
| TLA0238-4 | TLA0238-LFR1-3 | 172 | TLA0238-LCDR1-1 | 155 | TLA0238-LFR2-3 | 183 | TLA0238-LCDR2-1 | 160 | TLA0238-LFR3-3 | 192 | TLA0238-LCDR3-1 | 164 | TL0015-LFR4-3/TLA0238-LFR4-3 | 61 |
| TLA0238-2-1 | TLA0238-LFR1-3 | 172 | TLA0238-LCDR1-1 | 155 | TLA0238-LFR2-3 | 183 | TLA0238-LCDR2-1 | 160 | TLA0238-LFR3-3 | 192 | TLA0238-LCDR3-1 | 164 | TL0015-LFR4-3/TLA0238-LFR4-3 | 61 |
| TLA0238-2-2 | TLA0238-LFR1-3 | 172 | TLA0238-LCDR1-1 | 155 | TLA0238-LFR2-3 | 183 | TLA0238-LCDR2-1 | 160 | TLA0238-LFR3-3 | 192 | TLA0238-LCDR3-1 | 164 | TL0015-LFR4-3/TLA0238-LFR4-3 | 61 |
| TLA0238-5 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-1 | 164 | TLA0238-LFR4-4/TLA0241-LFR4-1 | 201 |
| TLA0238-6 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-1 | 164 | TLA0238-LFR4-4/TLA0241-LFR4-1 | 201 |
| TLA0238-7 | TLA0238-LFR1-5 | 174 | TLA0238-LCDR1-2 | 156 | TLA0238-LFR2-4 | 184 | TLA0238-LCDR2-2 | 161 | TLA0238-LFR3-5 | 193 | TLA0238-LCDR3-1 | 164 | TLA0238-LFR4-1 | 199 |
| TLA0238-8 | TLA0238-LFR1-6 | 175 | TLA0238-LCDR1-3 | 157 | TLA0238-LFR2-5 | 185 | TLA0238-LCDR2-2 | 161 | TLA0238-LFR3-6 | 194 | TLA0238-LCDR3-1 | 164 | TLA0238-LFR4-1 | 199 |
| TLA0238-9 | TLA0238-LFR1-7 | 176 | TLA0238-LCDR1-3 | 157 | TLA0238-LFR2-6 | 186 | TLA0238-LCDR2-3 | 162 | TLA0238-LFR3-7 | 195 | TLA0238-LCDR3-1 | 164 | TLA0238-LFR4-1 | 199 |
| TLA0238-10 | TLA0238-LFR1-8 | 177 | TLA0238-LCDR1-2 | 156 | TLA0238-LFR2-7 | 187 | TLA0238-LCDR2-2 | 161 | TLA0238-LFR3-8 | 196 | TLA0238-LCDR3-1 | 164 | TLA0238-LFR4-1 | 199 |

TABLE 1-4-continued

| antibody | VL LFR1 | SEQ ID | CDR1 | SEQ ID | LFR2 | SEQ ID | LCDR2 | SEQ ID | LFR3 | SEQ ID | LCDR3 | SEQ ID | LFR4 | SEQ ID |
|---|---|---|---|---|---|---|---|---|---|---|---|---|---|---|
| TLA0238-11 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-1 | 164 | TLA0238-LFR4-4/TLA0241-LFR4-1 | 201 |
| TLA0238-12 | TLA0238-LFR1-9 | 178 | TLA0238-LCDR1-4 | 158 | TLA0238-LFR2-8 | 188 | TLA0238-LCDR2-1 | 160 | TLA0238-LFR3-8 | 196 | TLA0238-LCDR3-1 | 164 | TLA0238-LFR4-1 | 199 |
| TLA0238-13 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-1 | 164 | TLA0238-LFR4-4/TLA0241-LFR4-1 | 201 |
| TLA0238-14 | TLA0238-LFR1-10 | 179 | TLA0238-LCDR1-2 | 156 | TLA0238-LFR2-7 | 187 | TLA0238-LCDR2-3 | 162 | TLA0238-LFR3-9 | 197 | TLA0238-LCDR3-1 | 164 | TLA0238-LFR4-1 | 199 |
| TLA0238-15 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-2 | 165 | TLA0238-LFR4-4/TLA0241-LFR4-1 | 201 |
| TLA0238-16 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-3 | 166 | TLA0238-LFR4-4/TLA0241-LFR4-1 | 201 |
| TLA0238-17 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-2 | 165 | TLA0238-LFR4-4/TLA0241-LFR4-1 | 201 |
| TLA0238-18 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-3 | 166 | TLA0238-LFR4-4/TLA0241-LFR4-1 | 201 |
| TLA0238-19 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-2 | 165 | TLA0238-LFR4-4/TLA0241-LFR4-1 | 201 |
| TLA0238-20 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-3 | 166 | TLA0238-LFR4-4/TLA0241-LFR4-1 | 201 |
| TLA0238-21 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-4 | 167 | TLA0238-LFR4-4/TLA0241-LFR4-1 | 201 |
| TLA0238-22 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-5 | 168 | TLA0238-LFR4-4/TLA0241-LFR4-1 | 201 |
| TLA0238-23 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-4 | 167 | TLA0238-LFR4-4/TLA0241-LFR4-1 | 201 |

TABLE 1-4-continued

| | VL | | | | | | | | | | | | | |
|---|---|---|---|---|---|---|---|---|---|---|---|---|---|---|
| antibody | LFR1 | SEQ ID | CDR1 | SEQ ID | LFR2 | SEQ ID | LCDR2 | SEQ ID | LFR3 | SEQ ID | LCDR3 | SEQ ID | LFR4 | SEQ ID |
| TLA0238-24 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-5 | 168 | TLA0238-LFR4-4/TLA0241-LFR4-1 | 201 |
| TLA0238-25 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-4 | 167 | TLA0238-LFR4-4/TLA0241-LFR4-1 | 201 |
| TLA0238-26 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-5 | 168 | TLA0238-LFR4-4/TLA0241-LFR4-1 | 201 |
| TLA0238-27 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-4 | 167 | TLA0238-LFR4-4/TLA0241-LFR4-1 | 201 |
| TLA0238-28 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-5 | 168 | TLA0238-LFR4-4/TLA0241-LFR4-1 | 201 |
| TLA0238-29 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-4 | 167 | TLA0238-LFR4-4/TLA0241-LFR4-1 | 201 |
| TLA0238-30 | TLA0238-LFR1-4/TLA0241-LFR1-2 | 173 | TLA0238-LCDR1-1 | 155 | TLA0238-LFR2-3 | 183 | TLA0238-LCDR2-1 | 160 | TL0015-LFR3-4/TLA0238-LFR3-4/TLA0241-LFR3-2 | 57 | TLA0238-LCDR3-5 | 168 | TLA0238-LFR4-4/TLA0241-LFR4-1 | 201 |

Isolated Antigen-Binding Protein-TLA-0241

In one aspect, the present disclosure provides an antigen-binding protein which specifically binds to TL1A and comprises a heavy chain variable region (VH). The VH comprises at least one heavy chain complementarity determining regions (HCDR). The VH may include at least one, two or three of HCDR1, HCDR2 or HCDR3. In some embodiments, HCDR 1, HCDR3 and HCDR3 are sequences as set forth in SEQ ID NO:235, 238 and 242 respectively.

HCDR3 of the antigen-binding protein may include amino acid sequence as set forth in SEQ ID NO: 242. For example, the sequence of HCDR3 of the antigen-binding protein may be defined by Kabat.

HCDR2 of the antigen-binding protein may include amino acid sequence as set forth in SEQ ID NO: 238. For example, the sequence of HCDR2 of the antigen-binding protein may be defined by Kabat.

In some embodiments, HCDR2 may be DINPNNGRTTYX94X95X96X97X98G (SEQ ID NO: 238). X94 may be A or N. X95 may be D or Q. X96 may be K or S. X97 may be F or V. X98 may be K or Q or T.

In some embodiments, HCDR2 may include an amino acid sequence as set forth in any one of SEQ ID NOs: 239-241.

HCDR1 of the antigen-binding protein may include amino acid sequence as set forth in SEQ ID NO: 235. For example, the sequence of HCDR1 of the antigen-binding protein may be defined by Kabat.

In some embodiments, HCDR1 may be DYYX99X100 (SEQ ID NO:235). X99 may be Lor M.

X100 may be N or H.

In some embodiments, HCDR1 may include an amino acid as set forth in any one of SEQ ID NOs: 236-237.

In some embodiments, the VH comprises HFR1, and C-terminus of HFR1 is directly or indirectly linked to the N-terminus of HCDR1. For example, the sequence of HFR1 of the antigen-binding protein may be defined by Kabat. HFR1 comprises an amino acid as set forth in SEQ ID NO: 243.

In some embodiments, HFR1 is X101IX102 X103TQSPX104 X105 X106S X107S X108G X109 X110VTITC (SEQ ID NO: 243). X101 may be A or D or E. X102 may be V or Q. X103 may be Lor M. X104 may be A or G or Por S or T. X105 may be S or T. X106 may be Lor V. X107 may be A or L. X108 may be Por V. X109 may be Dor E. X110 may be K or R.

In some embodiments, HFR1 is selected from an amino acid sequence as set forth in any one of SEQ ID NOs: 244-250.

In some embodiments, VH comprises HFR2, and HFR2 is located between HCDR1 and HCDR2. For example, the sequence of HFR2 of the antigen-binding protein may be defined by Kabat. HFR2 comprises an amino acid sequence as set forth in SEQ ID NO:251.

In some embodiments, HFR2 is WYQQKP X111 X112 X113P X114LLIY (SEQ ID NO:251). X111 may be D or G. X112 may be K or Q. X113 may be A or S. X114 may be K or Q.

In some embodiments, HFR2 is selected from an amino acid sequence as set forth in any one of SEQ ID NOs: 252-255.

In some embodiments, VH comprises HFR3, and HFR3 is located between HCDR2 and HCDR3. For example, the sequence of HFR3 of the antigen-binding protein may be defined by Kabat. HFR3 comprises an amino acid as set forth in SEQ ID NO:256.

In some embodiments, HFR3 is GVPX115RFSGSGSGTX116FTLTIX117SLX118X119ED X120ATYYC (SEQ ID NO:256). X115 may be A or D or S. X116 may be D or E or S. X117 may be S or N. X118 may be E or Q. X119 may be A or P. X120 may be A or F.

In some embodiments, HFR3 is selected from an amino acid sequence as set forth in any one of SEQ ID NOs: 257-262.

In some embodiments, VH comprises HFR4, and N-terminus of HFR4 is directly or indirectly linked to C-terminus of HCDR3. For example, the sequence of HFR4 of the antigen-binding protein may be defined by Kabat. HFR4 comprises an amino acid sequence as set forth in SEQ ID NO: 263.

In some embodiments, HFR4 is FGX121GTX122X123EX124K (SEQ ID NO:263). X121 may be A or Q. X122 may be Kor R. X123 may be Lor V. X124 may be I or L.

In some embodiments, HFR4 is selected from an amino acid sequence as set forth in any one of SEQ ID NOs: 264-268.

In some embodiments, the isolated antigen-binding protein further comprises a light chain variable region (VL), an VL comprises at least one light chain complementarity determining regions (LCDR). VL comprises LCDR1, LCDR2 and LCDR3, which is selected from an amino acid sequence as set forth in any one of SEQ ID NO: 269, SEQ ID NO:274 and SEQ ID NO:277 accordingly.

In some embodiments, VL comprises LCDR3 including an amino acid sequence as set forth in SEQ ID NO:277. For example, the sequence of LCDR3 of the antigen-binding protein may be defined by Kabat.

In some embodiments, VL comprises LCDR2 including an amino acid sequence as set forth in SEQ ID NO:274. For example, the sequence of LCDR2 of the antigen-binding protein may be defined by Kabat.

In some embodiments, LCDR2 is KTSNX125PS (SEQ ID NO:274). X125 may be L or R.

In some embodiments, LCDR2 is selected from an amino acid sequence as set forth in any one of SEQ ID NOs: 275-276.

In some embodiments, VL comprises LCDR1 including an amino acid sequence as set forth in SEQ ID NO:269. For example, the sequence of LCDR1 of the antigen-binding protein may be defined by Kabat.

In some embodiments, LCDR1 is SX126SSSIISNYX127X128 (SEQ ID NO:269). X126 may be A or T. X127 may be Lor S. X128 may be A or H.

In some embodiments, LCDR1 is selected from an amino acid sequence as set forth in any one of SEQ ID NOs: 270-273.

In some embodiments, VL comprises the LFR1, and C-terminus of the LFR1 is directly or indirectly linked to N-terminus of LCDR1. For example, the sequence of the LFR1 of the antigen-binding protein may be defined by Kabat. the LFR1 comprises an amino acid sequence as set forth in SEQ ID NO:278.

In some embodiments, the LFR1 is X129IX130X131TQSPX132X133X134SX135S X136GX137X138VTITC (SEQ ID NO:278).

X129 may be A or E or D. X130 may be Q or V. X131 may be Lor M. X132 may be A or G or Por S or T. X133 may be S or T. X134 may be Lor V. X135 may be Lor A. X136 may be Por V. X137 may be D or E. X138 may be K or R.

In some embodiments, the LFR1 comprises an amino acid sequence as set forth in any one of SEQ ID NOs: 47, 173, 279-284.

In some embodiments, VL comprises the LFR2, and the LFR2 is located between LCDR1 and LCDR2. For example, the sequence of the LFR2 of the antigen-binding protein may be defined by Kabat, the LFR2 comprises an amino acid sequence as set forth in SEQ ID NO:284.

In some embodiments, the LFR2 is WYQQKPX139 X140 X141P X142LLIY (SEQ ID NO: 284). X139 may be D or G. X140 may be K or Q. X141 may be A or S. X142 may be K or Q.

In some embodiments, the LFR2 comprises an amino acid sequence as set forth in any one of SEQ ID NOs: 52, 285-287.

In some embodiments, VL comprises the LFR3, and the LFR3 is located between LCDR2 and LCDR3. For example, the sequence of the LFR3 of the antigen-binding protein may be defined by Kabat. The LFR3 comprises an amino acid sequence as set forth in SEQ ID NO: 288.

In some embodiments, the LFR3 is GVPX143RFSGSGSGTX144FTLTIX145SLX146X147ED X148ATYYC (SEQ ID NO:288). X143 may be A or D or S. X144 may be D or E or S. X145 may be N or S. X146 may be E or Q. X147 may be A or P. X148 may be A or F.

In some embodiments, the LFR3 comprises an amino acid sequence as set forth in any one of SEQ ID NOs: 289-293 and 57.

In some embodiments, the isolated antigen-binding protein comprises the LFR4, and N-terminus of the LFR4 is directly or indirectly linked to C terminus of LCDR3. For example, the sequence of the LFR4 of the antigen-binding protein may be defined by Kabat. The LFR4 comprises an amino acid sequence as set forth in SEQ ID NO:294.

In some embodiments, the LFR4 is FG FGX148GTX149X150EX151K (SEQ ID NO: 294). X148 may be A or Q. X149 may be K or R. X150 may be Lor V. X151 may be I or L.

In some embodiments, the LFR4 comprises an amino acid sequence as set forth in any one of SEQ ID NOs: 295-296 and 201.

In some embodiments, VH comprises sequences as set forth in SEQ ID NOs: 297-230.

In some embodiments, VL comprises sequences as set forth in SEQ ID NOs: 308-317.

In some embodiments, the antigen-binding proteins described above are mentioned in Example 4, Tables 8 and 9.

In some embodiments, the distribution of antibodies for the TLA-0238 series is shown in the following table, with Table 1-5 showing the distribution of heavy chain components and Table 1-6 showing the distribution of light chain components. The technical solution of the present application includes, for the same antibody, a combination of HCDR1-3 in Table 1-5 and LCDR1-3 in Table 1-6. The technical solution of the present application includes, for the same antibody, a combination of VH in Table 1-5 and VL in Table 1-6.

TABLE 1-5

| Antibody no. | VH | | | | | | | | | | | | | |
|---|---|---|---|---|---|---|---|---|---|---|---|---|---|---|
| | HFR1 | SEQ ID | HCDR1 | SEQ ID | HFR2 | SEQ ID | HCDR2 | SEQ ID | HFR3 | SEQ ID | HCDR3 | SEQ ID | HFR4 | SEQ ID |
| TLA0241 | | | TLA0241-HCDR1-1 | 236 | | | TLA0241-HCDR2-1 | 239 | | | TLA0241-HCDR3-1 | 242 | | |
| TLA0241-1 | TLA0241-HFR1-1 | 244 | TLA0241-HCDR1-1 | 236 | TLA0241-HFR2-1 | 252 | TLA0241-HCDR2-2 | 240 | TLA0241-HFR3-1 | 257 | TLA0241-HCDR3-1 | 242 | TLA0241-HFR4-1 | 264 |
| TLA0241-2 | TLA0241-HFR1-2 | 245 | TLA0241-HCDR1-1 | 236 | TLA0241-HFR2-1 | 252 | TLA0241-HCDR2-2 | 240 | TLA0241-HFR3-2 | 258 | TLA0241-HCDR3-1 | 242 | TLA-0238-HFR4-4 | 152 |
| TLA0241-3 | TLA0241-HFR1-3 | 246 | TLA0241 HCDR1-2 | 237 | TLA0241-HFR2-2 | 253 | TLA0241-HCDR2-3 | 241 | TLA0241-HFR3-3 | 259 | TLA0241-HCDR3-1 | 242 | TLA0241-HFR4-5 | 268 |
| TLA0241-4 | TLA0241-HFR1-3 | 246 | TLA0241-HCDR1-2 | 237 | TLA0241-HFR2-3 | 254 | TLA0241-HCDR2-3 | 241 | TLA0241-HFR3-4 | 260 | TLA0241-HCDR3-1 | 242 | TLA0241-HFR4-3 | 266 |
| TLA0241-5 | TLA0241-HFR1-4 | 247 | TLA0241-HCDR1-2 | 237 | TLA0241-HFR2-3 | 254 | TLA0241-HCDR2-3 | 241 | TLA0241-HFR3-5 | 261 | TLA0241-HCDR3-1 | 242 | TLA0241-HFR4-5 | 268 |
| TLA0241-6 | TLA0241-HFR1-5 | 248 | TLA0241-HCDR1-1 | 236 | TLA0241-HFR2-1 | 252 | TLA0241-HCDR2-2 | 240 | TLA0241-HFR3-2 | 258 | TLA0241-HCDR3-1 | 242 | TLA-0238-HFR4-4 | 152 |
| TLA0241-7 | TLA0241-HFR1-3 | 246 | TLA0241-HCDR1-2 | 237 | TLA0241-HFR2-4 | 255 | TLA0241-HCDR2-3 | 241 | TLA0241-HFR3-4 | 260 | TLA0241-HCDR3-1 | 242 | TLA0241-HFR4-5 | 268 |
| TLA0241-8 | TLA0241-HFR1-2 | 245 | TLA0241-HCDR1-1 | 236 | TLA0241-HFR2-1 | 252 | TLA0241-HCDR2-2 | 240 | TLA0241-HFR3-2 | 258 | TLA0241-HCDR3-1 | 242 | TLA-0238-HFR4-5 | 153 |
| TLA0241-9 | TLA0241-HFR1-6 | 249 | TLA0241-HCDR1-2 | 237 | TLA0241-HFR2-3 | 254 | TLA0241-HCDR2-3 | 241 | TLA0241-HFR3-4 | 260 | TLA0241-HCDR3-1 | 242 | TLA0241-HFR4-5 | 268 |
| TLA0241-10 | TLA0241-HFR1-7 | 250 | TLA0241-HCDR1-2 | 237 | TLA0241-HFR2-2 | 253 | TLA0241-HCDR2-3 | 241 | TLA0241-HFR3-6 | 262 | TLA0241-HCDR3-1 | 242 | TLA0241-HFR4-3 | 266 |

TABLE 1-6

| Antibody No. | VL | | | | | | | | | | | | | |
|---|---|---|---|---|---|---|---|---|---|---|---|---|---|---|
| | LFR1 | SEQ ID | CDR1 | SEQ ID | LFR2 | SEQ ID | LCDR2 | SEQ ID | LFR3 | SEQ ID | LCDR3 | SEQ ID | LFR4 | SEQ ID |
| TLA0241 | | | TLA0241-LCDR1-1 | 270 | | | TLA0241-LCDR2-1 | 275 | | | TLA0241-LCDR3-1 | 277 | | |
| TLA0241-1 | TL0015-LFR1-2/ TLA0241-LFR1-1 | 47 | TLA0241-LCDR1-1 | 270 | TL0015-LFR2-4/ TLA0241-LFR2-1 | 52 | TLA0241-LCDR2-1 | 275 | TLA0241-LFR3-1 | 289 | TLA0241-LCDR3-1 | 277 | TLA0238-LFR4-4/ TLA0241-LFR4-1 | 201 |
| TLA0241-2 | TLA0238-LFR1-4/ TLA0241-LFR1-2 | 173 | TLA0241-LCDR1-1 | 270 | TL0015-LFR2-4/ TLA0241-LFR2-1 | 52 | TLA0241-LCDR2-1 | 275 | TL0015-LFR3-4/ TLA0238-LFR3-4/ TLA0241-LFR3-2 | 57 | TLA0241-LCDR3-1 | 277 | TLA0238-LFR4-4/ TLA0241-LFR4-1 | 201 |
| TLA0241-3 | TLA0241-LFR1-3 | 279 | TLA0241-LCDR1-2 | 271 | TLA0241-LFR2-2 | 285 | TLA0241-LCDR2-1 | 275 | TLA0241-LFR3-3 | 290 | TLA0241-LCDR3-1 | 277 | TLA0241-LFR4-2 | 295 |
| TLA0241-4 | TLA0241-LFR1-4 | 280 | TLA0241-LCDR1-2 | 271 | TLA0241-LFR2-3 | 286 | TLA0241-LCDR2-2 | 276 | TLA0241-LFR3-4 | 291 | TLA0241-LCDR3-1 | 277 | TLA0241-LFR4-2 | 295 |
| TLA0241-5 | TLA0241-LFR1-5 | 281 | TLA0241-LCDR1-2 | 271 | TLA0241-LFR2-4 | 287 | TLA0241-LCDR2-1 | 275 | TLA0241-LFR3-3 | 290 | TLA0241-LCDR3-1 | 277 | TLA0241-LFR4-3 | 296 |
| TLA0241-6 | TLA0241-LFR1-6 | 282 | TLA0241-LCDR1-1 | 270 | TL0015-LFR2-4/ TLA0241-LFR2-1 | 52 | TLA0241-LCDR2-1 | 275 | TL0015-LFR3-4/ TLA0238-LFR3-4/ TLA0241-LFR3-2 | 57 | TLA0241-LCDR3-1 | 277 | TLA0238-LFR4-4/ TLA0241-LFR4-1 | 201 |
| TLA0241-7 | TLA0241-LFR1-7 | 283 | TLA0241-LCDR1-3 | 272 | TLA0241-LFR2-2 | 285 | TLA0241-LCDR2-1 | 275 | TLA0241-LFR3-5 | 292 | TLA0241-LCDR3-1 | 277 | TLA0241-LFR4-2 | 295 |
| TLA0241-8 | TLA0238-LFR1-4/ TLA0241-LFR1-2 | 173 | TLA0241-LCDR1-1 | 270 | TL0015-LFR2-4/ TLA0241-LFR2-1 | 52 | TLA0241-LCDR2-1 | 275 | TL0015-LFR3-4/ TLA0238-LFR3-4/ TLA0241-LFR3-2 | 57 | TLA0241-LCDR3-1 | 277 | TLA0238-LFR4-4/ TLA0241-LFR4-1 | 201 |
| TLA0241-9 | TLA0241-LFR1-3 | 279 | TLA0241-LCDR1-2 | 271 | TLA0241-LFR2-4 | 287 | TLA0241-LCDR2-1 | 275 | TLA0241-LFR3-3 | 290 | TLA0241-LCDR3-1 | 277 | TLA0241-LFR4-3 | 296 |
| TLA0241-10 | TLA0241-LFR1-4 | 280 | TLA0241-LCDR1-4 | 273 | TLA0241-LFR2-2 | 285 | TLA0241-LCDR2-1 | 275 | TLA0241-LFR3-6 | 293 | TLA0241-LCDR3-1 | 277 | TLA0241-LFR4-3 | 296 |

Recombinant Antibodies

In the present application, the isolated antigen-binding protein or antibody may include a heavy chain constant region, said heavy chain constant region may include a constant region derived from IgG or a constant region derived from Ig Y.

For example, the isolated antigen-binding protein or antibody may include a constant region derived from IgG. For example, the isolated antigen-binding protein or antibody may include a heavy chain. The heavy chain may include a heavy chain variable region and a heavy chain constant region. The heavy chain variable region and the heavy chain constant region may be directly or indirectly connected. For example, the heavy chain variable region may be directly connected to the heavy chain constant region. For example, the heavy chain constant region may include a constant region derived from a protein selected from the group consisting of IgG1, IgG2, IgG3, and IgG4. In some embodiments, the heavy chain constant region may include a constant region derived from a protein selected from the group consisting of human IgG1, IgG2, IgG3, and IgG4. In some embodiments, the heavy chain constant region may include a constant region derived from IgG1. The heavy chain constant region may include a constant region derived from human IgG1. In some embodiments, the constant region may include L234A and L235A mutations. In some embodiments, the constant region may include M252Y, S254T, and T256E mutations, and in some embodiments, the constant region may include L234A, L235A, M252Y, S254T, and T256E mutations. The Fc constant region of the antigen-binding protein may comprise the amino acid sequence set forth in SEQ ID NO: 320 or SEQ ID NO: 321. CH1 may comprise the amino acid sequence set forth in SEQ ID NO: 319.

In the present application, the isolated antigen-binding protein or antibody may include a light chain constant region, said light chain constant region may include a constant region derived from Igκ or a constant region derived from Igλ. For example, said light chain constant region may include a Kappa light chain constant region, such as SEQ ID NO:318.

In some embodiments, the isolated antigen-binding protein or antibody may include a light chain and a heavy chain, wherein the light chain structure is: light chain variable region VL-light chain constant region, and the heavy chain structure is: heavy chain variable region VH-CH1-Fc constant region. The VH and VL may be a combination of the VH and VL of the antibodies of the same name in Tables 1-1 and 1-2, or a combination of the antibodies of the same name in Tables 1-3 or 1-4, or a combination of the antibodies of the same name in Tables 1-5 or 1-6. The light chain constant region may have the amino acid sequence set forth in SEQ ID NO:318. CH1 may have the amino acid sequence set forth in SEQ ID NO:319. The Fc constant region may comprise the amino acid sequence set forth in SEQ ID NO:320 or SEQ ID NO:321.

For example, the isolated antigen-binding protein or antibody described herein may include the following heavy chain and light chain combinations:

```
Heavy chain:
                                    (SEQ ID NO 339)
EIQLVESGGGLIQPGGSLRISCAVSGFSLSSYGVDWVRQAPGKGLEWLG

VIWGFGGTNYNSALKSRLTISKDNSKNTVYLQMNSLRAEDTAVYYCASG
```

-continued

```
NFDAMDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQT

YICNVNHKPSNTKVDKKVEPKSCDKTHTCPPCPAPEAAGGPSVFLFPPK

PKDTLYITREPEVTCVVVDVSHEDPEVKFNWYVDGVEVHNAKTKPREEQ

YNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLS

LSPGK

Light chain:
                                    (SEQ ID NO 340)
DIQMTQSPSSLSASVGDRVTITCRASQDISNYLNWYQQKPGKAVKLLIY

YTSRLHSGVPSRFSGSGSGTDYTLTISSLQPEDFATYFCQQGNTLPFTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

Peptides and Immunoconjugates

In another aspect, the present application provides one or more polypeptides, which may comprise an isolated antigen-binding protein of the present application.

In another aspect, the present application provides one or more immunoconjugates, which may comprise an isolated antigen-binding protein of the present application. In some embodiments, the immunoconjugate also comprises a pharmaceutically acceptable therapeutic agent.

Nucleic Acid, Vector, and Cell

In another aspect, the present application also provides one or more isolated nucleic acid molecules that may encode the isolated antigen-binding proteins described herein. For example, each of the one or more nucleic acid molecules may encode the entire antigen-binding protein or a portion thereof (e.g., one or more of the HCDR1-3 and the heavy chain variable regions).

The nucleic acid molecules described herein may be isolated. For example, it may be produced or synthesized by the following methods: (i) in vitro amplification, e.g., by polymerase chain reaction (PCR) amplification, (ii) clonal recombination, (iii) purification, e.g., by digestion and gel electrophoresis fractionation, or (iv) synthesis, e.g., by chemical synthesis. For example, the isolated nucleic acid may be a nucleic acid molecule prepared by recombinant DNA technology.

In the present application, the nucleic acids encoding the isolated antigen-binding proteins may be prepared by a variety of methods known in the art including, but not limited to, using reverse transcription PCR and PCR to obtain nucleic acid molecules of the isolated antigen-binding proteins described herein.

In another aspect, the present application provides one or more vectors comprising one or more nucleic acid molecules described herein. Each vector may comprise one or more of the nucleic acid molecules. In addition, the vector may also comprise other genes, such as marker genes that allow for selection of the vector in an appropriate host cell and under appropriate conditions. In addition, the vector may also comprise expression control elements that allow for the proper expression of the coding region in an appropriate host. Such control elements are well known to those skilled in the art and may include, for example, promoters, ribosome binding sites, enhancers, and other control elements that regulate gene transcription or mRNA translation, etc. In some embodiments, the expression control sequence is a regulatable element. The specific structure of the expression control sequences may vary depending on the function of the species or cell type, but typically comprise 5' non-transcribed sequences and 5' and 3' non-translated sequences involved in transcription and translation initiation, respectively, such as TATA cassettes, capping sequences, CAAT sequences, etc. For example, the 5' non-transcribed expression control sequence may comprise a promoter region, which may comprise a promoter sequence for transcription control of a functionally linked nucleic acid. The expression control sequences may also include enhancer sequences or upstream activator sequences. In the present application, suitable promoters may include, for example, promoters for SP6, T3, and T7 polymerases, human U6RNA promoters, CMV promoters, and artificial hybrid promoters thereof (e.g., CMV), wherein some portion of the promoter may be fused to some portion of the promoter of a gene for another cellular proteins (e.g., human GAPDH, glyceraldehyde-3-phosphate dehydrogenase), which may or may not comprise an additional intron. One or more nucleic acid molecules described herein can be operably linked to the expression control elements.

Such vectors may include, for example, plasmids, cosmids, viruses, phages, or other vectors commonly used in, for example, genetic engineering. For example, the vector may be an expression vector. For example, the vector may be a viral vector. The patient may be administered directly (in vivo) with the viral vector or may be administered indirectly, e.g., the patient may be administered with the cell treated with the virus in vitro (ex vivo). Viral vector technology is well known in the art and is described, for example, in Sambrook et al., (2001, Molecular Cloning: A Laboratory Manual, Cold Spring Harbor Laboratory, New York) and other virology and molecular biology manuals. Conventional virus-based systems may include retroviral vectors, lentiviral vectors, adenoviral vectors, adeno-associated viral vectors, and herpes simplex viral vectors for gene transfer. In some cases, retroviral, lentiviral, and adeno-associated viral methods can be used to transfer and integrate gene into the host genome for long term expression of the inserted gene. Lentiviral vectors are retroviral vectors capable of transducing or infecting non-dividing cells and typically producing higher viral titers. Lentiviral vectors may comprise a long terminal repeat 5' LTR and a truncated 3' LTR, a RRE, a rev response element (cPPT), a central termination sequence (CTS), and/or a post-translational regulatory element (WPRE). The vectors described herein can be introduced into cells.

According to another aspect, the present application provides a cell. The cell may comprise an isolated antigen-binding protein as described herein, a polypeptide as described herein, an immunoconjugate as described herein, one or more nucleic acid molecules and/or one or more vectors as described herein. For example, each or every cell may comprise a nucleic acid molecule or vector described herein. For example, each or every cell may comprise many (e.g., 2 or more) or multiple (e.g., 2 or more) kinds of nucleic acid molecules or vectors described herein. For example, the vectors described herein can be introduced into said host cells, such as prokaryotic cells (e.g., bacterial cells), CHO cells, NS/0 cells, HEK293T cells, 293F cells, or HEK293A cells, or other eukaryotic cells, such as cells from plants, fungal or yeast cells, etc. The vectors described herein can be introduced into the host cells by methods known in the art, such as electroporation, lipofectine transfection, lipofectamin transfection, etc. For example, the cells may include yeast cells. For example, the cells may include *E. coli* cells. For example, the cells may include mammalian cells. For example, the cells may include immune cells.

The cells may include immune cells. In some cases, the cells may include immune cells. For example, the cells may include T cells, B cells, natural killer cells (NK cells), macrophages, NKT cells, monocytes, dendritic cells, granulocytes, lymphocytes, leukocytes and/or peripheral blood mononuclear cells.

Pharmaceutical Composition and Pharmaceutical Combination

In another aspect, the present application provides a pharmaceutical composition. The pharmaceutical composition may comprise the isolated antigen-binding protein, the polypeptide, the immunoconjugate, the isolated nucleic acid molecule, the vector, the cell, and/or the pharmaceutically acceptable adjuvant and/or excipient as described herein. In the present application, the pharmaceutically acceptable adjuvants may include buffers, antioxidants, preservatives, low molecular weight polypeptides, proteins, hydrophilic polymers, amino acids, sugars, chelating agents, counter ions, metal complexes and/or nonionic surfactants. Any conventional media or agent is contemplated for the pharmaceutical compositions of the present application, unless they are incompatible with the cells described herein. In the present application, the pharmaceutically acceptable excipients may include an additive other than main drug in the pharmaceutical preparation, which may also be referred to as pharmaceutical necessities. For example, the excipients may include binders, fillers, disintegrants, and lubricants in tablets. For example, the excipients may include alcohol, vinegar, medicinal juice, etc. in traditional Chinese medicine pills. For example, the excipients may include the base portion of semi-solid formulation ointments and creams. For example, the excipients may include preservatives, antioxidants, flavoring agents, perfuming agents, solubilizing assistant, emulsifiers, solubilizers, osmotic pressure regulators, and colorants in liquid formulations.

Kits, Uses and Methods

In one aspect, the present application provides a method for detecting or assaying TL1A, said method may comprise using said isolated antigen-binding protein or said peptide.

In the present application, said method may comprise an in vitro method, an ex vivo method, a method for non-diagnostic or non-therapeutic purposes.

For example, said methods may comprise methods for detecting the presence and/or amount of TL1A for non-diagnostic purposes, which may comprise the following steps:

1) contacting a sample with an antigen-binding protein of the present application; and
2) detecting the presence and/or amount of said antigen-binding protein bound by the sample to determine the presence and/or expression level of TL1A in a sample obtained from a subject.

In another aspect, the present application provides a kit for TL1A, which may comprise the use of said isolated antigen-binding protein or said peptide.

In the present application, said kit may also include instructions for use, said instructions for use documenting a method for detecting the presence and/or level of TL1A. For example, said methods may include in vitro methods, ex vivo methods, methods for non-diagnostic or non-therapeutic purposes.

In another aspect, the present application provides a use of said isolated antigen-binding protein or said polypeptide in the preparation of a kit, said kit being usable for methods for detecting the presence and/or the amount of TL1A. For example, said methods may include in vitro methods, ex vivo methods, methods for non-diagnostic or non-therapeutic purposes.

In another aspect, the present application provides a method of inhibiting the binding of TL1A to DR3/TR6/DcR3 comprising administering to a subject in need thereof an effective amount of said isolated antigen-binding protein, said peptide, said immuno-fix, said isolated nucleic acid molecule, said vector, and/or said cell. Said methods may be in vitro or ex vivo methods.

In another aspect, the present application provides isolated antigen-binding proteins, said polypeptides, said immune-conjugates, said isolated nucleic acid molecules, said vectors, and said pharmaceutical compositions for use in the prevention, mitigation and/or treatment of a disease or condition.

In another aspect, in the present application, said kits and/or said pharmaceutical compositions are used for the prevention, mitigation and/or treatment of a disease or condition.

In another aspect, the present application provides the use of a pharmaceutical composition in the preparation of a drug, said drug being used for the prevention, alleviation and/or treatment of a disease or condition.

In another aspect, the present application provides a method of preventing and/or treating a disease or condition comprising administering to a subject in need thereof said isolated antigen-binding protein, said isolated nucleic acid molecule, said vector, said cell, said pharmaceutical composition.

The disease or condition disclosed herein may be an inflammatory disease, a fibrostenotic disease, or a fibrotic disease. In some instances, the disease or the condition is a TL1A-mediated disease or condition. The term, "TL1A-mediated disease or condition" refers to a disease or a condition pathology or pathogenesis that is driven, at least in part, by TL1A signaling. In some instances, the disease or the condition is immune-mediated disease or condition, such as those mediated by TL1A.

In some embodiments, the disease or the condition is an inflammatory disease or disorder that is mediated, at least in part, by TL1A signaling. Non-limiting examples of inflammatory disease include, allergy, ankylosing spondylitis, asthma, atopic dermatitis, autoimmune diseases or disorders, cancer, celiac disease, chronic obstructive pulmonary disease (COPD), chronic peptic ulcer, cystic fibrosis, diabetes (e.g., type 1 diabetes and type 2 diabetes), glomerulonephritis, gout, hepatitis (e.g., active hepatitis), an immune-mediated disease or disorder, inflammatory bowel disease (IBD) such as Crohn's disease and ulcerative colitis, myositis, osteoarthritis, pelvic inflammatory disease (PID), multiple sclerosis, neurodegenerative diseases of aging, periodontal disease (e.g., periodontitis), preperfusion injury transplant rejection, psoriasis, pulmonary fibrosis (e.g., idiopathic pulmonary fibrosis), rheumatic disease, scleroderma, sinusitis, tuberculosis.

In some embodiments, the disease or the condition is an autoimmune disease that is mediated, at least in part, by TL1A signaling. Non-limiting examples of autoimmune disease or disorder include Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopeniaurpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal MotorNeuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopeni purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Vogt-Koyanagi-Harada Disease.

In some embodiments, the disease or the condition is a cancer that is mediated, at least in part, by TL1A signaling.

Non-limiting examples of cancers include Adenoid Cystic Carcinoma, Adrenal Gland Cancer, Amyloidosis, Anal Cancer, Ataxia-Telangiectasia, Atypical Mole Syndrome, Basal Cell Carcinoma, Bile Duct Cancer, Birt Hogg Dube Syndrome, Bladder Cancer, Bone Cancer, Brain Tumor, Breast Cancer, Breast Cancer in Men, Carcinoid Tumor, Cervical Cancer, Colorectal Cancer, Ductal Carcinoma, Endometrial Cancer, Esophageal Cancer, Gastric Cancer, Gastrointestinal Stromal Tumor (GIST), HER2-Positive Breast Cancer, Islet Cell Tumor, Juvenile Polyposis Syndrome, Kidney Cancer, Laryngeal Cancer, Leukemia-Acute Lymphoblastic Leukemia, Leukemia-Acute Lymphocytic (ALL), Leukemia-Acute Myeloid AML, Leukemia-Adult, Leukemia-Childhood, Leukemia-Chronic Lymphocytic (CLL), Leukemia-Chronic Myeloid (CIVIL), Liver Cancer, Lobular Carcinoma, Lung Cancer, Lung Cancer-Small Cell (SCLC), Lung Cancer-Non-small Cell (NSCLC), Lymphoma-Hodgkin's, Lymphoma-Non-Hodgkin's, Malignant Glioma, Melanoma, Meningioma, Multiple Myeloma, Myelodysplastic Syndrome (MDS), Nasopharyngeal Cancer, Neuroendocrine Tumor, Oral Cancer, Osteosarcoma, Ovarian Cancer, Pancreatic Cancer, Pancreatic Neuroendocrine Tumors, Parathyroid Cancer, Penile Cancer, Peritoneal Cancer, Peutz-Jeghers Syndrome, Pituitary Gland Tumor, Polycythemia Vera, Prostate Cancer, Renal Cell Carcinoma, Retinoblastoma, Salivary Gland Cancer, Sarcoma, Sarcoma-Kaposi, Skin Cancer, Small Intestine Cancer, Stomach Cancer, Testicular Cancer, Thymoma, Thyroid Cancer, Uterine (Endometrial) Cancer, Vaginal Cancer, and Wilms' Tumor.

In some embodiments, the disease or the condition is an inflammatory bowel disease, such as Crohn's disease (CD) or ulcerative colitis (UC). A subject may suffer from fibrosis, fibrostenosis, or a fibrotic disease, either isolated or in combination with an inflammatory disease. In some cases, the CD is severe CD. The severe CD may result from inflammation that has led to the formation of scar tissue in the intestinal wall (fibrostenosis) and/or swelling. In some cases, the severe CD is characterized by the presence of fibrotic and/or inflammatory strictures. The strictures may be determined by computed tomography enterography (CTE), and magnetic resonance imaging enterography (MRE). The disease or condition may be characterized as refractory, which in some cases, means the disease is resistant to a standard treatment (e.g., anti-TNFα therapy). Non-limiting examples of standard treatment include glucocorticosteriods, anti-TNF therapy, anti-a4-b7 therapy (vedolizumab), anti-IL12p40 therapy (ustekinumab), Thalidomide, and Cytoxin.

In the present application, the subject may include a human or non-human animal. For example, the non-human animal may be selected from the group consisting of: a monkey, a chicken, a goose, a cat, a dog, a mouse, and a rat. In addition, a non-human animal may also include any animal species other than human, such as livestock animals, or rodents, or primates, or domestic animals, or poultry animals. The human can be Caucasian, African, Asian, Sumerian, or other ethnicity, or a hybrid of various ethnicities. As another example, the human may be the elderly, adults, adolescents, children or infants.

Effective amounts in human can be extrapolated from the effective amounts in experimental animals. For example, Freireich et al. described the interrelationship of dosages for animals and humans (based on milligrams per meter squared of body surface) (Freireich et al., Cancer Chemother. Rep. 50, 219 (1966)). Body surface area can be approximately determined from the height and weight of the patient. See, e.g., Scientific Tables, Geigy Pharmaceuticals, Ardsley, N. Y, 537 (1970).

Further Numbered Embodiments

Further numbered embodiments of the disclosure are provided below:

Embodiment 1

An isolated antigen-binding protein specifically binding to TNF-like protein A (TL1A), comprising a heavy chain variable region (VH), wherein the VH comprises at least one heavy chain complementarity-determining region (HCDR) comprising an amino acid sequence shown in SEQ ID NO:1, SEQ ID NO:5, or SEQ ID NO: 14.

Embodiment 2

The isolated antigen-binding protein of Embodiment 1, wherein the VH comprises an HCDR3 comprising an amino acid sequence as set forth in SEQ ID NO:14.

Embodiment 3

The isolated antigen-binding protein according to any one of Embodiments 1-2, wherein the HCDR3 comprises an amino acid sequence as set forth in any one SEQ ID NOs: 15-18.

Embodiment 4

The isolated antigen-binding protein according to any one of Embodiments 1-3, wherein the VH comprises an HCDR2 comprising an amino acid sequence as set forth in SEQ ID NO:5.

Embodiment 5

The isolated antigen-binding protein of Embodiment 4, wherein the HCDR2 comprises an amino acid sequence as set forth in any one of SEQ ID NOs: 6-13.

Embodiment 6

The isolated antigen-binding protein according to any one of Embodiments 1-5, wherein the VH comprises an HCDR1 which comprises an amino acid sequence as set forth in SEQ ID NO:1.

Embodiment 7

The isolated antigen-binding protein of Embodiment 6, wherein the HCDR1 comprises an amino acid sequence as set forth in any one of SEQ ID NOs: 2-4.

Embodiment 8

The isolated antigen-binding protein according to any one of Embodiments 1-7, wherein the VH comprises the HCDR1 as set forth in SEQ ID NO: 2, the HCDR2 as set forth in SEQ ID NO: 6, and the HCDR3 as set forth in SEQ ID NO: 15.

Embodiment 9

The isolated antigen-binding protein according to any one of Embodiments 1-7, wherein the VH comprises the HCDR1 as set forth in SEQ ID NO: 2, the HCDR2 as set forth in SEQ ID NO: 7, and the HCDR3 as set forth in SEQ ID NO: 15.

Embodiment 10

The isolated antigen-binding protein according to any one of Embodiments 1-7, wherein the VH comprises the HCDR1 as set forth in SEQ ID NO: 2, the HCDR2 as set forth in SEQ ID NO: 8, and the HCDR3 as set forth in SEQ ID NO: 15.

Embodiment 11

The isolated antigen-binding protein according to any one of Embodiments 1-7, wherein the VH comprises the HCDR1 as set forth in SEQ ID NO: 3, the HCDR2 as set forth in SEQ ID NO: 6, and the HCDR3 as set forth in SEQ ID NO: 15.

Embodiment 12

The isolated antigen-binding protein according to any one of Embodiments 1-7, wherein the VH comprises the HCDR1 as set forth in SEQ ID NO: 2, the HCDR2 as set forth in SEQ ID NO: 6, and the HCDR3 as set forth in SEQ ID NO: 16.

Embodiment 13

The isolated antigen-binding protein according to any one of Embodiments 1-7, wherein the VH comprises the HCDR1 as set forth in SEQ ID NO: 2, the HCDR2 as set forth in SEQ ID NO: 6, and the HCDR3 as set forth in SEQ ID NO: 17.

Embodiment 14

The isolated antigen-binding protein according to any one of Embodiments 1-7, wherein the VH comprises the HCDR1 as set forth in SEQ ID NO: 2, the HCDR2 as set forth in SEQ ID NO: 6, and the HCDR3 as set forth in SEQ ID NO: 18.

Embodiment 15

The isolated antigen-binding protein according to any one of Embodiments 1-7, wherein the VH comprises the HCDR1 as set forth in SEQ ID NO: 4, the HCDR2 as set forth in SEQ ID NO: 6, and the HCDR3 as set forth in SEQ ID NO: 15.

Embodiment 16

The isolated antigen-binding protein according to any one of Embodiments 1-7, wherein the VH comprises the HCDR1 as set forth in SEQ ID NO: 2, the HCDR2 as set forth in SEQ ID NO: 9, and the HCDR3 as set forth in SEQ ID NO: 15.

Embodiment 17

The isolated antigen-binding protein according to any one of Embodiments 1-7, wherein the VH comprises the HCDR1 as set forth in SEQ ID NO: 2, the HCDR2 as set forth in SEQ ID NO: 10, and the HCDR3 as set forth in SEQ ID NO: 15.

Embodiment 18

The isolated antigen-binding protein according to any one of Embodiments 1-7, wherein the VH comprises the HCDR1 as set forth in SEQ ID NO: 2, the HCDR2 as set forth in SEQ ID NO: 11, and the HCDR3 as set forth in SEQ ID NO: 15.

Embodiment 19

The isolated antigen-binding protein according to any one of Embodiments 1-7, wherein the VH comprises the HCDR1 as set forth in SEQ ID NO:2, the HCDR2 as set forth in SEQ ID NO: 12, and the HCDR3 as set forth in SEQ ID NO: 15.

Embodiment 20

The isolated antigen-binding protein according to any one of Embodiments 1-7, wherein the VH comprises the HCDR1 as set forth in SEQ ID NO: 2, the HCDR2 as set forth in SEQ ID NO: 13, and the HCDR3 as set forth in SEQ ID NO: 15.

Embodiment 21

The isolated antigen-binding protein according to any one of Embodiments 1-7, wherein the VH comprises the HCDR1 as set forth in SEQ ID NO: 3, the HCDR2 as set forth in SEQ ID NO: 6, and the HCDR3 as set forth in SEQ ID NO: 16.

Embodiment 22

The isolated antigen-binding protein according to any one of Embodiments 1-7, wherein the VH comprises the HCDR1 as set forth in SEQ ID NO: 3, the HCDR2 as set forth in SEQ ID NO: 6, and the HCDR3 as set forth in SEQ ID NO: 17.

Embodiment 23

The isolated antigen-binding protein according to any one of Embodiments 1-7, wherein the VH comprises the HCDR1 as set forth in SEQ ID NO: 3, the HCDR2 as set forth in SEQ ID NO: 9, and the HCDR3 as set forth in SEQ ID NO: 15.

Embodiment 24

The isolated antigen-binding protein according to any one of Embodiments 1-7, wherein the VH comprises the HCDR1 as set forth in SEQ ID NO: 3, the HCDR2 as set forth in SEQ ID NO: 10, and the HCDR3 as set forth in SEQ ID NO: 15.

Embodiment 25

The isolated antigen-binding protein according to any one of Embodiments 1-7, wherein the VH comprises the HCDR1 as set forth in SEQ ID NO: 3, the HCDR2 as set forth in SEQ ID NO: 11, and the HCDR3 as set forth in SEQ ID NO: 15.

Embodiment 26

The isolated antigen-binding protein according to any one of Embodiments 1-7, wherein the VH comprises the HCDR1 as set forth in SEQ ID NO: 2, the HCDR2 as set forth in SEQ ID NO: 9, and the HCDR3 as set forth in SEQ ID NO: 16.

Embodiment 27

The isolated antigen-binding protein according to any one of Embodiments 1-7, wherein the VH comprises the HCDR1 as set forth in SEQ ID NO: 2, the HCDR2 as set forth in SEQ ID NO: 10, and the HCDR3 as set forth in SEQ ID NO: 16.

Embodiment 28

The isolated antigen-binding protein according to any one of Embodiments 1-7, wherein the VH comprises the HCDR1 as set forth in SEQ ID NO: 2, the HCDR2 as set forth in SEQ ID NO: 11, and the HCDR3 as set forth in SEQ ID NO: 16.

Embodiment 29

The isolated antigen-binding protein according to any one of Embodiments 1-7, wherein the VH comprises the HCDR1 as set forth in SEQ ID NO: 2, the HCDR2 as set forth in SEQ ID NO: 12, and the HCDR3 as set forth in SEQ ID NO: 16.

Embodiment 30

The isolated antigen-binding protein according to any one of Embodiments 1-7, wherein the VH comprises the HCDR1 as set forth in SEQ ID NO: 2, the HCDR2 as set forth in SEQ ID NO: 10, and the HCDR3 as set forth in SEQ ID NO: 17.

Embodiment 31

The isolated antigen-binding protein according to any one of Embodiments 1-30, wherein the VH comprises an HFR1 and the HFR1 comprises an amino acid sequence of the SEQ ID NO:19.

Embodiment 32

The isolated antigen-binding protein according to Embodiment 31, wherein the HFR1 is selected from an amino acid sequence as set forth in any one of SEQ ID NO: 20-28.

Embodiment 33

The isolated antigen-binding protein according to any one of

Embodiments 1-32, wherein the VH comprises an HFR2 and the HFR2 comprises an amino acid sequence as set forth in SEQ ID NO:29.

Embodiment 34

The isolated antigen-binding protein according to any one of Embodiment 33, wherein the HFR2 is selected from an amino acid sequence as set forth in any one of SEQ ID NOs: 30-32.

Embodiment 35

The isolated antigen-binding protein according to any one of

Embodiments 1-34, wherein the VH comprises an HFR3 comprising an amino acid sequence as set forth in SEQ ID NO:33.

Embodiment 36

The isolated antigen-binding protein of Embodiment 35, wherein the HFR3 is selected from an amino acid sequence as set forth in any one of SEQ ID NOs: 34-40.

Embodiment 37

The isolated antigen-binding protein according to any one of Embodiments 1-36, wherein the VH comprises an HFR4 which comprises an amino acid sequence as set forth in SEQ ID NO:41.

Embodiment 38

The isolated antigen-binding protein according to any one of Embodiments 1-37, wherein the VH comprises the HFR1 as set forth in SEQ ID NO: 20, the HFR2 as set forth in SEQ ID NO: 30, the HFR3 as set forth in SEQ ID NO: 34, and the HFR4 as set forth in SEQ ID NO: 41.

Embodiment 39

The isolated antigen-binding protein according to any one of

Embodiments 1-37, wherein the VH comprises the HFR1 as set forth in SEQ ID NO: 21, the HFR2 as set forth in SEQ ID NO: 31, the HFR3 as set forth in SEQ ID NO: 35, and the HFR4 as set forth in SEQ ID NO: 41.

Embodiment 40

The isolated antigen-binding protein according to any one of

Embodiments 1-37, wherein the VH comprises the HFR1 as set forth in SEQ ID NO: 22, the HFR2 as set forth in SEQ ID NO: 32, the HFR3 as set forth in SEQ ID NO: 35, and the HFR4 as set forth in SEQ ID NO: 41.

Embodiment 41

The isolated antigen-binding protein according to any one of

Embodiments 1-37, wherein the VH comprises the HFR1 as set forth in SEQ ID NO: 23, the HFR2 as set forth in SEQ ID NO: 31, the HFR3 as set forth in SEQ ID NO: 36, and the HFR4 as set forth in SEQ ID NO: 41.

Embodiment 42

The isolated antigen-binding protein according to any one of Embodiments 1-37, wherein the VH comprises the HFR1 as set forth in SEQ ID NO: 23, the HFR2 as set forth in SEQ ID NO: 31, the HFR3 as set forth in SEQ ID NO: 37, and the HFR4 as set forth in SEQ ID NO: 41.

Embodiment 43

The isolated antigen-binding protein according to any one of Embodiments 1-37, wherein the VH comprises the HFR1 as set forth in SEQ ID NO: 23, the HFR2 as set forth in SEQ ID NO: 31, the HFR3 as set forth in SEQ ID NO: 35, and the HFR4 as set forth in SEQ ID NO: 41.

Embodiment 44

The isolated antigen-binding protein according to any one of Embodiments 1-37, wherein the VH comprises the HFR1 as set forth in SEQ ID NO: 24, the HFR2 as set forth in SEQ ID NO: 31, the HFR3 as set forth in SEQ ID NO: 38, and the HFR4 as set forth in SEQ ID NO: 41.

Embodiment 45

The isolated antigen-binding protein according to any one of Embodiments 1-37, wherein the VH comprises the HFR1 as set forth in SEQ ID NO: 25, the HFR2 as set forth in SEQ ID NO: 31, the HFR3 as set forth in SEQ ID NO: 37, and the HFR4 as set forth in SEQ ID NO: 41.

Embodiment 46

The isolated antigen-binding protein according to any one of Embodiments 1-37, wherein the VH comprises the HFR1 as set forth in SEQ ID NO: 25, the HFR2 as set forth in SEQ ID NO: 31, the HFR3 as set forth in SEQ ID NO: 39, and the HFR4 as set forth in SEQ ID NO: 41.

Embodiment 47

The isolated antigen-binding protein according to any one of Embodiments 1-37, wherein the VH comprises the HFR1 as set forth in SEQ ID NO: 25, the HFR2 as set forth in SEQ ID NO: 31, the HFR3 as set forth in SEQ ID NO: 40, and the HFR4 as set forth in SEQ ID NO: 41.

Embodiment 48

The isolated antigen-binding protein according to any one of Embodiments 1-37, wherein the VH comprises the HFR1 as set forth in SEQ ID NO: 26, the HFR2 as set forth in SEQ ID NO: 31, the HFR3 as set forth in SEQ ID NO: 35, and the HFR4 as set forth in SEQ ID NO: 41.

Embodiment 49

The isolated antigen-binding protein according to any one of Embodiments 1-37, wherein the VH comprises the HFR1 as set forth in SEQ ID NO: 25, the HFR2 as set forth in SEQ ID NO: 31, the HFR3 as set forth in SEQ ID NO: 35, and the HFR4 as set forth in SEQ ID NO: 41.

Embodiment 50

The isolated antigen-binding protein according to any one of Embodiments 1-37, wherein the VH comprises the HFR1 as set forth in SEQ ID NO: 27, the HFR2 as set forth in SEQ ID NO: 31, the HFR3 as set forth in SEQ ID NO: 35, and the HFR4 as set forth in SEQ ID NO: 41.

Embodiment 51

The isolated antigen-binding protein according to any one of Embodiments 1-37, wherein the VH comprises the HFR1 as set forth in SEQ ID NO: 28, the HFR2 as set forth in SEQ ID NO: 31, the HFR3 as set forth in SEQ ID NO: 35, and the HFR4 as set forth in SEQ ID NO: 41.

Embodiment 52

The isolated antigen-binding protein according to any one of Embodiments 1-51 further comprises a light chain variable region (VL) comprising at least one light chain complementarity-determining region (LCDR) comprising an amino acid sequence selected from SEQ ID NO: 42, SEQ ID NO: 43, and SEQ ID NO: 44.

Embodiment 53

The isolated antigen-binding protein according to Embodiment 52, wherein the VL comprises an LCDR3 comprising an amino acid sequence as set forth in SEQ ID NO: 44.

Embodiment 54

The isolated antigen-binding protein according to any one of Embodiments 52-53, wherein the VL comprises an LCDR2 which comprises an amino acid sequence as set forth in SEQ ID NO:43.

Embodiment 55

The isolated antigen-binding protein according to any one of Embodiments 52-54, wherein the VL comprises an LCDR1 which comprises an amino acid sequence as set forth in SEQ ID NO: 42.

Embodiment 56

The isolated antigen-binding protein according to any one of Embodiments 52-55, wherein the VL comprises an LFR1 comprising an amino acid sequence as set forth in SEQ ID NO:45.

Embodiment 57

The isolated antigen-binding protein of Embodiment 56, wherein the LFR1 comprises an amino acid sequence as set forth in any one of SEQ ID NOs: 46-47.

Embodiment 58

The isolated antigen-binding protein according to any one of Embodiments 52-57, wherein the VL comprises an LFR2 comprising an amino acid sequence as set forth in SEQ ID NO: 48.

Embodiment 59

The isolated antigen-binding protein according to Embodiment 58, wherein the LFR2 comprises an amino acid sequence as set forth in any one of SEQ ID NOS: 49-52.

Embodiment 60

The isolated antigen-binding protein according to any one of Embodiments 52-59, wherein the VL comprises an LFR3 comprising an amino acid sequence as set forth in SEQ ID NO:53.

Embodiment 61

The isolated antigen-binding protein according to Embodiment 60, wherein the LFR3 comprises an amino acid sequence as set forth in any one of SEQ ID NOs: 54-57.

Embodiment 62

The isolated antigen-binding protein according to any one of Embodiments 52-61, wherein the VL comprises an LFR4 comprising an amino acid sequence as set forth in SEQ ID NO:58.

Embodiment 63

The isolated antigen-binding protein according to Embodiment 62, wherein the LFR1 comprises an amino acid sequence as set forth in any one of SEQ ID NOs: 59-61.

Embodiment 64

The isolated antigen-binding protein according to any one of Embodiments 52-63, wherein the VL comprises the LFR1 as set forth in SEQ ID NO: 46, the LFR2 as set forth in SEQ ID NO: 49, the LFR3 as set forth in SEQ ID NO: 54, and the LFR4 as set forth in SEQ ID NO: 59.

Embodiment 65

The isolated antigen-binding protein according to any one of Embodiments 52-63, wherein the VL comprises the LFR1 as set forth in SEQ ID NO: 47, the LFR2 as set forth in SEQ ID NO: 50, the LFR3 as set forth in SEQ ID NO: 55, and the LFR4 as set forth in SEQ ID NO: 60.

Embodiment 66

The isolated antigen-binding protein according to any one of Embodiments 52-63, wherein the VL comprises the LFR1 as set forth in SEQ ID NO: 47, the LFR2 as set forth in SEQ ID NO: 51, the LFR3 as set forth in SEQ ID NO: 56, and the LFR4 as set forth in SEQ ID NO: 61.

Embodiment 67

The isolated antigen-binding protein according to any one of Embodiments 52-63, wherein the VL comprises the LFR1 as set forth in SEQ ID NO: 47, the LFR2 as set forth in SEQ ID NO: 52, the LFR3 as set forth in SEQ ID NO: 57, and the LFR4 as set forth in SEQ ID NO: 61.

Embodiment 68

The isolated antigen-binding protein according to any one of Embodiments 52-63, wherein the VL comprises the LFR1 as set forth in SEQ ID NO: 47, the LFR2 as set forth in SEQ ID NO: 52, the LFR3 as set forth in SEQ ID NO: 56, and the LFR4 as set forth in SEQ ID NO: 61.

Embodiment 69

The isolated antigen-binding protein according to any one of Embodiments 1-68, wherein the VH comprises a sequence as set forth in SEQ ID NOs: 62-99.

Embodiment 70

The isolated antigen-binding protein according to any one of Embodiments 1-69, wherein the VL comprises a sequence as set forth in SEQ ID NOs: 102-106.

Embodiment 71

An isolated antigen-binding protein specifically binding to TNF-like protein A (TL1A), comprising a heavy chain variable region (VH) comprising at least one heavy chain complementarity-determining region (HCDR) comprising an amino acid sequence selected from SEQ ID NO: 107, SEQ ID NO:115, and SEQ ID NO: 120.

Embodiment 72

The isolated antigen-binding protein of Embodiment 71, wherein the VH comprises an HCDR3 comprising an amino acid sequence as set forth in SEQ ID NO: 120.

Embodiment 73

The isolated antigen-binding protein according to any one of Embodiments 71-72, wherein the VH comprises the HCDR2 comprising an amino acid sequence as set forth in SEQ ID NO:115.

Embodiment 74

The isolated antigen-binding protein according to Embodiment 73, wherein the HCDR2 comprises an amino acid sequence as set forth in any one of SEQ ID NO: 116-119.

Embodiment 75

The isolated antigen-binding protein according to any one of Embodiments 71-74, wherein the VH comprises an HCDR1 which comprises an amino acid sequence as set forth in SEQ ID NO: 107.

Embodiment 76

The isolated antigen-binding protein according to Embodiment 75, wherein the HCDR1 comprises an amino acid sequence as set forth in any one of SEQ ID NOS: 108-114.

Embodiment 77

The isolated antigen-binding protein according to any one of Embodiments 71-76, wherein the VH comprises the HCDR1 as set forth in SEQ ID NO: 108, the HCDR2 as set forth in SEQ ID NO: 116, and the HCDR3 as set forth in SEQ ID NO: 120.

Embodiment 78

The isolated antigen-binding protein according to any one of Embodiments 71-76, wherein the VH comprises the HCDR1 as set forth in SEQ ID NO: 109, the HCDR2 as set forth in SEQ ID NO: 118, and the HCDR3 as set forth in SEQ ID NO: 120.

Embodiment 79

The isolated antigen-binding protein according to any one of Embodiments 71-76, wherein the VH comprises the HCDR1 as set forth in SEQ ID NO: 108, the HCDR2 as set forth in SEQ ID NO: 119, and the HCDR3 as set forth in SEQ ID NO: 120.

Embodiment 80

The isolated antigen-binding protein according to any one of Embodiments 71-76, wherein the VH comprises the HCDR1 as set forth in SEQ ID NO: 110, the HCDR2 as set forth in SEQ ID NO: 118, and the HCDR3 as set forth in SEQ ID NO: 120.

Embodiment 81

The isolated antigen-binding protein according to any one of Embodiments 71-76, wherein the VH comprises the HCDR1 as set forth in SEQ ID NO: 111, the HCDR2 as set forth in SEQ ID NO: 117, and the HCDR3 as set forth in SEQ ID NO: 120.

Embodiment 82

The isolated antigen-binding protein according to any one of Embodiments 71-76, wherein the VH comprises the HCDR1 as set forth in SEQ ID NO: 112, the HCDR2 as set forth in SEQ ID NO: 117, and the HCDR3 as set forth in SEQ ID NO: 120.

Embodiment 83

The isolated antigen-binding protein according to any one of Embodiments 71-76, wherein the VH comprises the HCDR1 as set forth in SEQ ID NO: 113, the HCDR2 as set forth in SEQ ID NO: 117, and the HCDR3 as set forth in SEQ ID NO: 120.

Embodiment 84

The isolated antigen-binding protein according to any one of Embodiments 71-76, wherein the VH comprises the HCDR1 as set forth in SEQ ID NO: 108, the HCDR2 as set forth in SEQ ID NO: 117, and the HCDR3 as set forth in SEQ ID NO: 120.

Embodiment 85

The isolated antigen-binding protein according to any one of Embodiments 71-76, wherein the VH comprises the HCDR1 as set forth in SEQ ID NO: 114, the HCDR2 as set forth in SEQ ID NO: 117, and the HCDR3 as set forth in SEQ ID NO: 120.

Embodiment 86

The isolated antigen-binding protein according to any one of Embodiments 71-85, wherein the VH comprises an HFR1 and the HFR1 comprises an amino acid sequence as set forth in SEQ ID NO:121.

Embodiment 87

The isolated antigen-binding protein according to Embodiment 86, wherein the HFR1 is selected from an amino acid sequence as set forth in any one of SEQ ID NOs: 122-132.

Embodiment 88

The isolated antigen-binding protein according to any one of Embodiments 71-87, wherein the VH comprises an HFR2 and the HFR2 comprises an amino acid sequence as set forth in SEQ ID NO: 133.

Embodiment 89

The isolated antigen-binding protein according to any one of Embodiment 88, wherein the HFR2 is selected from an amino acid sequence as set forth in any one of the SEQ ID NOs: 134-135, 30.

Embodiment 90

The isolated antigen-binding protein according to any one of Embodiments 71-159, wherein the VH comprises an HFR3 comprising an amino acid sequence as set forth in SEQ ID NO:136.

Embodiment 91

The isolated antigen-binding protein of Embodiment 90, wherein the HFR3 is selected from an amino acid sequence as set forth in any one of SEQ ID NOs: 137-148.

Embodiment 92

The isolated antigen-binding protein according to any one of Embodiments 71-91, wherein the VH comprises an HFR4 which comprises an amino acid sequence as set forth in SEQ ID NO: 149.

Embodiment 93

The isolated antigen-binding protein of Embodiment 92, wherein the HFR4 is selected from an amino acid sequence shown in any one of SEQ ID NOs: 150-153, 41.

Embodiment 94

The isolated antigen-binding protein according to any one of Embodiments 71-93, wherein the VH comprises the HFR1 as set forth in SEQ ID NO: 122, the HFR2 as set forth in SEQ ID NO: 134, the HFR3 as set forth in SEQ ID NO: 137, and the HFR4 as set forth in SEQ ID NO: 150.

Embodiment 95

The isolated antigen-binding protein according to any one of Embodiments 71-93, wherein the VH comprises the HFR1 as set forth in SEQ ID NO: 123, the HFR2 as set forth in SEQ ID NO: 135, the HFR3 as set forth in SEQ ID NO: 138, and the HFR4 as set forth in SEQ ID NO: 41.

Embodiment 96

The isolated antigen-binding protein according to any one of Embodiments 71-93, wherein the VH comprises the HFR1 as set forth in SEQ ID NO: 124, the HFR2 as set forth in SEQ ID NO: 135, the HFR3 as set forth in SEQ ID NO: 139, and the HFR4 as SEQ ID NO: 151.

Embodiment 97

The isolated antigen-binding protein according to any one of Embodiments 71-93, wherein the VH comprises the HFR1 as set forth in SEQ ID NO: 125, the HFR2 as set forth in SEQ ID NO: 135, the HFR3 as set forth in SEQ ID NO: 142, and the HFR4 as set forth in SEQ ID NO: 41.

Embodiment 98

The isolated antigen-binding protein according to any one of Embodiments 71-93, wherein the VH comprises the HFR1 as set forth in SEQ ID NO: 123, the HFR2 as set forth in SEQ ID NO: 135, the HFR3 as set forth in SEQ ID NO: 140, and the HFR4 as SEQ ID NO: 41.

Embodiment 99

The isolated antigen-binding protein according to any one of Embodiments 71-93, wherein the VH comprises the HFR1 as set forth in SEQ ID NO: 123, the HFR2 as set forth in SEQ ID NO: 135, the HFR3 as set forth in SEQ ID NO: 141, and the HFR4 as set forth in SEQ ID NO: 41.

Embodiment 100

The isolated antigen-binding protein according to any one of Embodiments 71-93, wherein the VH comprises the HFR1 as set forth in SEQ ID NO: 126, the HFR2 as set forth in SEQ ID NO: 135, the HFR3 as set forth in SEQ ID NO: 142, and the HFR4 as set forth in SEQ ID NO: 152.

Embodiment 101

The isolated antigen-binding protein according to any one of Embodiments 71-93, wherein the VH comprises the HFR1 as set forth in SEQ ID NO: 127, the HFR2 as set forth in SEQ ID NO: 30, the HFR3 as set forth in SEQ ID NO: 143, and the HFR4 as set forth in SEQ ID NO: 41.

Embodiment 102

The isolated antigen-binding protein according to any one of Embodiments 71-93, wherein the VH comprises the HFR1 as set forth in SEQ ID NO: 128, the HFR2 as set forth in SEQ ID NO: 30, the HFR3 as set forth in SEQ ID NO: 144, and the HFR4 as set forth in SEQ ID NO: 41.

Embodiment 103

The isolated antigen-binding protein according to any one of Embodiments 71-93, wherein the VH comprises the HFR1 as set forth in SEQ ID NO: 129, the HFR2 as set forth in SEQ ID NO: 30, the HFR3 as set forth in SEQ ID NO: 145, and the HFR4 as set forth in SEQ ID NO: 41.

Embodiment 104

The isolated antigen-binding protein according to any one of Embodiments 71-93, wherein the VH comprises the HFR1 as set forth in SEQ ID NO: 127, the HFR2 as set forth in SEQ ID NO: 30, the HFR3 as set forth in SEQ ID NO: 146, and the HFR4 as set forth in SEQ ID NO: 41.

Embodiment 105

The isolated antigen-binding protein according to any one of Embodiments 71-93, wherein the VH comprises the HFR1 as set forth in SEQ ID NO: 125, the HFR2 as set forth in SEQ ID NO: 135, the HFR3 as set forth in SEQ ID NO: 142, and the HFR4 as set forth in SEQ ID NO: 152.

Embodiment 106

The isolated antigen-binding protein according to any one of Embodiments 71-93, wherein the VH comprises the HFR1 as set forth in SEQ ID NO: 130, the HFR2 as set forth in SEQ ID NO: 30, the HFR3 as set forth in SEQ ID NO: 147, and the HFR4 as set forth in SEQ ID NO: 41.

Embodiment 107

The isolated antigen-binding protein according to any one of Embodiments 71-93, wherein the VH comprises the HFR1 as set forth in SEQ ID NO: 131, the HFR2 as set forth in SEQ ID NO: 135, the HFR3 as set forth in SEQ ID NO: 148, and the HFR4 as set forth in SEQ ID NO: 153.

Embodiment 108

The isolated antigen-binding protein according to any one of Embodiments 71-93, wherein the VH comprises the HFR1 as set forth in SEQ ID NO: 132, the HFR2 as set forth in SEQ ID NO: 30, the HFR3 as set forth in SEQ ID NO: 145, and the HFR4 as set forth in SEQ ID NO: 41.

Embodiment 109

The isolated antigen-binding protein according to any one of Embodiments 71-108 further comprises a light chain variable region (VL) comprising at least one light chain complementarity-determining region (LCDR) including an amino acid sequence selected from SEQ ID NO: 154, SEQ ID NO: 159, and SEQ ID NO: 163.

Embodiment 110

The isolated antigen-binding protein according to any one of Embodiments 71-109, wherein the VL comprises an LCDR3 comprising an amino acid sequence as set forth in SEQ ID NO:163.

Embodiment 111

The isolated antigen-binding protein of Embodiment 110, wherein the LCDR3 comprises an amino acid sequence as set forth in any one of SEQ ID NOs: 164-168.

Embodiment 112

The isolated antigen-binding protein according to any one of Embodiments 71-111, wherein the VL comprises an LCDR2 comprising an amino acid sequence as set forth in SEQ ID NO: 159.

Embodiment 113

The isolated antigen-binding protein according to Embodiment 112, wherein the LCDR2 comprises an amino acid sequence as set forth in any one of the SEQ ID NOs: 160-162.

Embodiment 114

The isolated antigen-binding protein according to any one of Embodiments 71-113, wherein the VL comprises an LCDR1 comprising an amino acid sequence as set forth in SEQ ID NO:154.

Embodiment 115

The isolated antigen-binding protein according to Embodiment 114, wherein the LCDR1 comprises an amino acid sequence as set forth in any one of SEQ ID NOS: 155-158.

Embodiment 116

The isolated antigen-binding protein according to any one of Embodiments 71-116, wherein the VL comprises the LCDR1 as set forth in SEQ ID NO: 157, the LCDR2 as set forth in SEQ ID NO: 161, and the LCDR3 as set forth in SEQ ID NO: 164.

Embodiment 117

The isolated antigen-binding protein according to any one of Embodiments 71-116, wherein the VL comprises the LCDR1 as set forth in SEQ ID NO: 157, the LCDR2 as set forth in SEQ ID NO: 162, and the LCDR3 as set forth in SEQ ID NO: 164.

Embodiment 118

The isolated antigen-binding protein according to any one of Embodiments 71-116, wherein the VL comprises the LCDR1 as set forth in SEQ ID NO: 156, the LCDR2 as set forth in SEQ ID NO: 161, and the LCDR3 as set forth in SEQ ID NO: 164.

Embodiment 119

The isolated antigen-binding protein according to any one of Embodiments 71-116, wherein the VL comprises the LCDR1 as set forth in SEQ ID NO: 158, the LCDR2 as set forth in SEQ ID NO: 160, and the LCDR3 as set forth in SEQ ID NO: 164.

Embodiment 120

The isolated antigen-binding protein according to any one of Embodiments 71-116, wherein the VL comprises the LCDR1 as set forth in SEQ ID NO: 155, the LCDR2 as set forth in SEQ ID NO: 160, and the LCDR3 as set forth in SEQ ID NO: 164.

Embodiment 121

The isolated antigen-binding protein according to any one of Embodiments 71-116, wherein the VL comprises the LCDR1 as set forth in SEQ ID NO: 156, the LCDR2 as set forth in SEQ ID NO: 162, and the LCDR3 as set forth in SEQ ID NO: 164.

Embodiment 122

The isolated antigen-binding protein according to any one of Embodiments 71-116, wherein the VL comprises the LCDR1 as set forth in SEQ ID NO: 155, the LCDR2 as set forth in SEQ ID NO: 160, and the LCDR3 as set forth in SEQ ID NO: 165.

Embodiment 123

The isolated antigen-binding protein according to any one of Embodiments 71-116, wherein the VL comprises the LCDR1 as set forth in SEQ ID NO: 155, the LCDR2 as set forth in SEQ ID NO: 160, and the LCDR3 as set forth in SEQ ID NO: 166.

Embodiment 124

The isolated antigen-binding protein according to any one of Embodiments 71-116, wherein the VL comprises the LCDR1 as set forth in SEQ ID NO: 155, the LCDR2 as set forth in SEQ ID NO: 160, and the LCDR3 as set forth in SEQ ID NO: 167.

Embodiment 125

The isolated antigen-binding protein according to any one of Embodiments 71-116, wherein the VL comprises the LCDR1 as set forth in SEQ ID NO: 155, the LCDR2 as set forth in SEQ ID NO: 160, and the LCDR3 as set forth in SEQ ID NO: 168.

Embodiment 126

The isolated antigen-binding protein according to any one of Embodiments 71-125, wherein the VL comprises an LFR1 including an amino acid sequence as set forth in SEQ ID NO:169.

Embodiment 127

The Isolated antigen-binding protein according to Embodiment 126, wherein the LFR1 comprises an amino acid sequence as set forth in any one of SEQ ID NOs: 170-179.

Embodiment 128

The isolated antigen-binding protein according to any one of Embodiments 71-127, wherein the VL comprises an LFR2 comprising an amino acid sequence as set forth in SEQ ID NO: 180.

Embodiment 129

The isolated antigen-binding protein of Embodiment 128, wherein the LFR2 comprises an amino acid sequence as set forth in any one of SEQ ID NOs: 181-188.

Embodiment 130

The isolated antigen-binding protein according to any one of Embodiments 71-129, wherein the VL comprises an LFR3 comprising an amino acid sequence as set forth in SEQ ID NO: 189.

Embodiment 131

The isolated antigen-binding protein of Embodiment 130, wherein the LFR3 comprises an amino acid sequence as set forth in any one of SEQ ID NOs: 190-197, 57.

Embodiment 132

The isolated antigen-binding protein according to any one of Embodiments 71-131, wherein the VL comprises an LFR4 comprising an amino acid sequence as set forth in SEQ ID NO: 198.

Embodiment 133

The isolated antigen-binding protein of Embodiment 132, wherein the LFR4 comprises an amino acid sequence as set forth in any one of SEQ ID NOs: 199-201, 61.

Embodiment 134

The isolated antigen-binding protein according to any one of Embodiments 71-133, wherein the VL comprises the LFR1 as set forth in SEQ ID NO: 170, the LFR2 as set forth in SEQ ID NO: 181, the LFR3 as set forth in SEQ ID NO: 190, and the LFR4 as set forth in SEQ ID NO: 199.

Embodiment 135

The isolated antigen-binding protein according to any one of Embodiments 71-133, wherein the VL comprises the LFR1 as set forth in SEQ ID NO: 171, the LFR2 as set forth in SEQ ID NO: 182, the LFR3 as set forth in SEQ ID NO: 191, and the LFR4 as set forth in SEQ ID NO: 200.

Embodiment 136

The isolated antigen-binding protein according to any one of Embodiments 71-133, wherein the VL comprises the LFR1 as set forth in SEQ ID NO: 172, the LFR2 as set forth in SEQ ID NO: 183, the LFR3 as set forth in SEQ ID NO: 192, and the LFR4 as set forth in SEQ ID NO: 61.

Embodiment 137

The isolated antigen-binding protein according to any one of Embodiments 71-133, wherein the VL comprises the LFR1 as set forth in SEQ ID NO: 174, the LFR2 as set forth in SEQ ID NO: 184, the LFR3 as set forth in SEQ ID NO: 57, and the LFR4 as set forth in SEQ ID NO: 199.

Embodiment 138

The isolated antigen-binding protein according to any one of Embodiments 71-133, wherein the VL comprises the LFR1 as set forth in SEQ ID NO: 175, the LFR2 as set forth in SEQ ID NO: 185, the LFR3 as set forth in SEQ ID NO: 193, and the LFR4 as set forth in SEQ ID NO: 199.

Embodiment 139

The isolated antigen-binding protein according to any one of Embodiments 71-133, wherein the VL comprises the LFR1 as set forth in SEQ ID NO: 176, the LFR2 as set forth in SEQ ID NO: 186, the LFR3 as set forth in SEQ ID NO: 194, and the LFR4 as set forth in SEQ ID NO: 199.

Embodiment 140

The isolated antigen-binding protein according to any one of Embodiments 71-133, wherein the VL comprises the LFR1 as set forth in SEQ ID NO: 177, the LFR2 as set forth in SEQ ID NO: 187, the LFR3 as set forth in SEQ ID NO: 195, and the LFR4 as set forth in SEQ ID NO: 199.

Embodiment 141

The isolated antigen-binding protein according to any one of Embodiments 71-133, wherein the VL comprises the LFR1 as set forth in SEQ ID NO: 178, the LFR2 as set forth in SEQ ID NO: 188, the LFR3 as set forth in SEQ ID NO: 196, and the LFR4 as set forth in SEQ ID NO: 199.

Embodiment 142

The isolated antigen-binding protein according to any one of Embodiments 71-133, wherein the VL comprises the LFR1 as set forth in SEQ ID NO: 179, the LFR2 as set forth in SEQ ID NO: 187, the LFR3 as set forth in SEQ ID NO: 195, and the LFR4 as set forth in SEQ ID NO: 199.

Embodiment 143

The isolated antigen-binding protein according to any one of Embodiments 71-133, wherein the VL comprises the LFR1 as set forth in SEQ ID NO: 173, the LFR2 as set forth in SEQ ID NO: 183, the LFR3 as set forth in SEQ ID NO: 192, and the LFR4 as set forth in SEQ ID NO: 201.

Embodiment 144

The isolated antigen-binding protein according to any one of Embodiments 71-143, wherein the VH comprises a sequence as set forth in SEQ ID NOs: 202-220, 332-334.

Embodiment 145

The isolated antigen-binding protein according to any one of Embodiments 71-144, wherein the VL comprises a sequence as set forth in SEQ ID NOs: 221-234, 335-338.

Embodiment 146

An isolated antigen-binding protein capable of specifically binding to TNF-like protein A (TL1A), comprising a heavy chain variable region (VH) comprising at least one heavy chain complementarity-determining region (HCDR) comprising an amino acid sequence selected from an amino acid sequence as set forth in SEQ ID NO:242, SEQ ID NO: 238, and SEQ ID NO:235.

Embodiment 147

The isolated antigen-binding protein of Embodiment 146, wherein the VH comprises an HCDR3 comprising an amino acid sequence as set forth in SEQ ID NO: 242.

Embodiment 148

The isolated antigen-binding protein according to any one of Embodiments 146-147, wherein the VH comprises an HCDR2 comprising an amino acid sequence as set forth in SEQ ID NO:238.

Embodiment 149

The isolated antigen-binding protein according to Embodiment 218, wherein the HCDR2 comprises an amino acid sequence as set forth in any one of the SEQ ID NOs: 239-241.

Embodiment 150

The isolated antigen-binding protein according to any one of Embodiments 146-149, wherein the VH comprises an HCDR1 comprising an amino acid sequence as set forth in SEQ ID NO:235.

Embodiment 151

The isolated antigen-binding protein of Embodiment 220, wherein the HCDR1 comprises an amino acid sequence as set forth in any one of SEQ ID NOs: 236-237.

Embodiment 152

The isolated antigen-binding protein according to any one of Embodiments 146-151, wherein the VH comprises the HCDR1 as set forth in SEQ ID NO: 108, the HCDR2 as set forth in SEQ ID NO: 116, and the HCDR3 as set forth in SEQ ID NO: 120.

Embodiment 153

The isolated antigen-binding protein according to any one of Embodiments 146-152, wherein the VH comprises the HCDR1 as set forth in SEQ ID NO: 236, the HCDR2 as set forth in SEQ ID NO: 239, and the HCDR3 as set forth in SEQ ID NO: 242.

Embodiment 154

The isolated antigen-binding protein according to any one of Embodiments 146-152, wherein the VH comprises the HCDR1 as set forth in SEQ ID NO: 236, the HCDR2 as set forth in SEQ ID NO: 240, and the HCDR3 as set forth in SEQ ID NO: 242.

Embodiment 155

The isolated antigen-binding protein according to any one of Embodiments 146-152, wherein the VH comprises the HCDR1 as set forth in SEQ ID NO: 237, the HCDR2 as set forth in SEQ ID NO: 241, and the HCDR3 as set forth in SEQ ID NO: 242.

Embodiment 156

The isolated antigen-binding protein according to any one of Embodiments 146-155, wherein the VH comprises an HFR1 comprising an amino acid sequence as set forth in SEQ ID NO:243.

Embodiment 157

The isolated antigen-binding protein of Embodiment 156, wherein the HFR1 is selected from an amino acid sequence as set forth in any one of SEQ ID NOs: 244-250.

Embodiment 158

The isolated antigen-binding protein according to any one of Embodiments 146-157, wherein the VH comprises the HFR2 and the HFR2 comprises an amino acid sequence as set forth in SEQ ID NO:251.

Embodiment 159

The isolated antigen-binding protein according to any one of Embodiment 158, wherein the HFR2 is selected from an amino acid sequence as set forth in any one of SEQ ID NOs: 252-255.

Embodiment 160

The isolated antigen-binding protein according to any one of Embodiments 146-159, wherein the VH comprises the HFR3 comprising an amino acid sequence as set forth in SEQ ID NO:256.

Embodiment 161

The isolated antigen-binding protein of Embodiment 160, wherein the HFR3 is selected from an amino acid sequence as set forth in any one of SEQ ID NOs: 257-262.

Embodiment 162

The isolated antigen-binding protein according to any one of Embodiments 146-161, wherein the VH comprises the HFR4 comprising an amino acid sequence as set forth in SEQ ID NO:263.

Embodiment 163

The isolated antigen-binding protein according to Embodiment 162, wherein the HFR4 is selected from an amino acid sequence as set forth in any one of SEQ ID NOs: 264-268.

Embodiment 164

The isolated antigen-binding protein according to any one of Embodiments 146-163, wherein the VH comprises the HFR1 as set forth in SEQ ID NO: 244, the HFR2 as set forth in SEQ ID NO: 252, the HFR3 as set forth in SEQ ID NO: 257, and the HFR4 as set forth in SEQ ID NO: 264.

Embodiment 165

The isolated antigen-binding protein according to any one of Embodiments 146-163, wherein the VH comprises the HFR1 as set forth in SEQ ID NO: 245, the HFR2 as set forth in SEQ ID NO: 252, the HFR3 as set forth in SEQ ID NO: 258, and the HFR4 as set forth in SEQ ID NO: 265.

Embodiment 166

The isolated antigen-binding protein according to any one of Embodiments 146-163, wherein the VH comprises the HFR1 as set forth in SEQ ID NO: 246, the HFR2 as set forth in SEQ ID NO: 253, the HFR3 as set forth in SEQ ID NO: 259, and the HFR4 as set forth in SEQ ID NO: 268.

Embodiment 167

The isolated antigen-binding protein according to any one of Embodiments 146-163, wherein the VH comprises the HFR1 as set forth in SEQ ID NO: 246, the HFR2 as set forth in SEQ ID NO: 254, the HFR3 as set forth in SEQ ID NO: 260, and the HFR4 as set forth in SEQ ID NO: 266.

Embodiment 168

The isolated antigen-binding protein according to any one of Embodiments 146-163, wherein the VH comprises the HFR1 as set forth in SEQ ID NO: 247, the HFR2 as set forth in SEQ ID NO: 254, the HFR3 as set forth in SEQ ID NO: 261, and the HFR4 as set forth in SEQ ID NO: 268.

Embodiment 169

The isolated antigen-binding protein according to any one of Embodiments 146-163, wherein the VH comprises the HFR1 as set forth in SEQ ID NO: 248, the HFR2 as set forth in SEQ ID NO: 252, the HFR3 as set forth in SEQ ID NO: 258, and the HFR4 as set forth in SEQ ID NO: 265.

Embodiment 170

The isolated antigen-binding protein according to any one of Embodiments 146-163, wherein the VH comprises the HFR1 as set forth in SEQ ID NO: 246, the HFR2 as set forth in SEQ ID NO: 255, the HFR3 as set forth in SEQ ID NO: 260, and the HFR4 as set forth in SEQ ID NO: 268.

Embodiment 171

The isolated antigen-binding protein according to any one of Embodiments 146-163, wherein the VH comprises the HFR1 as set forth in SEQ ID NO: 245, the HFR2 as set forth in SEQ ID NO: 252, the HFR3 as set forth in SEQ ID NO: 258, and the HFR4 as set forth in SEQ ID NO: 267.

Embodiment 172

The isolated antigen-binding protein according to any one of Embodiments 146-163, wherein the VH comprises the HFR1 as set forth in SEQ ID NO: 249, the HFR2 as set forth in SEQ ID NO: 254, the HFR3 as set forth in SEQ ID NO: 260, and the HFR4 as set forth in SEQ ID NO: 268.

Embodiment 173

The isolated antigen-binding protein according to any one of Embodiments 146-163, wherein the VH comprises the HFR1 as set forth in SEQ ID NO: 250, the HFR2 as set forth in SEQ ID NO: 253, the HFR3 as set forth in SEQ ID NO: 262, and the HFR4 as set forth in SEQ ID NO: 266.

Embodiment 174

The isolated antigen-binding protein as described in any one of Embodiments 146-173 further comprises a light chain variable region (VL) comprising at least one light chain complementarity-determining region (LCDR) comprising an amino acid sequence selected from SEQ ID NO: 269, SEQ ID NO: 274, and SEQ ID NO: 277.

Embodiment 175

The isolated antigen-binding protein according to any one of Embodiments 146-174, wherein the VL comprises an LCDR3 comprising an amino acid sequence as set forth in SEQ ID NO:277.

Embodiment 176

The isolated antigen-binding protein according to any one of Embodiments 146-175, wherein the VL comprises an LCDR2 comprising an amino acid sequence as set forth in SEQ ID NO:274.

Embodiment 177

The isolated antigen-binding protein according to Embodiment 176, wherein the LCDR2 comprises an amino acid sequence as set forth in any one of SEQ ID NOS: 275-276.

Embodiment 178

The isolated antigen-binding protein according to any one of Embodiments 146-177, wherein the VL comprises an LCDR1 comprising an amino acid sequence as set forth in SEQ ID NO:269.

Embodiment 179

The isolated antigen-binding protein according to Embodiment 178, wherein the LCDR1 comprises an amino acid sequence as set forth in any one of the SEQ ID NOs: 270-273.

Embodiment 180

The isolated antigen-binding protein according to any one of Embodiments 146-179, wherein the VL comprises the LCDR1 as set forth in SEQ ID NO: 270, the LCDR2 as set forth in SEQ ID NO: 275, and the LCDR3 as set forth in SEQ ID NO: 277.

Embodiment 181

The isolated antigen-binding protein according to any one of Embodiments 146-179, wherein the VL comprises the LCDR1 as set forth in SEQ ID NO: 271, the LCDR2 as set forth in SEQ ID NO: 275, and the LCDR3 as set forth in SEQ ID NO: 277.

Embodiment 182

The isolated antigen-binding protein according to any one of Embodiments 146-179, wherein the VL comprises the LCDR1 as set forth in SEQ ID NO: 272, the LCDR2 as set forth in SEQ ID NO: 275, and the LCDR3 as set forth in SEQ ID NO: 277.

Embodiment 183

The isolated antigen-binding protein according to any one of Embodiments 146-179, wherein the VL comprises the LCDR1 as set forth in SEQ ID NO: 273, the LCDR2 as set forth in SEQ ID NO: 275, and the LCDR3 as set forth in SEQ ID NO: 277.

Embodiment 184

The isolated antigen-binding protein according to any one of Embodiments 146-179, wherein the VL comprises the LCDR1 as set forth in SEQ ID NO: 271, the LCDR2 as set forth in SEQ ID NO: 276, and the LCDR3 as set forth in SEQ ID NO: 277.

Embodiment 185

The isolated antigen-binding protein according to any one of Embodiments 146-184, wherein the VL comprises an LFR1 comprising an amino acid sequence as set forth in SEQ ID NO:278.

Embodiment 186

The isolated antigen-binding protein according to Embodiment 185, wherein the LFR1 comprises an amino acid sequence as set forth in any one of SEQ ID NOS: 47, 173, 279-283.

Embodiment 187

The isolated antigen-binding protein according to any one of Embodiments 146-186, wherein the VL comprises an LFR2 comprising an amino acid sequence as set forth in SEQ ID NO:284.

Embodiment 188

The isolated antigen-binding protein of Embodiment 187, wherein the LFR2 comprises an amino acid sequence as set forth in any one of SEQ ID NOs: 52, 285-287.

Embodiment 189

The isolated antigen-binding protein according to any one of Embodiments 146-188, wherein the VL comprises an LFR3 which comprises an amino acid sequence as set forth in SEQ ID NO: 288.

Embodiment 190

The isolated antigen-binding protein of Embodiment 189, wherein the LFR3 comprises an amino acid sequence as set forth in any one of SEQ ID NOs: 289-293, 57.

Embodiment 191

The isolated antigen-binding protein according to any one of Embodiments 146-190, wherein the VL comprises an LFR4 comprising an amino acid sequence as set forth in SEQ ID NO:294.

Embodiment 192

The isolated antigen-binding protein of Embodiment 191, wherein the LFR4 comprises an amino acid sequence as set forth in any one of SEQ ID NOs: 201, 295-296.

Embodiment 193

The isolated antigen-binding protein according to any one of Embodiments 146-192, wherein the VL comprises the LFR1 as set forth in SEQ ID NO: 170, the LFR2 as set forth in SEQ ID NO: 181, the LFR3 as set forth in SEQ ID NO: 190, and the LFR4 as set forth in SEQ ID NO: 199.

Embodiment 194

The isolated antigen-binding protein according to any one of Embodiments 146-192, wherein the VL comprises the LFR1 as set forth in SEQ ID NO: 171, the LFR2 as set forth in SEQ ID NO: 182, the LFR3 as set forth in SEQ ID NO: 191, and the LFR4 as set forth in SEQ ID NO: 200.

Embodiment 195

The isolated antigen-binding protein according to any one of Embodiments 146-192, wherein the VL comprises the LFR1 as set forth in SEQ ID NO: 172, the LFR2 as set forth in SEQ ID NO: 183, the LFR3 as set forth in SEQ ID NO: 192, and the LFR4 as set forth in SEQ ID NO: 61.

Embodiment 196

The isolated antigen-binding protein according to any one of Embodiments 146-192, wherein the VL comprises the LFR1 as set forth in SEQ ID NO: 174, the LFR2 as set forth in SEQ ID NO: 184, the LFR3 as set forth in SEQ ID NO: 57, and the LFR4 as set forth in SEQ ID NO: 199.

Embodiment 197

The isolated antigen-binding protein according to any one of Embodiments 146-192, wherein the VL comprises the LFR1 as set forth in SEQ ID NO: 175, the LFR2 as set forth in SEQ ID NO: 185, the LFR3 as set forth in SEQ ID NO: 193, and the LFR4 as set forth in SEQ ID NO: 199.

Embodiment 198

The isolated antigen-binding protein according to any one of Embodiments 146-192, wherein the VL comprises the LFR1 as set forth in SEQ ID NO: 176, the LFR2 as set forth in SEQ ID NO: 186, the LFR3 as set forth in SEQ ID NO: 194, and the LFR4 as set forth in SEQ ID NO: 199.

Embodiment 199

The isolated antigen-binding protein according to any one of Embodiments 146-192, wherein the VL comprises the LFR1 as set forth in SEQ ID NO: 177, the LFR2 as set forth in SEQ ID NO: 187, the LFR3 as set forth in SEQ ID NO: 195, and the LFR4 as set forth in SEQ ID NO: 199.

Embodiment 200

The isolated antigen-binding protein according to any one of Embodiments 146-192, wherein the VL comprises the LFR1 as set forth in SEQ ID NO: 178, the LFR2 as set forth in SEQ ID NO: 188, the LFR3 as set forth in SEQ ID NO: 196, and the LFR4 as set forth in SEQ ID NO: 199.

Embodiment 201

The isolated antigen-binding protein according to any one of Embodiments 146-192, wherein the VL comprises the LFR1 as set forth in SEQ ID NO: 179, the LFR2 as set forth in SEQ ID NO: 187, the LFR3 as set forth in SEQ ID NO: 195, and the LFR4 as set forth in SEQ ID NO: 199.

Embodiment 202

The isolated antigen-binding protein according to any one of Embodiments 146-192, wherein the VL comprises the LFR1 as set forth in SEQ ID NO: 173, the LFR2 as set forth in SEQ ID NO: 183, the LFR3 as set forth in SEQ ID NO: 192, and the LFR4 as set forth in SEQ ID NO: 201.

Embodiment 203

The isolated antigen-binding protein according to any one of Embodiments 146-202, wherein the VH comprises a sequence as set forth in SEQ ID NOs: 202-220, 332-334.

Embodiment 204

The isolated antigen-binding protein according to any one of Embodiments 146-203, wherein the VL comprises a sequence as set forth in SEQ ID NOs: 221-234, 335-338.

Embodiment 205

The isolated antigen-binding protein according to any one of Embodiments 1-204, further comprises a heavy chain constant region of IgG and/or a light chain constant region of a human antibody.

Embodiment 206

The isolated antigen-binding protein according to any one of Embodiments 1-205, comprising a heavy chain constant region derived from IgG1, IgG2, IgG3, or IgG4.

Embodiment 207

The isolated antigen-binding protein according to any one of Embodiments 1-206 comprising a Kappa or Lambda light chain constant region.

Embodiment 208

The isolated antigen-binding protein according to any one of Embodiments 1-207, wherein the heavy chain constant region is derived from IgG, IgM, IgA, IgD, or IgE.

Embodiment 209

An isolated nucleic acid molecule encoding an isolated antigen-binding protein as described in any one of Embodiments 1-208.

Embodiment 210

An expression vector comprising nucleic acids according to Embodiment 209.

Embodiment 211

A host cell comprising nucleic acids isolated according to Embodiment 209 and/or the expression vector according to Embodiment 210.

Embodiment 212

A composition comprising the isolated antigen-binding protein according to any one of Embodiments 1-208 and an optionally pharmaceutical acceptable carrier.

Embodiment 213

A preparation method for isolated antigen-binding proteins for TL1A, comprising: culturing the host cells of Embodiment 211, and recovering the isolated antigen-binding proteins.

Embodiment 214

A method for treating TL1A-mediated disease or condition, which comprises:

1. administering a subject in need thereof the isolated antigen-binding protein according to any one of Embodiments 1-208, the isolated nucleic acid according to Embodiment 209, and/or the expression vector according to Embodiment 210, the host cell according to any one of Embodiment 211, and/or the composition according to Embodiment 212.

Embodiment 215

The isolated antigen-binding protein according to any one of Embodiments 1-208, the nucleic acid isolated according to Embodiment 209, the expression vector according to Embodiment 210, the host cell according to any one of Embodiment 211, and/or the composition according to Embodiment 212, which is used for the treatment of TL1A-mediated disease or condition.

Embodiment 216

Use of the Isolated antigen-binding proteins as described in any one of Embodiments 1-208, isolated nucleic acids according to Embodiment 209, and/or expression vectors according to Embodiment 210, host cells according to any one of Embodiment 211, or composition according to Embodiment 212 for the treatment of TL1A-mediated disease or condition.

Embodiment 217

Use of the isolated antigen-binding protein of Embodiments 1-208, the isolated nucleic acid according to Embodiment 209, the expression vector according to Embodiment 210, the host cell according to any one of Embodiment 211, and/or the composition according to Embodiment 212 in preparation a drug for the treatment of TL1A-mediated disease or condition.

Embodiment 218

The method as described in Embodiment 214, or the use as described in Embodiments 215-217, wherein the TL1A-mediated disease or condition is inflammatory disease.

Embodiment 219

The method or use as described in Embodiment 218, wherein the TL1A-mediated inflammatory disease is selected from one of the following: allergy, ankylosing spondylitis, asthma, atopic dermatitis, autoimmune diseases or disorders, cancer, celiac disease, chronic obstructive pulmonary disease (COPD), chronic peptic ulcer, cystic fibrosis, diabetes (e.g., type 1 diabetes and type 2 diabetes), glomerulonephritis, gout, hepatitis (e.g., active hepatitis), an immune-mediated disease or disorder, inflammatory bowel disease (IBD) such as Crohn's disease and ulcerative colitis, myositis, osteoarthritis, pelvic inflammatory disease (PID), multiple sclerosis, neurodegenerative diseases of aging, periodontal disease (e.g., periodontitis), preperfusion injury transplant rejection, psoriasis, pulmonary fibrosis (e.g., idiopathic pulmonary fibrosis), rheumatic disease, scleroderma, sinusitis, tuberculosis.

Embodiment 220

The method or use of Embodiment 219, wherein inflammatory bowel disease (IBD) comprises: Ulcerative colitis (UC) or Crohn's disease (CD).

Embodiment 221

The method as described in Embodiment 214, or the use as described in Embodiments 215-217, wherein the TL1A-mediated disease or condition are autoimmune diseases.

Embodiment 222

The method or use as described in Embodiment 221, wherein the TL1A-mediated autoimmune diseases are selected from one of the following: Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune urticaria, Axonal & neuronal neuropathy (AMAN), Bal disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenia purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal MotorNeuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjögren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenia purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Vogt-Koyanagi-Harada Disease.

Embodiment 223

The method as described in Embodiment 214, or the use as described in Embodiments 215-217, wherein the TL1A-mediated disease or condition is cancer.

Embodiment 224

The method as described in Embodiment 223, or the use described in Embodiments 215-217, wherein TL1A-mediated cancers are selected from one or more of the following: Adenoid Cystic Carcinoma, Adrenal Gland Cancer, Amyloidosis, Anal Cancer, Ataxia-Telangiectasia, Atypical Mole Syndrome, Basal Cell Carcinoma, Bile Duct Cancer, Birt Hogg Dube Syndrome, Bladder Cancer, Bone Cancer, Brain Tumor, Breast Cancer, Breast Cancer in Men, Carcinoid Tumor, Cervical Cancer, Colorectal Cancer, Ductal Carcinoma, Endometrial Cancer, Esophageal Cancer, Gastric Cancer, Gastrointestinal Stromal Tumor (GIST), HER2-Positive Breast Cancer, Islet Cell Tumor, Juvenile Polyposis Syndrome, Kidney Cancer, Laryngeal Cancer, Leukemia-Acute Lymphoblastic Leukemia, Leukemia-Acute Lymphocytic (ALL), Leukemia-Acute Myeloid AML, Leukemia-Adult, Leukemia—Childhood, Leukemia-Chronic Lymphocytic (CLL), Leukemia-Chronic Myeloid (CIVIL), Liver Cancer, Lobular Carcinoma, Lung Cancer, Lung Cancer-Small Cell (SCLC), Lung Cancer-Non-small Cell (NSCLC), Lymphoma-Hodgkin's, Lymphoma-Non-Hodgkin's, Malignant Glioma, Melanoma, Meningioma, Multiple Myeloma, Myelodysplastic Syndrome (MDS), Nasopharyngeal Cancer, Neuroendocrine Tumor, Oral Cancer, Osteosarcoma, Ovarian Cancer, Pancreatic Cancer, Pancreatic Neuroendocrine Tumors, Parathyroid Cancer, Penile Cancer, Peritoneal Cancer, Peutz-Jeghers Syndrome, Pituitary Gland Tumor, Polycythemia Vera, Prostate Cancer, Renal Cell Carcinoma, Retinoblastoma, Salivary Gland Cancer, Sarcoma, Sarcoma-Kaposi, Skin Cancer, Small Intestine Cancer, Stomach Cancer, Testicular Cancer, Thymoma, Thyroid Cancer, Uterine (Endometrial) Cancer, Vaginal Cancer, and Wilms' Tumor.

Embodiment 225

The isolated antigen-binding protein according to Embodiment 1, wherein the isolated antigen-binding protein includes VH including HCDR1 as set forth in SEQ ID NO: 2, HCDR2 as set forth in SEQ ID NO: 6, HCDR3 as set forth in SEQ ID NO: 15, and VL including LCDR1 as set forth in SEQ ID NO: 42, LCDR2 as set forth in SEQ ID NO: 43, and LCDR3 as set forth in SEQ ID NO: 44.

Embodiment 226

The isolated antigen-binding protein according to Embodiment 225, wherein the isolated antigen-binding protein includes VH as set forth in SEQ ID NO: 70 and VL as set forth in SEQ ID NO: 106.

Without intending to be bound by any theory, the following examples are intended merely to illustrate the fusion proteins, methods of preparation, uses, etc., of the present application and are not intended to limit the scope of the present application.

EXAMPLES

Example 1 SJL Mouse Immunization 1.1 Immunogen: Sequence that encoding human TL1A protein (UniprotKB NO. 095150), the DNA sequence of amino acids 72-251 in the extracellular region, was cloned into the mDeZ-Fc vector containing the Fc tag and a recombinant eukaryotic expression plasmid was prepared. The expression plasmid was transiently transfected into Expi293 cells and cultured in larger quantities, and the cell culture supernatant was collected four days later, and the cell culture supernatant was purified to obtain high-purity and biologically active huTL1A-Fc protein, which was frozen at −80° C. for later use. At the same time, cynomolgus monkey TL1A-his protein (UniprotKB NO. G7PRK8) and murine TL1A-his protein (UniprotKB NO. Q5UBV8) was constructed and prepared, and rat TL1A-his protein (Acrobiosystems, TLA-R5249) was purchased for subsequent related experiments. The corresponding protein amino acid sequences are shown in Table 1.

TABLE 1

| Amino acid sequences of related proteins | |
|---|---|
| Human TL1A (M1-L251) | MAEDLGLSFGETASVEMLPEHGSCRPKARSSSARWALTCCLVLLPFLAGLTTYLLVSQLRA QGEACVQFQALKGQEFAPSHQQVYAPLRADGDKPRAHLTVVRQTPTQHFKNQFPALHWEH ELGLAFTKNRMNYTNKFLLIPESGDYFIYSQVTFRGMTSECSEIRQAGRPNKPDSITVVITKV TDSYPEPTQLLMGTKSVCEVGSNWFQPIYLGAMFSLQEGDKLMVNVSDISLVDYTKEDKTF FGAFLL (SEQ ID 326) |
| Human sTL1A (L72-L251) | LKGQEFAPSHQQVYAPLRADGDKPRAHLTVVRQTPTQHFKNQFPALHWEHELGLAFTKNR MNYTNKFLLIPESGDYFIYSQVTFRGMTSECSEIRQAGRPNKPDSITVVITKVTDSYPEPTQLL MGTKSVCEVGSNWFQPIYLGAMFSLQEGDKLMVNVSDISLVDYTKEDKTFFGAFLL (SEQ ID 327) |
| Cyno sTL1A (L72-L251) | LKGQEFAPSHQQVYAPLRADGDKPRAHLTVVRQTPTQHLKNQFPALHWEHELGLAFTKNR MNYTNKFLLIPESGDYFVYSQVTFRGMTSECSEIRQAGRPNKPDSITVVITKVTDSYPEPTQL LMGTKSVCEVGSNWFQPIYLGAMFSLQEGDKLMVNVSDISLVDYTKEDKTFFGAFLL (SEQ ID 328) |
| Mouse sTL1A (A61-L252) | AGQLRVPGKDCMLRAITEERSEPSPQQVYSPPRGKPRAHLTIKKQTPAPHLKNQLSALHWEH DLGMAFTKNGMKYINKSLVIPESGDYFIYSQITFRGTTSVCGDISRGRRPNKPDSITVVITKVA DSYPEPARLLTGSKSVCEISNNWFQSLYLGAMFSLEEGDRLMVNVSDISLVDYTKEDKTFFG AFLL (SEQ ID 329) |
| Rat sTL1A (T61-I252) | TGQLRIPGKDCMFPTVTEERSAPSAQPVYTPSRDKPKAHLTIMRQTPVPHLKNELAALHWEN NLGMAFTKNRMNYTNKFLVIPESGDYFIYSQITFRGTTSECGDISRVRRPKKPDSITVVITKV ADSYPEPAHLLTGTKSVCEISSNWFQPIYLGAMESLEEGDRLMVNVSDISLVDYTKEDKTFF GAFLI (SEQ ID 330) |
| Human DR3-ECD (Q25-Q199) | QGGTRSPRCDCAGDFHKKIGLFCCRGCPAGHYLKAPCTEPCGNSTCLVCPQDTFLAWENHH NSECARCQACDEQASQVALENCSAVADTRCGCKPGWFVECQVSQCVSSSPFYCQPCLDCG ALHRHTRLLCSRRDTDCGTCLPGFYEHGDGCVSCPTSTLGSCPERCAAVCGWRQ (SEQ ID 331) |

1.2 SJL mouse immunization: 6-8 weeks old SJL mice were immunized with huTL1A-Fc protein. For primary immunization, 50 μg of huTL1A-Fc protein was emulsified with CFA adjuvant and intraperitoneally injected into mice. For subsequent booster immunization, 50 μg of huTL1A-Fc protein was mixed with RIBI adjuvant and intraperitoneally injected into mice. The interval between each immunization is 2 weeks. Serum was isolated after blood collection 7 days after the third immunization, serum antibody titers were detected by ELISA, and mice with high serum titers were selected for subsequent antibody screening.

Example 2 Antibody Screening 2.1 Screening of anti-TL1A antibody based on Single B sorting memory B cell technology: Biotin conjugation of huTL1A-his protein via a biotin labeling kit (ThermoFisher, A35389) was used to obtain huTL1A-his-Biotin protein. The spleen of mice with qualified immune titer was prepared into a single-cell suspension, and B cells were enriched by magnetic bead sorting, and the huTL1A-his-Biotin protein was incubated with the isolated B cells, and after the incubation, Streptavidin-PE was added, the positive B cells were sorted, and introduced into a 96-well plate to ensure that each well contained only one positive B cell, and sequencing analysis was arranged later.

2.2 Screening of anti-huTL1A murine monoclonal antibody based on phage display technology: total RNA was extracted from mouse spleen single cells using Trizol, RNA was reverse transcribed into cDNA, and then PCR-amplified VH and VL fragments were inserted into the phage vector, and the constructed phage was packaged into a phage library with a capacity of about 3.0E+8 by an auxiliary phage. After three rounds of phage library panning, clones identified as positive by ELISA were selected for sequencing analysis.

Example 3 Monoclonal Sequencing

The positive B cells sorted by Single B were cloned, RNA was extracted, reverse transcribed into cDNA, amplified, and then sequenced to obtain the VH and VL sequences of anti-huTL1A monoclonal antibody. The clones that were tested positive by Phage ELISA were sequenced to obtain the VH and VL amino acid sequences of the anti-huTL1A monoclonal antibody. The amino acid sequences of VH and VL for all monoclonal antibodies against huTL1A are shown in Table 2:

TABLE 2

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0014 | QIQLVQSGPELKKPGETVKISCKASGYTFT TYGMNWVKQSPGKGLKWMGWINTYSGV PTYADDFKGRFAFSLETSVNTAYLQINSLK TDDTATYFCAKDAYDNYAMDYWGQGTS VTVSS | 342 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPLTFG AGTKLELK | 544 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0015 | QIQLKESGPGLVAPSQSLSITCTVSGFSLSSYGVDWVRQSPGKGLEWLGVIWGFGGTNYNSALKSRLSISKDNSKSQVFLKMNSLQSDDSAIYYCASGNFDAMDYWGQGTSVTVSS | 343 | DIQMTQTTSSLSASLGDRVTISCRASQDISNYLNWYQQKPDGTVKLLIYYTSRLHSGVPSRFSGSGSGTDYSLTISNLEQEDIATYFCQQGNTLPFTFGSGTKLEIK | 478 |
| TLA0094 | DVQLQESGPGLVKPSQSLSLTCSVTDYSITSGYYWNWIRQFPGNKLEWMGYIHFDGSNDYNPSLKNRISITRDTSRNQFFLKLNSVTSEDTATYYCAREGTSYFDYWGQGTTLTVSS | 344 | DIKMTQSPSSMYASLGERVTITCKASQDINSYLSWFQQKPGKSPKTLIYRANRLVDGVPSRFSASGSGQDYSLTISSLEYEDMGIYYCLQCDEFPYTFGGGTKLEIK | 481 |
| TLA0095 | QIQLVQSGPELKKPGETVKISCKASGYTFTTYGMSWVKQAPGKYLKWMGWIDTYSGVPTYADDFKGRFAFSLETSANTAYLQINNLKNEDTATYFCANSFQFAYWGQGTLVTVSA | 345 | DIVLTQSPASLPVSLGQRATISCRASKSVSTSSYSYMHWYQQKPGQPPKLLIKYASNLESGVPARFSGSGSGTDFTLNIHPVEEEDAATYYCQHSKEFPWTFGGGTKLEIK | 479 |
| TLA0096 | DVQLQESGPGLVKPSQSLSLTCSVTGYSITSGYYWNWIRQFPGNKLEWMGCISYDGSNYYNPSLKNRISFTRDTSKNQFFLKLNSVTTDDTATYYCVREGTSYVDYWGQGTTLTVSS | 346 | DIKMTQSPSSMYASLGERVTITCKASQDINSFLSWFQQKPGKSPKTLIYRANRLVDGVPSRFSGSGSGQDYSLTISSLEYEDMGIYYCLQCDEFPYTFGGGTKLEIK | 480 |
| TLA0097 | DVQLQESGPGLVKPSQSLSLTCSVTDYSITSGYYWNWIRQFPGNKLEWMGYIHYDGSNDYNPSLKNRISITRDTSRNQFFLKLNSVTSEDTATYYCAREGTSYFDYWGQGTTLTVSS | 347 | DIKMTQSPSSMYASLGERVTITCKASQDINSYLSWFQQKPGKSPKTLIYRANRLVDGVPSRFSASGSGQDYSLTISSLEYEDMGIYYCLQCDEFPYTFGGGTKLEIK | 481 |
| TLA0098 | QVQLQQSGPELVRPGASVKISCKAPGYTFTSHWMQWVRQRPGQGLEWIGEIFPGSGTTYYNEKFQGKATLTVDTSSSTAYMQLSSLTSEDSSVHFCARGEGIYYPARSYGPLGYFDVWGTGTTVTVSS | 348 | DIVMTQSHKFMSTSVGDRVSITCKASQDVSTAVAWYQQKPGQSPKLLIYWASARHTGVPARFTGSGSGTDYTLTISSVQAEDLALYYCQQHYGTPPTFGGGTKLEIK | 482 |
| TLA0099 | QVQLQQPGAELVMPGASVKLSCKASGYTFTNYWMNWVKQRPRQGLEWIGETDPSNTYINYNQKFKGKATLTVDKSSNTAYMQLNSLTSEDSAVYYCARGGLPYYGMDYWGQGTSVTVSS | 349 | QIVLTQSPAIMSVSPGEKVTITCSATSRVTYMHWFQQKPGTAPKLWIYSTSNVASGVPARFSGSGSVTSYSLTISRMEAADAATYYCQQRSSYPPTFGGGTKLEIK | 483 |
| TLA0100 | QIQLVQSGPELKKPGETVKISCKASGSAFTTYGMSWVKQAPGEGLKWMGYIITYSGVPTYADDFKGRFAFSLETSASTAYLQINNLKNEDTATYFCTNFYYFDYWGQGTTLTVSS | 350 | DIMLTQSPASLTVSLGQRATISCRASKSVSTSSYTYMHWYQQKPGQPPKLLIKYASNLESGVPARFSGSGSGTDFILNIHPVEEEDAATYYCQHSREFPWTFGGGTKLEIK | 484 |
| TLA0101 | QIQLVQSGPELKKPGETVKISCKASGYTFTTFGMNWVKQAPGKDLKWMGWINTNSGVPTYADDFRGRFAFSMETSATTAYLQINNLKNEDTATYFCARGNWEGPGIWFAYWGQGTLVTVSA | 351 | DIVLTQSPASLAVSLGQRATISCRASKSVSTSSYNYMHWYQQKPGQPPKLLIKYASNLESGVPARFSGSGSGTDFTLNIHPVEEEDAATYYCQHSREFPWTFGGGTKLEIK | 485 |
| TLA0102 | QVQLQQPGTELVKPGASVKLSCKASGYTFTSYWMHWVKQRPGQGLEWIGNIDPNNDVINYNDKFKSKATLTVDKSSSTAYMQLSSLTSEDSGVYYCARGIYAGYWGQGTLVTVSA | 352 | QIVLTQSPALMSASPGEKVTMTCSASSSVSYMYWYQQKPRSSPKPWIYLTSNLASVPARFSGSGSGTSYSLTISSMEAEDAATYYCQQWIIYPPMLTFGAGTKLELK | 486 |
| TLA0103 | EVQLQQSGAELMKPGASVKLSCKATGYTFTGYWLEWVKQRPGHGLEWIGETLPGSGYNKYNEKFKGKATFTADTSSNTAHMQLSSLTTEDSAIYYCARRGSNYPYWYFDVWGTGTTVTVSS | 353 | DIVLTQSPASLAVSLGQRATISCKASQSVSFAGISLMHWYQQKPGQQPKLLIYRASNLEAGVPTRFSGSGSRTDFTLTINPVETDDVATYYCQQSNKDPTFGGGTKLELK | 487 |
| TLA0104 | QVQLKESGPGLVQPSQSLSITCTVSGFSLTSYGVHWVRQSPGKGLEWLGVIWSGGSTDYNAAFISRLSISKDNSKSQVFFKMNSLQADDTAIYYCARNDYDYAMDYWGQGTSVTVSS | 354 | DIVMTQSHKFMSTSVGDRVSITCKASQDVSTAVAWYQQKPGQSPKLLIYSASYRYTGVPDRFTGSGSGTDFTFTISSVQAEDLAVYYCHQHYSTPYTFGGGTKLEIKR | 488 |

TABLE 2-continued

Amino acid sequences of VH and VL of anti-TL1A antibodies screened by Single B and libraries

| Antibody NO. | Amino acid sequence (VH) | SEQ ID | Amino acid sequence (VL) | SEQ ID |
|---|---|---|---|---|
| TLA0105 | QVQLQQSGPELVKPGASVKVSCKASGYTF TRQDINWVKQRPGQGLEWIGWIYPRDGRT EYNEKFKGKVTLTVDTSSSTAYMELHSLT SEDSAVYFCATYGSSLDNWGQGTTLTVSS | 469 | DVVMTQTPLSLPVSLGDQASISCRSS QNIVHSNGDTYLDWFLQKPGQSPKL LIYKVSNRFSGVPDRFSGSGSGTDFTL KITRVESEDLGVYYCFQGSHDPYTFG GGTKLEIKR | 489 |
| TL10106 | QVQLQQSGPELVKPGASVKLSCKASGYTF TSIDINWVKQRPGQGLEWIGWIYPRDGRT DYNEKFKGKATLTVDTSSSTAYMELHSLT SEDSAVYFCARYTSSLDYWGQGTTLTVSS | 355 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0107 | EVKLEESGGGLVQPGGSMKLSCVASGFTF SNYWMNWVRQSPEKGLEWVAQIRLKSDN YATHYAESVKGRFTISRDDSKSNVYLQMN NLRAEDTGIYYCTPLLLRSIDYWGQGTTLT VSS | 356 | ENVLTQSPAIMSASPGERVTMTCSAS SSVSYMHWYQQKSSTSPKLWISDTS KLASGVPGRFSGSGSGNSYSLTISSME AEDVATYYCFQESGYPFTFGAGTKLE LK | 490 |
| TLA0108 | EVQLQQSGPELVKPGASVKLSCKASGYTF TSIDINWVKQRPGQGLEWIGWIYPRDGRT DYNEKFKGKATLTVDTSSSTAYMELHSLT SEDSAVYFCARYGSSLDYWGQGTTLTVSS | 357 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0109 | QIQLVQSGPELVKPGASVKLSCQASGYTFT NSDINWVKQRPGQGLEWIGWVYPRDGRT YYNEKFKGKATLTVDTSSSTAYMELYSLT SEDSAVYFCARYAYALNSWGQGTSVTVSS | 423 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0110 | QVQLQQSGPELVKPGASVKVSCKASGYTF TRQDINWVKQRPGQGLEWIGWIYPRDGRT EYNEKFKGKVTLTVDTSSSTAYMELHSLT SEDSAVYFCATYGSSLDNWGQGTTLTVSS | 469 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0111 | QVQLQQSGPELVKPGASVKLSCKASGYTF TNQDMNWVKQRPGQGLEWIGWIFPRDGR THHNENFKGKATLTVDTSSSTAYMELHSL TAEDSAVYFCAIYGFAMDQWGQGTSVTV SS | 358 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0112 | QVQLQQPGPELVKPGASVKLSCKASGYTF TNQDINWVKQRPGQGLEWIGWIFPRDGRT HYNENFKGKATLTVDTSSSTAYMELHSLT AEDSAVYFCAIYGIALDHWGQGTSVTVSS | 359 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0113 | QVQLQQSGPELVKPGASVKLSCKASGYTF TDYDVNWVKQRPGQGLEWIGWNYPRDG RTNYNEKFKGKATLTVDISSSTAYMELHS LTSEDSAVYFCARYGSALNVWGTGTTVTV SS | 420 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0114 | QVQLQQSGPELVKPGASVKLSCKASGYTF TNQDINWVKQRPGQGLEWIGWIFPRDGRT HYNENFKGKATLTVDTSSSTAYMELHSLT AEDSAVYFCAIYGFAMDHWGQGTSVTVS S | 447 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 191 |
| TLA0115 | QVQLQQSGPELVKPGASVKLSCRASGYTF TSYDINWVKQRPGQGLEWIGWNYPRDGR TDYNEKFKGKATLTVDTSSNTAYMELHSL TSEDSAVYFCTRYGSTLDVWGTGTTVTVS S | 414 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0116 | QVQLQQSGPELVKPGTSVKLSCKASGYTF TNQDINWVKQRPGQGLEWIGWIFPRDGRT HYNENFKGKATLTVDTSSSTAYMELHSLT AEDSAVYFCSIYGIAMDHWGQGTSVTVSS | 445 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0117 | QVQLQQPGPELVKPGASVKLSCKASGYTF TNQDINWVKQRPGQGLEWIGWIFPRDGRT HYNENFKGKATLTVDTSSSTAYMELHSLT AEDSAVYFCAIYGAAMDHWGQGTSVTVS S | 360 | DVVMTQTPLSLPVSLGDQASISCRSS QSIVHSNGDTYLEWYLQKPGQSPKLL IYKVSNRFSGVPDRFSGSGSGTDFTL KISRVEAEDLGVYYCFQGSHVPYTFG GGTKLEIKR | 491 |
| TLA0118 | EVKLEESGGGLVQPGGSMKLSCVASGFTF SNYWMNWVRQSPEKGLEWVAQIRLKSDN YATHYAESVKGRFTISRDDSKSSVYLQMN NLRAEDTGIYYCTPLLLRYFDVWGTGTTV TVSS | 361 | ENVLTQSPAIMSASPGEKVTMTCSAS SSVSYMHWYQQKSSTSPKLWIYDTS KLASGVPGRFSGSGSGNSYSLTISSME AEDVATYYCFQESGYPLTFGAGTKL ELK | 492 |
| TLA0119 | EVQLQQSVAELVRPGASVKLSCTASGFNIE DTYIHWVKQRPEQGLEWIGRIDPAHDKTK YAPKFQGKATITADTSSNTAYLQLSSLTSE DTAIYYCASTGPDWWGQGTTLTVSS | 362 | EILLTQSPAIIVASPGEKVTITCSATSS VIYMNWYQQKPGSSPKIWIYGISNLA SGVPARFSGSGSGTSFSFTINSMEAED VATYYCQQRSSYPFTFGSGTKLEIK | 493 |
| TLA0120 | QVQLQQSGAELVRPGTSVKMSCKASGYTF TNYWIGWTKQRPGHGLEWIGDIYPGGGYI NYNEKFKGKATLTADKSSSTAYMQFSSLT SEDSAIYYCAREGGYGSGQAWFPYWGQG TLVTVSA | 363 | DVQITQSPSYLAASPGETITMNCRAS KSIRKYLAWYQEKPGKSNKILIYSGS TLQSGIPSRFSGSGSGTDFTLTISSLEP EDFAMYYCQQHNEYPLTFGAGTKLE LK | 494 |
| TLA0121 | QVQLQQPGTELVRPGTSVKLSCKASGYTF TSYWMHWVKQRPGQGLEWIGVIEPSDSY TDYNQKFKGKATLTVDTSSSTAYMQLSSL TSEDSAVYYCARGDYDEVFAYWGQGTLV TVSA | 364 | QIVLTQSPAIMSASPGEKVTMTCSASS SVSYMHWYQQKSGTSLKRWIYDTSK LASGVPARFSGSGSGTSYSLTVSSME AEDAATYYCQQWTSTPYTFGGGTKL EIK | 495 |
| TLA0122 | QVQLQQPGAELVRPGTSVKLSCKASGYTF TSYWMHWVKQRPGQGLEWIGVIEPSDSY TDYDQKFKGKATLTVDTSSNTAYMQLSSL TSEDSAVYYCSRGDYDEVFAYWGQGTLV TVST | 365 | QIVLTQSPAIMSASPGEKVTMTCSASS SVSYMHWYQQKSGTSPKRWIYDTSK LASGVPARFSGSGSGTSYSLTISTMEA EDAATYYCQQWTSTPYTFGGGTKLE IK | 496 |
| TLA0123 | QVQLQQSGADLVRPGASVTLSCKASGYTF SDSEIHWVRQTPVHGLEWIGAIDPETGDIA YNQMFKDKATLTADKSSSTAYVELRSLTS EDSAVYYCTRYGGNSWHFDVWGTGTTVT VSS | 366 | DIQMTQTTSSLSASLGDRVTISCRASQ DITNYLNWYQQKPDGTVKLLIYSTSR LHSGVPSRFSGSGSGTDYSLTISNLEQ EDIATYFCQQGNTLPLTFGAGTKLEL K | 497 |
| TLA0124 | EFQLQQSGPELLKPGASVKISCKASGYSFT DYNINWVKQRNGKSLEWIGMINPKYGITD YNQKFKGKATLTVDQFSSTAYMQVNSLTS DDSAVYYCAREELGHWCFDVWGTGTTVT VSS | 367 | DIVMTQPQKFMPTSVGDRVSVTCKA SQNVGTNVAWYQQKAGQSPKVLIYS ASYRYSGVPDRFTGSGSGTAFTLTISN VQSEDLAEYFCHQYNNFPFSFGSGTM LEIK | 499 |
| TLA0125 | QVQLQQSGAELVRPGTSVKVSCKASGYAF TNYLIEWVNQRPGQGLEWIGVINPGSGGT KYNEKFKGKATLTADKSSSTAYMQLSSLT SEDSAVYFCAREGSAGPFDYWGQGTTLTV SS | 368 | DIKMTQSPSSMYASLGERVTITCKAS QDINSYLSWFQQKPGKSPKTLIYRAN RLLDGVPSRFSGSGSGQDYSLTISSLE YEDMGIYYCLQYDEFPYTFGGGTKL EIK | 498 |
| TLA0126 | EFQLQQSGPELVKPGASVKISCKASGYSFT DYNINWVKQRNGKSLEWIGMINPKYGITD YNQKFKGKATLTVDQFSSTAYMQVNSLTS DDSAVYYCAREELGHWCFDVWGTGTTVT VSS | 369 | DIVMTQPQKFMPTSVGDRVSVTCKA SQNVGTNVAWYQQKAGQSPKVLIYS ASYRYSGVPDRFTGSGSGTAFTLTISN VQSEDLAEYFCHQYNNFPFSFGSGTM LEIK | 499 |
| TLA0127 | EVQLQQSGPVLVKPGASVKMSCEASGYTL TDYYMNWVKQSHGKSLEWIGIINPYNGAS NFNQRFRGKASLTFGKSSNTAYMELNSLT SEDSAVYYCASDWDVGYWGQGTALTVSS | 370 | DIKMTQSPSSMYASLGDRVTITCKAS QDIDSYLSWFQQKPGKSPKTLMYHT NRLIVGVPSRFSGTGSGQDYALTISSL EYEDLGIYYCQQYDEFPSTFGSGTKL EIK | 500 |
| TLA0128 | EVQLVESGGDLVKPGGSLKLSCAASGFTFS RYGMSWVRQTPDKRLEWVATISSGGSDT YYPDSVKGRFTISRDNAKNTLYLQMSSLK SEDTAMYYCARHGYDYGHFDYWGQGTT LTVSS | 371 | DIQMTQTTSSLSASLGDRVTISCRASQ DISNYLNWYQQKPDGTVKLLIYYTSR LHSGVPSRFSGSGSGTDYSLTISNLDQ EDIATYFCQQGNTLPLTFGAGTKLEL K | 501 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0129 | EFQLQQSGPELVKPGASVKISCKASGYSFTDYNINWVKQSNGKSLEWIGVINPNYGITDYNQKFKGKATLTVDQSSSTAYMQLNSLTSEDSAVYYCAREELGHWCFDVWGTGTTVTVSS | 372 | DNVMTQSQKFMSTSVGDRVSVTCKASQNVGTNVAWYQQKAGQSPKVLIYSASYRYSGVPDRFTGSGSGTAFTLTISNVQSEDLAEYFCQQYNSFPFTFGSGTKLEIK | 502 |
| TLA0130 | QVTLKESGPGILQPSQTLNLTCSFSGFSLSTFGMGVGWIRQPSGEGLEWLAHIWWDDHEYYNPALKSRLTISKDTSKNQVFLKIANVDTADTATYYCNRGFVYWGQGTLVTVSA | 373 | DVVMTQTPLTLSVTIGQPASISCKSSQSLLDSDGKTYLSWLLQRPGQSPKRLIILVSKLDSGVPDRFTGSGSGTDFTLKISRVEAEDLGVYYCWQGTHFPQTFGGGTKLEIK | 503 |
| TLA0131 | QVQLQQSGPELVKPGTSVKLSCKASGYTFTSYDINWMKQRPGQGLEWIGWIFPRDGITKYNEKFKDKATLTVDTSSSAAYMELHSLTSEDSAVYFCARYGPAMDYWGQGTSVTVSS | 374 | DVLMTQAPLSLPVSLGDQASISCRSSQSIVHSNGDTYLDWYLQKPGQSLKLLIYKLSNRFSGVPDRFSGSGSGTDFTLKISRVEAEDLGVYHCFQGSHVPYTFGGGTKLEIK | 504 |
| TLA0132 | EVQLQQSGPELVKPGASVKLSCKASGYTFTNQDINWVKQRPGQGLEWIGWIFPRDGRTHYNENFKGKATLTVDTSSSTAYMELHSLTAEDSAVYFCAIYGIALDHWGQGTSVTVSS | 441 | DVVMTQTPLSLPVSLGDQASISCRSSQSIVHGNGNTYLEWYLQKPGQSPKLLIYKVSNRFSGVPDRFSGSGSGTDFTLKISRVEAEDLGVYYCFQGSHVPYTFGGGTKLELKR | 505 |
| TLA0133 | QIQLVQSGPELVKPGASVKVSCKASGYTFTRQDINWVKQRPGQGLEWIGWIYPRDGRTEYNEKFKGKVTLTVDTSSSTAYMELHSLTSEDSAVYFCATYGSSLDNWGQGTTLTVSS | 375 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLELKR | 506 |
| TLA0134 | EVQLQQSGPELVKPGASVKVSCKASGYTFTRQDINWVKQRPGQGLEWIGWIYPRDGSTKYNEKFKGKVTLTVDTSSSTAYMELHSLTSEDSAVYFCATYGSSLDNWGQGTTLTVSS | 376 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLELKR | 506 |
| TLA0135 | EVQLQQSGPELVKPGASVKLSCKASGYTFTNQDINWVKQRPGQGLEWIGWIFPRDGRTHYNENFKGKATLTVDTSSSTAYMELHSLTAEDSAVYFCAIYGIAMDHWGQGTSVTVSS | 377 | DVVMTQTPLSLPVSLGDQASISCRSSQSIVHSNGSTYLEWYLQKPGQSPKLLIYKVSNRFSGVPDRFSGSGSGTDFTLKISRVEAEDLGVYYCFQGSHVPYTFGGGTKLEIK | 507 |
| TLA0136 | QIQLVQSGPELVKPGASVKLSCKASGYTFTNYDINWVKQRPGQGLEWIGWIYPRDGSTYYNEKFKGKATLTVDTSSTTAYMEFHSLTSEDSAVYFCARYAYALNSWGQGTSVTVSS | 378 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIKR | 547 |
| TLA0137 | QVQLKQSGPELVRPGASVKLSCKASGYSFTSGDINWVKQRPGQGLEWIAWIYPRDGSTEYNEKFKGKATLTVDTSSSTAYMELHSLTSEDSAVYFCARYDCAFVYWGQGTLVTVSA | 379 | DVVMTQTPLSLPVSLGDQASISCRSSQNIVHSNGDTYLDWFLQKPGQSPQLLIYKVSNRFSGVPDRFSGSGSGTDFTLKISRVEAEDLGIYYCFQGSHVPYTFGGGTKLEIK | 508 |
| TLA0138 | QVQLQQSGPELVKPGASVKLSCKASGYTFTNQDINWVKQRPGQGLEWIGWIFPRDGRTHYNENFKGKATLTVDTSSSTAFMELHSLTAEDSAVYFCAIYGIALDHWGQGTSVTVSS | 380 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0139 | QVQLQQSGPELVKPGASVKLSCKASGYTFTDYDVNWVKQRPGQGLEWIGWNYPRDGRTNYNEKFKGKATLTVDISSSTAYMELHSLTSEDSAVYFCARYGSALNVWGTGTSVTVSS | 381 | DVVMTQTPLSLPVSLGDQASISCRSSQSIVHSNGDTYLDWFLQKPGQSPKLLIYKVSNRFSGVPDRFSGSGSGTDFTLKISRVEAEDLGVYYCFQGSHVPYTFGGGTKLEIK | 550 |
| TLA0140 | QIQLVQSGPELVKPGASVKLSCKASGYTFTKYDINWVKQRPGQGLEWIGWIYPRDGSTKYNEKFKGKATLTVDTSSNTAYMELHSLTSEDSAVYFCARYSAAMDYWGQGTSVTVSS | 382 | DVVMTQTPLSLPVSLGDQASISCRSSQNIVHSNGDTYLDWFLQKPGQSPKLLIYKVSNRFSGVPDRFSGSGSGTDFTLKISRVEAEDLGVYYCFQGSHVPYTFGGGTKLEIK | 538 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0141 | QVQLQQPGAELGKPGASVKLSCKASGYTF<br>TNYDINWVKQRPGQGLEWIGWNYPRDGR<br>TKYNEKFKGKATLTVDTSSSTAYMELHSL<br>TSEDSAVYFCARYGYAMDYWGQGTSVTV<br>SS | 383 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |
| TLA0142 | QVQLQQPGAELGKPGASVKLSCKASGYTF<br>TNYDINWMKLRPGQGLEWIGWNYPRDGR<br>TKYNEKFKGKATFTVDTSSSTAYMELHSL<br>TSEDSAVYFCARYGYAMDYWGQGTSVTV<br>SS | 384 | DVVMTQTPLSLPVSLGDQASISCRSS<br>QSIVHSNGHTYLEWYLQKPGQSPKLL<br>IYKVSNRFSGVPDRFSGSGSGTDFTL<br>KISRVEAEDLGVYYCFQGSHVPYTFG<br>GGTKLEIK | 509 |
| TLA0143 | QIQLVQSGPELVKPGASVKLSCRASGYTFT<br>SYDINWVKQRPGQGLEWIGWIFPRDGRTE<br>YNAKFKGKATLTVDTSSNTAYMELHSLTS<br>DDSAVYFCARYGSTLDVLGAGTTVTVSS | 385 | DVVMTQTPLSLPVSLGDQASISCRPS<br>QTIVHSNGDTYLDWFLQKPGQSPKLL<br>IYKVSNRFSGVPDRFSGSGSGTDFTL<br>KISRVEAEDLGVYYCFQGSHVPYTFG<br>GGTRLEIK | 510 |
| TLA0144 | EVQLQQSGPELVKPGASVKLSCKASGYTF<br>TNQDINWVKQRPGQGLEWIGWIFPRDGRT<br>HYNENFKDKATLTVDTSSSTAYMEVHSLT<br>AEDSAVYFCAIYGIALDHWGQGTSVTVSS | 386 | DVVMTQTPLSLPVSLGDQASISCRSS<br>QSIVHSNGDTYLDWFLQKPGQSPKLL<br>IYKVSNRFSGVPDRFSGSGSGTDFTL<br>KISRVEAEDLGVYYCFQGSHVPYTFG<br>GGTKLEIK | 550 |
| TLA0145 | QVQLQQSGPELVKPGASVKVSCKASGYTF<br>TRQDINWVKQRPGQGLEWIGWIYPRDGRT<br>EYNEKFKGKVTLTVDTSSSTAYMELHSLT<br>SEDSAVYFCATYGSSLDNWGQGTTLTVSS | 469 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |
| TLA0146 | QIQLVQSGPELVKPGASVKLSCKASGYTFT<br>RQDINWVKQRPGQGLEWIGWIYPRDGSTK<br>YNEKFKGKVTLTVDTSSSTAYMELHSLTS<br>EDSAVYFCATYGSSLDNWGQGTTLTVSS | 387 | DVVMTQTPLSLPVSLADQASISCRSS<br>QSIVHDNGDTYLEWYLQKPGQSPRL<br>LIYKVSNRFSGVPDRFSGSGSGTDFTL<br>KINRVEAEDLGVYYCFQGSHVPYTF<br>GGGTKLEIK | 552 |
| TLA0147 | QVQLQQSGPELVKPGASVKIPCKTSGYTFT<br>DYNINWVKRSHGKSLEWIGDINPDSGGTS<br>YNQRFKDKATLTVDKSSSTAYMELRSLTS<br>GDTAVYYCARWGYYGGRGFDYWGQGTT<br>LTVSS | 388 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPLTFG<br>DGTKLEIK | 511 |
| TLA0148 | QVQLQQSGAELGKPGASVKLSCKASGYTF<br>TNYDINWMKQRPGQGLEWIGWNYPRDGR<br>TKYNEKFKGKATLTVDTSSSTAYMELHSL<br>TSEDSAVYFCARYGYAMDYWGQGTSVTV<br>SS | 389 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |
| TLA0149 | EVQLQQSGPELVKPGASVKVSCKASGYTF<br>TRQDINWVKQRPGQGLEWIGWIYPRDGRT<br>EYNEKFKGKVTLTVDTSSSTAYMELHSLT<br>SEDSAVYFCATYGSSLDNWGQGTTLTVSS | 471 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |
| TLA0150 | EVQLQQSGPDLVKPGASVKLSCKASGYTF<br>ASYDINWVKQRPGQGLEWIGWIYPRDGRT<br>DYNEKFKGKATLTVDTSSSTAYMELHSLT<br>SEDSAVYFCARYGYALGYWGQGTSVTVS<br>S | 390 | DVVMTQTPLSLPVSLGDQASISCRSS<br>QSIVHSNGDTYLDWFLQKPGQSPKLL<br>IYKVSNRFSGVPDRFSGSGSGTDFTL<br>KITRVESEDLGVYYCFQGSHDPYTFG<br>GGTKLEIK | 512 |
| TLA0151 | QVQLQQSGPELAKPGASVKLSCKASGYTF<br>TSRDINWVKQRPGQGLEWIGWIYPRDGRT<br>NYNEKFKDKATLTVDTSSSTAYMDLHSLT<br>SEDSAVYFCATYGSSLDHWGQGTTLTVSS | 391 | DVVMTQTPLSLPVSLGDQASISCRSS<br>QSVVHNNGNTYLEWYLQKPGQSPKL<br>LIYKVSNRFSGVPDRFSGSGSGTDFTL<br>KISRVEAEDLGVYYCFQGSHVPYTFG<br>GGTKLELK | 513 |
| TLA0152 | EVQLQQSGPELVKPGASVKLSCKASGYTF<br>TNQDINWVKQRPGQGLEWIGWIFPRDGRT<br>HYNENFKGKATLTVDTSSSTAYMELHSLT<br>AEDSAVYFCAIYGAAMDHWGQGTSVTVS<br>S | 392 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0153 | QVQLQQSGPELVKPGTSVKLSCKASGYTFTDQDINWVKQRPGQGLEWIGWIFPRDGRTHYNEKFKGKATLTVDTSSSTAYMELHSLTSEDSAVYFCSIYGSAMDLWGQGTSVTVSS | 393 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0154 | QVQLQQSGPELVKPGASVKLSCKASGYTFTNQDINWVKQRPGQGLEWIGWIFPRDGRTHNNENFKGKATLTVDTSSSTAYMELHSLTAEDSAVYFCAIYGFAMDHWGQGTSVTVSS | 394 | DVVMTQTPLSLPVSLGNQASISCRSSQDIVHTNGDTYLDWYLQKPGQSPKLLIYKVSNRFSGVPDRFSGSGSGTDFTLKINRVEAEDLGVYYCFQGSHVPYTFGGGTKLELK | 528 |
| TLA0155 | QVQLQQSGPELVKPGASVKLSCKASGYTFTNQDINWVKQRPGQGLEWIGWIFPRDGRTHYNENFKGKATLTVDTSSSTAYMELHSLTAEDSAVYFCAIYGIALDHWGQGTSVTVSS | 443 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0156 | EVQLQQSGPELVKPGASVKLSCKASGYTSTSYDINWVKQRPGQGLEWIGWIYPRDGRTNYNEKFKGKATLTVDTSSSTAFMELHSLTSEDSAVYFCARYSAAMDYWGQGTSVTVSS | 395 | DVVMTQTPLSLPVSLGDQASISCRSSQSIVHSNGDTYLEWYLQKPGQSPKLLIYKVSNRFSGVPDRFSGSGSGTDFTLKISRVEAEDLGVYYCFQGSHVPYTFGGGTKLEIK | 514 |
| TLA0157 | QVQLQQPGSELVRPGASVKIPCKTSGYSFTDFNINWVRQSHGKSLEWIGDINPDSGGTIYNQKFKGKATLTVDKSSSTAYMELRSLTSEDTAVYYCARWGYYGGEGFDYWGQGTTLTVSS | 396 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPLTFGAGTKLELK | 544 |
| TLA0158 | QVQLQQSGPELVKPGASVKLSCKASGYTFTNQDINWVKQRPGQGLEWIGWIFPRDGRTHYNENFKGKATLTVDTSSNTAYMELHSLTAEDSAVYFCAIYGIALDHWGQGTSVTVSS | 442 | DVVMTQTPLSLPVSLGDQASISCRSSQTIVHSNGDTYLDWYLQKPGQSPKLLISKVSNRFSGVPDRFSGSGSGTDFTLKISSVEAEDLGVYYCFQGSHVPYTFGGGTKLEIK | 531 |
| TLA0159 | QIQLVQSGPELVKPGASVKLSCKASGYTFTSSDINWVKQRPGQGPEWIGWIYPRDGRTHYNEKFKGKATLTVDTSSSTAYMELHSLTSEDSAVYFCARYAYALNSWGQGTSVTVSS | 397 | DVVMTQTPLSLPVSLGDQASISCRSSQSIVHSNGDTYLEWYLQKPGQSPKLLIYKVSNRFSGVPDRFSGSGSGTDFTLKISRVEAEDLGVYYCFQGSHVPYTFGSGTKLEIK | 557 |
| TLA0160 | QVQLQQPGPELVKPGASVRVSCKASGYTFTRQDINWVKQRAGQGLEWIGWIYPRDGRTEYNEKFKGKVTLTVDTSSSTAYMELHSLTSEDSAVYFCATYGSSLDNWGQGATLTVSS | 398 | DVVMTQTPLSLPVSLGDQASISCRSSQSIVHSNGDTYLEWYLQKPGQSPKLLIYKVSNRFSGVPDRFSGSGSGTDFTLKISRVEAEDLGVYYCFQGSHVPYTFGGGTKLEIK | 514 |
| TLA0161 | QVQLQQSGPELVKPGASVKLSCKASGYTFTSYDINWVKQRPGQGLEWIGWIFPRDGDTKYNEKFKGKATLTVDTSSSTAFMELHSLTSEDSAVYFCARYGSTLDVWGTGTTVTVSS | 399 | DVVMTQTPLSLPVSLGDQASISCRSSQSIVHTNGDTYLDWYLQKPGQSPKLLIYKVSNRFSGVPDRFSGSGSGTDFTLKISRVEAEDLGVYYCFQGSHVPYTFGGGTKLEIK | 515 |
| TLA0162 | QIQLVQSGPELVMPGASVKLSCQASGYTFTNSDINWVKQRPGQGLEWIGWVYPGDGSTYYNEKFKGKATLTVDTSSSTAYMDLYSLTSEDSAVYFCARYAYALNSWGQGTSVTVSS | 400 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0163 | QIQLVQSGPELVKPGASVKLSCKASGYTFTNSDINWVKQRPGQGLEWIGWIYPRDGSTYYNEKFKGKATLTVDTSSTTAYMEFHSLTSEDSAVYFCARYAYALNSWGQGTSVTVSS | 401 | DVVMTQTPLSLPVSLGDQASISCRSSQSIVHDNGDTYLEWYLQKPGQSPKLLIYKVSNRFSGVPDRFSGSGSGTDFTLKINRVEAEDLGVYYCFQGSHVPYTFGGGTKLEIK | 516 |
| TLA0164 | QVQLQQSGPEVVKPGASVKLSCKASGYTFTSYDINWVKQRPGQGLEWIGWIFPRDGRTEYNEKFKDKATLTVDTSSSTAYMELHSLTSEDSAFYFCARYGSSLDYWGQGTTLTVSS | 402 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0165 | QIQLVQSGPELVKPGASVKLSCQASGYTFT<br>NSDINWVKQRPGQGLDWIGWVYPRDGST<br>YYNEKFKGKATLTVDTSSSTAYMELYSLT<br>SEDSAVYFCARYAYALNYWGQGTSVTVS<br>S | 403 | DVVMTQTPLSLPVSLGDQASISCRSS<br>QNIVHSNGNTYLEWYLQKPGQSPKL<br>LIYKVSNRFSGVPDRFSGSGSGTDFTL<br>KISRVEAEDLGVYYCFQGSHVPYTFG<br>GGTKLEIK | 517 |
| TLA0166 | QIQLVQSGPELVKPGASVKLSCKASGYTFT<br>SIDINWVKQRPGQGLEWIGWIYPRDGRTD<br>YNEKFKGKATLTVDTSSSTAYMELHSLTS<br>EDSAVYFCARYTSSLDYWGQGTTLTVSS | 404 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |
| TLA0167 | QVQLQQSGPELVKPGASVKLSCKASGYTF<br>TSIDINWVKQRPGQGLEWIGWIYPRDGRT<br>NYNEKFKGKATLTVDTSSSTAYMDLHSLT<br>SEDSAVYFCARYTSSLDYWGQGTTLTVSS | 405 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |
| TLA0168 | QVQLQQSGPELVKPGASVKLSCRASGYTF<br>TSYDINWVKQRPGQGLEWIGWNYPRDGR<br>TDYNEKFKGKATLTVDTSSNTAYMDLHSL<br>TSEDSAVYFCTRYGSTLDVWGTGTSVTVS<br>S | 406 | DVVMTQTPLSLPVSLGDQASISCRSS<br>QSIVHSNGDTYLDWFLQKPGQSPKLL<br>IYKVSNRFSGVPDRFSGSGSGTDFTL<br>KISRVEAEDLGVYYCFQGSHVPYTFG<br>GGTKLEIK | 550 |
| TLA0169 | QIQLVQSGPELVKPGASVKLSCQASGYTFT<br>NSDINWVKQRPGQGLEWIGWVYPRDGSA<br>YYNEKFKGKATLTVDTSSSTAYMELYSLT<br>SEDSAVYFCARYAYALNFWGQGTSVTVSS | 407 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLELK | 558 |
| TLA0170 | QVQLKQSGPELVKPGASVKVSCKASGYTF<br>TRQDINWVKQRPGQGLEWIGWIYPRDGRT<br>EYNEKFKGKVTLTVDTSSSTAYMELHSLT<br>SEDSAVYFCATYGSSLDNWGQGTTLTVSS | 408 | DVVMTQTPLSLPVSLADQASISCRSS<br>QSIVHDNGDTYLEWYLQKPGQSPRL<br>LIYKVSNRFSGVPDRFSGSGSGTDFTL<br>KINRVEAEDLGVYYCFQGSHVPYTF<br>GGGTKLEIK | 552 |
| TLA0171 | QVQLQQPGPELVKPGASVKLSCKASGYTF<br>TNQDINWVKQRPGQGLEWIGWIFPRDGRT<br>HYNEKFKGKATLTVDTSSSTAYMELHSLT<br>AEDSAVYFCAIYGSAMDQWGQGTSVTVS<br>S | 409 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |
| TLA0172 | EVQLQQSGPELVKPGASVKLSCKASGYTF<br>TNSDINWVKQRPGQGLEWIGWIYPRDGST<br>YYNEKFKGKATLTVDTSSTTAYMEFHSLT<br>SEDSAVYFCARYAYALNSWGQGTSVTVSS | 410 | DVVMTQTPLSLPVSLGDQASISCRSS<br>QSIVHSNGNTYLEWYLQKPGQSPKLL<br>IYKVSNRFSGVPDRFSGSGSGTDFTL<br>KISRVEAEDLGVYYCFQGSHVPYTFG<br>GGTKLEIK | 553 |
| TLA0173 | QVQLQQSGAELMKPGASVKLSCKATGYT<br>FTGYWLEWVKQRPGHGLEWIGETLPGSG<br>YNKYNEKFKGKATFTADTSSNTAHMQLSS<br>LTTEDSAIYYCARRGSNYPYWYFDVWGT<br>GTTVTVSS | 412 | DIVLTQSPASLAVSLGQRATISCRASE<br>SVDDYGISFMHWYQQKPGQPPKLLI<br>YRASNLESGIPARFSGSGSRTDFTLTI<br>DPVETDDVATYYCQQSYEDPPTFGA<br>GTKLEIK | 518 |
| TLA0174 | QVQLQQPGAELMKPGASVKLSCKATGYT<br>FTAYWLEWVKQRPGHGLEWIGEILPGSGY<br>AYYNAKFKGKATFTADISSNTAYMQLSGL<br>TTEDSAIYYCARRGSNYPYWYFDVWGTG<br>TTVTVSS | 411 | DIVLTQSPASLAVSLGQRATISCRASE<br>SVDNYGISFMHWYQQKPGQPPKLLV<br>YRASNLESGIPARFSGSGSRTDFTLTI<br>NPVETDDVATYYCQQSNKDPPTFGG<br>GTKLEIK | 519 |
| TLA0175 | QVQLQQSGAELMKPGASVKLSCKATGYT<br>FTGYWLEWVKQRPGHGLEWIGETLPGSG<br>YNKYNEKFKGKATFTADTSSNTAHMQLSS<br>LTTEDSAIYYCARRGSNYPYWYFDVWGT<br>GTTVTVSS | 412 | DIVLTQSPASLAVSLGQRATISCRASE<br>SVDNYGISFMHWYQQKPGQPPKLLI<br>YRASNLESGIPARFSGSGSRTDFTLTI<br>NPVETDDVATYYCQQSNKDPPTFGA<br>GTKLELK | 520 |
| TLA0176 | QVQLQQSGAELMKPGASVKLSCKATGYT<br>FTGYWLEWVKQRPGHGLEWIGETLPGSG<br>YNKYNEKFKGKATFTADTSSNTAHMQLSS<br>LTTEDSAIYYCARRGSNYPYWYFDVWGT<br>GTSVTVSS | 413 | DIVLTQSPASLAVSLGQRATISCRASK<br>SVSTSSYSYMHWYQQKPGQPPKLLIK<br>YASNLESGVPARFSGSGSGTDFTLNI<br>HPVEEEDAATYYCQHSREFPTFGGGT<br>KLEIK | 521 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0177 | QVQLQQSGPELVKPGASVKLSCRASGYTFTSYDINWVKQRPGQGLEWIGWNYPRDGRTDYNEKFKGKATLTVDTSSNTAYMELHSLTSEDSAVYFCTRYGSTLDVWGTGTTVTVSS | 414 | DVVMTQTPLSLPVSLGDQASISCRSSQNIVHSNGDTYLDWFLQKPGQSPKLLIYKVSNRFSGVPDRFSGSGSGTDFTLKISRVEAEDLGVYYCFQGSHVPYTFGGGTKLEIK | 538 |
| TLA0178 | QIQLVQSGPELVKPGASVKLSCRASGYTFTSYDINWVKQRPGQGLEWIGWNYPRDGRTDYNEKFKGKATLTVDTSSNTAYMELHSLTSEDSAVYFCTRYGSTLDVWGTGTTVTVSS | 415 | DVVMTQTPLSLPVSLGDQASISCRSSQSIVHSNGDTYLDWYLEKPGQSPKLLIYKVSNRFSGVPDRFSGSGSGTDFTLKISRVEAEDLGVYYCFQGSHVPYTFGGGTKLEIKR | 522 |
| TLA0179 | QVQLQQPGPELVKPGASVKLSCRASGYTFTSYDINWVKQRPGQGLEWIGWIFPRDGRTEYNAKFKGKATLTVDTSSNTAYMELHSLTSDDSAVYFCARYGSTLDVLGAGTTVTVSS | 416 | DVVMTQTPLSLPVSLGDQASISCRSSQSIVHNNGDTYLDWYLEKPGQSPKLLIYKVSNRFSGVPDRFSGSGSGTDFTLKISRVEAEDLGVYYCFQGSHVPYTFGGGTKLEIK | 533 |
| TLA0180 | EVQLQQSGPELVKPGASVKLSCRASGYTFTSYDINWVKQRPGQGLEWIGWIFPRDGRTEYNEKFKGKATLTVDTSSNTAYMELHSLTSEDSAVYFCARYGSTLDVWGTGTTVTVSS | 417 | DVVMTQTPLSLPVSLGDQASISCRSSQSIVHSNGDTYLDWFLQKPGQSPKLLIYKVSNRFSGVPDRFSGSGSGTDFTLKISRVEAEDLGVYYCFQGSHVPYTFGGGTKLELK | 529 |
| TLA0181 | QIQLVQSGPELVKPGASVKLSCRASGYTFTSYDINWVKQRPGQGLEWIGWIFPRDGRTEYNEKFKGKVTLTVDTSSNTAYMELHSLTSEDSAVYFCARYGSTLDVWGPGTTVTVSS | 418 | DVVMTQTPLSLPVSLGDQASISCRSSQSIVHNNGDTYLDWYLQKPGQSPKLLIYKVSNRFSGVPDRFSGSGSGTDFTLKISRVEAEDLGVYYCFQGSHVPYTFGGGTKLELK | 523 |
| TLA0182 | QVQLQQFGPELVKPGSSVKLSCKASGYTFTDYDVNWVKQRPGQGLEWIGWNYPRDGRTNYNEKFKGKATLTVDTSSSTAYMELHSLTSEDSAVYFCARYGSALNVWGTGTTVTVSS | 419 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLELK | 558 |
| TLA0183 | QVQLQQSGPELVKPGASVKLSCKASGYTFTDYDVNWVKQRPGQGLEWIGWNYPRDGRTNYNEKFKGKATLTVDISSSTAYMELHSLTSEDSAVYFCARYGSALNVWGTGTTVTVSS | 420 | DVVMTQTPLSLPVSLGDQASISCRSSQSIVHGNGNTYLEWYLQKPGQSPKLLIYKVSNRFSGVPDRFSGSGSGTDFTLKISRVEAEDLGVYYCFQGSHVPYTFGGGTKLEIK | 524 |
| TLA0184 | QVQLQQSGPELVKPGASVKLSCKASGYTFTDYDVNWVKQRPGQGLEWIGWNYPRDGRTNYNEKFKGKATLTVDISSSTAYMELHSLTSEDSAVYFCARYGSALNVWGTGTTVTVSS | 420 | DVVMTQTPLSLPVSLGDQASISCRSSQTIVHSNGDTYLDWYLQKPGQSPKLLISKVSNRFSGVPDRFSGSGSGTDFTLKISSVEAEDLGVYYCFQGSHVPYTFGGGTKLEIK | 531 |
| TLA0185 | QIQLVQSGPELVKPGASVKLSCQASGYTFTNSDINWVKQRPGQGLEWIGWVYPRDGSTYYNEKFKGKATLTVDTSSSTAYMELYSLTSEDSAVYFCARYAYALNSWGQGTSVTVSS | 421 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0186 | QIQLVQSGPELVKPGASVKLSCQASGYTFTNSDINWVKQRPGQGLEWIGWVYPRDGSTYYNEKFKAKATLTVDTSSSTAYMELYSLTSEDSAVYFCARYAYALNYWGQGTSVTVSS | 422 | DVVMTQTPLSLPVSLGDQASISCRSSQNIIHSNGDTYLDWFLQKPGQSPKLLIYKVSNRFSGVPDRFSGSGSGTDFTLKISRVEAEDLGVYYCFQGSHVPYTFGGGTKLEIK | 525 |
| TLA0187 | QIQLVQSGPELVKPGASVKLSCQASGYTFTNSDINWVKQRPGQGLEWIGWVYPRDGRTYYNEKFKGKATLTVDTSSSTAYMELYSLTSEDSAVYFCARYAYALNSWGQGTSVTVSS | 423 | DVVMTQTPLSLPVSLGDQASISCRSSQNIVHSNGDTYLEWYLQKPGQSPKLLIYKVSSRFSGVPDRFSGSGSGTDFTLKISRVEAEDLGIYYCFQGSHVPYTFGGGTKLEIK | 559 |
| TLA0188 | QIQLVQSGPELVKPGASVKLSCKASGYTFTNSDINWVKQRPGQGLEWIGWVYPRDGSTYYNEKFKGKATLTVDTSSSTAYMELHSLTSEDSAVYFCTRYAYALNSWGQGTSVTVSS | 424 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGRGDQAGNKT | 526 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0189 | QIQLVQSGPELVKPGASVKLSCKASGYTFTNSDINWVKQRPGQGLEWIGWIYPRDGSTYYNEKFKGKATLTVDTSSTTAYMEFHSLTSEDSAVYFCARYAYTLNSWGQGTSVTVSS | 425 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLELK | 558 5 5 8 |
| TLA0190 | EVQLQQSGAELARPGASVKMSCKASGYTFTNSDINWVKQRPGQGLEWIGWIYPRDGSTYYNEKFKGKATLTVDTSSSTAYMELHSLTSEDSAVYFCTRYAYALNSWGQGTSVTVSS | 426 | DVVMTQTPLSLPVSLGDQASISCRSSQSIVHSNGDTYLEWYLQKPGQSPKLLIYKVSNRFSGVPDRFSGSGSGTDFTLKISRVEAEDLGIYYCFQGSHVPYTFGGGTKLEIK | 527 |
| TLA0191 | QVQLQQSGPELVKPGASVKLSCKASGYTFTNSDINWVKQRPGQGLEWIGWIYPRDGSTYYNEKFKGKATLTVDTSSSTAYMELHSLTSEDSAVYFCTRYAYALNSWGQGTSVTVSS | 427 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0192 | EVQLQQSGPELVKPGASVKLSCQASGYTFTNSDINWVKQRPGQGLEWIGWVYPRDGRTYYNEKFKGKATLTVDTSSSTAYMELYSLTSEDSAVYFCARYAYALNSWGQGTSVTVSS | 428 | DVVMTQTPLSLPVSLGDQASISCRSSQNIVHSNGDTYLDWFLQKPGQSPKLLIYKVSNRFSGVPDRFSGSGSGTDFTLKISRVEAEDLGVYYCFQGSHVPYTFGGGTKLEIK | 538 |
| TLA0193 | EVQLQQSGPELVRPGASVKLSCKASGYSFTSGDINWVKQRPGQGLEWIAWIYPRDGSTEYNEKFKGKATLTVDTSSSTAYMELHSLTSEDSAVYFCARYDYAFVYWGQGTLVTVSA | 429 | DVVMTQTPLSLPVSLGNQASISCRSSQDIVHTNGDTYLDWYLQKPGQSPKLLIYKVSNRFSGVPDRFSGSGSGTDFTLKINRVEAEDLGVYYCFQGSHVPYTFGGGTKLELK | 528 |
| TLA0194 | EVQLQQSGPELVRPGTSVRLSCKTSGYTFTSRDINWVKQRPGQGLEWIAWIYPRDGSTEYNEKFKGKATLTVDTSSSTAYMELHSLTSEDSAVYFCTRYDYAFTYWGQGTLVTVSA | 430 | DVVMTQTPLSLPVSLGDQASISCRSSQSIVHSNGDTYLDWFLQKPGQSPKLLIYKVSNRFSGVPDRFSGSGSGTDFTLKISRVEAEDLGVYYCFQGSHVPYTFGGGTKLELK | 529 |
| TLA0195 | EVQLQQSGPEVVKPGASVKLSCKASGYTFTRNDINWVKQRPGQGLEWIGWIYPRDGSSKNNEKFKGKATLTVDTSSSTAYMELHSLTSEDSAVYFCARYDYAFVYWGQGTTVTVSS | 431 | DVVMTQTPLYLPVSLGDQASISCRSSQSIVHSNGDTYLDWFLQKPGQSPKLLIYKVSNRFSGVPDRFSGSGSGTDFTLKISRVEAEDLGVYYCFQGSHVPYTFGGGTKLELK | 530 |
| TLA0196 | EVQLQQSGPELVKPGASVKLSCKASGYTFTSYDINWVKQRPGQGLEWIGWIYPRDGRTKYSEKFKGKATLTVDTSSSTAYMELHSLTSEDSAVYFCARYGASMDYWGQGTSVTVSS | 432 | DVVMTQTPLSLPVSLGDQASISCRSSQTIVHSNGDTYLDWYLQKPGQSPKLLISKVSNRFSGVPDRFSGSGSGTDFTLKISSVEAEDLGVYYCFQGSHVPYTFGGGTKLEIK | 531 |
| TLA0197 | EVQLQQSGPELVKPGASVKLSCKASGYTFTSYDINWVKQSPGQGPEWIGWVYPRDGRTQYNEKFKGKATLTVDTSSSTAYMELHSLTSEDSAVYFCARYGASMDYWGQGTSVTVSS | 433 | DVVMTQTPLSLPVSLADQASISCRSSQSIVHDNGDTYLEWYLQKPGQSPKLLIYKVSNRFSGVPDRFSGSGSGTDFTLKISRVEAEDLGVYYCFQGSHVPYTFGGGTKLEIK | 532 |
| TLA0198 | EVQLQQSGPELAKPGASVKLSCKASGYTFTSYDINWVKQRPGQGLEWIGWIYPRDGNTNYNEKFKGKATLTVDTSSNTASMELHSLTSEDSAVYFCARYSAAMDYWGQGTSVTVSS | 434 | DVVMTQTPLSLPVSLGDQASISCRSSQNIVHSNGDTYLDWFLQKPGQSPKLLIYKVSNRFSGVPDRFSGSGSGTDFTLKISRVEAEDLGVYYCFQGSHVPYTFGGGTKLELK | 551 |
| TLA0199 | QVQLQQPGPELVKPGASVKLSCKASGYTSTSYDINWVKQRPGQGLEWIGWIYPRDGRTNYNEKFKGKATLTVDTSSSTAFMELHSLTSEDSAVYFCARYSAAMDYWGQGTSVTVSS | 435 | DVVMTQTPLSLPVSLGDQASISCRSSQSIVHNNGDTYLDWYLEKPGQSPKLLIYKVSNRFSGVPDRFSGSGSGTDFTLKISRVEAEDLGVYYCFQGSHVPYTFGGGTKLEIK | 533 |
| TLA0200 | QVQLQQSGPELVKPGASVKLSCKASGYTFTSYDINWVKQRPGQGLEWIGWIFPRDGRTNYNEKFKDKATLTVDTSSSTAFMELHRLTSEDSAVYFCARYSAAMDYWGQGTSVTVSS | 436 | DVVMTQTPLSLPVSLGDQASISCRSSQNIVHNNGDTYLDWFLQKPGQSPKLLIYKVSNRFSGVPDRFSGSGSGTDFTLKISRVEAEDLGVYYCFQGSHVPYTFGGGTKLELK | 534 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0201 | EVQLQQSGAELGKPGASVKLSCKASGYTFTNYDINWMKQRPGQGLEWIGWNYPRDGRTKYNEKFKGKATLTVDTSSSTAYMELHSLTSEDSAVYFCARYGYAMDYWGQGTSVTVSS | 437 | DVVMTQTPLSLPVSLGDQASISCKSSQSIVHSNGNTYLEWYLQKPGQSPKLLIYKVSNRFSGVPDRFSGSGSGTDFTLKISRVEAEDLGVYYCFQGSHVPYTFGGGTKLEIK | 535 |
| TLA0202 | QVQLQQSGPDLVKPGASVKLSCKASGYIFASYDLNWVKQRPGQGLEWIGWIYPRDGRTDYNEKFKGKATLTVDTSSSTAYMELHSLTSEDSAVYFCARYGYALDYWGQGTSVTVSS | 438 | DVVMTQTPLSLPVSLGDQASISCRSSQNIVHSNGDTYLEWYLQKPGQSPKLLIYKVSNRFSGVPDRFSGSGSGTDFTLKISRVEAEDLGVYYCFQGSYVPYTFGGGTKLEIK | 536 |
| TLA0203 | QIQLVQSGPELVKPGASVKVSCKASGYTFTRQDINWVKQRPGQGLEWIGWIYPRDGRTEYNEKFKGKATLTVDTSSSTAFMELHSLTSEDSAVYFCARYSAAMDYWGQGTSVTVSS | 439 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0204 | QIQLVQSGPELVKPGASVKLSCKASGYTFTNSDINWVKQRPGQGLEWIGWNYPRDGRTKYNEKFKGKATFTVDTSSSTAYMDLQSLTSEDSAVYFCTRYGSAMDYWGQGTSVTVSS | 440 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLELK | 558 |
| TLA0205 | EVQLQQSGPELVKPGASVKLSCKASGYTFTNQDINWVKQRPGQGLEWIGWIFPRDGRTHYNENFKGKATLTVDTSSSTAYMELHSLTAEDSAVYFCAIYGIALDHWGQGTSVTVSS | 441 | DVVMTQTPLSLPVSLGDQASISCRSSQNIVHSNGDTYLDWFLQKPGQSPKLLIYKVSNRFSGVPDRFSGSGSGTDFTLKISRVEAEDLGVYYCFQGSHVPYTFGGGTKLELK | 551 |
| TLA0206 | QVQLQQSGPELVKPGASVKLSCKASGYTFTNQDINWVKQRPGQGLEWIGWIFPRDGRTHYNENFKGKATLTVDTSSNTAYMELHSLTAEDSAVYFCAIYGIALDHWGQGTSVTVSS | 442 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0207 | QVQLQQSGPELVKPGASVKLSCKASGYTFTNQDINWVKQRPGQGLEWIGWIFPRDGRTHYNENFKGKATLTVDTSSSTAYMELHSLTAEDSAVYFCAIYGIALDHWGQGTSVTVSS | 443 | DVVMTQTPLSLPVSLGDQASISCRSSQNIVHSNGDTYLEWYLQKPGQSPKLLIYKVSNRFSGVPDRFSGSGSGTDFTLKISRVEAEDLGVYYCFQGSHVPYTFGGGTKLEIK | 537 |
| TLA0208 | QVQLQQSGPELVKPGASVKLSCKASGYTFTNQDINWVKQRPGQGLEWIGWIFPRDGRTHYNENFKGKATLTVDTSSSTAYMELHSLTAEDSAVYFCAIYGAAMDHWGQGTSVTVSS | 444 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK | 553 |
| TLA0209 | QVQLQQSGPELVKPGTSVKLSCKASGYTFTNQDINWVKQRPGQGLEWIGWIFPRDGRTHYNENFKGKATLTVDTSSSTAYMELHSLTAEDSAVYFCSIYGIAMDHWGQGTSVTVSS | 445 | DVVMTQTPLSLPVSLGDQASISCRSSQNIVHSNGDTYLDWFLQKPGQSPKLLIYKVSNRFSGVPDRFSGSGSGTDFTLKISRVEAEDLGVYYCFQGSHVPYTFGGGTKLEIK | 538 |
| TLA0210 | QVQLQQPGPELVKPGASVKLSCKASGYTFTNQDINWVKQRPGQGLEWIGWIFPRDGRTHNNENFKGKATLTVDTSSSTAYMELHSLTAEDSAVYFCAIYGFAMDHWGQGTSVTVSS | 446 | DVVMTQTPLSLPVSLGDQASISCRSSQSIVHSNGDTYLDWFLQKPGQSPKLLIYKVSNRFSGVPDRFSGSGSGTDFTLKISRVESEDLGVYYCFQGSHDPYTFGGGTKLEIK | 539 |
| TLA0211 | QVQLQQSGPELVKPGASVKLSCKASGYTFTNQDINWVKQRPGQGLEWIGWIFPRDGRTHYNENFKGKATLTVDTSSSTAYMELHSLTAEDSAVYFCAIYGFAMDHWGQGTSVTVSS | 447 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLELK | 558 |
| TLA0212 | QVQLQQPGPELVKPGASVKLSCKASGYTFTNQDINWVKQRPGQGLEWIGWIFPRDGRTHYNENFKGKATLTVDTSSSTAYMELHSLTAEDSAVYFCAIYGAAMDDWGQGTSVTVSS | 448 | DVVMTQTPLSLPVSLGDQASISCRSSQSIVHSNGNTYLEWYLQKPGQSPKLLIYKVSDRFSGVPDRFSGSGSGTDFTLKISRVEAEDLGVYYCFQGSHVPYTFGGGTKLEIK | 540 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0213 | QVQLQQPGPELVKPGASVKLSCKASGYTF TNQDINWVKQRPGQGLEWIGWIFPRDGRT HYNENFKGKATLTVDTSSSTAFMELHSLT AEDSAVYFCAIYGIALDHWGQGTSVTVSS | 449 | DVVMTQTPLSLPVSLGHQASISCRSS QSIVHSNGNTYLEWYLQKPGQSPKLL IYKVSNRFSGVPDRFSGSGSGTDFTL KISRVEAEDLGVYYCFQGSHVPYTFG GGTKLELK | 541 |
| TLA0213 | EVQLQQSGPELVKPGASVKLSCKASGYTF TNQDINWVKQRPGQGLEWIGWIFPRDGRT HYNENFKGKATLTVDTSSSTAYMELHSLT AEDSAVYFCAIYGFAMDHWGQGTSVTVS S | 450 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPYTFG GGTKLEIK | 553 |
| TLA0214 | EVQLQQSGPELVKPGASVKLSCKASGYTF TNQDINWVKQRPGQGLEWIGWNFPRDGR THYNENFKGKATLTVDTSSSTAYMELHSL TAEDSAVFFCAIYGFALDHWGQGTSVTVS S | 451 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPYTFG GGTKLELK | 558 |
| TLA0216 | QVQLQQSGPELVKPGASVKLSCKASGYTF TNQDINWVKQRPGQGLEWIGWIFPRDGRT HYNENFKGKATLTVDTSSSTAYMELHSLT AEDSAVYFCALYGFAMDQWGQGTSVTVS S | 452 | DVVMTQTPLSLPVSLADQASISCRSS QSIVHDNGDTYLEWYLQKPGQSPKL LIYKVSNRFSGVPDRFSGSGSGTDFTL KISRVEAEDLGVYYCFQGSHVPYTFG WRDQAGNKT | 542 |
| TLA0217 | EVQLQQSGPELVKPGASVKLSCKASGYTF TNQDINWVKQRPGQGLEWIGWIFPRDGRT HYNEKFKGKATLTVDTSSSTAYMELHSLT AEDSAVYFCAIYGSAMDQWGQGTSVTVS S | 453 | DVVMTQTPLSLPVSLGDQASISCRSS QSIVHSNGNTYLEWYLQKPGQSPKLL IYKASNRFSGVPDRFSGSGSGTDFTLR ISSVEAEDLGVYYCFQGSHVPYTFGG GTKLEIK | 513 |
| TLA0218 | EVQLQQSGPELVKPGTSVKIPCKTSGYTFT DYNINWVKQSHGKSLEWIGDINPDSGGTV YNQRFKDKATLTVDKSSSTAYMELRSLTS GDTAVYYCARWGYYDGRGFDYWGQGTT LTVSS | 454 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPLTFG AGTKLELK | 544 |
| TLA0219 | EVQLQQSGAELVRPGASVTLSCKASGYTF TDYEIHWVKQIPVHGLEWIGVFDPETGGA AYNQKFKGKAILTADKSSSTAYMELRSLT SEDSAVYYCTTPWLNYFEYWGQGTTLTVS S | 455 | DVVMTQTPLSLPVSLGDQASISCRSS QSLVHSNGNTYLHWYLQKPGQSPKL LIYKVSNRFSGVPDRFSGSGSGTDFTL KISRVEAEDLGVYFCSQSTHVPFTFGS GTKLEIK | 545 |
| TLA0220 | QVQLQQSVAELVRPGASVKLSCTASGFNIE DTYMHWVKQRPEQGLEWIGRVDPASGNT KYGPKFQGKATITADTSSNTAYLQLSSLSS ADTAIYYCSTWGLFDYWGQGTTLTVSS | 456 | EIVLTQSPALMSASPGEKVTITCSASS SVSYMHWFQQKPGTSPKLWIYSTSN LASGVPARFSGSGSGTSYSLTISRMEA EDAATYYCQQRSSYPFTFGSGTKLEI K | 546 |
| TLA0221 | QVQLQQPGPELVKPGASVKLSCKASGYTF TSIDINWVKQRPGQGLEWIGWIYPRDGRT HYNEKFKGKATLTVDTSSSTAYMELHSLT SEDSAVYFCARYTSSLDYWGQGTTLTVSS | 457 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPYTFG GGTKLEIKR | 547 |
| TLA0222 | QVQLQQSGPELVKPGASVKLSCKASGYTF TSIDINWVKQRPGQGLEWIGWIYPRDGRT DYNEKFKGKATLTVDTSSSTAYMELHSLT SEDSAVYFCARYGSSLDYWGQGTTLTVSS | 458 | DVVMTQTPLSLPVSLGDQASISCRSS QSIVHSNGDTYLDWFLQKPGQSPKLL IYKVSNRFSGVPDRFSGSGSGTDFTL KISRVEAEDLGVYYCFQGSHVPYTFG GGTKLEIK | 550 |
| TLA0223 | QVQLQQSGPELVKPGTSVRLSCKASGYTF TNSDINWVKQRPGQGLEWIGWIYPRDGRT DYNEKFKGKATLTVDTSSSTAYMELHSLT SEDSAVYFCARYGSSLYWGQGTTLTVSS | 459 | DVVMTQTPLSLPVSLGDQASISCRSS QNIVHSNGDTYLDWYLQKPGQSPKL LISKVSNRFSGVPDRFSGSGSGTDFTL KISRVEAEDLGVYYCFQGSHVPYTFG GGTKLEIK | 548 |
| TLA0224 | EVQLQQSGPELVKPGASVKLSCKASGYTF TSSDINWVKQRPGQGPEWIGWIYPRDGRT HYNEKFKGKATLTVDTSSSTAYMELHSLT SEDSAVYFCAPYGSSLAYWGQGTTLTVSS | 460 | DVVMTQTPLSLPVSLGDQASISCRSS QNIVHSNGDTYLDWFLQKPGQSPKL LISKVSNRFSGVPDRFSGSGSGTDFTL KISRVEAEDLGVYYCFQGSHVPYTFG GGTKLEIK | 549 |

TABLE 2-continued

Amino acid sequences of VH and VL of anti-TL1A antibodies screened by Single B and libraries

| Antibody NO. | Amino acid sequence (VH) | SEQ ID | Amino acid sequence (VL) | SEQ ID |
|---|---|---|---|---|
| TLA0225 | QIQLVQSGPELVKPGASVKLSCKASGYTFT SSDINWVKQRPGQGLEWIGWIYPRDGSTH YNENFKGKATLTVDTSSSTAYMELHSLTS EDSAVYFCAPYGSSLAYWGQGTTLTVSS | 461 | DVVMTQTPLSLPVSLGDQASISCRSS QSIVHSNGDTYLDWFLQKPGQSPKLL IYKVSNRFSGVPDRFSGSGSGTDFTL KISRVEAEDLGVYYCFQGSHVPYTFG GGTKLEIK | 550 |
| TLA0226 | QVQLKESGPEVVKPGASVKLSCKASGYTF TSYDINWVKQRPGQGLEWIGWIYPRDGRT EYNEKFKDKATLTVDTSSSTAYMELHSLT SEDSAVYFCARYGSSLDYWGQGTTLTVSS | 462 | DVVMTQTPLSLPVSLGDQASISCRSS QNIVHSNGDTYLDWFLQKPGQSPKL LIYKVSNRFSGVPDRFSGSGSGTDFTL KISRVEAEDLGVYYCFQGSHVPYTFG GGTKLELK | 551 |
| TLA0227 | QIQLVQSGPELVKPGASVKVSCKASGYTFT RQDINWVKQRPGQGLEWIGWIYPRDGSTK YNEKFKGKVTLTVDTSSSTAYMELHSLTS EDSAVYFCATYGSSLDNWGQGTTLTVSS | 463 | DVVMTQTPLSLPVSLADQASISCRSS QSIVHDNGDTYLEWYLQKPGQSPRL LIYKVSNRFSGVPDRFSGSGSGTDFTL KINRVEAEDLGVYYCFQGSHVPYTF GGGTKLEIK | 552 |
| TLA0228 | QVQLQQSGPELVKPGASVKVSCKASGYTF TRQDINWVKQRPGQGLEWIGWIYPRDGST KYNEKFKGKVTLTVDTSSSTAYMELHSLT SEDSAVYFCATYGSSLDNWGQGTTLTVSS | 464 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPYTFG GGTKLEIK | 553 |
| TLA0229 | QIQLVQSGPELVKPGASVKVSCKASGYTFT RQDINWVKQRPGQGLEWIGWIYPRDGRTE YNEKFKGKVTLTVDTSSSTAYMELHSLTP EDSAVYFCATYGSSLDNWGQGTTLTVSS | 465 | DVVMTQTPLSLPVSLGDQASISCRSS QSIVHNNGDTYLEWYLQKPGQSPKL LIYKVSNRFSGVPDRFSGSGSGTDFTL KISRVEAEDLGVYYCFQGSHVPYTFG GGTKLEIK | 554 |
| TLA0230 | QVQLKESGPELVKPGASVKVSCKASGYTF TRQDINWVKQRPGQGLEWIGWIYPRDGRT EYNEKFKGKVTLTVDTSSSTAYMELHSLT SEDSAVYFCATYGSSLDNWGQGTTLTVSS | 466 | DVVMTQTPLSLPVSLGDQASISCRSS QNIVHTNGDTYLDWYLQKPGQSPKL LIYKVSNRFSGVPDRFSGSGSGTDFTL KISRVEAEDLGVYYCFQGSHVPYTFG GGTKLELK | 555 |
| TLA0231 | QVQLQQSGAELAKPGASVKLSCKASGYTF TRQDINWVKQRPGQGLEWIGWIYPRDGRT EYNEKFKGKVTLTVDTSSSTAYMELHSLT SEDSAVYFCATYGSSLDNWGQGTTLTVSS | 467 | DVVMTQTPLSLPVSLGDQASISCRSS QTIVHSNGNTYLDWYLQKPGHSPQL LIYKVSNRFSGVPDRFSGSGSGTDFTL KISRVEAEDLGVYYCFQGSHVPYTFG GGTKLEIK | 556 |
| TLA0232 | QVQLQQPGPELVKPGASVKVSCKASGYTF TRQDINWVKQRPGQGLEWIGWIYPRDGRT EYNEKFKGKVTLTVDTSSNTAYMELHSLT SEDSAVYFCATYGSSLDNWGQGTTLTVSS | 468 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPYTFG SGTKLEIK | 557 |
| TLA0233 | QVQLQQSGPELVKPGASVKVSCKASGYTF TRQDINWVKQRPGQGLEWIGWIYPRDGRT EYNEKFKGKVTLTVDTSSSTAYMELHSLT SEDSAVYFCATYGSSLDNWGQGTTLTVSS | 469 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPYTFG GGTKLELK | 558 |
| TLA0234 | EVQLQQSGPELVKPGASVKVSCKASGYTF TRQDINWAKQRPGQGLEWIGWIYPRDGRT EYNEKFKGKVTLTVDTSSSTAYMELHSLT PEDSAVYFCATYGSSLDNWGQGTTLTVSS | 470 | DVVMTQTPLSLPVSLGDQASISCRSS QSIVHSNGNTYLEWYLQKPGQSPKLL IYKVSNRFSGVPDRFSGSGSGTDFTL KISRVEAEDLGVYYCFQGSHVPYTFG GGTKLELK | 558 |
| TLA0235 | EVQLQQSGPELVKPGASVKVSCKASGYTF TRQDINWVKQRPGQGLEWIGWIYPRDGRT EYNEKFKGKVTLTVDTSSSTAYMELHSLT SEDSAVYFCATYGSSLDNWGQGTTLTVSS | 471 | DVVMTQTPLSLPVSLGDQASISCRSS QNIVHSNGDTYLEWYLQKPGQSPKL LIYKVSSRFSGVPDRFSGSGSGTDFTL KISRVEAEDLGIYYCFQGSHVPYTFG GGTKLEIK | 559 |
| TLA0236 | EVQLQQSVAELVRPGASVKLSCTASGFNIE NTYIHWVKQRPEQGLEWIGRIDPASGNTK YAPKFQGKATITADTSSNTAYLQLSSLTSE DTAIYYCASTGPDYWGQGTTLTVSS | 472 | EILLTQSPAIIAASPGEKVTITCSASSS VSYMNWYQQKPGSSPKIWIYGISNLA SGVPARFSGSGSGTSFSFTINSMEAED VATYYCQQRSSYPFTFGSGTKLEIK | 560 |

TABLE 2-continued

Amino acid sequences of VH and VL of anti-TL1A antibodies screened by Single B and libraries

| Antibody NQ. | Amino acid sequence (VH) | SEQ ID | Amino acid sequence (VL) | SEQ ID |
|---|---|---|---|---|
| TLA0237 | QIQLVQSGPELKKPGETVEISCKASGYTFTTHGMNWVKQAPGKGLKWMGWINTFSGVPTYADDFRGRFDFFLATSASTAYLQINNLKNEDTATYFCARDYGTAYAMDSWGQGTSVTVSS | 473 | DVLMTQAPLSLPVSLGDQASISCRSNQTIVHSNGNTYLEWYLQKPGQSPKLLIYKVSNRFSGVPDRFSGSGSGTDFTLKISGVEAEDLGVYYCFQGSHVPLTFGAGTKLELN | 561 |
| TLA0238 | EVKVEESGGGLVQPGGSMKLSCIASGFTFSNYWMNWVRQSPEKGLEWVAQIRLKSDNYATHYAESVKGNFTISRDDSKSSVYLQMNNLRAEDTGIYYCTPLLLRYRDYWGQGTTLTVSS | 474 | ENVLTQSPAIMSASPGEKVTMTCSASSSVSYMHWYQQKSSTSPKLWIYDTSNLASGVPGRFSGSGSGNSYSLTISSMEAEDVATYYCFQENGHPFTFGGGTKLEMK | 562 |
| TLA0239 | EVQLQQSGPELVKPGASVKISCKASGYTFTDYYMNWVKQSHGKSLEWIGDVNPNSGGTSQNQKFKGKATLTVDKSSTTAYMELRSLTSEDSAVYHCARGSNYVGGFTYWGQGTLVAVSA | 475 | DILMTQSPSSMSVSLGDTVSITCHASQDIFSYIGWLQQKPGKSFKGLIHHGTNLEDGVPSRFRGNGSGADYSLTISSLESEDFADYYCVQYAQFPYTFGGGTKLEIK | 563 |
| TLA0240 | QVQLQQPGAELVKPGASVKLSCKASGYTFSNDWMHWVKQRPGRGLEWIGRIDPDSGGTKYNEKFKNKATLTVDKPSSTVYMQLSSLTSEDSAVYYCARSEGYYGSRSYFDYWGQGTTLTVSS | 476 | DIVMTQSPSSLRVSAGEKVTMSCKSSQSLLNSGNQKNYLAWYQQKPGQPPKLLIYGASTRESGVPDRFTGSGSGTDFTLTISSVQAEDLAVYYCQNDHSYPYTFGGGTKLEIK | 564 |
| TLA0241 | EFQLQQSGPELVKPGASVRISCKASGYTFTDYYLNWVKQSRGESLEWIGDINPNNGRTTYNQKFTGKATWTVDKSSSTVYMELRSLTSDDSAVYYCAREGGYGWYFDVWGTGTTVTVSS | 477 | EIVLTQSPTTMAASPGEKITITCSTSSSIISNYSHWYQQKPGFSPKLLIYKTSNLPSGVPARFSGSGSGTSYSLTIGTMEAEDAATYYCQQGSDMPITFGAGTKLELK | 565 |

The single underlined line represents the sequence of CDR1, CDR2, and CDR3. CDRs are defined by Kabat.

Example 4 Humanized Design and Identification of Anti-TL1A Murine Monoclonal Antibody 4.1 TLA0015 humanized design: according to the VH and VL amino acid sequences of TLA0015 murine monoclonal antibodies, the IGHV3-23/IGHV3-39/IGKV1-39 Germline sequences which has the highest homology in the human germline database were selected as templates, and the CDR regions of murine antibodies were transplanted to the corresponding humanized templates to obtain humanized sequences, and the heavy and light chain pairs were paired to obtain TLA0015 humanized antibody sequence pairs, the specific sequences are shown in Table 3 below

TABLE 3

TLA0015 humanized antibody amino acid sequences

| TLA0015 humanized antibody sequence | Amino acid sequence (VH) | SEQ ID NO | Amino acid sequence (VL) | SEQ ID NO |
|---|---|---|---|---|
| TLA0015 | QIQLKESGPGLVAPSQSLSITCTVSGFSLSSYGVDWVRQSPGKGLEWLGVIWGFGGTNYNSALKSRLSISKDNSKSQVFLKMNSLQSDDSAIYYCASGNFDAMDYWGQGTSVTVSS | 62 | DIQMTQTTSSLSASLGDRVTISCRASQDISNYLNWYQQKPDGTVKLLIYYTSRLHSGVPSRESGSGSGTDYSLTISNLEQEDIATYFCQQGNTLPFTFGSGTKLEIK | 102 |
| TLA0015-1 | EIQLLESGGGLVQPGGSLRLSCAVSGFSLSSYGVDWVRQAPGKGLEWVGVIWGFGGTNYNSALKSRLTISRDNSKNTLYLQMNSLRAEDTAVYYCASGNFDAMDYWGQGTLVTVSS | 63 | DIQMTQSPSSLSASVGDRVTITCRASQDISNYLNWYQQKPGKVVKLLIYYTSRLHSGVPSRFSGSGSGTDYTLTISSLQPEDVATYFCQQGNTLPFTFGPGTKLEIK | 103 |
| TLA0015-2 | EIQLLESGGGLVQPGGSLRLSCAVSGFSLSSYGVDWVRQAPGKGLEWVGVIWGFGGTNYNSALKSRLTISRDNSKNTLYLQMNSLRAEDTAVYYCASGNFDAMDYWGQGTLVTVSS | 63 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |

TABLE 3-continued

TLA0015 humanized antibody amino acid sequences

| TLA0015 humanized antibody sequence | Amino acid sequence (VH) | SEQ ID NO | Amino acid sequence (VL) | SEQ ID NO |
| --- | --- | --- | --- | --- |
| TLA0015-3 | EIQLLESGGGLVQPGGSLRISCAVSGFS<br>LSSYGVDWVRQAPGKGLEWLGVIWGF<br>GGTNYNSALKSRLTISKDNSKNTVYLQ<br>MNSLRAEDTAVYYCASGNFDAMDYW<br>GQGTLVTVSS | 64 | DIQMTQSPSSLSASVGDRVTITCRA<br>SQDISNYLNWYQQKPGKVVKLLI<br>YYTSRLHSGVPSRFSGSGSGTDYT<br>LTISSLQPEDVATYFCQQGNTLPFT<br>FGPGTKLEIK | 103 |
| TLA0015-4 | EIQLLESGGGLVQPGGSLRISCAVSGFS<br>LSSYGVDWVRQAPGKGLEWLGVIWGF<br>GGTNYNSALKSRLTISKDNSKNTVYLQ<br>MNSLRAEDTAVYYCASGNFDAMDYW<br>GQGTLVTVSS | 64 | DIQMTQSPSSLSASVGDRVTITCRA<br>SQDISNYLNWYQQKPGKAVKLLI<br>YYTSRLHSGVPSRFSGSGSGTDYT<br>LTISSLQPEDFATYFCQQGNTLPFT<br>FGQGTKLEIK | 106 |
| TLA0015-5 | EIQLVESGGGLVQPGGSLRISCAVSGFS<br>LSSYGVDWVRQSPGKGLEWLGVIWGF<br>GGTNYNSALKSRLTISKDNSKNTVYLQ<br>MNSLRAEDTAVYYCASGNFDAMDYW<br>GQGTLVTVSS | 65 | DIQMTQSPSSLSASVGDRVTITCRA<br>SQDISNYLNWYQQKPGKVVKLLI<br>YYTSRLHSGVPSRFSGSGSGTDYT<br>LTISSLQPEDVATYFCQQGNTLPFT<br>FGPGTKLEIK | 103 |
| TLA0015-6 | EIQLVESGGGLVQPGGSLRISCAVSGFS<br>LSSYGVDWVRQSPGKGLEWLGVIWGF<br>GGTNYNSALKSRLTISKDNSKNTVYLQ<br>MNSLRAEDTAVYYCASGNFDAMDYW<br>GQGTLVTVSS | 65 | DIQMTQSPSSLSASVGDRVTITCRA<br>SQDISNYLNWYQQKPGKAVKLLI<br>YYTSRLHSGVPSRFSGSGSGTDYT<br>LTISSLQPEDFATYFCQQGNTLPFT<br>FGQGTKLEIK | 106 |
| TLA0015-7 | EVQLLESGGGLVQPGGSLRLSCAVSGF<br>SLSSYGVDWVRQAPGKGLEWLGVIWG<br>FGGTNYNSALKSRFTISRDNSKNTVYL<br>QMNSLRAEDTAVYYCASGNFDAMDY<br>WGQGTLVTVSS | 66 | DIQMTQSPSSLSASVGDRVTITCRA<br>SQDISNYLNWYQQKPGKAVKLLI<br>YYTSRLHSGVPSRFSGSGSGTDYT<br>LTISSLQPEDFATYFCQQGNTLPFT<br>FGQGTKLEIK | 106 |
| TLA0015-8 | EVQLLESGGGLVQPGGSLRLSCAVSGF<br>SLSSYGVDWVRQAPGKGLEWLGVIWG<br>FGGTNYNSALKSRLTISRDNSKNTVYL<br>QMNSLRAEDTAVYYCASGNFDAMDY<br>WGQGTLVTVSS | 67 | DIQMTQSPSSLSASVGDRVTITCRA<br>SQDISNYLNWYQQKPGKAVKLLI<br>YYTSRLHSGVPSRFSGSGSGTDYT<br>LTISSLQPEDFATYFCQQGNTLPFT<br>FGQGTKLEIK | 106 |
| TLA0015-9 | EVQLLESGGGLVQPGGSLRLSCAVSGF<br>SLSSYGVDWVRQAPGKGLEWLGVIWG<br>FGGTNYNSALKSRLTISKDNSKNTVYL<br>QMNSLRAEDTAVYYCASGNFDAMDY<br>WGQGTLVTVSS | 68 | DIQMTQSPSSLSASVGDRVTITCRA<br>SQDISNYLNWYQQKPGKAVKLLI<br>YYTSRLHSGVPSRFSGSGSGTDYT<br>LTISSLQPEDFATYFCQQGNTLPFT<br>FGQGTKLEIK | 106 |
| TLA0015-10 | EIQLVESGGGLIQPGGSLRLSCAVSGFS<br>LSSYGVDWVRQAPGKGLEWLGVIWGF<br>GGTNYNSALKSRLTISRDNSKNTVYLQ<br>MNSLRAEDTAVYYCARGNFDAMDYW<br>GQGTLVTVSS | 69 | DIQMTQSPSSLSASVGDRVTITCRA<br>SQDISNYLNWYQQKPGKAVKLLI<br>YYTSRLHSGVPSRFSGSGSGTDYT<br>LTISSLQPEDFATYFCQQGNTLPFT<br>FGQGTKLEIK | 106 |
| TLA0015-11 | EIQLVESGGGLIQPGGSLRISCAVSGESL<br>SSYGVDWVRQAPGKGLEWLGVIWGFG<br>GTNYNSALKSRLTISKDNSKNTVYLQM<br>NSLRAEDTAVYYCASGNFDAMDYWG<br>QGTLVTVSS | 70 | DIQMTQSPSSLSASVGDRVTITCRA<br>SQDISNYLNWYQQKPGKAVKLLI<br>YYTSRLHSGVPSRFSGSGSGTDYT<br>LTISSLQPEDFATYFCQQGNTLPFT<br>FGQGTKLEIK | 106 |
| TLA0015-12 | EIQLVESGGGLIQPGGSLRISCAVSGESL<br>SSYGVDWVRQAPGKGLEWLGVIWGFG<br>GTNYNSALKSRLTISKDNSKNTVYLQM<br>NSLRAEDTAVYYCASGNFDAMDYWG<br>QGTLVTVSS | 70 | DIQMTQSPSSLSASVGDRVTITCRA<br>SQDISNYLNWYQQKPGKAPKLLIY<br>YTSRLHSGVPSRFSGSGSGTDFTLT<br>ISSLQPEDFATYYCQQGNTLPFTFG<br>QGTKLEIK | 104 |
| TLA0015-13 | EIQLVESGGGLIQPGGSLRISCAVSGESL<br>SSYGVDWVRQAPGKGLEWLGVIWGFG<br>GTNYNSALKSRLTISKDNSKNTVYLQM<br>NSLRAEDTAVYYCASGNFDAMDYWG<br>QGTLVTVSS | 70 | DIQMTQSPSSLSASVGDRVTITCRA<br>SQDISNYLNWYQQKPGKAPKLLIY<br>YTSRLHSGVPSRESGSGSGTDYTL<br>TISSLQPEDFATYFCQQGNTLPFTF<br>GQGTKLEIK | 105 |

TABLE 3-continued

TLA0015 humanized antibody amino acid sequences

| TLA0015 humanized antibody sequence | Amino acid sequence (VH) | SEQ ID NO | Amino acid sequence (VL) | SEQ ID NO |
|---|---|---|---|---|
| TLA0015-14 | EVQLLESGGGLVQPGGSLRLSCAVSGFSLSSYGVDWVRQAPGKGLEWLGVIWGFGGTNYNSALKSRFTISRDNSKNTVYLQMNSLRAEDTAVYYCASGNFDAMDYWGQGTLVTVSS | 66 | DIQMTQSPSSLSASVGDRVTITCRASQDISNYLNWYQQKPGKAPKLLIYYTSRLHSGVPSRFSGSGSGTDFTLTISSLQPEDFATYYCQQGNTLPFTFGQGTKLEIK | 104 |
| TLA0015-15 | EVQLLESGGGLVQPGGSLRLSCAVSGFSLSSYGVDWVRQAPGKGLEWLGVIWGFGGTNYNSALKSRLTISRDNSKNTVYLQMNSLRAEDTAVYYCASGNFDAMDYWGQGTLVTVSS | 67 | DIQMTQSPSSLSASVGDRVTITCRASQDISNYLNWYQQKPGKAPKLLIYYTSRLHSGVPSRFSGSGSGTDFTLTISSLQPEDFATYYCQQGNTLPFTFGQGTKLEIK | 104 |
| TLA0015-16 | EVQLLESGGGLVQPGGSLRLSCAVSGFSLSSYGVDWVRQAPGKGLEWLGVIWGFGGTNYNSALKSRFTISRDNSKNTVYLQMNSLRAEDTAVYYCASGNFDAMDYWGQGTLVTVSS | 66 | DIQMTQSPSSLSASVGDRVTITCRASQDISNYLNWYQQKPGKAPKLLIYYTSRLHSGVPSRFSGSGSGTDYTLTISSLQPEDFATYFCQQGNTLPFTFGQGTKLEIK | 105 |

Where single underline represents the sequence of FR1, FR2, FR3, FR4, and the rest portion is CDR1, CDR2, CDR3 in that order. CDRs are defined by Kabat.

TLA0015-11 was mutated to improve the active function of TLA0015-11-related antibodies, and 31 antibodies were designed and obtained, and the specific amino acid sequences are shown in Table 4.

TABLE 4

| Antibody NO. | VH | SEQ ID NO | VL | SEQ ID NO |
|---|---|---|---|---|
| TLa0015-17 | EIQLVESGGGLIQPGGSLRISCAVSGFSLSSYGVDWVRQAPGKGLEWLGVIWGFGGTNYNSALKSRLTIS**R**DNSKNTVYLQMNSLRAEDTAVYYCASGNFDAMDYWGQGTLVTVSS | 71 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLa0015-18 | EIQLVESGGGLIQPGGSLRISCAVSGFSLSSYGVDWVRQAPGKGLEWLGVIWGFGGTNYNSALKSRLTIS**V**DNSKNTVYLQMNSLRAEDTAVYYCASGNFDAMDYWGQGTLVTVSS | 72 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLa0015-19 | EIQLVESGGGLIQPGGSLRISCAVSGFSLSSYGVDWVRQAPGKGLEWLGVIWGFGGTNY**Q**SALKSRLTISKDNSKNTVYLQMNSLRAEDTAVYYCASGNFDAMDYWGQGTLVTVSS | 73 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLa0015-20 | EIQLVESGGGLIQPGGSLRISCAVSGFSLSSYGVDWVRQAPGKGLEWLGVIWGFGGTNYN**A**ALKSRLTISKDNSKNTVYLQMNSLRAEDTAVYYCASGNFDAMDYWGQGTLVTVSS | 74 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLa0015-21 | EIQLVESGGGLIQPGGSLRISCAVSGFSLSSYGVDWVRQAPGKGLEWLGVIWGFGGTNYNSALKSRLTIS**A**DNSKNTVYLQMNSLRAEDTAVYYCASGNFDAMDYWGQGTLVTVSS | 75 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-22 | EIQLVESGGGLIQPGGSLRISCAVSGFSLS**Y**YGVDWVRQAPGKGLEWLGVIWGFGGTNYNSALKSRLTISKDNSKNTVYLQMNSLRAEDTAVYYCASGNFDAMDYWGQGTLVTVSS | 76 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |

TABLE 4-continued

| Antibody NO. | VH | SEQ ID NO | VL | SEQ ID NO |
|---|---|---|---|---|
| TLA015-23 | EIQLVESGGGLIQPGGSLRISCAVSGFSLSS<br>YGVDWVRQAPGKGLEWLGVIWGFGGTN<br>YNSALKSRLTISKDNSKNTVYLQMNSLRA<br>EDTAVYYCASGN**Y**DAMDYWGQGTLVTV<br>SS | 77 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-24 | EIQLVESGGGLIQPGGSLRISCAVSGFSLSS<br>YGVDWVRQAPGKGLEWLGVIWGFGGTN<br>YNSALKSRLTISKDNSKNTVYLQMNSLRA<br>EDTAVYYCASG**D**FDAMDYWGQGTLVTV<br>SS | 78 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-25 | EIQLVESGGGLIQPGGSLRISCAVSGFSLSS<br>YGVDWVRQAPGKGLEWLGVIWGFGGTN<br>YNSALKSRLTISKDNSKNTVYLQMNSLRA<br>EDTAVYYCASG**L**FDAMDYWGQGTLVTV<br>SS | 79 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-26 | EIQLVESGGGLIQPGGSLRISCAVSGFSLS**T**<br>YGVDWVRQAPGKGLEWLGVIWGFGGTN<br>YNSALKSRLTISKDNSKNTVYLQMNSLRA<br>EDTAVYYCASGNFDAMDYWGQGTLVTV<br>SS | 80 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-27 | EIQLVESGGGLIQPGGSLRISCAVSGFSL**I**S<br>YGVDWVRQAPGKGLEWLGVIWGFGGTN<br>YNSALKSRLTISKDNSKNTVYLQMNSLRA<br>EDTAVYYCASGNFDAMDYWGQGTLVTV<br>SS | 81 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-28 | EIQLVESGGGLIQPGGSLRISCAVSGFSLSS<br>YGVDWVRQAPGKGLEWLGVIWGFGGTN<br>YN**P**ALKSRLTISKDNSKNTVYLQMNSLRA<br>EDTAVYYCASGNFDAMDYWGQGTLVTV<br>SS | 82 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106<br>0<br>6 |
| TLA015-29 | EIQLVESGGGLIQPGGSLRISCAVSGFSL**K**S<br>YGVDWVRQAPGKGLEWLGVIWGFGGTN<br>YNSALKSRLTISKDNSKNTVYLQMNSLRA<br>EDTAVYYCASGNFDAMDYWGQGTLVTV<br>SS | 83 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-30 | EIQLVESGGGLIQPGGSLRISCAVSGFSLSS<br>YGVDWVRQAPGKGLEWLGVIWGFGGT**H**<br>YNSALKSRLTISKDNSKNTVYLQMNSLRA<br>EDTAVYYCASGNFDAMDYWGQGTLVTV<br>SS | 84 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-31 | EIQLVESGGGLIQPGGSLRISCAVSGFSLSS<br>YGVDWVRQAPGKGLEWLG**R**IWGFGGTN<br>YNSALKSRLTISKDNSKNTVYLQMNSLRA<br>EDTAVYYCASGNFDAMDYWGQGTLVTV<br>SS | 85 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106<br>0 |
| TLA015-32 | EIQLVESGGGLIQPGGSLRISCAVSGF**D**LSS<br>YGVDWVRQAPGKGLEWLGVIWGFGGTN<br>YNSALKSRLTISKDNSKNTVYLQMNSLRA<br>EDTAVYYCASGNFDAMDYWGQGTLVTV<br>SS | 86 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-33 | EIQLVESGGGLIQPGGSLRISCAVSGFSLSS<br>YGVDWVRQAPGKGLEWLGVIWGFG**K**TN<br>YNSALKSRLTISKDNSKNTVYLQMNSLRA<br>EDTAVYYCASGNFDAMDYWGQGTLVTV<br>SS | 87 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |
| TLA015-34 | EIQLVESGGGLIQPGGSLRISCAVSGFSLSS<br>YGVDWVRQAPGKGLEWLGVIWGFGGT**D**<br>YNSALKSRLTISKDNSKNTVYLQMNSLRA<br>EDTAVYYCASGNFDAMDYWGQGTLVTV<br>SS | 88 | DIQMTQSPSSLSASVGDRVTITCRAS<br>QDISNYLNWYQQKPGKAVKLLIYYT<br>SRLHSGVPSRFSGSGSGTDYTLTISSL<br>QPEDFATYFCQQGNTLPFTFGQGTKL<br>EIK | 106 |

TABLE 4-continued

| Antibody NO. | VH | SEQ ID NO | VL | SEQ ID NO |
|---|---|---|---|---|
| TLA015-35 | EIQLVESGGGLIQPGGSLRISCAVSGFSLS**Y**YGVDWVRQAPGKGLEWLGVIWGFGGTNYNSALKSRLTISKDNSKNTVYLQMNSLRAEDTAVYYCASGN**Y**DAMDYWGQGTLVTVSS | 89 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-36 | EIQLVESGGGLIQPGGSLRISCAVSGFSLS**Y**YGVDWVRQAPGKGLEWLGVIWGFGGTNYNSALKSRLTISKDNSKNTVYLQMNSLRAEDTAVYYCASG**D**FDAMDYWGQGTLVTVSS | 90 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-37 | EIQLVESGGGLIQPGGSLRISCAVSGFSLS**Y**YGVDWVRQAPGKGLEWLGVIWGFGGTNYN**P**ALKSRLTISKDNSKNTVYLQMNSLRAEDTAVYYCASGNFDAMDYWGQGTLVTVSS | 91 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-38 | EIQLVESGGGLIQPGGSLRISCAVSGFSLS**Y**YGVDWVRQAPGKGLEWLGVIWGFGGT**H**YNSALKSRLTISKDNSKNTVYLQMNSLRAEDTAVYYCASGNFDAMDYWGQGTLVTVSS | 92 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-39 | EIQLVESGGGLIQPGGSLRISCAVSGFSLS**Y**YGVDWVRQAPGKGLEWLG**R**IWGFGGTNYNSALKSRLTISKDNSKNTVYLQMNSLRAEDTAVYYCASGNFDAMDYWGQGTLVTVSS | 93 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-40 | EIQLVESGGGLIQPGGSLRISCAVSGF**D**LS**Y**YGVDWVRQAPGKGLEWLGVIWGFGGTNYNSALKSRLTISKDNSKNTVYLQMNSLRAEDTAVYYCASGNFDAMDYWGQGTLVTVSS | 94 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-41 | EIQLVESGGGLIQPGGSLRISCAVSGFSL**I**SYGVDWVRQAPGKGLEWLGVIWGFGGTNYNSALKSRLTISKDNSKNTVYLQMNSLRAEDTAVYYCASGN**Y**DAMDYWGQGTLVTVSS | 95 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-42 | EIQLVESGGGLIQPGGSLRISCAVSGFSLSSYGVDWVRQAPGKGLEWLGVIWGFGGTNYN**P**ALKSRLTISKDNSKNTVYLQMNSLRAEDTAVYYCASGN**Y**DAMDYWGQGTLVTVSS | 96 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-43 | EIQLVESGGGLIQPGGSLRISCAVSGFSLSSYGVDWVRQAPGKGLEWLGVIWGFGGT**H**YNSALKSRLTISKDNSKNTVYLQMNSLRAEDTAVYYCASGN**Y**DAMDYWGQGTLVTVSS | 97 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-44 | EIQLVESGGGLIQPGGSLRISCAVSGFSLSSYGVDWVRQAPGKGLEWLG**R**IWGFGGTNYNSALKSRLTISKDNSKNTVYLQMNSLRAEDTAVYYCASGN**Y**DAMDYWGQGTLVTVSS | 98 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-45 | EIQLVESGGGLIQPGGSLRISCAVSGFSLSSYGVDWVRQAPGKGLEWLGVIWGFG**K**TNYNSALKSRLTISKDNSKNTVYLQMNSLRAEDTAVYYCASGN**Y**DAMDYWGQGTLVTVSS | 99 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |
| TLA015-46 | EIQLVESGGGLIQPGGSLRISCAVSGFSL**I**SYGVDWVRQAPGKGLEWLGVIWGFGGTNYNSALKSRLTISKDNSKNTVYLQMNSLRAEDTAVYYCASG**D**FDAMDYWGQGTLVTVSS | 100 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK | 106 |

TABLE 4-continued

| Antibody NO. | VH | SEQ ID NO | VL | SEQ ID NO |
|---|---|---|---|---|
| TLA015-47 | EIQLVESGGGLIQPGGSLRISCAVSGFSLSS YGVDWVRQAPGKGLEWLGVIWGFGGT**H** YNSALKSRLTISKDNSKNTVYLQMNSLRA EDTAVYYCASG**D**FDAMDYWGQGTLVTV SS | 101 | DIQMTQSPSSLSASVGDRVTITCRAS QDISNYLNWYQQKPGKAVKLLIYYT SRLHSGVPSRFSGSGSGTDYTLTISSL QPEDFATYFCQQGNTLPFTFGQGTKL EIK | 106 |

where the single underlined bolded amino acids represent the portion of the mutation compared to TLA0015-11.

4.2 TLA0238 humanized design: According to the VH and VL amino acid sequences TLA0238 murine monoclonal antibodies, IGHV3-15/IGHV3-7/IGKV3-11/IGKV1-39 Germline, which has the highest homology in the human germline database, was selected as a template, and the CDR region of the murine antibody was transplanted to the corresponding humanized template to obtain the humanized sequence, and the heavy and light chain pairs were paired to obtain TLA0238 humanized antibody sequence pairs, and some sequences were PTM Removal, the specific sequences are shown in Table 5

TABLE 5

| TLA00238 humanized antibody sequence | VH | SEQ ID NO | VL | SEQ ID NO |
|---|---|---|---|---|
| TLA0238-1 | EVQVVESGGGLVKPGGSLRLSCAASGF TFSNYWMNWVRQAPGKGLEWVAQIR LKSDNYATHYAESVKGNFTISRDDSKS TVYLQMNSLKTEDTAVYYCTPLLLRYR DYWGQGTLVTVSS | 203 | ENVLTQSPATLSLSPGERATMSCS ASSSVSYMHWYQQKPGQAPRLWI YDTSNLASGVPARFSGSGSGNDY TLTISSMEPEDFAVYYCFQENGHP FTFGGGTKVEMK | 222 |
| TLA0238-2 | EVQVVESGGGLVKPGGSLRLSCAASGF TFSNYWMNWVRQAPGKGLEWVAQIR LKSDNYATHYAESVKGNFTISRDDSKS TVYLQMNSLKTEDTAVYYCTPLLLRYR DYWGQGTLVTVSS | 203 | DNQLTQSPSSLSASVGDRVTITCS ASSSVSYMHWYQQKPGKAPKLWI YDTSNLASGVPGRFSGSGSGNDY TLTISSLQPEDFATYYCFQENGHPF TFGQGTKLEIK | 223 |
| TLA0238-3 | EVQVVESGGGLVQPGGSLRLSCIASGFT FSNYWMNWVRQAPGKGLEWVAQIRL KSDNYATHYAESVKGNFTISRDNAKSS VYLQMNSLRAEDTAVYYCTPLLLRYR DYWGQGTLLTVSS | 204 | ENVLTQSPATLSLSPGERATMSCS ASSSVSYMHWYQQKPGQAPRLWI YDTSNLASGVPARFSGSGSGNDY TLTISSMEPEDFAVYYCFQENGHP FTFGGGTKVEMK | 222 |
| TLA0238-4 | EVQVVESGGGLVQPGGSLRLSCIASGFT FSNYWMNWVRQAPGKGLEWVAQIRL KSDNYATHYAESVKGNFTISRDNAKSS VYLQMNSLRAEDTAVYYCTPLLLRYR DYWGQGTLLTVSS | 204 | DNQLTQSPSSLSASVGDRVTITCS ASSSVSYMHWYQQKPGKAPKLWI YDTSNLASGVPGRESGSGSGNDY TLTISSLQPEDFATYYCFQENGHPF TFGQGTKLEIK | 223 |
| TLA0238-2-1 | EVQVVESGGGLVKPGGSLRLSCAASGF TFSNYWMNWVRQAPGKGLEWVAQIR LKSDNYATHYAESVKGRFTISRDDSKS TVYLQMNSLKTEDTAVYYCTPLLLRYR DYWGQGTLVTVSS | 205 | DNQLTQSPSSLSASVGDRVTITCS ASSSVSYMHWYQQKPGKAPKLWI YDTSNLASGVPGRESGSGSGNDY TLTISSLQPEDFATYYCFQENGHPF TFGQGTKLEIK | 223 |
| TLA0238-2-2 | EVQVVESGGGLVKPGGSLRLSCAASGF TFSNYWMNWVRQAPGKGLEWVAQIR LKSDNYATHYAESVKGNFAISRDDSKS TVYLQMNSLKTEDTAVYYCTPLLLRYR DYWGQGTLVTVSS | 206 | DNQLTQSPSSLSASVGDRVTITCS ASSSVSYMHWYQQKPGKAPKLWI YDTSNLASGVPGRFSGSGSGNDY TLTISSLQPEDFATYYCFQENGHPF TFGQGTKLEIK | 223 |

Where the single underline represents the sequence of FR1, FR2, FR3, FR4, and the rest portion is CDR1, CDR2, CDR3 in that order. CDRs are defined by Kabat.

In addition, TLA0238 was humanized and the sequences obtained from the design are shown in Table 6

TABLE 6

| TLA00238 humanized antibody sequence | VH | SEQ ID NO | VL | SEQ ID NO |
|---|---|---|---|---|
| TLA0238-5 | EVQLVESGGGLVQPGGSLRLSCAASGF TFSNYWMNWVRQAPGKGLEWVAQIRL KSDNYATHYADSVKGRFTISRDNSKNT LYLQMNSLRAEDTAVYYCTPLLLRYRD YWGQGTLVTVSS | 219 | DIQMTQSPSSVSASVGDRVTITCS ASSSVSYMHWYQQKPGKAPKLW IYDTSNLASGVPSRFSGSGSGTDF TLTISSLQPEDFATYYCFQENGHP FTFGQGTKVEIK | 229 |
| TLA0238-6 | QVQLVESGGGVVQPGRSLRLSCAASGF TFSNYWMNWVRQAPGKGLEWVAQIRL KSDNYATHYADSVKGRFTISRDNSKNT LYLQMNSLRAEDTAVYYCTPLLLRYRD YWGQGTMVTVSS | 207 | DIQMTQSPSSVSASVGDRVTITCS ASSSVSYMHWYQQKPGKAPKLW IYDTSNLASGVPSRFSGSGSGTDF TLTISSLQPEDFATYYCFQENGHP FTFGQGTKVEIK | 229 |
| TLA0238-7 | EVKVEESGGGLVQPGGSLRLSCIASGFT FSNYWMHWVRQAPGKGLEWVGQIRL KSDNYATHYAASVKGRFTISRDNSKNT LYLQMNSLKTEDTAVYYCTPLLLRYRD YWGQGTLVTVSS | 208 | ENVLTQSPAIMSATPGEKVTITCS ASSSVSYLHWYQQKPGQSPQLWI YDTSNRASGVPDRFSGSGSGTDY TLTISSLQPEDVATYYCFQENGHP FTFGGGTKLEMK | 224 |
| TLA0238-8 | EVKVEESGGGLVQPGGSLKLSCIASGFT FSNYWMHWVRQAPGKGLEWVGQIRL KSDNYATHYAASVKGRFTISRDDSKNS LYLQMNSLRDEDTAVYYCTPLLLRYRD YWGQGTLVTVSS | 209 | EVVLTQSPAFLSVTPGEKVTITCS ASSSVSYLAWYQQKPGQSPRLWI YDTSNRASGVPDRFSGSGSGTDY TLTISSLQPEDFAVYYCFQENGHP FTFGGGTKLEMK | 225 |
| TLA0238-9 | EVKVEESGGGLVQPGGALRLSCIASGFT FSNYWMHWVRQAPGKGLEWVGQIRL KSDNYATHYAASVKGRFTISRDDSKNT LYLQMNSLRAEDTAVYYCTPLLLRYRD YWGQGTLVTVSS | 210 | ENVLTQSPAFMSATPGEKVTITCS ASSSVSYLAWYQQKPGKSPKLWI YDTSNLATGVPSRFSGSGSGTSYT LTISSLQPEDVATYYCFQENGHPF TFGGGTKLEMK | 226 |
| TLA0238-10 | EVKVEESGGGLVQPGGSLRLSCIASGFT FSNYWMHWVRQAPGKGLEWVGQIRL KSDNYATHYAASVKGRFTISRDDSKNS LYLQMNSLRAEDMAVYYCTPLLLRYR DYWGQGTLVTVSS | 211 | EIVLTQSPAFMSATPGEKVTITCS ASSSVSYLHWYQQKPDQSPKLWI YDTSNRASGVPDRFSGSGSGTDY TLTISSLEAEDAATYYCFQENGHP FTFGGGTKLEMK | 227 |
| TLA0238-11 | EVQLVESGGGLVQPGGSLRLSCAASGF TFSNYWMNWVRQAPGKGLEWVAQIRL KSDNYATHYADSVKGRFTISRDNSKNT LYLQMNSLRAEDTAVYYCTPLLLRYRD YWGQGTMVTVSS | 212 | DIQMTQSPSSVSASVGDRVTITCS ASSSVSYMHWYQQKPGKAPKLW IYDTSNLASGVPSRFSGSGSGTDF TLTISSLQPEDFATYYCFQENGHP FTFGQGTKVEIK | 229 |
| TLA0238-12 | EVKLEESGGGLVQPGGSLKLSCIASGFT FSNYWMHWVRQAPGKGLEWVGQIRL KSDNYATHYAASVKGRFTISRDDSKNT AYLQMNSLRAEDTAVYYCTPLLLRYR DYWGQGTLVTVSS | 213 | ETVLTQSPAFMSATPGEKVTITCS ASSSVSYLTWYQQKPGQSPKLWI YDTSNLASGVPDRFSGSGSGTDY TLTISSLEAEDAATYYCFQENGHP FTFGGGTKLEMK | 228 |
| TLA0238-13 | EVQLVESGGGLVKPGGSLRLSCAASGF TFSNYWMNWVRQAPGKGLEWVAQIRL KSDNYATHYAAPVKGRFTISRDDSKNT LYLQMNSLKTEDTAVYYCTPLLLRYRD YWGQGTTVTVSS | 214 | DIQMTQSPSSVSASVGDRVTITCS ASSSVSYMHWYQQKPGKAPKLW IYDTSNLASGVPSRFSGSGSGTDF TLTISSLQPEDFATYYCFQENGHP FTFGQGTKVEIK | 229 |
| TLA0238-14 | EVKLEESGGGLVQPGGALRLSCIASGFT FSNYWMSWVRQAPGKGLEWVGQIRLK SDNYATHYAASVKGRFTISRDDSKNTL YLQMNSLRAEDTAVYYCTPLLLRYRD YWGQGTLVTVSS | 215 | ENVLTQSPAFLSVTPGEKVTITCS ASSSVSYLHWYQQKPDQSPKLWI YDTSNLATGVPSRFSGSGSGTDYT LTISSLQPEDFATYYCFQENGHPF TFGGGTKLEMK | 230 |
| TLA0238-39 | EVQLVESGGGLVKPGGSLRLSCAASGFT FSNYWMNWVRQAPGKGLEWVGQIRL KSDNYATHYAESVKGRFTISRDDSKNTL YLQMNSLKTEDTAVYYCTTLLLRYRDY WGQGTLVTVSS | 332 | EIVLTQSPATLSLSPGERATLSCSAS SSVSYMHWYQQKPGQSPRLWIY DTSNLASGIPARFSGSGSGTDYTL TISSLEPEDFAVYYCFQENAHPFTF GGGTKVEIK | 335 |
| TLA0238-40 | EVQLVESGGGLVKPGGSLRLSCAASGFT FSNYWMNWVRQAPGKGLEWVGQIRL KSDNYATHYAESVKGRFTISRDDSKNTL YLQMNSLKTEDTAVYYCTTLLLRYRDY WGQGTLVTVSS | 332 | EIVLTQSPATLSLSPGERATLSCSAS SSVSYMHWYQQKPGQSPRLWIY DTSNLASGVPARFSGSGSGTDYTL TISSLEPEDFAVYYCFQENAHPFTF GGGTKVEIK | 336 |

TABLE 6-continued

| TLA00238 humanized antibody sequence | VH | SEQ ID NO | VL | SEQ ID NO |
|---|---|---|---|---|
| TLA0238-41 | EVQLVESGGGLVKPGGSLRLSCAASGFTFSNYWMNWVRQAPGKGLEWVGQIRLKSDNYATHYAESVKGRFTISRDDSKNTLYLQMNSLKTEDTAVYYCTTLLLRYRDYWGQGTLVTVSS | 332 | DIQMTQSPSSLSASVGDRVTITCSASSSVSYMHWYQQKPGKAPKLWIYDTSNLASGVPSRFSGSGSGTDYTLTISSLQPEDFATYYCFQENAHPFTFGQGTKLEIK | 337 |
| TLA0238-42 | EVQLVESGGGLVKPGGSLRLSCAASGFTFSNYWMNWVRQAPGKGLEWVGQIRLKSDNYATHYAESVKGRFTISRDDSKNTLYLQMNSLKTEDTAVYYCTTLLLRYRDYWGQGTLVTVSS | 332 | DIQLTQSPSSLSASVGDRVTITCSASSSVSYMHWYQQKPGKAPKLWIYDTSNLASGVPSRFSGSGSGTDYTLTISSLQPEDFATYYCFQENAHPFTFGQGTKLEIK | 338 |
| TLA0238-43 | EVQLVESGGGLVKPGGSLRLSCAASGFTFSNYWMNWVRQAPGKGLEWVGQIRLKSDNYATHYAESVKGRFTISRDDSKNTLYLQMNSLKTEDTAVYYCTPLLLRYRDYWGQGTLVTVSS | 333 | EIVLTQSPATLSLSPGERATLSCSASSSVSYMHWYQQKPGQSPRLWIYDTSNLASGIPARFSGSGSGTDYTLTISSLEPEDFAVYYCFQENAHPFTFGGGTKVEIK | 335 |
| TLA0238-44 | EVQLVESGGGLVKPGGSLRLSCAASGFTFSNYWMNWVRQAPGKGLEWVGQIRLKSDNYATHYAESVKGRFTISRDDSKNTLYLQMNSLKTEDTAVYYCTPLLLRYRDYWGQGTLVTVSS | 333 | EIVLTQSPATLSLSPGERATLSCSASSSVSYMHWYQQKPGQSPRLWIYDTSNLASGVPARFSGSGSGTDYTLTISSLEPEDFAVYYCFQENAHPFTFGGGTKVEIK | 336 |
| TLA0238-45 | EVQLVESGGGLVKPGGSLRLSCAASGFTFSNYWMNWVRQAPGKGLEWVGQIRLKSDNYATHYAESVKGRFTISRDDSKNTLYLQMNSLKTEDTAVYYCTPLLLRYRDYWGQGTLVTVSS | 333 | DIQMTQSPSSLSASVGDRVTITCSASSSVSYMHWYQQKPGKAPKLWIYDTSNLASGVPSRFSGSGSGTDYTLTISSLQPEDFATYYCFQENAHPFTFGQGTKLEIK | 337 |
| TLA0238-46 | EVQLVESGGGLVKPGGSLRLSCAASGFTFSNYWMNWVRQAPGKGLEWVGQIRLKSDNYATHYAESVKGRFTISRDDSKNTLYLQMNSLKTEDTAVYYCTPLLLRYRDYWGQGTLVTVSS | 333 | DIQLTQSPSSLSASVGDRVTITCSASSSVSYMHWYQQKPGKAPKLWIYDTSNLASGVPSRFSGSGSGTDYTLTISSLQPEDFATYYCFQENAHPFTFGQGTKLEIK | 338 |
| TLA0238-47 | EVQLVESGGGLVKPGGSLRLSCAASGFTFSNYWMNWVRQAPGKGLEWVAQIRLKSDNYATHYAESVKGRFTISRDDSKNTLYLQMNSLKTEDTAVYYCTPLLLRYRDYWGQGTLVTVSS | 334 | EIVLTQSPATLSLSPGERATLSCSASSSVSYMHWYQQKPGQSPRLWIYDTSNLASGIPARFSGSGSGTDYTLTISSLEPEDFAVYYCFQENAHPFTFGGGTKVEIK | 335 |
| TLA0238-48 | EVQLVESGGGLVKPGGSLRLSCAASGFTFSNYWMNWVRQAPGKGLEWVAQIRLKSDNYATHYAESVKGRFTISRDDSKNTLYLQMNSLKTEDTAVYYCTPLLLRYRDYWGQGTLVTVSS | 334 | EIVLTQSPATLSLSPGERATLSCSASSSVSYMHWYQQKPGQSPRLWIYDTSNLASGVPARFSGSGSGTDYTLTISSLEPEDFAVYYCFQENAHPFTFGGGTKVEIK | 336 |
| TLA0238-49 | EVQLVESGGGLVKPGGSLRLSCAASGFTFSNYWMNWVRQAPGKGLEWVAQIRLKSDNYATHYAESVKGRFTISRDDSKNTLYLQMNSLKTEDTAVYYCTPLLLRYRDYWGQGTLVTVSS | 334 | DIQMTQSPSSLSASVGDRVTITCSASSSVSYMHWYQQKPGKAPKLWIYDTSNLASGVPSRFSGSGSGTDYTLTISSLQPEDFATYYCFQENAHPFTFGQGTKLEIK | 337 |

TABLE 6-continued

| TLA00238 humanized antibody sequence | VH | SEQ ID NO | VL | SEQ ID NO |
|---|---|---|---|---|
| TLA0238-50 | EVQLVESGGGLVKPGGSLRLSCAASGFTFSNYWMNWVRQAPGKGLEWVAQIRLKSDNYATHYAESVKGRFTISRDDSKNTLYLQMNSLKTEDTAVYYCTPLLLRYRDYWGQGTLVTVSS | 334 | DIQLTQSPSSLSASVGDRVTITCSASSSVSYMHWYQQKPGKAPKLWIYDTSNLASGVPSRFSGSGSGTDYTLTISSLQPEDFATYYCFQENAHPFTFGQGTKLEIK | 338 |

Where the single underline represents the sequence of FR1, FR2, FR3, FR4, and the rest portion is CDR1, CDR2, CDR3 in that order. CDRs are defined by Kabat.

Eleven antibodies were designed by mutating the amino acids of the protein post-translational modification risk sites present in the TLA0238-5 antibody, and the specific antibody sequences are shown in Table 7.

TABLE 7

| antibody | VH | SEQ ID NO | VL | SEQ ID NO |
|---|---|---|---|---|
| TLA0238-15 | EVQLVESGGGLVQPGGSLRLSCAASGFTFSNYIMNWVRQAPGKGLEWVAQIRLKSDNYATHYADSVKGRFTISRDNSKNTLYLQMNSLRAEDTAVYYCTPLLLRYRDYWGQGTLVTVSS | 216 | DIQMTQSPSSVSASVGDRVTITCSASSSVSYMHWYQQKPGKAPKLWIYDTSNLASGVPSRFSGSGSGTDFTLTISSLQPEDFATYYCFQESGHPFTFGQGTKVEIK | 231 |
| TLA0238-16 | EVQLVESGGGLVQPGGSLRLSCAASGFTFSNYIMNWVRQAPGKGLEWVAQIRLKSDNYATHYADSVKGRFTISRDNSKNTLYLQMNSLRAEDTAVYYCTPLLLRYRDYWGQGTLVTVSS | 216 | DIQMTQSPSSVSASVGDRVTITCSASSSVSYMHWYQQKPGKAPKLWIYDTSNLASGVPSRFSGSGSGTDFTLTISSLQPEDFATYYCFQENEHPFTFGQGTKVEIK | 232 |
| TLA0238-17 | EVQLVESGGGLVQPGGSLRLSCAASGFTFSNYLMNWVRQAPGKGLEWVAQIRLKSDNYATHYADSVKGRFTISRDNSKNTLYLQMNSLRAEDTAVYYCTPLLLRYRDYWGQGTLVTVSS | 217 | DIQMTQSPSSVSASVGDRVTITCSASSSVSYMHWYQQKPGKAPKLWIYDTSNLASGVPSRFSGSGSGTDFTLTISSLQPEDFATYYCFQESGHPFTFGQGTKVEIK | 231 |
| TLA0238-18 | EVQLVESGGGLVQPGGSLRLSCAASGFTFSNYLMNWVRQAPGKGLEWVAQIRLKSDNYATHYADSVKGRFTISRDNSKNTLYLQMNSLRAEDTAVYYCTPLLLRYRDYWGQGTLVTVSS | 217 | DIQMTQSPSSVSASVGDRVTITCSASSSVSYMHWYQQKPGKAPKLWIYDTSNLASGVPSRFSGSGSGTDFTLTISSLQPEDFATYYCFQENEHPFTFGQGTKVEIK | 232 |
| TLA0238-19 | EVQLVESGGGLVQPGGSLRLSCAASGFTFSNYMMNWVRQAPGKGLEWVAQIRLKSDNYATHYADSVKGRFTISRDNSKNTLYLQMNSLRAEDTAVYYCTPLLLRYRDYWGQGTLVTVSS | 218 | DIQMTQSPSSVSASVGDRVTITCSASSSVSYMHWYQQKPGKAPKLWIYDTSNLASGVPSRFSGSGSGTDFTLTISSLQPEDFATYYCFQESGHPFTFGQGTKVEIK | 231 |
| TLA0238-20 | EVQLVESGGGLVQPGGSLRLSCAASGFTFSNYMMNWVRQAPGKGLEWVAQIRLKSDNYATHYADSVKGRFTISRDNSKNTLYLQMNSLRAEDTAVYYCTPLLLRYRDYWGQGTLVTVSS | 218 | DIQMTQSPSSVSASVGDRVTITCSASSSVSYMHWYQQKPGKAPKLWIYDTSNLASGVPSRFSGSGSGTDFTLTISSLQPEDFATYYCFQENEHPFTFGQGTKVEIK | 232 |
| TLA0238-21 | EVQLVESGGGLVQPGGSLRLSCAASGFTFSNYIMNWVRQAPGKGLEWVAQIRLKSDNYATHYADSVKGRFTISRDNSKNTLYLQMNSLRAEDTAVYYCTPLLLRYRDYWGQGTLVTVSS | 216 | DIQMTQSPSSVSASVGDRVTITCSASSSVSYMHWYQQKPGKAPKLWIYDTSNLASGVPSRFSGSGSGTDFTLTISSLQPEDFATYYCFQEEGHPFTFGQGTKVEIK | 233 |
| TLA0238-22 | EVQLVESGGGLVQPGGSLRLSCAASGFTFSNYIMNWVRQAPGKGLEWVAQIRLKSDNYATHYADSVKGRFTISRDNSKNTLYLQMNSLRAEDTAVYYCTPLLLRYRDYWGQGTLVTVSS | 216 | DIQMTQSPSSVSASVGDRVTITCSASSSVSYMHWYQQKPGKAPKLWIYDTSNLASGVPSRFSGSGSGTDFTLTISSLQPEDFATYYCFQENAHPFTFGQGTKVEIK | 234 |

TABLE 7-continued

| antibody | VH | SEQ ID NO | VL | SEQ ID NO |
|---|---|---|---|---|
| TLA0238-23 | EVQLVESGGGLVQPGGSLRLSCAASGFTFS<br>NY**L**MNWVRQAPGKGLEWVAQIRLKSDNY<br>ATHYADSVKGRFTISRDNSKNTLYLQMNS<br>LRAEDTAVYYCTPLLLRYRDYWGQGTLVT<br>VSS | 217 | DIQMTQSPSSVSASVGDRVTITCSAS<br>SSVSYMHWYQQKPGKAPKLWIYDT<br>SNLASGVPSRFSGSGSGTDFTLTISSL<br>QPEDFATYYCFQE**E**GHPFTFGQGTK<br>VEIK | 233 |
| TLA0238-24 | EVQLVESGGGLVQPGGSLRLSCAASGFTFS<br>NY**L**MNWVRQAPGKGLEWVAQIRLKSDNY<br>ATHYADSVKGRFTISRDNSKNTLYLQMNS<br>LRAEDTAVYYCTPLLLRYRDYWGQGTLVT<br>VSS | 217 | DIQMTQSPSSVSASVGDRVTITCSAS<br>SSVSYMHWYQQKPGKAPKLWIYDT<br>SNLASGVPSRFSGSGSGTDFTLTISSL<br>QPEDFATYYCFQEN**A**HPFTFGQGTK<br>VEIK | 234 |
| TLA0238-25 | EVQLVESGGGLVQPGGSLRLSCAASGFTFS<br>NY**M**MNWVRQAPGKGLEWVAQIRLKSDN<br>YATHYADSVKGRFTISRDNSKNTLYLQMN<br>SLRAEDTAVYYCTPLLLRYRDYWGQGTLV<br>TVSS | 218 | DIQMTQSPSSVSASVGDRVTITCSAS<br>SSVSYMHWYQQKPGKAPKLWIYDT<br>SNLASGVPSRFSGSGSGTDFTLTISSL<br>QPEDFATYYCFQE**E**GHPFTFGQGTK<br>VEIK | 233 |
| TLA0238-26 | EVQLVESGGGLVQPGGSLRLSCAASGFTFS<br>NY**M**MNWVRQAPGKGLEWVAQIRLKSDN<br>YATHYADSVKGRFTISRDNSKNTLYLQMN<br>SLRAEDTAVYYCTPLLLRYRDYWGQGTLV<br>TVSS | 218 | DIQMTQSPSSVSASVGDRVTITCSAS<br>SSVSYMHWYQQKPGKAPKLWIYDT<br>SNLASGVPSRFSGSGSGTDFTLTISSL<br>QPEDFATYYCFQEN**A**HPFTFGQGTK<br>VEIK | 234 |
| TLA0238-27 | EVQLVESGGGLVQPGGSLRLSCAASGFTFS<br>NYWMNWVRQAPGKGLEWVAQIRLKSDN<br>YATHYADSVKGRFTISRDNSKNTLYLQMN<br>SLRAEDTAVYYCTPLLLRYRDYWGQGTLV<br>TVSS | 219 | DIQMTQSPSSVSASVGDRVTITCSAS<br>SSVSYMHWYQQKPGKAPKLWIYDT<br>SNLASGVPSRFSGSGSGTDFTLTISSL<br>QPEDFATYYCFQE**E**GHPFTFGQGTK<br>VEIK | 233 |
| TLA0238-28 | EVQLVESGGGLVQPGGSLRLSCAASGFTFS<br>NYWMNWVRQAPGKGLEWVAQIRLKSDN<br>YATHYADSVKGRFTISRDNSKNTLYLQMN<br>SLRAEDTAVYYCTPLLLRYRDYWGQGTLV<br>TVSS | 219 | DIQMTQSPSSVSASVGDRVTITCSAS<br>SSVSYMHWYQQKPGKAPKLWIYDT<br>SNLASGVPSRFSGSGSGTDFTLTISSL<br>QPEDFATYYCFQEN**A**HPFTFGQGTK<br>VEIK | 234 |
| TLA0238-29 | EVQLVESGGGLVQPGGSLRLSCAASGFTFS<br>NY**Y**MNWVRQAPGKGLEWVAQIRLKSDNY<br>ATHYADSVKGRFTISRDNSKNTLYLQMNS<br>LRAEDTAVYYCTPLLLRYRDYWGQGTLVT<br>VSS | 220 | DIQMTQSPSSVSASVGDRVTITCSAS<br>SSVSYMHWYQQKPGKAPKLWIYDT<br>SNLASGVPSRFSGSGSGTDFTLTISSL<br>QPEDFATYYCFQE**E**GHPFTFGQGTK<br>VEIK | 233 |
| TLA0238-30 | EVQLVESGGGLVQPGGSLRLSCAASGFTFS<br>NY**Y**MNWVRQAPGKGLEWVAQIRLKSDNY<br>ATHYADSVKGRFTISRDNSKNTLYLQMNS<br>LRAEDTAVYYCTPLLLRYRDYWGQGTLVT<br>VSS | 220 | DIQMTQSPSSVSASVGDRVTITCSAS<br>SSVSYMHWYQQKPGKAPKLWIYDT<br>SNLASGVPSRFSGSGSGTDFTLTISSL<br>QPEDFATYYCFQEN**A**HPFTFGQGTK<br>VEIK | 234 |

where the single underlined bolded amino acids represent the portion of the mutation compared to TLA0238-5.

4.3 TLA0241 humanized design: humanizing the TLA0241, and the sequences obtained by the design are shown in Table 8.

TABLE 8

| TLA0241 humanized number | VH | SEQ ID NO | VL | SEQ ID NO |
|---|---|---|---|---|
| TLA0241-1 | EVQLVESGGGLVQPGGSLRLSCSASGYTF<br>TDYYLNWVRQAPGKGLEWIGDINPNNG<br>RTTYADSVKGRFTISRDNSKNTLYLQMSS<br>LRAEDTAVYYCAREGGYGWYFDVWGR<br>GTLVTVSS | 298 | DIQMTQSPSSLSASVGDRVTITCST<br>SSSIISNYSHWYQQKPGKAPKLLIY<br>KTSNLPSGVPSRFSGSGSGTEFTLTI<br>SSLQPEDFATYYCQQGSDMPITFG<br>QGTKVEIK | 309 |
| TLA0241-2 | QVQLVESGGGVVQPGRSLRLSCAASGYT<br>FTDYYLNWVRQAPGKGLEWIGDINPNNG<br>RTTYADSVKGRFTISRDNSKNTLYLQMN<br>SLRAEDTAVYYCAREGGYGWYFDVWG<br>QGTMVTVSS | 299 | DIQMTQSPSSVSASVGDRVTITCST<br>SSSIISNYSHWYQQKPGKAPKLLIY<br>KTSNLPSGVPSRESGSGSGTDFTLTI<br>SSLQPEDFATYYCQQGSDMPITFG<br>QGTKVEIK | 315 |

TABLE 8-continued

| TLA0241 humanized number | VH | SEQ ID NO | VL | SEQ ID NO |
|---|---|---|---|---|
| TLA0241-3 | EVQLQQSGPEVKKPGASVRISCKASGYTF TDYYMHWVRQAPGQGLEWIGDINPNNG RTTYNQKFQGRVTITRDTSSSTAYMELRS LRSDDTAVYYCAREGGYGWYFDVWGT GTTVTVSS | 300 | EIVLTQSPTTLSLSPGEKVTITCSAS SSIISNYLHWYQQKPGKSPKLLIYK TSNLPSGVPSRESGSGSGTDFTLTIN SLEAEDAATYYCQQGSDMPITFGA GTRLELK | 310 |
| TLA0241-4 | EVQLQQSGPEVKKPGASVRISCKASGYTF TDYYMHWVQQAPGKGLEWIGDINPNNG RTTYNQKFQGRVTITADKSTSTAYMELR SLRSDDTAVYYCAREGGYGWYFDVWGT GTLVTVSS | 301 | EIVLTQSPPTLSLSPGEKVTITCSAS SSIISNYLHWYQQKPGQSPQLLIYK TSNRPSGVPDRFSGSGSGTDFTLTI NSLEAEDAATYYCQQGSDMPITFG AGTRLELK | 311 |
| TLA0241-5 | ELQLQQSGPEVKKPGASVRISCKASGYTE TDYYMHWVQQAPGKGLEWIGDINPNNG RTTYNQKFQGRVTITADKSTSTAYMELR SLTSDDTAVYYCAREGGYGWYFDVWGT GTTVTVSS | 302 | EIVLTQSPGTLSLSPGEKVTITCSAS SSIISNYLHWYQQKPDQSPKLLIYK TSNLPSGVPSRFSGSGSGTDFTLTIN SLEAEDAATYYCQQGSDMPITFGA GTKLELK | 312 |
| TLA0241-6 | EVQLLESGGGLVQPGGSLRLSCAASGYTF TDYYLNWVRQAPGKGLEWIGDINPNNG RTTYADSVKGRFTISRDNSKNTLYLQMN SLRAEDTAVYYCAREGGYGWYFDVWG QGTMVTVSS | 303 | AIQLTQSPSSLSASVGDRVTITCSTS SSIISNYSHWYQQKPGKAPKLLIYK TSNLPSGVPSRFSGSGSGTDFTLTIS SLQPEDFATYYCQQGSDMPITFGQ GTKVEIK | 313 |
| TLA0241-7 | EVQLQQSGPEVKKPGASVRISCKASGYTE TDYYMHWVRQAPGEGLEWIGDINPNNG RTTYNQKFQGRVTITADKSTSTAYMELR SLRSDDTAVYYCAREGGYGWYFDVWGT GTTVTVSS | 304 | EIVLTQSPATLSLSPGEKVTITCSAS SSIISNYSAWYQQKPGKSPKLLIYK TSNLPSGVPARFSGSGSGTDFTLTI NSLEAEDAATYYCQQGSDMPITFG AGTRLELK | 314 |
| TLA0241-8 | QVQLVESGGGVVQPGRSLRLSCAASGYT FTDYYLNWVRQAPGKGLEWIGDINPNNG RTTYADSVKGRFTISRDNSKNTLYLQMN SLRAEDTAVYYCAREGGYGWYFDVWG QGTTVTVSS | 305 | DIQMTQSPSSVSASVGDRVTITCST SSSIISNYSHWYQQKPGKAPKLLIY KTSNLPSGVPSRFSGSGSGTDFTLTI SSLQPEDFATYYCQQGSDMPITFG QGTKVEIK | 315 |
| TLA0241-9 | EIQLQQSGAEEKKPGASVRISCKASGYTF TDYYMHWVQQAPGKGLEWIGDINPNNG RTTYNQKFQGRVTITADKSTSTAYMELR SLRSDDTAVYYCAREGGYGWYFDVWGT GTTVTVSS | 306 | EIVLTQSPTTLSLSPGEKVTITCSAS SSIISNYLHWYQQKPDQSPKLLIYK TSNLPSGVPSRFSGSGSGTDFTLTIN SLEAEDAATYYCQQGSDMPITFGA GTKLELK | 316 |
| TLA0241-10 | ELQLQQSGAEVKKPGASVRISCKASGYTF TDYYMHWVRQAPGQGLEWIGDINPNNG RTTYNQKFQGRVTITADKSTSTAYMELR SLRSDDMAVYYCAREGGYGWYFDVWG TGTLVTVSS | 307 | EIVLTQSPPTLSLSPGEKVTITCSAS SSIISNYLAWYQQKPGKSPKLLIYK TSNLPSGVPSRFSGSGSGTSFTLTIN SLEAEDAATYYCQQGSDMPITFGA GTKLELK | 317 |

The single underline represents the sequence of FR1, FR2, FR3, FR4, and the rest portion is CDR1, CDR2, CDR3 in that order. CDRs are defined by Kabat.

The VH and VL amino acid sequences of the control antibodies RVT-3101 and MK-7240 were obtained according to their published patents, and the specific amino acid sequences are shown in Table 9.

TABLE 9

| Abs | amino acid sequence (VH) | amino acid sequence (VL) |
|---|---|---|
| RVT-3101 | QVQLVQSGAEVKKPGASVKVSCKASGYDF TYYGISWVRQAPGQGLEWMGWISTYNGNT HYARMLQGRVTMTTDTSTRTAYMELRSLR SDDTAVYYCARENYYGSGAYRGGMDVWGQ GTTVTVSS (SEQ ID NO: 322) | EIVLTQSPATLSLSPGERATLSCRASQSVSSYLAW YQQKPGQAPRLLIYDASNRATGIPARFSGSGSGT DFTLTISSLEPEDFAVYYCQQRSNWPWTFGQGTK VEIK (SEQ ID NO: 323) |
| MK-7240 | QVQLVQSGAEVKKPGASVKVSCKASGFDI QDTYMHWVKQRPGQGLEWMGRIDPASGHT KYDPKFQVRVTITRDTSTSTVYLELSSLR SEDTAVYYCARSGGLPDVWGQGTTVTVSS (SEQ ID NO: 324) | EIVLTQSPGTLSLSPGERATLSCRASSSVSYMYW YQQKPGQAPRPLIYATSNLASGIPDRFSGSGSGTD FTLTISRLEPEDFAVYYCQQWEGNPRTFGGGTKL EIK (SEQ ID NO: 325) |

Figure 1B:
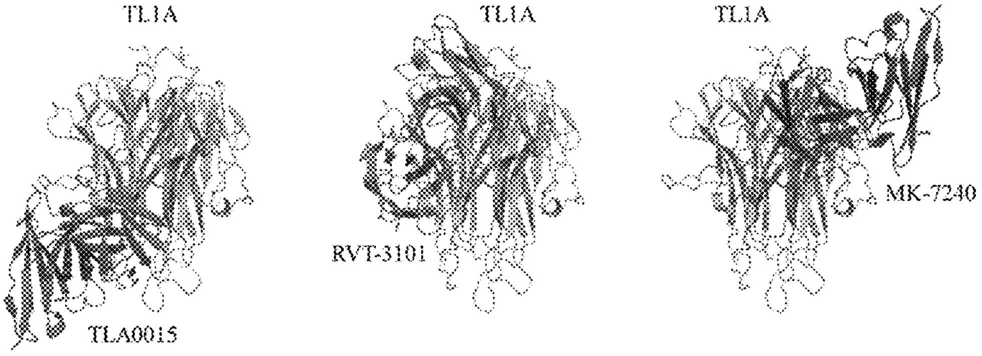
FIG. 1B shows the predicted structure of different anti-TL1A antibodies binding with TL1A antigen as described in the present application (side view)
Figure 2A:
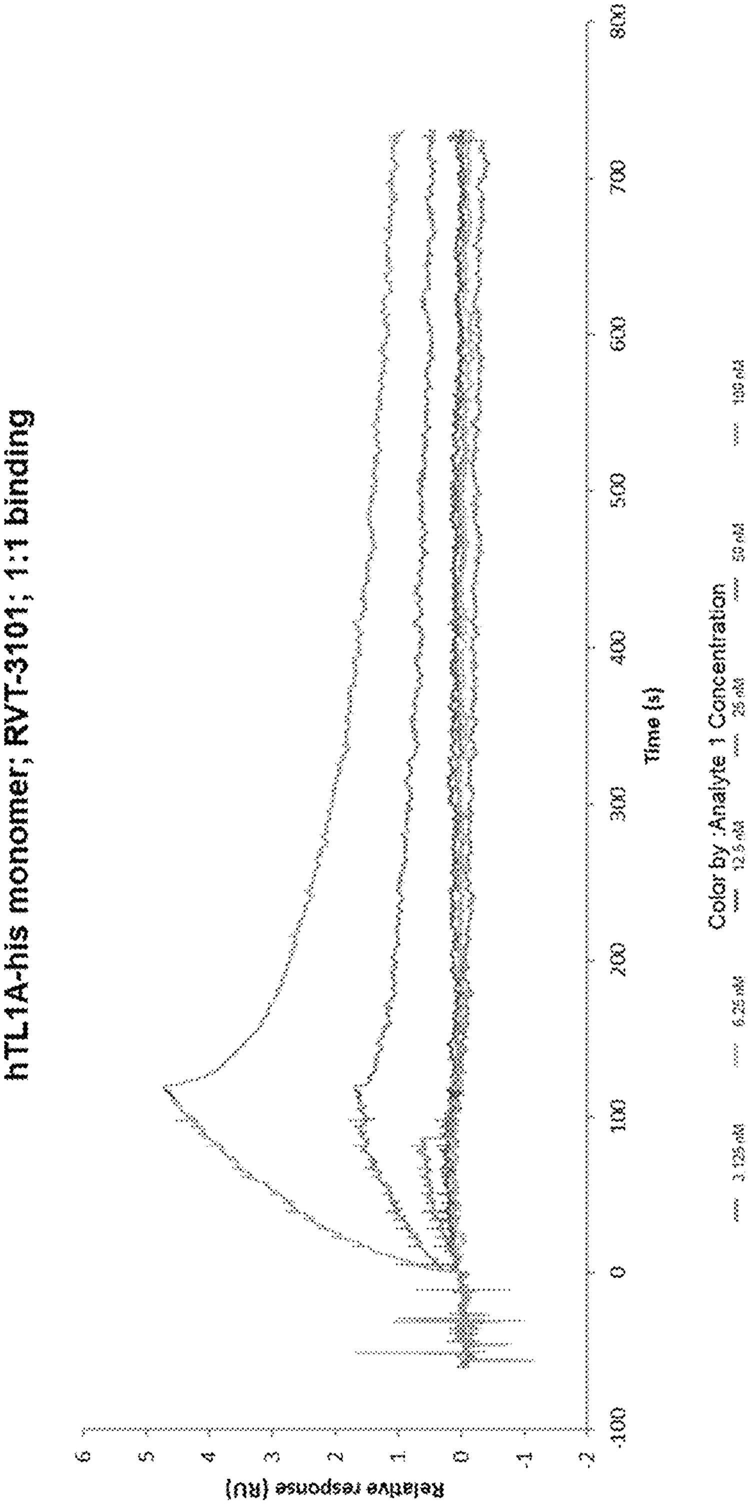
FIGS. 2A-2D show the binding curves of different anti-TL1A antibodies described in the present application to human TL1A-his monomeric protein, and the curve from top to bottom indicates that the concentration is from high to low.
Figure 2B:
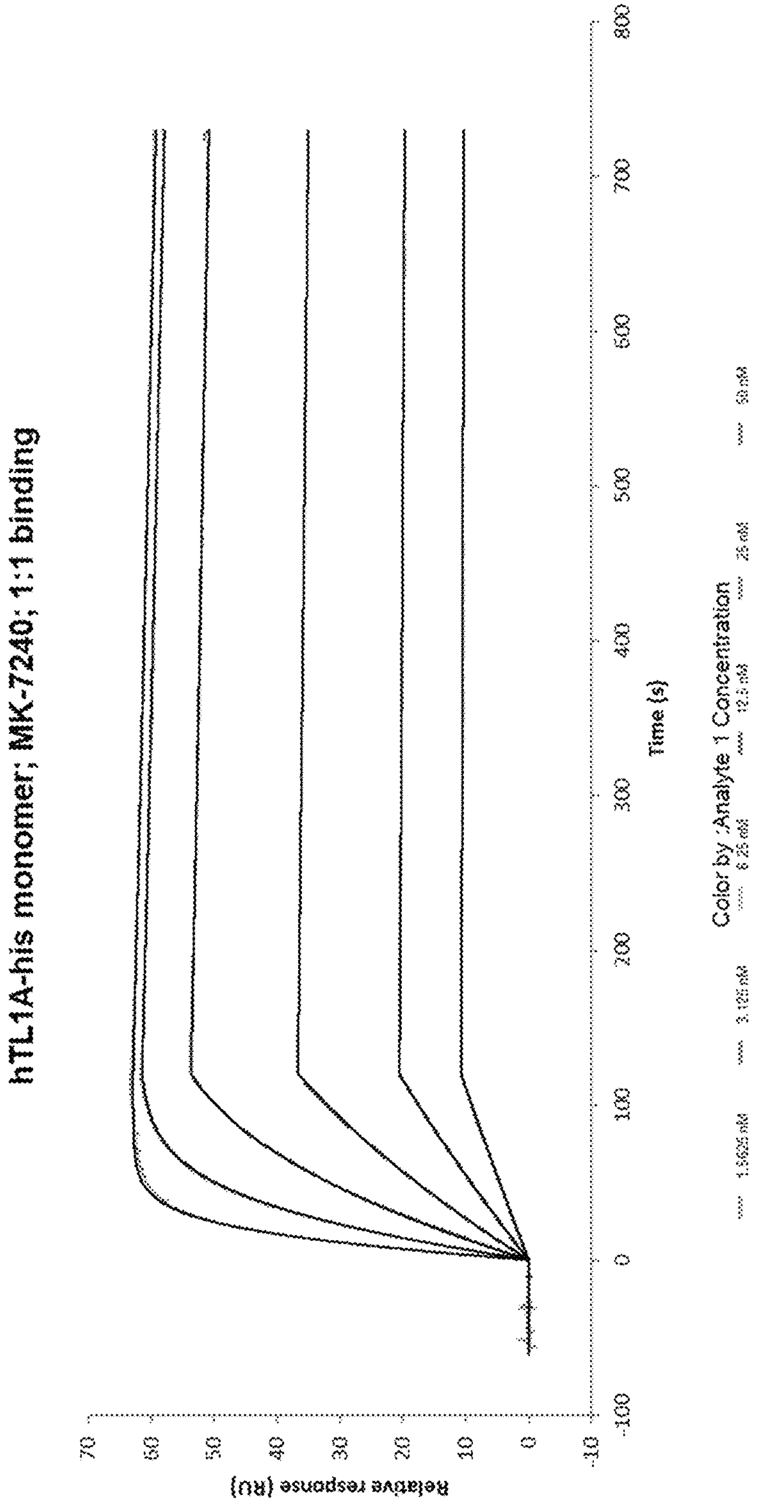
Figure 2C:
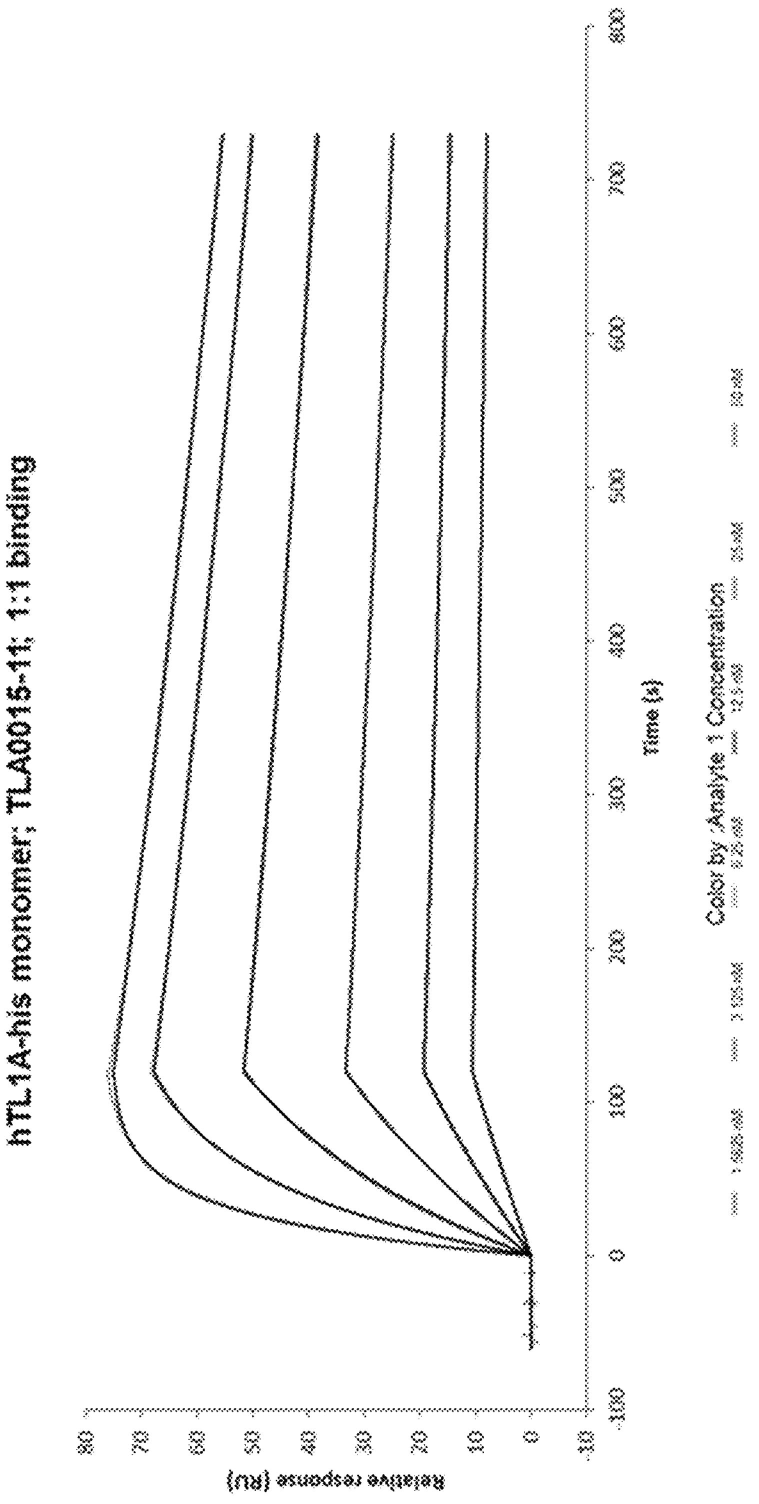
Figure 2D:
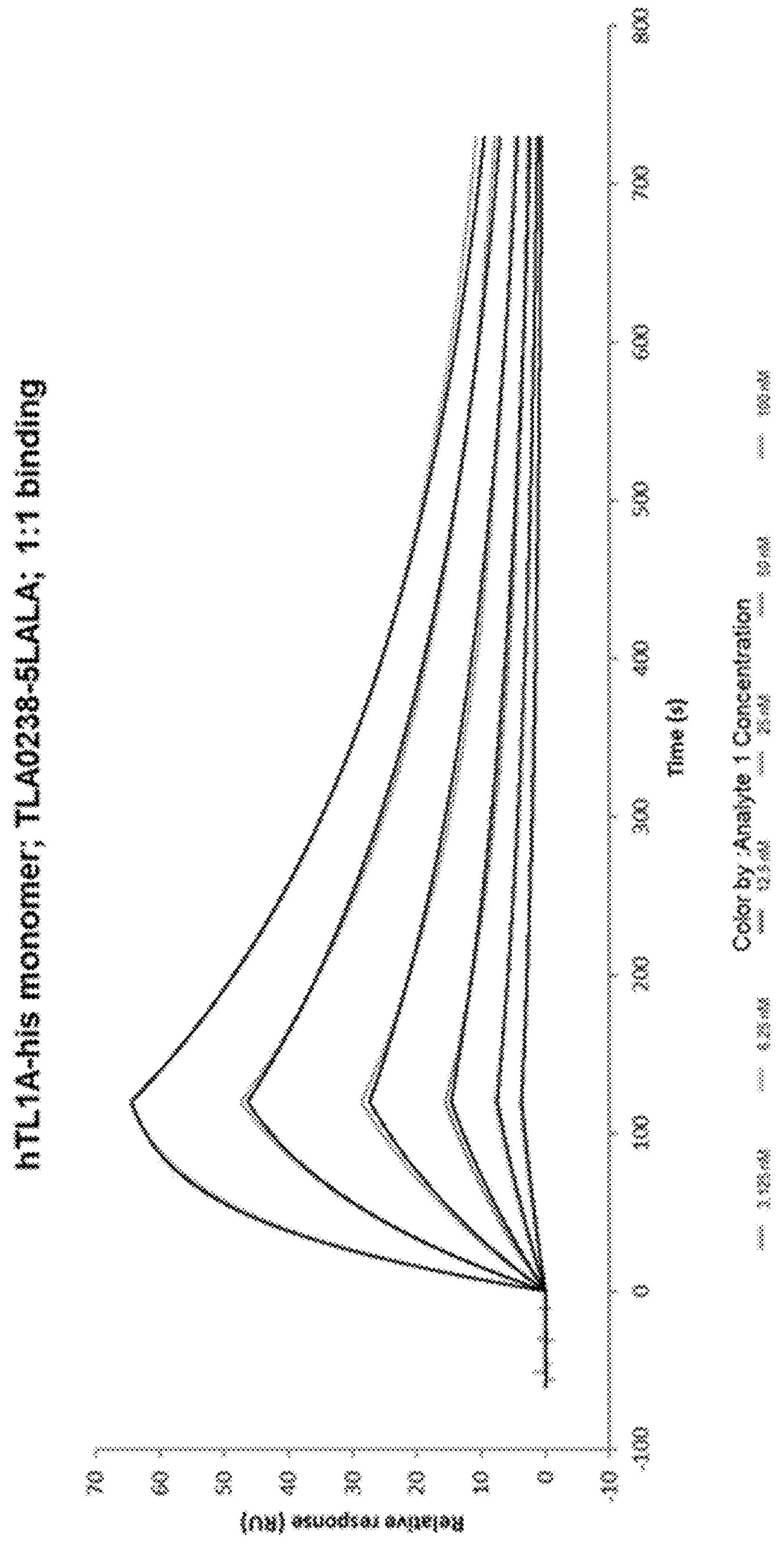
Figure 3A:
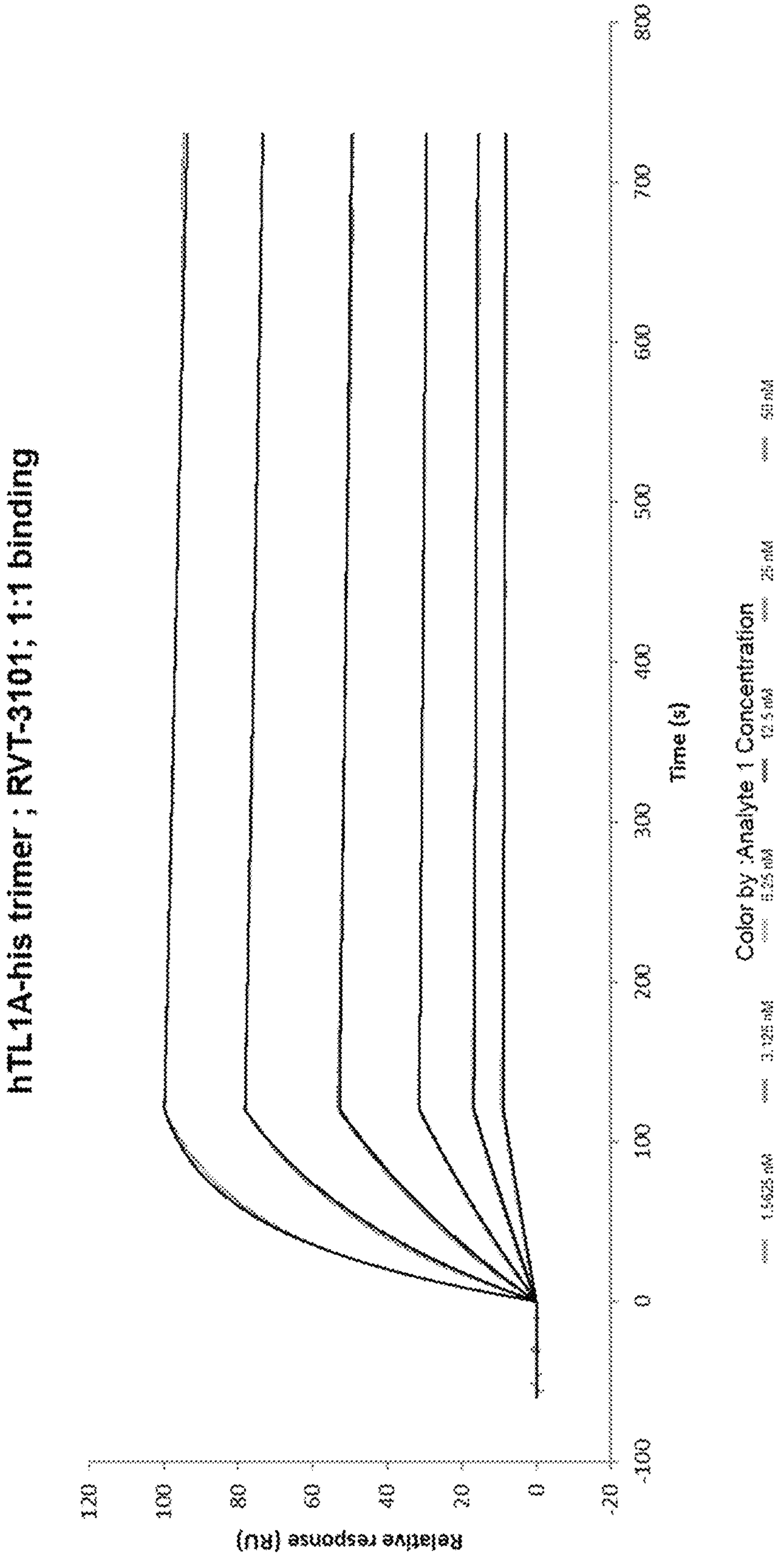
FIGS. 3A-3D show the binding curves of different anti-TL1A antibodies as described in the present application to human TL1A-his trimeric protein, and the curve from top to bottom indicates that the concentration is from high to low.
Figure 3B:
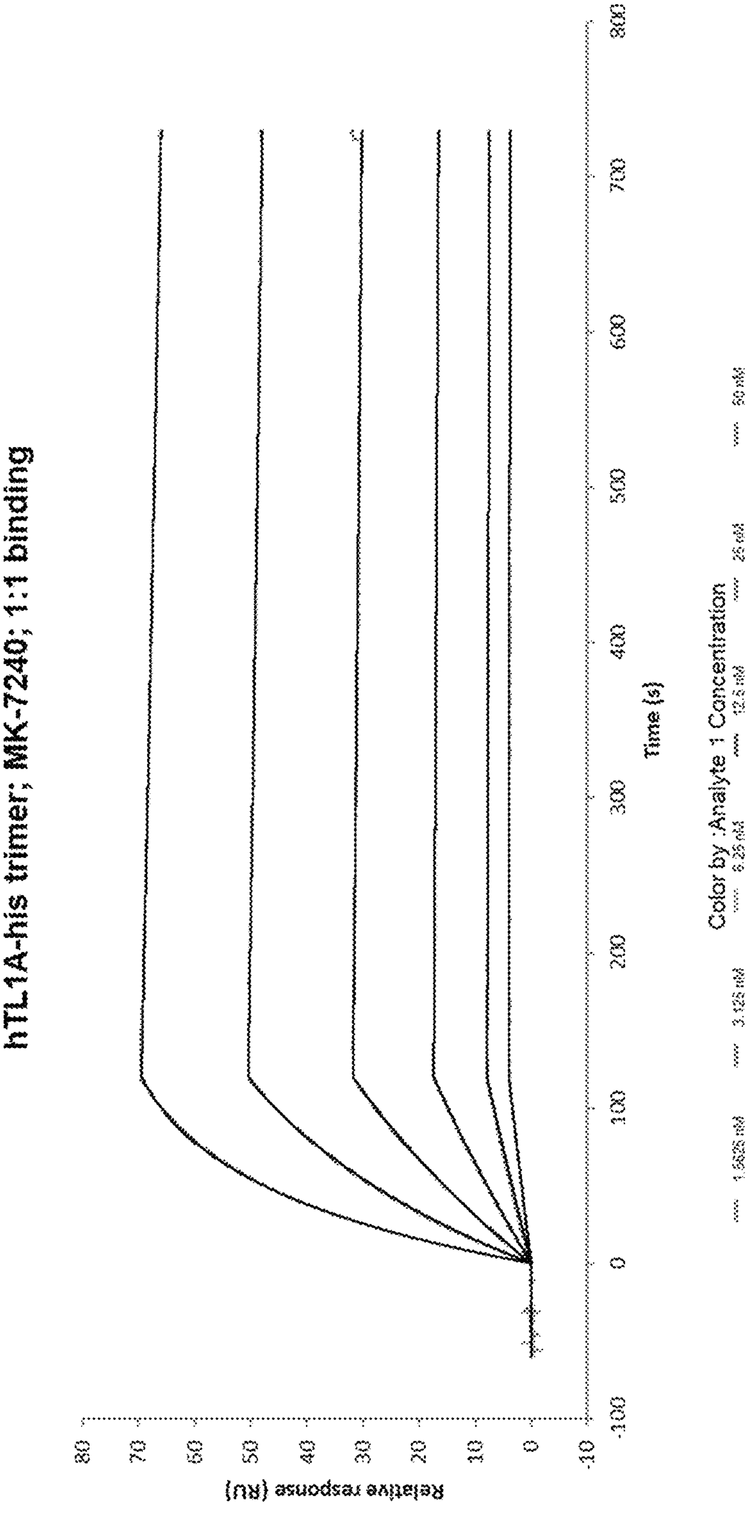
Figure 3C:
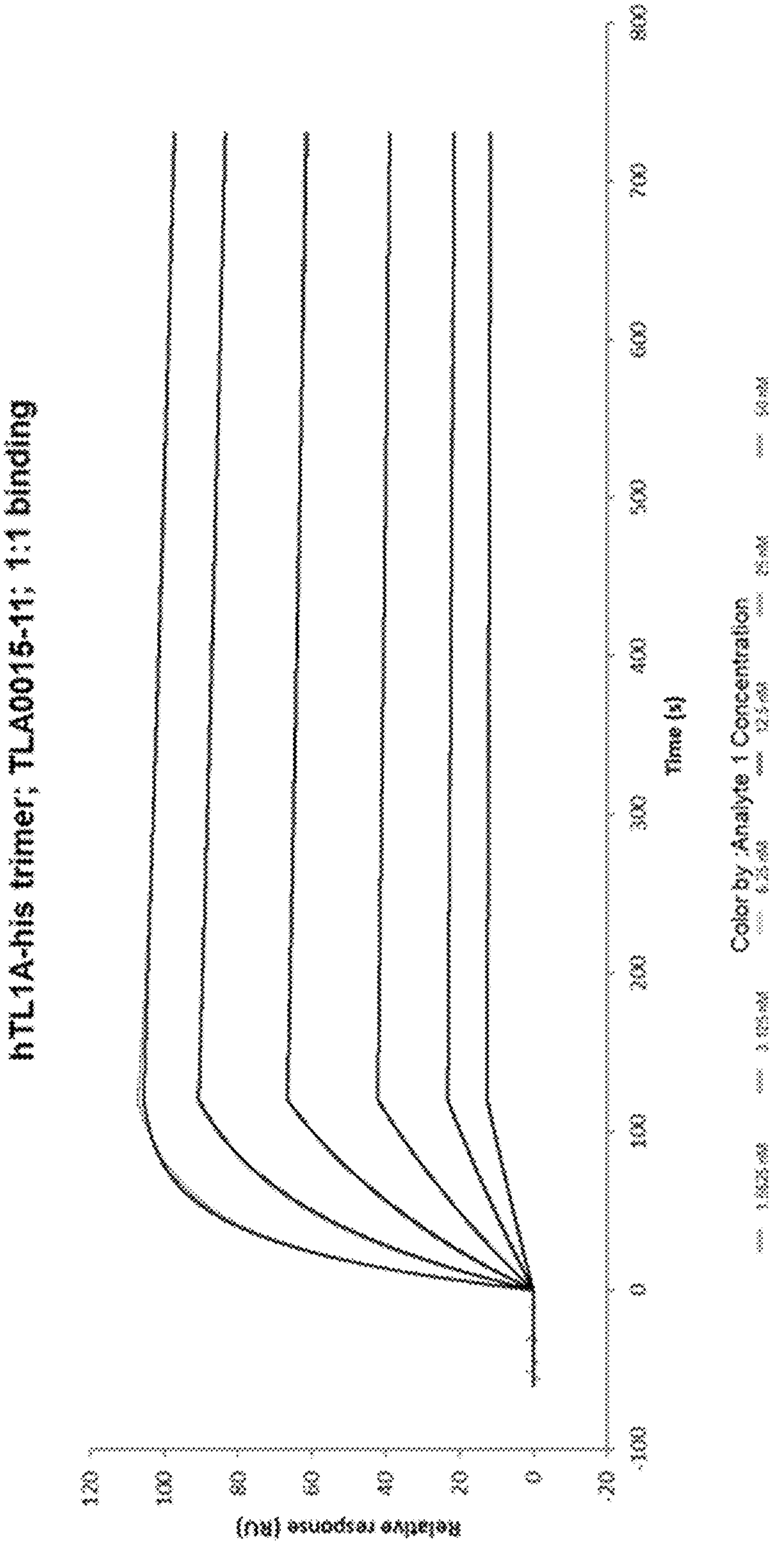
Figure 3D:
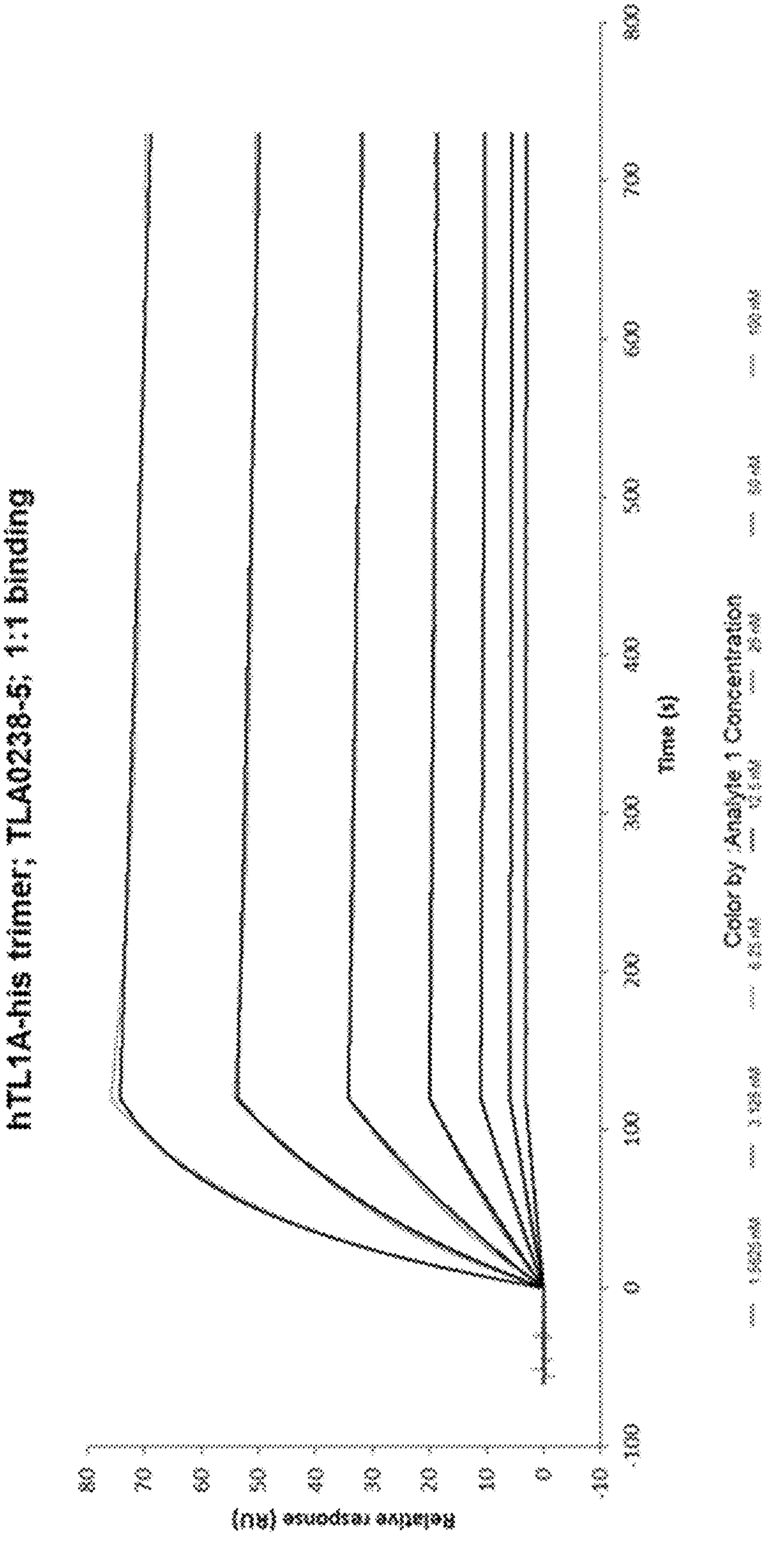
Figure 4A:
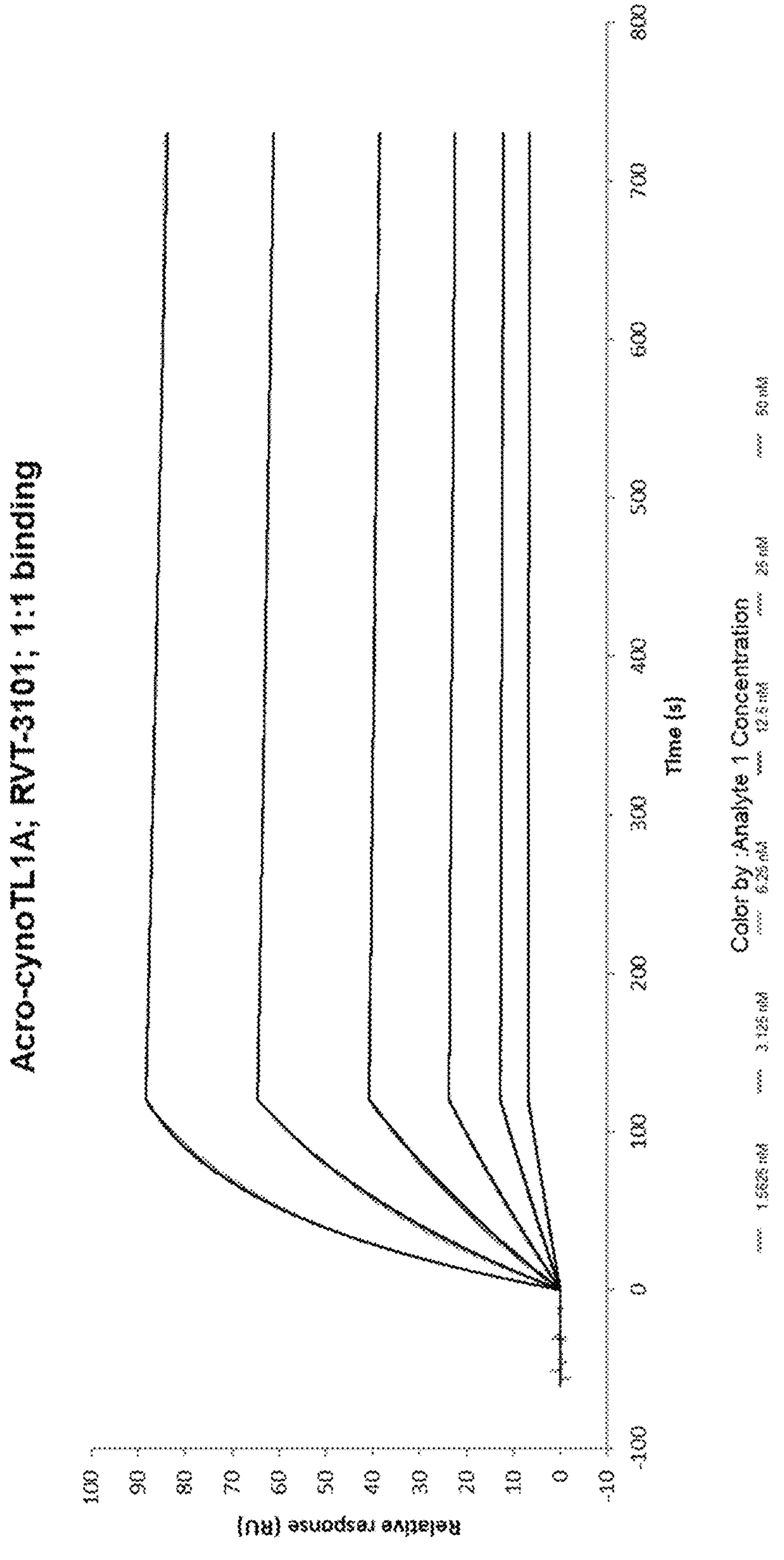
FIGS. 4A-4D show different anti-TL1A antibody binding curves to monkey TL1A-his protein as described in the present application, and the curve from top to bottom indicates that the concentration is from high to low.
Figure 4B:
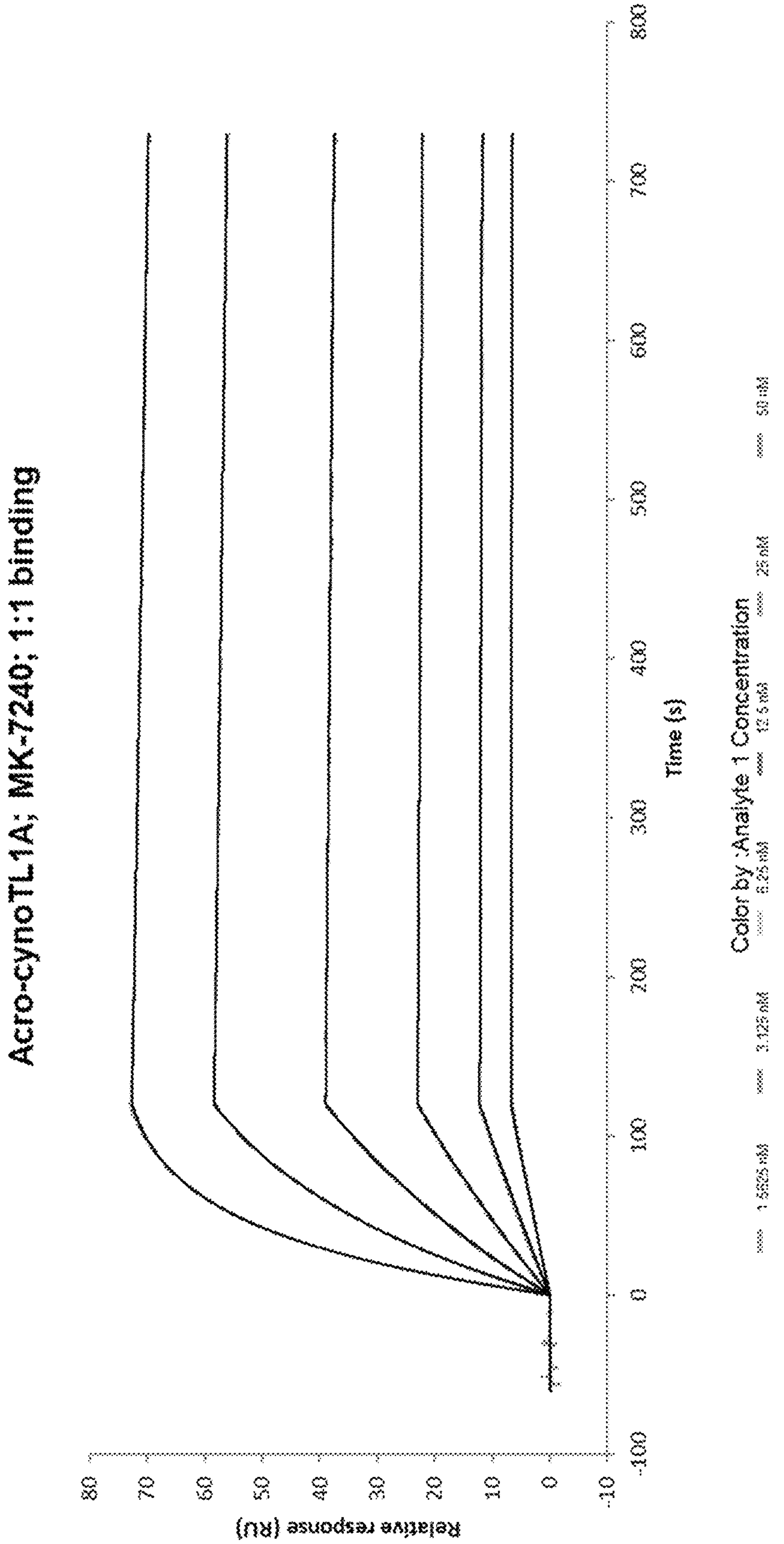
Figure 4C:
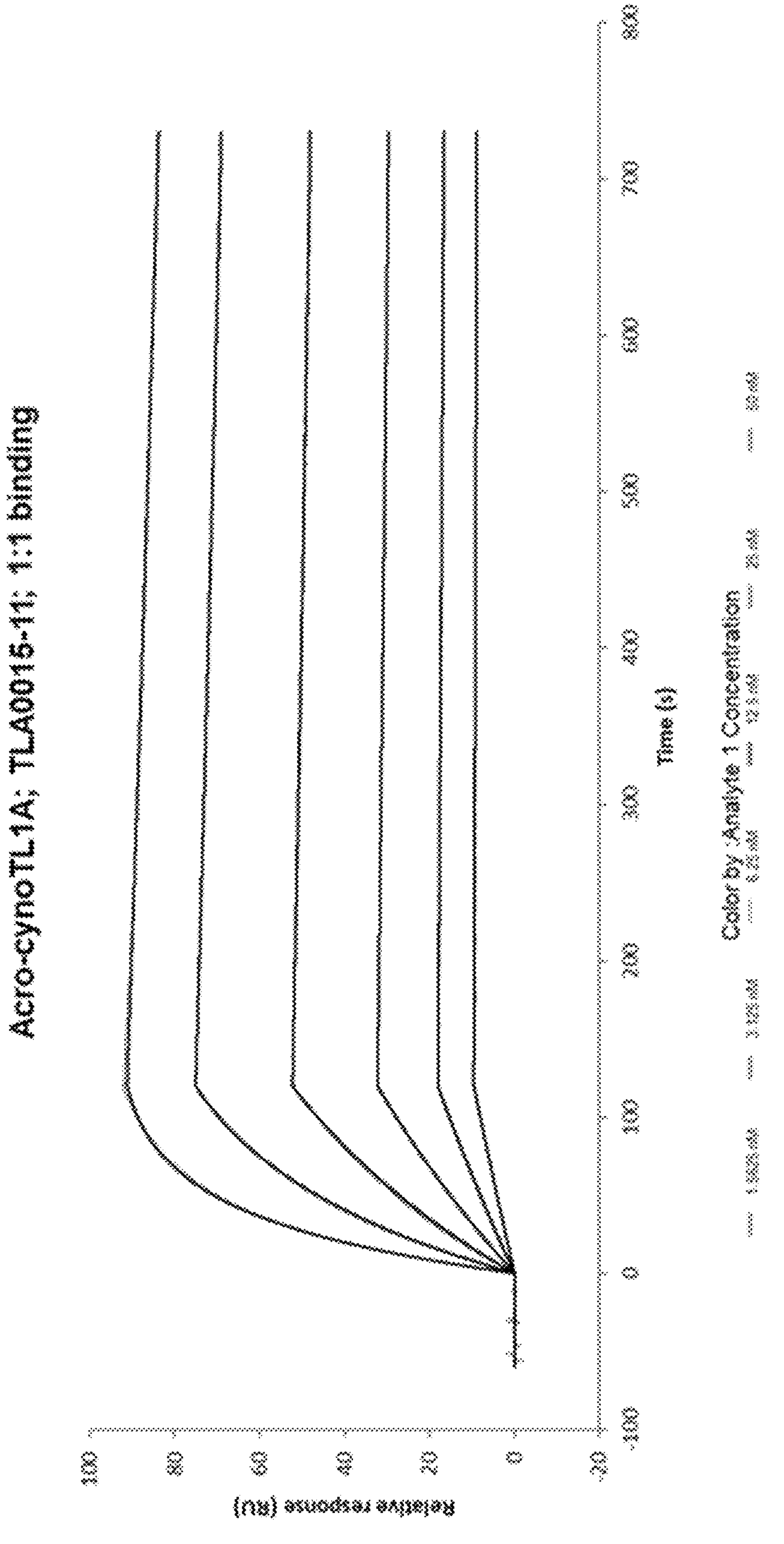
Figure 4D:
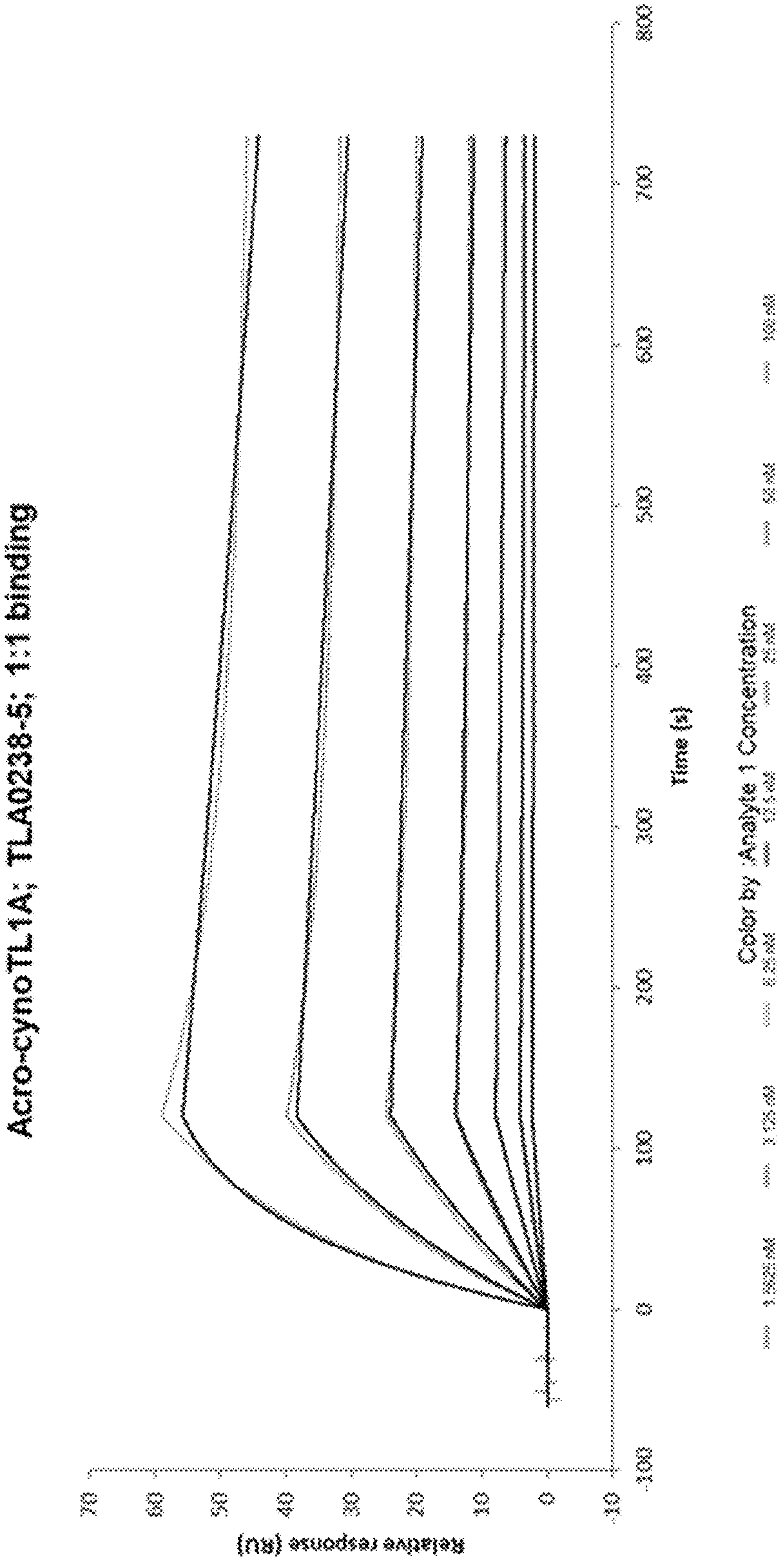

Example 5 Antibody-Antigen Complex Structure Prediction of Anti-TL1A Monoclonal Antibody The anti-antibody complex structure prediction model was used to predict the crystal structure of TL1A monomer and the anti-TL1A TLA0015, MK-7240 and RVT-3101, and the high-quality complex structure was obtained. The results of the composite structure prediction are shown in FIGS. 1A and 1B.

Example 6 Recombinant Antibody Expression and Purification

The VH and VL sequences of the antibodies obtained by sequencing after Single B sorting and phage library panning were constructed as human IgG1 type, with Kappa as the light chain. The amino acid sequences of the Cκ, CH1 and Fc constant region (containing L234A, L235A, M252Y, S254T and T256E mutations) for constructing the antibody are shown in Table 10. The antibody heavy chain and light chain DNA fragments were subcloned into pcDNA3.4 vector, the recombinant plasmid was extracted and co-transfected into CHO cells, and after 7 days of cell culture, the culture medium was filtered through high-speed centrifugation and microporous filter membrane, and then loaded onto a Protein A affinity chromatography column, the protein was eluted with sodium acetate buffer eluent at pH 3.4, and dialyzed to PBS at pH 7.4, and the absorbance value of 280 nm was read by using a NanoDrop instrument to detect the protein concentration. The antibody obtained in this example are used in the tests of the following examples.

TABLE 10

| | |
|---|---|
| Cκ | RTVAAPSVFIFPPSDEQLKSGTASVVCLLNNFYPREAKVQ WKVDNALQSGNSQESVTEQDSKDSTYSLSSTLTLSKADYE KHKVYACEVTHQGLSSPVTKSFNRGEC (SEQ ID NO 318) |
| CH1 | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSC (SEQ ID NO 319) |
| Fc (No mutation) | DKTHTCPPCPAPELLGGPSVFLFPPKPKDTLMISRTPEVT CVVVDVSHEDPEVKFNWYVDGVEVHNAKTKPREEQYNSTY RVVSVLTVLHQDWLNGKEYKCKVSNKALPAPIEKTISKAK GQPREPQVYTLPPSRDELTKNQVSLTCLVKGFYPSDIAVE WESNGQPENNYKTTPPVLDSDGSFFLYSKLTVDKSRWQQG NVFSCSVMHEALHNHYTQKSLSLSPGK (SEQ ID NO 341) |
| Fc (L234A, L235A) | DKTHTCPPCPAPEAAGGPSVFLFPPKPKDTLMISRTPEVT CVVVDVSHEDPEVKFNWYVDGVEVHNAKTKPREEQYNSTY RVVSVLTVLHQDWLNGKEYKCKVSNKALPAPIEKTISKAK GQPREPQVYTLPPSRDELTKNQVSLTCLVKGFYPSDIAVE WESNGQPENNYKTTPPVLDSDGSFFLYSKLTVDKSRWQQG NVFSCSVMHEALHNHYTQKSLSLSPGK (SEQ ID NO 320) |
| Fc (L234A, L235A, M252Y, S254T, T256E) | DKTHTCPPCPAPEAAGGPSVFLFPPKPKDTLYITREPEVT CVVVDVSHEDPEVKFNWYVDGVEVHNAKTKPREEQYNSTY RVVSVLTVLHQDWLNGKEYKCKVSNKALPAPIEKTISKAK GQPREPQVYTLPPSRDELTKNQVSLTCLVKGFYPSDIAVE WESNGQPENNYKTTPPVLDSDGSFFLYSKLTVDKSRWQQG NVFSCSVMHEALHNHYTQKSLSLSPGK (SEQ ID NO 321) |

Example 7 Biacore Detects the Affinity of the Antibody to the TL1A-his Protein The affinity of the multiple antibodies prepared by example 6 with human TL1A-his monomeric protein, human TL1A-his trimeric protein, monkey TL1A-his protein and rat TL1A-his protein is detected based on a Biacore biomolecular interaction instrument.

Figure 5A:
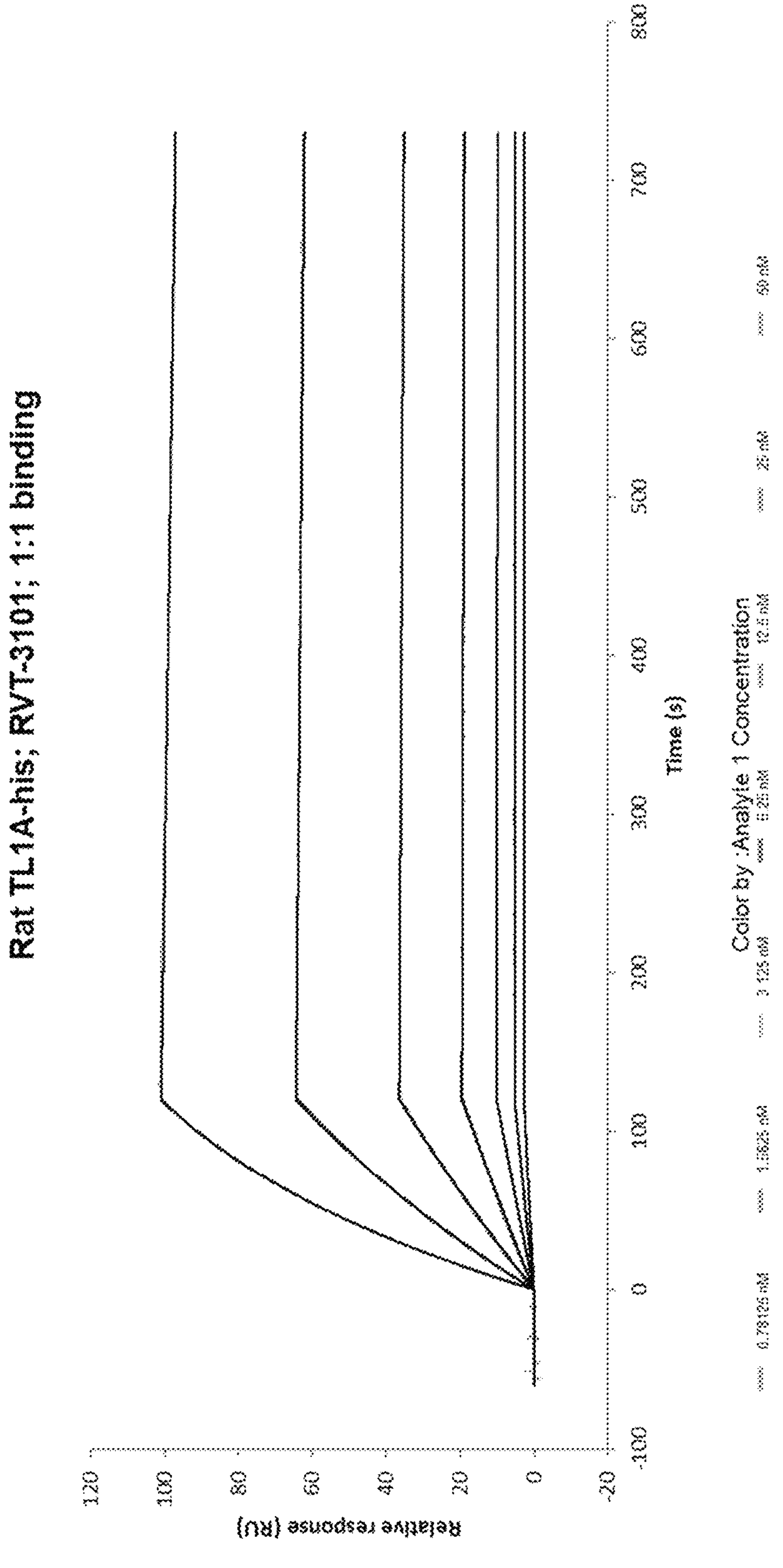
FIGS. 5A-5B show binding curves of different anti-TL1A antibodies described in the present application to rat TL1A-his protein, and the curve from top to bottom indicates that the concentration is from high to low.
Figure 5B:
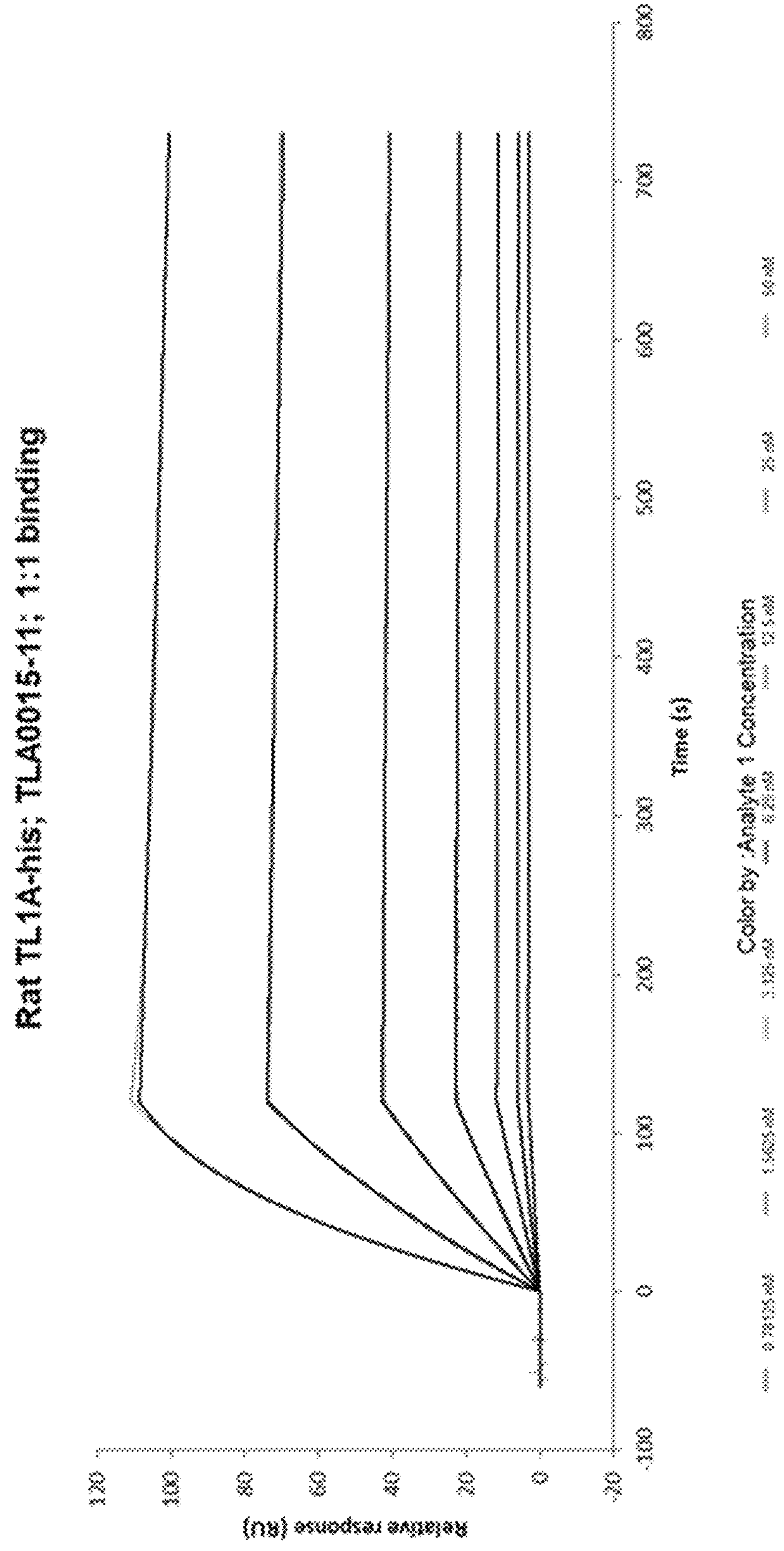
Figure 6A:
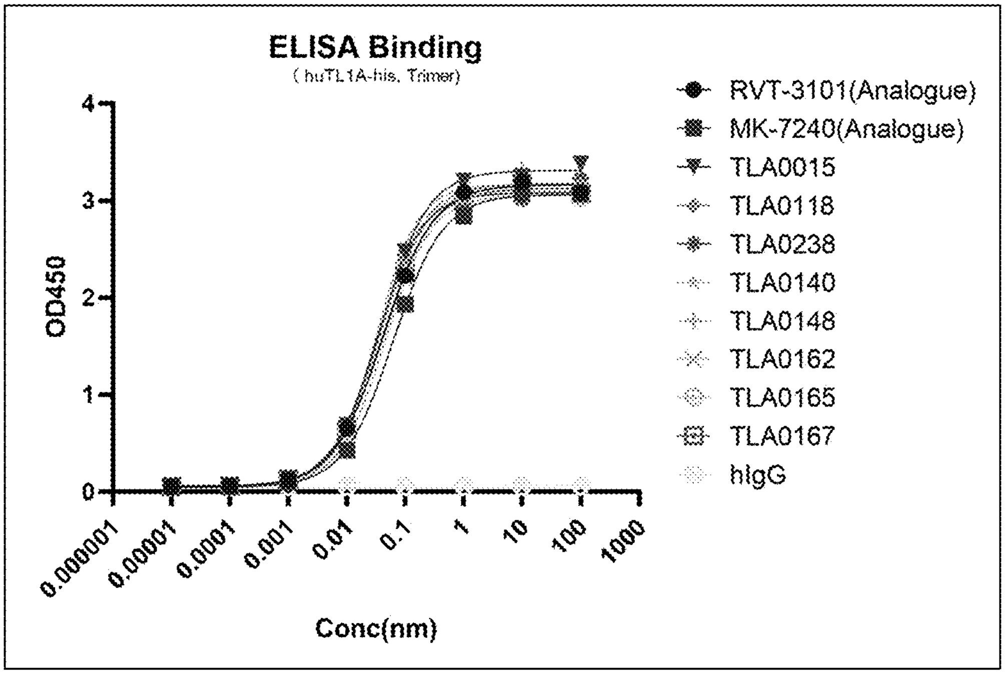
FIG. 6A showing the results of an ELISA assay for the binding ability of anti-TL1A antibodies described in the present application to human TL1A-his (trimer)
Figure 6B:
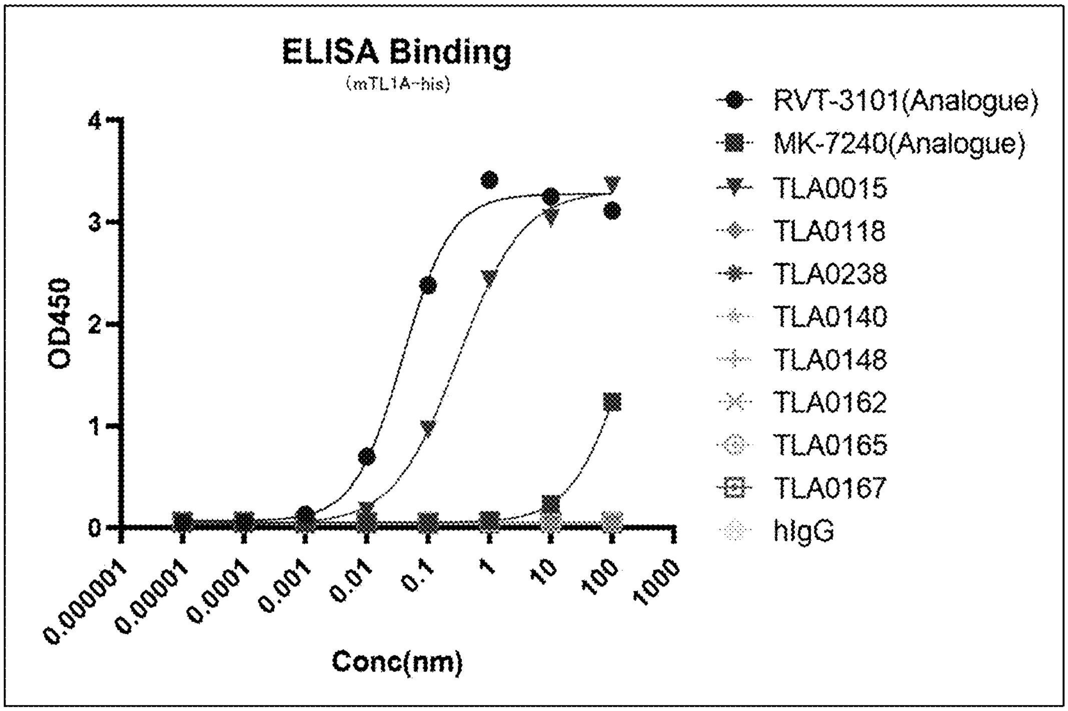
FIG. 6B showing the results of the ELISA assay detecting the binding capacity of the anti-TL1A antibody described in the present application to murine TL1A-his protein.
Figure 6C:
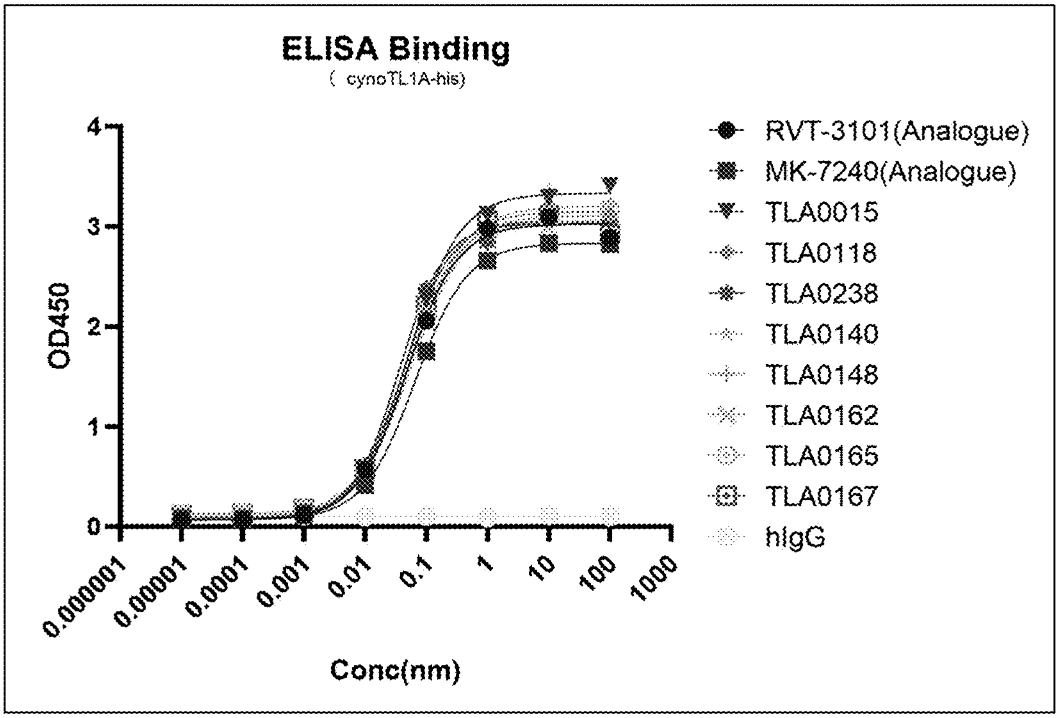
FIG. 6C shows the results of the ELISA assay for the binding capacity assay of the anti-TL1A antibody described in the present application to the monkey TL1A-his protein.
Figure 6D:
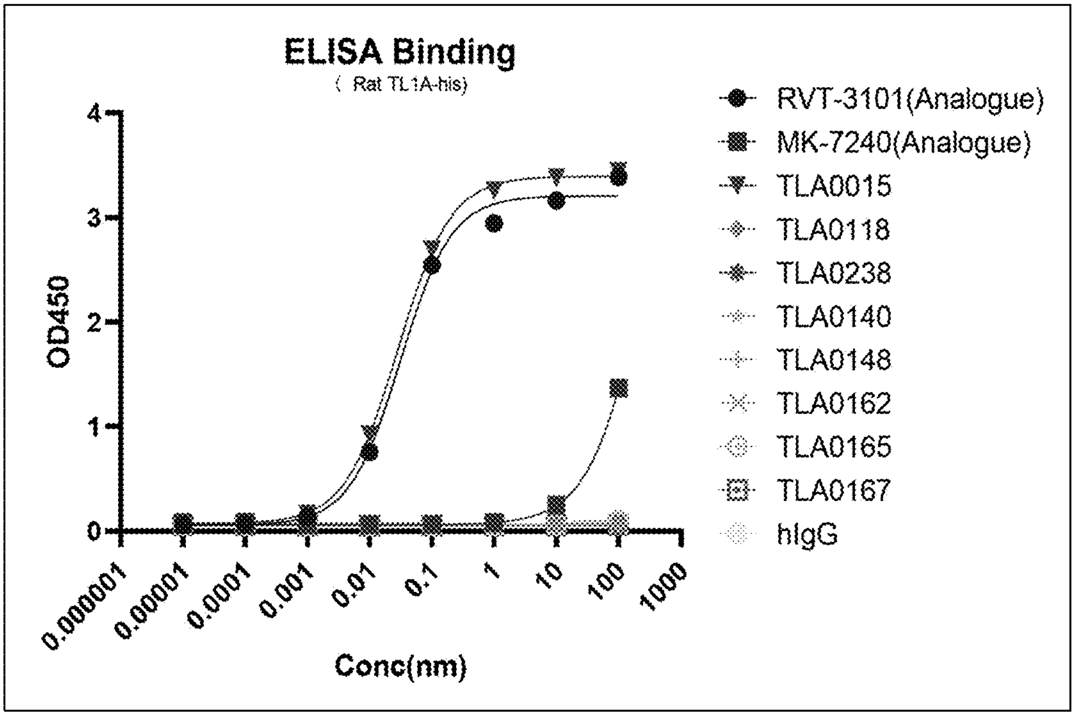
FIG. 6D shows the results of the ELISA assay for the binding capacity assay of the anti-TL1A antibody described in the present application to rat TL1A-his protein.

A certain amount of antibody to be tested was captured with the biosensor chip Protein A (GE, 29127556) affinity, and then a series of antigens (50 nM, 25 nM, 12.5 nM, 6.25 nM, 3.125 nM, 1.5625 nM) were passed on the surface of the chip to detect the reaction signal in real time to obtain binding and dissociation curves. After the completion of each cycle of dissociation, the biochips are washed and regenerated with 10 mM glycine-hydrochloric acid solution pH 1.5 (GE, BR-1003-54). The experimental data were fitted to a 1:1 model using Biacore Insight Evaluation Software 5.0 to calculate the value of the affinity. The binding curve of anti-TL1A antibody to human TL1A monomeric protein is shown in FIG. 2. The binding curve of the anti-TL1A antibody to the human TL1A trimeric protein is shown in FIG. 3: The binding curves of anti-TL1A antibody to monkey TL1A protein are shown in FIG. 4. The binding curves of anti-TL1A antibody to rat TL1A protein are shown in FIG. 5, and the affinity KD values are shown in Table 11.

TABLE 11

| Abs | Antigen | ka (1/Ms) | kd (1/s) | KD (M) |
|---|---|---|---|---|
| RVT-3101 (Analogue) | hTL1A-his monomer | | No binding | |
| MK-7240 (Analogue) | | 1.83e+06 | 1.00e−04 | 5.47e−11 |
| TLA0015-11 | | 8.39e+05 | 5.05e−04 | 6.02e−10 |
| TLA0238-5 | | 2.66e+05 | 3.91e−03 | 1.47e−08 |
| RVT-3101 (Analogue) | hTL1A-his trimer | 4.70e+05 | 1.04e−04 | 2.21e−10 |
| MK-7240 (Analogue) | | 3.93e+05 | 8.50e−05 | 2.16e−10 |
| TLA0015-11 | | 6.84e+05 | 1.36e−04 | 1.99e−10 |
| TLA0238-5 | | 1.86e+05 | 1.23e−04 | 6.57e−10 |
| RVT-3101 (Analogue) | cynoTL1A-his | 3.53e+05 | 8.79e−05 | 2.49e−10 |
| MK-7240 (Analogue) | | 5.38e+05 | 6.73e−05 | 1.25e−10 |
| TLA0015-11 | | 5.54e+05 | 1.40e−04 | 2.53e−10 |
| TLA0238-5 | | 2.10e+05 | 3.97e−04 | 1.89e−09 |
| RVT-3101 (Analogue) | Rat TL1A-his | 2.42e+05 | 6.87e−05 | 2.84e−10 |
| TLA0015-11 | | 5.54e+05 | 1.43e−04 | 2.58e−10 |

Example 8 ELISA Detects the Binding Ability of Anti-TL1A Antibody to TL1A-his Protein The binding ability of a plurality of antibodies prepared by example 6 of the present invention to human TL1A-his trimeric protein, mouse TL1A-his protein, monkey TL1A-his protein and rat TL1A-his protein is detected based on ELISA assay. The binding capacity of different antibodies is determined by comparing their binding curves to TL1A-his protein.

Recombinant human TL1A-his trimeric protein, murine TL1A-his, monkey TL1A-his, and rat TL1A-his protein was diluted to 2 μg/ml in PBS at 100 μl/well, respectively, added to the plate (coated with an equal amount of BSA as a control), and incubated overnight at 4° C. Remove the coating solution and incubate at 200 μl/well with 5% BSA blocking solution for 2 h at room temperature. Remove the blocking solution, wash three times with 250 μl/well 0.5% % PBST, then dilute the anti-TL1A specific antibody to 100 nM with the blocking solution, dilute 10-fold to form 8 concentration gradients (the highest concentration is 100 nM), add 100 μl/well sequentially to the blocked microplate plate, and incubate for 1 hour at room temperature. Wash the plate 3 times with PBST (remove residual droplets with absorbent paper) at 100 μl/well, add goat anti-human IgG antibody containing HRP label, and incubate for 45 min at room temperature. Wash the plate 5 times with 0.5‰ PBST at 100 μl/well, add TMB solution, incubate for 5 min at room temperature in the dark, at 100 μl/well, add stop solution, stop the substrate chromogenic reaction, read the OD value at 450 nm with a microplate reader, analyze the data with a GraphPad and calculate the EC50 (Table 12).

TABLE 12

EC50 values of anti-TL1A monoclonal antibody binding to TL1A protein ELISA in different species

| Abs | ELISA Binding EC50(nM) | | | |
|---|---|---|---|---|
| | huTL1A-his | Mouse TL1A-his | Cyno TL1A-his | Rat TL1A-his |
| RVT-3101 (Analogue) | 0.04 | 0.04 | 0.05 | 0.03 |
| MK-7240 (Analogue) | 0.06 | NA | 0.065 | NA |
| TLA0015 | 0.04 | 0.31 | 0.05 | 0.03 |
| TLA0118 | 0.04 | NA | 0.05 | NA |
| TLA0238 | 0.03 | | 0.04 | |
| TLA0140 | 0.03 | | 0.05 | |
| TLA0148 | 0.04 | | 0.05 | |
| TLA0162 | 0.05 | | 0.06 | |
| TLA0165 | 0.04 | | 0.05 | |
| TLA0167 | 0.04 | | 0.05 | |

The results of the assay are shown in FIG. 6, TLA0015, TLA0118, TLA0140, TLA0148, TLA0162, TLA00165, TLA0167, TLA0238 showed good binding activity with both human TL1A trimer protein and monkey TL1A protein, among which TLA0015 showed good binding activity with mouse TL1A protein and rat TL1A protein. TLA0015 also showed good binding activity to rat TL1A protein.

Example 9 FACS Detects the Binding Ability of Anti-TL1A Antibody to 293-TL1A Cell Line Based on flow cytometry assay, the binding ability of a plurality of antibodies prepared by example 6 to human TL1A molecules expressed on the surface of CHO-K1 cells was detected. The binding capacity of different antibodies was determined by comparing the binding curves of different antibodies to human TL1A molecules expressed on the surface of CHO-K1 cells.

The DNA sequence encoding the full-length protein of human TL1A was cloned into mDeZ (Zeocin resistance gene) vector, transiently transfected into CHO-K1 cells, and screened for 7 days by adding 100 μg/mL Zeocin (final concentration) after 24 h. After subcloning, a CHO-K1 cell line with high expression of human TL1A on the cell surface (CHO-K1-huTL1A) was obtained.

Figure 7:
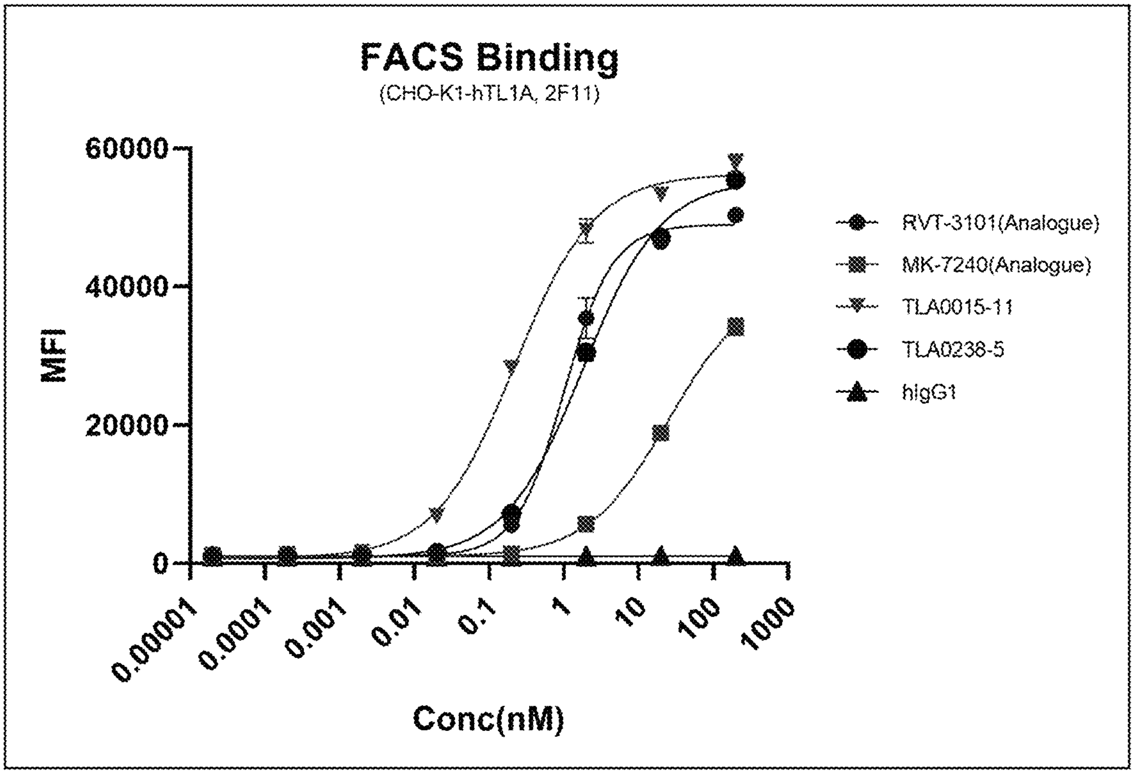
FIG. 7 shows the binding capacity of the anti-TL1A antibody described in the present application to CHO-K1-huTL1A cells.

In this experiment, CHO-K1 cells (CHO-K1-huTL1A) with high expression of human TL1A full-length protein on the cell surface were used as the target cells, and CHO-K1 cells were used as the negative control. CHO-K1-huTL1A and CHO-K1 cells were washed three times with staining buffer (PBS+2% FBS (Gibco, Cat #10091148)+5 mM EDTA (Gibco, Cat #15575020)) at 450 g each for 5 min and the supernatant was discarded. Resuspend cells in staining buffer and adjust the cell density to $1\times10^6$ cell/mL, 100 μL/well, and add to a 96-well plate. Anti-TL1A antibody and positive control antibody were diluted to 200 nM, 10-fold stepwise dilution of 8 gradients (maximum concentration 200 nM), 100 μL/well, added to a 96-well plate, and mixed well with CHO-K1-huTL1A cells. After 30 min of incubation at 4° C., the cells are washed twice in PBS to remove unbound antibodies to be tested. Add 100 μL/well of goat anti-human IgG-PE and incubate at 4° C. for 30 min. Centrifuge at 300 g for 5 min and wash the cells twice in PBS to remove unbound secondary antibody. Finally, the cells were resuspended in 200 μl PBS, and the binding capacity of the anti-TL1A antibody to CHO-K1-huTL1A cells was determined by a Beckman Coulter CytoFLEX flow cytometer. The resulting data were fitted and analyzed by GraphPad Prism software. The experimental results are shown in FIG. 7 and Table 13, and TLA0015-11 and TLA0238-5 have strong binding capacity to the CHO-K1-huTL1A cell line.

TABLE 13

EC50 of anti-TL1A antibody binding to CHO-K1-huTL1A cells

| Abs | EC50(nM) | Top MFI |
|---|---|---|
| RVT-3101 (Analogue) | 1.02 | 49017 |
| MK-7240 (Analogue) | 24.95 | 40329 |
| TLA0015-11 | 0.41 | 56310 |
| TLA0238-5 | 1.81 | 55419 |

Example 10 FACS Detects the Ability of TL1A Antibody to Block the Binding of TL1A-his to 293-DR3 Cells The ability of multiple antibodies prepared by example 6 to block the binding of huTL1A-his protein to human DR3 (DR3: UniprotKB NO. Q93038) expressed on the surface of Expi293 cells was detected based on a flow cytometry assay. The blocking ability of huTL1A-his protein is determined by comparing the curves of different antibody concentrations blocking huTL1A-his protein to 293-huDR3 cells.

Figure 8:
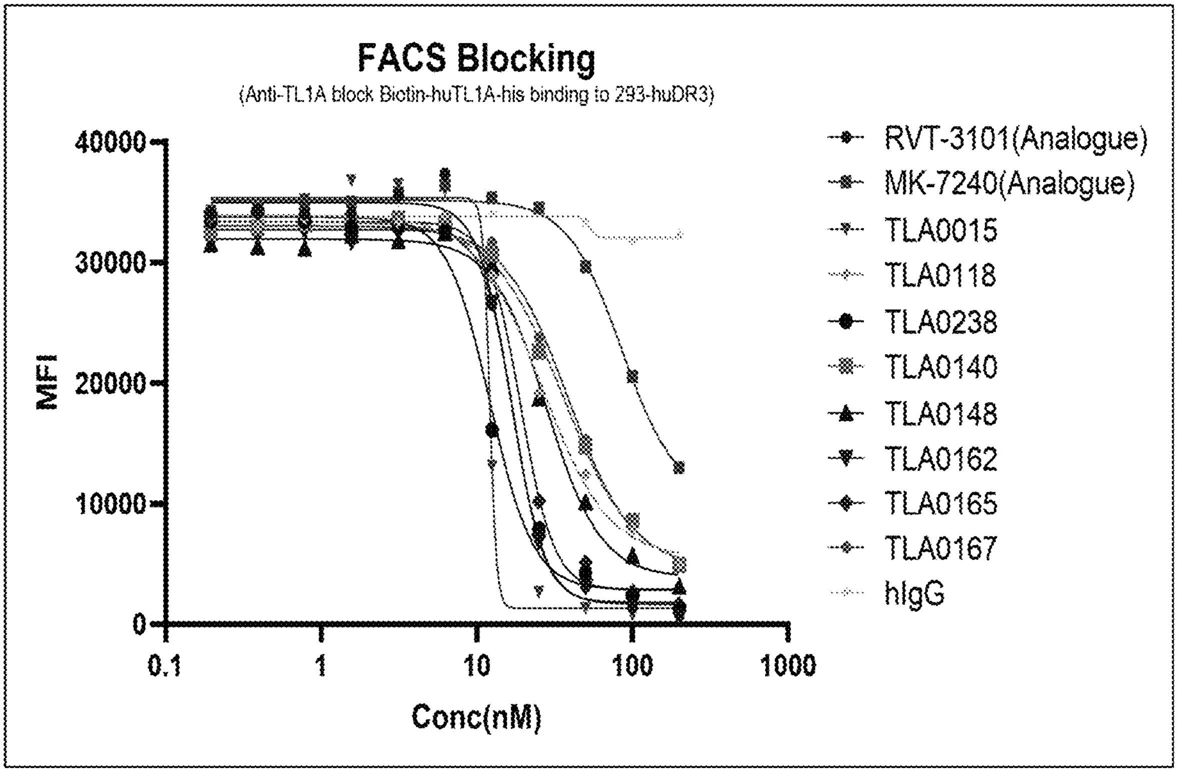
FIG. 8 shows the anti-TL1A antibody described in the present application blocking TL1A-his protein binding to 293-DR3 cells.

The DNA sequence of the receptor DR3 extracellular domain protein encoding TL1A was cloned into the mDeZ-TM (with transmembrane sequence and Zeocin resistance gene) vector, transiently transfected into Expi293 cells, and 100 μg/mL Zeocin (final concentration) was added 24 h later for 7 days to obtain the Expi293 cell line (293-huDR3) expressing human DR3 on the cell surface. The huTL1A-his-Biotin protein was obtained by Biotin conjugation using a biotin labeling kit (ThermoFisher, A35389). FACS Binding was used to determine the EC80 concentration of protein binding between huTL1A-his-Biotin protein and 293-huDR3 cells. Wash 293-huDR3 cells three times with staining buffer (PBS+2% FBS (Gibco, Cat #10091148)+5 mM EDTA (Gibco, Cat #15575020)) at 300 g each for 5 min and discard the supernatant. Resuspend cells in PBS, adjust the cell density to $5\times10^5$ cells/mL, 100 μL/well, add to a 96-well plate, centrifuge to remove the supernatant, and add 2*EC80 concentration of huTL1A-his-Biotin protein, 50 μL/well. Anti-TL1A antibody and positive control antibody were diluted to 400 nM, 2-fold stepwise dilution of 12 gradients (up to 200 nM final concentration) at 50 μL/well, added to 96-well plates, and mixed well with huTL1A-his-Biotin protein and 293-huDR3 cells. Incubate at 4° C. for 30 min. Cells are washed twice in PBS to remove unbound antibodies to be tested. Add 100 μL/well of Streptavidin-PE secondary antibody and incubate at 4° C. for 30 min. Centrifuge at 300 g for 5 min and wash the cells twice in PBS to remove unbound secondary antibody. Finally, the cells were resuspended in 200 μl PBS, and the ability of the anti-TL1A antibody to block the binding of TL1A protein to 293-huDR3 cells was determined by a Beckman Coulter CytoFLEX flow cytometer. The resulting data were fitted and analyzed by GraphPad Prism software. The results are shown in FIG. 8 and Table 14, and the antibodies to TLA0015, TLA0118, TLA0140, TLA0148, TLA0162, TLA00165, TLA0167, and TLA0238 all have the ability to block the binding of TL1A-his protein to 293-DR3 cells.

TABLE 14

Anti-TL1A antibody blocking activity-IC50 values

| Abs | IC50 (nM) | Bottom (MFI) |
|---|---|---|
| RVT-3101 (Analogue) | 16.68 | 1668 |
| MK-7240 (Analogue) | 85.05 | 10492 |
| TLA0015 | 12.10 | 1326 |
| TLA0118 | 26.21 | 5403 |
| TLA0238 | 12.19 | 2855 |
| TLA0140 | 35.79 | 4416 |
| TLA0148 | 28.08 | 3886 |
| TLA0162 | 17.27 | 1802 |
| TLA0165 | 19.15 | 2826 |
| TLA0167 | 38.48 | 4581 |

Figure 9:
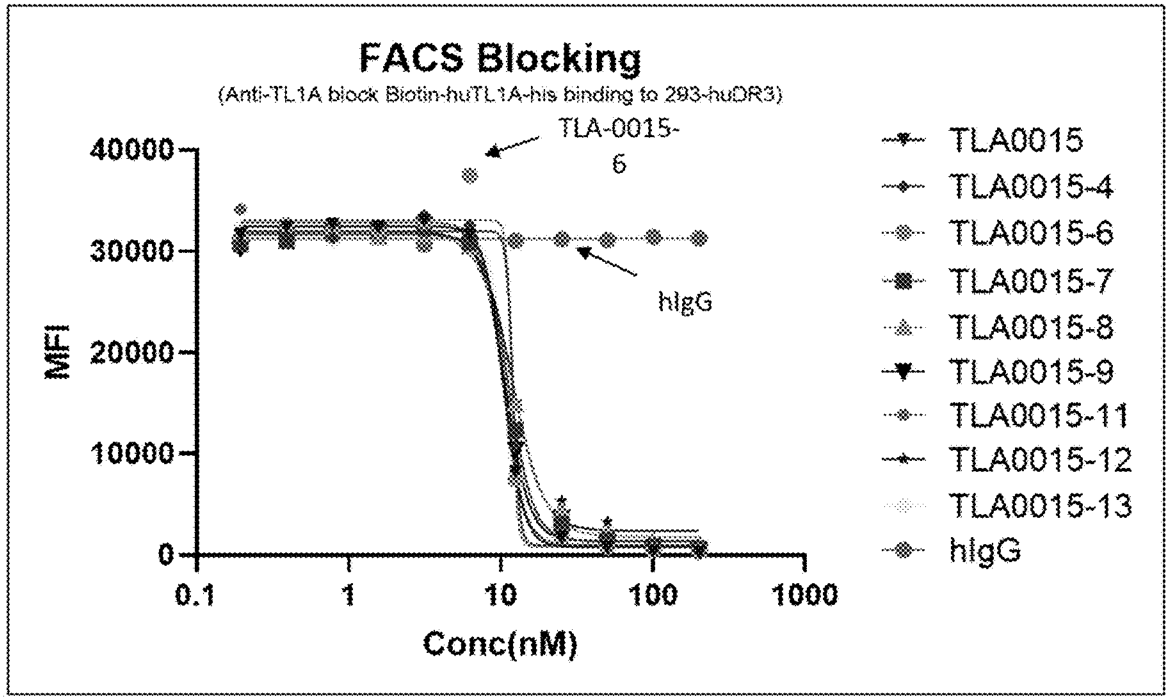
FIG. 9 shows the blocking activity of anti-TLA0015 humanized antibodies described in this application.

The blocking effect of TLA0015 humanized antibody on human TL1A-his trimeric protein was detected, and the specific results are shown in FIG. 9 and Table. 15

TABLE 15

TLA0015 humanized antibody blocking activity-IC50 values

| Abs | IC50 (nM) | Bottom (MFI) |
|---|---|---|
| TLA0015 | 10.52 | 263 |
| TLA0015-4 | 12.03 | 327 |
| TLA0015-6 | 11.83 | 300 |
| TLA0015-7 | 11.29 | 605 |
| TLA0015-8 | 11.89 | 1059 |
| TLA0015-9 | 10.76 | 519 |
| TLA0015-11 | 10.33 | 363 |
| TLA0015-12 | 11.92 | 916 |
| TLA0015-13 | 11.01 | 642 |

Figure 10:
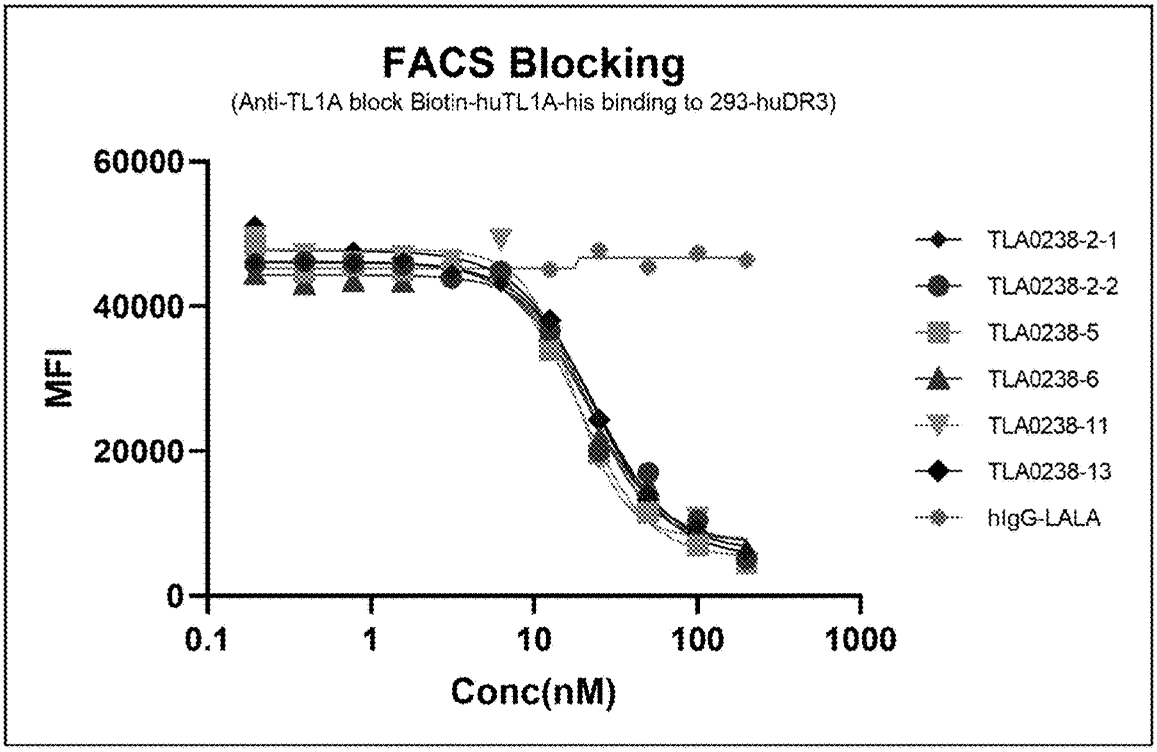
FIG. 10 shows the TLA0238 humanized antibody blocking activity as described in this application.

The blocking effect of TLA0238 humanized antibody on human TL1A-his protein was detected, and the specific results are shown in FIG. 10 and Table 16.

TABLE 16

TLA0238 humanized antibody blocking activity-IC50

| Abs | IC50 (nM) | Bottom (MFI) |
|---|---|---|
| TLA0238-2-1 | 23.92 | 6053 |
| TLA0238-2-2 | 21.06 | 5117.9 |
| TLA0238-5 | 19.29 | 4534.9 |
| TLA0238-6 | 22.29 | 6333.3 |
| TLA0238-11 | 17.64 | 4485.9 |
| TLA0238-13 | 22.99 | 5570.1 |

Example 11 Fluorescent Reporter Gene Method to Detect the Ability of TL1A Antibody to Inhibit NF-κB Signaling Pathway A luciferase reporter gene-based method was used to test the ability of the plurality of antibodies of the present invention obtained by example 6 to inhibit the NF-κB signaling pathway in soluble or membrane-bound TL1A-activated TF-1 (endogenously expressing DR3) cells. The TF-1-NFκB-Luc cell line was purchased from Genomeditech Biotechnology Ltd (GM-C30289, H_TNFSF15 (TL1A) Reporter Cell Line) and screened using NF-κB-Luciferase lentiviral infection of TF-1 cells.

Figure 11A:
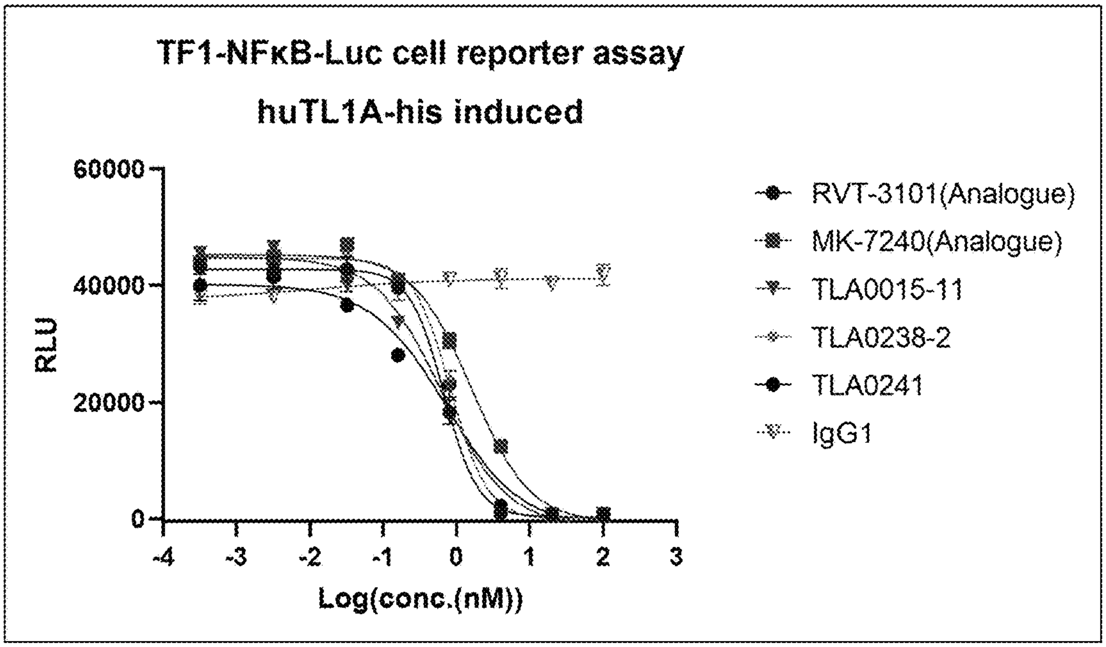
FIGS. 11A-11D show the inhibition of soluble TL1A-activated NF-κB signaling pathway by the anti-TL1A antibodies described in this application.
Figure 11B:
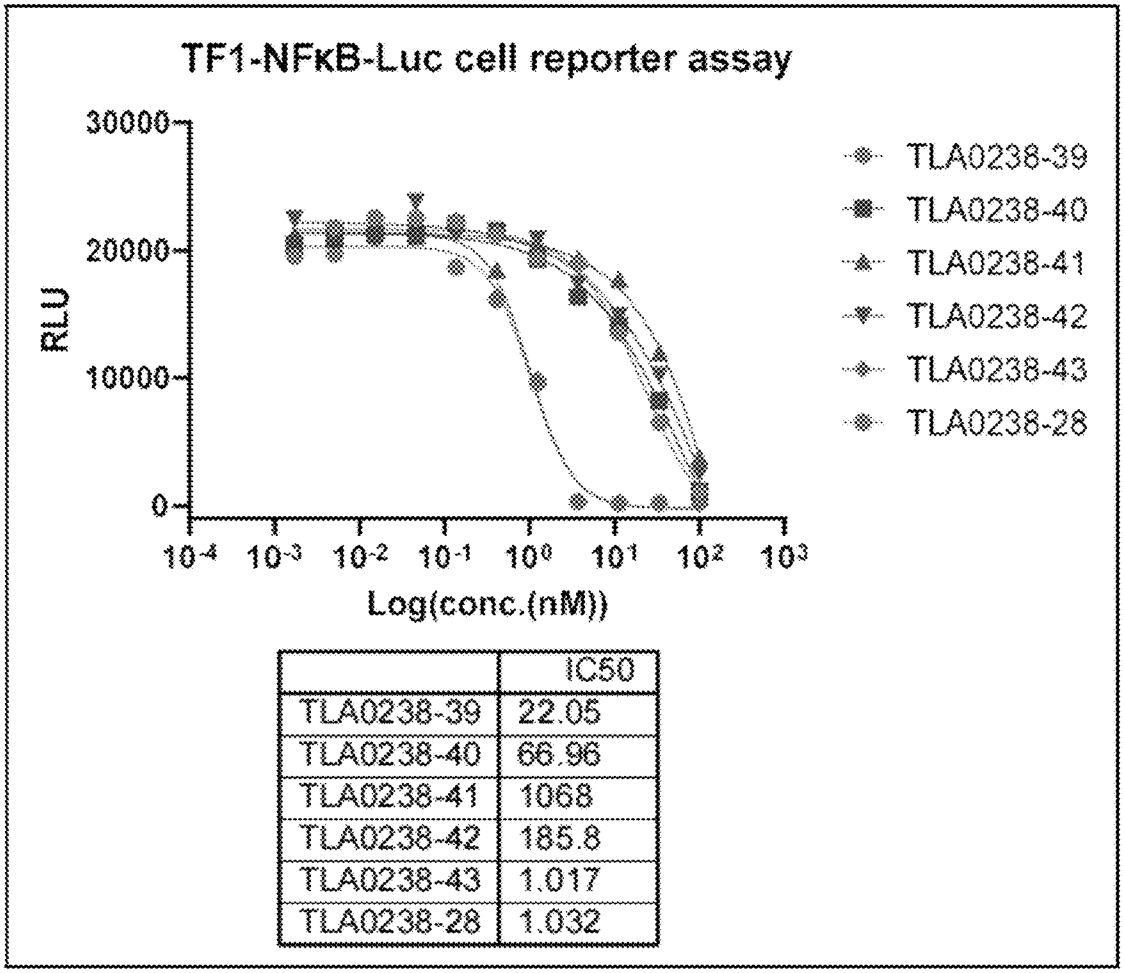
Figure 11C:
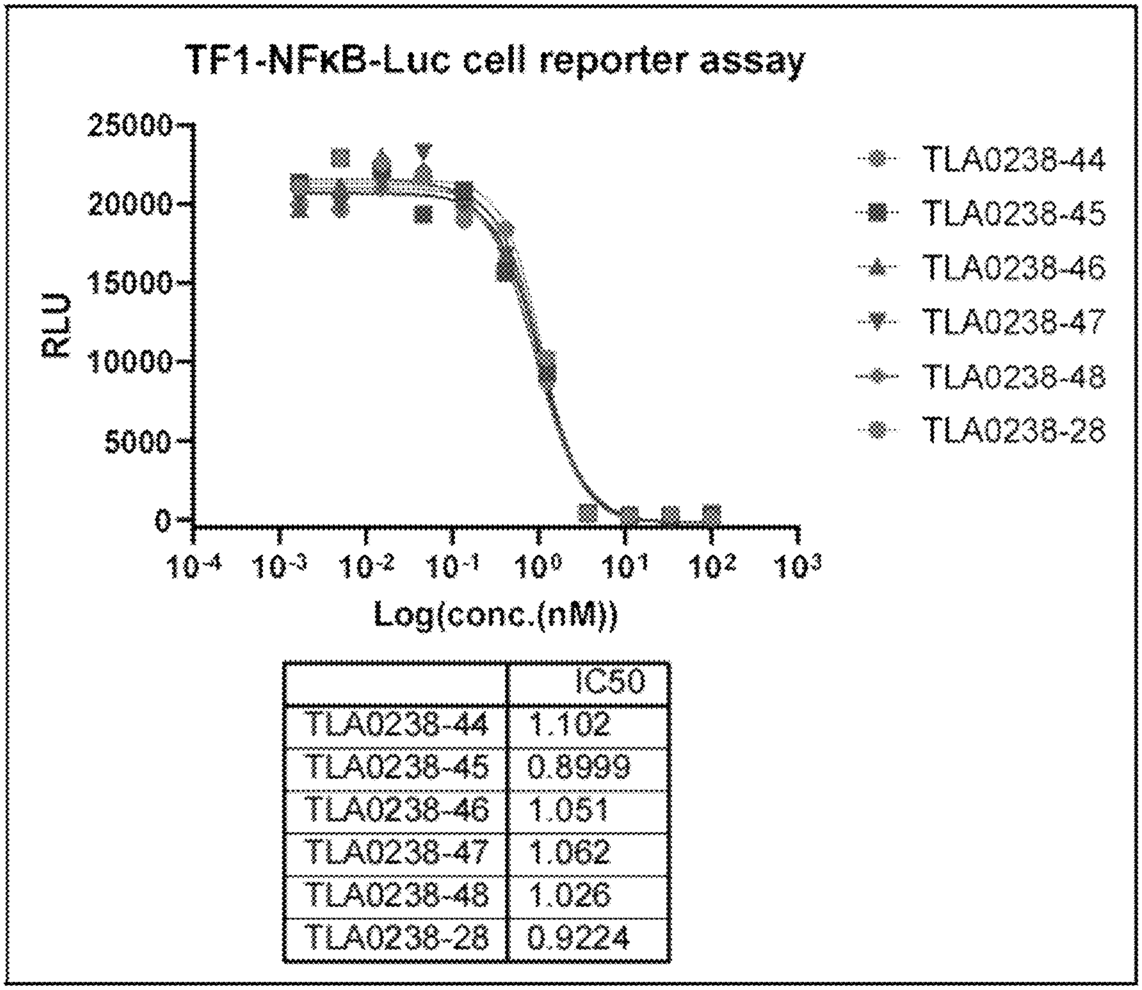
Figure 11D:
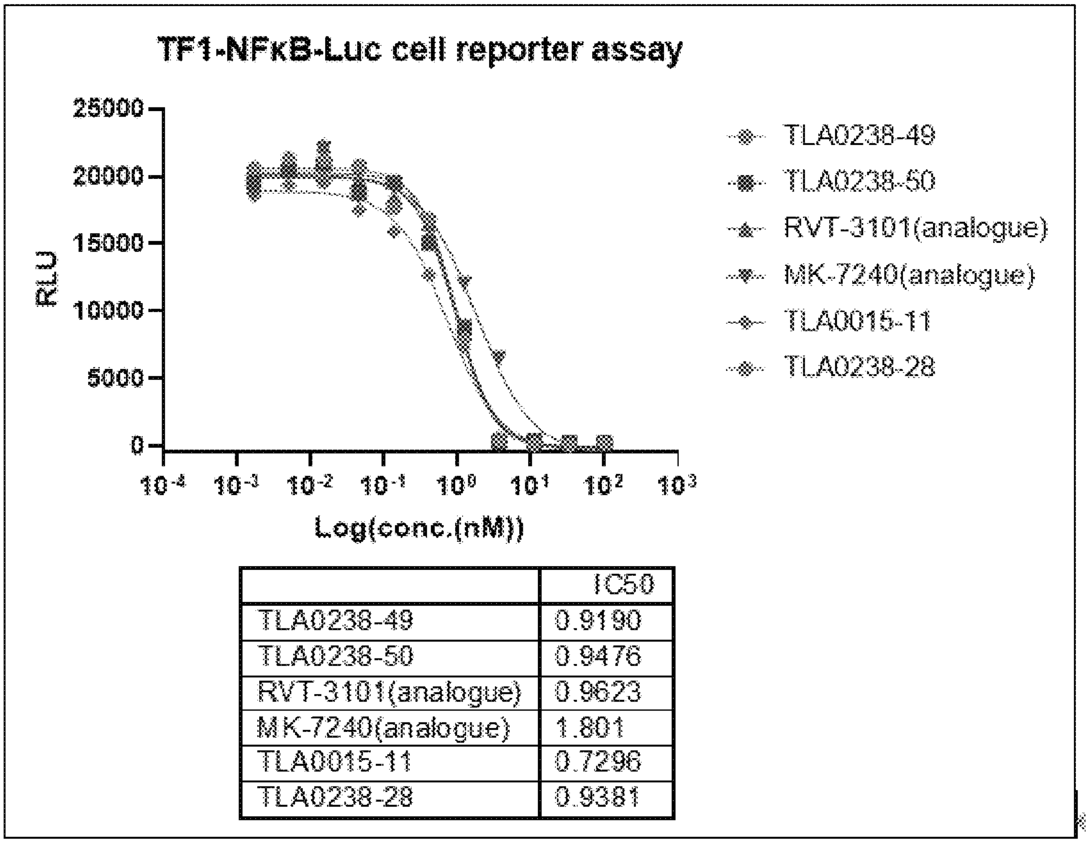

Fluorescent reporter gene method for soluble TL1A protein activation. In this study, TF1-NFκB-luc cells were used to detect the biological activity of anti-TL1A antibody to inhibit the DR3-NFκB signaling pathway activated by soluble TL1A. In this experiment, 3× of the analytical concentration of huTL1A-his antigen solution was prepared with analytical buffer (RPMI 1640 medium+1% FBS) at 0.9 μg/ml (final concentration of 0.3 μg/ml) and added to a white 96-well flat-bottom plate at 40 μl/well. Prepare 3× analytical concentrations of anti-TL1A antibody with a maximum concentration of 300 nM (final concentration of 100 nM), 5-fold serial dilution for a total of 8 concentration points. After the antibody is diluted, 40 μl/well is added to the above white 96-well flat-bottom plate, and then the white 96-well flat-bottom plate is placed in a carbon dioxide incubator to pre-incubate the TL1A antibody and antigen for 1 h. During the antibody and antigen pre-incubation, TF1-NFκB-luc cells were centrifuged (300 g, 5 min) and then resuspended with analysis buffer and counted, and the cell density was adjusted to 5E5 cells/ml. After the antigen and antibody incubation time is over, take out the white 96-well flat-bottom plate, inoculate TF1-NFκB-luc cells with adjusted density at 40 μl/well, and continue to incubate in a carbon dioxide incubator for 6 h. At the end of the incubation, remove the white 96-well flat-bottom plate from the incubator, add 60 μl of Bio-Lite Luciferase Assay reagent (Vazyme, DD1201-02) to each well, shake slightly for 5 minutes, and read the RLU value on a multimode microplate reader. Graphpad was used to plot the logarithm of the sample concentration with the measured signal values, and the results are shown in FIG. 11A and Table 17: TLA0015-11, TLA0238-2, and TLA0241 antibodies all have good activity to inhibit the NF-κB signaling pathway activated by soluble TL1A. In addition, the results of the inhibitory activity of other humanized antibodies of TLA0238 are shown in FIGS. 11B, 11C and 11D. As shown in the figures, the inhibitory activity of antibodies TLA0238-43, TLA0238-44, TLA0238-45, TLA0238-46, TLA0238-47, TLA0238-48, TLA0238-49 and TLA0238-50 are all very good.

TABLE 17

Anti-TL1A antibody inhibits the NF-κB signaling pathway-IC50 values activated by soluble TL1A

| Abs | IC50 (nM) |
|---|---|
| RVT-3101 (Analogue) | 0.674 |
| MK-7240 (Analogue) | 1.622 |
| TLA0015-11 | 0.631 |
| TLA0238-2 | 0.829 |
| TLA0241 | 0.725 |

Figure 12:
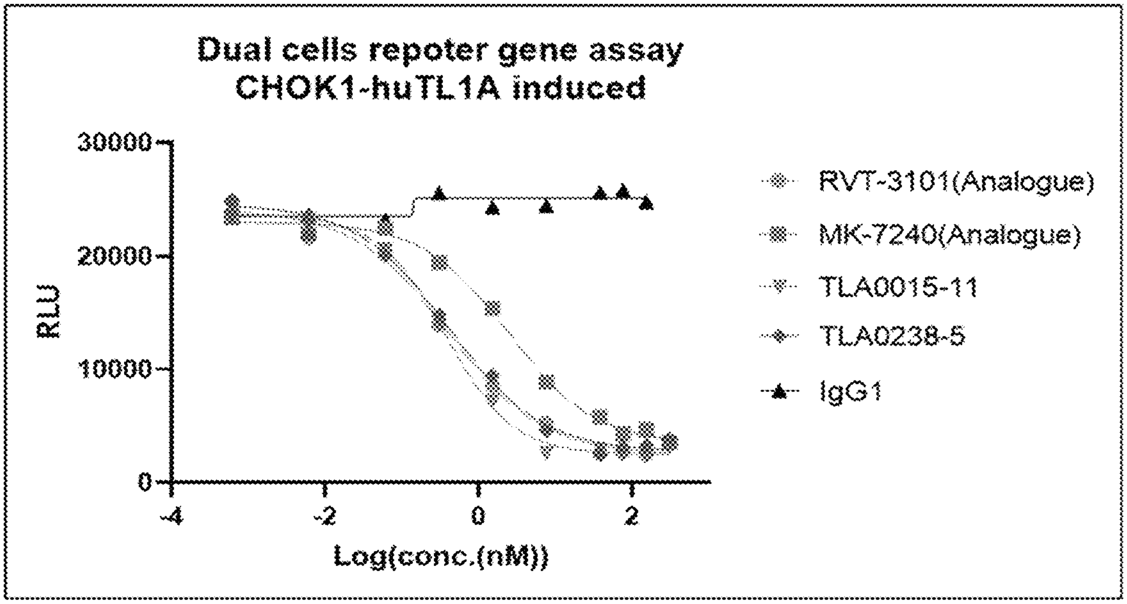
FIG. 12 shows the inhibition of the membrane-bound TL1A-activated NF-κB signaling pathway by the anti-TL1A antibodies described in this application.

Fluorescent reporter method for membrane-bound TL1A activation. In this study, CHO-K1-TL1A cells (overexpressing human full-length TL1A were constructed on CHO-K1 cells) and TF1-NFκB-luc cells were used to evaluate the biological activity of anti-TL1A antibody against membrane-bound TL1A-DR3-NFκB signaling pathway. CHO-K1-TL1A cells were digested, centrifuged (300 g, 5 min), resuspended with F-12K complete medium and counted, the cell density was adjusted to 5E5 cells/ml, and 100 μl/well seeded in white 96-well flat-bottom plates were cultured overnight. The next day, prepare 2× analytical concentrations of anti-TL1A antibody with analytical buffer (RPMI 1640 medium+1% FBS) at a maximum concentration of 200 nM (final concentration of 100 nM).), 5-fold serial dilution for a total of 8 concentration points. After diluting the antibody, remove the white 96-well flat-bottom plate inoculated with CHO-K1-TL1A cells, aspirate the culture supernatant, and add 50 μl of the above diluted antibody to each well. Continue to pre-incubate the white 96-well flat-bottom plate in a CO2 incubator for 30 min. During the pre-incubation, TF1-NFκB-luc cells were centrifuged (300 g, 5 min) and then resuspended with analysis buffer and counted, and the cell density was adjusted to 1E6 cells/ml. After the pre-incubation time is over, remove the white 96-well flat-bottom plate and inoculate TF1-NFκB-luc cells with adjusted density at 50 μl/well. Place the white 96-well flat-bottom plate in a carbon dioxide incubator and continue to incubate for 6 h. At the end of the incubation, remove the white 96-well flat-bottom plate from the incubator, add 50 μl of Bio-Lite Luciferase Assay reagent to each well, and read the RLU value on a multimode microplate reader after 5 min of slight shaking. The results of the logarithm of the sample concentration and the measured signal value were shown in FIG. 12 and Table 18, and both TLA0015-11 and TLA0238-5 antibodies had good activity in inhibiting the NF-κB signaling pathway activated by membrane-bound TL1A.

TABLE 18

Anti-TL1A antibody inhibits membrane-bound TL1A-activated NF-κB signaling

| Abs | EC50 (nM) |
|---|---|
| RVT-3101 (Analogue) | 0.393 |
| MK-7240 (Analogue) | 2.450 |
| TLA0015-11 | 0.363 |
| TLA0238-5 | 0.401 |

Example 12 Detection of the Ability of Anti-TL1A Antibody to Inhibit TL1A-DR3-Activated Caspase3/7

A method based on the Caspase-Glo® 3/7 Assay System Activity Detection Kit (Promega, Cat #G8092) was used to assay the ability of the plurality of antibodies of the present invention, prepared by example 6, to inhibit the TL1A-induced apoptosis signaling pathway in TF-1 (endogenously expressing DR3) cells. The inhibitory capacity was determined by comparing the curves of caspase3/7 activity of TF-1 cells inhibited by different antibody concentrations.

Figure 13:
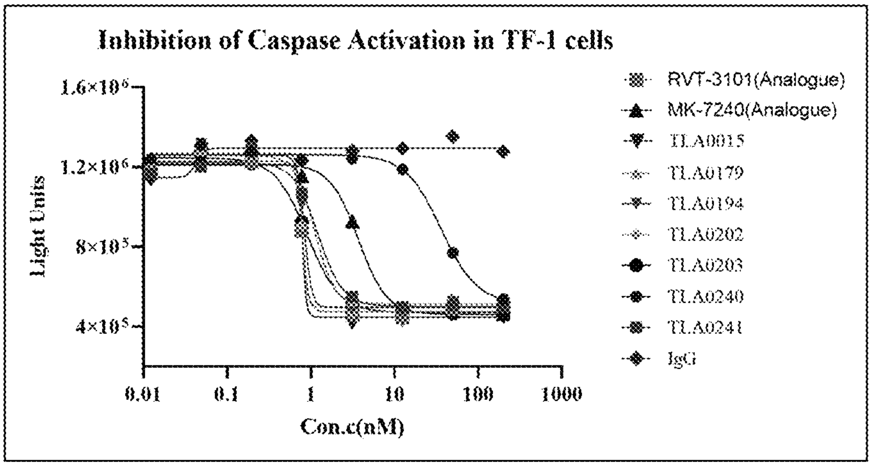
FIG. 13 shows the inhibition of TL1A-activated Caspase3/7 activity by an anti-TL1A antibody as described in the present application.

The huTL1A-his protein was configured to a 4× working concentration of 16 nM: the Cycloheximide small molecule drug was configured to a 4× working concentration of 10 μg/ml. 25 μl of the mixture was added to each well in a white-bottomed 96-well plate. Antibody starting concentration was configured as 10 nM, 2-fold dilution, 8 concentrations, 25 μl of each in a white-bottomed 96-well plate. Pre-incubate the above mixture at 37° C. for 1h. At the same time, centrifuge the TF-1 cells (300 g for 5 min) and resuspend them with buffer (1640 medium+10% FBS) and count them, and adjust the cell density to 1E6 cells/ml. When the incubation time of the antigen-antibody is over, take out the white 96-well plate, inoculate the TF-1 cells according to the adjusted density of 50 μl/well, and add 25 μl to each well in the white 96-well plate. After incubation, take out the white 96-well flat-bottom plate, inoculate with the adjusted density of TF-1 cells at 50 μl/well, and continue to incubate for 6 h in a carbon dioxide incubator. After incubation, take out the plate from the incubator and equilibrate the plate at room temperature for about 30 min, and take out the Caspase-Glo® 3/7 Assay System reagent beforehand and equilibrate the plate at room temperature. Add Caspase-Glo® 3/7 Assay System reagent, 50 μl per well, shake the shaker at 300 rpm for 30 s, and then let it stand for 15-30 min to make the cells fully lysed, and then read the RLU value on the multifunctional enzyme labeling instrument, and then make a four-parameter fit plot with the measured RLU value after taking the logarithm of the sample concentration using the Graphpad, the results are shown in FIG. 13 and Table 19. The results are shown in FIG. 13 and Table 19. TLA0015, TLA0179, TLA0194, TLA0202, TLA0203 and TLA0241 antibodies all functioned well to inhibit Caspase3/7 activity.

TABLE 19

Inhibition of TL1A-activated caspase3/7 activity by anti-TL1A antibody-IC50

| Abs | IC50 (nM) |
|---|---|
| RVT-3101 (Analogue) | 0.79 |
| MK-7240 (Analogue) | 3.70 |
| TLA0015 | 0.80 |
| TLA0179 | 1.10 |
| TLA0194 | 0.84 |
| TLA0202 | 0.79 |
| TLA0203 | 0.91 |
| TLA0240 | 36.20 |
| TLA0241 | 1.22 |

Figure 14A:
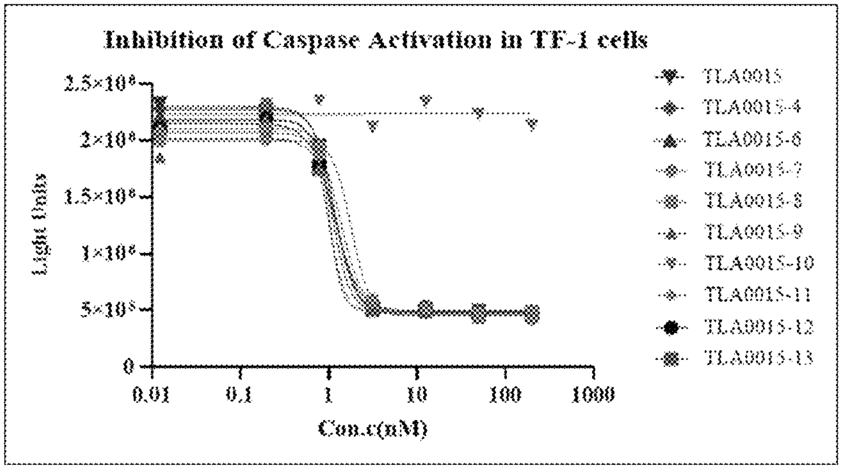
FIGS. 14A-14B show the inhibition of TL1A-activated Caspase3/7 activity by the TLA0015 humanized antibodies described in this application.
Figure 14B:
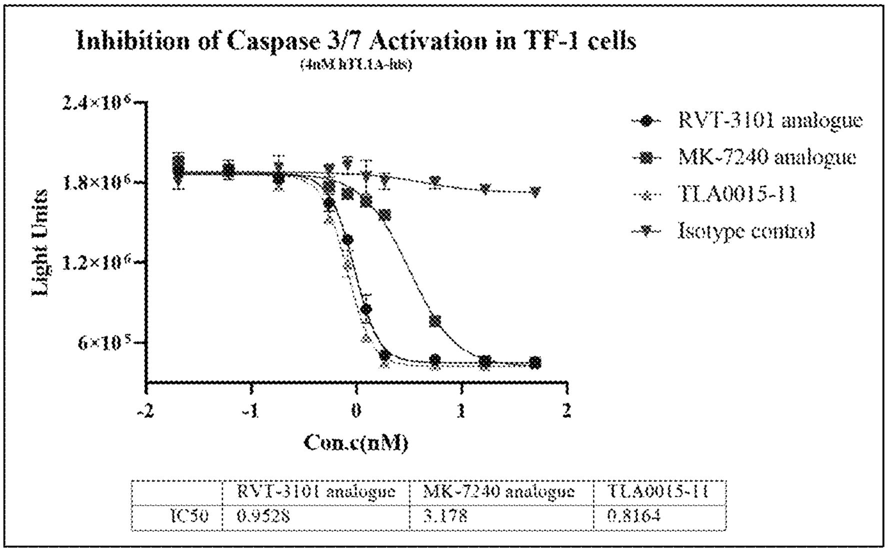
Figure 15A:
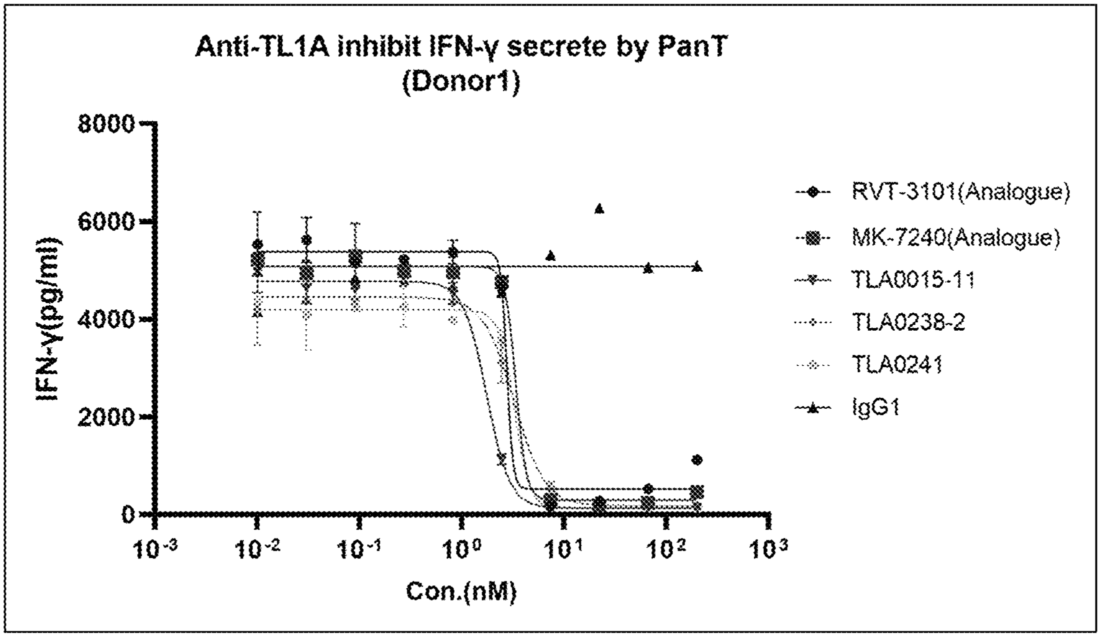
FIG. 15A shows that the anti-TL1A antibody described in this application inhibits IFN-γ secretion by T cells (Donor 1)
Figure 15B:
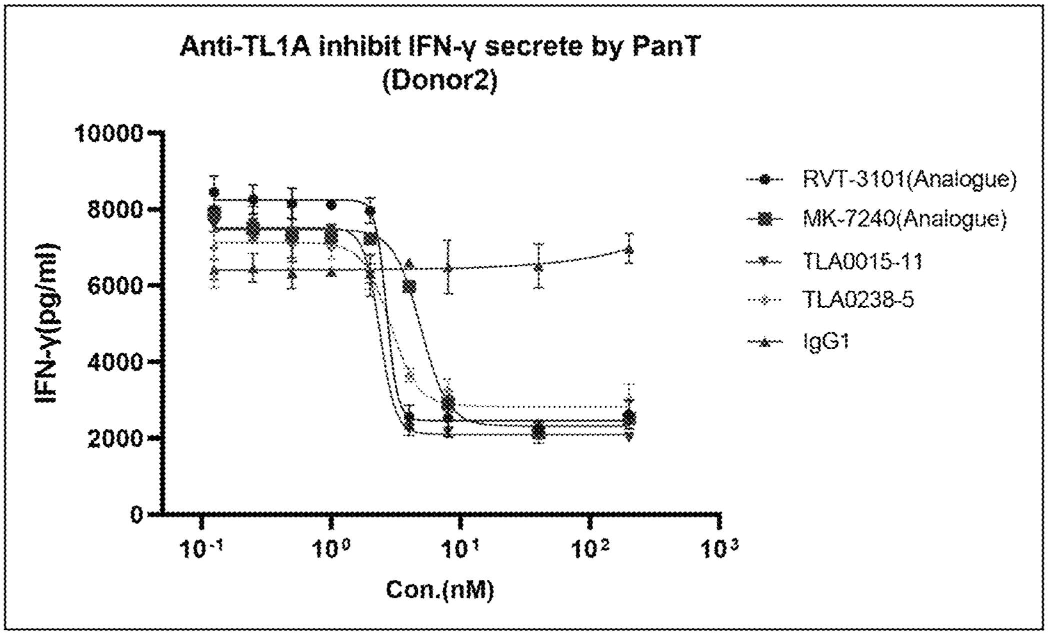
FIG. 15B shows an anti-TL1A antibody as described in the present application inhibiting IFN-γ secretion by T cells (Donor 2)
Figure 15C:
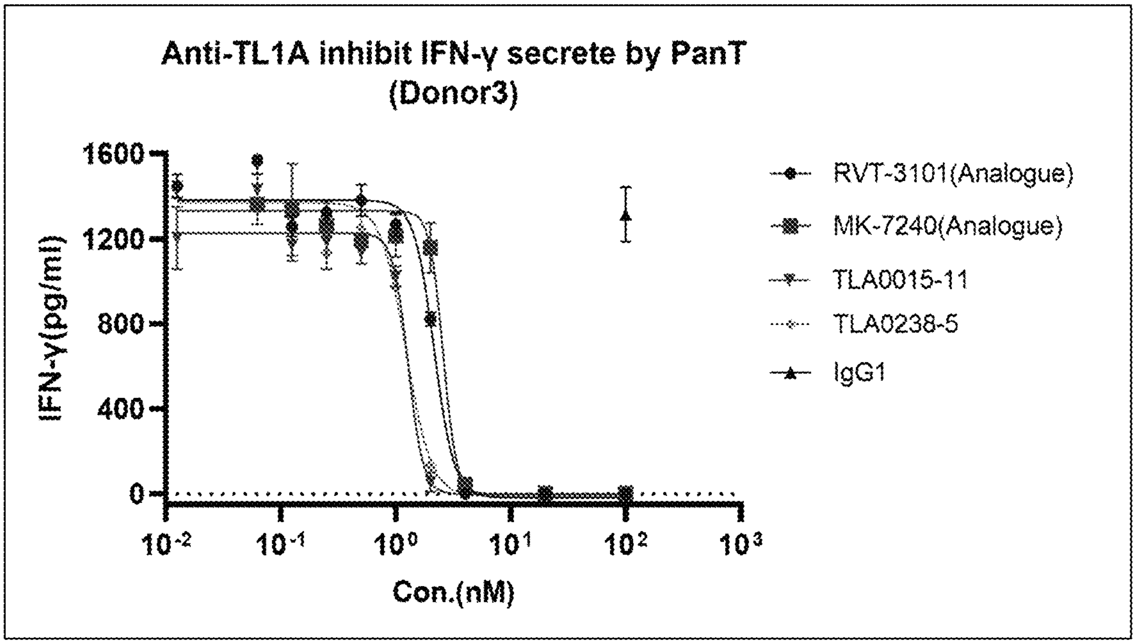
FIG. 15C shows an anti-TL1A antibody as described in the present application inhibiting IFN-γ secretion by T cells (Donor 3)
Figure 15D:
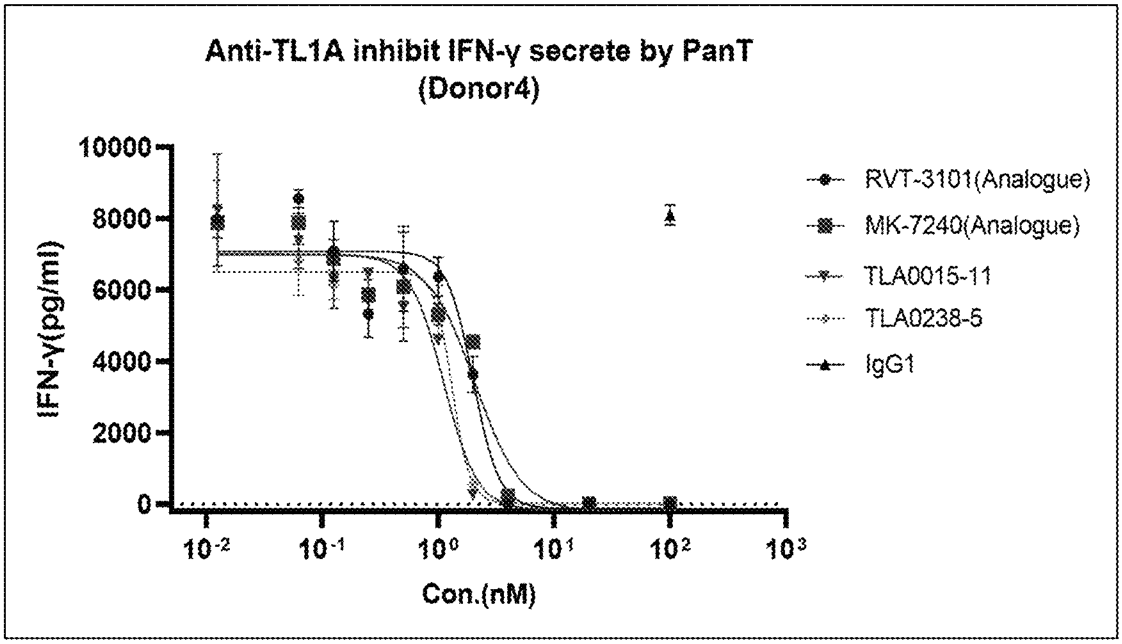
FIG. 15D shows an anti-TL1A antibody inhibiting IFN-γ secretion by T cells as described in the present application (Donor 4)

To test the ability of TLA0015 humanized antibodies to inhibit the TL1A-induced apoptosis signaling pathway in TF-1 cells. TLA0015 humanized antibodies (FIG. 14 and Table 20) have a good function of inhibiting caspase 3/7 activity. In addition, the activity difference between the humanized antibody TLA0015-11 and the control antibody was compared. As shown in FIG. 14C, the inhibitory activity of TLA0015-11 was superior to that of the control antibodies RVT-3101 and MK-7240.

TABLE 20

Inhibition of TL1A-activated caspase3/7 activity by TLA0015 humanized antibody

| Abs | IC50 (nM) |
|---|---|
| TLA0015 | 1.16 |
| TLA0015-4 | 1.15 |
| TLA0015-6 | 1.10 |
| TLA0015-7 | 1.80 |
| TLA0015-8 | 1.37 |
| TLA0015-9 | 1.25 |
| TLA0015-10 | 2.40 |
| TLA0015-11 | 1.03 |
| TLA0015-12 | 1.16 |
| TLA0015-13 | 0.98 |

Figure 16A:
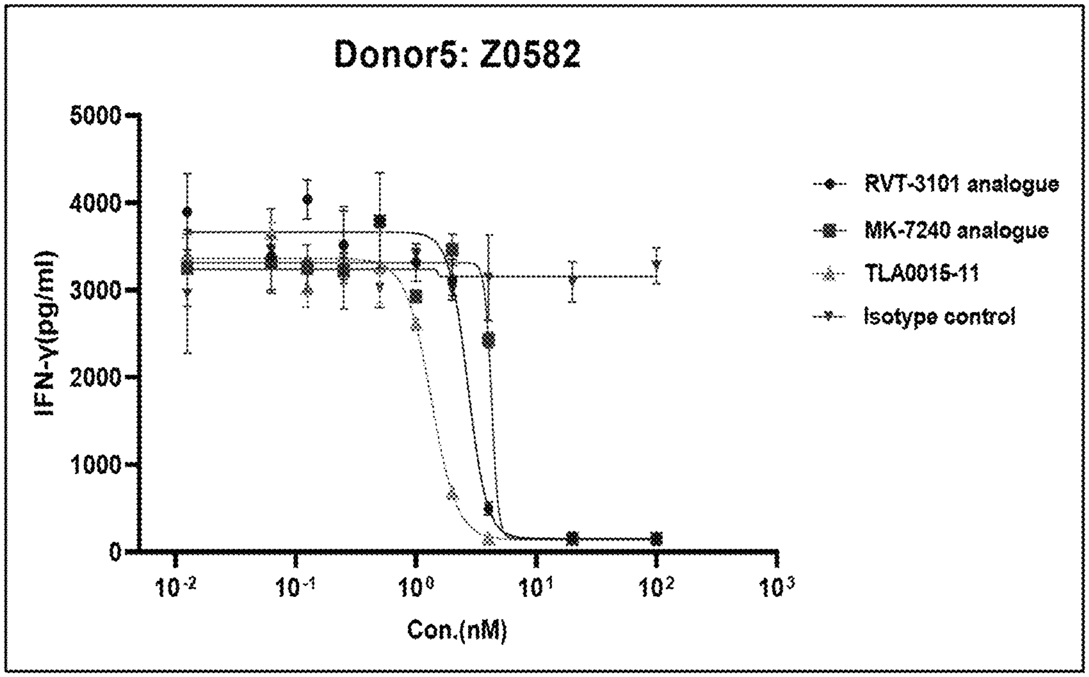
FIGS. 16A-16C shows an anti-TL1A antibody as described in the present application inhibiting TNF-α secretion by T cells (Donor 5-7)
Figure 16B:
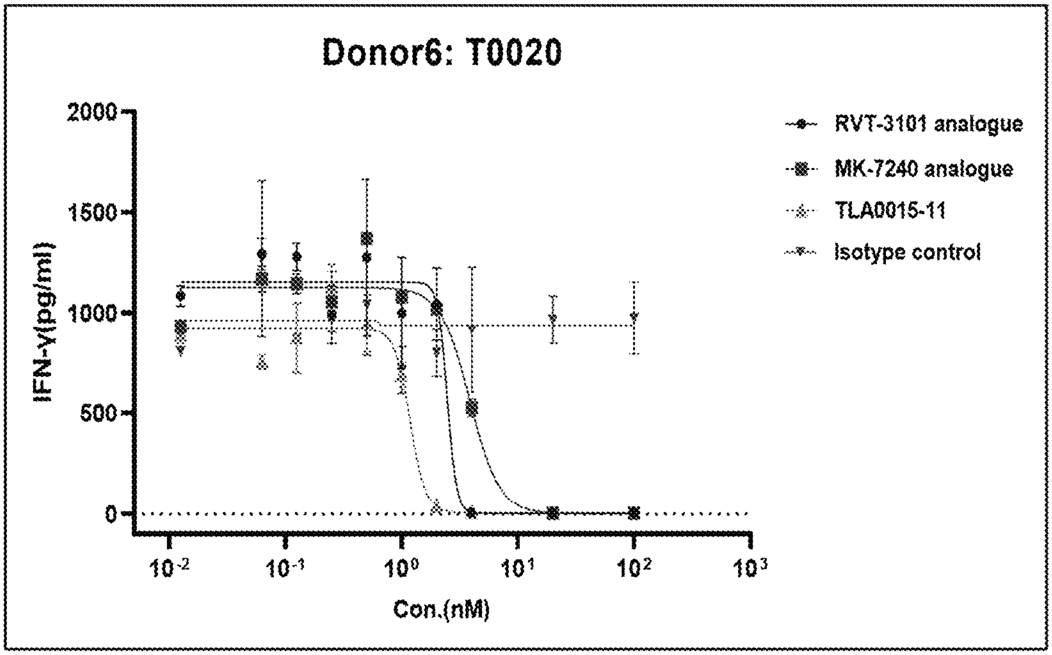
Figure 16C:
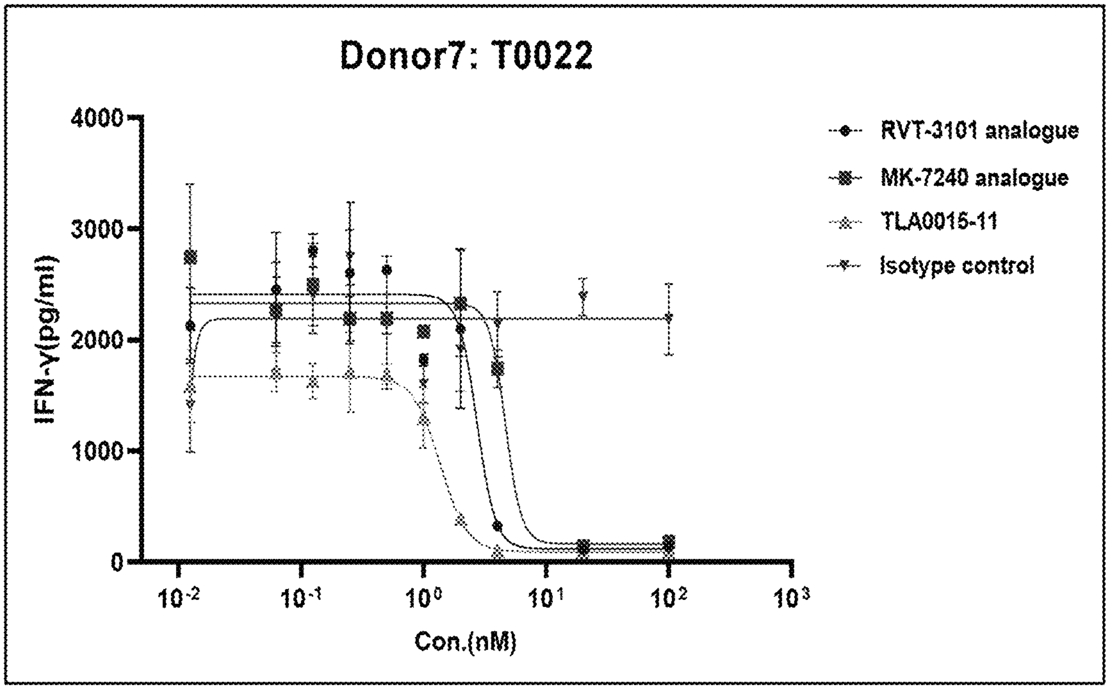

Example 13 Detection of the Inhibitory Effect of Anti-TL1A Antibody on T Cells In this study, the inhibitory ability of anti-huTL1A antibody to immune cell activation was evaluated by measuring the amount of cytokines in the culture supernatant of CD3+ T cells isolated from fresh healthy human peripheral blood. Fresh healthy human PBMCs (purchased from Saili Bio) were centrifuged (500 g for 5 min) and the supernatant was discarded, and the cells were resuspended with PBS (containing 2% FBS+5 mM EDTA), counted, and the cell density was adjusted to 5E7 cells/mL. Use the CD3 negative selection kit (Biolegend, Cat #480131) to sort T cells according to the kit instructions. T cells were washed twice with PBS, centrifuged at 500 g each for 5 min, and the supernatant was discarded. Resuspend T cells with RPMI 1640 complete medium, count, adjust the cell density to 1.5E6 cells/mL, 100 μl/well, and add to a 96-well plate. Complete culture with RPMI 1640 was prepared with TL1A (final concentration 10 nM), IL-12 (final concentration 0.5 ng/ml), IL-18 (final concentration 5 ng/mL) mixed solution, 50 μl/well, and added to a 96-well plate. Dilute the antibody to be tested to 800 nM, followed by a 3-fold stepwise dilution of 10 gradients (final concentration up to 200 nM), 50 μl/well add to a 96-well plate. The 96-well plate was placed in a carbon dioxide incubator, incubated for 24 hours, removed, centrifuged at 500 g for 5 minutes, and the supernatant was aspirated and placed on ice for later use. The amount of cytokine IFN-γ in the supernatant was detected using the BD™ Cytometric Bead Array (human IFN-γ) kit. Prepare the standard according to the instructions, dilute the sample, 50 μl/well per well, and add to the 96-well plate. Prepare Capture beads solution at 50 μl/well per well, add to a 96-well plate, and incubate the standard/sample with the Capture beads solution for 1 h. Dilute the detection antibody solution according to the instructions, 50 μl/well per well, add to a 96-well plate, and incubate for a total of 2 h. Centrifuge at 300 g for 5 min, discard the supernatant, and wash with wash buffer. Centrifuge again at 300 g for 5 min, discard the supernatant, resuspend with wash buffer, 70 μl/well, and determine the amount of cytokine IFN-γ by Beckman CytoFLEX flow cytometer. The obtained data were fitted and analyzed by GraphPad Prism software, and the results are shown in FIG. 15, and both TLA0015-11 and TLA0238-5 have good inhibition activity of IFN-γ in PBMCs in different healthy people. The inhibitory activity of TLA0015-11 on IFN-γ secretion by T cells was tested in several different PBMCs at the same time, and the results are shown in FIGS. 16A-16C. TLA0015-11 has a very good inhibitory activity against IFN-γ in three different PBMCs, and the inhibitory activity is better than that of the control antibodies RVT-3101 (analog) and MK-7240 (analog).

Figure 17:
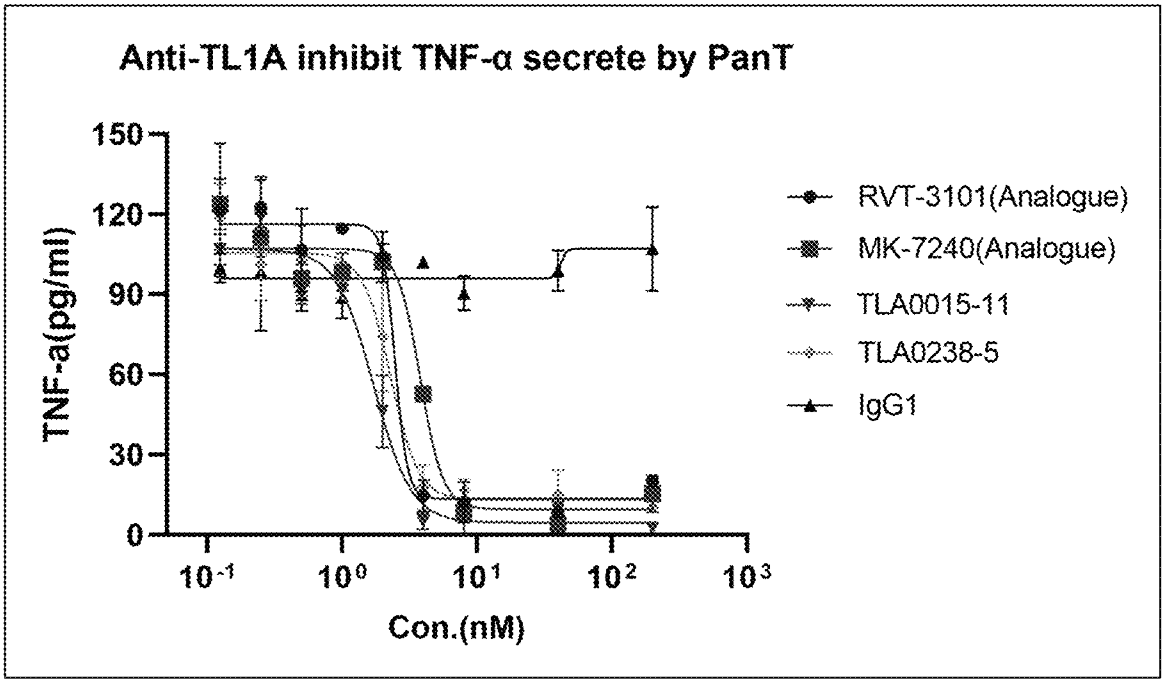
FIG. 17 shows inhibition of TNF-α secretion by T cells by an anti-TL1A antibody as described in the present application.

The amount of cytokine TNF-α in the supernatant was also detected using the BD™ Cytometric Bead Array Human TNF Flex Set. Prepare the standard according to the instructions, dilute the sample, 50 μl/well per well, and add to a 96-well plate. Prepare Capture beads solution at 50 μl/well per well, add to a 96-well plate, and incubate the standard/sample with Capture beads solution for 1 h. Dilute the detection antibody solution according to the instructions, 50 μl/well per well, add to a 96-well plate, and incubate for a total of 2 h. Centrifuge at 300 g for 5 min, discard the supernatant, and wash with wash buffer. Centrifuge again at 300 g for 5 min, discard the supernatant, resuspend with 70 μl wash buffer, and determine the cytokine content by Beckman CytoFLEX flow cytometer. The resulting data were fitted and analyzed by GraphPad Prism software. As shown in FIG. 17, both TLA0015-11 and TLA0238-5 have good activity against TNF-α.

Example 14 Detection of Cross-Reactivity of Anti-TL1A Antibody with Proteins of the Same Family The experiment is based on an ELISA assay to detect the binding ability of a plurality of antibodies prepared by example 6 of the present invention to other proteins of the same family as TL1A. The specificity of the TL1A antibody is determined by detecting whether the antibody binds to the TL1A family of proteins. TL1A homo proteins include: FasL (36% homology to TL1A sequence), TRAIL (35% homology to TL1A sequence), LIGHT (31% homology to TL1A sequence), TNF-β (30% homology to TL1A sequence), and TNF-α (29% homology to TL1A sequence).

TL1A homologous family proteins: FasL (Acrobiosystems, Cat #FAL-H5241), TRAIL (Acrobiosystems, Cat #TRL-H5259), LIGHT (Acrobiosystems, Cat #LIT-H5242), TNF-β (Acrobiosystems, Cat #TNB-H52H3) and TNF-α (Acrobiosystems, Cat #TNA-H5228) were purchased for the preparation of positive control antibodies to the same family of proteins. FasL-his, TRAIL-his, LIGHT-his, TNF-β-his and TNF-α-his proteins were diluted to 2 μg/ml in PBS at 100 μl/well, respectively, added to the enzyme labeled plates (coated with an equal amount of BSA as a control), and left at 4° C. overnight. The coating solution was removed, 5% BSA blocking solution was added at 200 μl/well and was left at room temperature for 2 hours. Remove the blocking solution, wash three times with 250 μl/well of 0.5%. PBST, then dilute anti-TL1A antibody and positive antibodies of each protein of the same family to 100 nM with the blocking solution, and add them sequentially to the blocked plates with 100 μl/well, and leave at room temperature for 1 hour. The plate was washed 3 times with PBST (residual droplets were removed with absorbent paper), and HRP-labeled goat anti-human IgG antibody was added at 100 μl/well and left at room temperature for 45 min. Wash the plate with 0.5%. PBST for 5 times, in 100 μl/well, add TMB solution, and leave it at room temperature and avoid light for 5 minutes, add termination solution in 100 μl/well to terminate the color development reaction of the substrate, and read the OD value at 450 nm with enzyme marker. The results are shown in Table 21: Anti-TL1A specific monoclonal antibodies TLA0015, TLA0238 and TLA0241 all did not bind to other proteins of the same family.

TABLE 21

Anti-TL1A antibody binding detection to the same family protein

| Abs | FasL | TRAIL | LIGHT | TNF-β | TNF α |
|---|---|---|---|---|---|
| TLA0015 | 0.05 | 0.05 | 0.05 | 0.05 | 0.05 |
| TLA0238 | 0.05 | 0.05 | 0.05 | 0.05 | 0.05 |
| TLA0241 | 0.05 | 0.05 | 0.05 | 0.05 | 0.05 |
| Cytokine Abs | 3.30 | 2.64 | 3.29 | 1.81 | 3.65 |

Example 15 Detection of Anti-TL1A Antibody Tm Value Detection

The experiment is based on a Panta instrument to detect the Tm values of a plurality of antibodies prepared by example 6 of the present invention. The Panta instrument includes micro-differential scanning fluorescence (nanoDSF) technology, which tracks the folding state of a protein by detecting its endogenous fluorescence. The ratio of the fluorescence signal changes with increasing temperature or chemical denaturant concentration, thus determining the protein stability parameter Tm value. The specific Tm values of each antibody are shown in Table 22.

TABLE 22

The body Tm value of the anti-TL1A antibody

| Abs | Tm(° C.) | |
|---|---|---|
| | Tm1(° C.) | Tm2(° C.) |
| RVT-3101 (Analogue) | 71.65 | 79.21 |
| MK-7240 (Analogue) | 65.05 | 81.44 |
| TLA0015-11 | 75.62 | NA |
| TLA0238-2-1 | 69.92 | NA |
| TLA0238-5 | 69.60 | NA |

Example 16 Detection of ADCC Activity of Anti-TL1A Antibody TLA0015-11 by Fluorescent Reporter Gene Method In this experiment Jurkat-ADCC fluorescent reporter gene cells were used to detect the ADCC activity of anti-TL1A antibody TLA0015-11. The effector cells used in this study were Jurkat-ADCC cells overexpressing FcγRIIIa and downstream fluorescent reporter genes, and the ADCC activity of the TLA0015-11 antibody was reflected by determining the expression of fluorescent reporter genes in the effector cells. The Jurkat-ADCC cell line was purchased from Triple Excellence Bio (XHB604, Human FcgR3a/CD16a NF-AT-Jurkat Cell Line).

Figure 18:
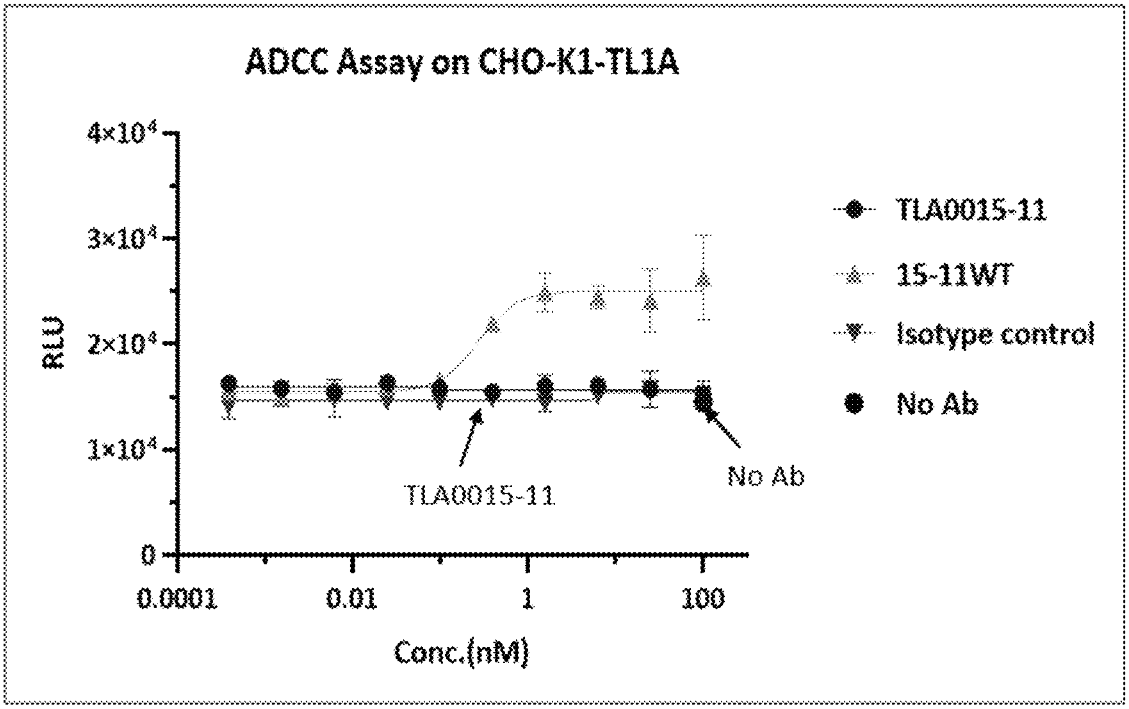
FIG. 18 shows the ADCC activity of the TLA0015-11 antibody described in the present application.

CHO-K1-TL1A cells were digested and centrifuged, and the cell density was adjusted to 2E5 cells/mL using analytical buffer (phenol red-free RPMI1640 medium+4% FBS+1% Penicillin Streptomycin), and the target cells were inoculated into white 96-well flat-bottomed plates with 50 μl per well. 3× analytical buffer was used to prepare 3× analytical concentration of TLA0015-11 monoclonal antibody, positive control antibody 15-11WT (Fc is human IgG1 wild type Fc) and negative control antibody Isotype control, the highest concentration point is 300 nM (final concentration is 100 nM), 4-fold gradient dilution, a total of 10 concentration points. After the antibody was diluted, it was added to the white 96-well flat-bottomed plate as described above at 50 μl/well. The density of Jurkat-ADCC effector cells was then adjusted to 1E6 cells/mL with analytical buffer, and 50 μl/well was added to the white 96-well flat-bottomed plate and incubated in a carbon dioxide incubator for 6 h. After incubation, the white 96-well flat-bottomed plate was taken out of the incubator, and 40 μl of Bio-Lite Luciferase Assay Reagent was added to each well. (Vazyme, DD1201-02) per well, and read the RLU value on a multifunctional enzyme marker after 5 minutes of gentle shaking. A four-parameter fit plot of the sample concentration logarithmically versus the measured signal value was performed using Graphpad, and the results are shown in FIG. 18: anti-TL1A antibody TLA0015-11 has no ADCC activity.

Example 17 CDC Activity of Anti-TL1A Antibody TLA0015-11 Detected by Human Complement Serum In this experiment, human complement serum was used to detect whether anti-TL1A antibody TLA0015-11 has CDC activity at in vitro level.

Figure 19:
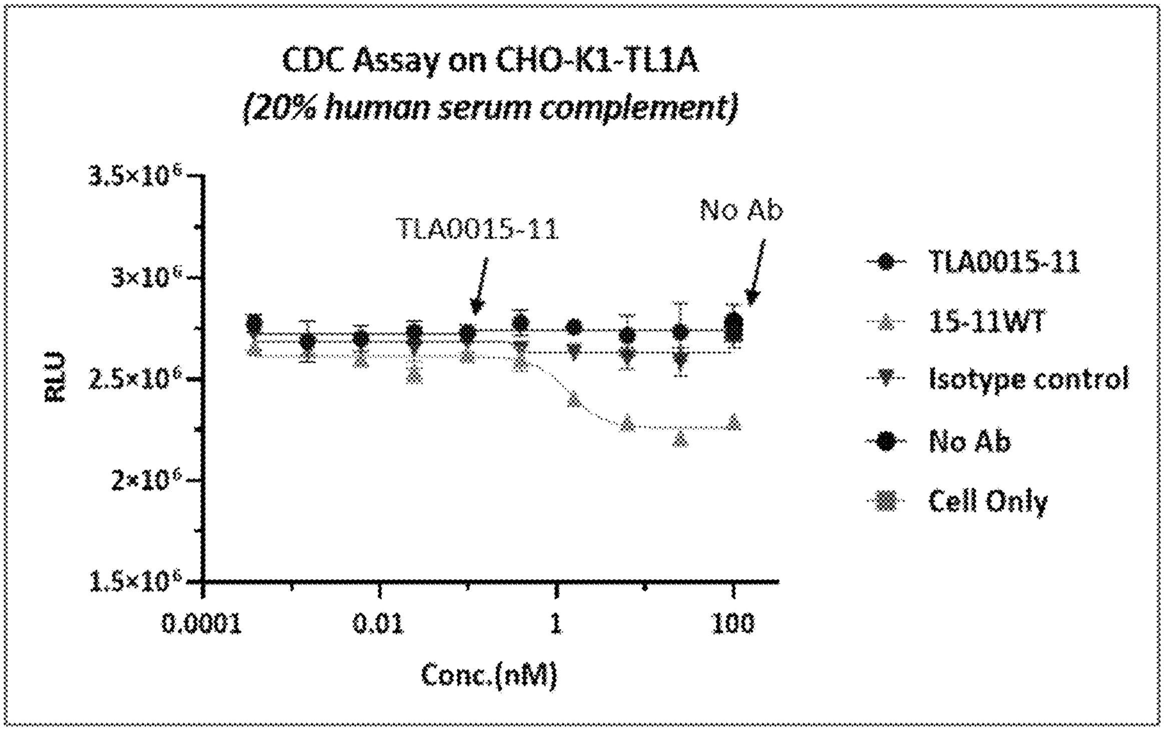
FIG. 19 shows the TLA0015-11 antibody CDC activity as described in the present application.
Figure 20A:
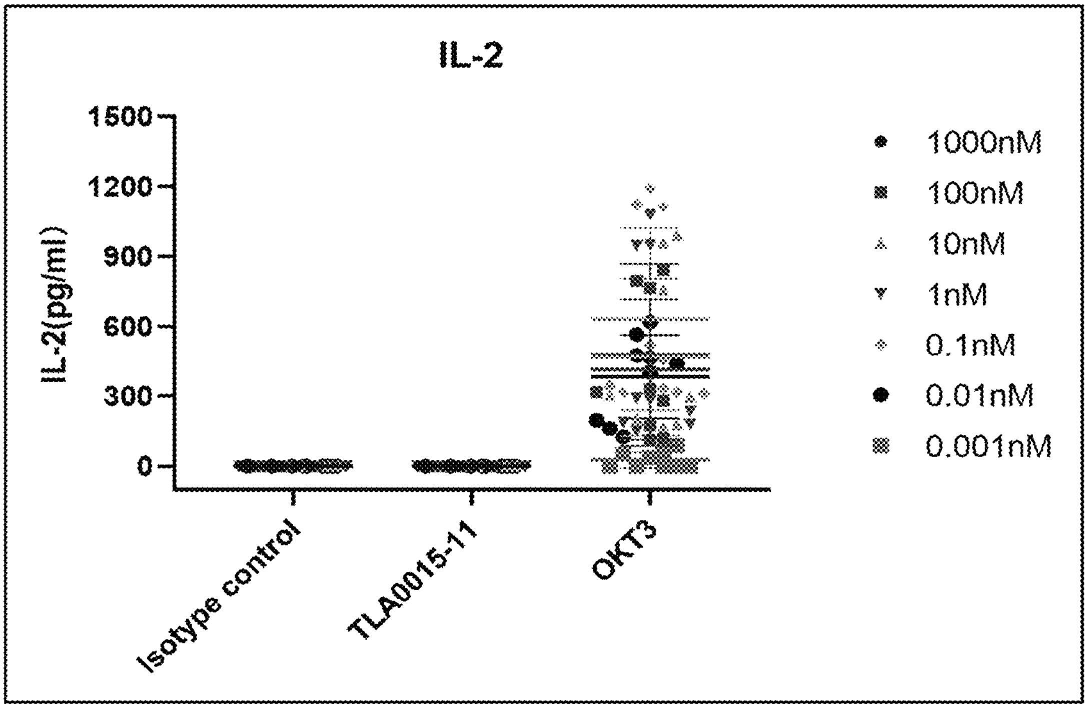
FIGS. 20A-20F show the effect of the TLA0015-11 antibodies described in this application on cytokine release.
Figure 20B:
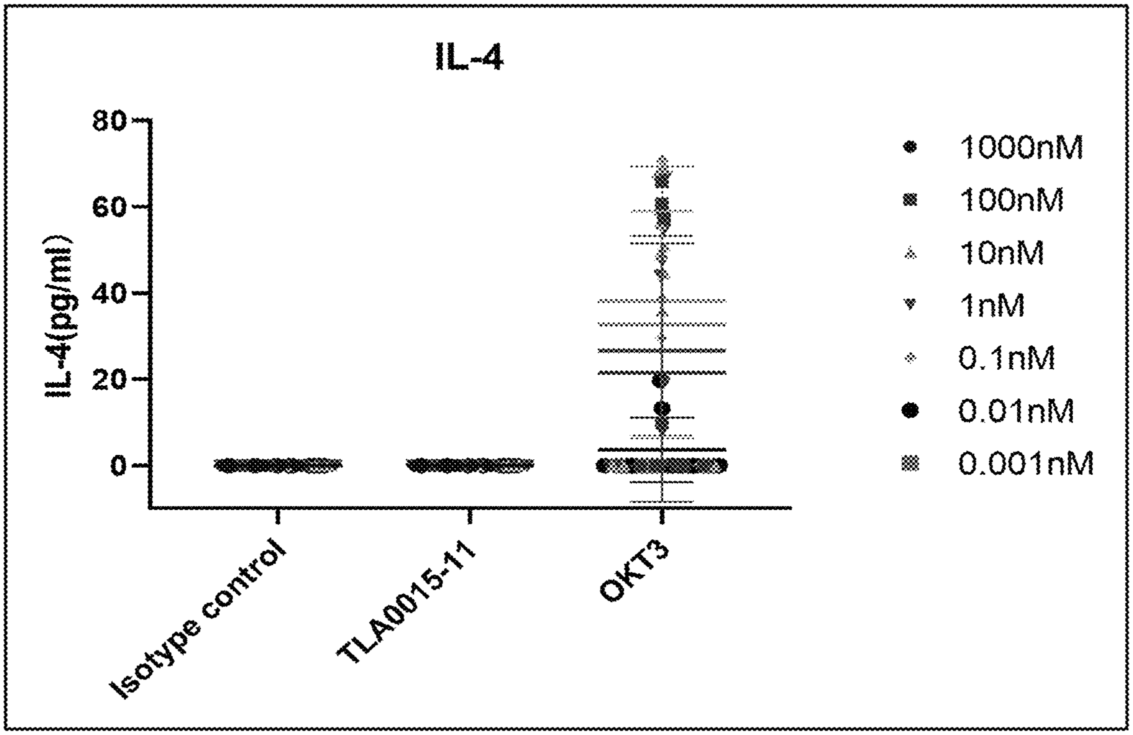
Figure 20C:
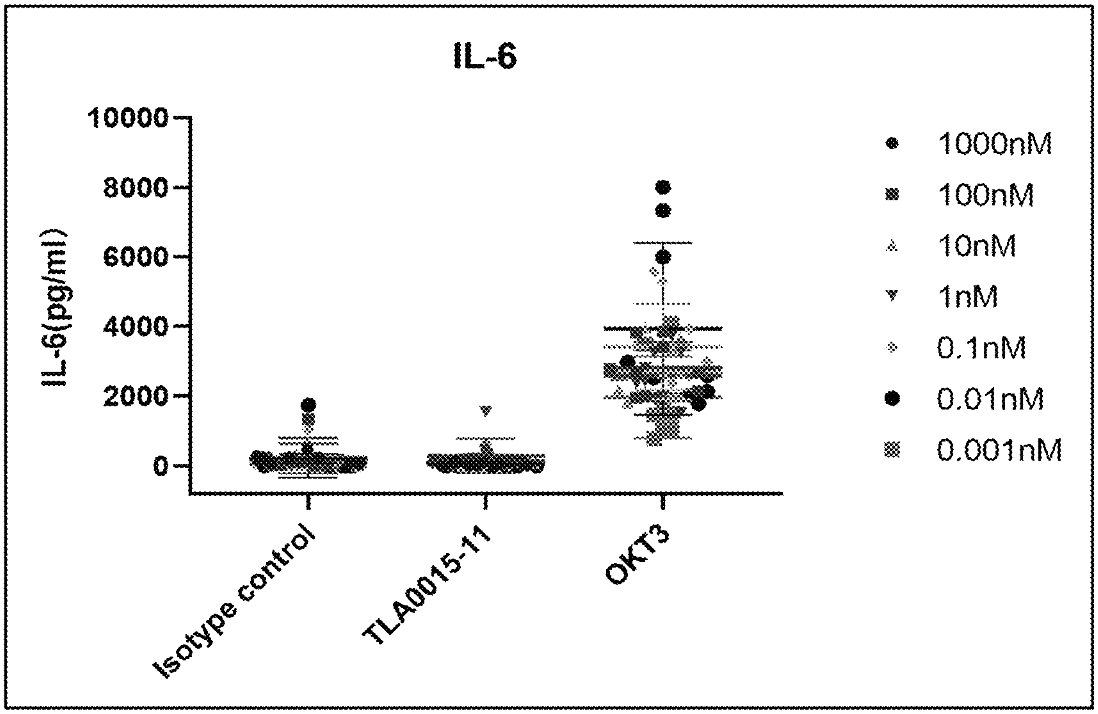
Figure 20D:
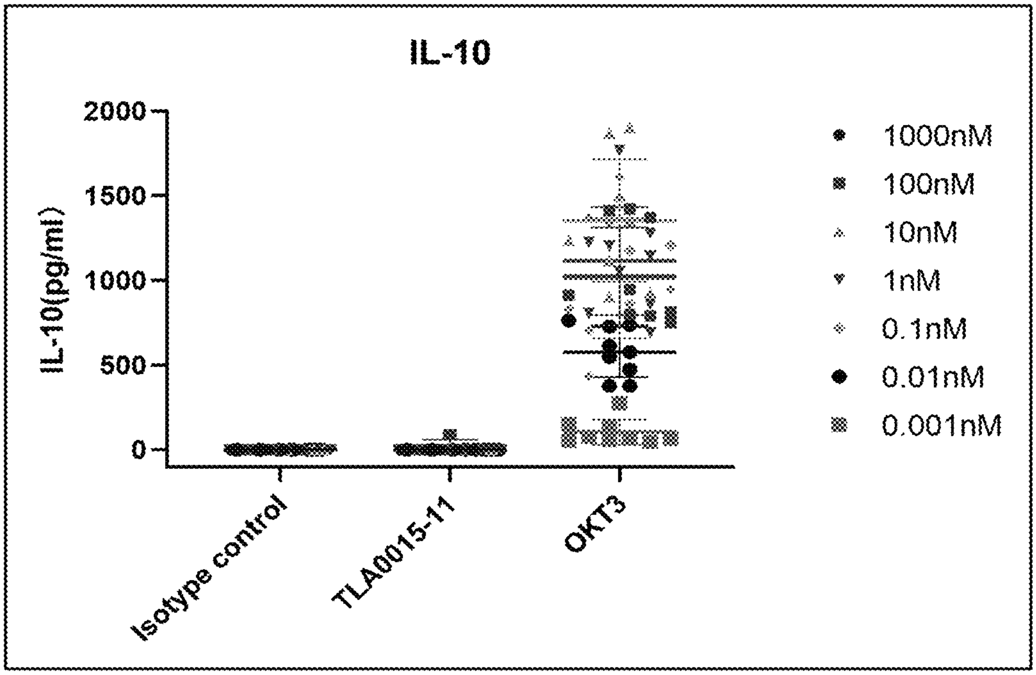
Figure 20E:
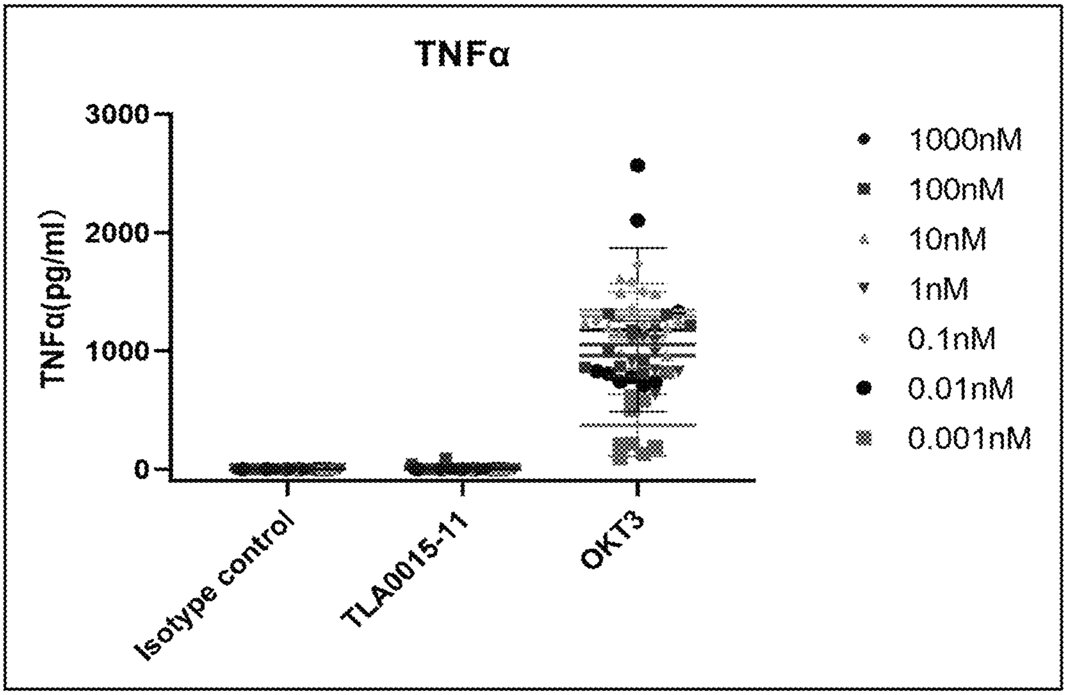
Figure 20F:
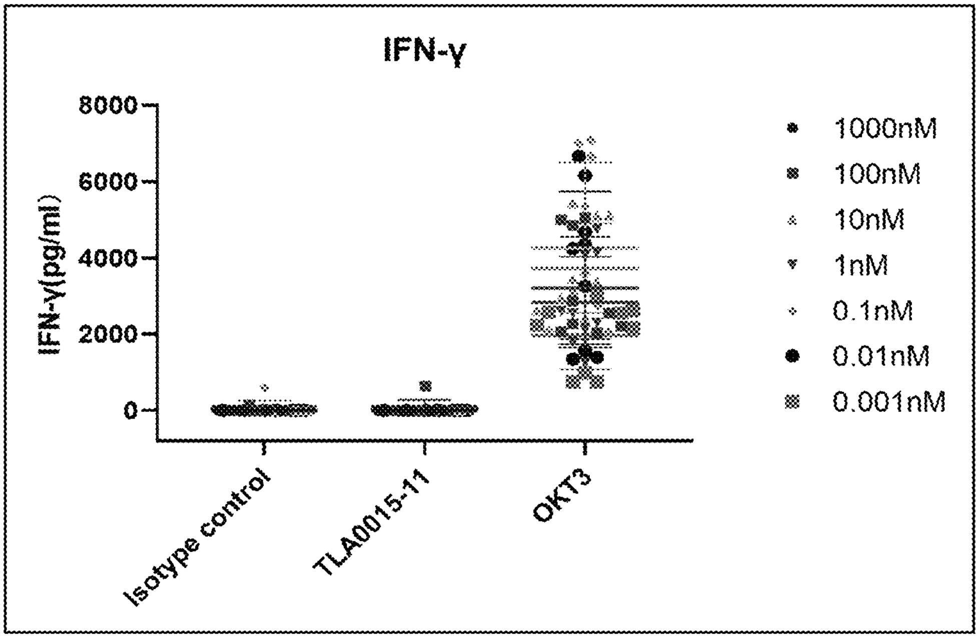
Figure 21A:
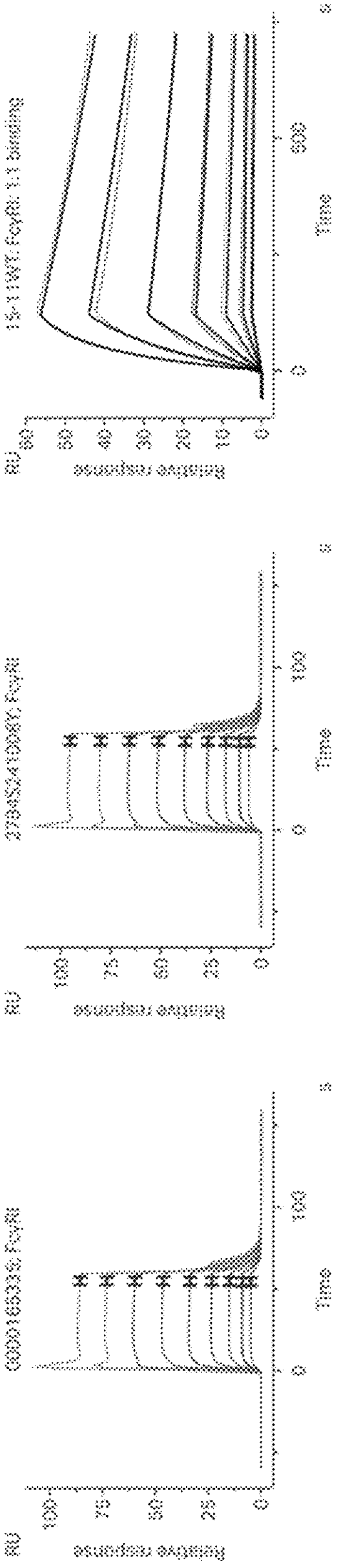
FIGS. 21A-21K show the affinity results of the TLA0015-11 antibody described in the present application to different Fcγ receptors, complement C1q, and FcRn proteins.
Figure 21B:
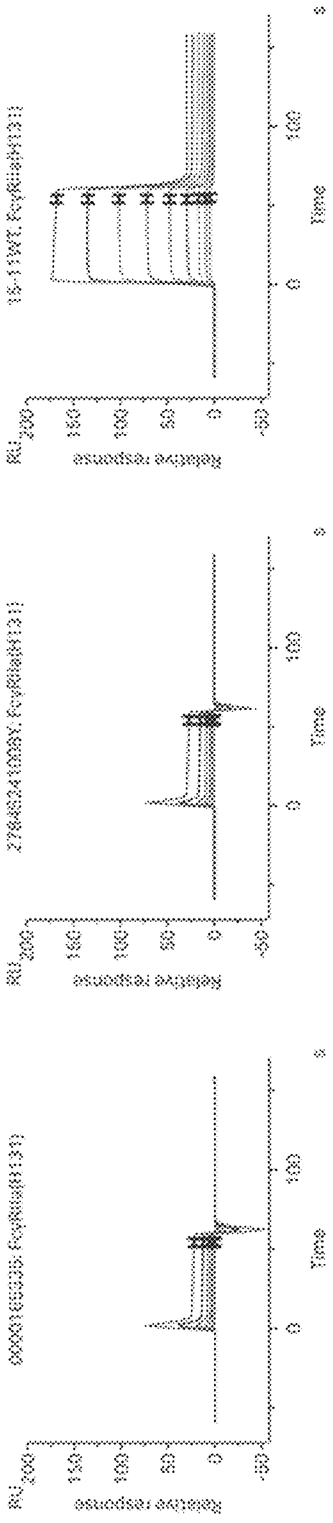
Figure 21C:
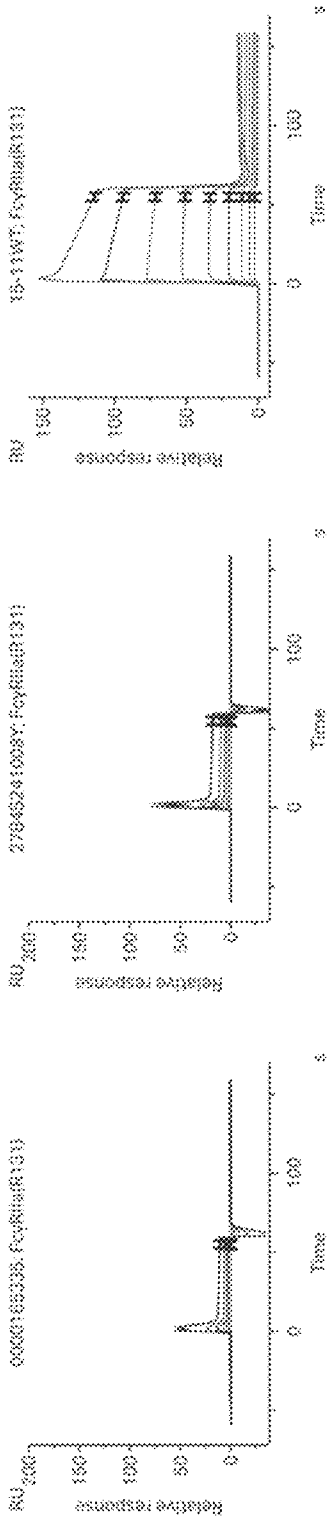
Figure 21D:
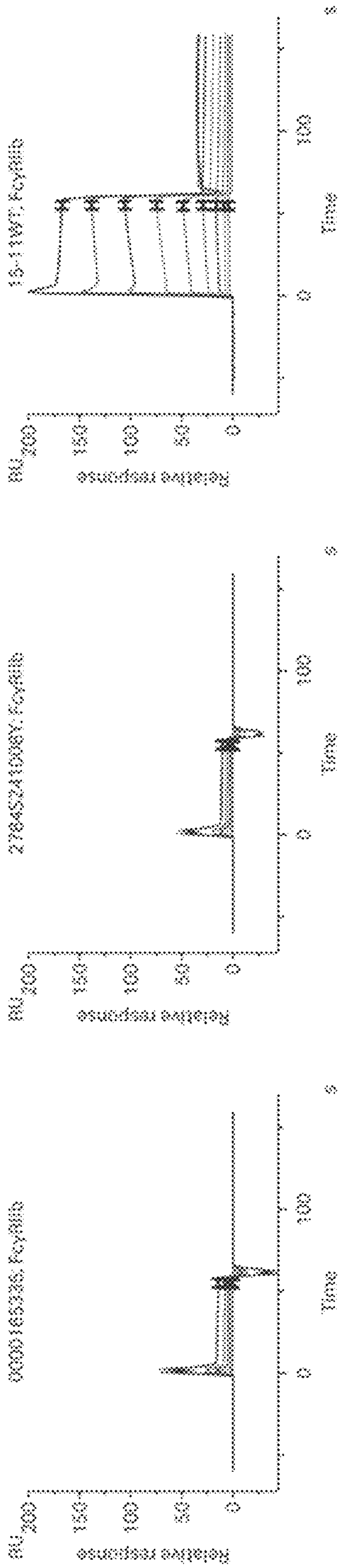
Figure 21E:
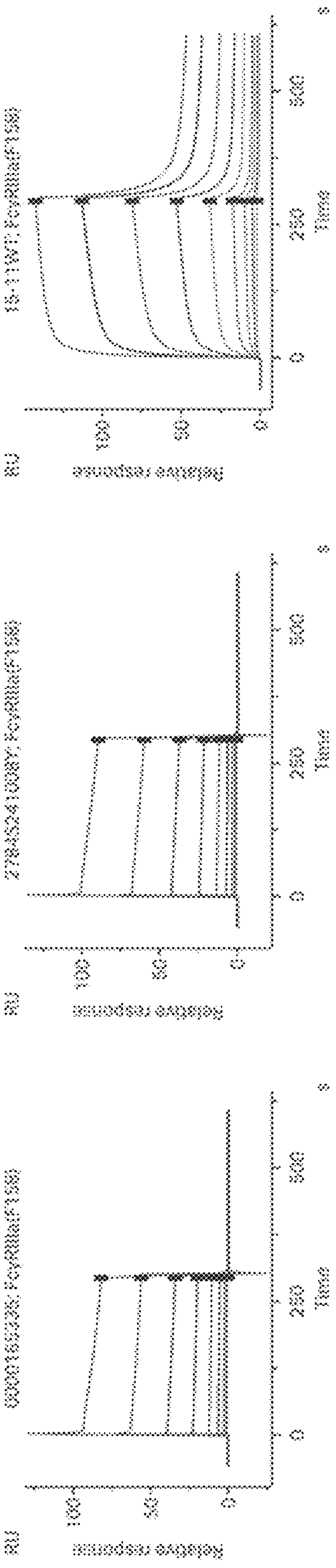
Figure 21F:
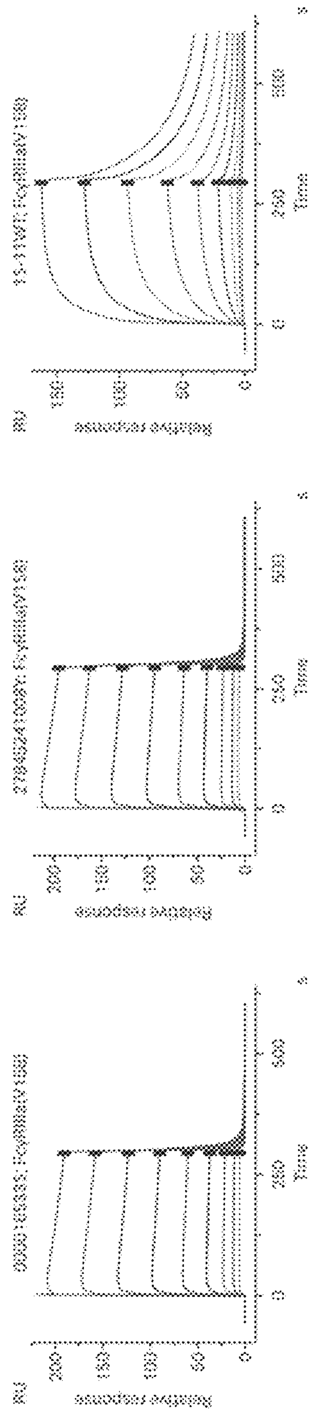
Figure 21G:
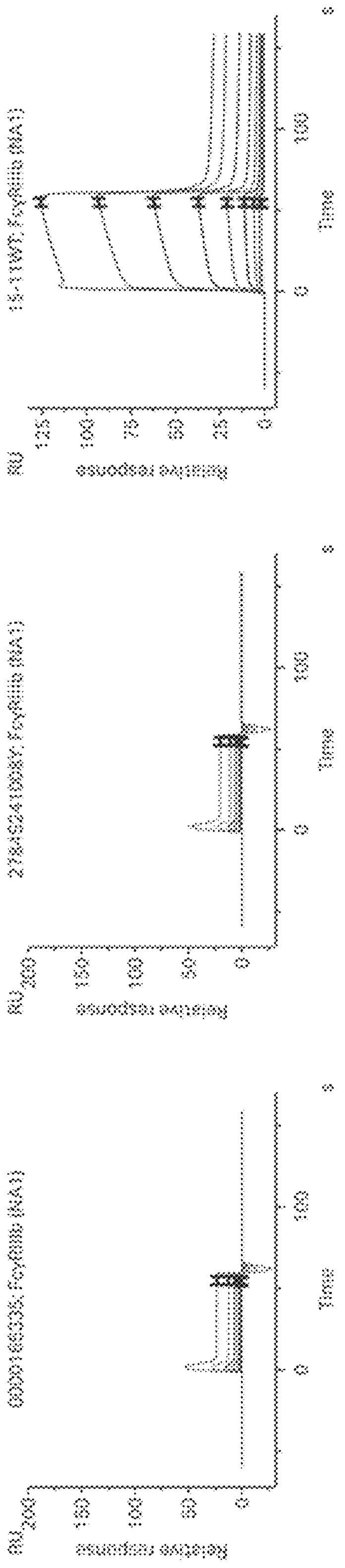
Figure 21H:
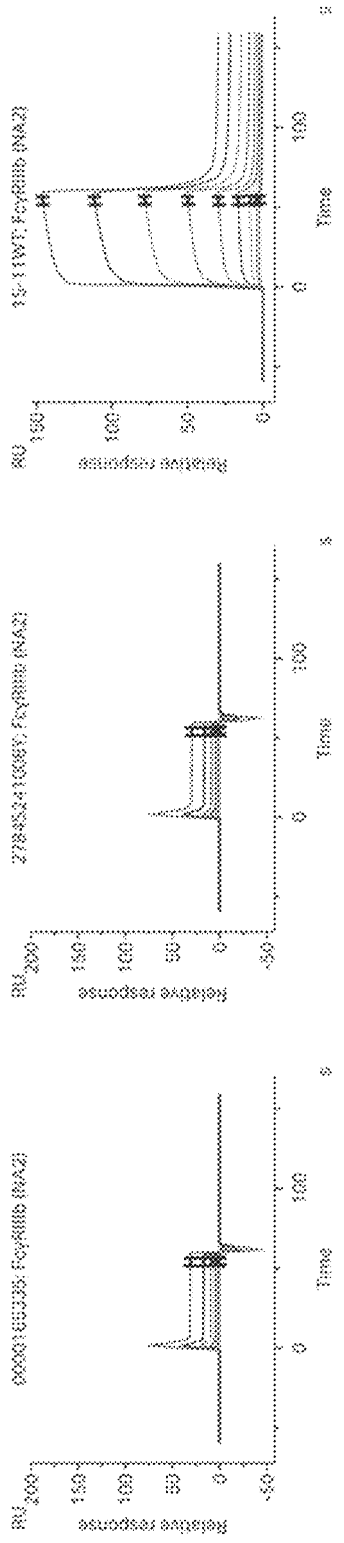
Figure 21I:
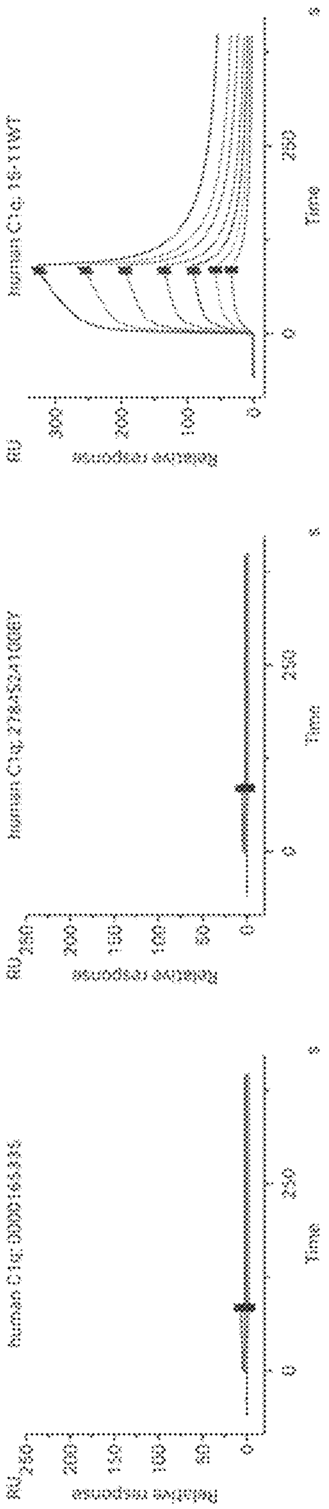
Figure 21J:
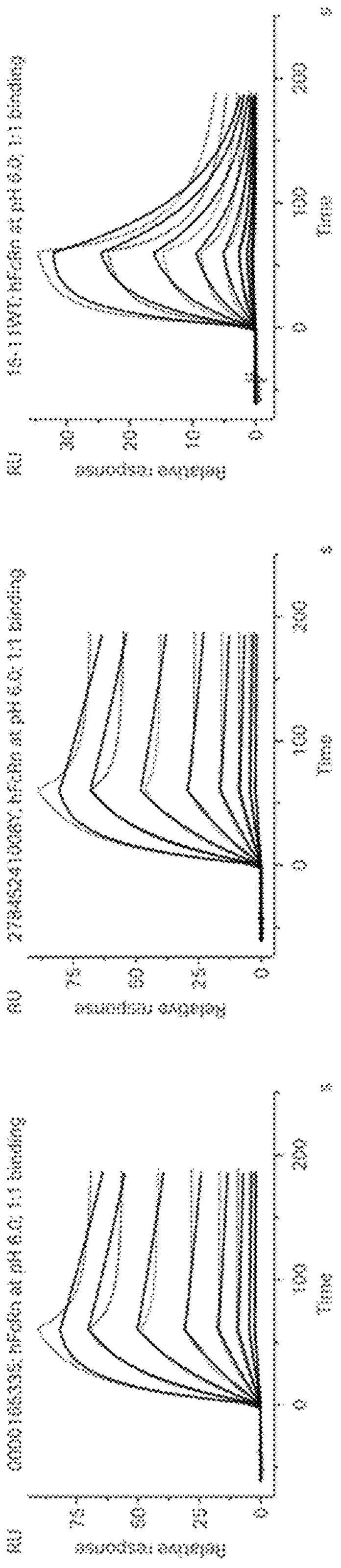
Figure 21K:
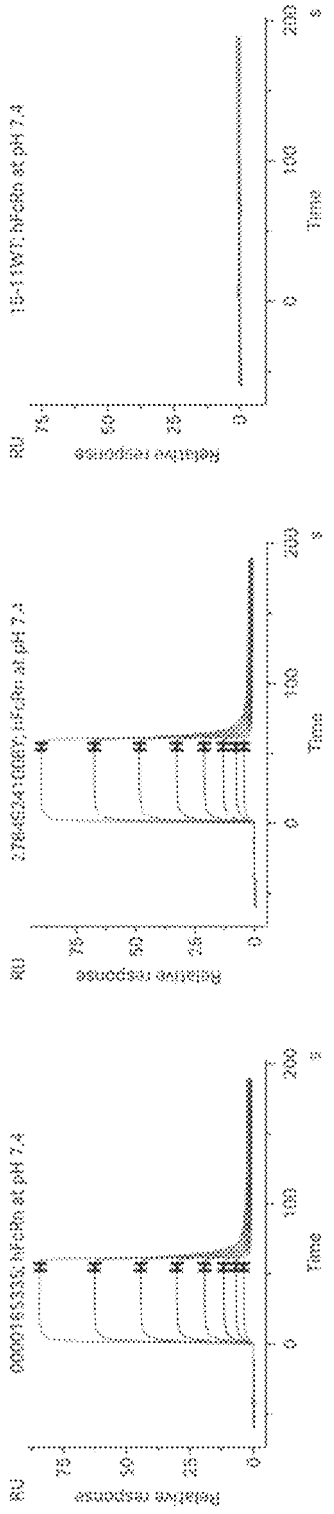

CHO-K1-TL1A cells were digested and centrifuged, and the cell density was adjusted to 6.7E5 cells/mL using analytical buffer (phenol red-free RPMI1640 medium+4% FBS+1% Penicillin Streptomycin), and target cells were inoculated into white 96-well flat-bottomed plates with 30 μl per well. 2× of analytical buffer was used to prepare the analyzed concentration of anti-TL1A antibody TLA0015-11, positive control antibody 15-11WT and negative control antibody Isotype control, the highest concentration point is 200 nM (final concentration is 100 nM), 4-fold gradient dilution, a total of 10 concentration points. After the antibody was diluted, it was added to the above white 96-well flat-bottom plate at 50 μl/well. At the same time, Normal Human Serum Complement (QuidelOrtho, A113) was added to the white 96-well plate at 20 μl/well, and the white 96-well plate was incubated in a carbon dioxide incubator for 4 h. At the end of the incubation, the white 96-well plate was removed from the incubator, and 50 μl of the Normal Human Serum Complement (QuidelOrtho, A113) was added to each well. Cell Counting-Lite 2.0 Luminescent Cell Viability Assay Reagent (Vazyme, DD1101-02) was added to each well, and the RLU values were read on a multifunctional enzyme marker after 5 minutes of gentle shaking. A four-parameter fit plot of the sample concentration logarithmically plotted against the measured signal value using Graphpad was performed, and the results are shown in FIG. 19: monoclonal antibody TLA0015-11 has no CDC activity.

Example 18 Detection of Cytokine Release Activity Mediated by Anti-TL1A Antibody TLA0015-11

This experiment was performed to evaluate whether TLA0015-11 monoclonal antibody can mediate cytokine release syndrome using human peripheral blood single nucleated cells in vitro. The TLA0015-11 antibody and negative control antibody IgG1-LALA were diluted with 1640 complete medium to prepare 2× analyzed concentrations of the antibody with a maximum concentration of 2 μM (final concentration of 1 μM), and the positive control antibody was OKT3 with a maximum concentration of 200 nM (final concentration of 100 nM). All antibodies were diluted according to a 10-fold gradient with a total of 6 concentration points, and 3 replicate wells were made for each concentration point. The diluted antibodies were added to 96-well round bottom plates at 50 μl per well. PBMC from three different donors were resuscitated, quickly thawed and transferred to centrifuge tubes with 9 ml 1640 complete medium beforehand, the supernatant was discarded after centrifugation (400 g, 5 min), fresh 1640 complete medium was added to resuspend and counted, and the cell density was adjusted to be 6E6 cells/ml, and the cell density was adjusted to be 6E6 cells/ml. Add 50 μl per well into the above 96-well round bottom plate (3E5 PBMC per well), and incubate in a CO2 incubator for 24 h. After incubation, remove the 96-well round bottom plate, centrifuge at 400 g for 5 min, and pipette 50 μl of culture supernatant from each well into a new 96-well V-bottom plate, then incubate in accordance with the BD™ Cytometric Bead Array (CBA) Human Thl/Thl Array. (CBA) Human Thl/Th2 Cytokine Cytometric Bead Array (CBA) Kit II (BD, Cat #551809) instructions, and then processed to detect the content of multiple cytokines (IL-2, IL-4, IL-6, IL-10, TNF-α, IFN-γ) in cell supernatants. The samples were collected on a flow cytometer (Agilent, NovoCyte Penteon), analyzed by FCAP Array v3 software, and finally plotted against the antibody concentration versus the concentration of each cytokine by Graphpad, and the results are shown in FIGS. 20A-20F. The effect of TLA0015-11 monoclonal antibody on IL-2, IL-4, IL-6, IL-10, the TNF-α, and IFN-γ cytokines were not stimulated.

Example 19 Biacore Detection of the Affinity of Anti-TL1A Antibodies to Different Fc Receptors and Complement Proteins The affinity of the TLA0015-11 antibody to different Fc receptors and complement C1q protein was tested using the Biacore biomolecular interaction instrument.

In the detection experiment, the CM5 chip captured anti-his antibodies and then captured different Fc receptor proteins, including Human FcγRI (ACRO, FCA-H52H1) protein, Human FcγRIIa (H131) (ACRO, CD1-H5223) protein, Human FcγRIIa (R131) (ACRO, CDA-H5221) protein, Human FcγRIIb (ACRO, CDB-H5228) protein, Human FeyRIIIa (F158) (ACRO, CDA-H5220) protein, Human FcγRIIIa (V158) (ACRO, CD8-H52H4) protein, Human FcγRIIIb (NA1) (ACRO, CDB-H5227) protein, Human FcγRIIIb (NA2) (ACRO, CDB-H5222) protein, complement C1q (Complement Technology, A099) protein, and human FcRn (ACRO, FCM-H5286) protein. Two batches of TLA0015-11 antibody (batch 2784S241008Y and batch 0000165335) were used as analytes to measure binding activity to each protein. 15-11 WT antibody without Fc mutations (i.e., the Fc of TLA0015-11 in Example 6 was replaced with an Fc sequence without mutation) was also used as a control.

Binding and dissociation curves for different batches of TLA0015-11 antibody and the 15-11 WT antibody without Fc mutations to FeyRI, FcγRIIa (H131), FcγRIIa (R131), FcγRIIb, FcγRIIIa (F158), FcγRIIIa (V158), FcγRIIIb (NA1), FcγRIIIb (NA2), C1q. FcRn (pH 6.0), and FcRn (pH 7.4) are shown in FIGS. 21A-21K, and specific affinity values are shown in Table 23. The TLA0015-11 antibody has reduced affinity for various Fc receptors and complement proteins due to the introduction of the L234A/L235A (LALA) mutations in its Fc region. Consistent with expectations, TLA0015-11 antibody from different batches showed very weak or even no affinity for various Fcγ receptors and complement C1q proteins. In contrast, the 15-11 WT antibody, which did not undergo Fc mutations, showed moderate affinity for various Fc receptors and complement proteins, all stronger than that of the HX15001 antibody. The TLA0015-11 antibody, which incorporates the M252Y, S254T, and T256E (YTE) mutations in its Fc region, has increased its affinity for FcRn at low pH. Consistent with expectations, the TLA0015-11 antibody from different batches showed strong affinity for FcRn at pH 6.0, surpassing that of the 15-11 WT antibody.

TABLE 23

Affinity results of HX15001 antibody to Fc receptors and complement C1q protein

| Protein | antibody | $k_a$ (1/Ms) | $k_d$ (1/s) | $K_D$ (M) |
|---|---|---|---|---|
| Human FcγRI | 0000165335 | | NA | 5.79E−06 |
| | 2784S241008Y | | NA | 6.04E−06 |
| | 15-11WT | 5.44E+05 | 4.69E−04 | 8.63E−10 |
| Human FcγRIIa (H131) | 0000165335 | | NA | Weak or no binding |
| | 2784S241008Y | | NA | Weak or no binding |
| | 15-11WT | | NA | 2.61E−06 |
| Human FcγRIIa (R131) | 0000165335 | | NA | Weak or no binding |
| | 2784S241008Y | | NA | Weak or no binding |
| | 15-11WT | | NA | 4.57E−06 |
| Human FcγRIIb | 0000165335 | | NA | Weak or no binding |
| | 2784S241008Y | | NA | Weak or no binding |
| | 15-11WT | | NA | 9.10E−06 |
| Human FcγRIIIa (F158) | 0000165335 | | NA | 3.41E−05 |
| | 2784S241008Y | | NA | 3.62E−05 |
| | 15-11WT | | NA | 8.38E−07 |
| Human FcγRIIIa (V158) | 0000165335 | | NA | 8.11E−06 |
| | 2784S241008Y | | NA | 7.55E−06 |
| | 15-11WT | | NA | 2.00E−07 |
| Human FcγRIIIb (NA1) | 0000165335 | | NA | Weak or no binding |
| | 2784S241008Y | | NA | Weak or no binding |
| | 15-11WT | | NA | 5.38E−06 |
| Human FcγRIIIb (NA2) | 0000165335 | | NA | Weak or no binding |
| | 2784S241008Y | | NA | Weak or no binding |
| | 15-11WT | | NA | 4.10E−06 |
| Human C1q | 0000165335 | | NA | Weak or no binding |
| | 2784S241008Y | | NA | Weak or no binding |
| | 15-11WT | | NA | 3.82E−08 |
| Human FcRn at pH 6.0 | 0000165335 | | NA | 1.19E−09 |
| | 2784S241008Y | | NA | 1.25E−09 |
| | 15-11WT | | NA | 1.36E−08 |
| Human FcRn at pH 7.4 | 0000165335 | | NA | 1.75E−06 |
| | 2784S241008Y | | NA | 1.66E−06 |
| | 15-11WT | | NA | Weak or no binding |

Example 20 Pharmacokinetics of Anti-TL1A Antibodies in hFcRn Transgenic Mice

In this experiment, B-hFcRn transgenic mice were used to study the pharmacokinetics of anti-TL1A antibodies. FcRn is the receptor for antibody IgG, and its binding is pH-dependent. In a weakly acidic environment, the IgG-Fc segment exhibits a high affinity for FcRn, while in a neutral or alkaline environment, the IgG-Fc segment exhibits a low affinity for FcRn. When IgG is non-specific pinocytosis by cells, it enters the endosome in an acidic environment, and shows a high affinity binding to FcRn on the endosomal membrane, and then is transported to the cell membrane by the circulating endosome, at this time, under alkaline conditions, the affinity between the IgG-Fc segment and FcRn is very low, and IgG is released from the FcRn into the blood circulation, thereby increasing the half-life of IgG. When M252Y, S254T and T256E mutations are introduced into IgG-Fc, the binding ability of Fc to FcRn receptors can be enhanced, and the half-life of IgG can be better extended. B-hFcRn transgenic mice (Catalog: 110001) were purchased from Biocytogen, and the mouse FcRn gene was knocked out on the C57BL/6 strain mice, and the human FcRn gene was knocked in, and the transgenic mouse only expressed the human FcRn receptor protein, but not the mouse FcRn receptor, so it can be used for metabolic kinetic studies of antibody drugs.

Female B-hFcRn transgenic mice with SPF grade (Catalog: 110001) were purchased from Biocytogen (Beijing)

Pharmaceutical Technology Co., Ltd., and after the animals were quarantined, 10 mice were randomly assigned to each antibody, divided into 2 groups, 5 mice in each group, and blood was collected alternately. Each mouse is injected with 1 mg/kg of anti-TL1A antibody through the tail vein, followed by alternating blood sampling at time points in Table 23. Blood was collected by mandibular vein by collecting 20 μl/time point/piece, leaving it at room temperature for 1 h, and centrifugation (8000 rpm, centrifugation for 5 min) at room temperature. Recombinant human TL1A-his protein was diluted to 1 μg/ml with PBS at 100 μl/well, added to the plate (coated with an equal amount of BSA as a control), and incubated overnight at 4° C. Remove the coating solution, add blocking solution at 200 μl/well, and incubate for 2 h at room temperature. Remove the blocking solution and wash three times at 250 μl/well with 0.5%. PBST and pat dry for later use. Dilute the serum sample to the appropriate ratio using the blocking solution and add it to the blocked plate. The standard curves were used using RVT-3101, MK-7240, and TLA0015-11 starting at 100 nM with 2-fold dilutions for a total of 20 concentration gradients (maximum concentration of 100 nM), sequentially added to the blocked plate at 100 μl/well, and incubated for 1 h at room temperature. Wash the plate 3 times with 0.5%. PBST at 100 μl/well, add HRP-labeled goat anti-human IgG antibody, and incubate for 45 min at room temperature. Wash the plate 5 times with 0.5%. PBST, add TMB at 100 μl/well, incubate at room temperature in the dark for 5 min, at 100 μl/well, add stop solution, stop the substrate chromogenic reaction, read the OD value at 450 nm with a microplate reader, analyze the data with a GraphPad, plot and calculate the half-life (T1/2).

Figure 22:
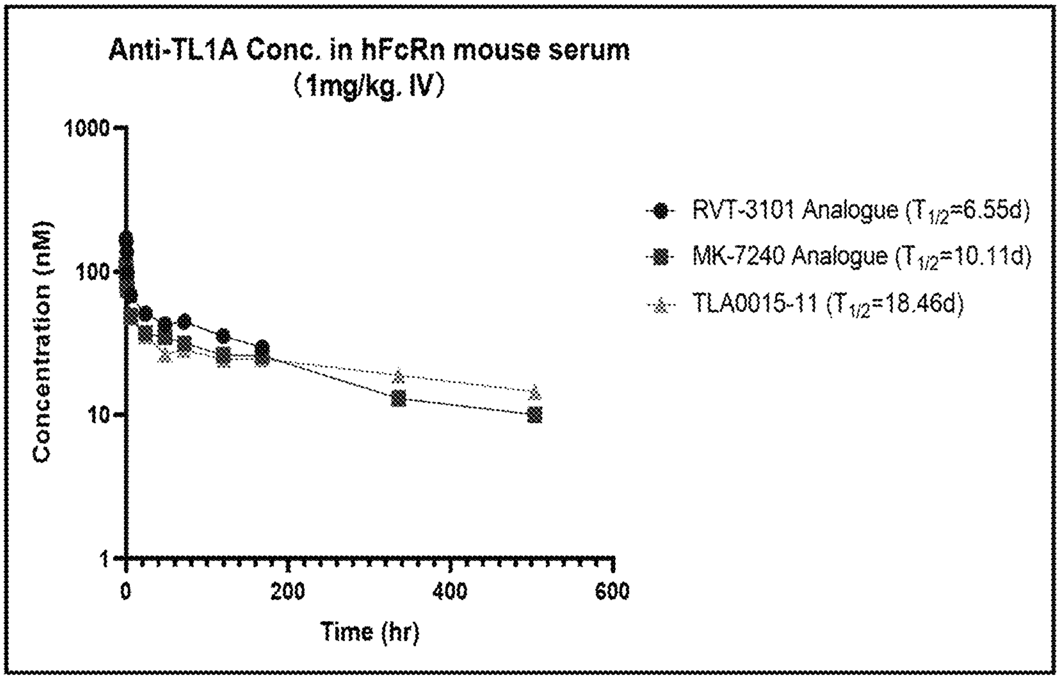
FIG. 22 shows the anti-TL1A antibody described in this application in PK assay in B-hFcRn transgenic mice.
Figure 23:
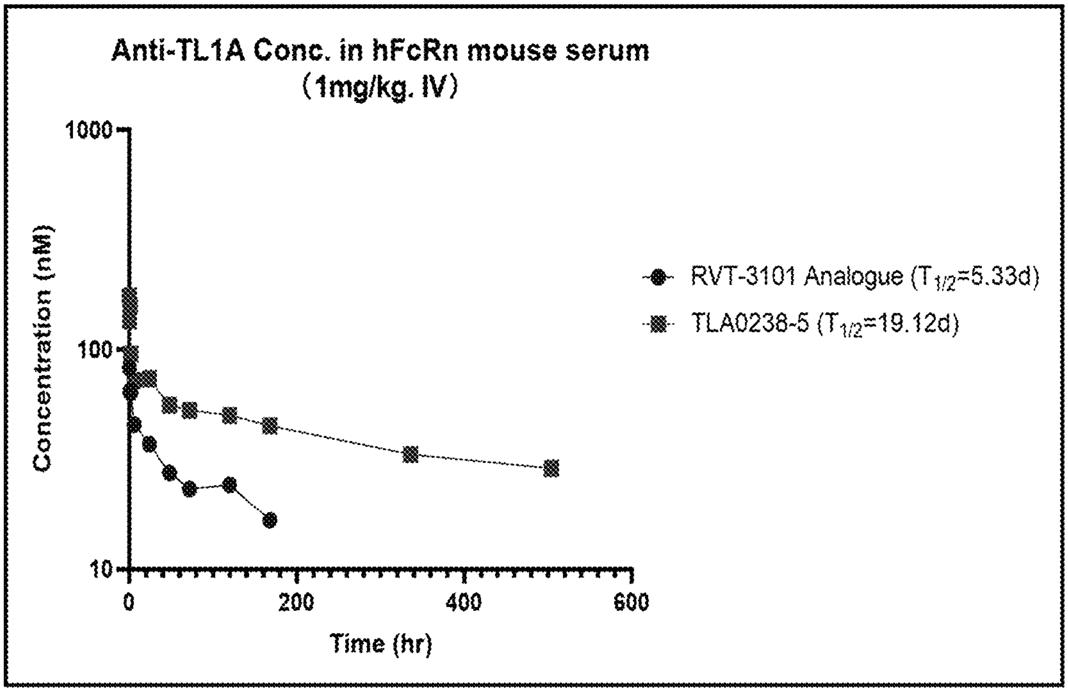
FIG. 23 shows the anti-TL1A antibody described in this application PK assay in B-hFcRn transgenic mice.

The results of the same batch of RVT-3101, MK-7240 and TLA0015-11 antibodies are shown in FIG. 22, the half-life T1/2 of the TLA0015-11 antibody in hFcRn mice is 18.46 days, and the concentration of the control antibody RVT-3101 in the serum samples on day 14 and day 21 is below the lower limit of detection. In addition, the results of the same batch of RVT-3101 and TLA0238-5 antibodies are shown in FIG. 23, the half-life T1/2 time of TLA0238-5 antibody in hFcRn mice is 19.12 days, and the concentration of control antibody RVT-3101 in serum samples on day 14 and day 21 is below the lower limit of detection.

TABLE 24

| PK blood collection time point | | | | | | | | | | | | | |
|---|---|---|---|---|---|---|---|---|---|---|---|---|---|
| Mice | Point-in-time | | | | | | | | | | | | |
| 1 | 5 min | | 1 h | | 6 hours | | 48 h | | 96 h | | 7 d | | 21 d |
| 2 | | | | | | | | | | | | | |
| 3 | | | | | | | | | | | | | |
| 4 | | | | | | | | | | | | | |
| 5 | | | | | | | | | | | | | |
| 6 | | 30 min | | 2 hours | | 24 h | | 72 h | | 120 h | | 14 d | |
| 7 | | | | | | | | | | | | | |
| 8 | | | | | | | | | | | | | |
| 9 | | | | | | | | | | | | | |
| 10 | | | | | | | | | | | | | |

Example 21 Efficacy of Anti-TL1A Antibody in DSS-Induced hTL1A Transgenic Mouse Enteritis Model In this experiment, TL1A humanized transgenic mice were used to investigate the efficacy of anti-TL1A antibodies in a DSS-induced mouse model of enteritis. TL1A humanized transgenic mouse B-hTL1A mice (Catalog: 111997) was purchased from Biocytogen (Beijing) Pharmaceutical Technology Co., Ltd., the humanized transgenic mouse knocked out the mouse TL1A gene on the C57BL/6 strain mouse, and knocked in the human TL1A gene, the transgenic mouse only expressed the human TL1A protein, not the mouse TL1A protein. After dissolving DSS in drinking water, the intestinal epithelial cells of mice were destroyed after drinking water containing DSS, and non-specific immune cells released cytokines, which eventually led to the destruction of the integrity of the mucosal barrier, and the mice showed obvious weight loss, loose stool, blood in the stool and granulocyte infiltration, which were extremely similar to human ulcerative colitis in terms of clinical symptoms and pathological features. A DSS-induced mouse enteritis model was used to verify the efficacy of anti-TL1A antibody in enteritis.

Figure 24:
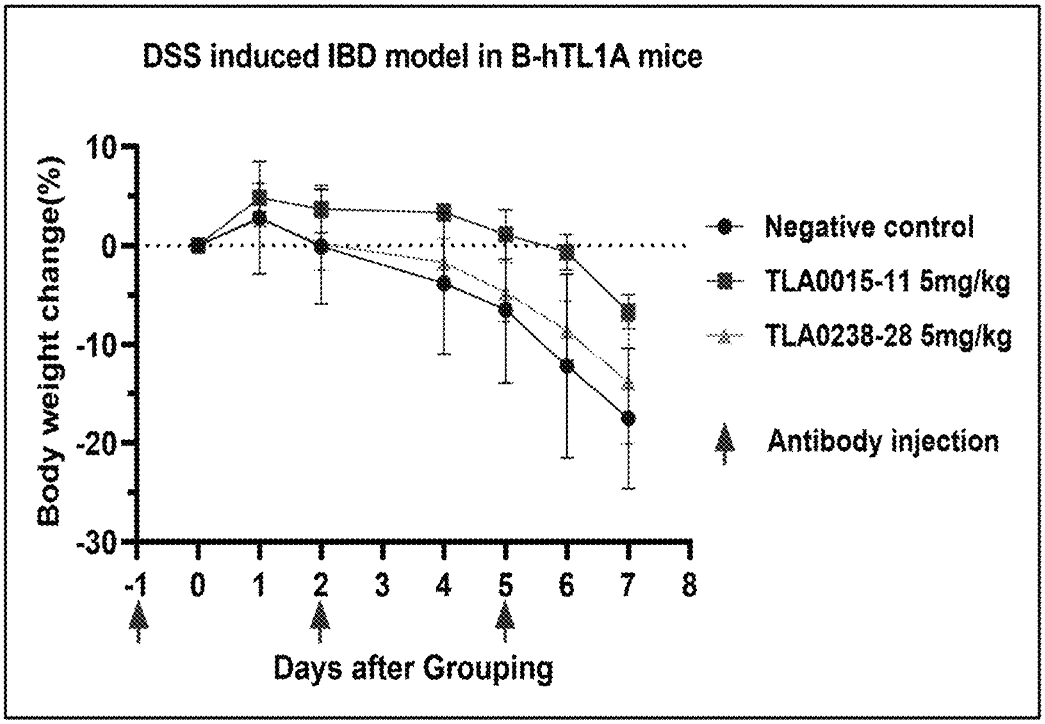
FIG. 24 shows the effect of anti-TL1A antibodies described in the present application on body weight changes in B-hTL1A humanized transgenic mice in the DSS-induced enteritis model.
Figure 25:
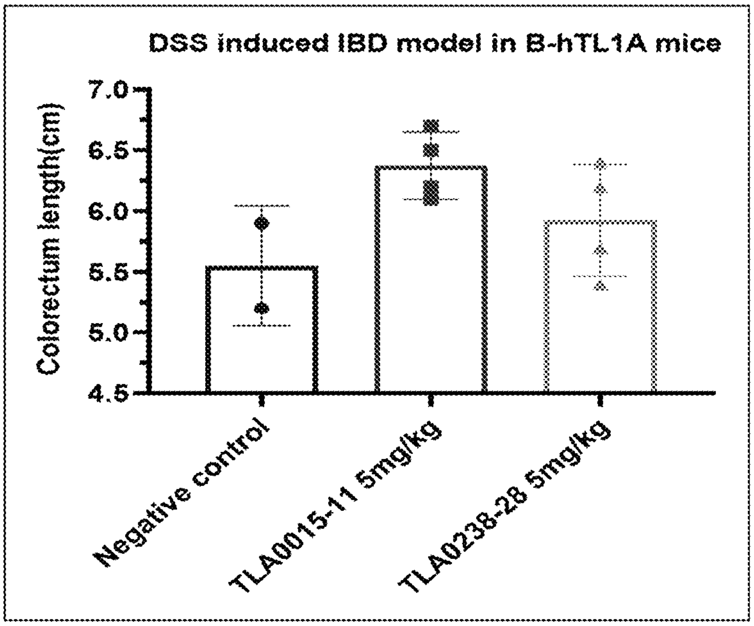
FIG. 25 shows the effect of anti-TL1A antibodies described in the present application on colorectal length in B-hTL1A humanized transgenic mice in a DSS-induced enteritis model.

Ten B-hTL1A transgenic mice were randomly divided into three groups, including two mice in the negative control group, four mice in each of the TLA0015-11 monoclonal antibody group and the TLA0238-28 monoclonal antibody group. The drug was injected into the tail vein on day 0, day 3 and day 6, respectively, at a dose of 5 mg/kg: Mice were given drinking water dissolved in 4% DSS from day 2 to day 8. During the experiment, the weight of the experimental animals was measured and recorded every day, and the daily activities of the animals were observed. Experimental animal fecal traits are scored daily (0=normal, 1=moist/sticky, 2=fluffy, 3=liquid). At the end of the experiment on the 8th day, all experimental animals were euthanized by suffocation with excess carbon dioxide, after which the abdominal cavity was cut, the colon was removed, and the length of the colon was recorded. The results of weight change are shown in FIG. 24, and it can be seen from the negative control group that the weight loss of mice after DSS-induced enteritis was significant, while the weight loss of mice in the TLA0015-11 monoclonal antibody administration group was significantly less than that of the negative control. The results of the change in colorectal length are shown in FIG. 25, and it can be seen from the negative control group that the colorectal length of mice was significantly shortened after DSS-induced enteritis, while the colorectal length of mice in the TLA0015-11 monoclonal antibody administration group was significantly restored. In summary, it can be seen that TLA0015-11 antibody has a good therapeutic effect in a DSS-induced enteritis model.

To explore the relationship between the efficacy of TLA0015-11 antibody and the dose in the DSS-induced enteritis model, three dose groups were designed, namely, 1 mg/kg, 3 mg/kg and 10 mg/kg, and the specific groupings are shown in Table 25, and the experiments were carried out as described above.

Figure 26A:
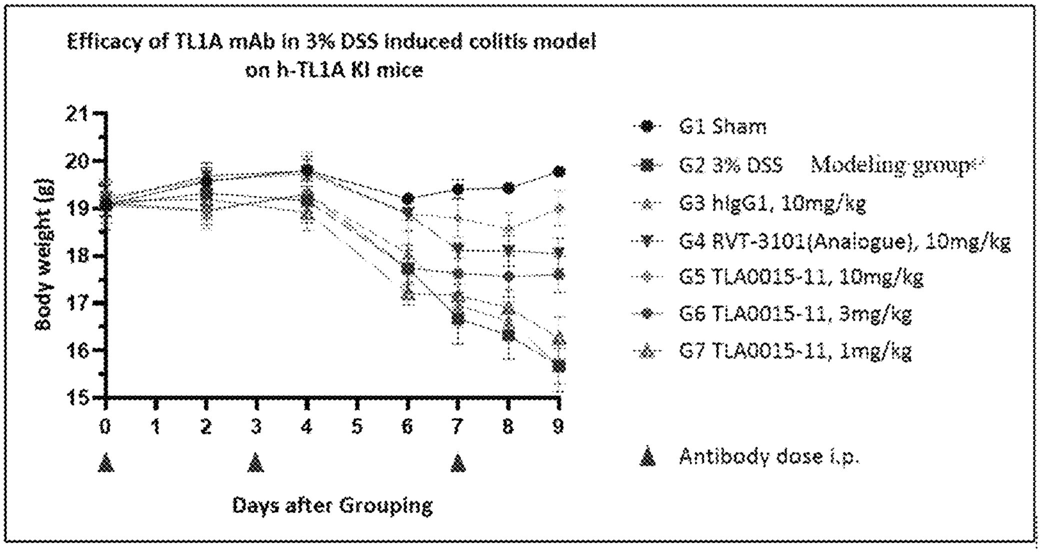
FIGS. 26A-26B show the effect of the anti-TL1A antibodies described in the present application on the change in body weight of B-hTL1A humanized transgenic mice in a DSS-induced enteritis model.
Figure 26B:
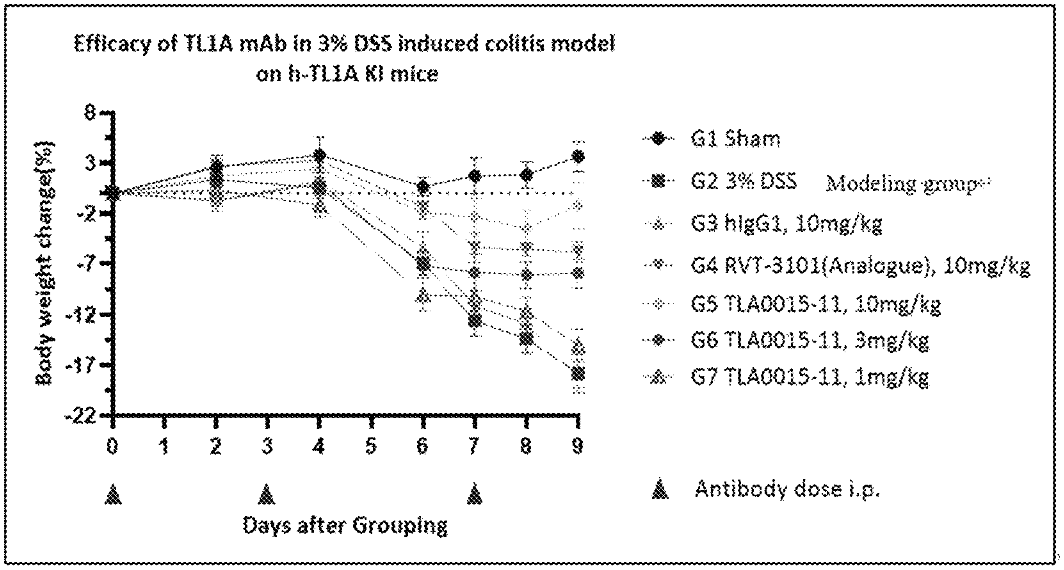
Figure 27:
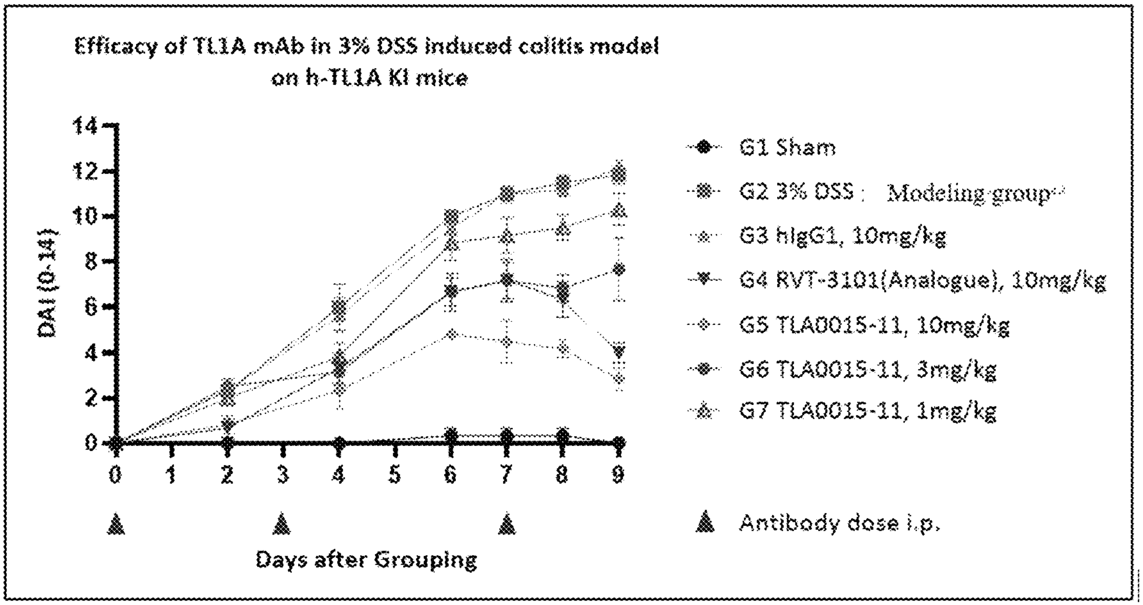
FIG. 27 shows the results of the anti-TL1A antibody described in the present application for daily scoring of B-hTL1A humanized transgenic mice in a DSS-induced enterocolitis model.
Figure 28A:
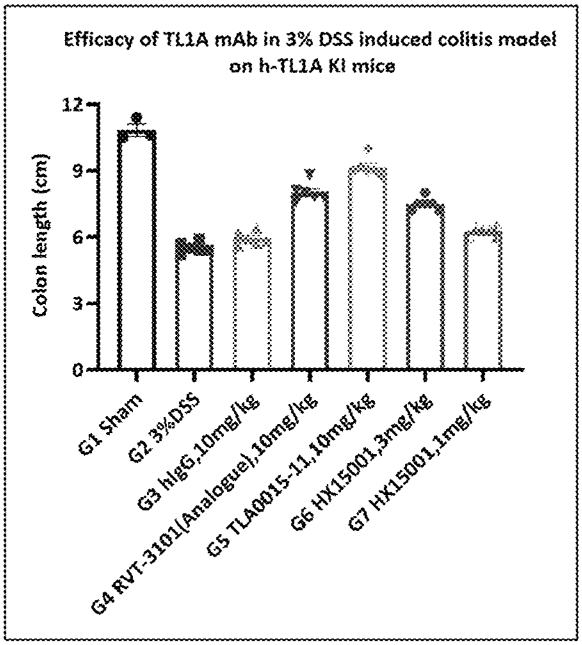
FIGS. 28A-28B show the effect of anti-TL1A antibodies described in the present application on colorectal length in B-hTL1A humanized transgenic mice in a DSS-induced enteritis model.
Figure 28B:
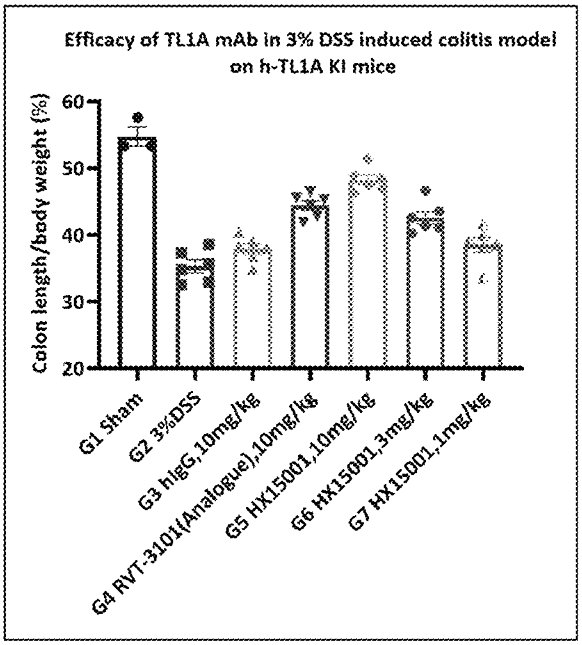
Figure 29A:
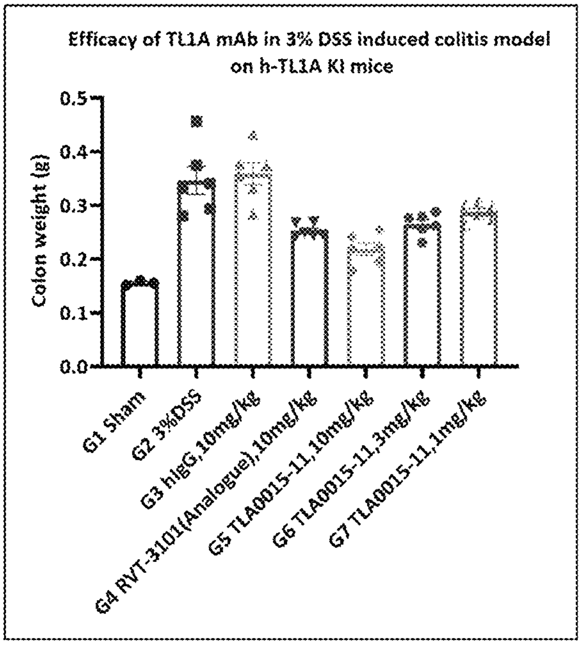
FIGS. 29A-29B show the effect of anti-TL1A antibodies described in the present application on colorectal weight in B-hTL1A humanized transgenic mice in a DSS-induced enteritis model.
Figure 29B:
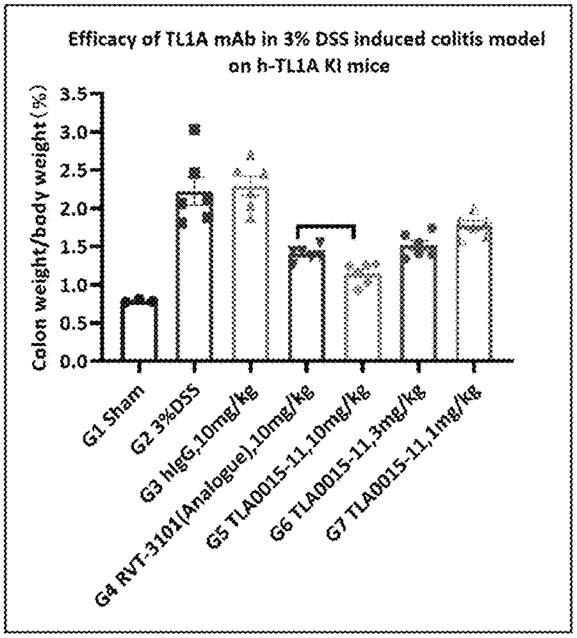

Experimental results: the results of the body weight changes of mice in each group are shown in FIG. 26A and FIG. 26B, and it can be seen that the body weights of mice in the modeling group and the IgG-negative control group were significantly decreased, and TLA0015-11 monoclonal antibody had a very good pharmacodynamic activity at the doses of 3 mg/kg and 10 mg/kg, and TLA0015-11 monoclonal antibody had a weak pharmacodynamic activity in the case of 1 mg/kg: the control antibodyRVT-3101 also had good pharmacodynamic activity. The results of daily scoring are shown in FIG. 27, in which the high dose group of TLA0015-11 antibody was scored better than the low dose group, and the potency was better than the control antibody RVT-3101 at the dose of 10 mg/kg. At the end of the experiment, all mice survived, and there was no difference in the survival curves. After the mice were dissected, the results of colorectal length are shown in FIGS. 28A and 28B, and the results of colorectal weight are shown in FIGS. 29A and 29B. The efficacy was seen in both the TLA0015-11 and RVT-3101 dosing groups, with a clear efficacy-dose relationship for TLA0015-11, with the higher the dose, the better the efficacy. In conclusion, TLA0015-11 antibody has a good in vivo pharmacodynamic activity in the DSS-induced murine enteritis model, and the pharmacodynamic effect is dose-related.

TABLE 25

Grouping of mice and details of drug administration (DSS-induced enteritis model)

| Group | Animal | Number of Animals | Modeling | Treatment | Dosing |
|---|---|---|---|---|---|
| G1 | hTL1A | 3 | — | — | — |
| G2 | mice | 6 | DSS | — | — |
| G3 | | 6 | | hIgG1 | 10 mg/kg, 3 dose |
| G4 | | 6 | | RVT-3101 (Analogue) | 10 mg/kg, 3 dose |
| G5 | | 6 | | TLA0015-11 | 10 mg/kg, 3 dose |
| G6 | | 6 | | TLA0015-11 | 3 mg/kg, 3 dose |
| G7 | | 6 | | TLA0015-11 | 1 mg/kg, 3 dose |

Example 22 Efficacy of Anti-TL1A Antibody in TNBS-Induced Enteritis Model in hTL1A Transgenic Mice In this experiment, hTL1A transgenic mice were used to study the in vivo pharmacodynamic activity of anti-TL1A antibodies in a TNBS-induced model of enterocolitis. TNBS-treated mice establish a preclinical model that mimics clinical Crohn's disease (CD), which produces a Th1-mediated immune response characterized by infiltration of CD4+ T cells, neutrophils, and macrophages that develops laterally progressive inflammation that leading to colitis. Therefore, the TNBS-induced enteritis model can be used to evaluate the in vivo pharmacodynamic activity of antibody drugs.

Forty-four male hTL1A transgenic mice were randomly divided into six groups based on body weight, including four mice in the G1 negative control group, eight mice in each of the G2 modeling group, G3 hIgG-negative control group, G4 RVT-3101 (analog) drug group, G5 MK-7240 (analog) drug group, and G6 TLA0015-11 administration group, and the detailed grouping of the mice is shown in Table 26. day 1 began intraperitoneal administration of the drug at three-day intervals for a total of three administrations. All animals were fasted on Day 0:100 μl of 60% ethanol was given (i.r.) rectally to the G1 negative control group on Day 1, and 100 μl of 2% TNBS was given (i.r.) rectally to the G2 to G6 groups and feed was resumed to all animals to induce acute enterocolitis. During the experiment, the body weights of the experimental animals were measured and recorded daily, and the daily activities of the animals were observed: the fecal traits of the experimental animals were scored daily (0=normal, 1=moist/sticky, 2=fluffy, 3=liquid). At the end of the experiment on day 9, all experimental animals were euthanized using excess carbon dioxide asphyxiation after which the abdominal cavity was cut open, the colon was removed, and the length of the colon was recorded.

Figure 30A:
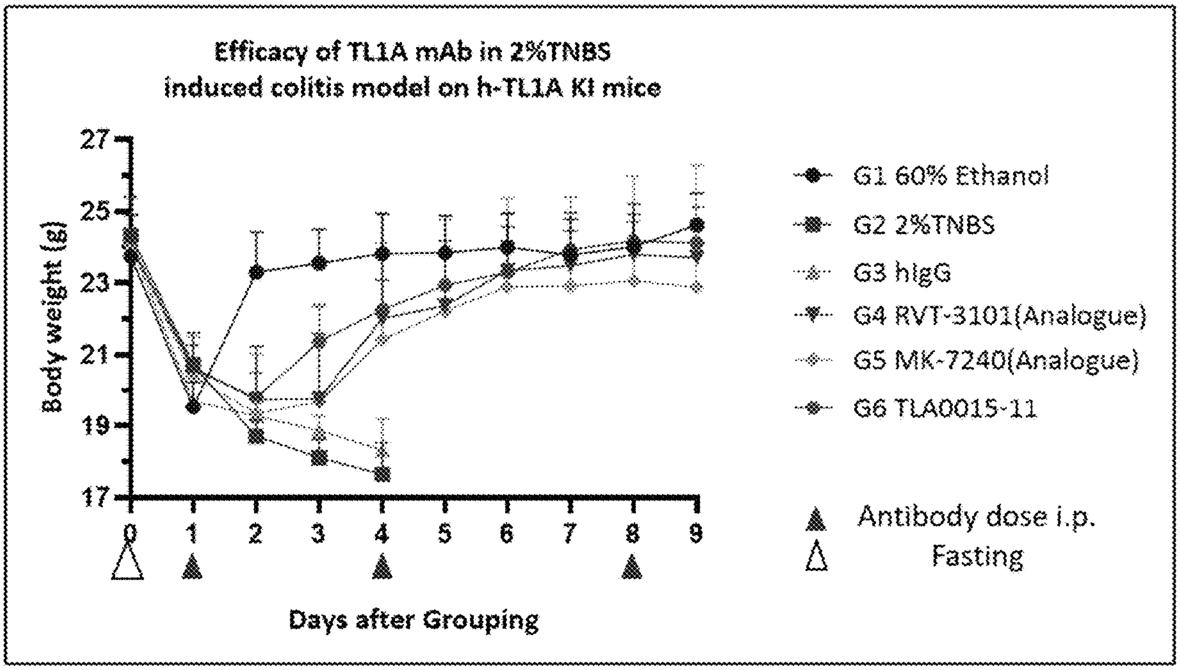
FIGS. 30A-30B show the effect of the anti-TL1A antibodies described in the present application on the change in body weight of B-hTL1A humanized transgenic mice in a TNBS-induced enteritis model.
Figure 30B:
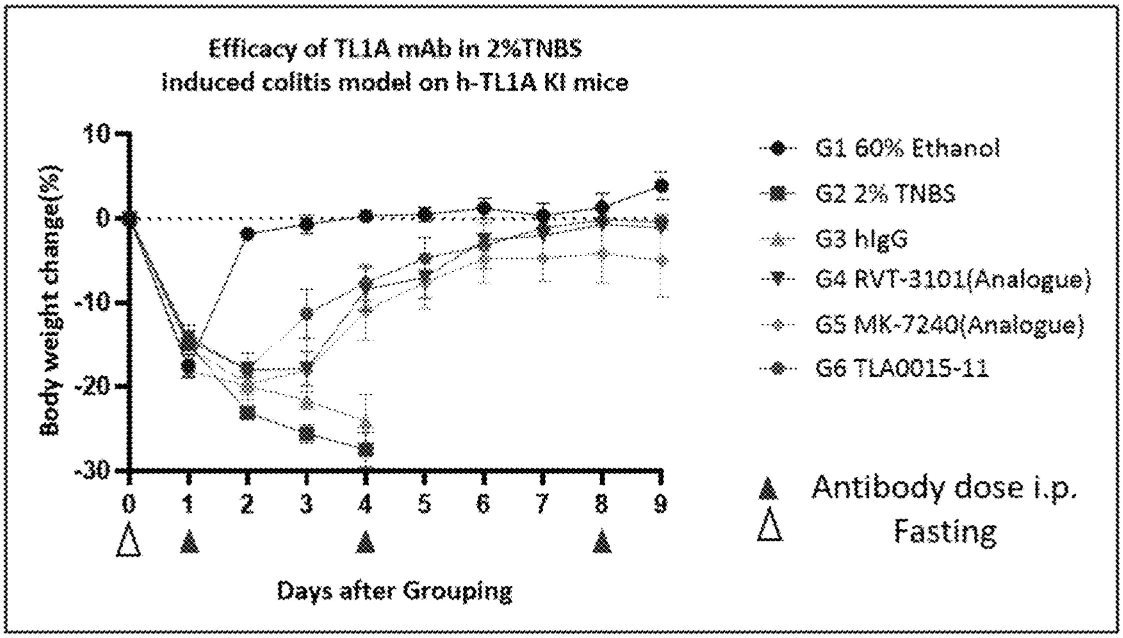
Figure 31:
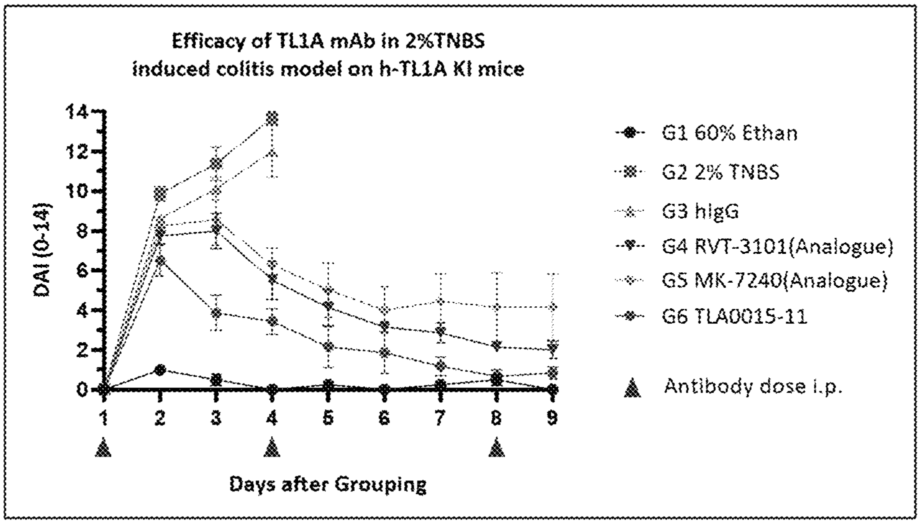
FIG. 31 shows the results of the anti-TL1A antibody described in the present application for daily scoring of B-hTL1A humanized transgenic mice in a TNBS-induced enterocolitis model.
Figure 32:
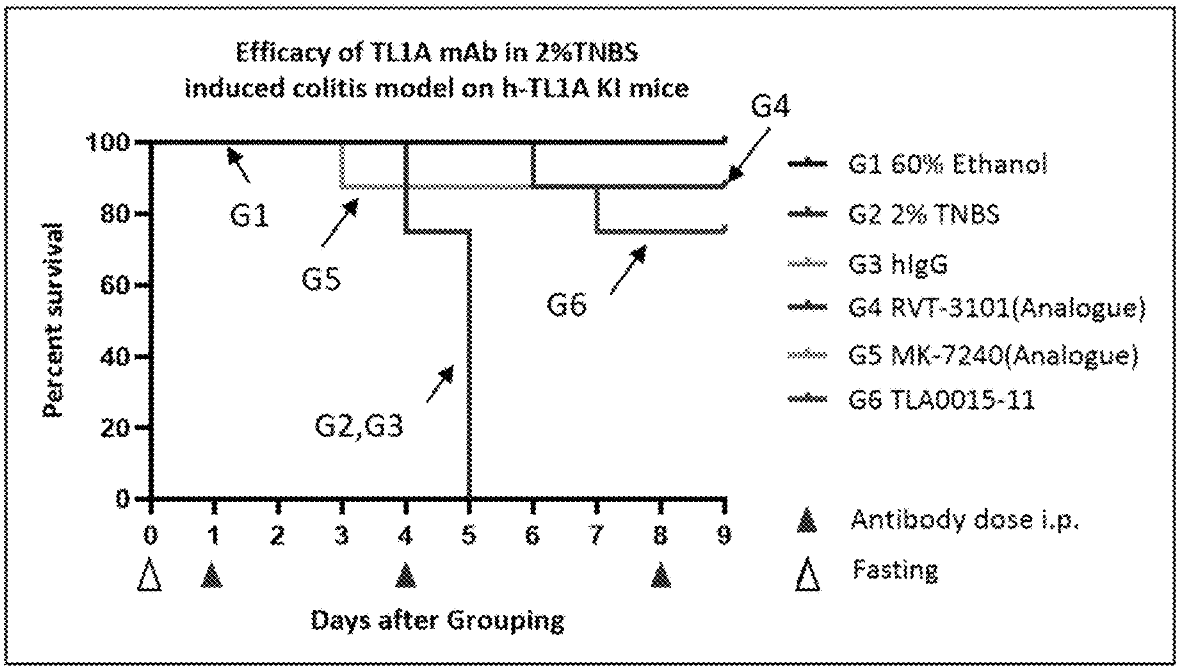
FIG. 32 shows the effect of the anti-TL1A antibodies described in the present application on the survival curves of B-hTL1A humanized transgenic mice in a TNBS-induced enteritis model.
Figure 33A:
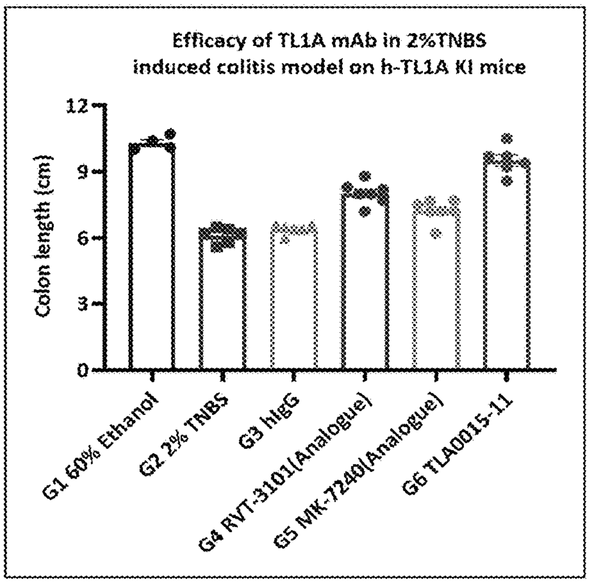
FIGS. 33A-33B show the effect of the anti-TL1A antibodies described in the present application on colorectal length in B-hTL1A humanized transgenic mice in a TNBS-induced enteritis model.
Figure 33B:
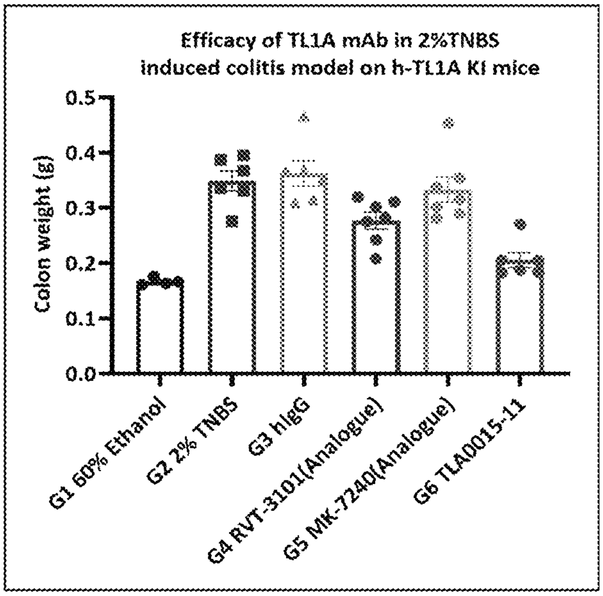
Figure 34A:
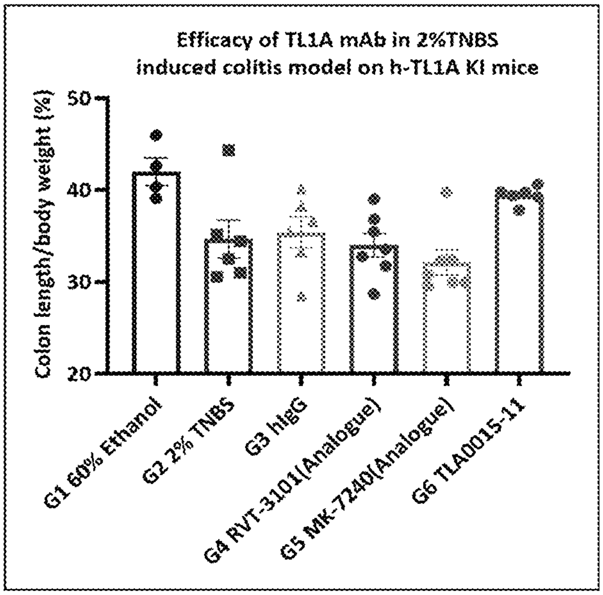
FIGS. 34A-34B show the effect of anti-TL1A antibodies described in the present application on colorectal weight in B-hTL1A humanized transgenic mice in a TNBS-induced enteritis model.
Figure 34B:
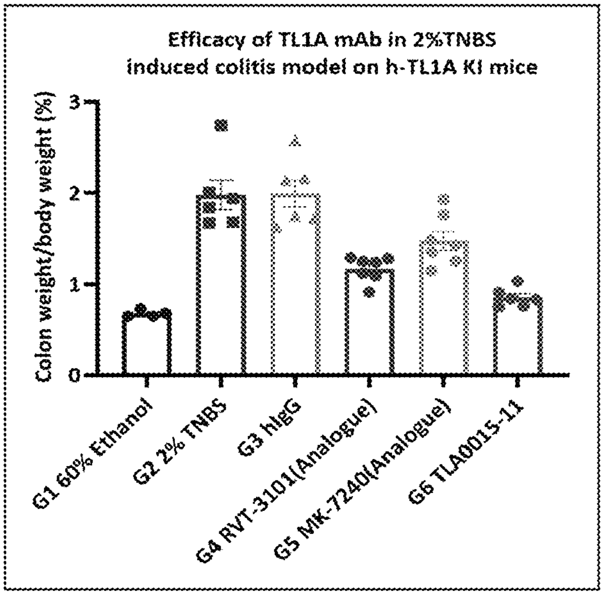

At the end of the experiment, the results were statistically analyzed, in which the results of mice weight changes are shown in FIG. 30A and FIG. 30B, and the weight regain of mice can be seen in the RVT-3101 (analog) drug group, the MK-7240 (analog) drug group, and the TLA0015-11 administration group when compared with the G2 modeling group. From the results of daily activity scores (FIG. 31), the scores of RVT-3101 (analog) drug group, MK-7240 (analog) drug group and TLA0015-11 administration group started to decrease after day 2. The results of the animal survival curves are shown in FIG. 32, in which all mice in the modeling group and hIgG-negative control group died at day 5. At the end of day 9, some mice in the three TL1A antibody-administered groups also died. Colorectal length and weight were measured after dissection, and the results of colorectal length in mice are shown in FIGS. 33A and 33B, and the results of colorectal weight are shown in FIGS. 34A and 34B. Significant shortening of colorectal length and increase in colorectal weight were seen in the G2 modeling group. efficacy of the drug could be seen in RVT-3101, MK-7240 and TLA0015-11.

TABLE 26

Grouping of mice and details of drug administration (TNBS-induced enteritis model)

| Group | Animal | Number of Animals | Modeling | Treatment | Dosing |
|---|---|---|---|---|---|
| G1 | hTL1A | 4 | — | — | — |
| G2 | mice | 8 | TNBS | — | — |
| G3 | | 8 | | hIgG1 | 10 mg/kg, 3 dose |
| G4 | | 8 | | RVT-3101 (Analogue) | 10 mg/kg, 3 dose |
| G5 | | 8 | | MK-7240 (Analogue) | 10 mg/kg, 3 dose |
| G6 | | 8 | | TLA0015-11 | 10 mg/kg, 3 dose |

To explore the relationship between the efficacy of TLA0015-11 antibody and the dose in the TNBS-induced enteritis model, three dose groups were designed, which were 1 mg/kg, 3 mg/kg and 10 mg/kg, and the specific groupings are shown in Table 27, and the experiments were carried out as described above.

Figure 35A:
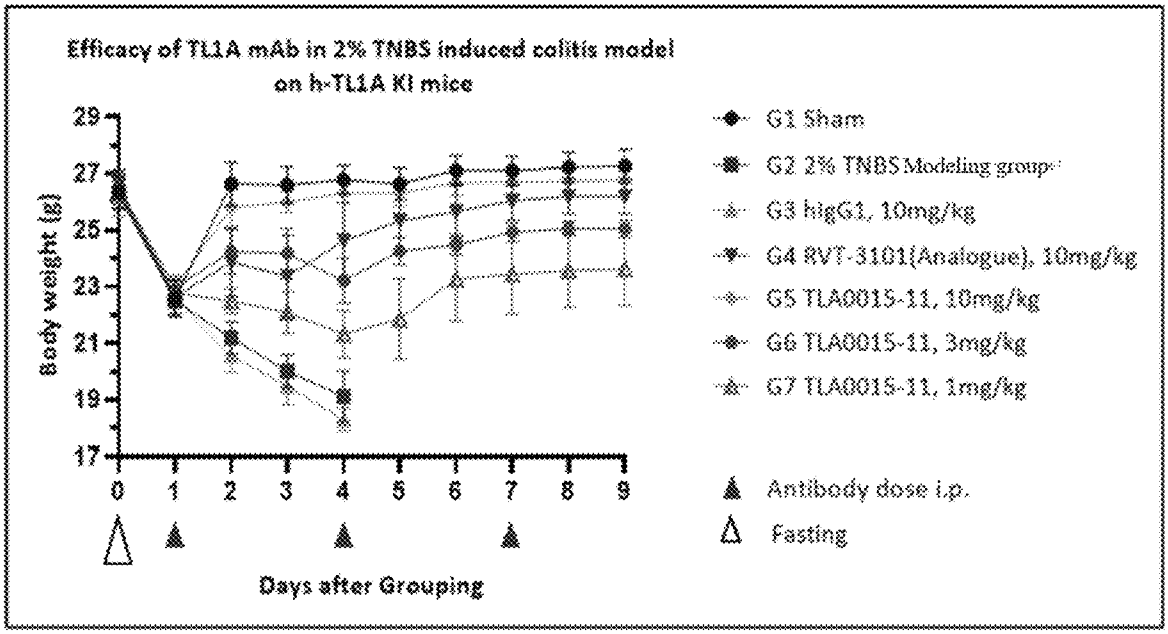
FIGS. 35A-35B show the effect of anti-TL1A antibodies described in the present application on the change in body weight of B-hTL1A humanized transgenic mice in a TNBS-induced enteritis model.
Figure 35B:
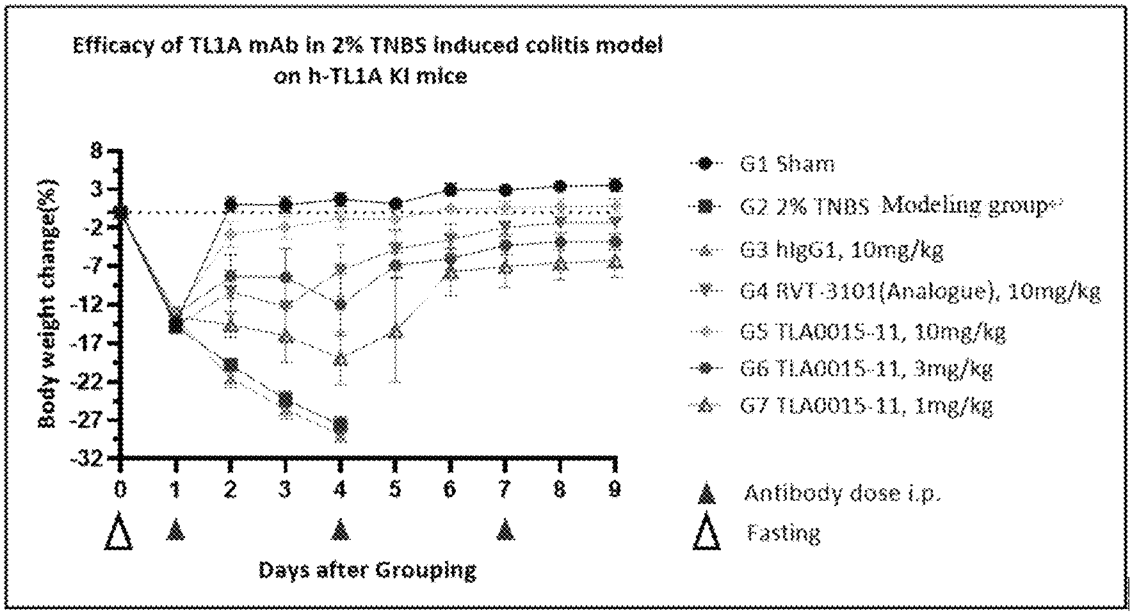
Figure 36:
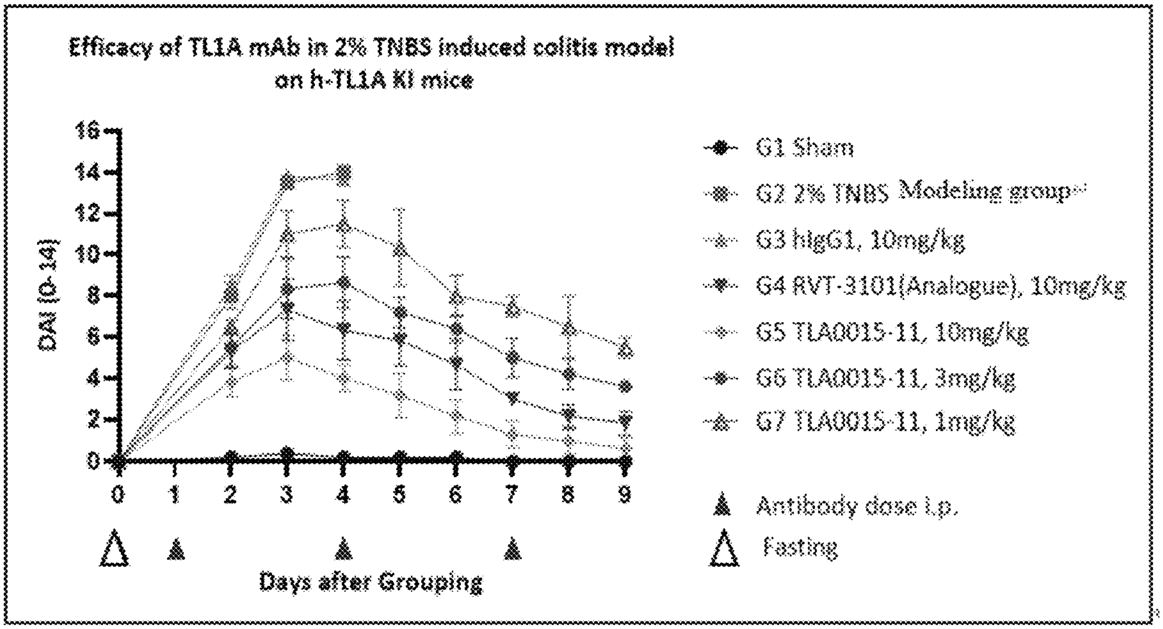
FIG. 36 shows the results of the anti-TL1A antibody described in the present application for daily scoring of B-hTL1A humanized transgenic mice in a TNBS-induced enterocolitis model.
Figure 37:
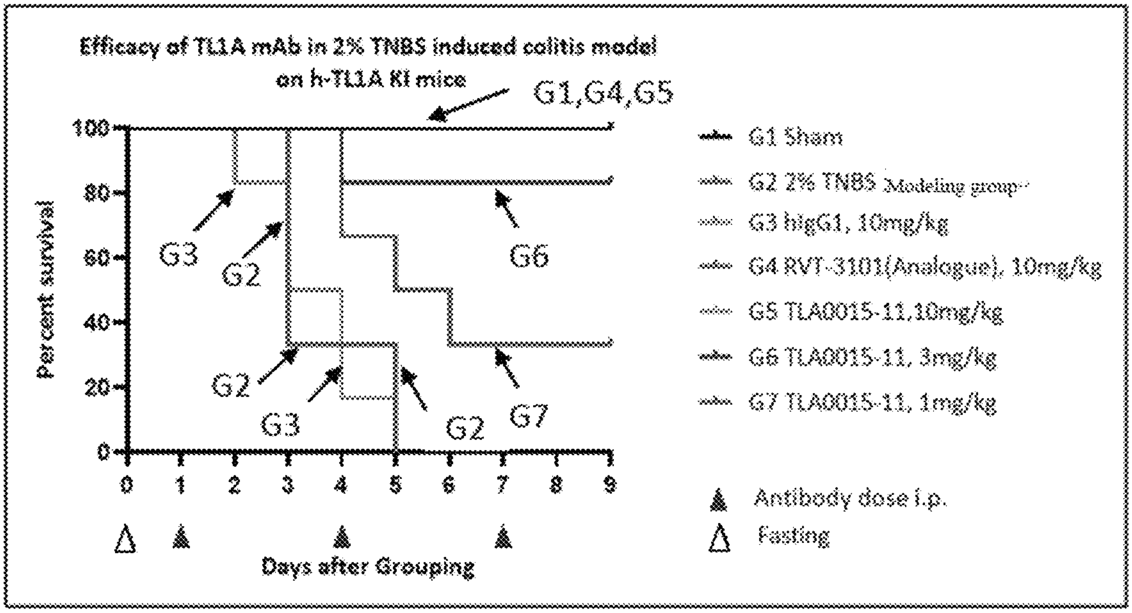
FIG. 37 shows the effect of the anti-TL1A antibodies described in the present application on the survival curves of B-hTL1A humanized transgenic mice in a TNBS-induced enteritis model.
Figure 38A:
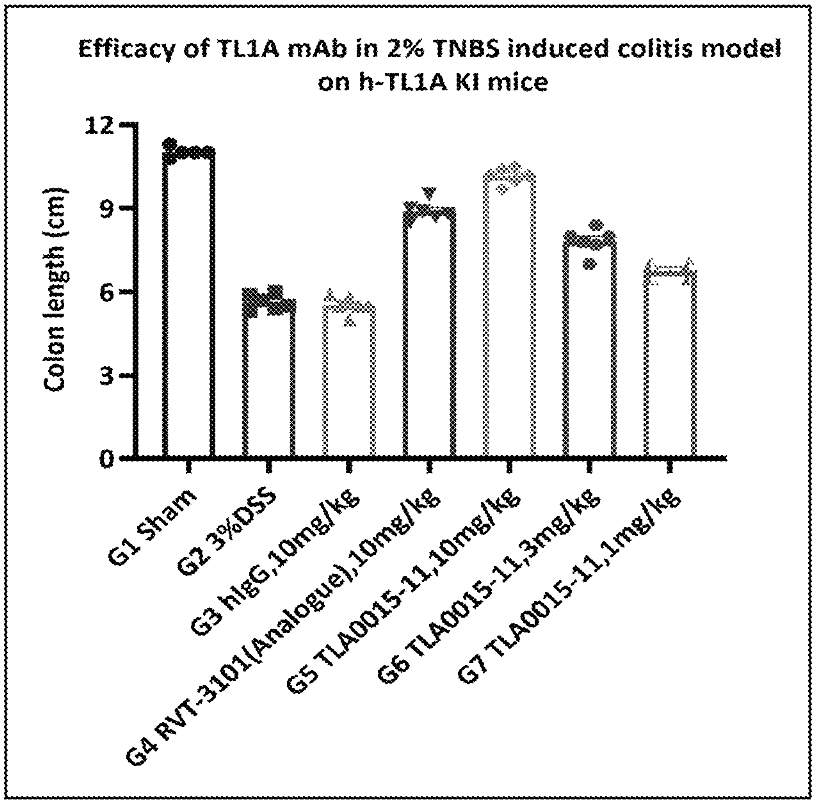
FIGS. 38A-38B show the effect of the anti-TL1A antibodies described in the present application on colorectal length in B-hTL1A humanized transgenic mice in a TNBS-induced enteritis model.
Figure 38B:
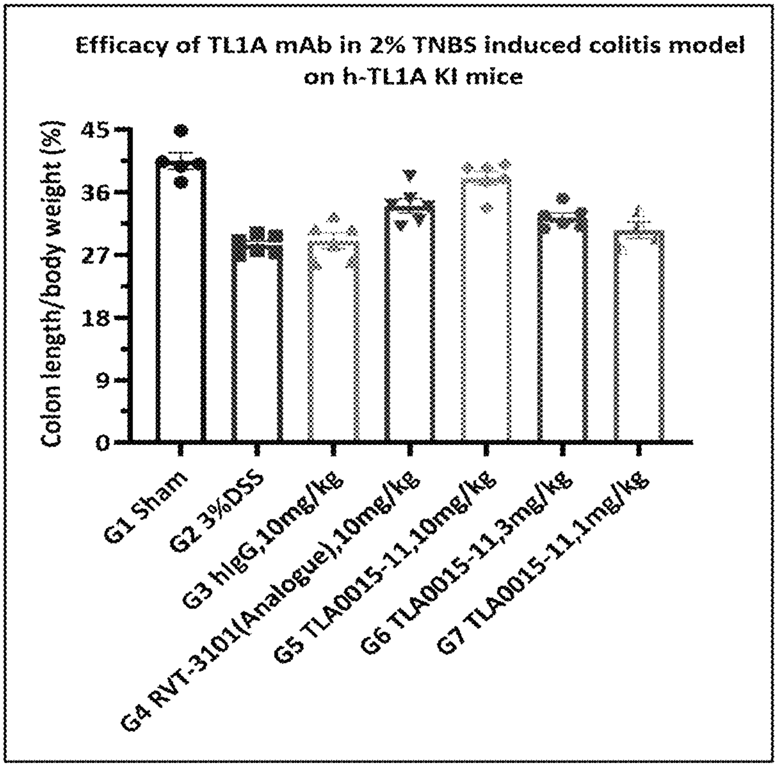
Figure 39A:
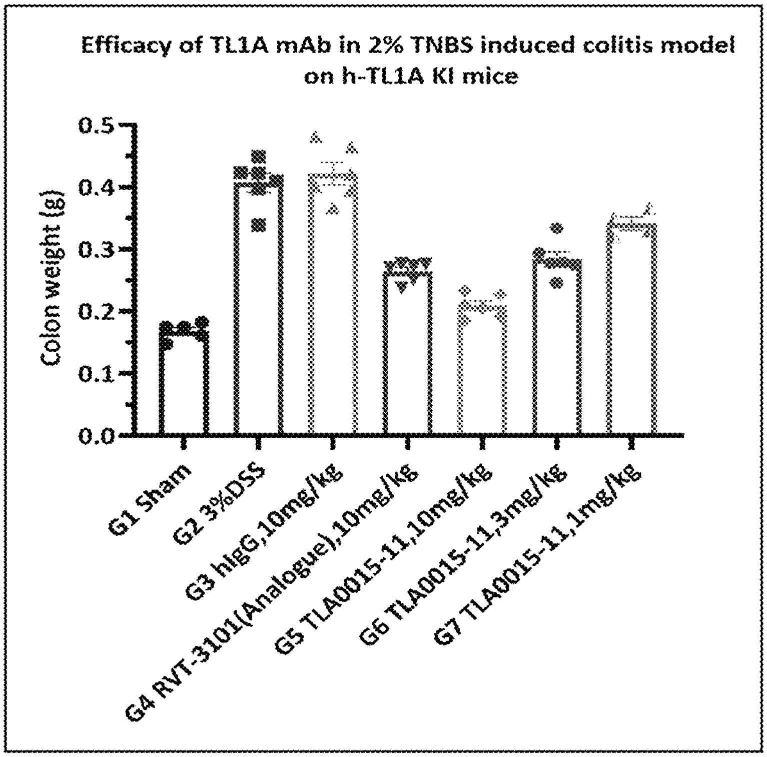
FIGS. 39A-39B show the effect of anti-TL1A antibodies described in the present application on colorectal weight in B-hTL1A humanized transgenic mice in a TNBS-induced enteritis model.
Figure 39B:
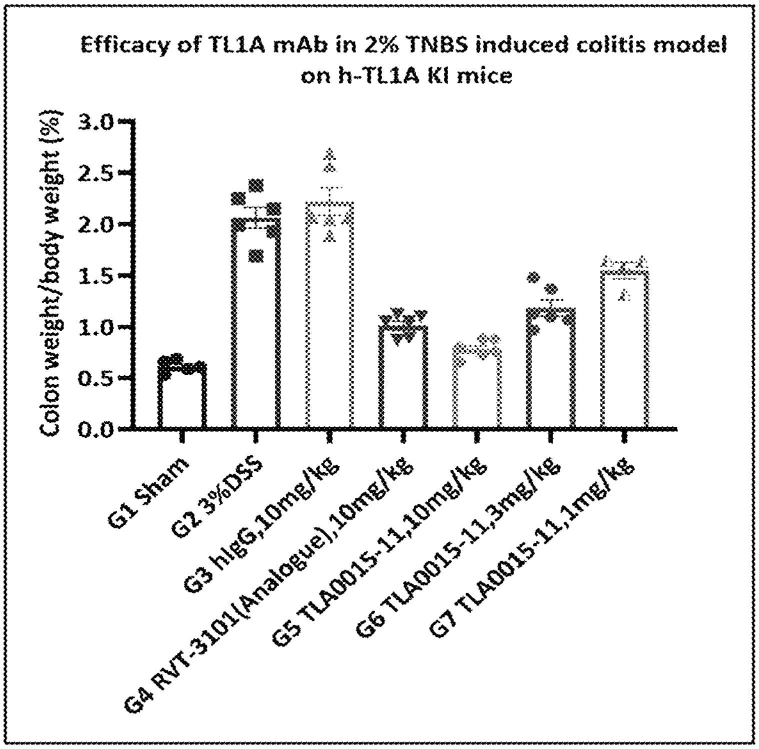

Experimental results: the results of the body weight changes of mice in each group are shown in FIGS. 35A and 35B, and it can be seen that the body weights of mice in both the modeling group and the IgG-negative control group were significantly decreased, and TLA0015-11 monoclonal antibody had a very good pharmacodynamic activity at the doses of 3 mg/kg and 10 mg/kg, and TLA0015-11 monoclonal antibody had a weak pharmacodynamic activity in the case of 1 mg/kg: the control antibodyRVT-3101 also had good pharmacodynamic activity. The results of daily scoring are shown in FIG. 36, in which the TLA0015-11 antibody high-dose group scored better than the low-dose group and was more potent than the control antibody RVT-3101 at a dose of 10 mg/kg. The results of the animal survival curves are shown in FIG. 37, in which all the mice in the modeling group and the hIgG-negative control group were dead at the end of day 5. At the end of day 9, no mice died at the dose of 10 mg/kg for RVT-3101 and TLA0015-11; one mouse died at the dose of 3 mg/kg for TLA0015-11; and four mice died at the dose of 1 mg/kg. After the mice were dissected, the results of colorectal length are shown in FIGS. 38A and 38B, and the results of colorectal weight are shown in FIGS. 39A and 39B. The efficacy of the drug was seen in both the TLA0015-11 and RVT-3101 dosing groups, with a clear dose-dependent efficacy of TLA0015-11, with the higher the dose, the better the efficacy. In conclusion, TLA0015-11 antibody has good in vivo pharmacodynamic activity in TNBS-induced murine enteritis model, and the pharmacodynamic effect is dose-related.

TABLE 27

Grouping of mice and details of drug administration (TNBS-induced enteritis model)

| Group | Animal | Number of Animals | Modeling | Treatment | Dosing |
|---|---|---|---|---|---|
| G1 | hTL1A | 3 | — | — | — |
| G2 | mice | 6 | TNBS | — | — |
| G3 | | 6 | | hIgG1 | 10 mg/kg, 3 dose |
| G4 | | 6 | | RVT-3101 (Analogue) | 10 mg/kg, 3 dose |
| G5 | | 6 | | TLA0015-11 | 10 mg/kg, 3 dose |
| G6 | | 6 | | TLA0015-11 | 3 mg/kg, 3 dose |
| G7 | | 6 | | TLA0015-11 | 1 mg/kg, 3 dose |

In summary, the sequences used in the present application are shown in the table below, wherein [ ] represents that the position can be arbitrarily replaced by the amino acids shown in [ ].

| c | LABEL | SEQ |
|---|---|---|
| 1 | TLA0015-HCDR1 | [STY]YGVD |
| 2 | TLA0015-HCDR1-1 | SYGVD |
| 3 | TLA0015 HCDR1-2 | YYGVD |
| 4 | TLA0015-HCDR1-3 | TYGVD |
| 5 | TLA0015-HCDR2 | [RV]IWGFG[GK]T[DHN]Y[NQ][APS]ALKS |
| 6 | TLA0015-HCDR2-1 | VIWGFGGTNYNSALKS |
| 7 | TLA0015-HCDR2-2 | VIWGFGGTNYQSALKS |
| 8 | TLA0015-HCDR2-3 | VIWGFGGTNYNAALKS |
| 9 | TLA0015-HCDR2-4 | VIWGFGGTNYNPALKS |
| 10 | TLA0015-HCDR2-5 | VIWGFGGTHYNSALKS |
| 11 | TLA0015-HCDR2-6 | RIWGFGGTNYNSALKS |
| 12 | TLA0015-HCDR2-7 | VIWGFGKTNYNSALKS |
| 13 | TLA0015-HCDR2-8 | VIWGFGGTDYNSALKS |
| 14 | TLA0015-HCDR3 | G[DLN][FY]DAMDY |
| 15 | TLA0015-HCDR3-1 | GNFDAMDY |
| 16 | TLA0015-HCDR3-2 | GNYDAMDY |
| 17 | TLA0015-HCDR3-3 | GDFDAMDY |
| 18 | TLA0015-HCDR3-4 | GLEDAMDY |

-continued

| c | LABEL | SEQ |
|---|---|---|
| 19 | TLA0015-HFR1 | E[IV]QL[LV]ESGGGL[IV]QPGGSLR[IL]SCAVSGF[DS]L[IKS] |
| 20 | TLA0015-HFR1-1 | EIQLLESGGGLVQPGGSLRLSCAVSGFSLS |
| 21 | TLA0015-HFR1-2 | EIQLLESGGGLVQPGGSLRISCAVSGFSLS |
| 22 | TLA0015-HFR1-3 | EIQLVESGGGLVQPGGSLRISCAVSGFSLS |
| 23 | TLA0015-HFR1-4 | EVQLLESGGGLVQPGGSLRLSCAVSGFSLS |
| 24 | TLA0015-HFR1-5 | EIQLVESGGGLIQPGGSLRLSCAVSGFSLS |
| 25 | TLA0015-HFR1-6 | EIQLVESGGGLIQPGGSLRISCAVSGFSLS |
| 26 | TLA0015-HFR1-7 | EIQLVESGGGLIQPGGSLRISCAVSGFSLI |
| 27 | TLA0015-HFR1-8 | EIQLVESGGGLIQPGGSLRISCAVSGFSLK |
| 28 | TLA0015-HFR1-9 | EIQLVESGGGLIQPGGSLRISCAVSGFDLS |
| 29 | TLA0015-HFR2 | WVRQ[AS]PGKGLEW[LV]G |
| 30 | TLA0015-HFR2-1/TLA-0238-HFR2-3 | WVRQAPGKGLEWVG |
| 31 | TLA0015 HFR2-2 | WVRQAPGKGLEWLG |
| 32 | TLA0015-HFR2-3 | WVRQSPGKGLEWLG |
| 33 | TLA0015-HFR3 | R[FL]TIS[AKRV]DNSKNT[LV]YLQMNSLRAEDTAVYYCA[RS] |
| 34 | TLA0015-HFR3-1 | RLTISRDNSKNTLYLQMNSLRAEDTAVYYCAS |
| 35 | TLA0015-HFR3-2 | RLTISKDNSKNTVYLQMNSLRAEDTAVYYCAS |
| 36 | TLA0015-HFR3-3 | RFTISRDNSKNTVYLQMNSLRAEDTAVYYCAS |
| 37 | TLA0015-HFR3-4 | RLTISRDNSKNTVYLQMNSLRAEDTAVYYCAS |
| 38 | TLA0015-HFR3-5 | RLTISRDNSKNTVYLQMNSLRAEDTAVYYCAR |
| 39 | TLA0015-HFR3-6 | RLTISVDNSKNTVYLQMNSLRAEDTAVYYCAS |
| 40 | TLA0015-HFR3-7 | RLTISADNSKNTVYLQMNSLRAEDTAVYYCAS |
| 41 | TLA0015-HFR4-1/TLA-0238-HFR4-2 | WGQGTLVTVSS |

-continued

| c | LABEL | SEQ |
|---|---|---|
| 42 | TLA0015-LCDR1-1 | RASQDISNYLN |
| 43 | TL0015-LCDR2-1 | YTSRLHS |
| 44 | TL0015-LCDR3-1 | QQGNTLPFT |
| 45 | TL0015-LFR1 | DIQMTQ[ST][PT]SSLSASVGDRVTI[TS]C |
| 46 | TL0015-LFR1-1 | DIQMTQTTSSLSASLGDRVTISC |
| 47 | TL0015-LFR1-2/TLA0241-LFR1-1 | DIQMTQSPSSLSASVGDRVTITC |
| 48 | TL0015-LFR2 | WYQQKPGK[AV][PV]KLLIY |
| 49 | TL0015-LFR2-1 | WYQQKPDGTVKLLIY |
| 50 | TL0015-LFR2-2 | WYQQKPGKVVKLLIY |
| 51 | TL0015-LFR2-3 | WYQQKPGKAVKLLIY |
| 52 | TL0015-LFR2-4/TLA0241-LFR2-1 | WYQQKPGKAPKLLIY |
| 53 | TL0015-LFR3 | GVPSRFSGSGSGTD[FY]TLTISSLQPED[FV]ATY[FY]C |
| 54 | TL0015-LFR3-1 | GVPSRFSGSGSGTDYSLTISNLEQEDIATYFC |
| 55 | TL0015 LFR3-2 | GVPSRFSGSGSGTDYTLTISSLQPEDVATYFC |
| 56 | TL0015-LFR3-3 | GVPSRFSGSGSGTDYTLTISSLQPEDFATYFC |
| 57 | TL0015-LFR3-4/TLA0238-LFR3-4/TLA0241-LFR3-2 | GVPSRFSGSGSGTDFTLTISSLQPEDFATYYC |
| 58 | TL0015-LFR4 | FG[PQ]GTKLEIK |
| 59 | TL0015-LFR4-1 | FGSGTKLEIK |
| 60 | TL0015-LFR4-2 | FGPGTKLEIK |
| 61 | TL0015-LFR4-3/TLA0238-LFR4-3 | FGQGTKLEIK |
| 62 | TLA0015-VH-1 | QIQLKESGPGLVAPSQSLSITCTVSGFSLSSYGVDWVRQSPGKGLEWLGVIWGFGGTNYN SALKSRLSISKDNSKSQVFLKMNSLQSDDSAIYYCASGNFDAMDYWGQGTSVTVSS |

-continued

| c | LABEL | SEQ |
|---|---|---|
| 63 | TLA0015-VH-2 | EIQLLESGGGLVQPGGSLRLSCAVSGFSLSSYGVDWVRQAPGKGLEWVGVIWGFGGTN YNSALKSRLTISRDNSKNTLYLQMNSLRAEDTAVYYCASGNFDAMDYWGQGTLVTVSS |
| 64 | TLA0015-VH-3 | EIQLLESGGGLVQPGGSLRISCAVSGFSLSSYGVDWVRQAPGKGLEWLGVIWGFGGTNY NSALKSRLTISKDNSKNTVYLQMNSLRAEDTAVYYCASGNFDAMDYWGQGTLVTVSS |
| 65 | TLA0015-VH-4 | EIQLVESGGGLVQPGGSLRISCAVSGFSLSSYGVDWVRQSPGKGLEWLGVIWGFGGTNY NSALKSRLTISKDNSKNTVYLQMNSLRAEDTAVYYCASGNFDAMDYWGQGTLVTVSS |
| 66 | TLA0015-VH-5 | EVQLLESGGGLVQPGGSLRLSCAVSGFSLSSYGVDWVRQAPGKGLEWLGVIWGFGGTN YNSALKSRFTISRDNSKNTVYLQMNSLRAEDTAVYYCASGNFDAMDYWGQGTLVTVSS |
| 67 | TLA0015-VH-6 | EVQLLESGGGLVQPGGSLRLSCAVSGFSLSSYGVDWVRQAPGKGLEWLGVIWGFGGTN YNSALKSRLTISRDNSKNTVYLQMNSLRAEDTAVYYCASGNFDAMDYWGQGTLVTVSS |
| 68 | TLA0015 VH-7 | EVQLLESGGGLVQPGGSLRLSCAVSGFSLSSYGVDWVRQAPGKGLEWLGVIWGFGGTN YNSALKSRLTISKDNSKNTVYLQMNSLRAEDTAVYYCASGNFDAMDYWGQGTLVTVSS |
| 69 | TLA0015-VH-8 | EIQLVESGGGLIQPGGSLRLSCAVSGFSLSSYGVDWVRQAPGKGLEWLGVIWGFGGTNY NSALKSRLTISRDNSKNTVYLQMNSLRAEDTAVYYCARGNFDAMDYWGQGTLVTVSS |
| 70 | TLA0015-VH-9 | EIQLVESGGGLIQPGGSLRISCAVSGFSLSSYGVDWVRQAPGKGLEWLGVIWGFGGTNY NSALKSRLTISKDNSKNTVYLQMNSLRAEDTAVYYCASGNFDAMDYWGQGTLVTVSS |
| 71 | TLA0015-VH-10 | EIQLVESGGGLIQPGGSLRISCAVSGFSLSSYGVDWVRQAPGKGLEWLGVIWGFGGTNY NSALKSRLTISRDNSKNTVYLQMNSLRAEDTAVYYCASGNFDAMDYWGQGTLVTVSS |
| 72 | TLA0015-VH-11 | EIQLVESGGGLIQPGGSLRISCAVSGFSLSSYGVDWVRQAPGKGLEWLGVIWGFGGTNY NSALKSRLTISVDNSKNTVYLQMNSLRAEDTAVYYCASGNFDAMDYWGQGTLVTVSS |
| 73 | TLA0015-VH-12 | EIQLVESGGGLIQPGGSLRISCAVSGFSLSSYGVDWVRQAPGKGLEWLGVIWGFGGTNY QSALKSRLTISKDNSKNTVYLQMNSLRAEDTAVYYCASGNFDAMDYWGQGTLVTVSS |
| 74 | TLA0015-VH-13 | EIQLVESGGGLIQPGGSLRISCAVSGFSLSSYGVDWVRQAPGKGLEWLGVIWGFGGTNY NAALKSRLTISKDNSKNTVYLQMNSLRAEDTAVYYCASGNFDAMDYWGQGTLVTVSS |
| 75 | TLA0015-VH-14 | EIQLVESGGGLIQPGGSLRISCAVSGFSLSSYGVDWVRQAPGKGLEWLGVIWGFGGTNY NSALKSRLTISADNSKNTVYLQMNSLRAEDTAVYYCASGNFDAMDYWGQGTLVTVSS |
| 76 | TLA0015-VH-15 | EIQLVESGGGLIQPGGSLRISCAVSGFSLSYYGVDWVRQAPGKGLEWLGVIWGFGGTNY NSALKSRLTISKDNSKNTVYLQMNSLRAEDTAVYYCASGNFDAMDYWGQGTLVTVSS |
| 77 | TLA0015-VH-16 | EIQLVESGGGLIQPGGSLRISCAVSGFSLSSYGVDWVRQAPGKGLEWLGVIWGFGGTNY NSALKSRLTISKDNSKNTVYLQMNSLRAEDTAVYYCASGNYDAMDYWGQGTLVTVSS |
| 78 | TLA0015-VH-17 | EIQLVESGGGLIQPGGSLRISCAVSGFSLSSYGVDWVRQAPGKGLEWLGVIWGFGGTNY NSALKSRLTISKDNSKNTVYLQMNSLRAEDTAVYYCASGDFDAMDYWGQGTLVTVSS |
| 79 | TLA0015-VH-18 | EIQLVESGGGLIQPGGSLRISCAVSGFSLSSYGVDWVRQAPGKGLEWLGVIWGFGGTNY NSALKSRLTISKDNSKNTVYLQMNSLRAEDTAVYYCASGLFDAMDYWGQGTLVTVSS |
| 80 | TLA0015-VH-19 | EIQLVESGGGLIQPGGSLRISCAVSGFSLSTYGVDWVRQAPGKGLEWLGVIWGFGGTNY NSALKSRLTISKDNSKNTVYLQMNSLRAEDTAVYYCASGNFDAMDYWGQGTLVTVSS |
| 81 | TLA0015-VH-20 | EIQLVESGGGLIQPGGSLRISCAVSGFSLISYGVDWVRQAPGKGLEWLGVIWGFGGTNYN SALKSRLTISKDNSKNTVYLQMNSLRAEDTAVYYCASGNFDAMDYWGQGTLVTVSS |
| 82 | TLA0015-VH-21 | EIQLVESGGGLIQPGGSLRISCAVSGFSLSSYGVDWVRQAPGKGLEWLGVIWGFGGTNY NPALKSRLTISKDNSKNTVYLQMNSLRAEDTAVYYCASGNFDAMDYWGQGTLVTVSS |
| 83 | TLA0015-VH-22 | EIQLVESGGGLIQPGGSLRISCAVSGFSLKSYGVDWVRQAPGKGLEWLGVIWGFGGTNY NSALKSRLTISKDNSKNTVYLQMNSLRAEDTAVYYCASGNFDAMDYWGQGTLVTVSS |
| 84 | TLA0015-VH-23 | EIQLVESGGGLIQPGGSLRISCAVSGFSLSSYGVDWVRQAPGKGLEWLGVIWGFGGTHY NSALKSRLTISKDNSKNTVYLQMNSLRAEDTAVYYCASGNFDAMDYWGQGTLVTVSS |
| 85 | TLA0015-VH-24 | EIQLVESGGGLIQPGGSLRISCAVSGFSLSSYGVDWVRQAPGKGLEWLGRIWGFGGTNY NSALKSRLTISKDNSKNTVYLQMNSLRAEDTAVYYCASGNFDAMDYWGQGTLVTVSS |
| 86 | TLA0015-VH-25 | EIQLVESGGGLIQPGGSLRISCAVSGFDLSSYGVDWVRQAPGKGLEWLGVIWGFGGTNY NSALKSRLTISKDNSKNTVYLQMNSLRAEDTAVYYCASGNFDAMDYWGQGTLVTVSS |
| 87 | TLA0015-VH-26 | EIQLVESGGGLIQPGGSLRISCAVSGFSLSSYGVDWVRQAPGKGLEWLGVIWGFGKTNY NSALKSRLTISKDNSKNTVYLQMNSLRAEDTAVYYCASGNFDAMDYWGQGTLVTVSS |
| 88 | TLA0015-VH-27 | EIQLVESGGGLIQPGGSLRISCAVSGFSLSSYGVDWVRQAPGKGLEWLGVIWGFGGTDY NSALKSRLTISKDNSKNTVYLQMNSLRAEDTAVYYCASGNFDAMDYWGQGTLVTVSS |

-continued

| c | LABEL | SEQ |
|---|---|---|
| 89 | TLA0015-VH-28 | EIQLVESGGGLIQPGGSLRISCAVSGFSLSYYGVDWVRQAPGKGLEWLGVIWGFGGTNYNSALKSRLTISKDNSKNTVYLQMNSLRAEDTAVYYCASGNYDAMDYWGQGTLVTVSS |
| 90 | TLA0015-VH-29 | EIQLVESGGGLIQPGGSLRISCAVSGFSLSYYGVDWVRQAPGKGLEWLGVIWGFGGTNYNSALKSRLTISKDNSKNTVYLQMNSLRAEDTAVYYCASGDFDAMDYWGQGTLVTVSS |
| 91 | TLA0015-VH-30 | EIQLVESGGGLIQPGGSLRISCAVSGFSLSYYGVDWVRQAPGKGLEWLGVIWGFGGTNYNPALKSRLTISKDNSKNTVYLQMNSLRAEDTAVYYCASGNFDAMDYWGQGTLVTVSS |
| 92 | TLA0015-VH-31 | EIQLVESGGGLIQPGGSLRISCAVSGFSLSYYGVDWVRQAPGKGLEWLGVIWGFGGTHYNSALKSRLTISKDNSKNTVYLQMNSLRAEDTAVYYCASGNFDAMDYWGQGTLVTVSS |
| 93 | TLA0015-VH-32 | EIQLVESGGGLIQPGGSLRISCAVSGFSLSYYGVDWVRQAPGKGLEWLGRIWGFGGTNYNSALKSRLTISKDNSKNTVYLQMNSLRAEDTAVYYCASGNFDAMDYWGQGTLVTVSS |
| 94 | TLA0015-VH-33 | EIQLVESGGGLIQPGGSLRISCAVSGFDLSYYGVDWVRQAPGKGLEWLGVIWGFGGTNYNSALKSRLTISKDNSKNTVYLQMNSLRAEDTAVYYCASGNFDAMDYWGQGTLVTVSS |
| 95 | TLA0015-VH-34 | EIQLVESGGGLIQPGGSLRISCAVSGFSLISYGVDWVRQAPGKGLEWLGVIWGFGGTNYNSALKSRLTISKDNSKNTVYLQMNSLRAEDTAVYYCASGNYDAMDYWGQGTLVTVSS |
| 96 | TLA0015-VH-35 | EIQLVESGGGLIQPGGSLRISCAVSGFSLSSYGVDWVRQAPGKGLEWLGVIWGFGGTNYNPALKSRLTISKDNSKNTVYLQMNSLRAEDTAVYYCASGNYDAMDYWGQGTLVTVSS |
| 97 | TLA0015-VH-36 | EIQLVESGGGLIQPGGSLRISCAVSGFSLSSYGVDWVRQAPGKGLEWLGVIWGFGGTHYNSALKSRLTISKDNSKNTVYLQMNSLRAEDTAVYYCASGNYDAMDYWGQGTLVTVSS |
| 98 | TLA0015-VH-37 | EIQLVESGGGLIQPGGSLRISCAVSGFSLSSYGVDWVRQAPGKGLEWLGRIWGFGGTNYNSALKSRLTISKDNSKNTVYLQMNSLRAEDTAVYYCASGNYDAMDYWGQGTLVTVSS |
| 99 | TLA0015-VH-38 | EIQLVESGGGLIQPGGSLRISCAVSGFSLSSYGVDWVRQAPGKGLEWLGVIWGFGKTNYNSALKSRLTISKDNSKNTVYLQMNSLRAEDTAVYYCASGNYDAMDYWGQGTLVTVSS |
| 100 | TLA0015-VH-39 | EIQLVESGGGLIQPGGSLRISCAVSGFSLISYGVDWVRQAPGKGLEWLGVIWGFGGTNYNSALKSRLTISKDNSKNTVYLQMNSLRAEDTAVYYCASGDFDAMDYWGQGTLVTVSS |
| 101 | TLA0015-VH-40 | EIQLVESGGGLIQPGGSLRISCAVSGFSLSSYGVDWVRQAPGKGLEWLGVIWGFGGTHYNSALKSRLTISKDNSKNTVYLQMNSLRAEDTAVYYCASGDFDAMDYWGQGTLVTVSS |
| 102 | TLA0015-VL-1 | DIQMTQTTSSLSASLGDRVTISCRASQDISNYLNWYQQKPDGTVKLLIYYTSRLHSGVPSRFSGSGSGTDYSLTISNLEQEDIATYFCQQGNTLPFTFGSGTKLEIK |
| 103 | TLA0015-VL-2 | DIQMTQSPSSLSASVGDRVTITCRASQDISNYLNWYQQKPGKVVKLLIYYTSRLHSGVPSRFSGSGSGTDYTLTISSLQPEDVATYFCQQGNTLPFTFGPGTKLEIK |
| 104 | TLA0015-VL-3 | DIQMTQSPSSLSASVGDRVTITCRASQDISNYLNWYQQKPGKAPKLLIYYTSRLHSGVPSRFSGSGSGTDFTLTISSLQPEDFATYYCQQGNTLPFTFGQGTKLEIK |
| 105 | TLA0015-VL-4 | DIQMTQSPSSLSASVGDRVTITCRASQDISNYLNWYQQKPGKAPKLLIYYTSRLHSGVPSRFSGSGSGTDYTLTISSLQPEDFATYFCQQGNTLPFTFGQGTKLEIK |
| 106 | TLA0015-VL-5 | DIQMTQSPSSLSASVGDRVTITCRASQDISNYLNWYQQKPGKAVKLLIYYTSRLHSGVPSRFSGSGSGTDYTLTISSLQPEDFATYFCQQGNTLPFTFGQGTKLEIK |
| 107 | TLA-0238-HCDR1 | NY[ILMYW]M[NHS] |
| 108 | TLA-0238-HCDR1-1 | NYWMN |
| 109 | TLA-0238-HCDR1-2 | NYWMH |
| 110 | TLA-0238-HCDR1-3 | NYWMS |
| 111 | TLA-0238-HCDR1-4 | NYIMN |
| 112 | TLA-0238-HCDR1-5 | NYLMN |

-continued

| c | LABEL | SEQ |
|---|---|---|
| 113 | TLA-0238-HCDR1-6 | NYMMN |
| 114 | TLA-0238-HCDR1-7 | NYYMN |
| 115 | TLA-0238-HCDR2 | QIRLKSDNYATHYA[ADE][PS]VKG |
| 116 | TLA-0238-HCDR2-1 | QIRLKSDNYATHYAESVKG |
| 117 | TLA-0238-HCDR2-2 | QIRLKSDNYATHYADSVKG |
| 118 | TLA-0238-HCDR2-3 | QIRLKSDNYATHYAASVKG |
| 119 | TLA-0238-HCDR2-4 | QIRLKSDNYATHYAAPVKG |
| 120 | TLA-0238-HCDR3-1 | LLLRYRDY |
| 121 | TLA-0238-HFR1 | [EQ]V[KQ][LV][EV]ESGGG[LV]V[KQ]PG[GR][AS]L[KR]LSC[AIJASGFTFS |
| 122 | TLA-0238-HFR1-1 | EVKVEESGGGLVQPGGSMKLSCIASGFTFS |
| 123 | TLA-0238-HFR1-2 | EVQVVESGGGLVKPGGSLRLSCAASGFTFS |
| 124 | TLA-0238-HFR1-3 | EVQVVESGGGLVQPGGSLRLSCIASGFTFS |
| 125 | TLA-0238-HFR 1-4 | EVQLVESGGGLVQPGGSLRLSCAASGFTFS |
| 126 | TLA-0238-HFR1-5 | QVQLVESGGGVVQPGRSLRLSCAASGFTFS |
| 127 | TLA-0238-HFR1-6 | EVKVEESGGGLVQPGGSLRLSCIASGFTFS |
| 128 | TLA-0238-HFR1-7 | EVKVEESGGGLVQPGGSLKLSCIASGFTFS |
| 129 | TLA-0238-HFR1-8 | EVKVEESGGGLVQPGGALRLSCIASGFTFS |
| 130 | TLA-0238-HFR1-9 | EVKLEESGGGLVQPGGSLKLSCIASGFTFS |
| 131 | TLA-0238-HFR1-10 | EVQLVESGGGLVKPGGSLRLSCAASGFTFS |
| 132 | TLA-0238-HFR1-11 | EVKLEESGGGLVQPGGALRLSCIASGFTFS |
| 133 | TLA-0238-HFR2 | WVRQ[AS]P[EG]KGLEWV[AG] |
| 134 | TLA-0238-HFR2-1 | WVRQSPEKGLEWVA |
| 135 | TLA-0238-HFR2-2 | WVRQAPGKGLEWVA |
| 136 | TLA-0238-HFR3 | [NR]F[AT]ISRD[DN][AS]K[NS][ST][ALV]YLQMNSL[KR][ADT]ED[MT]AVYYCTP |
| 137 | TLA-0238-HFR3-1 | NFTISRDDSKSSVYLQMNNLRAEDTGIYYCTP |
| 138 | TLA-0238-HFR3-2 | NFTISRDDSKSTVYLQMNSLKTEDTAVYYCTP |

-continued

| c | LABEL | SEQ |
|---|---|---|
| 139 | TLA-0238-HFR3-3 | NFTISRDNAKSSVYLQMNSLRAEDTAVYYCTP |
| 140 | TLA-0238-HFR3-4 | RFTISRDDSKSTVYLQMNSLKTEDTAVYYCTP |
| 141 | TLA-0238-HFR3-5 | NFAISRDDSKSTVYLQMNSLKTEDTAVYYCTP |
| 142 | TLA-0238-HFR3-6 | RFTISRDNSKNTLYLQMNSLRAEDTAVYYCTP |
| 143 | TLA-0238-HFR3-7 | RFTISRDNSKNTLYLQMNSLKTEDTAVYYCTP |
| 144 | TLA-0238-HFR3-8 | RFTISRDDSKNSLYLQMNSLRDEDTAVYYCTP |
| 145 | TLA-0238-HFR3-9 | RFTISRDDSKNTLYLQMNSLRAEDTAVYYCTP |
| 146 | TLA-0238-HFR3-10 | RFTISRDDSKNSLYLQMNSLRAEDMAVYYCTP |
| 147 | TLA-0238-HFR3-11 | RFTISRDDSKNTAYLQMNSLRAEDTAVYYCTP |
| 148 | TLA-0238-HFR3-12 | RFTISRDDSKNTLYLQMNSLKTEDTAVYYCTP |
| 149 | TLA-0238-HFR4 | WGQGT[LMT][LV]TVSS |
| 150 | TLA-0238-HFR4-1 | WGQGTTLTVSS |
| 151 | TLA-0238-HFR4-3 | WGQGTLLTVSS |
| 152 | TLA-0238-HFR4-4 | WGQGTMVTVSS |
| 153 | TLA-0238-HFR4-5 | WGQGTTVTVSS |
| 154 | TLA0238-LCDR1 | SASSSVSY[LM][AHT] |
| 155 | TLA0238-LCDR1-1 | SASSSVSYMH |
| 156 | TLA0238-LCDR1-2 | SASSSVSYLH |
| 157 | TLA0238-LCDR1-3 | SASSSVSYLA |
| 158 | TLA0238-LCDR1-4 | SASSSVSYLT |
| 159 | TLA0238-LCDR2 | DTSN[LR]A[ST] |
| 160 | TLA0238-LCDR2-1 | DTSNLAS |
| 161 | TLA0238-LCDR2-2 | DTSNRAS |
| 162 | TLA0238-LCDR2-3 | DTSNLAT |
| 163 | TLA0238-LCDR3 | FQE[NSE][GEA]HPFT |
| 164 | TLA0238-LCDR3-1 | FQENGHPFT |

-continued

| c | LABEL | SEQ |
|---|---|---|
| 165 | TLA0238-LCDR3-2 | FQESGHPFT |
| 166 | TLA0238-LCDR3-3 | FQENEHPFT |
| 167 | TLA0238-LCDR3-4 | FQEEGHPFT |
| 168 | TLA0238-LCDR3-5 | FQENAHPFT |
| 169 | TLA0238-LFR1 | [DE][INTV][QV][LM]TQSP[AS][FIST][LMV]S[ALV][ST][PV]G[DE][KR][AV]T[IM][ST]C |
| 170 | TLA0238-LFR1-1 | ENVLTQSPAIMSASPGEKVTMTC |
| 171 | TLA0238-LFR1-2 | ENVLTQSPATLSLSPGERATMSC |
| 172 | TLA0238-LFR1-3 | DNQLTQSPSSLSASVGDRVTITC |
| 173 | TLA0238-LFR1-4/TLA0241-LFR1-2 | DIQMTQSPSSVSASVGDRVTITC |
| 174 | TLA0238-LFR1-5 | ENVLTQSPAIMSATPGEKVTITC |
| 175 | TLA0238-LFR1-6 | EVVLTQSPAFLSVTPGEKVTITC |
| 176 | TLA0238-LFR1-7 | ENVLTQSPAFMSATPGEKVTITC |
| 177 | TLA0238-LFR1-8 | EIVLTQSPAFMSATPGEKVTITC |
| 178 | TLA0238-LFR1-9 | ETVLTQSPAFMSATPGEKVTITC |
| 179 | TLA0238-LFR1-10 | ENVLTQSPAFLSVTPGEKVTITC |
| 180 | TLA0238-LFR2 | WYQQKP[DG][KQ][AS]P[KQR]LWIY |
| 181 | TLA0238-LFR2-1 | WYQQKSSTSPKLWIY |
| 182 | TLA0238-LFR2-2 | WYQQKPGQAPRLWIY |
| 183 | TLA0238-LFR2-3 | WYQQKPGKAPKLWIY |
| 184 | TLA0238-LFR2-4 | WYQQKPGQSPQLWIY |
| 185 | TLA0238-LFR2-5 | WYQQKPGQSPRLWIY |
| 186 | TLA0238-LFR2-6 | WYQQKPGKSPKLWIY |
| 187 | TLA0238-LFR2-7 | WYQQKPDQSPKLWIY |
| 188 | TLA0238-LFR2-8 | WYQQKPGQSPKLWIY |
| 189 | TLA0238-LFR3 | GVP[ADGS]RFSGSGSG[NT][DS][FY]TLTISS[LM][EQ][AP]ED[AFV]A[TV]YYC |

-continued

| c | LABEL | SEQ |
|---|---|---|
| 190 | TLA0238-LFR3-1 | GVPGRFSGSGSGNSYSLTISSMEAEDVATYYC |
| 191 | TLA0238-LFR3-2 | GVPARFSGSGSGNDYTLTISSMEPEDFAVYYC |
| 192 | TLA0238-LFR3-3 | GVPGRFSGSGSGNDYTLTISSLQPEDFATYYC |
| 193 | TLA0238-LFR3-5 | GVPDRFSGSGSGTDYTLTISSLQPEDVATYYC |
| 194 | TLA0238-LFR3-6 | GVPDRFSGSGSGTDYTLTISSLQPEDFAVYYC |
| 195 | TLA0238-LFR3-7 | GVPSRFSGSGSGTSYTLTISSLQPEDVATYYC |
| 196 | TLA0238-LFR3-8 | GVPDRFSGSGSGTDYTLTISSLEAEDAATYYC |
| 197 | TLA0238-LFR3-9 | GVPSRFSGSGSGTDYTLTISSLQPEDFATYYC |
| 198 | TLA0238 LFR4 | FG[GQ]GTK[LV]E[IM]K |
| 199 | TLA0238-LFR4-1 | FGGGTKLEMK |
| 200 | TLA0238-LFR4-2 | FGGGTKVEMK |
| 201 | TLA0238-LFR4-4/TLA0241-LFR4-1 | FGQGTKVEIK |
| 202 | TLA0238-VH-1 | EVKVEESGGGLVQPGGSMKLSCIASGFTFSNYWMNWVRQSPEKGLEWVAQIRLKSDNYATHYAESVKGNFTISRDDSKSSVYLQMNNLRAEDTGIYYCTPLLLRYRDYWGQGTTLTVSS |
| 203 | TLA0238-VH-2 | EVQVVESGGGLVKPGGSLRLSCAASGFTFSNYWMNWVRQAPGKGLEWVAQIRLKSDNYATHYAESVKGNFTISRDDSKSTVYLQMNSLKTEDTAVYYCTPLLLRYRDYWGQGTLVTVSS |
| 204 | TLA0238-VH-3 | EVQVVESGGGLVQPGGSLRLSCIASGFTFSNYWMNWVRQAPGKGLEWVAQIRLKSDNYATHYAESVKGNFTISRDNAKSSVYLQMNSLRAEDTAVYYCTPLLLRYRDYWGQGTLLTVSS |
| 205 | TLA0238-VH-4 | EVQVVESGGGLVKPGGSLRLSCAASGFTFSNYWMNWVRQAPGKGLEWVAQIRLKSDNYATHYAESVKGRFTISRDDSKSTVYLQMNSLKTEDTAVYYCTPLLLRYRDYWGQGTLVTVSS |
| 206 | TLA0238-VH-5 | EVQVVESGGGLVKPGGSLRLSCAASGFTFSNYWMNWVRQAPGKGLEWVAQIRLKSDNYATHYAESVKGNFAISRDDSKSTVYLQMNSLKTEDTAVYYCTPLLLRYRDYWGQGTLVTVSS |
| 207 | TLA0238-VH-6 | QVQLVESGGGVVQPGRSLRLSCAASGFTFSNYWMNWVRQAPGKGLEWVAQIRLKSDNYATHYADSVKGRFTISRDNSKNTLYLQMNSLRAEDTAVYYCTPLLLRYRDYWGQGTMVTVSS |
| 208 | TLA0238-VH-7 | EVKVEESGGGLVQPGGSLRLSCIASGFTFSNYWMHWVRQAPGKGLEWVGQIRLKSDNYATHYAASVKGRFTISRDNSKNTLYLQMNSLKTEDTAVYYCTPLLLRYRDYWGQGTLVTVSS |
| 209 | TLA0238-VH-8 | EVKVEESGGGLVQPGGSLKLSCIASGFTFSNYWMHWVRQAPGKGLEWVGQIRLKSDNYATHYAASVKGRFTISRDDSKNSLYLQMNSLRDEDTAVYYCTPLLLRYRDYWGQGTLVTVSS |
| 210 | TLA0238-VH-9 | EVKVEESGGGLVQPGGALRLSCIASGFTFSNYWMHWVRQAPGKGLEWVGQIRLKSDNYATHYAASVKGRFTISRDDSKNTLYLQMNSLRAEDTAVYYCTPLLLRYRDYWGQGTLVTVSS |

-continued

| c | LABEL | SEQ |
|---|---|---|
| 211 | TLA0238-VH-10 | EVKVEESGGGLVQPGGSLRLSCIASGFTFSNYWMHWVRQAPGKGLEWVGQIRLKSDNYATHYAASVKGRFTISRDDSKNSLYLQMNSLRAEDMAVYYCTPLLLRYRDYWGQGTLVTVSS |
| 212 | TLA0238-VH-11 | EVQLVESGGGLVQPGGSLRLSCAASGFTFSNYWMNWVRQAPGKGLEWVAQIRLKSDNYATHYADSVKGRFTISRDNSKNTLYLQMNSLRAEDTAVYYCTPLLLRYRDYWGQGTMVTVSS |
| 213 | TLA0238-VH-12 | EVKLEESGGGLVQPGGSLKLSCIASGFTFSNYWMHWVRQAPGKGLEWVGQIRLKSDNYATHYAASVKGRFTISRDDSKNTAYLQMNSLRAEDTAVYYCTPLLLRYRDYWGQGTLVTVSS |
| 214 | TLA0238-VH-13 | EVQLVESGGGLVKPGGSLRLSCAASGFTFSNYWMNWVRQAPGKGLEWVAQIRLKSDNYATHYAAPVKGRFTISRDDSKNTLYLQMNSLKTEDTAVYYCTPLLLRYRDYWGQGTTVTVSS |
| 215 | TLA0238-VH-14 | EVKLEESGGGLVQPGGALRLSCIASGFTFSNYWMSWVRQAPGKGLEWVGQIRLKSDNYATHYAASVKGRFTISRDDSKNTLYLQMNSLRAEDTAVYYCTPLLLRYRDYWGQGTLVTVSS |
| 216 | TLA0238-VH-15 | EVQLVESGGGLVQPGGSLRLSCAASGFTFSNYIMNWVRQAPGKGLEWVAQIRLKSDNYATHYADSVKGRFTISRDNSKNTLYLQMNSLRAEDTAVYYCTPLLLRYRDYWGQGTLVTVSS |
| 217 | TLA0238-VH-16 | EVQLVESGGGLVQPGGSLRLSCAASGFTFSNYLMNWVRQAPGKGLEWVAQIRLKSDNYATHYADSVKGRFTISRDNSKNTLYLQMNSLRAEDTAVYYCTPLLLRYRDYWGQGTLVTVSS |
| 218 | TLA0238-VH-17 | EVQLVESGGGLVQPGGSLRLSCAASGFTFSNYMMNWVRQAPGKGLEWVAQIRLKSDNYATHYADSVKGRFTISRDNSKNTLYLQMNSLRAEDTAVYYCTPLLLRYRDYWGQGTLVTVSS |
| 219 | TLA0238-VH-18 | EVQLVESGGGLVQPGGSLRLSCAASGFTFSNYWMNWVRQAPGKGLEWVAQIRLKSDNYATHYADSVKGRFTISRDNSKNTLYLQMNSLRAEDTAVYYCTPLLLRYRDYWGQGTLVTVSS |
| 220 | TLA0238-VH-19 | EVQLVESGGGLVQPGGSLRLSCAASGFTFSNYYMNWVRQAPGKGLEWVAQIRLKSDNYATHYADSVKGRFTISRDNSKNTLYLQMNSLRAEDTAVYYCTPLLLRYRDYWGQGTLVTVSS |
| 221 | TLA0238-VL-1 | ENVLTQSPAIMSASPGEKVTMTCSASSSVSYMHWYQQKSSTSPKLWIYDTSNLASGVPGRFSGSGSGNSYSLTISSMEAEDVATYYCFQENGHPFTFGGGTKLEMK |
| 222 | TLA0238-VL-2 | ENVLTQSPATLSLSPGERATMSCSASSSVSYMHWYQQKPGQAPRLWIYDTSNLASGVPARFSGSGSGNDYTLTISSMEPEDFAVYYCFQENGHPFTFGGGTKVEMK |
| 223 | TLA0238-VL-3 | DNQLTQSPSSLSASVGDRVTITCSASSSVSYMHWYQQKPGKAPKLWIYDTSNLASGVPGRFSGSGSGNDYTLTISSLQPEDFATYYCFQENGHPFTFGQGTKLEIK |
| 224 | TLA0238-VL-4 | ENVLTQSPAIMSATPGEKVTITCSASSSVSYLHWYQQKPGQSPQLWIYDTSNRASGVPDRFSGSGSGTDYTLTISSLQPEDVATYYCFQENGHPFTFGGGTKLEMK |
| 225 | TLA0238-VL-5 | EVVLTQSPAFLSVTPGEKVTITCSASSSVSYLAWYQQKPGQSPRLWIYDTSNRASGVPDRFSGSGSGTDYTLTISSLQPEDFAVYYCFQENGHPFTFGGGTKLEMK |
| 226 | TLA0238-VL-6 | ENVLTQSPAFMSATPGEKVTITCSASSSVSYLAWYQQKPGKSPKLWIYDTSNLATGVPSRFSGSGSGTSYTLTISSLQPEDVATYYCFQENGHPFTFGGGTKLEMK |
| 227 | TLA0238-VL-7 | EIVLTQSPAFMSATPGEKVTITCSASSSVSYLHWYQQKPDQSPKLWIYDTSNRASGVPDRFSGSGSGTDYTLTISSLEAEDAATYYCFQENGHPFTFGGGTKLEMK |
| 228 | TLA0238-VL-8 | ETVLTQSPAFMSATPGEKVTITCSASSSVSYLTWYQQKPGQSPKLWIYDTSNLASGVPDRFSGSGSGTDYTLTISSLEAEDAATYYCFQENGHPFTFGGGTKLEMK |
| 229 | TLA0238-VL-9 | DIQMTQSPSSVSASVGDRVTITCSASSSVSYMHWYQQKPGKAPKLWIYDTSNLASGVPSRFSGSGSGTDFTLTISSLQPEDFATYYCFQENGHPFTFGQGTKVEIK |
| 230 | TLA0238-VL-10 | ENVLTQSPAFLSVTPGEKVTITCSASSSVSYLHWYQQKPDQSPKLWIYDTSNLATGVPSRFSGSGSGTDYTLTISSLQPEDFATYYCFQENGHPFTFGGGTKLEMK |
| 231 | TLA0238-VL-11 | DIQMTQSPSSVSASVGDRVTITCSASSSVSYMHWYQQKPGKAPKLWIYDTSNLASGVPSRFSGSGSGTDFTLTISSLQPEDFATYYCFQESGHPFTFGQGTKVEIK |

-continued

| c | LABEL | SEQ |
|---|---|---|
| 232 | TLA0238-VL-12 | DIQMTQSPSSVSASVGDRVTITCSASSSVSYMHWYQQKPGKAPKLWIYDTSNLASGVPSRFSGSGSGTDFTLTISSLQPEDFATYYCFQENEHPFTFGQGTKVEIK |
| 233 | TLA0238-VL-13 | DIQMTQSPSSVSASVGDRVTITCSASSSVSYMHWYQQKPGKAPKLWIYDTSNLASGVPSRFSGSGSGTDFTLTISSLQPEDFATYYCFQEEGHPFTFGQGTKVEIK |
| 234 | TLA0238-VL-14 | DIQMTQSPSSVSASVGDRVTITCSASSSVSYMHWYQQKPGKAPKLWIYDTSNLASGVPSRFSGSGSGTDFTLTISSLQPEDFATYYCFQENAHPFTFGQGTKVEIK |
| 235 | TLA0241-HCDR1 | DYY[LM][HN] |
| 236 | TLA0241-HCDR1-1 | DYYLN |
| 237 | TLA0241-HCDR1-2 | DYYMH |
| 238 | TLA0241-HCDR2 | DINPNNGRTTY[AN][DQ][KS][FV][KQT]G |
| 239 | TLA0241-HCDR2-1 | DINPNNGRTTYNQKFTG |
| 240 | TLA0241-HCDR2-2 | DINPNNGRTTYADSVKG |
| 241 | TLA0241-HCDR2-3 | DINPNNGRTTYNQKFQG |
| 242 | TLA0241-HCDR3-1 | EGGYGWYFDV |
| 243 | TLA0241-HFR1 | [EQ][ILV]QL[LQV][EQ]SG[AGP][EG][ELV][KV][KQ]PG[AGR]S[LV]R[IL]SC[AKS]ASGYTFT |
| 244 | TLA0241-HFR1-1 | EVQLVESGGGLVQPGGSLRLSCSASGYTFT |
| 245 | TLA0241-HFR1-2 | QVQLVESGGGVVQPGRSLRLSCAASGYTFT |
| 246 | TLA0241-HFR1-3 | EVQLQQSGPEVKKPGASVRISCKASGYTFT |
| 247 | TLA0241-HFR1-4 | ELQLQQSGPEVKKPGASVRISCKASGYTFT |
| 248 | TLA0241-HFR1-5 | EVQLLESGGGLVQPGGSLRLSCAASGYTFT |
| 249 | TLA0241-HFR1-6 | EIQLQQSGAEEKKPGASVRISCKASGYTFT |
| 250 | TLA0241-HFR1-7 | ELQLQQSGAEVKKPGASVRISCKASGYTFT |
| 251 | TLA0241-HFR2 | WV[QR]QAPG[EKQ]GLEWIG |
| 252 | TLA0241-HFR2-1 | WVRQAPGKGLEWIG |
| 253 | TLA0241-HFR2-2 | WVRQAPGQGLEWIG |
| 254 | TLA0241-HFR2-3 | WVQQAPGKGLEWIG |
| 255 | TLA0241-HFR2-4 | WVRQAPGEGLEWIG |
| 256 | TLA0241-HFR3 | R[FV]TI[ST][AR]D[KNT]S[KST][NS]T[AL]Y[LM][EQ][LM][NRS]SL[RT][AS][DE]D[MT]AVYYCAR |
| 257 | TLA0241-HFR3-1 | RFTISRDNSKNTLYLQMSSLRAEDTAVYYCAR |

-continued

| c | LABEL | SEQ |
|---|---|---|
| 258 | TLA0241-HFR3-2 | RFTISRDNSKNTLYLQMNSLRAEDTAVYYCAR |
| 259 | TLA0241-HFR3-3 | RVTITRDTSSSTAYMELRSLRSDDTAVYYCAR |
| 260 | TLA0241-HFR3-4 | RVTITADKSTSTAYMELRSLRSDDTAVYYCAR |
| 261 | TLA0241-HFR3-5 | RVTITADKSTSTAYMELRSLTSDDTAVYYCAR |
| 262 | TLA0241-HFR3-6 | RVTITADKSTSTAYMELRSLRSDDMAVYYCAR |
| 263 | TLA0241-HFR4 | WG[QRT]GT[LMT]VTVSS |
| 264 | TLA0241-HFR4-1 | WGRGTLVTVSS |
| 265 | TLA0241-HFR4-2 | WGQGTMVTVSS |
| 266 | TLA0241-HFR4-3 | WGTGTLVTVSS |
| 267 | TLA0241-HFR4-4 | WGQGTTVTVSS |
| 268 | TLA0241-HFR4-5 | WGTGTTVTVSS |
| 269 | TLA0241-LCDR1 | S[AT]SSSIISNY[LS][AH] |
| 270 | TLA0241-LCDR1-1 | STSSSIISNYSH |
| 271 | TLA0241-LCDR1-2 | SASSSIISNYLH |
| 272 | TLA0241-LCDR1-3 | SASSSIISNYSA |
| 273 | TLA0241-LCDR1-4 | SASSSIISNYLA |
| 274 | TLA0241-LCDR2 | KTSN[LR]PS |
| 275 | TLA0241-LCDR2-1 | KTSNLPS |
| 276 | TLA0241-LCDR2-2 | KTSNRPS |
| 277 | TLA0241-LCDR3-1 | QQGSDMPIT |
| 278 | TLA0241-LFR1 | [ADE]I[QV][LM]TQSP[AGPST][ST][LV]S[AL]S[PV]G[DE][KR]VTITC |
| 279 | TLA0241-LFR1-3 | EIVLTQSPTTLSLSPGEKVTITC |
| 280 | TLA0241-LFR1-4 | EIVLTQSPPTLSLSPGEKVTITC |
| 281 | TLA0241 LFR1-5 | EIVLTQSPGTLSLSPGEKVTITC |

-continued

| c | LABEL | SEQ |
|---|---|---|
| 282 | TLA0241-LFR1-6 | AIQLTQSPSSLSASVGDRVTITC |
| 283 | TLA0241-LFR1-7 | EIVLTQSPATLSLSPGEKVTITC |
| 284 | TLA0241-LFR2 | WYQQKP[DG][KQ][AS]P[KQ]LLIY |
| 285 | TLA0241-LFR2-2 | WYQQKPGKSPKLLIY |
| 286 | TLA0241-LFR2-3 | WYQQKPGQSPQLLIY |
| 287 | TLA0241-LFR2-4 | WYQQKPDQSPKLLIY |
| 288 | TLA0241-LFR3 | GVP[ADS]RFSGSGSGT[DES]FTLTI[NS]SL[EQ][AP]ED[AF]ATYYC |
| 289 | TLA0241-LFR3-1 | GVPSRFSGSGSGTEFTLTISSLQPEDFATYYC |
| 290 | TLA0241-LFR3-3 | GVPSRFSGSGSGTDFTLTINSLEAEDAATYYC |
| 291 | TLA0241-LFR3-4 | GVPDRFSGSGSGTDFTLTINSLEAEDAATYYC |
| 292 | TLA0241-LFR3-5 | GVPARFSGSGSGTDFTLTINSLEAEDAATYYC |
| 293 | TLA0241-LFR3-6 | GVPSRFSGSGSGTSFTLTINSLEAEDAATYYC |
| 294 | TLA0241-LFR4 | FG[AQ]GT[KR][LV]E[IL]K |
| 295 | TLA0241-LFR4-2 | FGAGTRLELK |
| 296 | TLA0241-LFR4-3 | FGAGTKLELK |
| 297 | TLA0241-VH-1 | EFQLQQSGPELVKPGASVRISCKASGYTFTDYYLNWVKQSRGESLEWIGDINPNNGRTTYNQKFTGKATWTVDKSSSTVYMELRSLTSDDSAVYYCAREGGYGWYFDVWGTGTTVTVSS |
| 298 | TLA0241-VH-2 | EVQLVESGGGLVQPGGSLRLSCSASGYTFTDYYLNWVRQAPGKGLEWIGDINPNNGRTTYADSVKGRFTISRDNSKNTLYLQMSSLRAEDTAVYYCAREGGYGWYFDVWGRGTLVTVSS |
| 299 | TLA0241-VH-3 | QVQLVESGGGVVQPGRSLRLSCAASGYTFTDYYLNWVRQAPGKGLEWIGDINPNNGRTTYADSVKGRFTISRDNSKNTLYLQMNSLRAEDTAVYYCAREGGYGWYFDVWGQGTMVTVSS |
| 300 | TLA0241-VH-4 | EVQLQQSGPEVKKPGASVRISCKASGYTFTDYYMHWVRQAPGQGLEWIGDINPNNGRTTYNQKFQGRVTITRDTSSSTAYMELRSLRSDDTAVYYCAREGGYGWYFDVWGTGTTVTVSS |
| 301 | TLA0241-VH-5 | EVQLQQSGPEVKKPGASVRISCKASGYTFTDYYMHWVQQAPGKGLEWIGDINPNNGRTTYNQKFQGRVTITADKSTSTAYMELRSLRSDDTAVYYCAREGGYGWYFDVWGTGTLVTVSS |
| 302 | TLA0241-VH-6 | ELQLQQSGPEVKKPGASVRISCKASGYTFTDYYMHWVQQAPGKGLEWIGDINPNNGRTTYNQKFQGRVTITADKSTSTAYMELRSLTSDDTAVYYCAREGGYGWYFDVWGTGTTVTVSS |
| 303 | TLA0241-VH-7 | EVQLLESGGGLVQPGGSLRLSCAASGYTFTDYYLNWVRQAPGKGLEWIGDINPNNGRTTYADSVKGRFTISRDNSKNTLYLQMNSLRAEDTAVYYCAREGGYGWYFDVWGQGTMVTVSS |
| 304 | TLA0241-VH-8 | EVQLQQSGPEVKKPGASVRISCKASGYTFTDYYMHWVRQAPGEGLEWIGDINPNNGRTTYNQKFQGRVTITADKSTSTAYMELRSLRSDDTAVYYCAREGGYGWYFDVWGTGTTVTVSS |

-continued

| c | LABEL | SEQ |
|---|---|---|
| 305 | TLA0241-VH-9 | QVQLVESGGGVVQPGRSLRLSCAASGYTFTDYYLNWVRQAPGKGLEWIGDINPNNGRT TYADSVKGRFTISRDNSKNTLYLQMNSLRAEDTAVYYCAREGGYGWYFDVWGQGTTV TVSS |
| 306 | TLA0241-VH-10 | EIQLQQSGAEEKKPGASVRISCKASGYTFTDYYMHWVQQAPGKGLEWIGDINPNNGRTT YNQKFQGRVTITADKSTSTAYMELRSLRSDDTAVYYCAREGGYGWYFDVWGTGTTVTV SS |
| 307 | TLA0241-VH-11 | ELQLQQSGAEVKKPGASVRISCKASGYTFTDYYMHWVRQAPGQGLEWIGDINPNNGRT TYNQKFQGRVTITADKSTSTAYMELRSLRSDDMAVYYCAREGGYGWYFDVWGTGTLVT VSS |
| 308 | TLA0241-VL-1 | EIVLTQSPTTMAASPGEKITITCSTSSSIISNYSHWYQQKPGFSPKLLIYKTSNLPSGVPARF SGSGSGTSYSLTIGTMEAEDAATYYCQQGSDMPITFGAGTKLELK |
| 309 | TLA0241-VL-2 | DIQMTQSPSSLSASVGDRVTITCSTSSSIISNYSHWYQQKPGKAPKLLIYKTSNLPSGVPSR FSGSGSGTEFTLTISSLQPEDFATYYCQQGSDMPITFGQGTKVEIK |
| 310 | TLA0241-VL-3 | EIVLTQSPTTLSLSPGEKVTITCSASSSIISNYLHWYQQKPGKSPKLLIYKTSNLPSGVPSRF SGSGSGTDFTLTINSLEAEDAATYYCQQGSDMPITFGAGTRLELK |
| 311 | TLA0241-VL-4 | EIVLTQSPPTLSLSPGEKVTITCSASSSIISNYLHWYQQKPGQSPQLLIYKTSNRPSGVPDRF SGSGSGTDFTLTINSLEAEDAATYYCQQGSDMPITFGAGTRLELK |
| 312 | TLA0241-VL-5 | EIVLTQSPGTLSLSPGEKVTITCSASSSIISNYLHWYQQKPDQSPKLLIYKTSNLPSGVPSRF SGSGSGTDFTLTINSLEAEDAATYYCQQGSDMPITFGAGTKLELK |
| 313 | TLA0241-VL-6 | AIQLTQSPSSLSASVGDRVTITCSTSSSIISNYSHWYQQKPGKAPKLLIYKTSNLPSGVPSRF SGSGSGTDFTLTISSLQPEDFATYYCQQGSDMPITFGQGTKVEIK |
| 314 | TLA0241-VL-7 | EIVLTQSPATLSLSPGEKVTITCSASSSIISNYSAWYQQKPGKSPKLLIYKTSNLPSGVPARF SGSGSGTDFTLTINSLEAEDAATYYCQQGSDMPITFGAGTRLELK |
| 315 | TLA0241-VL-8 | DIQMTQSPSSVSASVGDRVTITCSTSSSIISNYSHWYQQKPGKAPKLLIYKTSNLPSGVPSR FSGSGSGTDFTLTISSLQPEDFATYYCQQGSDMPITFGQGTKVEIK |
| 316 | TLA0241-VL-9 | EIVLTQSPTTLSLSPGEKVTITCSASSSIISNYLHWYQQKPDQSPKLLIYKTSNLPSGVPSRF SGSGSGTDFTLTINSLEAEDAATYYCQQGSDMPITFGAGTKLELK |
| 317 | TLA0241-VL-10 | EIVLTQSPPTLSLSPGEKVTITCSASSSIISNYLAWYQQKPGKSPKLLIYKTSNLPSGVPSRF SGSGSGTSFTLTINSLEAEDAATYYCQQGSDMPITFGAGTKLELK |
| 318 | CK | RTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |
| 319 | CH1 | ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSC |
| 320 | Fc(L234A, L235A) | DKTHTCPPCPAPEAAGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 321 | Fc(L234A, L235A, M252Y, S254T, T256E) | DKTHTCPPCPAPEAAGGPSVFLFPPKPKDTLYITREPEVTCVVVDVSHEDPEVKFNWYVD GVEVHNAKTKPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK |
| 322 | RVT-3101-VH | QVQLVQSGAEVKKPGASVKVSCKASGYDFTYYGISWVRQAPGQGLEWMGWISTYNGN THYARMLQGRVTMTTDTSTRTAYMELRSLRSDDTAVYYCARENYYGSGAYRGGMDVW GQGTTVTVSS |
| 323 | RVT-3101-VL | EIVLTQSPATLSLSPGERATLSCRASQSVSSYLAWYQQKPGQAPRLLIYDASNRATGIPARF SGSGSGTDFTLTISSLEPEDFAVYYCQQRSNWPWTFGQGTKVEIK |
| 324 | MK-7240-VH | QVQLVQSGAEVKKPGASVKVSCKASGFDIQDTYMHWVKQRPGQGLEWMGRIDPASGH TKYDPKFQVRVTITRDTSTSTVYLELSSLRSEDTAVYYCARSGGLPDVWGQGTTVTVSS |
| 325 | MK-7240-VL | EIVLTQSPGTLSLSPGERATLSCRASSSVSYMYWYQQKPGQAPRPLIYATSNLASGIPDRES GSGSGTDFTLTISRLEPEDFAVYYCQQWEGNPRTFGGGTKLEIK |
| 326 | Human TL1A (M1-L251) | MAEDLGLSFGETASVEMLPEHGSCRPKARSSSARWALTCCLVLLPFLAGLTTYLLVSQLR AQGEACVQFQALKGQEFAPSHQQVYAPLRADGDKPRAHLTVVRQTPTQHFKNQFPALH WEHELGLAFTKNRMNYTNKFLLIPESGDYFIYSQVTFRGMTSECSEIRQAGRPNKPDSIT VVITKVTDSYPEPTQLLMGTKSVCEVGSNWFQPIYLGAMFSLQEGDKLMVNVSDISLVD YTKEDKTFFGAFLL |

-continued

| c | LABEL | SEQ |
|---|---|---|
| 327 | Human STL1A (L72-L251) | LKGQEFAPSHQQVYAPLRADGDKPRAHLTVVRQTPTQHFKNQFPALHWEHELGLAFTK NRMNYTNKFLLIPESGDYFIYSQVTFRGMTSECSEIRQAGRPNKPDSITVVITKVTDSYPE PTQLLMGTKSVCEVGSNWFQPIYLGAMFSLQEGDKLMVNVSDISLVDYTKEDKTFFGAF LL |
| 328 | Cyno sTL1A (L72-L251) | LKGQEFAPSHQQVYAPLRADGDKPRAHLTVVRQTPTQHLKNQFPALHWEHELGLAFTK NRMNYTNKFLLIPESGDYFVYSQVTFRGMTSECSEIRQAGRPNKPDSITVVITKVTDSYP EPTQLLMGTKSVCEVGSNWFQPIYLGAMFSLQEGDKLMVNVSDISLVDYTK EDKTFFGAFLL |
| 329 | Mouse STL1A (A61-L252) | AGQLRVPGKDCMLRAITEERSEPSPQQVYSPPRGKPRAHLTIKKQTPAPHLKNQLSALH WEHDLGMAFTKNGMKYINKSLVIPESGDYFIYSQITFRGTTSVCGDISRGRRPNKPDSITV VITKVADSYPEPARLLTGSKSVCEISNNWFQSLYLGAMFSLEEGDRLMVNVSDISLVDYT KEDKTFFGAFLL |
| 330 | Rat STL1A(T61-I252) | TGQLRIPGKDCMFPTVTEERSAPSAQPVYTPSRDKPKAHLTIMRQTPVPHLKNELAALH WENNLGMAFTKNRMNYTNKFLVIPESGDYFIYSQITFRGTTSECGDISRVRRPKKPDSITV VITKVADSYPEPAHLLTGTKSVCEISSNWFQPIYLGAMESLEEGDRLMVNVSDISLVDYTK EDKTFFGAFLI |
| 331 | Human DR3-ECD(Q25-Q199) | QGGTRSPRCDCAGDFHKKIGLFCCRGCPAGHYLKAPCTEPCGNSTCLVCPQDTFLAWEN HHNSECARCQACDEQASQVALENCSAVADTRCGCKPGWFVECQVSQCVSSSPFYCQPC LDCGALHRHTRLLCSRRDTDCGTCLPGFYEHGDGCVSCPTSTLGSCPERCAAVCGWRQ |
| 332 | TLA0238-VH20 | EVQLVESGGGLVKPGGSLRLSCAASGFTFSNYWMNWVRQAPGKGLEWVGQIRLKSDN YATHYAESVKGRFTISRDDSKNTLYLQMNSLKTEDTAVYYCTTLLLRYRDYWGQGTLVT VSS |
| 333 | TLA0238-VH21 | EVQLVESGGGLVKPGGSLRLSCAASGFTFSNYWMNWVRQAPGKGLEWVGQIRLKSDN YATHYAESVKGRFTISRDDSKNTLYLQMNSLKTEDTAVYYCTPLLLRYRDYWGQGTLVT VSS |
| 334 | TLA0238-VH22 | EVQLVESGGGLVKPGGSLRLSCAASGFTFSNYWMNWVRQAPGKGLEWVAQIRLKSDN YATHYAESVKGRFTISRDDSKNTLYLQMNSLKTEDTAVYYCTPLLLRYRDYWGQGTLVT VSS |
| 335 | TLA0238-VL-15 | EIVLTQSPATLSLSPGERATLSCSASSSVSYMHWYQQKPGQSPRLWIYDTSNLASGIPARFS GSGSGTDYTLTISSLEPEDFAVYYCFQENAHPFTFGGGTKVEIK |
| 336 | TLA0238-VL-16 | EIVLTQSPATLSLSPGERATLSCSASSSVSYMHWYQQKPGQSPRLWIYDTSNLASGVPARF SGSGSGTDYTLTISSLEPEDFAVYYCFQENAHPFTFGGGTKVEIK |
| 337 | TLA0238 VL-17 | DIQMTQSPSSLSASVGDRVTITCSASSSVSYMHWYQQKPGKAPKLWIYDTSNLASGVPS RFSGSGSGTDYTLTISSLQPEDFATYYCFQENAHPFTFGQGTKLEIK |
| 338 | TLA0238-VL-18 | DIQLTQSPSSLSASVGDRVTITCSASSSVSYMHWYQQKPGKAPKLWIYDTSNLASGVPSR FSGSGSGTDYTLTISSLQPEDFATYYCFQENAHPFTFGQGTKLEIK |
| 339 | HC | EIQLVESGGGLIQPGGSLRISCAVSGFSLSSYGVDWVRQAPGKGLEWLGVIWGFGGTNY NSALKSRLTISKDNSKNTVYLQMNSLRAEDTAVYYCASGNFDAMDYWGQGTLVTVSSA STKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCPAPEAAGGPS VFLFPPKPKDTLYITREPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPGK |
| 340 | LC | DIQMTQSPSSLSASVGDRVTITCRASQDISNYLNWYQQKPGKAVKLLIYYTSRLHSGVPS RFSGSGSGTDYTLTISSLQPEDFATYFCQQGNTLPFTFGQGTKLEIKRTVAAPSVFIFPPSDE QLKSGTASVVCLLNNFYPREAKVQWKVDNALQSGNSQESVTEQDSKDSTYSLSSTLTLS KADYEKHKVYACEVTHQGLSSPVTKSFNRGEC |
| 341 | Fc(No mutation) | DKTHTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK |
| 342 | mice-1 | QIQLVQSGPELKKPGETVKISCKASGYTFTTYGMNWVKQSPGKGLKWMGWINTYSGVP TYADDFKGRFAFSLETSVNTAYLQINSLKTDDTATYFCAKDAYDNYAMDYWGQGTSV TVSS |
| 343 | mice-2 | QIQLKESGPGLVAPSQSLSITCTVSGFSLSSYGVDWVRQSPGKGLEWLGVIWGFGGTNY NSALKSRLSISKDNSKSQVFLKMNSLQSDDSAIYYCASGNFDAMDYWGQGTSVTVSS |
| 344 | mice-3 | DVQLQESGPGLVKPSQSLSLTCSVTDYSITSGYYWNWIRQFPGNKLEWMGYIHFDGSND YNPSLKNRISITRDTSRNQFFLKLNSVTSEDTATYYCAREGTSYFDYWGQGTTLTVSS |

-continued

| c | LABEL | SEQ |
|---|---|---|
| 345 | mice-4 | QIQLVQSGPELKKPGETVKISCKASGYTFTTYGMSWVKQAPGKYLKWMGWIDTYSGVPTYADDFKGRFAFSLETSANTAYLQINNLKNEDTATYFCANSFQFAYWGQGTLVTVSA |
| 346 | mice-5 | DVQLQESGPGLVKPSQSLSLTCSVTGYSITSGYYWNWIRQFPGNKLEWMGCISYDGSNYYNPSLKNRISFTRDTSKNQFFLKLNSVTTDDTATYYCVREGTSYVDYWGQGTTLTVSS |
| 347 | mice-6 | DVQLQESGPGLVKPSQSLSLTCSVTDYSITSGYYWNWIRQFPGNKLEWMGYIHYDGSNDYNPSLKNRISITRDTSRNQFFLKLNSVTSEDTATYYCAREGTSYFDYWGQGTTLTVSS |
| 348 | mice-7 | QVQLQQSGPELVRPGASVKISCKAPGYTFTSHWMQWVRQRPGQGLEWIGEIFPGSGTTYYNEKFQGKATLTVDTSSSTAYMQLSSLTSEDSSVHFCARGEGIYYPARSYGPLGYFDVWGTGTTVTVSS |
| 349 | mice-8 | QVQLQQPGAELVMPGASVKLSCKASGYTFTNYWMNWVKQRPRQGLEWIGETDPSNTYINYNQKFKGKATLTVDKSSNTAYMQLNSLTSEDSAVYYCARGGLPYYGMDYWGQGTSVTVSS |
| 350 | mice-9 | QIQLVQSGPELKKPGETVKISCKASGSAFTTYGMSWVKQAPGEGLKWMGYIITYSGVPTYADDFKGRFAFSLETSASTAYLQINNLKNEDTATYFCTNFYYFDYWGQGTTLTVSS |
| 351 | mice-10 | QIQLVQSGPELKKPGETVKISCKASGYTFTTFGMNWVKQAPGKDLKWMGWINTNSGVPTYADDFRGRFAFSMETSATTAYLQINNLKNEDTATYFCARGNWEGPGIWFAYWGQGTLVTVSA |
| 352 | mice-11 | QVQLQQPGTELVKPGASVKLSCKASGYTFTSYWMHWVKQRPGQGLEWIGNIDPNNDVINYNDKFKSKATLTVDKSSSTAYMQLSSLTSEDSGVYYCARGIYAGYWGQGTLVTVSA |
| 353 | mice-12 | EVQLQQSGAELMKPGASVKLSCKATGYTFTGYWLEWVKQRPGHGLEWIGETLPGSGYNKYNEKFKGKATFTADTSSNTAHMQLSSLTTEDSAIYYCARRGSNYPYWYFDVWGTGTTVTVSS |
| 354 | mice-13 | QVQLKESGPGLVQPSQSLSITCTVSGFSLTSYGVHWVRQSPGKGLEWLGVIWSGGSTDYNAAFISRLSISKDNSKSQVFFKMNSLQADDTAIYYCARNDYDYAMDYWGQGTSVTVSS |
| 355 | mice-14 | QVQLQQSGPELVKPGASVKLSCKASGYTFTSIDINWVKQRPGQGLEWIGWIYPRDGRTDYNEKFKGKATLTVDTSSSTAYMELHSLTSEDSAVYFCARYTSSLDYWGQGTTLTVSS |
| 356 | mice-15 | EVKLEESGGGLVQPGGSMKLSCVASGFTFSNYWMNWVRQSPEKGLEWVAQIRLKSDNYATHYAESVKGRFTISRDDSKSNVYLQMNNLRAEDTGIYYCTPLLLRSIDYWGQGTTLTVSS |
| 357 | mice-16 | EVQLQQSGPELVKPGASVKLSCKASGYTFTSIDINWVKQRPGQGLEWIGWIYPRDGRTDYNEKFKGKATLTVDTSSSTAYMELHSLTSEDSAVYFCARYGSSLDYWGQGTTLTVSS |
| 358 | mice-17 | QVQLQQSGPELVKPGASVKLSCKASGYTFTNQDMNWVKQRPGQGLEWIGWIFPRDGRTHHNENFKGKATLTVDTSSSTAYMELHSLTAEDSAVYFCAIYGFAMDQWGQGTSVTVSS |
| 359 | mice-18 | QVQLQQPGPELVKPGASVKLSCKASGYTFTNQDINWVKQRPGQGLEWIGWIFPRDGRTHYNENFKGKATLTVDTSSSTAYMELHSLTAEDSAVYFCAIYGIALDHWGQGTSVTVSS |
| 360 | mice-19 | QVQLQQPGPELVKPGASVKLSCKASGYTFTNQDINWVKQRPGQGLEWIGWIFPRDGRTHYNENFKGKATLTVDTSSSTAYMELHSLTAEDSAVYFCAIYGAAMDHWGQGTSVTVSS |
| 361 | mice-20 | EVKLEESGGGLVQPGGSMKLSCVASGFTFSNYWMNWVRQSPEKGLEWVAQIRLKSDNYATHYAESVKGRFTISRDDSKSSVYLQMNNLRAEDTGIYYCTPLLLRYFDVWGTGTTVTVSS |
| 362 | mice-21 | EVQLQQSVAELVRPGASVKLSCTASGFNIEDTYIHWVKQRPEQGLEWIGRIDPAHDKTKYAPKFQGKATITADTSSNTAYLQLSSLTSEDTAIYYCASTGPDWWGQGTTLTVSS |
| 363 | mice-22 | QVQLQQSGAELVRPGTSVKMSCKASGYTFTNYWIGWTKQRPGHGLEWIGDIYPGGGYINYNEKFKGKATLTADKSSSTAYMQFSSLTSEDSAIYYCAREGGYGSGQAWFPYWGQGTLVTVSA |
| 364 | mice-23 | QVQLQQPGTELVRPGTSVKLSCKASGYTFTSYWMHWVKQRPGQGLEWIGVIEPSDSYTDYNQKFKGKATLTVDTSSSTAYMQLSSLTSEDSAVYYCARGDYDEVFAYWGQGTLVTVSA |
| 365 | mice-24 | QVQLQQPGAELVRPGTSVKLSCKASGYTFTSYWMHWVKQRPGQGLEWIGVIEPSDSYTDYDQKFKGKATLTVDTSSNTAYMQLSSLTSEDSAVYYCSRGDYDEVFAYWGQGTLVTVST |
| 366 | mice-25 | QVQLQQSGADLVRPGASVTLSCKASGYTFSDSEIHWVRQTPVHGLEWIGAIDPETGDIAYNQMFKDKATLTADKSSSTAYVELRSLTSEDSAVYYCTRYGGNSWHFDVWGTGTTVTVSS |

-continued

| c | LABEL | SEQ |
|---|---|---|
| 367 | mice-26 | EFQLQQSGPELLKPGASVKISCKASGYSFTDYNINWVKQRNGKSLEWIGMINPKYGITDYNQKFKGKATLTVDQFSSTAYMQVNSLTSDDSAVYYCAREELGHWCFDVWGTGTTVTVSS |
| 368 | mice-27 | QVQLQQSGAELVRPGTSVKVSCKASGYAFTNYLIEWVNQRPGQGLEWIGVINPGSGGTKYNEKFKGKATLTADKSSSTAYMQLSSLTSEDSAVYFCAREGSAGPFDYWGQGTTLTVSS |
| 369 | mice-28 | EFQLQQSGPELVKPGASVKISCKASGYSFTDYNINWVKQRNGKSLEWIGMINPKYGITDYNQKFKGKATLTVDQFSSTAYMQVNSLTSDDSAVYYCAREELGHWCFDVWGTGTTVTVSS |
| 370 | mice-29 | EVQLQQSGPVLVKPGASVKMSCEASGYTLTDYYMNWVKQSHGKSLEWIGIINPYNGASNFNQRFRGKASLTFGKSSNTAYMELNSLTSEDSAVYYCASDWDVGYWGQGTALTVSS |
| 371 | mice-30 | EVQLVESGGDLVKPGGSLKLSCAASGFTFSRYGMSWVRQTPDKRLEWVATISSGGSDTYYPDSVKGRFTISRDNAKNTLYLQMSSLKSEDTAMYYCARHGYDYGHFDYWGQGTTLTVSS |
| 372 | mice-31 | EFQLQQSGPELVKPGASVKISCKASGYSFTDYNINWVKQSNGKSLEWIGVINPNYGITDYNQKFKGKATLTVDQSSSTAYMQLNSLTSEDSAVYYCAREELGHWCFDVWGTGTTVTVSS |
| 373 | mice-32 | QVTLKESGPGILQPSQTLNLTCSFSGFSLSTFGMGVGWIRQPSGEGLEWLAHIWWDDHEYYNPALKSRLTISKDTSKNQVFLKIANVDTADTATYYCNRGFVYWGQGTLVTVSA |
| 374 | mice-33 | QVQLQQSGPELVKPGTSVKLSCKASGYTFTSYDINWMKQRPGQGLEWIGWIFPRDGITKYNEKFKDKATLTVDTSSSAAYMELHSLTSEDSAVYFCARYGPAMDYWGQGTSVTVSS |
| 375 | mice-34 | QIQLVQSGPELVKPGASVKVSCKASGYTFTRQDINWVKQRPGQGLEWIGWIYPRDGRTEYNEKFKGKVTLTVDTSSSTAYMELHSLTSEDSAVYFCATYGSSLDNWGQGTTLTVSS |
| 376 | mice-35 | EVQLQQSGPELVKPGASVKVSCKASGYTFTRQDINWVKQRPGQGLEWIGWIYPRDGSTKYNEKFKGKVTLTVDTSSSTAYMELHSLTSEDSAVYFCATYGSSLDNWGQGTTLTVSS |
| 377 | mice-36 | EVQLQQSGPELVKPGASVKLSCKASGYTFTNQDINWVKQRPGQGLEWIGWIFPRDGRTHYNENFKGKATLTVDTSSSTAYMELHSLTAEDSAVYFCAIYGIAMDHWGQGTSVTVSS |
| 378 | mice-37 | QIQLVQSGPELVKPGASVKLSCKASGYTFTNYDINWVKQRPGQGLEWIGWIYPRDGSTYYNEKFKGKATLTVDTSSTTAYMEFHSLTSEDSAVYFCARYAYALNSWGQGTSVTVSS |
| 379 | mice-38 | QVQLKQSGPELVRPGASVKLSCKASGYSFTSGDINWVKQRPGQGLEWIAWIYPRDGSTEYNEKFKGKATLTVDTSSSTAYMELHSLTSEDSAVYFCARYDCAFVYWGQGTLVTVSA |
| 380 | mice-39 | QVQLQQSGPELVKPGASVKLSCKASGYTFTNQDINWVKQRPGQGLEWIGWIFPRDGRTHYNENFKGKATLTVDTSSSTAFMELHSLTAEDSAVYFCAIYGIALDHWGQGTSVTVSS |
| 381 | mice-40 | QVQLQQSGPELVKPGASVKLSCKASGYTFTDYDVNWVKQRPGQGLEWIGWNYPRDGRTNYNEKFKGKATLTVDISSSTAYMELHSLTSEDSAVYFCARYGSALNVWGTGTSVTVSS |
| 382 | mice-41 | QIQLVQSGPELVKPGASVKLSCKASGYTFTKYDINWVKQRPGQGLEWIGWIYPRDGSTKYNEKFKGKATLTVDTSSNTAYMELHSLTSEDSAVYFCARYSAAMDYWGQGTSVTVSS |
| 383 | mice-42 | QVQLQQPGAELGKPGASVKLSCKASGYTFTNYDINWVKQRPGQGLEWIGWNYPRDGRTKYNEKFKGKATLTVDTSSSTAYMELHSLTSEDSAVYFCARYGYAMDYWGQGTSVTVSS |
| 384 | mice-43 | QVQLQQPGAELGKPGASVKLSCKASGYTFTNYDINWMKLRPGQGLEWIGWNYPRDGRTKYNEKFKGKATFTVDTSSSTAYMELHSLTSEDSAVYFCARYGYAMDYWGQGTSVTVSS |
| 385 | mice-44 | QIQLVQSGPELVKPGASVKLSCRASGYTFTSYDINWVKQRPGQGLEWIGWIFPRDGRTEYNAKFKGKATLTVDTSSNTAYMELHSLTSDDSAVYFCARYGSTLDVLGAGTTVTVSS |
| 386 | mice-45 | EVQLQQSGPELVKPGASVKLSCKASGYTFTNQDINWVKQRPGQGLEWIGWIFPRDGRTHYNENFKDKATLTVDTSSSTAYMEVHSLTAEDSAVYFCAIYGIALDHWGQGTSVTVSS |
| 387 | mice-46 | QIQLVQSGPELVKPGASVKLSCKASGYTFTRQDINWVKQRPGQGLEWIGWIYPRDGSTKYNEKFKGKVTLTVDTSSSTAYMELHSLTSEDSAVYFCATYGSSLDNWGQGTTLTVSS |
| 388 | mice-47 | QVQLQQSGPELVKPGASVKIPCKTSGYTFTDYNINWVKRSHGKSLEWIGDINPDSGGTSYNQRFKDKATLTVDKSSSTAYMELRSLTSGDTAVYYCARWGYYGGRGFDYWGQGTTLTVSS |
| 389 | mice-48 | QVQLQQSGAELGKPGASVKLSCKASGYTFTNYDINWMKQRPGQGLEWIGWNYPRDGRTKYNEKFKGKATLTVDTSSSTAYMELHSLTSEDSAVYFCARYGYAMDYWGQGTSVTVSS |

-continued

| c | LABEL | SEQ |
|---|---|---|
| 390 | mice-49 | EVQLQQSGPDLVKPGASVKLSCKASGYTFASYDINWVKQRPGQGLEWIGWIYPRDGRT DYNEKFKGKATLTVDTSSSTAYMELHSLTSEDSAVYFCARYGYALGYWGQGTSVTVSS |
| 391 | mice-50 | QVQLQQSGPELAKPGASVKLSCKASGYTFTSRDINWVKQRPGQGLEWIGWIYPRDGRT NYNEKFKDKATLTVDTSSSTAYMDLHSLTSEDSAVYFCATYGSSLDHWGQGTTLTVSS |
| 392 | mice-51 | EVQLQQSGPELVKPGASVKLSCKASGYTFTNQDINWVKQRPGQGLEWIGWIFPRDGRT HYNENFKGKATLTVDTSSSTAYMELHSLTAEDSAVYFCAIYGAAMDHWGQGTSVTVSS |
| 393 | mice-52 | QVQLQQSGPELVKPGTSVKLSCKASGYTFTDQDINWVKQRPGQGLEWIGWIFPRDGRT HYNEKFKGKATLTVDTSSSTAYMELHSLTSEDSAVYFCSIYGSAMDLWGQGTSVTVSS |
| 394 | mice-53 | QVQLQQSGPELVKPGASVKLSCKASGYTFTNQDINWVKQRPGQGLEWIGWIFPRDGRT HNNENFKGKATLTVDTSSSTAYMELHSLTAEDSAVYFCAIYGFAMDHWGQGTSVTVSS |
| 395 | mice-54 | EVQLQQSGPELVKPGASVKLSCKASGYTSTSYDINWVKQRPGQGLEWIGWIYPRDGRT NYNEKFKGKATLTVDTSSSTAFMELHSLTSEDSAVYFCARYSAAMDYWGQGTSVTVSS |
| 396 | mice-55 | QVQLQQPGSELVRPGASVKIPCKTSGYSFTDFNINWVRQSHGKSLEWIGDINPDSGGTIY NQKFKGKATLTVDKSSSTAYMELRSLTSEDTAVYYCARWGYYGGEGFDYWGQGTTLT VSS |
| 397 | mice-56 | QIQLVQSGPELVKPGASVKLSCKASGYTFTSSDINWVKQRPGQGPEWIGWIYPRDGRTH YNEKFKGKATLTVDTSSSTAYMELHSLTSEDSAVYFCARYAYALNSWGQGTSVTVSS |
| 398 | mice-57 | QVQLQQPGPELVKPGASVRVSCKASGYTFTRQDINWVKQRAGQGLEWIGWIYPRDGRT EYNEKFKGKVTLTVDTSSSTAYMELHSLTSEDSAVYFCATYGSSLDNWGQGATLTVSS |
| 399 | mice-58 | QVQLQQSGPELVKPGASVKLSCKASGYTFTSYDINWVKQRPGQGLEWIGWIFPRDGDT KYNEKFKGKATLTVDTSSSTAFMELHSLTSEDSAVYFCARYGSTLDVWGTGTTVTVSS |
| 400 | mice-59 | QIQLVQSGPELVMPGASVKLSCQASGYTFTNSDINWVKQRPGQGLEWIGWVYPGDGST YYNEKFKGKATLTVDTSSSTAYMDLYSLTSEDSAVYFCARYAYALNSWGQGTSVTVSS |
| 401 | mice-60 | QIQLVQSGPELVKPGASVKLSCKASGYTFTNSDINWVKQRPGQGLEWIGWIYPRDGSTY YNEKFKGKATLTVDTSSTTAYMEFHSLTSEDSAVYFCARYAYALNSWGQGTSVTVSS |
| 402 | mice-61 | QVQLQQSGPEVVKPGASVKLSCKASGYTFTSYDINWVKQRPGQGLEWIGWIFPRDGRT EYNEKFKDKATLTVDTSSSTAYMELHSLTSEDSAFYFCARYGSSLDYWGQGTTLTVSS |
| 403 | mice-62 | QIQLVQSGPELVKPGASVKLSCQASGYTFTNSDINWVKQRPGQGLDWIGWVYPRDGST YYNEKFKGKATLTVDTSSSTAYMELYSLTSEDSAVYFCARYAYALNYWGQGTSVTVSS |
| 404 | mice-63 | QIQLVQSGPELVKPGASVKLSCKASGYTFTSIDINWVKQRPGQGLEWIGWIYPRDGRTD YNEKFKGKATLTVDTSSSTAYMELHSLTSEDSAVYFCARYTSSLDYWGQGTTLTVSS |
| 405 | mice-64 | QVQLQQSGPELVKPGASVKLSCKASGYTFTSIDINWVKQRPGQGLEWIGWIYPRDGRTN YNEKFKGKATLTVDTSSSTAYMDLHSLTSEDSAVYFCARYTSSLDYWGQGTTLTVSS |
| 406 | mice-65 | QVQLQQSGPELVKPGASVKLSCRASGYTFTSYDINWVKQRPGQGLEWIGWNYPRDGRT DYNEKFKGKATLTVDTSSNTAYMDLHSLTSEDSAVYFCTRYGSTLDVWGTGTSVTVSS |
| 407 | mice-66 | QIQLVQSGPELVKPGASVKLSCQASGYTFTNSDINWVKQRPGQGLEWIGWVYPRDGSA YYNEKFKGKATLTVDTSSSTAYMELYSLTSEDSAVYFCARYAYALNFWGQGTSVTVSS |
| 408 | mice-67 | QVQLKQSGPELVKPGASVKVSCKASGYTFTRQDINWVKQRPGQGLEWIGWIYPRDGRT EYNEKFKGKVTLTVDTSSSTAYMELHSLTSEDSAVYFCATYGSSLDNWGQGTTLTVSS |
| 409 | mice-68 | QVQLQQPGPELVKPGASVKLSCKASGYTFTNQDINWVKQRPGQGLEWIGWIFPRDGRT HYNEKFKGKATLTVDTSSSTAYMELHSLTAEDSAVYFCAIYGSAMDQWGQGTSVTVSS |
| 410 | mice-69 | EVQLQQSGPELVKPGASVKLSCKASGYTFTNSDINWVKQRPGQGLEWIGWIYPRDGSTY YNEKFKGKATLTVDTSSTTAYMEFHSLTSEDSAVYFCARYAYALNSWGQGTSVTVSS |
| 411 | mice-70 | QVQLQQPGAELMKPGASVKLSCKATGYTFTAYWLEWVKQRPGHGLEWIGEILPGSGY AYYNAKFKGKATFTADISSNTAYMQLSGLTTEDSAIYYCARRGSNYPYWYFDVWGTGT TVTVSS |
| 412 | mice-71 | QVQLQQSGAELMKPGASVKLSCKATGYTFTGYWLEWVKQRPGHGLEWIGETLPGSGY NKYNEKFKGKATFTADTSSNTAHMQLSSLTTEDSAIYYCARRGSNYPYWYFDVWGTGT TVTVSS |
| 413 | mice-72 | QVQLQQSGAELMKPGASVKLSCKATGYTFTGYWLEWVKQRPGHGLEWIGETLPGSGY NKYNEKFKGKATFTADTSSNTAHMQLSSLTTEDSAIYYCARRGSNYPYWYFDVWGTGT SVTVSS |

-continued

| c | LABEL | SEQ |
|---|---|---|
| 414 | mice-73 | QVQLQQSGPELVKPGASVKLSCRASGYTFTSYDINWVKQRPGQGLEWIGWNYPRDGRTDYNEKFKGKATLTVDTSSNTAYMELHSLTSEDSAVYFCTRYGSTLDVWGTGTTVTVSS |
| 415 | mice-74 | QIQLVQSGPELVKPGASVKLSCRASGYTFTSYDINWVKQRPGQGLEWIGWNYPRDGRTDYNEKFKGKATLTVDTSSNTAYMELHSLTSEDSAVYFCTRYGSTLDVWGTGTTVTVSS |
| 416 | mice-75 | QVQLQQPGPELVKPGASVKLSCRASGYTFTSYDINWVKQRPGQGLEWIGWIFPRDGRTEYNAKFKGKATLTVDTSSNTAYMELHSLTSDDSAVYFCARYGSTLDVLGAGTTVTVSS |
| 417 | mice-76 | EVQLQQSGPELVKPGASVKLSCRASGYTFTSYDINWVKQRPGQGLEWIGWIFPRDGRTEYNEKFKGKATLTVDTSSNTAYMELHSLTSEDSAVYFCARYGSTLDVWGTGTTVTVSS |
| 418 | mice-77 | QIQLVQSGPELVKPGASVKLSCRASGYTFTSYDINWVKQRPGQGLEWIGWIFPRDGRTEYNEKFKGKVTLTVDTSSNTAYMELHSLTSEDSAVYFCARYGSTLDVWGPGTTVTVSS |
| 419 | mice-78 | QVQLQQFGPELVKPGSSVKLSCKASGYTFTDYDVNWVKQRPGQGLEWIGWNYPRDGRTNYNEKFKGKATLTVDTSSSTAYMELHSLTSEDSAVYFCARYGSALNVWGTGTTVTVSS |
| 420 | mice-79 | QVQLQQSGPELVKPGASVKLSCKASGYTFTDYDVNWVKQRPGQGLEWIGWNYPRDGRTNYNEKFKGKATLTVDISSSTAYMELHSLTSEDSAVYFCARYGSALNVWGTGTTVTVSS |
| 421 | mice-80 | QIQLVQSGPELVKPGASVKLSCQASGYTFTNSDINWVKQRPGQGLEWIGWVYPRDGSTYYNEKFKGKATLTVDTSSSTAYMELYSLTSEDSAVYFCARYAYALNSWGQGTSVTVSS |
| 422 | mice-81 | QIQLVQSGPELVKPGASVKLSCQASGYTFTNSDINWVKQRPGQGLEWIGWVYPRDGSTYYNEKFKAKATLTVDTSSSTAYMELYSLTSEDSAVYFCARYAYALNYWGQGTSVTVSS |
| 423 | mice-82 | QIQLVQSGPELVKPGASVKLSCQASGYTFTNSDINWVKQRPGQGLEWIGWVYPRDGRTYYNEKFKGKATLTVDTSSSTAYMELYSLTSEDSAVYFCARYAYALNSWGQGTSVTVSS |
| 424 | mice-83 | QIQLVQSGPELVKPGASVKLSCKASGYTFTNSDINWVKQRPGQGLEWIGWVYPRDGSTYYNEKFKGKATLTVDTSSSTAYMELHSLTSEDSAVYFCTRYAYALNSWGQGTSVTVSS |
| 425 | mice-84 | QIQLVQSGPELVKPGASVKLSCKASGYTFTNSDINWVKQRPGQGLEWIGWIYPRDGSTYYNEKFKGKATLTVDTSSTTAYMEFHSLTSEDSAVYFCARYAYTLNSWGQGTSVTVSS |
| 426 | mice-85 | EVQLQQSGAELARPGASVKMSCKASGYTFTNSDINWVKQRPGQGLEWIGWIYPRDGSTYYNEKFKGKATLTVDTSSSTAYMELHSLTSEDSAVYFCTRYAYALNSWGQGTSVTVSS |
| 427 | mice-86 | QVQLQQSGPELVKPGASVKLSCKASGYTFTNSDINWVKQRPGQGLEWIGWIYPRDGSTYYNEKFKGKATLTVDTSSSTAYMELHSLTSEDSAVYFCTRYAYALNSWGQGTSVTVSS |
| 428 | mice-87 | EVQLQQSGPELVKPGASVKLSCQASGYTFTNSDINWVKQRPGQGLEWIGWVYPRDGRTYYNEKFKGKATLTVDTSSSTAYMELYSLTSEDSAVYFCARYAYALNSWGQGTSVTVSS |
| 429 | mice-88 | EVQLQQSGPELVRPGASVKLSCKASGYSFTSGDINWVKQRPGQGLEWIAWIYPRDGSTEYNEKFKGKATLTVDTSSSTAYMELHSLTSEDSAVYFCARYDYAFVYWGQGTLVTVSA |
| 430 | mice-89 | EVQLQQSGPELVRPGTSVRLSCKTSGYTFTSRDINWVKQRPGQGLEWIAWIYPRDGSTEYNEKFKGKATLTVDTSSSTAYMELHSLTSEDSAVYFCTRYDYAFTYWGQGTLVTVSA |
| 431 | mice-90 | EVQLQQSGPEVVKPGASVKLSCKASGYTFTRNDINWVKQRPGQGLEWIGWIYPRDGSSKNNEKFKGKATLTVDTSSSTAYMELHSLTSEDSAVYFCARYDYAFVYWGQGTTVTVSS |
| 432 | mice-91 | EVQLQQSGPELVKPGASVKLSCKASGYTFTSYDINWVKQRPGQGLEWIGWIYPRDGRTKYSEKFKGKATLTVDTSSSTAYMELHSLTSEDSAVYFCARYGASMDYWGQGTSVTVSS |
| 433 | mice-92 | EVQLQQSGPELVKPGASVKLSCKASGYTFTSYDINWVKQSPGQGPEWIGWVYPRDGRTQYNEKFKGKATLTVDTSSSTAYMELHSLTSEDSAVYFCARYGASMDYWGQGTSVTVSS |
| 434 | mice-93 | EVQLQQSGPELAKPGASVKLSCKASGYTFTSYDINWVKQRPGQGLEWIGWIYPRDGNTNYNEKFKGKATLTVDTSSNTASMELHSLTSEDSAVYFCARYSAAMDYWGQGTSVTVSS |
| 435 | mice-94 | QVQLQQPGPELVKPGASVKLSCKASGYTSTSYDINWVKQRPGQGLEWIGWIYPRDGRTNYNEKFKGKATLTVDTSSSTAFMELHSLTSEDSAVYFCARYSAAMDYWGQGTSVTVSS |
| 436 | mice-95 | QVQLQQSGPELVKPGASVKLSCKASGYTFTSYDINWVKQRPGQGLEWIGWIFPRDGRTNYNEKFKDKATLTVDTSSSTAFMELHRLTSEDSAVYFCARYSAAMDYWGQGTSVTVSS |
| 437 | mice-96 | EVQLQQSGAELGKPGASVKLSCKASGYTFTNYDINWMKQRPGQGLEWIGWNYPRDGRTKYNEKFKGKATLTVDTSSSTAYMELHSLTSEDSAVYFCARYGYAMDYWGQGTSVTVSS |

-continued

| c | LABEL | SEQ |
|---|---|---|
| 438 | mice-97 | QVQLQQSGPDLVKPGASVKLSCKASGYIFASYDLNWVKQRPGQGLEWIGWIYPRDGRT DYNEKFKGKATLTVDTSSSTAYMELHSLTSEDSAVYFCARYGYALDYWGQGTSVTVSS |
| 439 | mice-98 | QIQLVQSGPELVKPGASVKVSCKASGYTFTRQDINWVKQRPGQGLEWIGWIYPRDGRTE YNEKFKGKATLTVDTSSSTAFMELHSLTSEDSAVYFCARYSAAMDYWGQGTSVTVSS |
| 440 | mice-99 | QIQLVQSGPELVKPGASVKLSCKASGYTFTNSDINWVKQRPGQGLEWIGWNYPRDGRT KYNEKFKGKATFTVDTSSSTAYMDLQSLTSEDSAVYFCTRYGSAMDYWGQGTSVTVSS |
| 441 | mice-100 | EVQLQQSGPELVKPGASVKLSCKASGYTFTNQDINWVKQRPGQGLEWIGWIFPRDGRT HYNENFKGKATLTVDTSSSTAYMELHSLTAEDSAVYFCAIYGIALDHWGQGTSVTVSS |
| 442 | mice-101 | QVQLQQSGPELVKPGASVKLSCKASGYTFTNQDINWVKQRPGQGLEWIGWIFPRDGRT HYNENFKGKATLTVDTSSNTAYMELHSLTAEDSAVYFCAIYGIALDHWGQGTSVTVSS |
| 443 | mice-102 | QVQLQQSGPELVKPGASVKLSCKASGYTFTNQDINWVKQRPGQGLEWIGWIFPRDGRT HYNENFKGKATLTVDTSSSTAYMELHSLTAEDSAVYFCAIYGIALDHWGQGTSVTVSS |
| 444 | mice-103 | QVQLQQSGPELVKPGASVKLSCKASGYTFTNQDINWVKQRPGQGLEWIGWIFPRDGRT HYNENFKGKATLTVDTSSSTAYMELHSLTAEDSAVYFCAIYGAAMDHWGQGTSVTVSS |
| 445 | mice-104 | QVQLQQSGPELVKPGTSVKLSCKASGYTFTNQDINWVKQRPGQGLEWIGWIFPRDGRT HYNENFKGKATLTVDTSSSTAYMELHSLTAEDSAVYFCSIYGIAMDHWGQGTSVTVSS |
| 446 | mice-105 | QVQLQQPGPELVKPGASVKLSCKASGYTFTNQDINWVKQRPGQGLEWIGWIFPRDGRT HNNENFKGKATLTVDTSSSTAYMELHSLTAEDSAVYFCAIYGFAMDHWGQGTSVTVSS |
| 447 | mice-106 | QVQLQQSGPELVKPGASVKLSCKASGYTFTNQDINWVKQRPGQGLEWIGWIFPRDGRT HYNENFKGKATLTVDTSSSTAYMELHSLTAEDSAVYFCAIYGFAMDHWGQGTSVTVSS |
| 448 | mice-107 | QVQLQQPGPELVKPGASVKLSCKASGYTFTNQDINWVKQRPGQGLEWIGWIFPRDGRT HYNENFKGKATLTVDTSSSTAYMELHSLTAEDSAVYFCAIYGAAMDDWGQGTSVTVSS |
| 449 | mice-108 | QVQLQQPGPELVKPGASVKLSCKASGYTFTNQDINWVKQRPGQGLEWIGWIFPRDGRT HYNENFKGKATLTVDTSSSTAFMELHSLTAEDSAVYFCAIYGIALDHWGQGTSVTVSS |
| 450 | mice-109 | EVQLQQSGPELVKPGASVKLSCKASGYTFTNQDINWVKQRPGQGLEWIGWIFPRDGRT HYNENFKGKATLTVDTSSSTAYMELHSLTAEDSAVYFCAIYGFAMDHWGQGTSVTVSS |
| 451 | mice-110 | EVQLQQSGPELVKPGASVKLSCKASGYTFTNQDINWVKQRPGQGLEWIGWNFPRDGRT HYNENFKGKATLTVDTSSSTAYMELHSLTAEDSAVFFCAIYGFALDHWGQGTSVTVSS |
| 452 | mice-111 | QVQLQQSGPELVKPGASVKLSCKASGYTFTNQDINWVKQRPGQGLEWIGWIFPRDGRT HYNENFKGKATLTVDTSSSTAYMELHSLTAEDSAVYFCALYGFAMDQWGQGTSVTVSS |
| 453 | mice-112 | EVQLQQSGPELVKPGASVKLSCKASGYTFTNQDINWVKQRPGQGLEWIGWIFPRDGRT HYNEKFKGKATLTVDTSSSTAYMELHSLTAEDSAVYFCAIYGSAMDQWGQGTSVTVSS |
| 454 | mice-113 | EVQLQQSGPELVKPGTSVKIPCKTSGYTFTDYNINWVKQSHGKSLEWIGDINPDSGGTV YNQRFKDKATLTVDKSSSTAYMELRSLTSGDTAVYYCARWGYYDGRGFDYWGQGTTL TVSS |
| 455 | mice-114 | EVQLQQSGAELVRPGASVTLSCKASGYTFTDYEIHWVKQIPVHGLEWIGVEDPETGGAA YNQKFKGKAILTADKSSSTAYMELRSLTSEDSAVYYCTTPWLNYFEYWGQGTTLTVSS |
| 456 | mice-115 | QVQLQQSVAELVRPGASVKLSCTASGFNIEDTYMHWVKQRPEQGLEWIGRVDPASGNT KYGPKFQGKATITADTSSNTAYLQLSSLSSADTAIYYCSTWGLFDYWGQGTTLTVSS |
| 457 | mice-116 | QVQLQQPGPELVKPGASVKLSCKASGYTFTSIDINWVKQRPGQGLEWIGWIYPRDGRTH YNEKFKGKATLTVDTSSSTAYMELHSLTSEDSAVYFCARYTSSLDYWGQGTTLTVSS |
| 458 | mice-117 | QVQLQQSGPELVKPGASVKLSCKASGYTFTSIDINWVKQRPGQGLEWIGWIYPRDGRTD YNEKFKGKATLTVDTSSSTAYMELHSLTSEDSAVYFCARYGSSLDYWGQGTTLTVSS |
| 459 | mice-118 | QVQLQQSGPELVKPGTSVRLSCKASGYTFTNSDINWVKQRPGQGLEWIGWIYPRDGRT DYNEKFKGKATLTVDTSSSTAYMELHSLTSEDSAVYFCARYGSSLYWGQGTTLTVSS |
| 460 | mice-119 | EVQLQQSGPELVKPGASVKLSCKASGYTFTSSDINWVKQRPGQGPEWIGWIYPRDGRTH YNEKFKGKATLTVDTSSSTAYMELHSLTSEDSAVYFCAPYGSSLAYWGQGTTLTVSS |
| 461 | mice-120 | QIQLVQSGPELVKPGASVKLSCKASGYTFTSSDINWVKQRPGQGLEWIGWIYPRDGSTH YNENFKGKATLTVDTSSSTAYMELHSLTSEDSAVYFCAPYGSSLAYWGQGTTLTVSS |

-continued

| c | LABEL | SEQ |
|---|---|---|
| 462 | mice-121 | QVQLKESGPEVVKPGASVKLSCKASGYTFTSYDINWVKQRPGQGLEWIGWIYPRDGRTEYNEKFKDKATLTVDTSSSTAYMELHSLTSEDSAVYFCARYGSSLDYWGQGTTLTVSS |
| 463 | mice-122 | QIQLVQSGPELVKPGASVKVSCKASGYTFTRQDINWVKQRPGQGLEWIGWIYPRDGSTKYNEKFKGKVTLTVDTSSSTAYMELHSLTSEDSAVYFCATYGSSLDNWGQGTTLTVSS |
| 464 | mice-123 | QVQLQQSGPELVKPGASVKVSCKASGYTFTRQDINWVKQRPGQGLEWIGWIYPRDGSTKYNEKFKGKVTLTVDTSSSTAYMELHSLTSEDSAVYFCATYGSSLDNWGQGTTLTVSS |
| 465 | mice-124 | QIQLVQSGPELVKPGASVKVSCKASGYTFTRQDINWVKQRPGQGLEWIGWIYPRDGRTEYNEKFKGKVTLTVDTSSSTAYMELHSLTPEDSAVYFCATYGSSLDNWGQGTTLTVSS |
| 466 | mice-125 | QVQLKESGPELVKPGASVKVSCKASGYTFTRQDINWVKQRPGQGLEWIGWIYPRDGRTEYNEKFKGKVTLTVDTSSSTAYMELHSLTSEDSAVYFCATYGSSLDNWGQGTTLTVSS |
| 467 | mice-126 | QVQLQQSGAELAKPGASVKLSCKASGYTFTRQDINWVKQRPGQGLEWIGWIYPRDGRTEYNEKFKGKVTLTVDTSSSTAYMELHSLTSEDSAVYFCATYGSSLDNWGQGTTLTVSS |
| 468 | mice-127 | QVQLQQPGPELVKPGASVKVSCKASGYTFTRQDINWVKQRPGQGLEWIGWIYPRDGRTEYNEKFKGKVTLTVDTSSNTAYMELHSLTSEDSAVYFCATYGSSLDNWGQGTTLTVSS |
| 469 | mice-128 | QVQLQQSGPELVKPGASVKVSCKASGYTFTRQDINWVKQRPGQGLEWIGWIYPRDGRTEYNEKFKGKVTLTVDTSSSTAYMELHSLTSEDSAVYFCATYGSSLDNWGQGTTLTVSS |
| 470 | mice-129 | EVQLQQSGPELVKPGASVKVSCKASGYTFTRQDINWAKQRPGQGLEWIGWIYPRDGRTEYNEKFKGKVTLTVDTSSSTAYMELHSLTPEDSAVYFCATYGSSLDNWGQGTTLTVSS |
| 471 | mice-130 | EVQLQQSGPELVKPGASVKVSCKASGYTFTRQDINWVKQRPGQGLEWIGWIYPRDGRTEYNEKFKGKVTLTVDTSSSTAYMELHSLTSEDSAVYFCATYGSSLDNWGQGTTLTVSS |
| 472 | mice-131 | EVQLQQSVAELVRPGASVKLSCTASGFNIENTYIHWVKQRPEQGLEWIGRIDPASGNTKYAPKFQGKATITADTSSNTAYLQLSSLTSEDTAIYYCASTGPDYWGQGTTLTVSS |
| 473 | mice-132 | QIQLVQSGPELKKPGETVEISCKASGYTFTTHGMNWVKQAPGKGLKWMGWINTFSGVPTYADDFRGRFDFFLATSASTAYLQINNLKNEDTATYFCARDYGTAYAMDSWGQGTSVTVSS |
| 474 | mice-133 | EVKVEESGGGLVQPGGSMKLSCIASGFTFSNYWMNWVRQSPEKGLEWVAQIRLKSDNYATHYAESVKGNFTISRDDSKSSVYLQMNNLRAEDTGIYYCTPLLLRYRDYWGQGTTLTVSS |
| 475 | mice-134 | EVQLQQSGPELVKPGASVKISCKASGYTFTDYYMNWVKQSHGKSLEWIGDVNPNSGGTSQNQKFKGKATLTVDKSSTTAYMELRSLTSEDSAVYHCARGSNYVGGFTYWGQGTLVAVSA |
| 476 | mice-135 | QVQLQQPGAELVKPGASVKLSCKASGYTFSNDWMHWVKQRPGRGLEWIGRIDPDSGGTKYNEKFKNKATLTVDKPSSTVYMQLSSLTSEDSAVYYCARSEGYYGSRSYFDYWGQGTTLTVSS |
| 477 | mice-136 | EFQLQQSGPELVKPGASVRISCKASGYTFTDYYLNWVKQSRGESLEWIGDINPNNGRTTYNQKFTGKATWTVDKSSSTVYMELRSLTSDDSAVYYCAREGGYGWYFDVWGTGTTVTVSS |
| 478 | mice-137 | DIQMTQTTSSLSASLGDRVTISCRASQDISNYLNWYQQKPDGTVKLLIYYTSRLHSGVPSRFSGSGSGTDYSLTISNLEQEDIATYFCQQGNTLPFTFGSGTKLEIK |
| 479 | mice-138 | DIVLTQSPASLPVSLGQRATISCRASKSVSTSSYSYMHWYQQKPGQPPKLLIKYASNLESGVPARFSGSGSGTDFTLNIHPVEEEDAATYYCQHSKEFPWTFGGGTKLEIK |
| 480 | mice-139 | DIKMTQSPSSMYASLGERVTITCKASQDINSFLSWFQQKPGKSPKTLIYRANRLVDGVPSRFSGSGSGQDYSLTISSLEYEDMGIYYCLQCDEFPYTFGGGTKLEIK |
| 481 | mice-140 | DIKMTQSPSSMYASLGERVTITCKASQDINSYLSWFQQKPGKSPKTLIYRANRLVDGVPSRFSASGSGQDYSLTISSLEYEDMGIYYCLQCDEFPYTFGGGTKLEIK |
| 482 | mice-141 | DIVMTQSHKFMSTSVGDRVSITCKASQDVSTAVAWYQQKPGQSPKLLIYWASARHTGVPARFTGSGSGTDYTLTISSVQAEDLALYYCQQHYGTPPTFGGGTKLEIK |
| 483 | mice-142 | QIVLTQSPAIMSVSPGEKVTITCSATSRVTYMHWFQQKPGTAPKLWIYSTSNVASGVPARFSGSGSVTSYSLTISRMEAADAATYYCQQRSSYPPTFGGGTKLEIK |
| 484 | mice-143 | DIMLTQSPASLTVSLGQRATISCRASKSVSTSSYTYMHWYQQKPGQPPKLLIKYASNLESGVPARFSGSGSGTDFILNIHPVEEEDAATYYCQHSREFPWTFGGGTKLEIK |
| 485 | mice-144 | DIVLTQSPASLAVSLGQRATISCRASKSVSTSSYNYMHWYQQKPGQPPKLLIKYASNLESGVPARFSGSGSGTDFTLNIHPVEEEDAATYYCQHSREFPWTFGGGTKLEIK |

-continued

| c | LABEL | SEQ |
|---|---|---|
| 486 | mice-145 | QIVLTQSPALMSASPGEKVTMTCSASSSVSYMYWYQQKPRSSPKPWIYLTSNLASGVPA RFSGSGSGTSYSLTISSMEAEDAATYYCQQWIIYPPMLTFGAGTKLELK |
| 487 | mice-146 | DIVLTQSPASLAVSLGQRATISCKASQSVSFAGISLMHWYQQKPGQQPKLLIYRASNLEA GVPTRFSGSGSRTDFTLTINPVETDDVATYYCQQSNKDPTFGGGTKLELK |
| 488 | mice-147 | DIVMTQSHKFMSTSVGDRVSITCKASQDVSTAVAWYQQKPGQSPKLLIYSASYRYTGVP DRFTGSGSGTDFTFTISSVQAEDLAVYYCHQHYSTPYTFGGGTKLEIKR |
| 489 | mice-148 | DVVMTQTPLSLPVSLGDQASISCRSSQNIVHSNGDTYLDWFLQKPGQSPKLLIYKVSNRF SGVPDRFSGSGSGTDFTLKITRVESEDLGVYYCFQGSHDPYTFGGGTKLEIKR |
| 490 | mice-149 | ENVLTQSPAIMSASPGERVTMTCSASSSVSYMHWYQQKSSTSPKLWISDTSKLASGVPG RFSGSGSGNSYSLTISSMEAEDVATYYCFQESGYPFTFGAGTKLELK |
| 491 | mice-150 | DVVMTQTPLSLPVSLGDQASISCRSSQSIVHSNGDTYLEWYLQKPGQSPKLLIYKVSNRF SGVPDRFSGSGSGTDFTLKISRVEAEDLGVYYCFQGSHVPYTFGGGTKLEIKR |
| 492 | mice-151 | ENVLTQSPAIMSASPGEKVTMTCSASSSVSYMHWYQQKSSTSPKLWIYDTSKLASGVPG RFSGSGSGNSYSLTISSMEAEDVATYYCFQESGYPLTFGAGTKLELK |
| 493 | mice-152 | EILLTQSPAIIVASPGEKVTITCSATSSVIYMNWYQQKPGSSPKIWIYGISNLASGVPARFS GSGSGTSFSFTINSMEAEDVATYYCQQRSSYPFTFGSGTKLEIK |
| 494 | mice-153 | DVQITQSPSYLAASPGETITMNCRASKSIRKYLAWYQEKPGKSNKILIYSGSTLQSGIPSRF SGSGSGTDFTLTISSLEPEDFAMYYCQQHNEYPLTFGAGTKLELK |
| 495 | mice-154 | QIVLTQSPAIMSASPGEKVTMTCSASSSVSYMHWYQQKSGTSLKRWIYDTSKLASGVPA RFSGSGSGTSYSLTVSSMEAEDAATYYCQQWTSTPYTFGGGTKLEIK |
| 496 | mice-155 | QIVLTQSPAIMSASPGEKVTMTCSASSSVSYMHWYQQKSGTSPKRWIYDTSKLASGVPA RFSGSGSGTSYSLTISTMEAEDAATYYCQQWTSTPYTFGGGTKLEIK |
| 497 | mice-156 | DIQMTQTTSSLSASLGDRVTISCRASQDITNYLNWYQQKPDGTVKLLIYSTSRLHSGVPS RFSGSGSGTDYSLTISNLEQEDIATYFCQQGNTLPLTFGAGTKLELK |
| 498 | mice-157 | DIKMTQSPSSMYASLGERVTITCKASQDINSYLSWFQQKPGKSPKTLIYRANRLLDGVPS RFSGSGSGQDYSLTISSLEYEDMGIYYCLQYDEFPYTFGGGTKLEIK |
| 499 | mice-158 | DIVMTQPQKFMPTSVGDRVSVTCKASQNVGTNVAWYQQKAGQSPKVLIYSASYRYSG VPDRFTGSGSGTAFTLTISNVQSEDLAEYFCHQYNNFPFSFGSGTMLEIK |
| 500 | mice-159 | DIKMTQSPSSMYASLGDRVTITCKASQDIDSYLSWFQQKPGKSPKTLMYHTNRLIVGVPS RFSGTGSGQDYALTISSLEYEDLGIYYCQQYDEFPSTFGSGTKLEIK |
| 501 | mice-160 | DIQMTQTTSSLSASLGDRVTISCRASQDISNYLNWYQQKPDGTVKLLIYYTSRLHSGVPS RFSGSGSGTDYSLTISNLDQEDIATYFCQQGNTLPLTFGAGTKLELK |
| 502 | mice-161 | DNVMTQSQKFMSTSVGDRVSVTCKASQNVGTNVAWYQQKAGQSPKVLIYSASYRYSG VPDRFTGSGSGTAFTLTISNVQSEDLAEYFCQQYNSFPFTFGSGTKLEIK |
| 503 | mice-162 | DVVMTQTPLTLSVTIGQPASISCKSSQSLLDSDGKTYLSWLLQRPGQSPKRLIILVSKLDS GVPDRFTGSGSGTDFTLKISRVEAEDLGVYYCWQGTHFPQTFGGGTKLEIK |
| 504 | mice-163 | DVLMTQAPLSLPVSLGDQASISCRSSQSIVHSNGDTYLDWYLQKPGQSLKLLIYKLSNRF SGVPDRFSGSGSGTDFTLKISRVEAEDLGVYHCFQGSHVPYTFGGGTKLEIK |
| 505 | mice-164 | DVVMTQTPLSLPVSLGDQASISCRSSQSIVHGNGNTYLEWYLQKPGQSPKLLIYKVSNRF SGVPDRFSGSGSGTDFTLKISRVEAEDLGVYYCFQGSHVPYTFGGGTKLELKR |
| 506 | mice-165 | DVVMTQTPLSLPVSLGDQASISCRSSQSIVHSNGNTYLEWYLQKPGQSPKLLIYKVSNRF SGVPDRFSGSGSGTDFTLKISRVEAEDLGVYYCFQGSHVPYTFGGGTKLELKR |
| 507 | mice-166 | DVVMTQTPLSLPVSLGDQASISCRSSQSIVHSNGSTYLEWYLQKPGQSPKLLIYKVSNRF SGVPDRFSGSGSGTDFTLKISRVEAEDLGVYYCFQGSHVPYTFGGGTKLEIK |
| 508 | mice-167 | DVVMTQTPLSLPVSLGDQASISCRSSQNIVHSNGDTYLDWFLQKPGQSPQLLIYKVSNRF SGVPDRFSGSGSGTDFTLKISRVEAEDLGIYYCFQGSHVPYTFGGGTKLEIK |
| 509 | mice-168 | DVVMTQTPLSLPVSLGDQASISCRSSQSIVHSNGHTYLEWYLQKPGQSPKLLIYKVSNRF SGVPDRFSGSGSGTDFTLKISRVEAEDLGVYYCFQGSHVPYTFGGGTKLEIK |
| 510 | mice-169 | DVVMTQTPLSLPVSLGDQASISCRPSQTIVHSNGDTYLDWFLQKPGQSPKLLIYKVSNRF SGVPDRFSGSGSGTDFTLKISRVEAEDLGVYYCFQGSHVPYTFGGGTRLEIK |
| 511 | mice-170 | DVVMTQTPLSLPVSLGDQASISCRSSQSIVHSNGNTYLEWYLQKPGQSPKLLIYKVSNRF SGVPDRFSGSGSGTDFTLKISRVEAEDLGVYYCFQGSHVPLTFGDGTKLEIK |

-continued

| c | LABEL | SEQ |
|---|---|---|
| 512 | mice-171 | DVVMTQTPLSLPVSLGDQASISCRSSQSIVHSNGDTYLDWFLQKPGQSPKLLIYKVSNRF SGVPDRFSGSGSGTDFTLKITRVESEDLGVYYCFQGSHDPYTFGGGTKLEIK |
| 513 | mice-172 | DVVMTQTPLSLPVSLGDQASISCRSSQSVVHNNGNTYLEWYLQKPGQSPKLLIYKVSNR FSGVPDRFSGSGSGTDFTLKISRVEAEDLGVYYCFQGSHVPYTFGGGTKLELK |
| 514 | mice-173 | DVVMTQTPLSLPVSLGDQASISCRSSQSIVHSNGDTYLEWYLQKPGQSPKLLIYKVSNRF SGVPDRFSGSGSGTDFTLKISRVEAEDLGVYYCFQGSHVPYTFGGGTKLEIK |
| 515 | mice-174 | DVVMTQTPLSLPVSLGDQASISCRSSQSIVHTNGDTYLDWYLQKPGQSPKLLIYKVSNRF SGVPDRFSGSGSGTDFTLKISRVEAEDLGVYYCFQGSHVPYTFGGGTKLEIK |
| 516 | mice-175 | DVVMTQTPLSLPVSLGDQASISCRSSQSIVHDNGDTYLEWYLQKPGQSPKLLIYKVSNRF SGVPDRFSGSGSGTDFTLKINRVEAEDLGVYYCFQGSHVPYTFGGGTKLEIK |
| 517 | mice-176 | DVVMTQTPLSLPVSLGDQASISCRSSQNIVHSNGNTYLEWYLQKPGQSPKLLIYKVSNRF SGVPDRFSGSGSGTDFTLKISRVEAEDLGVYYCFQGSHVPYTFGGGTKLEIK |
| 518 | mice-177 | DIVLTQSPASLAVSLGQRATISCRASESVDDYGISFMHWYQQKPGQPPKLLIYRASNLES GIPARFSGSGSRTDFTLTIDPVETDDVATYYCQQSYEDPPTFGAGTKLEIK |
| 519 | mice-178 | DIVLTQSPASLAVSLGQRATISCRASESVDNYGISFMHWYQQKPGQPPKLLVYRASNLES GIPARFSGSGSRTDFTLTINPVETDDVATYYCQQSNKDPPTFGGGTKLEIK |
| 520 | mice-179 | DIVLTQSPASLAVSLGQRATISCRASESVDNYGISFMHWYQQKPGQPPKLLIYRASNLES GIPARFSGSGSRTDFTLTINPVETDDVATYYCQQSNKDPPTFGAGTKLELK |
| 521 | mice-180 | DIVLTQSPASLAVSLGQRATISCRASKSVSTSSYSYMHWYQQKPGQPPKLLIKYASNLES GVPARFSGSGSGTDFTLNIHPVEEEDAATYYCQHSREFPTFGGGTKLEIK |
| 522 | mice-181 | DVVMTQTPLSLPVSLGDQASISCRSSQSIVHSNGDTYLDWYLEKPGQSPKLLIYKVSNRF SGVPDRFSGSGSGTDFTLKISRVEAEDLGVYYCFQGSHVPYTFGGGTKLEIKR |
| 523 | mice-182 | DVVMTQTPLSLPVSLGDQASISCRSSQSIVHNNGDTYLDWYLQKPGQSPKLLIYKVSNRF SGVPDRFSGSGSGTDFTLKISRVEAEDLGVYYCFQGSHVPYTFGGGTKLELK |
| 524 | mice-183 | DVVMTQTPLSLPVSLGDQASISCRSSQSIVHGNGNTYLEWYLQKPGQSPKLLIYKVSNRF SGVPDRFSGSGSGTDFTLKISRVEAEDLGVYYCFQGSHVPYTFGGGTKLEIK |
| 525 | mice-184 | DVVMTQTPLSLPVSLGDQASISCRSSQNIIHSNGDTYLDWFLQKPGQSPKLLIYKVSNRFS GVPDRFSGSGSGTDFTLKISRVEAEDLGVYYCFQGSHVPYTFGGGTKLEIK |
| 526 | mice-185 | DVVMTQTPLSLPVSLGDQASISCRSSQSIVHSNGNTYLEWYLQKPGQSPKLLIYKVSNRF SGVPDRFSGSGSGTDFTLKISRVEAEDLGVYYCFQGSHVPYTFGRGDQAGNKT |
| 527 | mice-186 | DVVMTQTPLSLPVSLGDQASISCRSSQSIVHSNGDTYLEWYLQKPGQSPKLLIYKVSNRF SGVPDRFSGSGSGTDFTLKISRVEAEDLGIYYCFQGSHVPYTFGGGTKLEIK |
| 528 | mice-187 | DVVMTQTPLSLPVSLGNQASISCRSSQDIVHTNGDTYLDWYLQKPGQSPKLLIYKVSNRF SGVPDRFSGSGSGTDFTLKINRVEAEDLGVYYCFQGSHVPYTFGGGTKLELK |
| 529 | mice-188 | DVVMTQTPLSLPVSLGDQASISCRSSQSIVHSNGDTYLDWFLQKPGQSPKLLIYKVSNRF SGVPDRFSGSGSGTDFTLKISRVEAEDLGVYYCFQGSHVPYTFGGGTKLELK |
| 530 | mice-189 | DVVMTQTPLYLPVSLGDQASISCRSSQSIVHSNGDTYLDWFLQKPGQSPKLLIYKVSNRF SGVPDRFSGSGSGTDFTLKISRVEAEDLGVYYCFQGSHVPYTFGGGTKLELK |
| 531 | mice-190 | DVVMTQTPLSLPVSLGDQASISCRSSQTIVHSNGDTYLDWYLQKPGQSPKLLISKVSNRF SGVPDRFSGSGSGTDFTLKISSVEAEDLGVYYCFQGSHVPYTFGGGTKLEIK |
| 532 | mice-191 | DVVMTQTPLSLPVSLADQASISCRSSQSIVHDNGDTYLEWYLQKPGQSPKLLIYKVSNRF SGVPDRFSGSGSGTDFTLKISRVEAEDLGVYYCFQGSHVPYTFGGGTKLEIK |
| 533 | mice-192 | DVVMTQTPLSLPVSLGDQASISCRSSQSIVHNNGDTYLDWYLEKPGQSPKLLIYKVSNRF SGVPDRFSGSGSGTDFTLKISRVEAEDLGVYYCFQGSHVPYTFGGGTKLEIK |
| 534 | mice-193 | DVVMTQTPLSLPVSLGDQASISCRSSQNIVHNNGDTYLDWFLQKPGQSPKLLIYKVSNRF SGVPDRFSGSGSGTDFTLKISRVEAEDLGVYYCFQGSHVPYTFGGGTKLELK |
| 535 | mice-194 | DVVMTQTPLSLPVSLGDQASISCKSSQSIVHSNGNTYLEWYLQKPGQSPKLLIYKVSNRF SGVPDRFSGSGSGTDFTLKISRVEAEDLGVYYCFQGSHVPYTFGGGTKLEIK |

-continued

| c | LABEL | SEQ |
|---|---|---|
| 536 | mice-195 | DVVMTQTPLSLPVSLGDQASISCRSSQNIVHSNGDTYLEWYLQKPGQSPKLLIYKVSNRFSGVPDRFSGSGSGTDFTLKISRVEAEDLGVYYCFQGSYVPYTFGGGTKLEIK |
| 537 | mice-196 | DVVMTQTPLSLPVSLGDQASISCRSSQNIVHSNGDTYLEWYLQKPGQSPKLLIYKVSNRFSGVPDRFSGSGSGTDFTLKISRVEAEDLGVYYCFQGSHVPYTFGGGTKLEIK |
| 538 | mice-197 | DVVMTQTPLSLPVSLGDQASISCRSSQNIVHSNGDTYLDWFLQKPGQSPKLLIYKVSNRFSGVPDRFSGSGSGTDFTLKISRVEAEDLGVYYCFQGSHVPYTFGGGTKLEIK |
| 539 | mice-198 | DVVMTQTPLSLPVSLGDQASISCRSSQSIVHSNGDTYLDWFLQKPGQSPKLLIYKVSNRFSGVPDRFSGSGSGTDFTLKISRVESEDLGVYYCFQGSHDPYTFGGGTKLEIK |
| 540 | mice-199 | DVVMTQTPLSLPVSLGDQASISCRSSQSIVHSNGNTYLEWYLQKPGQSPKLLIYKVSDRFSGVPDRFSGSGSGTDFTLKISRVEAEDLGVYYCFQGSHVPYTFGGGTKLEIK |
| 541 | mice-200 | DVVMTQTPLSLPVSLGHQASISCRSSQSIVHSNGNTYLEWYLQKPGQSPKLLIYKVSNRFSGVPDRFSGSGSGTDFTLKISRVEAEDLGVYYCFQGSHVPYTFGGGTKLELK |
| 542 | mice-201 | DVVMTQTPLSLPVSLADQASISCRSSQSIVHDNGDTYLEWYLQKPGQSPKLLIYKVSNRFSGVPDRFSGSGSGTDFTLKISRVEAEDLGVYYCFQGSHVPYTFGWRDQAGNKT |
| 543 | mice-202 | DVVMTQTPLSLPVSLGDQASISCRSSQSIVHSNGNTYLEWYLQKPGQSPKLLIYKASNRFSGVPDRFSGSGSGTDFTLRISSVEAEDLGVYYCFQGSHVPYTFGGGTKLEIK |
| 544 | mice-203 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPLTFGAGTKLELK |
| 545 | mice-204 | DVVMTQTPLSLPVSLGDQASISCRSSQSLVHSNGNTYLHWYLQKPGQSPKLLIYKVSNRFSGVPDRFSGSGSGTDFTLKISRVEAEDLGVYFCSQSTHVPFTFGSGTKLEIK |
| 546 | mice-205 | EIVLTQSPALMSASPGEKVTITCSASSSVSYMHWFQQKPGTSPKLWIYSTSNLASGVPARFSGSGSGTSYSLTISRMEAEDAATYYCQQRSSYPFTFGSGTKLEIK |
| 547 | mice-206 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIKR |
| 548 | mice-207 | DVVMTQTPLSLPVSLGDQASISCRSSQNIVHSNGDTYLDWYLQKPGQSPKLLISKVSNRFSGVPDRFSGSGSGTDFTLKISRVEAEDLGVYYCFQGSHVPYTFGGGTKLEIK |
| 549 | mice-208 | DVVMTQTPLSLPVSLGDQASISCRSSQNIVHSNGDTYLDWFLQKPGQSPKLLISKVSNRFSGVPDRFSGSGSGTDFTLKISRVEAEDLGVYYCFQGSHVPYTFGGGTKLEIK |
| 550 | mice-209 | DVVMTQTPLSLPVSLGDQASISCRSSQSIVHSNGDTYLDWFLQKPGQSPKLLIYKVSNRFSGVPDRFSGSGSGTDFTLKISRVEAEDLGVYYCFQGSHVPYTFGGGTKLEIK |
| 551 | mice-210 | DVVMTQTPLSLPVSLGDQASISCRSSQNIVHSNGDTYLDWFLQKPGQSPKLLIYKVSNRFSGVPDRFSGSGSGTDFTLKISRVEAEDLGVYYCFQGSHVPYTFGGGTKLELK |
| 552 | mice-211 | DVVMTQTPLSLPVSLADQASISCRSSQSIVHDNGDTYLEWYLQKPGQSPRLLIYKVSNRFSGVPDRFSGSGSGTDFTLKINRVEAEDLGVYYCFQGSHVPYTFGGGTKLEIK |
| 553 | mice-212 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLEIK |
| 554 | mice-213 | DVVMTQTPLSLPVSLGDQASISCRSSQSIVHNNGDTYLEWYLQKPGQSPKLLIYKVSNRFSGVPDRFSGSGSGTDFTLKISRVEAEDLGVYYCFQGSHVPYTFGGGTKLEIK |
| 555 | mice-214 | DVVMTQTPLSLPVSLGDQASISCRSSQNIVHTNGDTYLDWYLQKPGQSPKLLIYKVSNRFSGVPDRFSGSGSGTDFTLKISRVEAEDLGVYYCFQGSHVPYTFGGGTKLELK |
| 556 | mice-215 | DVVMTQTPLSLPVSLGDQASISCRSSQTIVHSNGNTYLDWYLQKPGHSPQLLIYKVSNRFSGVPDRFSGSGSGTDFTLKISRVEAEDLGVYYCFQGSHVPYTFGGGTKLEIK |
| 557 | mice-216 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGSGTKLEIK |
| 558 | mice-217 | DVVMTQTPLSLPVSLGDQASISCRSSQSIVHSNGNTYLEWYLQKPGQSPKLLIYKVSNRFSGVPDRFSGSGSGTDFTLKISRVEAEDLGVYYCFQGSHVPYTFGGGTKLELK |
| 559 | mice-218 | DVVMTQTPLSLPVSLGDQASISCRSSQNIVHSNGDTYLEWYLQKPGQSPKLLIYKVSSRFSGVPDRFSGSGSGTDFTLKISRVEAEDLGIYYCFQGSHVPYTFGGGTKLEIK |
| 560 | mice-219 | EILLTQSPAIIAASPGEKVTITCSASSSVSYMNWYQQKPGSSPKIWIYGISNLASGVPARFSGSGSGTSFSFTINSMEAEDVATYYCQQRSSYPFTFGSGTKLEIK |
| 561 | mice-220 | DVLMTQAPLSLPVSLGDQASISCRSNQTIVHSNGNTYLEWYLQKPGQSPKLLIYKVSNRFSGVPDRFSGSGSGTDFTLKISGVEAEDLGVYYCFQGSHVPLTFGAGTKLELN |

-continued

| c | LABEL | SEQ |
|---|---|---|
| 562 | mice-221 | ENVLTQSPAIMSASPGEKVTMTCSASSSVSYMHWYQQKSSTSPKLWIYDTSNLASGVPG RFSGSGSGNSYSLTISSMEAEDVATYYCFQENGHPFTFGGGTKLEMK |
| 563 | mice-222 | DILMTQSPSSMSVSLGDTVSITCHASQDIFSYIGWLQQKPGKSFKGLIHHGTNLEDGVPSR FRGNGSGADYSLTISSLESEDFADYYCVQYAQFPYTFGGGTKLEIK |
| 564 | mice-223 | DIVMTQSPSSLRVSAGEKVTMSCKSSQSLLNSGNQKNYLAWYQQKPGQPPKLLIYGAST RESGVPDRFTGSGSGTDFTLTISSVQAEDLAVYYCQNDHSYPYTFGGGTKLEIK |
| 565 | mice-224 | EIVLTQSPTTMAASPGEKITITCSTSSSIISNYSHWYQQKPGFSPKLLIYKTSNLPSGVPARF SGSGSGTSYSLTIGTMEAEDAATYYCQQGSDMPITFGAGTKLELK |

The invention claimed is:

1. An isolated antigen-binding protein specifically binding to TNF-like protein A (TL1A), wherein the antigen-binding protein is a monoclonal antibody comprising a heavy chain as set forth in SEQ ID NO: 339 and a light chain as set forth in SEQ ID NO: 340.

2. A composition comprising the isolated antigen-binding protein according to claim 1 and a pharmaceutical acceptable carrier.

3. A method for treating a TLIA-mediated disease, comprising administering a subject in need thereof the isolated antigen-binding protein according to claim 1.

4. The method of claim 3, wherein the TL1A-mediated disease is inflammatory bowel disease.

5. The method of claim 4, wherein the inflammatory bowel disease includes Ulcerative colitis or Crohn's disease.

* * * * *